United States Patent
Hirasawa et al.

(10) Patent No.: US 10,287,251 B2
(45) Date of Patent: May 14, 2019

(54) PYRAZOLE DERIVATIVE OR PHARMACEUTICALLY ACCEPTABLE SALT THEREOF

(71) Applicant: KISSEI PHARMACEUTICAL CO., LTD., Matsumoto-shi, Nagano (JP)

(72) Inventors: Hideaki Hirasawa, Azumino (JP); Fumiya Tanada, Azumino (JP); Yousuke Mutai, Azumino (JP); Nobuhiko Fushimi, Azumino (JP); Junichi Kobayashi, Azumino (JP); Yoshiro Kijima, Azumino (JP)

(73) Assignee: KISSEI PHARMACEUTICAL CO., LTD., Matsumoto-shi, Nagano (JP)

( * ) Notice: Subject to any disclaimer, the term of this patent is extended or adjusted under 35 U.S.C. 154(b) by 0 days.

(21) Appl. No.: 15/736,016

(22) PCT Filed: Jun. 22, 2016

(86) PCT No.: PCT/JP2016/068445
§ 371 (c)(1),
(2) Date: Dec. 13, 2017

(87) PCT Pub. No.: WO2016/208602
PCT Pub. Date: Dec. 29, 2016

(65) Prior Publication Data
US 2018/0170879 A1 Jun. 21, 2018

(30) Foreign Application Priority Data
Jun. 23, 2015 (JP) .................. 2015-126046

(51) Int. Cl.
*C07D 231/12* (2006.01)
*C07D 401/14* (2006.01)
(Continued)

(52) U.S. Cl.
CPC .......... *C07D 231/12* (2013.01); *A61K 31/415* (2013.01); *A61K 31/4155* (2013.01); *A61K 31/4178* (2013.01); *A61K 31/4192* (2013.01); *A61K 31/4196* (2013.01); *A61K 31/427* (2013.01); *A61K 31/436* (2013.01); *A61K 31/437* (2013.01); *A61K 31/4375* (2013.01); *A61K 31/444* (2013.01); *A61K 31/4439* (2013.01); *A61K 31/454* (2013.01); *A61K 31/4709* (2013.01); *A61K 31/4725* (2013.01); *A61K 31/497* (2013.01); *A61K 31/501* (2013.01); *A61K 31/506* (2013.01); *A61K 31/5377* (2013.01); *A61P 13/10* (2018.01); *C07D 401/04* (2013.01); *C07D 401/12* (2013.01); *C07D 401/14* (2013.01); *C07D 403/12* (2013.01); *C07D 405/14* (2013.01); *C07D 409/14* (2013.01); *C07D 417/12* (2013.01); *C07D 471/04* (2013.01); *C07D 491/052* (2013.01)

(58) Field of Classification Search
CPC ................ C07D 231/12; C07D 401/14; C07D 491/052; C07D 417/12
See application file for complete search history.

(56) References Cited

U.S. PATENT DOCUMENTS

| 2004/0215284 A1 | 10/2004 | Leonardi et al. |
| 2004/0266840 A1 | 12/2004 | Singh et al. |

(Continued)

FOREIGN PATENT DOCUMENTS

| GB | 1 366 035 A | 9/1974 |
| JP | 2000-256358 A | 9/2000 |

(Continued)

OTHER PUBLICATIONS

Kyu-Tae Chang, et al., "Regioselective synthesis of pyrazoles via the ring cleavage of 3-substituted N-alkylated 3-hydroxyisoindolin-1-ones", J. Chem. Soc. Perkin Trans. 1, 2002, pp. 207-210.

(Continued)

*Primary Examiner* — Laura L Stockton
(74) *Attorney, Agent, or Firm* — Sughrue Mion, PLLC

(57) ABSTRACT

The present invention is to provide a novel pyrazole derivative, or a pharmaceutically acceptable salt thereof, a pharmaceutical composition comprising the same, and a pharmaceutical use thereof.

The present invention provides a compound represented by the formula (I) or a pharmaceutically acceptable salt thereof, which has TRPM8 inhibitory effects:

[Chem.]

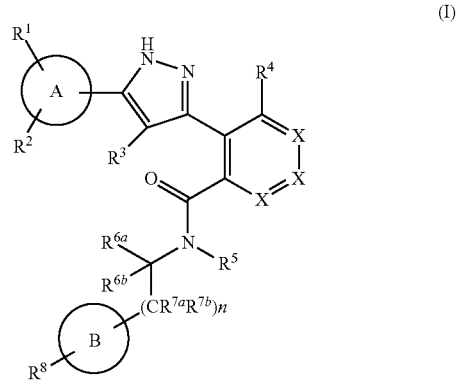

(I)

wherein ring A is $C_{6-10}$ aryl or the like; X is $CR^{4a}$ or the like; $R^1$ and $R^2$ are a hydrogen atom or the like; $R^3$ is a hydrogen atom or the like; $R^4$ is a hydrogen atom or the like; ring B is $C_{6-10}$ aryl or the like; $R^5$ is a hydrogen atom or the like; $R^{6a}$ is a hydrogen atom or the like; $R^{7a}$ is a hydrogen atom or the like; $R^{7b}$ is a hydrogen atom or the like; $R^{6b}$ is a hydrogen atom or the like; $R^8$ is a hydrogen atom or the like; n is 0, 1 or 2. Therefore, the compound represented by the formula (I) of the present invention or a pharmaceutically acceptable salt thereof is useful as an agent for treating or preventing diseases or symptoms caused by hyperexcitability or disorder of afferent neurons.

18 Claims, No Drawings

(51) Int. Cl.

| | |
|---|---|
| *C07D 491/052* | (2006.01) |
| *C07D 417/12* | (2006.01) |
| *C07D 403/12* | (2006.01) |
| *C07D 405/14* | (2006.01) |
| *A61K 31/436* | (2006.01) |
| *A61K 31/415* | (2006.01) |
| *A61K 31/4155* | (2006.01) |
| *A61K 31/4178* | (2006.01) |
| *A61K 31/4192* | (2006.01) |
| *A61K 31/4196* | (2006.01) |
| *A61K 31/427* | (2006.01) |
| *A61K 31/437* | (2006.01) |
| *A61K 31/4375* | (2006.01) |
| *A61K 31/4439* | (2006.01) |
| *A61K 31/444* | (2006.01) |
| *A61K 31/454* | (2006.01) |
| *A61K 31/4709* | (2006.01) |
| *A61K 31/4725* | (2006.01) |
| *A61K 31/497* | (2006.01) |
| *A61K 31/501* | (2006.01) |
| *A61K 31/506* | (2006.01) |
| *A61K 31/5377* | (2006.01) |
| *C07D 401/04* | (2006.01) |
| *C07D 401/12* | (2006.01) |
| *C07D 409/14* | (2006.01) |
| *C07D 471/04* | (2006.01) |
| *A61P 13/10* | (2006.01) |

(56) References Cited

U.S. PATENT DOCUMENTS

| | | |
|---|---|---|
| 2007/0197532 A1 | 8/2007 | Cao et al. |
| 2012/0202783 A1 | 8/2012 | Branstetter et al. |
| 2014/0309220 A1 | 10/2014 | Hadida-Ruah et al. |
| 2016/0115119 A1 | 4/2016 | Hirasawa et al. |

FOREIGN PATENT DOCUMENTS

| | | | |
|---|---|---|---|
| JP | 2009-515997 A | 4/2009 | |
| JP | 2010-536922 A | 12/2010 | |
| WO | 01/12627 A1 | 2/2001 | |
| WO | WO-2001/87287 A2 * | 11/2001 | ............ A61K 31/00 |
| WO | 02/00651 A2 | 1/2002 | |
| WO | 2004/018463 A2 | 3/2004 | |
| WO | 2004/067002 A2 | 8/2004 | |
| WO | 2004/099164 A1 | 11/2004 | |
| WO | 2006/088903 A2 | 8/2006 | |
| WO | 2007/017093 A1 | 2/2007 | |
| WO | 2009/012430 A1 | 1/2009 | |
| WO | 2009/027346 A2 | 3/2009 | |
| WO | 2011/050200 A1 | 4/2011 | |
| WO | 2011/109587 A1 | 9/2011 | |
| WO | 2013/067248 A1 | 5/2013 | |
| WO | 2014/181788 A1 | 11/2014 | |

OTHER PUBLICATIONS

International Search Report for PCT/JP2016/068445 dated Sep. 20, 2016 [PCT/ISA/210].

Communication dated Nov. 15, 2018 from the European Patent Office in counterpart Application No. 16814372.5.

\* cited by examiner

PYRAZOLE DERIVATIVE OR PHARMACEUTICALLY ACCEPTABLE SALT THEREOF

CROSS REFERENCE TO RELATED APPLICATIONS

This application is a National Stage of International Application No. PCT/JP2016/068445, filed on Jun. 22, 2016, which claims priority from Japanese Patent Application No. 2015-126046, filed on Jun. 23, 2015.

TECHNICAL FIELD

The present invention relates to an pyrazole derivative, which is useful as a pharmaceutical, or a pharmaceutically acceptable salt thereof, a pharmaceutical composition comprising the same, and a pharmaceutical use thereof.

BACKGROUND ART

Transient Receptor Potential (TRP) channels are non-selective cation channels activated by various stimuli such as temperature, chemical compounds, etc., and divided into TRPM, TRPA, TRPV, TRPC, TRPP, TRPML, and TRPN families. Further, the TRPM family includes TRPM1, TRPM2, TRPM3, TRPM4a, TRPM4b, TRPM5, TRPM6, TRPM 7 and TRPM8 channels (See, for example, Non-patent literature 1).

TRPM8, also known as CMR1 (cold and menthol sensitive receptor-1), is the eighth member of the TRPM family cloned in 2002 (See, for example, Non-patent literature 2), and is activated by cold temperature (8° C.-28° C.) or chemical compounds which evoke cold sensation such as menthol or icilin (See, for example, Non-patent literature 1 and 2). In addition to the primary afferent nerve (A-delta and C-fibers) and the trigeminal nerve, TRPM8 expression is also reported in taste papillae, vascular endothelium, the aorta, pulmonary arteries, the prostate, the male genital tract (See, for example, Non-patent literature 3), nerve fibers scattered in the human suburothelium (See, for example, Non-patent literature 4), prostate cancer (See, for example, Non-patent literature 5) and oral squamous carcinoma (See, for example, Non-patent literature 6).

In TRPM8 knockout mice, both lack of cold perception and deficiency in hypersensitivity to cold stimulation after nerve injury or inflammation are observed (See, for example, Non-patent literature 3).

In nervous system disorders, increase of TRPM8 expression and involvement in the hypersensitivity to cold in rats with sciatic nerve injury was reported (See, for example, Non-patent literature 7). It is reported that peripheral nerve injury evoked by oxaliplatin increases TRPM8 expression in mice and rats, and that TRPM8 is involved in the cold hypersensitivity evoked by oxaliplatin (See, for example, Non-patent literature 8 and 9). From the fact that patients taking oxaliplatin have increased reactivity to menthol compared with healthy volunteers, TRPM8 is considered to be involved in peripheral neuropathic pain evoked by oxaliplatin in humans as well as in rodents (See, for example, Non-patent literature 10).

In regards to the urinary tract diseases, TRPM8 is reported to be involved in the frequent urination symptoms evoked by cold temperature in rats (See, for example, Non-patent literature 11). Because of the expression in neurons projecting dichotomizing axons into both the skin and the bladder of rats, TRPM8 is considered to be involved in the urinary urgency evoked by cold (See, for example, Non-patent literature 12). In cats and patients with upper central nervous disorders such as stroke and spinal cord injury, infusion of a small amount of cold water into the bladder evokes micturition reflex that is not observed in normal volunteers, and this reflex is increased by the addition of menthol (See, for example, Non-patent literature 13 and 14). In cats, this reflex is decreased according to desensitization of C-fibers, so menthol-sensitive C-fibers are considered to be involved in the reflex (See, for example, Non-patent literature 13).

In patients with idiopathic detrusor overactivity or painful bladder syndrome, it is reported that TRPM8 expression is increased in nerve fibers in the suburothelium, and that TRPM8 expression correlates with the frequency of urination and pain scores (See, for example, Non-patent literature 15). Therefore, it is likely that TRPM8 plays an important role in the bladder afferent pathway during the bladder filling.

Accordingly, treatment or prevention of diseases or symptoms caused by the activation of TRPM8 are expected by inhibiting TRPM8.

Whereas a compound represented by the formula (A) has been described as a pyrazole derivative (see, for example, Non-patent literature 16):

[Chem.1]

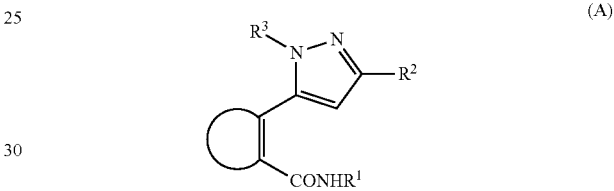

wherein, $R^1$, $R^2$, and $R^3$ have the same meanings as defined in Non-patent literature 16.

However, the compounds described in Non-patent literature 16 have a different structure from the compounds of the present invention. Further, anything is neither described nor suggested about TRPM8 inhibitors. And, compounds described in Patent literatures 1 to 9 have different structures from the compounds of the present invention. Further, anything is neither described nor suggested about TRPM8 inhibitors.

CITATION LIST

Non-Patent Literature

Non-patent literature 1: Makoto Tominaga, "Folia Pharmacologica Japonica", 2004, Vol. 124, p. 219-227

Non-patent literature 2: McKemy D D. et al., "Nature" 2002, Vol. 416, p. 52-58

Non-patent literature 3: Broad L M. et al., "Expert Opin Ther Targets", 2009, Vol. 13, p. 69-81

Non-patent literature 4: Andersson K E. et al., "BJU Int", 2010, Vol. 106, p.1114-1127

Non-patent literature 5: Zhang L. et al., "Endocr Relat Cancer", 2006, Vol. 13, p.27-38

Non-patent literature 6: Okamono Y. et al., "Int J Oncol", 2012, Vol. 40, p.1431-1440

Non-patent literature 7: Su L. et al., "BMC Neurosci", 2011, Vol.12, p.120

Non-patent literature 8: Kawashiri T. et al., "Mol Pain", 2012, Vol. 8, p.7

Non-patent literature 9: Gauchan P. et al., "Neurosci Lett", 2009, Vol. 458, p.93-95

Non-patent literature 10: Kono T. et al., "Brain Behave", 2012, Vol. 2, 68-73

Non-patent literature 11: Lei Z. et al., "Neurourol Urodyn", 2012, doi: 10.1002/nau.22325

Non-patent literature 12: Shibata Y. et al., "Neuroreport", 2011, Vol. 22, p.61-67

Non-patent literature 13: Lindstrom S. et al., "Acta Physiol Scand", 1991, Vol.141, p.1-10

Non-patent literature 14: Geirsson G. et al., "J Urol", 1993, Vol. 150, 427-430

Non-patent literature 15: Mukerji G. et al., "BMC Urol", 2006, Vol. 6, p.6

Non-patent literature 16: J. Chem. Soc. perkin Trans. 1, 2002, p. 207-210

Patent literature

Patent literature 1: Japanese patent publication (Tokuhyo) No. 2009-515997 gazette.
Patent literature 2: International publication No. WO2006/088903 pamphlet.
Patent literature 3: International publication No. WO2004/099164 pamphlet.
Patent literature 4: International publication No. WO2002/000651 pamphlet.
Patent literature 5: Japanese patent publication No. 2000-256358 gazette.
Patent literature 6: International publication No. WO2004/067002 pamphlet.
Patent literature 7: International publication No. WO2004/018463 pamphlet.
Patent literature 8: International publication No. WO2001/012627 pamphlet.
Patent literature 9: Japanese patent publication (Tokuhyo) No. 2010-536922 gazette.

SUMMARY OF THE INVENTION

Problem to be Solved by the Invention

The present invention is to provide a novel pyrazole derivative, or a pharmaceutically acceptable salt thereof, a pharmaceutical composition comprising the same, and a pharmaceutical use thereof.

Means for Solving the Problems

The present inventors have conducted extensive studies to find pyrazole derivatives, and as a result found that a compound represented by formula (I) of the present invention or a pharmaceutically acceptable salt thereof have a potent TRPM8 inhibition, thereby completing the present invention.

That is, the means for solving the above-described objects are as shown below.

[1] A compound represented by the formula (I) or a pharmaceutically acceptable salt thereof.

[Chem.2]

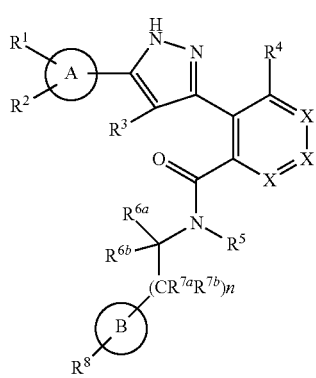

(I)

wherein
ring A is $C_{3-6}$ cycloalkyl, $C_{6-10}$ aryl or heterocycle;
X is independently $CR^{4a}$ or a nitrogen atom;
$R^1$ and $R^2$ are independently a hydrogen atom, a halogen atom, hydroxy, amino, formyl, hydroxy $C_{1-6}$ alkyl, $C_{1-6}$ alkoxy, $C_{1-6}$ alkyl, halo $C_{1-6}$ alkyl, cyano, $C_{1-6}$ alkylsulfonylamino, imidazolyl, 1,3-dioxolyl or mono(di)$C_{1-6}$ alkoxy $C_{1-6}$ alkyl;
$R^3$ is a hydrogen atom, a halogen atom, $C_{1-6}$ alkyl or formyl;
$R^4$ and $R^{4a}$ are independently a hydrogen atom, a halogen atom, hydroxy, $C_{1-6}$ alkyl, $C_{1-6}$ alkoxy, $C_{1-6}$ alkoxy $C_{1-6}$ alkoxy, halo $C_{1-6}$ alkyl, halo $C_{1-6}$ alkoxy, hydroxy $C_{1-6}$ alkyl, hydroxy $C_{1-6}$ alkoxy, cyano, carbamoyl, $C_{1-6}$ alkoxycarbonyl $C_{1-6}$ alkoxy, $C_{7-10}$ aralkyloxy $C_{7-10}$ aralkyloxy $C_{1-6}$ alkoxy or 1,3-dioxolyl;
ring B is $C_{6-10}$ aryl or heterocycle;
$R^5$ is a hydrogen atom, $C_{1-6}$ alkyl, mono(di)hydroxy $C_{1-6}$ alkyl, $C_{1-6}$ alkoxy(hydroxy)$C_{1-6}$ alkyl, carboxy $C_{1-6}$ alkyl or $C_{1-6}$ alkoxycarbonyl $C_{1-6}$ alkyl;
$R^{6a}$ is a hydrogen atom, $C(=O)R^9$, $C(=O)NR^{10}R^{11}$, $-CR^{12}R^{13}R^{14}$ or a group selected from the following formula:

[Chem.3]

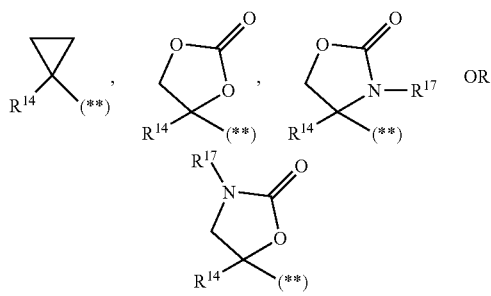

wherein, (**) is a bonding site;
$R^{7a}$ is independently a hydrogen atom, a fluorine atom, hydroxy, hydroxy $C_{1-6}$ alkyl, $C_{1-6}$ alkyl, $C_{1-6}$ alkoxy, $C_{1-6}$ alkoxy $C_{1-6}$ alkyl or amino $C_{1-6}$ alkyl;
$R^{7b}$ is independently a hydrogen atom, a fluorine atom or $C_{1-6}$ alkyl, or one of $R^5$ and $R^{6a}$ may bind together with ring B to form 6-membered ring or may bind together with $R^{7a}$ to form 5-membered ring;
$R^{6b}$ is a hydrogen atom or $C_{1-6}$ alkyl;
$R^8$ is a hydrogen atom, a halogen atom, $C_{1-6}$ alkyl, $C_{1-6}$ alkoxy, hydroxy, amino, cyano, $C_{1-6}$ alkoxycarbonyl, $C_{1-6}$ alkoxy $C_{1-6}$ alkoxy, carbamoyl, $C_{1-6}$ alkoxy $C_{1-6}$ alkyl, carboxy, azido, halo $C_{1-6}$ alkyl or tetrazolyl;
$R^9$ is hydroxy, $C_{1-6}$ alkyl or hydroxy pyrrolidinyl;
$R^{10}$ and $R^{11}$ are independently a hydrogen atom, $C_{1-6}$ alkyl, hydroxy $C_{1-6}$ alkyl, mono(di)$C_{1-6}$ alkylamino $C_{1-6}$ alkyl, pyrrolidinyl or piperidinyl;
$R^{12}$, $R^{13}$ and $R^{14}$ are independently a hydrogen atom, hydroxy, $C_{1-6}$ alkyl, $NR^{15}R^{16}$, $R^{15}R^{16}N-C_{1-6}$ alkyl, $C_{1-6}$ alkoxy, mono(di)hydroxy $C_{1-6}$ alkyl, carbamoyl, $C_{7-10}$ aralkyloxy $C_{1-6}$ alkyl, $C_{1-6}$ alkoxy $C_{1-6}$ alkyl, a fluorine atom or fluoro $C_{1-6}$ alkyl;
$R^{15}$ is a hydrogen atom, $C_{1-6}$ alkyl, ($C_{1-6}$ alkyl)carbonyl or $C_{7-10}$ aralkyl;
$R^{16}$ is a hydrogen atom, $C_{1-6}$ alkyl or C7-10 aralkyl;
$R^{17}$ is a hydrogen atom or $C_{1-6}$ alkyl;
n is 0, 1 or 2.

[2] The compound according to [1] or a pharmaceutical acceptable salt thereof: wherein, ring A is $C_{3-6}$ cycloalkyl, $C_{6-10}$ aryl, pyridyl, benzo[1,3]dioxolyl or thienyl; ring B is $C_{6-10}$ aryl or heterocycle selected from the group consisting of the following: pyridyl, pyrimidyl, piperidinyl, morpholinyl, thiazolyl, pyrazinyl, pyrazolyl, imidazolyl, pyridazinyl, azaindolizinyl, indolyl, isoquinolyl, triazolyl, tetrazolyl and dihydropyrimidinyl.

[3] The compound according to [2] or a pharmaceutically acceptable salt thereof: wherein n is 1.

[4] The compound according to [3] or a pharmaceutically acceptable salt thereof: wherein ring A is phenyl; X is $CR^{4a}$.

[5] The compound according to [4] or a pharmaceutically acceptable salt thereof: wherein $R^5$ is a hydrogen atom.

[6] The compound according to [5] or a pharmaceutically acceptable salt thereof: wherein $R^{6a}$ is a hydrogen atom, $C(=O)R^9$, $C(=O)NR^{10}R^{11}$, $-CR^{12}R^{13}R^{14}$ or a group selected from the following formula:

[Chem.4]

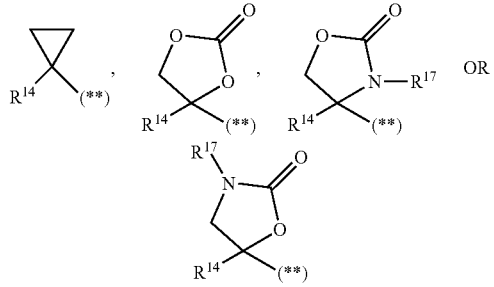

wherein, (**) is a bonding site;
$R^{7a}$ is a hydrogen atom, a fluorine atom, hydroxy, hydroxy $C_{1-6}$ alkyl, $C_{1-6}$ alkyl, $C_{1-6}$ alkoxy, $C_{1-6}$ alkoxy $C_{1-6}$ alkyl or amino $C_{1-6}$ alkyl;
$R^{7b}$ is a hydrogen atom, a fluorine atom or $C_{1-6}$ alkyl, or $R^{6a}$ may bind together with ring B or $R^{7a}$ to form the following formula:

[Chem.5]

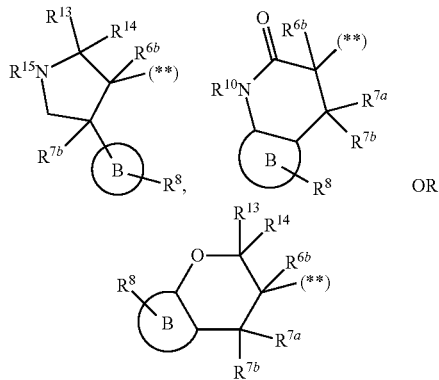

(**) is a bonding site.

[7] The compound according to [6] or a pharmaceutically acceptable salt thereof: wherein X is CH.

[8] The compound according to [7] or a pharmaceutically acceptable salt thereof: wherein $R^1$ and $R^2$ are not hydrogen atoms at the same time.

[9] The compound according to [8] or a pharmaceutically acceptable salt thereof: wherein $R^{6b}$, $R^{7a}$ and $R^{7b}$ are a hydrogen atom.

[10] The compound according to any one of [1] to [9] or a pharmaceutically acceptable salt thereof: wherein $R^{6a}$ is $-CR^{12}R^{13}R^{14}$;
$R^{12}$ is hydroxy or mono(di)hydroxy $C_{1-6}$ alkyl.

[11] A compound selected from the group consisting of following compounds:

[Chem.6]

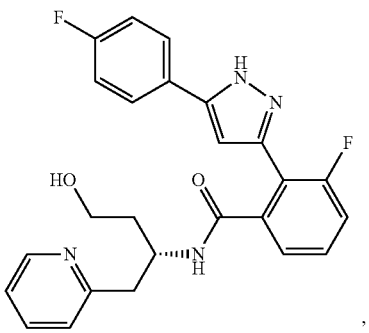

,

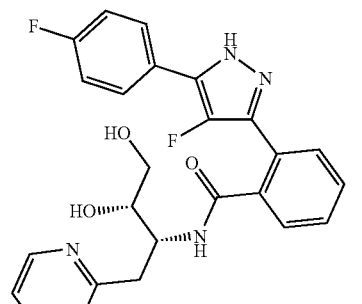

,

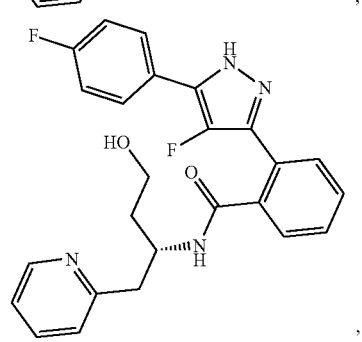

,

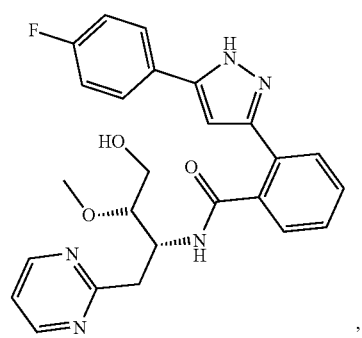

,

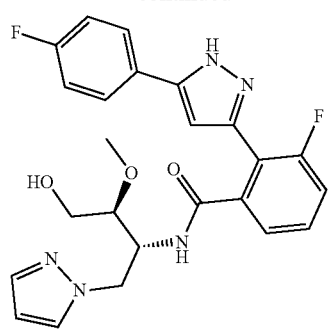
,
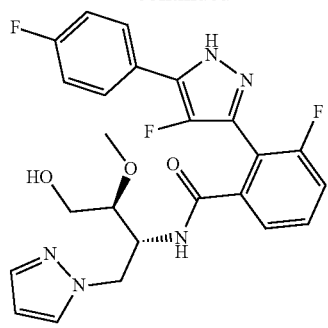
,
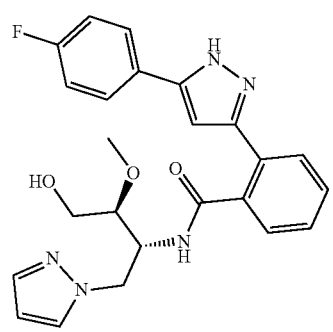
,
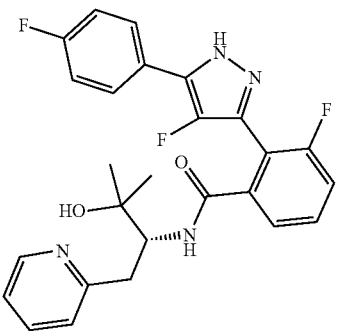
,
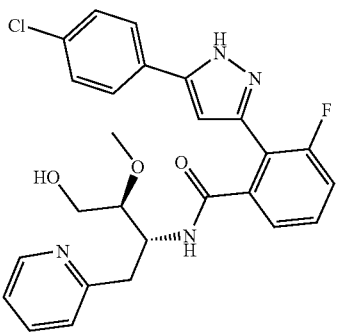
,
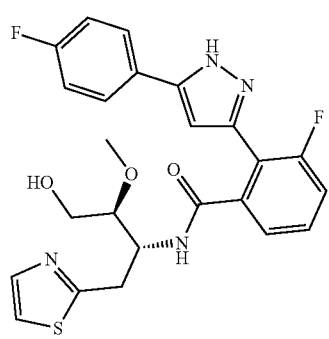
,
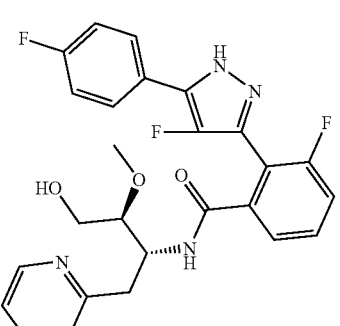
,
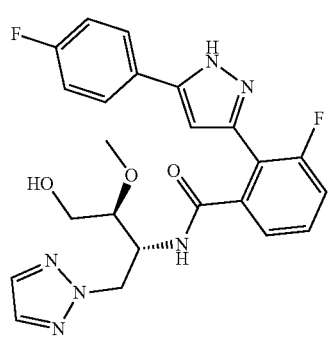
,
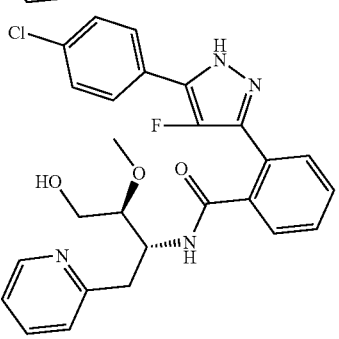
, -continued
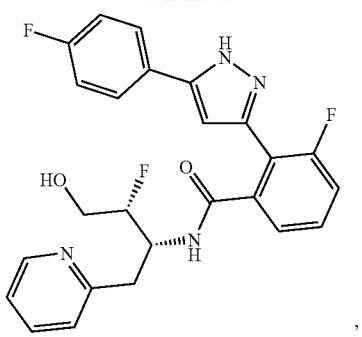
,
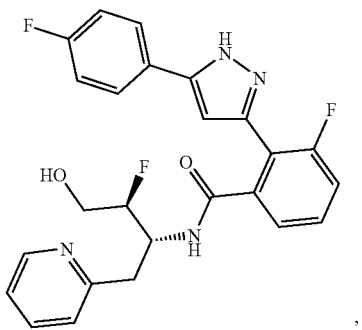
,
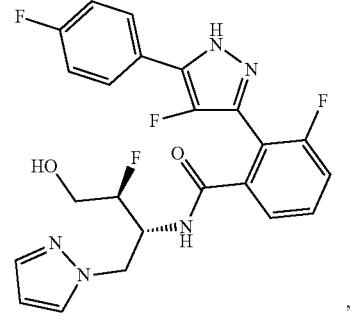
,
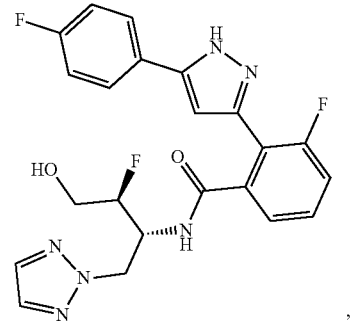
,
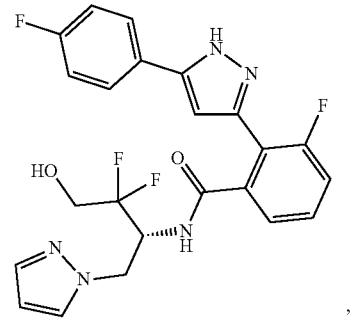
,
-continued
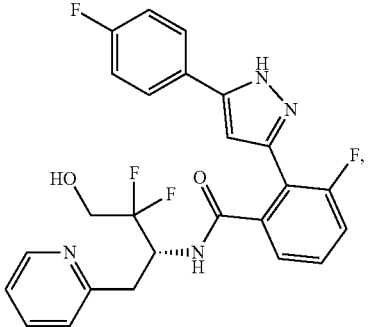
,
[Chem.7]
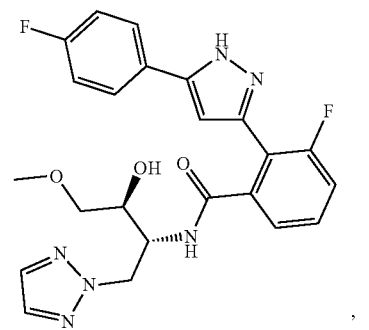
,
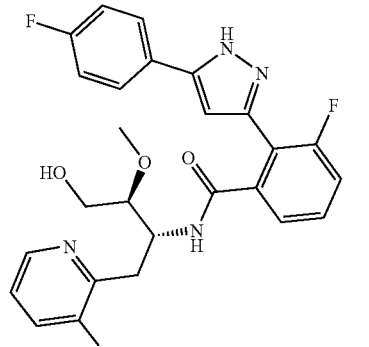
,
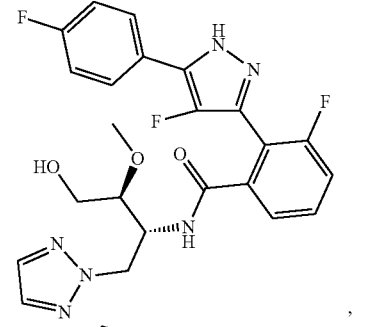
,
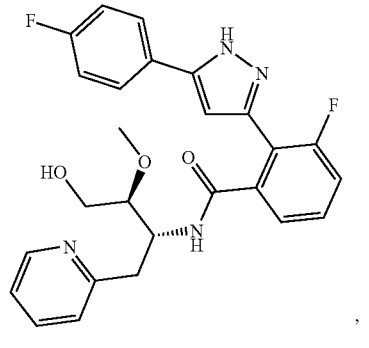
, 11
-continued

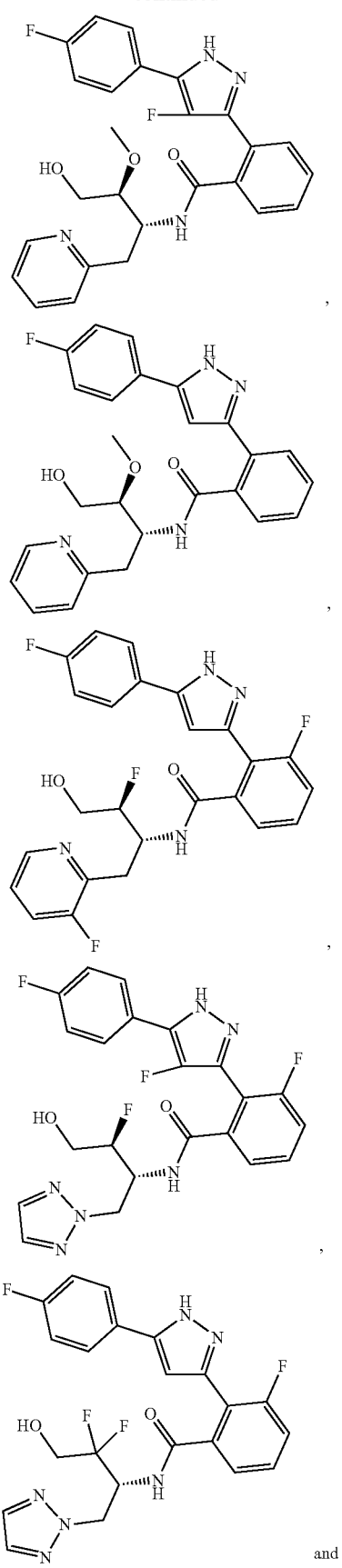

, and

12
-continued

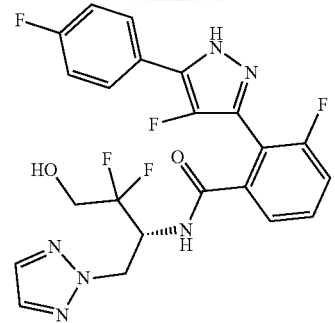

or a pharmaceutically acceptable salt thereof.

[12] A pharmaceutical composition comprising the compound according to any one of [1] to [11] or a pharmaceutically acceptable salt thereof, and pharmaceutical additive.

[13] The pharmaceutical composition according to [12], which is an pharmaceutical composition for use in the treatment or prevention of a disease or a symptom caused by hyperexcitability or a disorder of afferent neurons.

In an embodiment, the means for solving the above-described objects are the following [14] and [15].

[14] A method for preventing or treating a disease or a symptom caused by hyperexcitability or a disorder of afferent neurons, comprising administering an effective amount of the compound according to any one of [1] to [11] or a pharmaceutically acceptable salt thereof.

[15] Use of the compound according to any one of [1] to [11] or a pharmaceutically acceptable salt thereof for the manufacture of a pharmaceutical composition for preventing or treating a disease or a symptom caused by hyperexcitability or a disorder of afferent neurons.

Effect of the Invention

The compound represented by the formula (I) of the present invention or a pharmaceutically acceptable salt thereof exhibits a potent inhibitory effect in for example a confirmation test of inhibitory effects on icilin-induced wet-dog shakes which is a similar method described in International publication No. WO2009/012430. Therefore, the compound represented by the formula (I) of the present invention or a pharmaceutically acceptable salt thereof is useful as an agent for treating or preventing diseases or symptoms caused by hyperexcitability or disorder of afferent neurons.

MODE FOR CARRYING OUT THE INVENTION

The terms in the specification are defined.

The "halogen atom" means a fluorine atom, a chlorine atom, a bromine atom, or an iodine atom. It is preferably a fluorine atom or a chlorine atom.

The term "$C_{1-6}$ alkyl" means an alkyl group having 1 to 6 carbon atoms, which may be branched. Examples thereof include methyl, ethyl, propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, n-hexyl, isohexyl, and the like.

The "$C_{1-6}$ alkoxy" means an alkoxy group having 1 to 6 carbon atoms, which may be branched. Examples thereof include methoxy, propoxy, isopropoxy, butoxy, isobutoxy, sec-butoxy, tert-butoxy, pentyloxy, hexyloxy, and the like.

The term "halo $C_{1-6}$ alkyl" means the above $C_{1-6}$ alkyl substituted by 1 to 5 of the same or different halogen atoms. Examples thereof include monofluoromethyl, difluoromethyl, trifluoromethyl, 2-chloroethyl, 2-fluoroethyl, 2,2-difluoroethyl, 1,1-difluoroethyl, 1,2-difluoroethyl, 2,2,2-trifluoroethyl, 1,1,2,2,2-pentafluoroethyl, 2,2,2-trichloroethyl, 3-fluoropropyl, 2-fluoropropyl, 1-fluoropropyl, 3,3-difluoropropyl, 2,2-difluoropropyl, 1,1-difluoropropyl, 1-fluorobutyl, 1-fluoropentyl, 1-fluorohexyl, and the like.

The term "fluoro $C_{1-6}$ alkyl" means the above $C_{1-6}$ alkyl substituted by 1 to 5 fluoro atoms.

The term "halo $C_{1-6}$ alkoxy" means the above $C_{1-6}$ alkoxy substituted by 1 to 5 of the same or different halogen atoms. Examples thereof include monofluoromethoxy, difluoromethoxy, trifluoromethoxy, 2-chloroethoxy, 2-fluoroethoxy, 2,2-difluoroethoxy, 1,1-difluoroethoxy, 1,2-difluoroethoxy, 2,2,2-trifluoroethoxy, 1,1,2,2,2-pentafluoroethoxy, 2,2,2-trichloroethoxy, 3-fluoropropoxy, 2-fluoropropoxy, 1-fluoropropoxy, 3,3-difluoropropoxy, 2,2-difluoropropoxy, 1,1-difluoropropoxy, 4-fluorobutoxy, 5-fluoropentyloxy, 6-fluorohexyloxy, and the like.

The term "hydroxy $C_{1-6}$ alkyl" means the above $C_{1-6}$ alkyl substituted by hydroxy. Examples thereof include hydroxymethyl, 1-hydroxyethyl, 2-hydroxypropan-2-yl, 2-hydroxyethyl, 2-hydroxy-2-methylpropyl, 3-hydroxypropyl, and the like.

The term "mono(di)hydroxy $C_{1-6}$ alkyl" means the above $C_{1-6}$ alkyl substituted by one or two of hydroxy. Examples thereof include hydroxymethyl, 1-hydroxyethyl, 2-hydroxypropan-2-yl, 2-hydroxyethyl, 2-hydroxy-2-methylpropyl, 3-hydroxypropyl, 1,2-dihydroxyethyl, 1,3-dihydroxypropyl and the like.

The term "hydroxy $C_{1-6}$ alkoxy" means the above $C_{1-6}$ alkoxy substituted by hydroxy. Examples thereof include hydroxymethoxy, 1-hydroxyethoxy, 2-hydroxypropan-2-yloxy, 2-hydroxyethoxy, 2-hydroxy-2-methylpropoxy, 3-hydroxypropoxy, and the like.

The term "$C_{1-6}$ alkoxy $C_{1-6}$ alkyl" means the above $C_{1-6}$ alkyl substituted by the above $C_{1-6}$ alkoxy.

The term "mono(di)$C_{1-6}$ alkoxy $C_{1-6}$ alkyl" means the above $C_{1-6}$ alkyl substituted by one or two of the above $C_{1-6}$ alky. These $C_{1-6}$ alkoxy may be different in the case of di-substitution.

The term "$C_{1-6}$ alkoxy $C_{1-6}$ alkoxy" means the above $C_{1-6}$ alkoxy substituted by the above $C_{1-6}$ alkoxy.

The term "$C_{6-10}$ aryl" means phenyl or naphthyl.

The "$C_{7-10}$ aralkyl" means alkyl having 1 to 4 carbon atoms substituted by phenyl. Examples thereof include benzyl, phenethyl and the like.

The "$C_{7-10}$ aralkyloxy" means alkoxy having 1 to 4 carbon atoms substituted by phenyl. Examples thereof include benzyloxy, phenethyloxy and the like.

The term "($C_{7-10}$ aralkyloxy)$C_{1-6}$ alkyl" means the above $C_{1-6}$ alkyl substituted by the above $C_{7-10}$ aralkyloxy.

The term "($C_{7-10}$ aralkyloxy)$C_{1-6}$ alkoxy" means the above $C_{1-6}$ alkoxy substituted by the above $C_{7-10}$ aralkyloxy.

The term "carboxy $C_{4-6}$ alkyl" means the above $C_{1-6}$ alkyl substituted by carboxy.

The term "amino $C_{1-6}$ alkyl" means the above $C_{1-6}$ alkyl substituted by amino.

The term "mono(di)$C_{1-6}$ alkylamino $C_{1-6}$ alkyl" means the above amino $C_{1-6}$ alkyl substituted by one or two of the above $C_{1-6}$ alkyl. These $C_{1-6}$ alkyl may be different in the case of di-substitution.

The term "$C_{1-6}$ alkylsulfonylamino" means a group represented by ($C_{1-6}$ alkyl)-$SO_2NH$—. Examples thereof include methylsulfonylamino, ethylsulfonylamino, propylsulfonylamino, isopropylsulfonylamino, butylsulfonylamino, isobutylsulfonylamino, sec-butylsulfonylamino, pentylsulfonylamino, hexylsulfonylamino, and the like.

The term "($C_{1-6}$ alkyl)carbonyl" means carbonyl substituted by the above $C_{1-6}$ alkyl. Examples thereof include acetyl, ethylcarbonyl, propylcarbonyl, isopropylcarbonyl, isobutylcarbonyl, butylcarbonyl, sec-butylcarbonyl, tert-butylcarbonyl, pentylcarbonyl, hexylcarbonyl, and the like.

The term "$C_{1-6}$ alkoxycarbonyl" means carbonyl substituted by the above $C_{1-6}$ alkoxy. Examples thereof include methoxy carbonyl, ethoxycarbonyl, propoxycarbonyl, isopropoxycarbonyl, isobutoxycarbonyl, butoxycarbonyl, sec-butoxycarbonyl, tert-butoxycarbonyl, pentyloxycarbonyl, hexyloxycarbonyl, and the like.

The term "$C_{1-6}$ alkoxycarbonyl $C_{1-6}$ alkyl" means the above $C_{1-6}$ alkyl substituted by the above $C_{1-6}$ alkoxycarbonyl.

The term "$C_{1-6}$ alkoxycarbonyl $C_{1-6}$ alkoxy" means the above $C_{1-6}$ alkoxy substituted by the above $C_{1-6}$ alkoxycarbonyl.

The term "$C_{3-6}$ cycloalkyl" means monocyclic saturated alicyclic hydrocarbon having 3 to 6 carbon atoms. Examples thereof include cyclopropyl, cyclobutyl, cyclopentyl, and cyclohexyl.

The term "$C_{1-6}$ alkoxy(hydroxy)$C_{1-6}$ alkyl" means the above $C_{1-6}$ alkyl substituted by the above $C_{1-6}$ alkoxy and hydroxy. Examples thereof include 1-hydroxy-2-methoxyethyl, 1-hydroxy-3-methoxypropyl, 2-hydroxy-3-methoxypropyl, 1-methoxy-2-hydroxyethyl, 1-methoxy-3-hydroxypropyl, 2-methoxy-3-hydroxypropyl, and the like.

The term "heterocycle" means 5 or 6-membered heterocycle having any 1 to 4 hetero atoms selected from a sulfur atom, an oxygen atom and a nitrogen atom, examples thereof include aromatic heterocycle such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, 1-oxidopyridyl, pyridazinyl, pyrimidinyl, pyrazinyl, furazanyl and the like, unsaturated heterocycle such as pyrrolinyl, imidazolinyl, pyrazolinyl, dihydropyranyl, dihydrothiopyranyl, dihydropyridyl, dihydropyrimidinyl and the like, and saturated heterocycle such as morphonyl, thiomorphonyl, pyrrolidinyl, imidazolidinyl, pyrazolidinyl, piperidinyl, piperazinyl, tetrahydrofuranyl and the like. Furthermore, the above "heterocycle" may be fused with other cyclic groups, examples thereof include isobenzofuranyl, benzoxazolyl, benzoisoxazolyl, benzothiazolyl, benzoisothiazolyl, chromenyl, chromanonyl, xanthenyl, phenoxathiinyl, indolizinyl isoindolizinyl, indolyl, indazolyl, purinyl, quinolizinyl, isoquinolyl, quinolyl, phthalazinyl, naphthyridinyl, quinoxalinyl, quinazolinyl, carbazolyl, carbolinyl, acridinyl, isoindolinyl, 2,3-dihydrobenzofuranyl, imidazo[1,2-a]pyridyl, imidazo[1,2-a]pyrazinyl, benzo[1,3]dioxolyl, benzothienyl, 5,6,7,8-tetrahydroimidazo[1,2-a]pyrazinyl, azaindolizinyl and the like.

As "heterocycle" of ring A, preferably, pyridyl, benzo[1,3]dioxolyl or thienyl can be illustrated.

As "heterocycle" of ring B, preferably, pyridyl, pyrimidyl, piperidinyl, morpholinyl, thiazolyl, pyrazinyl, pyrazolyl, imidazolyl, pyridazinyl, azaindolizinyl, indolyl, isoquinolyl, triazolyl, tetrazolyl or dihydropyrimidinyl can be illustrated. More preferably, 2-pyridyl, 2-pyrimidyl, 1-pyrazolyl, 1,2,3-triazol-2-yl, 2-thiazolyl or 4-thiazolyl.

Hereinafter, the present invention is described in more detail.

The compound represented by the formula (I) of the present invention also include stereoisomers such as optical isomers, geometric isomers, tautomers and the like thereof.

An optical isomer of the compound represented by the formula (I) of the present invention may have either of an R configuration and an S configuration at the respective asymmetric carbon atoms. Also, any of the optical isomers thereof and a mixture of the optical isomers are encompassed by the present invention. Further, in the mixture of the optical active bodies, racemic bodies including equal amounts of the respective optical isomers are also encompassed within the scope of the present invention. In the case where the compound represented by the formula (I) of the present invention is a solid or crystal racemic body, the racemic compound, the racemic mixture, and the racemic solid solution are also encompassed within the scope of the present invention.

In the case where a compound represented by the formula (I) has the geometrical isomers, all geometrical isomers are included in the scope of the present invention.

Furthermore, in the case where tautomers of the compound represented by the formula (I) of the present invention exist, the present invention includes any of the tautomers. For example, tautomers such as the following the formula (I) and the formula (I') can be illustrated.

[Chem.8]

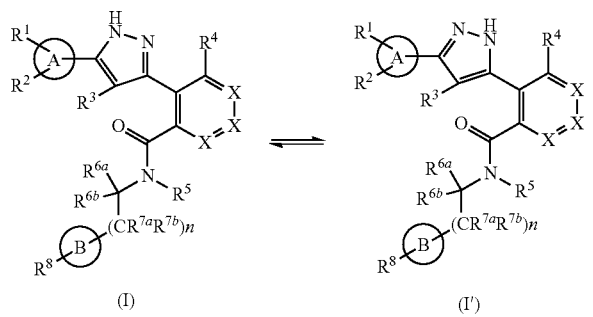

A compound represented by the formula (I) of the present invention can be converted into pharmaceutically acceptable salts thereof according to a general method if necessary. Such a salt may be presented as an acid addition salt or a salt with a base.

Examples of the acid addition salt can include acid addition salts with mineral acids such as hydrochloric acid, hydrobromic acid, hydroiodic acid, sulfuric acid, nitric acid, phosphoric acid and the like, and acid addition salts with organic acids such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid, and the like.

Examples of the salt with a base can include salts with inorganic bases, such as a sodium salt, a potassium salt, a calcium salt, a magnesium salt, and the like, and salts with organic bases such as piperidine, morpholine, pyrrolidine, arginine, lysine, and the like.

Moreover a compound represented by the formula (I) or a pharmaceutically acceptable salt thereof also includes a solvate with a pharmaceutically acceptable solvent such as water, ethanol and the like.

TRPM8 is a cation channel that expression is observed in dorsal root ganglion, trigeminal ganglion and so on. The TRPM8 inhibitor reduces the amount of cations influxing into cells through TRPM8 and thus suppresses the increase of the intracellular cation concentration. Based on this mechanism, the TRPM8 inhibitor is useful as an agent for treating or preventing lower urinary tract symptoms (LUTS), in particular overactive bladder syndrome (OAB) and the like by supression of hyperexcited afferent neuron activity.

Further, TRPM8 inhibitory activity can be evaluated by the efficacy inhibiting the wet-dog shake action which is induced by the administration of Icilin, TRPM8 agonist. Furthermore, an effect on overactive bladder (OAB) can be evaluated by an elongation of micturition interval against overactive bladder induced by acetic acid in accordance with a similar method described in J. Urol., 2001, 166, 1142.

As other embodiment of a compound represented by the formula (I) of the present invention:
wherein ring A is phenyl;
X is $CR^{4a}$;
$R^1$ is a hydrogen atom;
$R^2$ is a halogen atom;
$R^3$ is a hydrogen atom or a halogen atom;
$R^4$ and $R^{4a}$ are independently a hydrogen atom or a halogen atom;
ring B is phenyl, 2-pyridyl, 2-pyrimidyl, 1,2,3-triazol-2-yl or 1-pyrazolyl;
$R^5$ is a hydrogen atom;
$R^{6a}$ is $C(=O)NR^{10}R^{11}$ or $-CR^{12}R^{13}R^{14}$;
$R^{7a}$ is a hydrogen atom or $C_{1-6}$ alkyl;
$R^{7b}$ is a hydrogen atom;
$R^{6b}$ is a hydrogen atom;
$R^8$ is a hydrogen atom or a halogen atom;
$R^{10}$ and $R^{11}$ are a hydrogen atom;
$R^{12}$, $R^{13}$ and $R^{14}$ are independently a hydrogen atom, hydroxy, $C_{1-6}$ alkoxy, hydroxy $C_{1-6}$ alkyl or a fluorine atom;
n is 1.

As other embodiment of a compound represented by the formula (I) of the present invention:
wherein ring A is phenyl;
X is $CR^{4a}$;
$R^1$ is a hydrogen atom or a halogen atom;
$R^2$ is a hydrogen atom or a halogen atom;
$R^3$ is a hydrogen atom or a halogen atom;
$R^4$ and $R^{4a}$ are independently a hydrogen atom, a halogen atom or halo $C_{1-6}$ alkoxy;
ring B is phenyl, 2-pyridyl, 2-pyrimidyl, 2-thiazolyl, 4-thiazolyl, 1-pyrazolyl, 2-imidazolyl or 1,2,3-triazol-2-yl;
$R^5$ is a hydrogen atom;
$R^{6a}$ is a hydrogen atom, $C(=O)NR^{10}R^{11}$, $-CR^{12}R^{13}R^{14}$ or a group selected from the following formula:

[Chem.9]

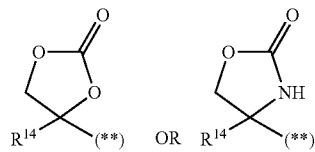

wherein, (**) is a bonding site;
$R^{7a}$ is a hydrogen atom, a fluorine atom, hydroxy, $C_{1-6}$ alkyl or $C_{1-6}$ alkoxy;
$R^{7b}$ is a hydrogen atom, a fluorine atom or $C_{1-6}$ alkyl;
$R^{6b}$ is a hydrogen atom or $C_{1-6}$ alkyl;
$R^8$ is a hydrogen atom, a halogen atom, $C_{1-6}$ alkyl, $C_{1-6}$ alkoxy, cyano or halo $C_{1-6}$ alkyl;

$R^{10}$ and $R^{11}$ are a hydrogen atom;

$R^{12}$, $R^{13}$ and $R^{14}$ are independently a hydrogen atom, hydroxy, $C_{1-6}$ alkoxy $C_{1-6}$ alkyl, $C_{1-6}$ alkyl, $NR^{15}R^{16}$, $C_{1-6}$ alkoxy, mono(di)hydroxy $C_{1-6}$ alkyl, carbamoyl, a fluorine atom or fluoro $C_{1-6}$ alkyl;

$R^{15}$ and $R^{16}$ are a hydrogen atom;

n is 1.

In an embodiment of a compound represented by the formula (I) of the present invention, 6-membered ring formed by one of $R^5$ and $R^{6a}$ bind together with ring B is a group represented by the following formula.

[Chem.10]

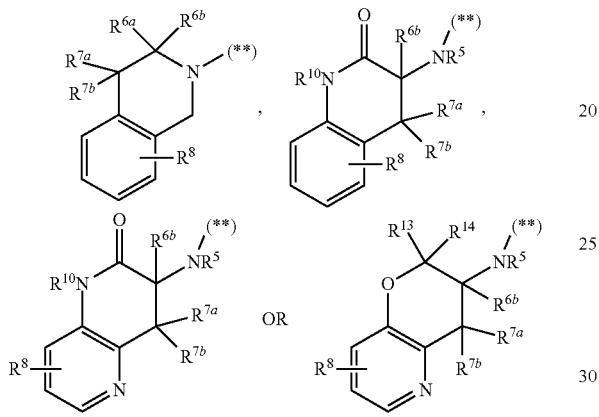

wherein, symbols have the same meaning as described in the above-described [1].

In an embodiment of a compound represented by the formula (I) of the present invention, 5-membered ring formed by one of $R^5$ and $R^{6a}$ bind together with $R^{7a}$ is a group represented by the following formula.

[Chem.11]

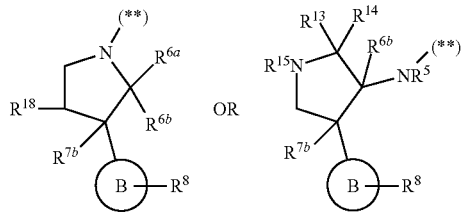

wherein, $R^{18}$ is amino or hydroxy $C_{1-6}$ alkyl, and other symbols have the same meaning as in the above-described [1].

Method for Producing Compound Represented by the Formula (I) of the Present Invention A compound represented by the formula (I) of the present invention or a pharmaceutically acceptable salt thereof can be prepared by a method shown in the following or a similar method thereto, or a method described in literatures or a similar method thereto.

Compound (4) shown in Scheme 1 can be prepared according to methods described in Journal of Organic Chemistry, 77 (8), 3887-3906; 2012. or a similar method thereto.

Schem 1

[Chem. 12]

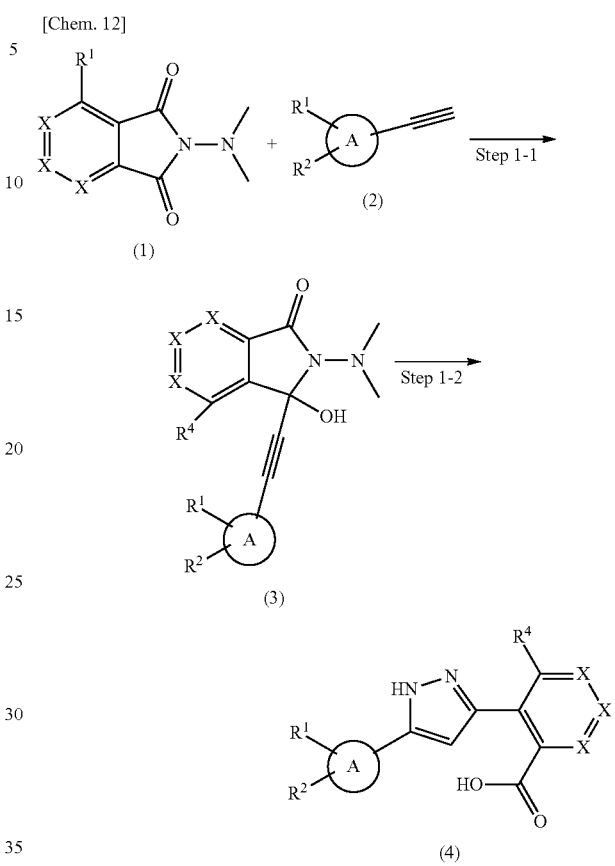

wherein ring A, $R^1$, $R^2$, $R^4$ and X have the same meanings as defined above.

Respectively, Compound (1) and Compound (2) can be commercially available, or can be prepared by a method described in literature or a similar method thereto.

Compound (4) can also be prepared according to methods shown in Scheme 2.

Scheme 2

[Chem. 13]

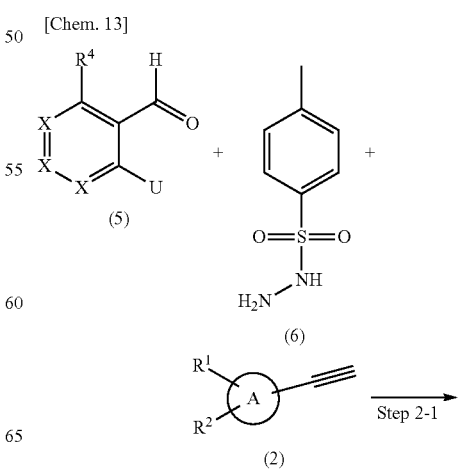

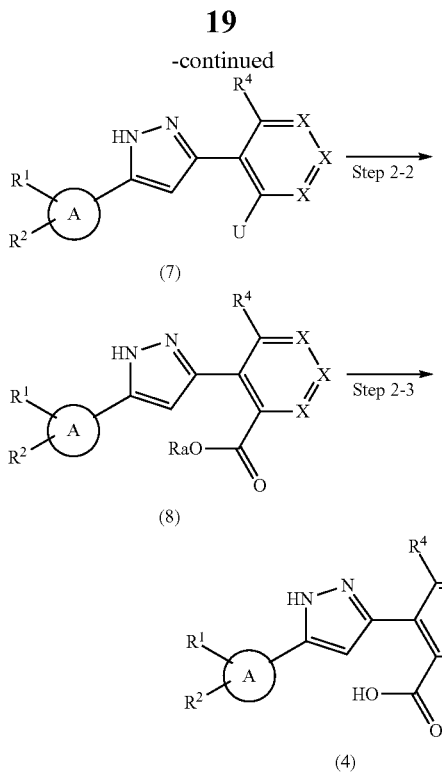

wherein ring A, $R^1$, $R^2$, $R^4$ and X have the same meanings as defined above, U is a leaving group such as a chlorine atom, a bromine atom, an iodine atom or the like, and Ra is $C_{1-6}$ alkyl.

Step 2-1

Compound (7) can be prepared by reacting Compound (5) with Compound (6) in a solvent and then reacting the obtained compound with Compound (2) in the presence of a base. As the solvent, toluene, benzene, acetonitrile, tetrahydrofuran, 1,4-dioxane and the like can be used. As the base, sodium hydroxide, sodium methoxide, sodium ethoxide, potassium tert-butoxide, potassium carbonate, cesium carbonate and the like can be used. The reaction temperature is at 0° C. to solvent reflux temperature, and the reaction time is usually from 2 hours to 3 days, varying based on a used material, solvent and reaction temperature or the like.

Respectively, Compound (5) and Compound (2) can be commercially available, or can be prepared by a method described in literature or a similar method thereto.

Step 2-2

Compound (8) can be prepared by reacting Compound (7) with carbon monoxide in the presence of RaOH, a base and a palladium catalyst in a solvent. As the solvent, N,N-dimethylformamide, N,N-dimethylacetamide, N-methylpyrrolidone, dimethylsulfoxide and the like can be used. As the RaOH, n-propanol, n-butanol and the like can be used. As the base, triethylamine, N,N-diisopropylethylamine and the like can be used. As the palladium catalyst, palladium(II) acetate, bis(triphenylphosphine)palladium(II)dichloride, [1,1'-bis(diphenylphosphino)ferrocene]palladium(II)dichloride, tetrakis(triphenylphosphine)palladium(0) and the like can be used. This step may also be performed with the addition of a ligand such as 1,3-bis(diphenylphosphino)propane, 1,1'-bis(diphenylphosphino)ferrocene and bis(adamantan-1-yl)(butyl)phosphine as necessary. The reaction temperature is at room temperature to solvent reflux temperature, and the reaction time is usually from 2 hours to 3 days, varying based on a used material, solvent and reaction temperature or the like.

Step 2-3

Compound (4) can be prepared by hydrolysis of Compound (8) in a solvent using a base. As the solvent, methanol, ethanol, acetonitrile, tetrahydrofuran, 1,4-dioxane, water, a mixed solvent thereof and the like can be used. As the base, sodium hydroxide, potassium hydroxide, lithium hydroxide and the like can be used. The reaction temperature is at room temperature to solvent reflux temperature, and the reaction time is from 30 minutes to 3 days, varying based on a used material, solvent and reaction temperature or the like. This step may also be performed using acid hydrolysis or hydrogenolysis, and methods described in Theodora W. Greene & Peter G. M. Wuts Eds., "Greene's Protective Groups in Organic Synthesis," fourth edition, Wiley-Interscience, 2006 can be used.

Compound (7) can also be prepared according to methods shown in Scheme 3.

Scheme 3

[Chem. 14]

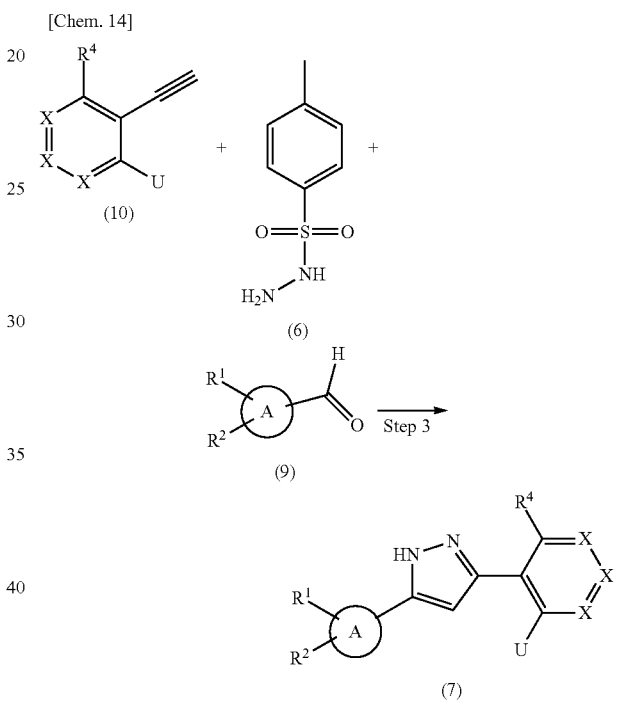

wherein ring A, $R^1$, $R^2$, $R^4$, X and U have the same meanings as defined above.

Step 3

Compound (7) can be prepared in a similar manner to that described in Step 2-1 using Compound (9), Compound (6), a base and Compound (10).

Respectively, Compound (10) and Compound (9) can be commercially available, or can be prepared by a method described in literature or a similar method thereto.

Compound (13) or Compound (13a) can be prepared according to methods shown in Scheme 4.

Scheme 4

[Chem.15]

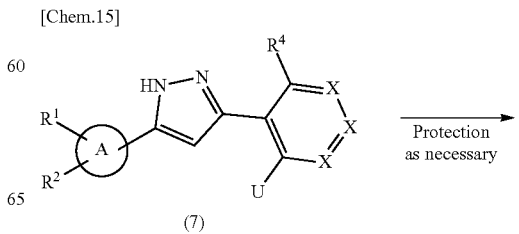

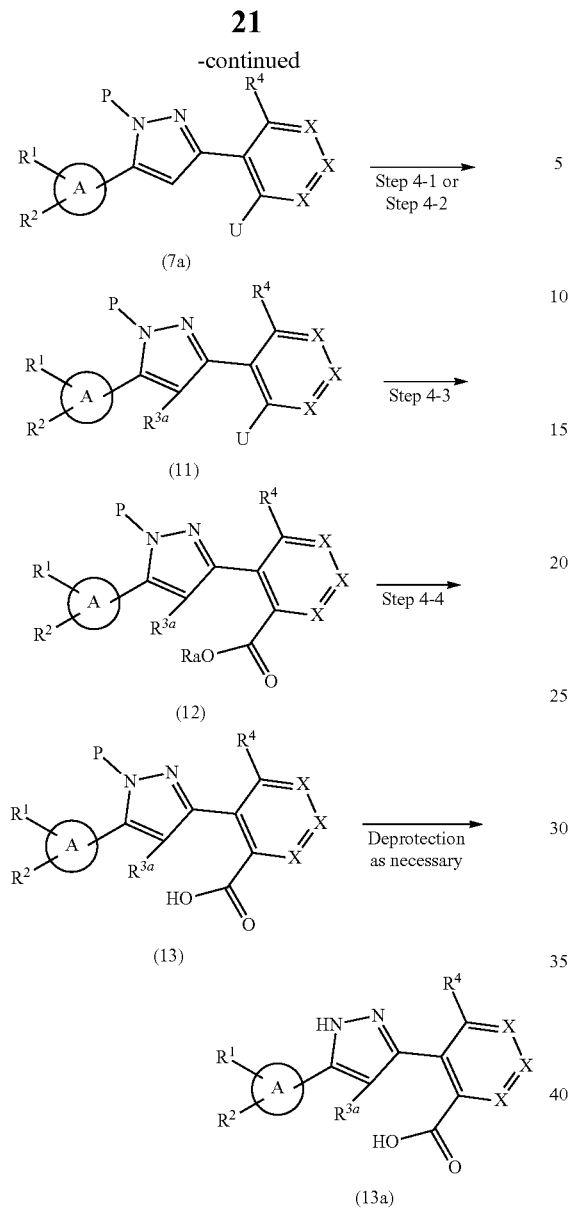

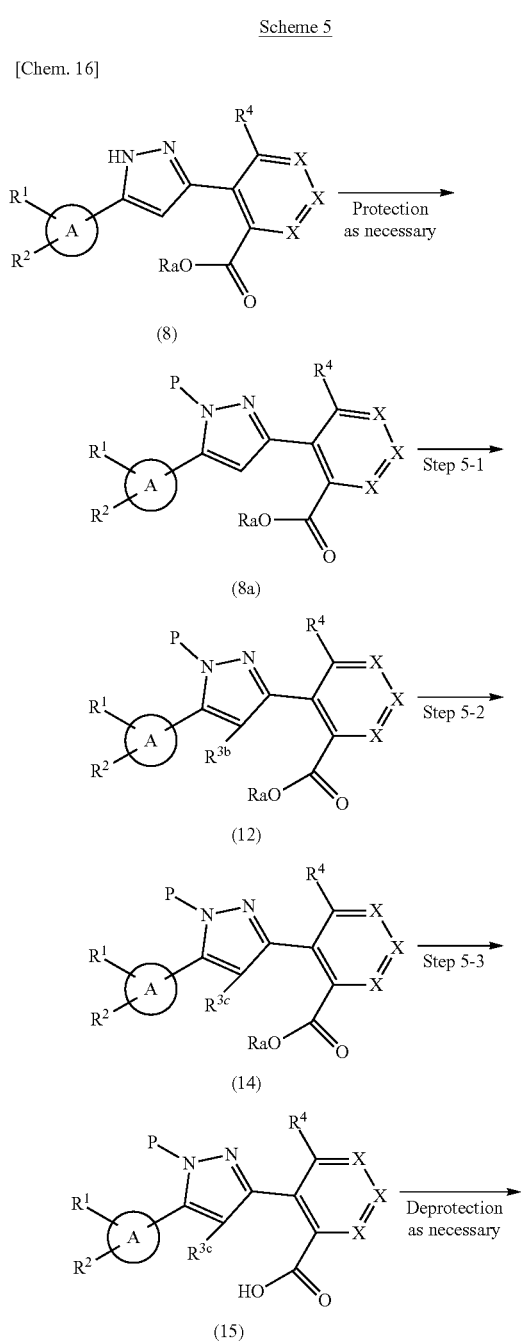

wherein ring A, $R^1$, $R^2$, $R^4$, X, U and Ra have the same meanings as defined above; $R^{3a}$ is a fluorine atom or a chlorine atom; and P is a hydrogen atom or a protective group.

Step 4-1

Compound (11) can be prepared by reacting Compound (7a) with a fluorination reagent in a solvent when $R^{3a}$ is a fluorine atom. As the solvent, acetonitrile, acetone, dichloromethane, 1,2-dichloroethane and the like can be used. As a fluorination reagent, N-fluoro-N'-(chloromethyl)triethylene diammonium(bistetrafluoroborate), N-fluorobenzenesulfonimide, 1-fluoro-2,4,6-trimethylpyridinium tetrafluoroborate and the like can be used. The reaction temperature is at 0° C. to solvent reflux temperature, and the reaction time is usually from 1 hour to 3 days, varying based on a used material, solvent and reaction temperature or the like.

Step 4-2

Compound (11) can be prepared by reacting Compound (7a) with a chlorination reagent in a solvent when $R^{3a}$ is a chlorine atom. As the solvent, dichloromethane, acetonitrile, N,N-dimethylformamide, N,N-dimethylacetamide, tetrahydrofuran and the like can be used. As the chlorination reagent, N-chlorosuccinimide, thionyl chloride and the like can be used. The reaction temperature is at 0° C. to solvent reflux temperature, and the reaction time is usually from 1 hour to 3 days, varying based on a used material, solvent and reaction temperature or the like.

Step 4-3 to Step 4-4

Compound (13) can be prepared in a similar manner to that described in Step 2-2 to Step 2-3 using Compound (11).

Compound (15) or Compound (15a) can be prepared according to methods shown in Scheme 5.

Scheme 5

[Chem. 16]

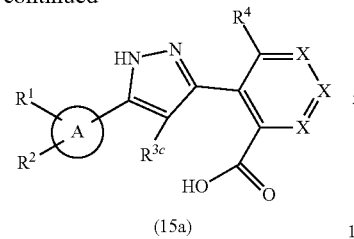

(15a)

wherein ring A, $R^1$, $R^2$, $R^4$, X, P and Ra have the same meanings as defined above; $R^{3b}$ is a bromine atom, and $R^{3c}$ is $C_{1-6}$ alkyl.

Step 5-1

Compound (12) can be prepared by reacting Compound (8a) with a bromination reagent in a solvent. As the solvent, dichloromethane, chloroform, acetonitrile, N,N-dimethylformamide, N,N-dimethylacetamide, tetrahydrofuran and the like can be used. As the bromination reagent, N-bromosuccinimide, tribromoisocyanuric acid, bromine and the like can be used. The reaction temperature is at 0° C. to solvent reflux temperature, and the reaction time is usually from 1 hour to 3 days, varying based on a used material, solvent and reaction temperature or the like.

Step 5-2

Compound (14) can be prepared by reacting Compound (12) with alkylboronic acid or the anhydride thereof in the presence of a base and a palladium catalyst in a solvent. As the solvent, toluene, acetonitrile, N,N-dimethylformamide, tetrahydrofuran and the like can be used. As the base, cesium carbonate, potassium carbonate, triethylamine, N,N-diisopropylethylamine and the like can be used. As the alkylboronic acid or the anhydride thereof, trimethylboroxine, methylboronic acid, ethylboronic acid, butylboronic acid and the like can be used. As the palladium catalyst, palladium(II)acetate, bis(triphenylphosphine)palladium(II) dichloride, [1,1'-bis(diphenylphosphino)ferrocene]palladium(II)dichloride, tetrakis(triphenylphosphine)palladium (0) and the like can be used. This step may also be performed with the addition of a ligand such as 1,3-bis(diphenylphosphino)propane, 1,1'-bis(diphenylphosphino)ferrocene and bis(adamantan-1-yl)(butyl)phosphine as necessary. The reaction temperature is at 0° C. to solvent reflux temperature, and the reaction time is usually from 1 hour to 3 days, varying based on a used material, solvent and reaction temperature or the like.

Step 5-3

Compound (15) can be prepared in a similar manner to that described in Step 2-3 using Compound (14).

Optically active Compound (21) can be prepared according to methods shown in Scheme 6.

Scheme 6

[Chem.17]

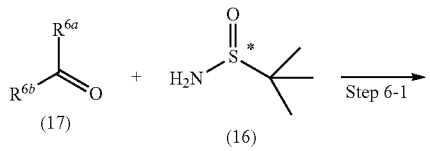

(17)  (16)

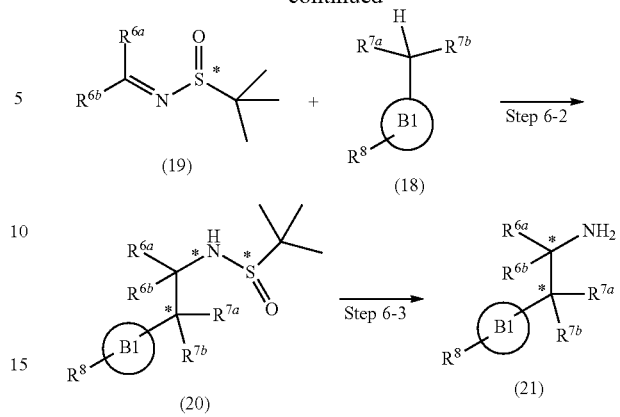

wherein $R^{6a}$, $R^{6b}$, $R^{7a}$ and $R^{7b}$ have the same meanings as defined above; ring B1 is $C_{6-10}$ aryl or heterocycle which does not include NH; $R^{8'}$ is $R^8$ having the same meaning as defined above with the proviso that this $R^8$ does not include hydroxy, amino, carbamoyl and carboxy; and * shows a chiral atom.

Step 6-1

Compound (19) can be prepared by reacting Compound (17) with Compound (16) in a solvent in the presence of Lewis acid. As the solvent, tetrahydrofuran, cyclopentyl methyl ether, 1,4-dioxane, toluene and the like can be used. As Lewis acid, tetraethyl orthotitanate, tetraisopropyl orthotitanate and the like can be used. The reaction temperature is at 0° C. to solvent reflux temperature, and the reaction time is usually from 1 hour to 3 days, varying based on a used material, solvent and reaction temperature or the like.

Respectively, Compound (16) and Compound (17) can be commercially available, or can be prepared by a method described in literature or a similar method thereto.

Step 6-2

Compound (20) can be prepared by reacting Compound (18) with Compound (19) in a solvent in the presence of a base. Such methods for preparing optically active amine using Elman's imine are well-known to those skilled in the art, and it can be prepared, for example, by using methods described in Chemical Reviews 2010, 110, 3600-3740. As the solvent, tetrahydrofuran, 1,4-dioxane, toluene and the like can be used. As the base, n-butyllithium, lithium diisopropylamide, bis(trifluoromethanesulfonyl)imide lithium and the like can be used. The reaction temperature is at −78° C. to room temperature, and the reaction time is usually from 1 hour to 12 hours, varying based on a used material, solvent and reaction temperature or the like.

Compound (18) can be commercially available, or can be prepared by a method described in literature or a similar method thereto.

Step 6-3

Compound (21) can be prepared by reacting Compound (20) in a solvent using an acid. As the solvent, tetrahydrofuran, 1,4-dioxane, methanol, ethanol, acetonitrile, water, a mixed solvent thereof and the like can be used. Examples of the acid include hydrogen chloride, trifluoroacetic acid, acetic acid, sulfuric acid and the like. The reaction temperature is at 0° C. to solvent reflux temperature, and the reaction time is usually from 10 minutes to 1 day, varying based on a used material, solvent and reaction temperature or the like.

Compound 21a) or Compound (21b) can be prepared according to methods shown in Scheme 7.

Scheme 7

[Chem. 18]

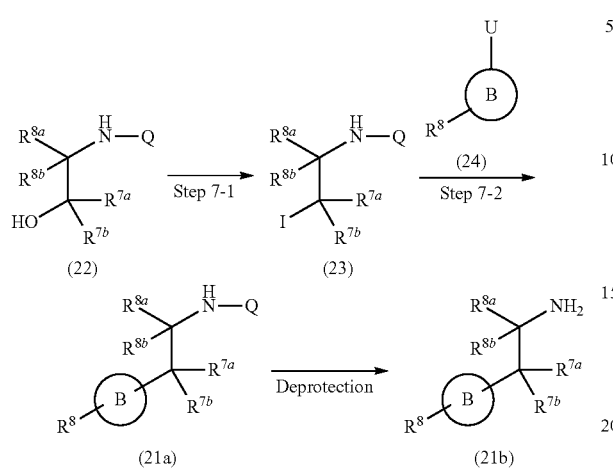

Scheme 8

[Chem.19]

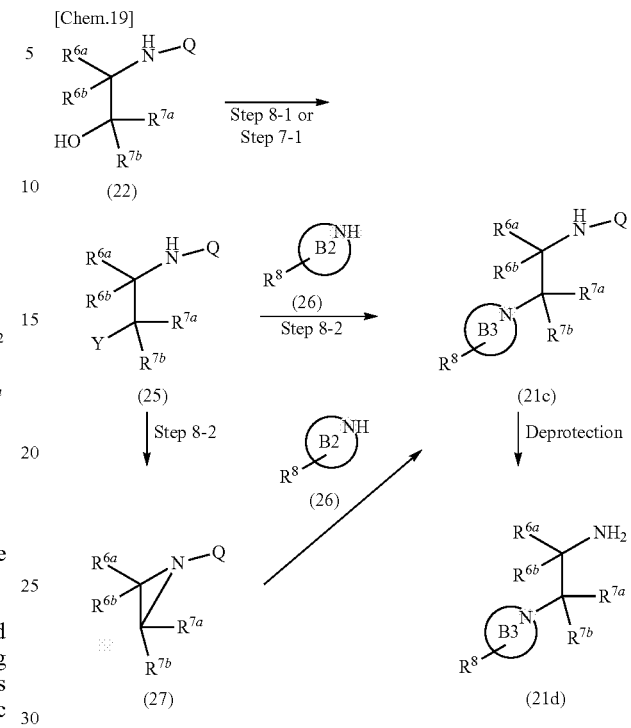

wherein ring B, $R^{6a}$, $R^{6b}$, $R^{7a}$, $R^{7b}$, $R^8$ and U have the same meanings as defined above; Q is a protective group.

Step 7-1

Compound (23) can be prepared by reacting Compound (22) with a organic phosphorus compound and a iodinating agent in a solvent in the presence of a base. Such methods for substitution of hydroxy to an iodine atom using a organic phosphorus compound and a iodinating agent are well-known to those skilled in the art, and it can be prepared, for example, by using methods described in Angewandte Chemie International Edition in English 1975, 14, 801-811 or a similar method thereto. As the solvent, tetrahydrofuran, acetonitrile, dichloromethane, acetone, N,N-dimethylformamide, N,N-dimethylacetamide and the like can be used. As the base, imidazole, pyridine and the like can be used. As the iodinating agent, iodine, sodium iodide and the like can be used. As the organic phosphorus compound, triphenylphosphine, tri(n-butyl)phosphine and the like can be used. The reaction temperature is at 0° C. to solvent reflux temperature, and the reaction time is usually from 30 minutes to 1 day, varying based on a used material, solvent and reaction temperature or the like.

Compound (22) can be commercially available, or can be prepared by a method described in literature or a similar method thereto.

Step 7-2

Compound (21a) can be prepared by reacting Compound (23) with zinc in a solvent and then reacting the obtained compound with Compound (24) in the presence of a palladium catalyst. As the solvent, N,N-dimethylformamide, N,N-dimethylacetamide, toluene, acetonitrile, tetrahydrofuran and the like can be used. As the palladium catalyst, palladium(II)acetate, bis(triphenylphosphine)palladium(II) dichloride, [1,1'-bis(diphenylphosphino)ferrocene] palladium(II)dichloride, tetrakis(triphenylphosphine)palladium(0), bis(dibenzylideneacetone)dipalladium(0), tris(dibenzylideneacetone)dipalladium(0), dichlorobis[di-tert-butyl(4-dimethylaminophenyl)phosphino]palladium(II) and the like can be used. The reaction temperature is at 0° C. to solvent reflux temperature, and the reaction time is usually from 30 minutes to 1 day, varying based on a used material, solvent and reaction temperature or the like.

Compound (24) can be commercially available, or can be prepared by a method described in literature or a similar method thereto.

Compound (21c) or Compound (21d) can be prepared according to methods shown in Scheme 8.

wherein $R^{6a}$, $R^{6b}$, $R^{7a}$, $R^{7b}$, $R^8$ and Q have the same meanings as defined above; ring B2 is heterocycle which includes NH; ring B3 is nitrogen-containing heterocycle; Y is a leaving group such as methanesulfonyloxy, p-toluenesulfonyloxy, an iodine atom and the like.

Step 8-1

Compound (25) can be prepared by reacting Compound (22) with sulfonyl halide or sulfonic anhydride in the presence of a base in a solvent. As the solvent, dichloromethane, 1,2-dichloroethane, tetrahydrofuran, acetonitrile and the like can be used. As the base, pyridine, triethylamine, N,N-diisopropylethylamine and the like can be used. As the sulfonyl halide, p-toluenesulfonyl chloride, methanesulfonyl chloride and the like can be used. As the sulfonic anhydride, trifluoromethanesulfonic anhydride and the like can be used. The reaction temperature is at 0° C. to solvent reflux temperature, and the reaction time is usually from 30 minutes to 1 day, varying based on a used material, solvent and reaction temperature or the like.

Step 8-2

Compound (21c) can be prepared by reacting Compound (25) with Compound. (26) in a solvent in the presence of a base. Moreover, Compound (21c) can also be prepared by reacting Compound (25) in a solvent in the presence of a base to give Compound (27), and then reacting obtained compound with Compound (26). As the solvent, N,N-dimethylformamide, N,N-dimethylacetamide, toluene, acetonitrile, tetrahydrofuran and the like can be used. As the base, cesium carbonate, potassium carbonate, pyridine, triethylamine, N,N-diisopropylethylamine, potassium tert-butoxide, sodium hydride and the like can be used. The reaction temperature is at 0° C. to solvent reflux temperature, and the reaction time is usually from 30 minutes to 3 days, varying based on a used material, solvent and reaction temperature or the like.

Compound (26) can be commercially available, or can be prepared by a method described in literature or a similar method thereto.

Compound (21d) can also be prepared according to methods shown in Scheme 9.

Scheme 9

[Chem. 20]

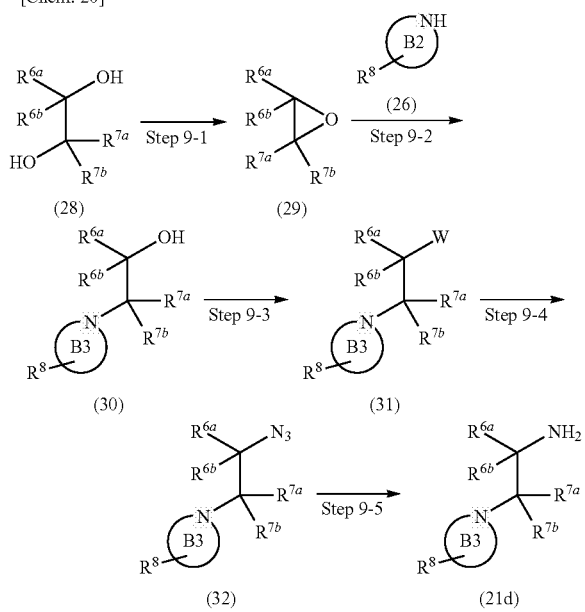

wherein ring B2, ring B3, $R^{6a}$, $R^{6b}$, $R^{7a}$, $R^{7b}$ and $R^8$ have the same meanings as defined above; W is a leaving group such as methanesulfonyloxy, p-toluenesulfonyloxy and the like.

Step 9-1

Compound (29) can be prepared by reacting Compound (28) with a organic phosphorus compound, in a solvent in the presence of an azo reagent. As the solvent, tetrahydrofuran, acetonitrile, 1,4-dioxane, toluene and the like can be used. As the organic phosphorus compound, triphenylphosphine, tri(n-butyl)phosphine and the like can be used. As the azo reagent, azodicarboxylic acid diisopropyl ester, azodicarboxylic acid diethyl ester, azodicarbonyldipiperazine and the like can be used. The reaction temperature is at room temperature to solvent reflux temperature, and the reaction time is from 30 minutes to 2 days, varying based on a used material, solvent and reaction temperature or the like.

Compound (28) can be commercially available, or can be prepared by a method described in literature or a similar method thereto.

Step 9-2

Compound (30) can be prepared by reacting Compound (29) with Compound (26) in a solvent in the presence or absence of a base. As the solvent, N,N-dimethylformamide, N,N-dimethylacetamide, toluene, acetonitrile, tetrahydrofuran and the like can be used. As the base, cesium carbonate, potassium carbonate, pyridine, triethylamine, N,N-diisopropylethylamine, potassium tert-butoxide, sodium hydride and the like can be used. The reaction temperature is at 0° C. to solvent reflux temperature, and the reaction time is usually from 30 minutes to 2 days, varying based on a used material, solvent and reaction temperature or the like.

Step 9-3

Compound (31) can be prepared in a similar manner to that described in Step 8-1 using Compound (30).

Step 9-4

Compound (32) can be prepared by reacting Compound (31) with an azidation reagent in a solvent. As the solvent, N,N-dimethylformamide, N,N-dimethylacetamide, tetrahydrofuran, acetonitrile, 1,4-dioxane, toluene and the like can be used. As the azidation reagent, sodium azide and the like can be used. The reaction temperature is at room temperature to solvent reflux temperature, and the reaction time is from 30 minutes to 2 days, varying based on a used material, solvent and reaction temperature or the like.

Step 9-5

Compound (21d) can be prepared by reacting Compound (32) with hydrogen in a solvent in the presence of a catalyst. As the solvent, methanol, ethanol, ethyl acetate, tetrahydrofuran, acetic acid and the like can be used. As the catalyst, palladium-carbon, platinum-carbon and the like can be used. The reaction temperature is at room temperature to solvent reflux temperature, and the reaction time is from 30 minutes to 1 day, varying based on a used material, solvent and reaction temperature or the like. Moreover, Compound (21d) can be prepared by reacting Compound (32) with a organic phosphorus compound and water in a solvent. As the solvent, tetrahydrofuran, 1,4-dioxane and the like can be used. As the organic phosphorus compound, triphenylphospine, tri(n-butyl)phosphine and the like can be used. The reaction temperature is at room temperature to solvent reflux temperature, and the reaction time is usually from 1 hour to 3 days, varying based on a used material, solvent and reaction temperature or the like.

A compound represented by the formula (I) of the present invention can be prepared according to methods shown in scheme 10.

Scheme 10

[Chem. 21]

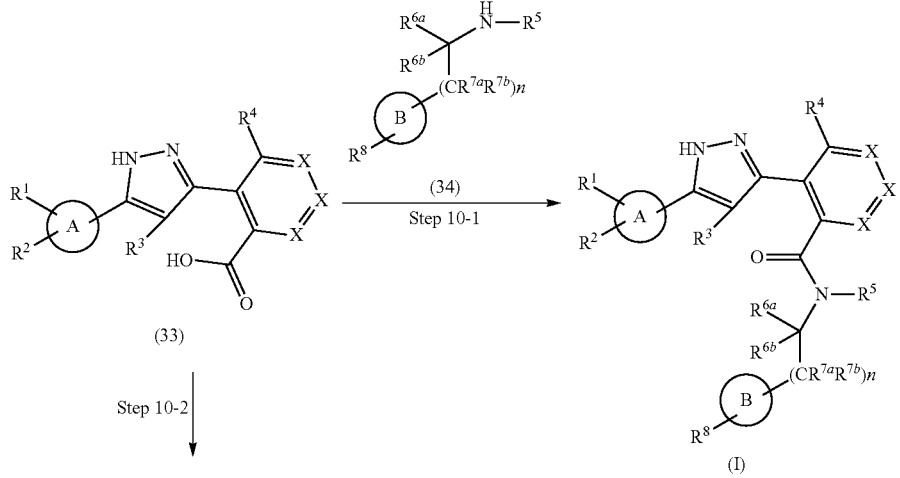

-continued

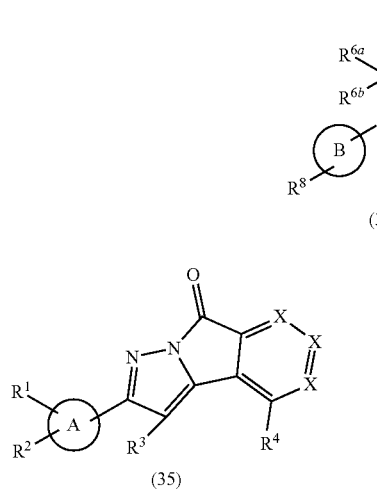

(34)

(35)

wherein ring A, ring B, $R^1$, $R^2$, $R^3$, $R^4$, $R^5$, $R^{6a}$, $R^{6b}$, $R^{7a}$, $R^{7b}$, $R^8$, X and n have the same meanings as defined above.

Step 10-1

The compound represented by the formula (1) can be prepared by reacting Compound (33) with a condensing reagent and Compound (34) in a solvent in the presence or absence of a base. As the solvent, N,N-dimethylformamide, N-methylpyrrolidone, N,N-dimethylacetamide, tetrahydrofuran, acetonitrile, 1 4-dioxane, toluene, methanol and water and the like can be used. As the base, triethylamine, N,N-diisopropylethylamine, pyridine and the like can be used. As the condensing reagent, 1-ethyl-3-(3-dimethylaminopropyl) carbodiimide, N,N'-carbonyldiimidazole, benzotriazol-1-yloxytris(dimethylamino)phosphonium hexafluorophosphate, 4-(4,6-dimethoxy-1,3,5-triazin-2-yl)-4-methylmorpholinium chloride, propylphosphonic acid anhydride and the like can be used.

This step may also be performed with the addition of an activator such as 1-hydroxybenzotriazole, 1-hydroxyazabenzotriazole as necessary. The reaction temperature is at room temperature to solvent reflux temperature, and the reaction time is from 30 minutes to 7 days, varying based on a used material, solvent and reaction temperature or the like.

Respectively, Compound (33) and Compound (34) can also be commercially available, or can be prepared by a method described in literature or a similar method thereto.

Step 10-2

The compound represented by the formula (I) can also be prepared by reacting Compound (33) in a solvent in the presence of a base and a condensing reagent to give Compound (35), and then reacting obtained compound with Compound (34). As the solvent, N,N-dimethylformamide, N-methylpyrrolidone, N,N-dimethylacetamide, tetrahydrofuran, acetonitrile, 1,4-dioxane, toluene, methanol and water and the like can be used. As the base, triethylamine, N,N-diisopropylethylamine, pyridine and the like can be used. As the condensing reagent, 1-ethyl-3-(3-dimethylaminopropyl) carbodiimide, N,N'-carbonyldiimidazole, 1H-benzotriazol-1-yloxytris(dimethylamino)phosphonium hexafluorophosphate, 4-(4,6-dimethoxy-1,3,5-triazin-2-yl)-4-methylmorpholinium chloride, propylphosphonic acid anhydride and the like can be used. This step may also be performed with the addition of a activator such as 1-hydroxybenzotriazole, 1-hydroxyazabenzotriazole as necessary. The reaction temperature is at room temperature to solvent reflux temperature, and the reaction time is from 30 minutes to 7 days, varying based on a used material, solvent and reaction temperature or the like.

The compound represented by the formula (I) of the present invention can also be prepared according to methods shown in scheme 11.

Scheme 11

[Chem. 22]

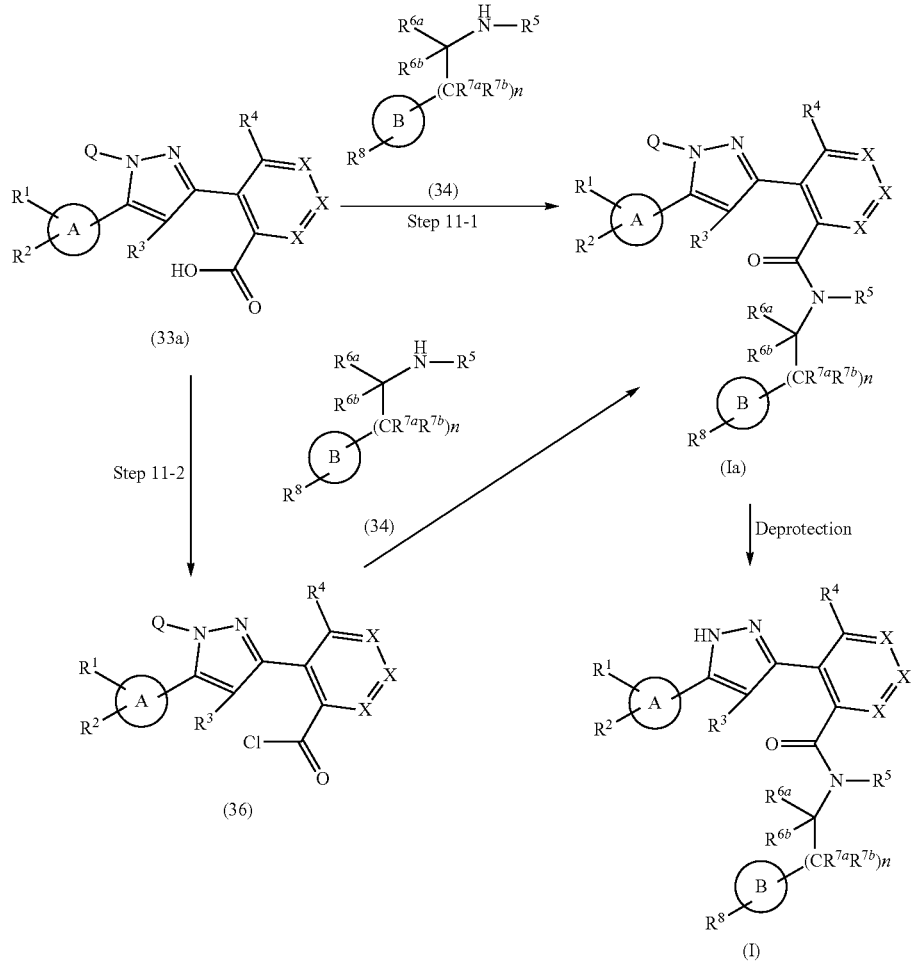

wherein ring A, ring B, $R^1$, $R^2$, $R^3$, $R^4$, $R^5$, $R^{6a}$, $R^{6b}$, $R^{7a}$, $R^{7b}$, $R^8$, Q, X and n have the same meanings as defined above.

Step 11-1

Compound (Ia) can be prepared in a similar manner to that described in Step 10-1 using Compound (33a).

Compound (33a) can be commercially available, or can also be prepared by a method described in literature or a similar method thereto.

Step 11-2

Compound (Ia) can be prepared by reacting Compound (33a) with a chlorination reagent in a solvent to give Compound (36), and then reacting the obtained compound with Compound (34) in the presence or absence of a base. As the solvent, dichloromethane, 1,2-dichloroethane and the like can be used. As the chlorination reagent, 1-chloro-N,N,2-trimethylpropenylamine, thionyl chloride, oxalyl chloride and the like can be used. As the base, triethylamine, N,N-diisopropylethylamine, pyridine and the like can be used. This step may also be performed with the addition of a activator such as N,N-dimethylformamide as necessary. The reaction temperature is at room temperature to solvent reflux temperature, and the reaction time is from 30 minutes to 3 days, varying based on a used material, solvent and reaction temperature or the like.

The above-mentioned schemes are exemplary for preparing compounds represented by the formula (I) of the present invention and synthetic intermediates thereof. These can be variously modified into schemes which can be easily understood by those skilled in the art.

Moreover, where a protecting group is required depending on the type of the functional group, protection and deprotection operations can be appropriately carried out in combination according to conventional methods. Examples regarding the type of protecting groups, protection and deprotection include the methods described in Theodora W. Greene & Peter G. M. Wuts Eds., "Greene's Protective Groups in Organic Synthesis," fourth edition, Wiley-Interscience, 2006 and Peter G. M. Wuts Eds., "Greene's Protective Groups in Organic Synthesis," fifth edition, Wiley-Interscience, 2014.

The compound represented by the formula (I) of the present invention or an intermediate used for a preparing pharmaceutically acceptable salt thereof can be isolated/purified, as necessary, by solvent extraction, crystallization/recrystallization, chromatography, preparative high performance liquid chromatography, or the like, which are isolation/purification means well-known to a skilled person in the art of the relevant field.

A pharmaceutical composition comprising a compound represented by the formula (I) of the present invention or a pharmaceutically acceptable salt thereof as an active ingredient can be administered in various dosage forms depending on their usages. Examples of such dosage forms include powders, granules, fine granules, dry syrups, tablets, capsules, injections, liquids, ointments, suppositories, plasters, sublinguals, and the like, which are administered orally or parenterally, These pharmaceutical compositions can be prepared by appropriately mixing or diluting/dissolving with appropriate pharmaceutical additives such as an excipient, a disintegrant, a binder, a lubricant, a diluent, a buffering agent, a tonicity agent, a preservative, a wetting agent, an emulsifier, a dispersant, a stabilizer, a solubilizing aid, and the like by a publicly-known method according to the dosage form. Moreover, when the compound represented by the formula (I) of the present invention or a pharmaceutically acceptable salt thereof is used in combination with agents other than the TRPM8 inhibitor, the pharmaceutical compositions can be prepared by formulating the respective active ingredients simultaneously or separately in the same way as described above.

The compound represented by the formula (I) of the present invention or a pharmaceutically acceptable salt thereof exhibits potent inhibitory effects based on its TRPM8 inhibition in the confirmation test of inhibitory effects on icilin-induced wet-dog shakes. Accordingly, a pharmaceutical comprising the compound represented by the formula (I) of the present invention or a pharmaceutically acceptable salt thereof as an active ingredient can be used as an agent for treating or preventing diseases or symptoms caused by the activation of TRPM8.

"A disease or a symptom caused by the activation of TRPM8" means a disease or a symptom caused by hyperexcitability or a disorder of afferent neurons.

Examples of "a disease or a symptom caused by hyperexcitability or a disorder of afferent neurons" include anxietas, depression, lower urinary tract symptoms (LUTS), algi, circulatory disorder, itch, pins-and-needles sensation, hives and the like.

In an embodiment, the compound represented by the formula (I) of the present invention or a pharmaceutically acceptable salt thereof is particularly useful as an agent for treating or preventing lower urinary tract symptoms (LUTS) or algi, among diseases or symptoms caused by hyperexcitability or disorder of afferent neurons.

"Lower urinary tract symptoms (LUTS)" means symptom caused by lower urinary tract dysfunction and the like, and examples of "lower urinary tract dysfunction" include overactive bladder, detrusor overactivity, nocturia, cystitis such as interstitial cystitis and the like, prostatitis such as chronic prostatitis and the like, painful bladder syndrome, hypersensitive bladder syndrome, urinary incontinence, benign prostatic hyperplasia, ankylurethria and the like. Preferably, it includes overactive bladder, detrusor overactivity, interstitial cystitis and painful bladder syndrome.

Examples of "circulatory disorder" include cold-induced rhinitis, Raynaud disease and the like.

Examples of "algi" include tooth pain, peripheral nerve injury evoked by oxaliplatin, migraine, postoperative pain, cold allodynia, peripheral nerve pain evoked by anticancer agent, diabetic peripheral neuropathy and the like. Preferably, it includes tooth pain, peripheral nerve injury evoked by oxaliplatin, migraine, postoperative pain and cold allodynia.

The compound represented by the formula (I) of the present invention or a pharmaceutically acceptable salt thereof can also be appropriately used in combination with at least one agent other than the TRPM8 inhibitor.

Examples of the agent that can be used in combination with the compound represented by the formula (I) of the present invention or a pharmaceutically acceptable salt thereof include an opioid analgesic agent, a non-steroidal anti-inflammatory drug (NSAID), a barbiturate sedative, a benzodiazepine drug having sedating properties, a $H_1$ blocker having sedating properties, a sedative, a skeletal muscle relaxant, a NMDA receptor antagonist, an α-adrenoceptor modulator, a tricyclic antidepressant, an anti-seizure drug, a tachykinin antagonist (NK antagonist), a muscarinic receptor antagonist, a COX-2 selective inhibitor, a coal tar analgesic, a neuroleptic agent, a TRPV1 agonist, a TRPV1 inhibitor, a β-adrenoceptor blocker, a local anesthetic agent, a corticosteroid, a 5-HT receptor agonist, a $5\text{-HT}_{2A}$ receptor antagonist, a cholinergic analgesic, PDE5 inhibitor, PDE9 inhibitor, α2δ ligand, a cannabinoid, a metabotropic glutamate receptor 1 antagonist (mGluR1 antagonist), a metabotropic glutamate receptor 5 antagonist (mGluR5 antagonist), a serotonin reuptake inhibitor, a noradrenaline reuptake inhibitor, a serotonin-noradrenaline reuptake inhibitor, an inducible nitric oxide synthase inhibitor (iNOS inhibitor), an acetylcholine esterase inhibitor (AChE inhibitor), an EP4 antagonist, a leukotriene B4 antagonist, a 5-lipoxygenase inhibitor, a sodium channel blocker, a 5-HT3 antagonist, a chemotherapeutic agent, an EP1 antagonist, a β3 adrenoceptor agonist, a TRPV1 inhibitor, a TRPV3 inhibitor, a TRPV4 inhibitor, a T-type calcium channel inhibitor, an ASIC inhibitor, a P2X inhibitor, a Trk inhibitor, a FAAH inhibitor, a botulinus toxin, a 5α-reductase inhibitor, an anti-NGF antibody, an NGF modulator, a depressant of IgE production, a histamine H2 inhibitor, a bladder mucosal protectant, a NOS activity regulator, a bladder muscle relaxant, a GABA reuptake inhibitor, a GABA receptor regulator, a GABA aminotransferase inhibitor and the like.

Furthermore, concrete examples of the agent that is used in combination are illustrated, as below, but the content of the present invention is not limited thereto. Further, examples of the concrete compounds include a free form thereof and other pharmaceutically acceptable salts.

Examples of "an α-adrenoceptor modulator" can include doxazosin, tamsulosin, silodosin, clonidine, guanfacine, dexmedetomidine tizanidine, moxonidine, and the like.

Examples of "a muscarinic receptor antagonist" can include oxybutynin, tolterodine, propiverine, darifenacin, solifenacin, temiverine, ipratropium bromide, trospium, propantheline, temiverine, imidafenacin, fesoterodine, and the like.

Examples of "EP1 antagonist" can include GSK-269984A, ONO-8539 and the like.

Examples of "a β3 adrenoceptor agonist" can include mirabegron, solabegron, TRK-380, and the like.

Examples of "a bladder mucosal protectant" can include pentosan polysulphate, hyaluronic acid, chondroitin sulfate, and the like.

When the compound represented by the formula (I) of the present invention or a pharmaceutically acceptable salt thereof is administrated in combination with one or more of the above-described agents, the present invention includes all administration methods following 1) to 5):

1) simultaneous administration by a combination preparation, 2) simultaneous administration by the same administration pathway as a separate formulation,
3) simultaneous administration by a different administration pathway as a separate formulation,
4) administration at different times by the same administration pathway as a separate formulation, and
5) administration at different times by a different administration pathway as a separate formulation.

Further, in the case of administration at different times as a separate formulation as in 4) or 5), the order of administration of the compound represented by the formula (I) of the present invention or a pharmaceutically acceptable salt thereof and the above-described agents that is administrated in combination is not particularly limited.

Furthermore, the compounds of the present invention or a pharmaceutically acceptable salt thereof can be administrated appropriately in combination with one or more of the above-described agents to achieve an advantageous effect that is equal to or more than an additive effect in prevention or treatment of the above-described diseases. Alternatively, as compared with a case of being administrated alone, the amount used can be reduced, or the side effect of the agent(s) without TRPM8 inhibitor used together can be mitigated, or the side effect of the agent(s) without TRPM8 inhibitor used together can be avoided or mitigated.

The pharmaceutical composition of the present invention can be administered systemically or locally, and orally or parenterally (nasal, pulmonary, intravenous, rectal, subcutaneous, intramuscular, transdermal routes, and the like).

When the pharmaceutical composition of the present invention is employed for actual therapy, the administration amount of the active ingredient, which is the compound represented by the formula (I) of the present invention or a pharmaceutically acceptable salt thereof, is appropriately determined depending on the age, gender, and weight of the patient, the extent of disease and therapy and the like. For example, in the case of oral administration, it can be appropriately administered in the range of about 1 to 3000 mg per day for an adult (regarded as a body weight of 60 kg), in one portion or in several divided portions. The daily dose as an oral administration agent is preferably from 10 to 1000 mg, and more preferably from 20 to 400 mg. For example, in the case of parenteral administration, it can be appropriately administered in the range of about 0.6 to 300 mg per day for an adult, in one portion or in several divided portions. The daily dose as a parenteral administration agent is preferably from 1 to 100 mg, and more preferably from 6 to 60 mg. Moreover, the administration amount of the compound represented by the formula (I) or a pharmaceutically acceptable salt thereof which is the active ingredient of the TRPM8 inhibitor of the present invention can be reduced according to the administration amount of agents other than TRPM8 inhibitor.

Hereinbelow, the present invention is illustrated in detail with reference to Examples, Reference Examples, and Test Examples, but the scope of the present invention is not limited thereto.

Among the symbols used in each of Reference Examples, Examples and Tables, Ref. Ex. means Reference Example Number, Ex. No. means Example Number, Strc. means chemical structural formula, P.D. means spectral data, and P.C. means purification condition. * means a chiral atom. Rel. means relative configuration. $^1$H-NMR means a proton nuclear magnetic resonance spectrum, CDCl$_3$ means chloroform-d, and DMSO-d$_6$ means dimethylsulfoxide-d$_6$, and CD$_3$OD means methanol-d$_4$. Further, MS means mass spectrometry. ESI-MS means electrospray ionization mass spectrometry. RT means retention time of high-performance liquid chromatography. SiO2 means column chromatography on silica gel, and APS means column chromatography on aminopropylated silica gel. When a mixture of stereoisomers was separated/purified using normal-phase column chromatography, low polarity product and LP means a former eluted compound, high polarity product and HP means a latter eluted compound. TBS means tert-butyldimethylsilyl, TBDPS means tert-butyldiphenylsilyl, Bn means benzyl, MOM means methoxymethyl, Cbz means benzyloxycarbonyl, Boc means tert-butoxycarbonyl, and Bu means n-butyl.

As described above, the present invention also includes tautomers of the compound represented by the formula (I). Thus, compound names in Reference Examples and Examples, and chemical structural formulas in Tables are not limited to compound names thereof and chemical structural formulas thereof in Tables, and include their tautomers thereof.

In each Reference Example, the irradiation of the microwave used Biotage Initiator.

In each Example, high-performance liquid chromatography and ESI-MS were performed on the following conditions.

Instrument: 6520 Accurate-Mass Q-TOF instrument (Agilent)
Column: Inertsil ODS-4 (GL-science) 2.1×50 mm, 3 μm
Flow rate: 0.75 mL/min.
Gradient:

TABLE 1

| Method A | | |
|---|---|---|
| Time (minute) | 0.1% HCO$_2$H/H$_2$O (%) | 0.1% HCO$_2$H/MeCN (%) |
| 0 | 80 | 20 |
| 5 | 10 | 90 |
| 6 | 10 | 90 |

TABLE 2

| Method B | | |
|---|---|---|
| Time (minute) | 10 mM AcONH$_4$ solution (%) | MeCN (%) |
| 0 | 80 | 20 |
| 5 | 10 | 90 |
| 6 | 10 | 90 |

REFERENCE EXAMPLE 1-1-1

2-[5-(3-Fluorophenyl)-1H-pyrazol-3-yl]benzoic acid

The title compound was obtained according to methods described in Journal of Organic Chemistry, 77 (8), 3887-3906; 2012 or a similar method thereto. Structural formula, spectral data and purification condition are shown in Table 3.

REFERENCE EXAMPLES 1-1-2 TO 1-1-16

Reference Examples 1-1-2 to 1-1-16 were synthesized in a manner similar to that of Reference Example 1-1-1 by using the corresponding materials. Structural formula, spectral data and purification condition are shown in Table 3 to Table 4.

REFERENCE EXAMPLE 1-2-1

4-Ethenyl-1-fluoro-3-methoxybenzene

To a mixture of 4-bromo-1-fluoro-3-methoxybenzene (0.513 g), trimethylsilylacetylene (0.737 g) in tetrahydrofuran (5 mL) were added triethylamine (3.795 g), bistriphenylphosphine palladium(II)dichloride (0.175 g) and copper (I) iodide (0.048 g), and the mixture was stirred for 1 hour at 110° C. under microwave irradiation. The mixture was filtered through a pad of celite. To the filtrate was added a saturated aqueous solution of ammonium chloride, and the crude product was extracted with ethyl acetate. The organic layer was washed with brine, and dried over anhydrous magnesium sulfate. The solvent was removed under reduced pressure, and the residue was dissolved in tetrahydrofuran (5 mL). To the mixture was added a solution of tetra-n-butylammonium fluoride in tetrahydrofuran (1 mol/L, 5 mL) under ice-cooling, and the mixture was stirred for 30 minutes. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford the title compound (0.375 g). Structural formula, spectral data and purification condition are shown in Table 5.

REFERENCE EXAMPLE 1-2-2

Reference Example 1-2-2 was synthesized in a manner similar to that of Reference Example 1-2-1 by using the corresponding materials. Structural formula, spectral data and purification condition are shown in Table 5.

REFERENCE EXAMPLE 1-3-1

A mixture of 3-bromo-2-[5-(4-fluorophenyl)-1-(methoxymethyl)-1H-pyrazol-3-yl]benzamide and 3-bromo-2-[5-(4-fluorophenyl)-2-(methoxymethyl)-2H-pyrazol-3-yl]benzamide To a solution of 2,6-dibromobenzaldehyde (1.6 g) in toluene (40 mL) was added p-toluenesulfonylhydrazine (1.13 g), and the mixture was stirred at 110° C. for 1.5 hours. The reaction mixture was allowed to cool to room temperature. To the mixture was added sodium ethoxide (1.65 g), and the mixture was stirred for 10 minutes. To the mixture was added 1-ethynyl-4-fluorobenzene (1.09 g), and the mixture was stirred at 110° C. for 20 hours. The reaction mixture was diluted with ethyl acetate and the mixture was washed with water and brine successively, and dried over anhydrous magnesium sulfate. The solvent was removed under reduced pressure, and the residue was purified by silica gel column chromatography (eluent: ethyl acetate/n-hexane) to afford 3-(2,6-dibromophenyl)-5-(4-fluorophenyl)-1H-pyrazole (0.35 g). To a solution of the product (0.35 g) in N,N-dimethylformamide (2 mL) were added cesium carbonate (0.86 g) and chloromethylmethylether (0.14 g), and the mixture was stirred at 60° C. for 1 day. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 3-(2,6-dibromophenyl)-5-(4-fluorophenyl)-1-(methoxymethyl)-1H-pyrazole and 3-(2,6-dibromophenyl)-5-(4-fluorophenyl)-2-(methoxymethyl)-2H-pyrazole (0.30 g). The product (0.30 g) was dissolved in tetrahydrofuran (3 mL). To the mixture was added dropwise a solution of n-butyllithium in n-hexane (2.6 mol/L, 0.51 mL) at −78° C., and the mixture was stirred at the same temperature for 30 minutes. To the mixture was added a large excess of dry ice, then the mixture was allowed to warm to room temperature. The mixture was stirred for 1 hour. The reaction mixture was acidified with hydrochloric acid (1 mol/L), and the crude product was extracted with ethyl acetate. The organic layer was washed with brine, and dried over anhydrous magnesium sulfate. The solvent was removed under reduced pressure to afford a mixture of 3-bromo-2-[5-(4-fluorophenyl)-1-(methoxymethyl)-1H-pyrazol-3-yl]benzoic acid and 3-bromo-2-[5-(4-fluorophenyl)-2-(methoxymethyl)-2H-pyrazol-3-yl]benzoic acid (0.27 g). To the product (0.27 g) was added N,N-dimethylformamide (2 mL). To the mixture were added 1-hydroxybenzotriazole monohydrate (0.21 g), ammonium chloride (0.36 g), triethylamine (0.69 g) and 1-ethyl-3-(3-dimethylaminopropyl)carbodiimide hydrochloride (0.26 g), and the mixture was stirred at room temperature for 4 hours. To the reaction mixture was added water, and the crude product was extracted with dichloromethane. The organic layer was washed with brine, and dried over anhydrous magnesium sulfate. The solvent was removed under reduced pressure, and the residue was purified by silica gel column chromatography (eluent: ethyl acetate/methanol) to afford the title compound (0.127g). Structural formula, spectral data and purification condition are shown in Table 5.

REFERENCE EXAMPLE 1-4-1

3-Methyl-2-(5-phenyl-1H-pyrazol-3-yl)benzoic acid

A mixture of 2-iodo-3-methylbenzoic acid ethyl ester (2.93 g), trimethylsilylacetylene (1.19 g), bis(triphenylphosphine)palladium(II)dichloride (354 mg), copper (I) iodide (38 mg) and triethylamine (20 mL) was stirred at 95° C. under an argon atmosphere for 3 hours. The mixture was filtered through a pad of celite, and the filtrate was concentrated under reduced pressure. The residue was purified by silica gel column chromatography (eluent: ethyl acetate/n-hexane) to afford 3-methyl-2-(trimethylsilylethynyl)benzoic acid ethyl ester (2.47 g). To a solution of the product (2.47 g) in methanol (25 mL) was added potassium carbonate (2.67 g) at room temperature. The mixture was stirred overnight, and the mixture was poured into water. The crude product was extracted with ethyl acetate. The organic layer was washed with water, and then was concentrated under reduced pressure. The residue was purified by silica gel column chromatography (eluent: ethyl acetate/n-hexane). The obtained crude product was purified by column chromatography on aminopropylated silica gel (eluent: n-hexane/ethyl acetate) to afford 2-ethynyl-3-methylbenzoic acid methyl ester (2.20 g). To a solution of benzaldehyde (447 mg) in toluene (1.8 mL) was added p-toluenesulfonylhydrazine (784 mg) at room temperature, and the mixture was stirred at 50° C. for 1.5 hours. The mixture was allowed to cool to room temperature. To the mixture was added sodium ethoxide (716 mg), and the mixture was stirred for 15 minutes. To the mixture was added a solution of 2-ethynyl-3-methylbenzoic acid methyl ester (2.2 g) in toluene (12 mL), and the mixture was stirred at 90° C. overnight. The mixture was cooled to room temperature and hydrochloric acid (1 mol/L, 16 mL) was added. The crude product was extracted with ethyl acetate, and the extract was concentrated under reduced pressure. The residue was purified by silica gel column chromatography (eluent: ethyl acetate/n-hexane) to afford the title compound (229 mg). Structural formula, spectral data and purification condition are shown in Table 5.

REFERENCE EXAMPLE 1-5-1

2-Bromo-6-methoxymethoxybenzaldehyde

To a solution of 2-bromo-6-hydroxybenzaldehyde (1.47 g) in N,N-dimethylformamide (15 mL) was added sodium hydride (60% dispersion in oil, 380 mg) at 0° C. and the mixture was stirred at 0° C. for 10 minutes. To the mixture was added chloromethylmethylether (707 mg), and the mixture was stirred at 0° C. to room temperature for 3 hours. The reaction mixture was poured into water, and the mixture was extracted with ethyl acetate. The organic layer was washed with water, and then was concentrated under reduced pressure. The residue was purified by silica gel column chromatography (eluent: ethyl acetate/n-hexane) to afford the title compound (690 mg). Structural formula, spectral data and purification condition are shown in Table 5.

REFERENCE EXAMPLE 1-6-1

3-(2-Bromo-6-fluorophenyl)-5-(4-fluorophenyl)-1H-pyrazole

To a solution of 2-bromo-6-fluorobenzaldehyde (4.439 g) in toluene (96 mL) was added p-toluenesulfonylhydrazine (4.072 g), and the mixture was stirred at 110° C. for 3 hours. The mixture was allowed to cool to room temperature, and to the mixture were added sodium ethoxide (4.464 g) and a solution of 1-ethynyl-4-fluorobenzene (3.94 g) in toluene (68 mL). The mixture was stirred at 110° C. for 16 hours. The reaction mixture was diluted with ethyl acetate and the mixture was washed with water and brine successively, and dried over sodium sulfate. The solvent was removed under reduced pressure, and the residue was purified by silica gel column chromatography (eluent: ethyl acetate/n-hexane) to afford the title compound (3.283 g). Structural formula, spectral data and purification condition are shown in Table 6.

REFERENCE EXAMPLES 1-6-2 TO 1-6-42

Reference Examples 1-6-2 to 1-6-42 were synthesized in a manner similar to that of Reference Example 1-6-1 by using the corresponding materials. Structural formula, spectral data and purification condition are shown in Table 6 to Table 10.

REFERENCE EXAMPLE 1-7-1

3-(2-Bromophenyl)-5-(thiophen-2-yl)-1H-pyrazole

To a solution of thiophene-2-carbaldehyde (207 mg) in toluene (12 mL) was added p-toluene sulfonylhydrazine (343 mg). The mixture was stirred at 50° C. for 1.5 hours, and the mixture was allowed to cool to room temperature. To the mixture was added sodium ethoxide (313 mg), and the mixture was stirred for 15 minutes. To the mixture was added a solution of 1-bromo-2-ethynylbenzene (1.00 g) in toluene mL), and the mixture was stirred at 90° C. overnight. The mixture was diluted with ethyl acetate. The mixture was washed with water, and then the mixture was concentrated under reduced pressure. The residue was purified by silica gel column chromatography (eluent: ethyl acetate/n-hexane) to afford the title compound (42 mg). Structural formula, spectral data and purification condition are shown in Table 11.

REFERENCE EXAMPLES 1-7-2 TO 1-7-4

Reference Examples 1-7-2 to 1-7-4 were synthesized in a manner similar to that of Reference Example 1-7-1 by using the corresponding materials. Structural formula, spectral data and purification condition are shown in Table 11.

REFERENCE EXAMPLE 1-8-1

A mixture of 3-(2-bromophenly-1-methoxymethyl-5-phenyl-1H-pyrazole and 3-(2-bromophenyl)-2-methoxymethyl-5-phenyl-2H-pyrazole To a solution of 3-(2-bromophenyl)-5-phenyl-1H-pyrazole (272 mg) in N,N-dimethylformamide (4 mL) was added sodium hydride (60% dispersion in oil, 43 mg) at 0° C., and the mixture was stirred for 10 minutes. To the mixture was added chloromethylmethylether (81 mg), and the mixture was stirred at room temperature overnight. The mixture was poured into water, and the crude product was extracted with ethyl acetate. The extract was washed with water, and then was concentrated under reduced pressure. The residue was purified by silica gel column chromatography (eluent: ethyl acetate/n-hexane) to afford the title compound (282 mg). Structural formula, spectral data and purification condition are shown in Table 12.

REFERENCE EXAMPLES 1-8-2 TO 1-8-6

Reference Examples 1-8-2 to 1-8-6 were synthesized in a manner similar to that of Reference Example 1-8-1 by using the corresponding materials. Structural formula, spectral data and purification condition are shown in Table 12 to Table 13.

REFERENCE EXAMPLE 1-9-1

A mixture of 2-[1-(methoxymethyl)-5-phenyl-1H-pyrazol-3-yl]benzoic acid and 2-[2-(methoxymethyl)-5-phenyl-2H-pyrazol-3-yl]benzoic acid To a mixture of 3-(2-bromophenyl)-1-methoxymethyl-5-phenyl-1H-pyrazole and 3-(2-bromophenyl)-2-methoxymethyl-5-phenyl-2H-pyrazole (140 mg) were added n-propanol (2 mL) and N-methylpyrrolidone (1 mL). To the mixture were added 1,1'-bis(diphenylphosphino)ferrocene (23 mg), 1,1'-bis(diphenylphosphino)ferrocene palladium(II)dichloride dichloromethane adduct (34 mg) and triethylamine (120 mg). The mixture was stirred at 100° C. under a carbon monoxide atmosphere overnight. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 2-[1-(methoxymethyl)-5-phenyl-1H-pyrazol-3-yl]benzoic acid propyl ester and 2-[2-(methoxymethyl)-5-phenyl-2H-pyrazol-3-yl]benzoic acid propyl ester (90 mg). To a mixture of the product (90 mg) and methanol (2 mL) was added an aqueous solution of sodium hydroxide (2 mol/L, 0.5 mL), and the mixture was stirred at 60° C. for 2.5 hours. The reaction mixture was allowed to cool to room temperature. To the mixture were added hydrochloric acid (2 mol/L, 0.55 mL) and water, and the crude product was extracted with ethyl acetate. The organic layer was washed with brine, and dried over anhydrous magnesium sulfate. The solvent was removed under reduced pressure to afford the title compound (45 mg). Structural formula, spectral data and purification condition are shown in Table 14.

REFERENCE EXAMPLES 1-9-2 TO 1-9-3

Reference Examples 1-9-2 to 1-9-3 were synthesized in a manner similar to that of Reference Example 1-9-1 by using the corresponding materials. Structural formula, spectral data and purification condition are shown in Table 15.

REFERENCE EXAMPLE 1-10-1

A mixture of 2-{5-[4-(imidazol-1-yl)phenyl]-1-methoxymethyl-1H-pyrazol-3-yl}benzoic acid and 2-{5-[4-(imidazol-1-yl)phenyl]-2-methoxymethyl-2H-pyrazol-3-yl}benzoic acid A mixture of 3-(2-bromophenyl)-5-[4-(imidazol-1-yl)phenyl]-1-methoxymethyl-1H-pyrazole and 3-(2-bromophenyl)-5-[4-(imidazol-1-yl)phenyl]-2-methoxymethyl-2H-pyrazole (248 mg) was dissolved in a mixture of dimethylsulfoxide (3 mL) and n-butyl alcohol (2 mL). To the mixture were added 1,3-bis(diphenylphosphino)propane (25 mg) and N,N-diisopropylethylamine (392 mg), and the mixture was placed under an argon atmosphere. To the mixture was added palladium(II)acetate (14 mg), and the mixture was stirred at 110° C. under a carbon monoxide atmosphere overnight. The reaction mixture was filtered through a pad of celite, and to the filtrate was added water. The crude product was extracted with ethyl acetate. The extract was washed with water, and then was concentrated under reduced pressure. The residue was purified by aminopropyl silica gel column chromatography (eluent: ethyl acetate/n-hexane) to afford a mixture of 2-{5-[4-(imidazol-1-yl)phenyl]-1-methoxymethyl-1H-pyrazol-3-yl}benzoic acid butyl ester and 2-{5-[4-(imidazol-1-yl)phenyl]1-2-methoxymethyl-2H-pyrazol-3-yl}benzoic acid butyl ester (198 mg). The product (198 mg) was dissolved in a mixture of tetrahydrofuran (2 mL), methanol (1 mL) and water (1 mL). To the mixture was added lithium hydroxide monohydrate (160 mg), and the mixture was stirred at 50° C. overnight. To the mixture was added hydrochloric acid (1 mol/L, 3.81 mL). The crude product was extracted with ethyl acetate. The extract was washed with water, and dried over anhydrous magnesium sulfate. The solvent was removed under reduced pressure to afford the title compound (113 mg). Structural formula, spectral data and purification condition are shown in Table 15.

REFERENCE EXAMPLE 1-11-1

3-Fluoro-2-[4-fluoro-5-(4-fluorophenyl)-1H-pyrazol-3-yl]benzoic acid

A solution of 3-(2-bromo-6-fluorophenyl)-5-(4-fluorophenyl)-1H-pyrazole (0.30 g) in acetonitrile (3 mL) was added Selectfluor® (0.38 g), and the mixture was stirred at 80° C. overnight. The reaction mixture was allowed to cool to room temperature. To the reaction mixture was added a saturated aqueous solution of sodium bicarbonate, and the crude product was extracted with ethyl acetate. The extract was washed with brine, and dried over anhydrous magnesium sulfate. The solvent was removed under reduced pressure, and the residue was purified by silica gel column chromatography (eluent: ethyl acetate/n-hexane) to afford 3-(2-bromo-6-fluorophenyl)-4-fluoro-5-(4-fluorophenyl)-1H-pyrazole (0.22 g). To a mixture of the product (0.22 g), n-propanol (3 mL) and N-methylpyrrolidone (1 mL) were added triethylamine (0.19 g), 1,1'-bis(diphenylphosphino)ferrocene (0.035 g) and 1,1'-bis(diphenylphosphino)ferrocene palladium(II)dichloride dichloromethane adduct (0.051 g), and the mixture was stirred at 100° C. under a carbon monoxide atmosphere for 5 hours. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford 3-fluoro-2-[4-fluoro-5-(4-fluorophenyl)-1H-pyrazol-3-yl]benzoic acid propyl ester (0.113 g). To a solution of the product (0.113 g) in methanol (1 mL) was added an aqueous solution of sodium hydroxide (2 mol/L, 0.9 mL), and the mixture was stirred at 60° C. for 1.5 hours. The reaction mixture was allowed to cool to room temperature. To the mixture was added hydrochloric acid (2 mol/L, 0.94 mL). The precipitate was collected by filtration to afford the title compound (80 mg). Structural formula, spectral data and purification condition are shown in Table 16.

REFERENCE EXAMPLES 1-11-2 TO 1-11-4

Reference Examples 1-11-2 to 1-11-4 were synthesized in a manner similar to that of Reference Example 1-11-1 by using the corresponding materials. Structural formula, spectral data and purification condition are shown in Table 16.

REFERENCE EXAMPLE 1-12-1

3-Fluoro-2-(5-phenyl-1H-pyrazol-3-yl)benzoic acid

To a suspension of 3-(2-bromo-6-fluorophenyl)-5-phenyl-1H-pyrazole (150 mg) in n-propanol (3 mL) were added dimethylsulfoxide (1 mL), triethylamine (72 mg), 1,3-bis(diphenylphosphino)propane (20 mg) and palladium(II)acetate (11 mg), and the mixture was stirred at 100° C. under a carbon monoxide atmosphere overnight. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford 3-fluoro-2-(5-phenyl-1H-pyrazol-3-yl)benzoic acid propyl ester (120 mg). To a solution of the product (120 mg) in methanol (2 mL) was added an aqueous solution of sodium hydroxide (2 mol/L, 750 μL), and the mixture was stirred at 60° C. for 1 hour. To the reaction mixture was added hydrochloric acid (2 mol/L, 800 μL). The crude product was extracted with ethyl acetate. The extract was washed with water, and dried over anhydrous magnesium sulfate. The solvent was removed under reduced pressure to afford the title compound (86 mg). Structural formula, spectral data and purification condition are shown in Table 17.

REFERENCE EXAMPLES 1-12-2 TO 1-12-6

Reference Examples 1-12-2 to 1-12-6 were synthesized in a manner similar to that of Reference Example 1-12-1 by using the corresponding materials. Structural formula, spectral data and purification condition are shown in Table 17.

REFERENCE EXAMPLE 1-13-1

3-Fluoro-2-[5-(4-fluorophenyl)-1H-pyrazol-3-yl] benzoic acid

To a suspension of 3-(2-bromo-6-fluorophenyl)-5-(4-fluorophenyl)-1H-pyrazole (1.163 g) in n-propanol (22 mL) were added N-methylpyrrolidone (7.5 mL), triethylamine (1.053 g), 1,1'-bis(diphenylphosphino)ferrocene (0.192 g) and 1,1'-bis(diphenylphosphino)ferrocene palladium(II)dichloride dichloromethane adduct (0.284 g), and the mixture was stirred at 100° C. under a carbon monoxide atmosphere for 10 hours. The reaction mixture was allowed to cool to room temperature. To the mixture were added hydrochloric acid (1 mol/L), and the crude product was extracted with ethyl acetate. The organic layer was washed with water and brine, and dried over sodium sulfate. The solvent was removed under reduced pressure, and the residue was purified by silica gel column chromatography (eluent: ethyl acetate/n-hexane) to afford 3-fluoro-2-[5-(4-fluorophenyl)-1H-pyrazol-3-yl]benzoic acid propyl ester (1.114 g). To a solution of the product (1.114 g) in methanol (10 mL) was added an aqueous solution of sodium hydroxide (2 mol/L, 10 mL), and the mixture was stirred at room temperature for 10 hours. To the reaction mixture was added hydrochloric acid (1 mol/L) under ice-cooling. The precipitate was collected by filtration, and dried under reduced pressure to afford the title compound (0.844 g). Structural formula, spectral data and purification condition are shown in Table 18.

REFERENCE EXAMPLES 1-13-2 TO 1-13-17

Reference Examples 1-13-2 to 1-13-17 were synthesized in a manner similar to that of Reference Example 1-13-1 by using the corresponding materials. Structural formula, spectral data and purification condition are shown in Table 18 to Table 19.

REFERENCE EXAMPLE 1-14-1

A mixture of 2-(4-chloro-1-methoxymethyl-5-phenyl-1H-pyrazol-3-yl)benzoic acid and 2-(4-chloro-2-methoxymethyl-5-phenyl-2H-pyrazol-3-yl)benzoic acid A mixture of 3-(2-bromophenyl)-1-methoxymethyl-5-phenyl-1H-pyrazole and 3-(2-bromophenyl)-2-methoxymethyl-5-phenyl-2H-pyrazole (2.0 g) was dissolved in a mixture of dimethylsulfoxide (30 ML) and n-butyl alcohol (20 mL). To the mixture were added 1,3-bis(diphenylphosphino)propane (240 mg) and N,N-diisopropylethylamine (3.77 g), and the mixture was placed under an argon atmosphere. To the mixture was added palladium(II) acetate (130 mg), and the mixture was stirred at 110° C. under a carbon monoxide atmosphere overnight. The reaction mixture was filtered through a pad of celite, and to the filtrate was added hydrochloric acid (0.5 mol/L). The crude product was extracted with ethyl acetate. The extract was washed with water and a saturated aqueous solution of sodium bicarbonate, and then was concentrated under reduced pressure. The residue was purified by silica gel column chromatography (eluent: ethyl acetate/n-hexane) to afford a mixture of 2-(1-methoxymethyl-5-phenyl-1H-pyrazol-3-yl)benzoic acid butyl ester and 2-(2-methoxymethyl-5-phenyl-2H-pyrazol-3-yl)benzoic acid butyl ester (1.52 g). The product (200 mg) was dissolved in dichloromethane (4 mL). To the mixture was added N-chlorosuccinimide (88 mg) at room temperature, and the mixture was stirred overnight. The mixture was purified by silica gel column chromatography (eluent: ethyl acetate/n-hexane) to afford a mixture of 2-(4-chloro-1-methoxymethyl-5-phenyl-1H-pyrazol-3-yl)benzoic acid butyl ester and 2-(4-chloro-2-methoxymethyl-5-phenyl-2H-pyrazol-3-yl)benzoic acid butyl ester (240 mg). The product (219 mg) was dissolved in a mixture of tetrahydrofuran (1 mL), methanol (0.5 mL) and water (0.5 mL). To the mixture was added lithium hydroxide monohydrate (168 mg), and the mixture was stirred at 50° C. overnight. To the mixture was added hydrochloric acid (2 mol/L, 4 mL). The crude product was extracted with ethyl acetate. The extract was washed with water, and dried over anhydrous magnesium sulfate. The solvent was removed under reduced pressure to afford the title compound (188 mg). Structural formula, spectral data and purification condition are shown in Table 20.

REFERENCE EXAMPLE 1-14-2

Reference Example 1-14-2 was synthesized in a manner similar to that of Reference Example 1-14-1 by using the corresponding materials. Structural formula, spectral data and purification condition are shown in Table 20.

REFERENCE EXAMPLE 1-15-1

A mixture of 2-(4-bromo-1-methoxymethyl-5-phenyl-1H-pyrazol-3-yl)benzoic acid butyl ester and 2-(4-bromo-2-methoxymethyl-5-phenyl-2H-pyrazol-3-yl)benzoic acid butyl ester A mixture of 3-(2-bromophenyl)-1-methoxymethyl-5-phenyl-1H-pyrazole and 3-(-bromophenyl)-2-methoxymethyl-5-phenyl-2H-pyrazole (2.0 g) was dissolved in a mixture of dimethylsulfoxide (30 mL) and n-butyl alcohol (20 mL). To the mixture were added 1,3-bis(diphenylphosphino)propane (240 mg) and N,N-diisopropylethylamine (377 g), and the mixture was placed under an argon atmosphere. To the mixture was added palladium(II)acetate (130 mg), and the mixture was stirred at 110° C. under a carbon monoxide atmosphere overnight. The reaction mixture was filtered through a pad of celite, and to the filtrate was added hydrochloric acid (0.5 mol/L). The crude product was extracted with ethyl acetate. The extract was washed with water and a saturated aqueous solution of sodium bicarbonate, and then was concentrated under reduced pressure. The residue was purified by silica gel column chromatography (eluent: ethyl acetate/n-hexane) to afford a mixture of 2-(1-methoxymethyl-5-phenyl-1 H-pyrazol-3-yl) benzoic acid butyl ester and 2-(2-methoxymethyl-5-phenyl-2H-pyrazol-3-yl)benzoic acid butyl ester (1.52 g). The product (1.22 g) was dissolved in dichloromethane (20 mL). To mixture was added N-bromosuccinimide (715 mg) at room temperature, and the mixture was stirred overnight. The mixture was purified by silica gel column chromatography (eluent: ethyl acetate/n-hexane) to afford the title compound (1.29 g). Structural formula, spectral data and purification condition are shown in Table 20.

REFERENCE EXAMPLE 1-15-2

Reference Example 1-15-2 was synthesized in a manner similar to that of Reference Example 1-15-1 by using the corresponding materials. Structural formula, spectral data and purification condition are shown in Table 20.

REFERENCE EXAMPLE 1-16-1

A mixture of 2-(1-methoxymethyl-4-methyl-5-phenyl-1H-pyrazol-3-yl)benzoic acid and 2-(2-methoxymethyl-4-methyl-5-phenyl-2H-pyrazol-3-yl) benzoic acid To N,N-dimethylformamide (3 mL) were added a mixture of 2-(4-bromo-1-methoxymethyl-5-phenyl-1H-pyrazol-3-yl)benzoic acid butyl ester and 2-(4-bromo-2-methoxymethyl-5-phenyl-2H-pyrazol-3-yl)benzoic acid butyl ester (109 mg), 2,4,6-trimethylboroxine (62 mg) and potassium carbonate (170 mg). The mixture was placed under an argon atmosphere. To the mixture was added [1,1'-bis(diphenylphosphino)ferrocene]palladium(II)dichloride dichloromethane adduct (20 mg), and the mixture was stirred at 110° C. for 3 hours. The mixture was diluted with ethyl acetate, and then was filtered through a pad of celite. The extract was washed with water twice, and then was concentrated under reduced pressure. The residue was purified by silica gel column chromatography (eluent: ethyl acetate/n-hexane) to afford a mixture of 2-(-methoxymethyl-4-methyl-5-phenyl-1H-pyrazol-3-yl) acid butyl ester and 2-(2-methoxymethyl-4-methyl-5-phenyl-2H-pyrazol-3-yl)benzoic acid butyl ester (93 mg). The product (93 mg) was dissolved in a mixture of tetrahydrofuran (1 mL), methanol (0.5 mL) and water (0.5 mL). To the mixture was added lithium hydroxide monohydrate (118 mg), and the mixture was stirred at 50° C. overnight. To the mixture was added hydrochloric acid (2 mol/L, 2.81 mL). The crude product was extracted with ethyl acetate. The extract was washed with water, and dried over anhydrous magnesium sulfate. The solvent was removed under reduced pressure to afford the title compound (79 mg). Structural formula, spectral data and purification condition are shown in Table 21.

REFERENCE EXAMPLE 1-16-2

Reference Example 1-16-2 was synthesized in a manner similar to that of Reference Example 1-16-1 by using the corresponding materials. Structural formula, spectral data and purification condition are shown in Table 21.

REFERENCE EXAMPLE 1-17-1

A mixture of 2-(1-methoxymethyl-5-phenyl4-vinyl-1H-pyrazol-3-yl)benzoic acid and 2-(2-methoxymethyl-5-phenyl-4-vinyl-2H-pyrazol-3-yl)benzoic acid To a toluene (6 mL) were added a mixture of 2-(4-bromo-1-methoxymethyl-5-phenyl-1H-pyrazol-3-yl)benzoic acid butyl ester and 2-(4-bromo-2-methoxymethyl-5-phenyl-2H-pyrazol-3-yl)benzoic acid butyl ester (500 mg), tributyl(vinyl)tin (536 mg) and tetrakis(triphenylphosphine)palladium (0) (130 mg). The mixture was stirred under reflux for 6 hours. The mixture was allowed to cool to 0° C. To the mixture was added an aqueous solution of potassium fluoride (0.5 mol/L, 5 mL), and the resulting mixture was stirred at room temperature for 10 minutes. The mixture was filtered through a pad of celite, and the insoluble compound was washed with ethyl acetate. The filtrate was washed with water, and then concentrated under reduced pressure. The residue was purified by silica gel column chromatography (eluent: ethyl acetate/n-hexane) to afford a mixture of 2-(1-methoxymethyl-5-phenyl-4-vinyl-1H-pyrazol-3-yl)benzoic acid butyl ester and 2-(2-methoxymethyl-5-phenyl-4-vinyl-2H-pyrazol-3-yl)benzoic acid butyl ester (0.44 g). The product (0.44 g) was dissolved in a mixture of tetrahydrofuran (6 mL), methanol (3 mL) and water (3 mL). To the mixture was added lithium hydroxide monohydrate (303 mg), and the mixture was stirred at 50° C. overnight. To the mixture was added hydrochloric acid (2 mol/L. 3.61 mL). The crude product was extracted with ethyl acetate. The extract was washed with water, and dried over anhydrous magnesium sulfate. The solvent was removed under reduced pressure to afford the title compound (377 mg). Structural formula, spectral data and purification condition are shown in Table 21.

REFERENCE EXAMPLE 1-18-1

4-Fluoro-2-(4-fluorophenyl)-8H-pyrazolo[5,1-a] isoindol-8-one

To a suspension of 3-fluoro-2-[5-(4-fluorophenyl)-1H-pyrazol-3-yl]benzoic acid (0.20 g) in dichloromethane (2 mL) were added N,N-diisopropylethylamine (0.30 g) and a solution of T3P® in N,N-dimethylformamide (1.6 mol/L, 0.79 mL), and the mixture was stirred at room temperature for 0.5 hours. To the reaction mixture was added water, and the crude product was extracted with ethyl acetate. The organic layer was washed with brine, and dried over anhydrous magnesium sulfate. The solvent was removed under reduced pressure to afford the title compound (0.19 g). Structural formula, spectral data and purification condition are shown in Table 22.

REFERENCE EXAMPLES 1-18-2 TO 1-18-3

Reference Examples 1-18-2 to 1-18-3 were synthesized in a manner similar to that of Reference Example 1-18-1 by using the corresponding materials. Structural formula, spectral data and purification condition are shown in Table 22.

REFERENCE EXAMPLE 1-19-1

3-Hydroxy-2-(2-methoxymethyl-5-phenyl-2H-pyrazol-3-yl)-N-[2-(pyridin-2-yl)ethyl]benzamide A mixture of 3-(2-benzyloxy-6-bromophenyl)-1-methoxymethyl-5-phenyl-1H-pyrazole and 3-(2-benzyloxy-6-bromophenyl)-2-methoxymethyl-5-phenyl-2H-pyrazole (1.63 g) was dissolved in dimethylsulfoxide (20 mL). To the mixture were added. 1,3-bis(diphenylphosphino)propane (302 mg), N,N-diisopropylethylamine (1.41 g) and 2-(pyridin-2-yl)ethylamine (1.33 g), and the mixture was placed under an argon atmosphere. To the mixture was added palladium(II)acetate (164 mg), and the mixture was stirred at 110° C. under a carbon monoxide atmosphere overnight. The reaction mixture was filtered through a pad of celite, and to the filtrate was added water. The crude product was extracted with ethyl acetate. The extract was washed with water, and then was concentrated under reduced pressure. The residue was purified by silica gel column chromatography (eluent: ethyl acetate/n-hexane-ethyl acetate/methanol) to afford 3-benzyloxy-2-(1-methoxymethyl-5-phenyl-1H-pyrazol-3-yl)-N-[2-(pyridin-2-yl)ethyl]benzamide (393 mg) and 3-benzyloxy-2-(2-methoxymethyl-5-phenyl-2H-pyrazol-3-yl)-N-[2-(pyridin-2-yl)ethyl]benzamide (736 mg). To the product (736 mg) in tetrahydrofuran (20 mL) was added 10% palladium-carbon (50% wet, 140 mg), and the mixture was stirred at room temperature under a hydrogen atmosphere overnight. To the mixture was added 10% palladium-carbon (50% wet, 140 mg), and the mixture was stirred at 70° C. for 8 hours. The reaction mixture was filtered through a pad of celite, and the filtrate was concentrated under reduced pressure. The residue was purified by silica gel column chromatography (eluent: ethyl acetate/methanol) to afford the title compound (525 mg). Structural formula, spectral data and purification condition are shown in Table 22.

REFERENCE EXAMPLE 1-20-1

A mixture of 3-cyano-2-[5-(4-fluorophenyl)-1-(methoxymethyl)-1H-pyrazol-3-yl]benzoic acid and 3-cyano-2-[5-(4-fluorophenyl)-2-(methoxymethyl)-2H-pyrazol-3-yl]benzoic acid A mixture of 3-bromo-2-[5-(4-fluorophenyl)-1-(methoxymethyl)-1H-pyrazol-3-yl]benzamide and 3-bromo-2-[5-(4-fluorophenyl)-2-(methoxymethyl)-2H-pyrazol-3-yl]benzamide (0.11 g) was dissolved in ethyl acetate (1 mL). To the mixture was added a solution of T3P® in ethyl acetate (1.7 mol/L, 1 mL), and the mixture was stirred for 3 hours under reflux. The reaction mixture was allowed to cool to room temperature, and then concentrated under reduced pressure. The residue was purified by silica gel column chromatography (eluent: ethyl acetate/n-hexane) to afford a mixture of 3-bromo-2-[5-(4-fluorophenyl)-1-(methoxymethyl)-1H-pyrazol-3-yl]benzonitrile and 3-bromo-2-[5-(4-fluorophenyl)-2-(methoxymethyl)-2H-pyrazol-3-yl]benzonitrile (0.090 g). A mixture of the product (90 mg), n-propanol (3 mL), N-methylpyrrolidone (1 mL), triethylamine (70 mg), 1,1'-bis(diphenylphosphino)ferrocene (20 mg) and 1,1'-bis(diphenylphosphino)ferrocene palladium(II)dichloride dichloromethane adduct (29 mg) was stirred at 100° C. under a carbon monoxide atmosphere for 5 hours. The reaction mixture was allowed to cool to room temperature. To the reaction mixture were added hydrochloric acid (1 mol/L) and water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 3-cyano-2-[5-(4-fluorophenyl)-1-(methoxymethyl)-1H-pyrazol-3-yl]benzoic acid propyl ester and 3-cyano-2-[5-(4-fluorophenyl)-2-(methoxymethyl)-2H-pyrazol-3-yl]benzoic acid propyl ester. To the product were added methanol (1 mL) and an aqueous solution of sodium hydroxide (2 mol/L, 470 µL), and the mixture was stirred at 60° C. for 1.5 hours. The reaction mixture was acidified with hydrochloric acid (2 mol/L). The crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/methanol) to afford the title compound (45 mg). Structural formula, spectral data and purification condition are shown in Table 23.

REFERENCE EXAMPLE 1-21-1

A mixture of 2-[5-(4-fluorophenyl)-1-(methoxymethyl)-1H-pyrazol-3-yl]-3-[(methoxymethoxy)methyl]benzoic acid and 2-[5-(4-fluorophenyl)-2-(methoxymethyl)-2H-pyrazol-3-yl]-3-[(methoxymethoxy)methyl]benzoic acid A mixture of 3-(2,6-dibromophenyl)-5-(4-fluorophenyl)-1-(methoxymethyl)-1H-pyrazole and 3-(2,6-dibromophenyl)-5-(4-fluorophenyl)-2-(methoxymethyl)-2H-pyrazole (145 mg) was dissolved in tetrahydrofuran (3 mL). To the mixture was added dropwise a solution of n-butyllithium in n-hexane (2.6 mol/L, 0.25 mL) at −78° C., and the mixture was stirred at the same temperature for 30 minutes. To the mixture was added N,N-dimethylformamide (40 µL), and the mixture was stirred at −78° C. for 30 minutes. The mixture was allowed to warm to room temperature. To the reaction mixture was added water, and the crude product was extracted with ethyl acetate. The organic layer was washed with brine, and dried over anhydrous magnesium sulfate. The solvent was removed under reduced pressure. To the residue was added methanol (1 mL). To the mixture was added sodium borohydride (13 mg) under ice-cooling, and the mixture was stirred at room temperature for 1 hour. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of {3-bromo-2-[5-(4-fluorophenyl)-1-(methoxymethyl)-1H-pyrazol-3-yl]phenyl}methanol and {3-bromo-2-[5-(4-fluorophenyl)-2-(methoxymethyl)-2H-pyrazol-3-yl]phenyl}methanol (20 mg). The product (20 mg) was dissolved in tetrahydrofuran (2 mL). To the mixture were added sodium hydride (60% dispersion in oil, 5 mg) and chloromethyl methyl ether (17 mg) under ice-cooling. The mixture was stirred at 60° C. for 3 hours. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 3-{2-bromo-6-[(methoxymethoxy)methyl]phenyl}-5-(4-fluorophenyl)-1-(methoxymethyl)-1H-pyrazole and 3-{2-bromo-6-[(methoxymethoxy)methyl]phenyl}-5-(4-fluorophenyl)-2-(methoxymethyl)-2H-pyrazole (22 mg). To the product (22 mg) were added n-propanol (3 mL) and N-methylpyrrolidone (1 mL). To the mixture were added triethylamine (15 mg), 1,1'-bis(diphenylphosphino)ferrocene (4 mg) and 1,1'-bis(diphenylphosphino)ferrocene palladium(II)dichloride dichloromethane adduct (6 mg), and the mixture was stirred at 100° C. under a carbon monoxide atmosphere for 5 hours. The reaction mixture was allowed to cool to room temperature. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 2-[5-(4-fluorophenyl)-1-(methoxymethyl)-1H-pyrazol-3-yl]-3-[(methoxymethoxy)methyl]benzoic acid propyl ester and 2-[5-(4-fluorophenyl)-2-(methoxymethyl)-2H-pyrazol-3-yl]-3-[(methoxymethoxy)methyl]benzoic acid propyl ester. To the product were added methanol (1 mL) and a solution of sodium hydroxide (2 mol/L, 200 µL), and the mixture was stirred at 60° C. for 1.5 hours. The reaction mixture was acidified with hydrochloric acid (2 mol/L). The crude product was extracted with ethyl acetate. The organic layer was washed with water and brine, and dried over anhydrous magnesium sulfate. The solvent was removed under reduced pressure to afford the title compound (20 mg). Structural formula, spectral data and purification condition are shown in Table 23.

REFERENCE EXAMPLE 1-22-1

2-Bromo-4-(1,3-dioxolan-2-yl)benzaldehyde

To a solution of 2-bromo-4-formylbenzoic acid methyl ester (1.867 g) in toluene (50 mL) were added ethylene glycol (4.767 g) and p-toluenesulfonic acid monohydrate (0.146 g), and the mixture was refluxed at 150° C. for 18 hours. The reaction mixture was allowed to cool to room temperature. To the reaction mixture was added a saturated aqueous solution of sodium carbonate, and the crude product was extracted with ethyl acetate. The organic layer was washed with water and brine, and dried over anhydrous magnesian sulfate. The solvent was removed under reduced pressure, and the residue was purified by silica gel column chromatography (eluent: ethyl acetate/n-hexane) to afford 2-bromo-4-(1,3-dioxolan-2-yl)benzoic acid methyl ester (1.792 g). To a suspension of lithium aluminium hydride (0.286 g) in tetrahydrofuran (9 mL) was added a solution of 2-bromo-4-(1,3-dioxolan-2-yl)benzoic acid methyl ester (1.446 g) in tetrahydrofuran (8 mL) under ice-cooling, and the mixture was stirred at room temperature for 1 hour. To the reaction mixture was added water. The mixture was diluted with diethyl ether, and the mixture was stirred for 30 minutes. The reaction mixture was filtered through a pad of celite, and the filtrate was concentrated under reduced pressure to afford [2-bromo-4-(1,3-dioxolan-2-yl)phenyl]methanol (1.196 g). To a solution of the product (1.196 g) in dichloromethane (30 mL) were added iodobenzene diacetate (1.634 g) and AZADOL® (0.070 g) under ice-cooling, and the mixture was stirred at room temperature overnight. To the reaction mixture were added 10% aqueous sodium sulfite solution and a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford the title compound (0.938 g). Structural formula, spectral data and purification condition are shown in Table 23.

REFERENCE EXAMPLE 1-23-1

A mixture of 2-[5-(4-fluorophenyl)-1-(methoxymethyl)-4-methyl-1H-pyrazol-3-yl]benzoic acid and 2-[5-(4-fluorophenyl)-2-(methoxymethyl)-4-methyl-2H-pyrazol-3-yl]benzoic acid To a suspension of 3-(2-bromophenyl)-5-(4-fluorophenyl)-1H-pyrazole (0.6 g) in n-propanol (12 mL) were added N-methylpyrrolidone (4 mL), triethylamine (0.574 g), 1,1'-bis(diphenylphosphino)ferrocene (0.105 g) and 1,1'-bis(diphenylphosphino)ferrocene palladium(II)dichloride dichloromethane adduct (0.154 g), and the mixture was stirred at 100° C. under a carbon monoxide atmosphere for 10 hours. The reaction mixture was allowed to cool to room temperature. To the reaction mixture was added hydrochloric acid (1 mol/L), and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane) to afford 2-[5-(4-fluorophenyl)-1H-pyrazol-3-yl]benzoic acid propyl ester (0.545 g). To a solution of the product (0.545 g) in N,N-dimethylformamide (8 mL) were added cesium carbonate (2.735 g) and chloromethyl methyl ether (0.338 g), and the mixture was stirred at 60° C. for 13 hours. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 2-[5-(4-fluorophenyl)-1-(methoxymethyl)-1H-pyrazol-3-yl]benzoic acid propyl ester and 2-[5-(4-fluorophenyl)-2-(methoxymethyl)-2H-pyrazol-3-yl]benzoic acid propyl ester (0.30 g). To the product (0.320 g) was added dichloromethane (8 mL). To the mixture was added N-bromosuccinimide (0.155 g), and the mixture was stirred at room temperature overnight. The reaction mixture was concentrated under reduced pressure, and the residue was purified by silica gel column chromatography (eluent: ethyl acetate/n-hexane) to afford a mixture of 2-[4-bromo-5-(4-fluorophenyl)-1-(methoxymethyl)-1H-pyrazol-3-yl]benzoic acid propyl ester and 2-[4-bromo-5-(4-fluorophenyl)-2-(methoxymethyl)-2H-pyrazol-3-yl]benzoic acid propyl ester (0.388 g). The product (0.200 g) was dissolved in N,N-dimethylformamide (4 mL). To the mixture were added potassium carbonate (0.309 g), trimethylboroxine (0.112 g) and 1,1'-bis(diphenylphosphino)ferrocene palladium(II)dichloride dichloromethane adduct (0.183 g), and the mixture was stirred at 110° C. for 3 hours. The reaction mixture was diluted with ethyl acetate, and then was filtered through a pad of celite. The filtrate was washed with water, and then was concentrated under reduced pressure. The residue was purified by silica gel column chromatography (eluent: ethyl acetate/n-hexane) to afford a mixture of 2-[5-(4-fluorophenyl)-1-(methoxymethyl)-4-methyl-1H-pyrazol-3-yl]benzoic acid propyl ester and 2-[5-(4-fluorophenyl)-2-(methoxymethyl)-4-methyl-2H-pyrazol-3-yl]benzoic acid propyl ester (0.131 g). To the mixture (0.131 g) were added methanol (1 mL) and a solution of sodium hydroxide (2 mol/L, 1 mL), and the mixture was stirred at 60° C. for 2 hours. To the reaction mixture was added hydrochloric acid (2 mol/L, 1 mL), and then the precipitate was collected by filtration to afford the title compound (0.103 g). Structural formula, spectral data and purification condition are shown in Table 24.

REFERENCE EXAMPLE 1-24-1

A mixture of 2-[5-(4-fluorophenyl)-1-(methoxymethyl)-4-chloro-1H-pyrazol-3-yl]benzoic acid and 2-[5-(4-fluorophenyl)-2-(methoxymethyl)-4-chloro-2H-pyrazol-3-yl]benzoic acid A mixture of 2-[5-(4-fluorophenyl)-1-(methoxymethyl)-1H-pyrazol-3-yl]benzoic acid propyl ester and 2-[5-(4-fluorophenyl)-2-(methoxymethyl)-2H-pyrazol-3-yl]benzoic acid propyl ester (0.214 g) was dissolved in dichloromethane (5 mL). To the mixture was added sulfuryl chloride (0.090 g), and the mixture was stirred at room temperature for 2 hours. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 2-[4-chloro-5-(4-fluorophenyl)-1-(methoxymethyl)-1H-pyrazol-3-yl]benzoic acid propyl ester and 2-[4-chloro-5-(4-fluorophenyl)-2-(methoxymethyl)-2H-pyrazol-3-yl]benzoic acid propyl ester (0.174 g). To the product (0.160 g) were added methanol (2 mL) and an aqueous solution of sodium hydroxide (2 mol/L, 1 mL), and the mixture was stirred at 60° C. for 2 hours. To the reaction mixture was added hydrochloric acid (2 mol/L, 1 mL), and then the precipitate was collected by filtration to afford the title compound (0.126 g). Structural formula, spectral data and purification condition are shown in Table 24.

REFERENCE EXAMPLE 1-25-1

3-(5-Phenyl-1H-pyrazol-3-yl)pyridine-2-carboxylic acid

A mixture of 2-bromo-3-(1-methoxymethyl-5-phenyl-1H-pyrazol-3-yl)pyridine and 2-bromo-3-(2-methoxymethyl-5-phenyl-2H-pyrazol-3-yl)pyridine (1.61 g) was dissolved in a mixture of dimethylsulfoxide (18 mL) and n-butyl alcohol (6 mL). To the mixture were added 1,3-bis(diphenylphosphino)propane (193 mg) and N,N-diisopropylethylamine (3.02 g), and the mixture was placed under an argon atmosphere. To the mixture was added palladium(II) acetate (104 mg), and the mixture was stirred at 110° C. under a carbon monoxide atmosphere overnight. The reaction mixture was filtered through a pad of celite, and to the filtrate was added hydrochloric acid (0.5 mol/L). The crude product was extracted with ethyl acetate. The extract was washed with water and a saturated aqueous solution of sodium bicarbonate, and then was concentrated under reduced pressure. The residue was purified by silica gel column chromatography (eluent: ethyl acetate/n-hexane) to afford a mixture of 3-(1-methoxymethyl-5-phenyl-1H-pyrazol-3-yl)pyridine-2-carboxylic acid butyl ester and 3-(2-methoxymethyl-5-phenyl-2H-pyrazol-3-yl)pyridine-2-carboxylic acid butyl ester (558 mg). The product (558 mg) was dissolved in ethanol (5 mL). To the mixture was added a solution of hydrogen chloride in ethyl acetate (4 mol/L, 10 mL). The mixture was stirred at 60° C. for 2 hours and the mixture was poured into a saturated aqueous solution of sodium bicarbonate. The crude product was extracted with ethyl acetate. The extract was washed with a saturated aqueous solution of sodium bicarbonate and water, and then was concentrated under reduced pressure to afford 3-(5-phenyl-1H-pyrazol-3-yl)pyridine-2-carboxylic acid butyl ester (364 mg). To the mixture of the product (364 mg) in a mixture of tetrahydrofuran (2 mL), methanol (1 ml) and water (1 mL) was added lithium hydroxide monohydrate (274 mg), and the mixture was stirred at 60° C. overnight. To the mixture was added hydrochloric acid (2 mol/L, 6.53 mL). The insoluble compound was collected by filtration, washed with water, and dried under reduced pressure to afford the title compound (253 mg). Structural formula, spectral data and purification condition are shown in Table 24.

REFERENCE EXAMPLE 1-26-1

A mixture of 3-fluoro-2-[4-fluoro-5-(4-fluorophenyl)-1-(methoxymethyl)-1H-pyrazol-3-yl]benzoic acid and 3-fluoro-2-[4-fluoro-5-(4-fluorophenyl)-2-(methoxymethyl)-2H-pyrazol-3-yl]benzoic acid To a mixture of 3-(2-bromo-6-fluorophenyl)-5-(4-fluorophenyl)-1-(methoxymethyl)-1H-pyrazole and 3-(2-bromo-6-fluorophenyl)-5-(4-fluorophenyl)(methoxymethyl)-2H-pyrazole (0.391 g) were added n-propanol (6 mL) and N-methylpyrrolidone (2 mL). To the mixture were added triethylamine (0.313 g), 1,1'-bis(diphenylphosphino)ferrocene (0.057 g) and 1,1'-bis(diphenylphosphino)ferrocene palladium(II)dichloride dichloromethane adduct (0.085 g), and the mixture was stirred at 100° C. under a carbon monoxide atmosphere for 10 hours. The reaction mixture was allowed to cool to room temperature. To the reaction mixture was added hydrochloric acid (1 mol/L), and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane) to afford a mixture of 3-fluoro-2-[5-(4-fluorophenyl)-1-(methoxymethyl)-1H-pyrazol-3-yl]benzoic acid propyl ester and 3-fluoro-2-[5-(4-fluorophenyl)-2-(methoxymethyl)-2H-pyrazol-3-yl]benzoic acid propyl ester (0.264 g). To a mixture of the product (0.264 g) and acetonitrile (2.3 mL) was added Selectfluor® (0.294 g), and the mixture was stirred at 80° C. overnight. The reaction mixture was allowed to cool to room temperature. The reaction mixture was poured into a saturated aqueous solution of sodium bicarbonate, and the crude product was extracted with ethyl acetate. The extract was washed with water, and dried over anhydrous magnesium sulfate. The solvent was removed under reduced pressure, and the residue was purified by silica gel column chromatography (eluent: ethyl acetate/n-hexane) to afford a mixture of 3-fluoro-2-[4-fluoro-5-(4-fluorophenyl)-1-(methoxymethyl)-1H-pyrazol-3-yl]benzoic acid propyl ester and 3-fluoro-2-[4-fluoro-5-(4-fluorophenyl)-2-(methoxymethyl)-2H-pyrazol-3-yl]benzoic acid propyl ester (0.140 g). The product (0.140 g) was dissolved in methanol (2.4 mL). To the mixture was added an aqueous solution of sodium hydroxide (2 mol/L, 1 mL), and the mixture was stirred at 60° C. for 10 hours. To the reaction mixture was added hydrochloric acid (2 mol/L, 1 mL), and then the precipitate was collected by filtration to afford the title compound (0.112 g). Structural formula, spectral data and purification condition are shown in Table 24.

REFERENCE EXAMPLE 1-27-1

3-Fluoro-2-[5-(4-fluorophenyl)-1H-pyrazol-3-yl] benzonitrile

A mixture of 3-(2-bromo-6-fluorophenyl)-5-(4-fluorophenyl)-1H-pyrazole (3.00 g), copper (I) cyanide (0.96 g), copper (I) iodide (0.34 g) and N-methylpyrrolidone (21 mL) was stirred at 120° C. for 1.5 hours. The reaction mixture was allowed to cool to 0° C. To the reaction mixture were added an aqueous solution of 28% ammonia (20 mL), water (20 mL) and ethyl acetate/n-hexane (10/1), and the mixture was stirred for 30 minutes. The mixture was partitioned between water and ethyl acetate/n-hexane (10/1). The aqueous layer was extracted three times with ethyl acetate/n-hexane (10/1). The combined organic layer was washed with water and brine. To the organic layer were added an aqueous solution of 28% ammonia (40 mL) and water (40 mL), and the mixture was stirred for 30 minutes. To the mixture was added water, and the crude product was extracted with ethyl acetate/n-hexane (10/1). The organic layer was washed with water and brine, and dried over anhydrous magnesium sulfate. The solvent was removed under reduced pressure to afford the title compound (2.51 g). Structural formula, spectral data and purification condition are shown in Table 24.

TABLE 3

| Ref. Ex. | Strc. | P.D. | P.C. |
|---|---|---|---|
| 1-1-1 | (3-fluorophenyl-pyrazole-benzoic acid structure) | MS (ESI, m/z): 283 (M + H)+ | Without purification |
| 1-1-2 | (methoxy-fluorophenyl-pyrazole-benzoic acid structure) | MS (ESI, m/z): 313 (M + H)+ | Without purification |
| 1-1-3 | (pyridinyl-pyrazole-benzoic acid structure) | MS (ESI, m/z): 266 (M + H)+ | Without purification |
| 1-1-4 | (BnO-phenyl-pyrazole-benzoic acid structure) | MS (ESI, m/z): 371 (M + H)+ | Column: SiO2 EtOAc/n-Hexane |
| 1-1-5 | (chloro-fluorophenyl-pyrazole-benzoic acid structure) | MS (ESI, m/z): 317 (M + H)+ | Without purification |
| 1-1-6 | (chloro-methylphenyl-pyrazole-benzoic acid structure) | MS (ESI, m/z): 313 (M + H)+ | Without purification |

TABLE 3-continued

| Ref. Ex. | Strc. | P.D. | P.C. |
|---|---|---|---|
| 1-1-7 | | MS (ESI, m/z): 313 (M + H)+ | Without purification |
| 1-1-8 | | MS (ESI, m/z): 297 (M + H)+ | Without purification |
| 1-1-9 | | MS (ESI, m/z): 313 (M + H)+ | Without purification |

TABLE 4

| Ref. Ex. | Strc. | P.D. | P.C. |
|---|---|---|---|
| 1-1-10 | | | Without purification |
| 1-1-11 | | | Without purification |
| 1-1-12 | | MS (ESI, m/z): 297 (M + H)+ | Without purification |
| 1-1-13 | | | Without purification |

TABLE 4-continued

| Ref. Ex. | Strc. | P.D. | P.C. |
| --- | --- | --- | --- |
| 1-1-14 | | MS (ESI, m/z): 308 (M + H)+ | Without purification |
| 1-1-15 | | MS (ESI, m/z): 209 (M + H)+ | Without purification |
| 1-11-16 | | MS (ESI, m/z): 313 (M + H)+ | Without purification |

TABLE 5

| Ref. Ex. | Strc. | P.D. | P.C. |
| --- | --- | --- | --- |
| 1-2-1 | | $^1$H-NMR (CDCl$_3$) δ ppm: 3.03-3.04 (1H, m), 3.89 (3H, s), 6.98-7.10 (3H, m). | Column: SiO2 EtOAc/n-Hexane |
| 1-2-2 | | $^1$H-NMR (CDCl$_3$) δ ppm: 3.04 (1H, s), 3.98-4.20 (4H, m), 6.07 (1H, s), 6.97-7.08 (1H, m), 7.43-7.51 (1H, m), 7.65-7.72 (1H, m). | Column: SiO2 EtOAc/n-Hexane |

TABLE 5-continued

| Ref. Ex. | Strc. | P.D. | P.C. |
|---|---|---|---|
| 1-3-1 | | MS (ESI, m/z): 405, 407 (M + H)+ | Column: SiO2<br>EtOAc/MeOH |
| 1-4-1 | | MS (ESI, m/z): 279 (M + H)+ | Column: SiO2<br>EtOAc/n-Hexane |
| 1-5-1 | | $^1$H-NMR (CDCl$_3$) δ ppm: 3.52 (3H, s) 5.28 (2H, s), 7.16-7.34 (4H, m), 10.44 (1H, s). | Column: SiO2<br>EtOAc/n-Hexane |

TABLE 6

| Ref. Ex. | Strc. | P.D. | P.C. |
|---|---|---|---|
| 1-6-1 | | MS (ESI, m/z): 335, 337 (M + H)+ | Column: SiO2<br>EtOAc/n-Hexane |
| 1-6-2 | | MS (ESI, m/z): 317, 319 (M + H)+ | Column: SiO2<br>EtOAc/n-Hexane |

TABLE 6-continued

| Ref. Ex. | Strc. | P.D. | P.C. |
|---|---|---|---|
| 1-6-3 | [structure: 3-(2-fluorophenyl)-5-(2-bromophenyl)-1H-pyrazole] | | Column: SiO2<br>EtOAc/n-Hexane |
| 1-6-4 | [structure: 3-(pyridin-3-yl)-5-(2-bromophenyl)-1H-pyrazole] | MS (ESI, m/z): 300, 302 (M + H)+ | Filtration of the DCH suspension. |
| 1-6-5 | [structure: 3-(2-aminophenyl)-5-(2-bromophenyl)-1H-pyrazole] | MS (ESI, m/z): 314, 316 (M + H)+ | Column: SiO2<br>EtOAc/n-Hexane |
| 1-6-6 | [structure: 3-(2-(diethoxymethyl)phenyl)-5-(2-bromophenyl)-1H-pyrazole] | MS (ESI, m/z): 339, 401 (M − H)− | Column: SiO2<br>EtOAc/n-Hexane |
| 1-6-7 | [structure: 3-phenyl-5-(2-bromo-6-fluorophenyl)-1H-pyrazole] | MS (ESI, m/z): 317, 319 (M + H)+ | Column: SiO2<br>EtOAc/n-Hexane |
| 1-6-8 | [structure: 3-phenyl-5-(2-bromo-6-chlorophenyl)-1H-pyrazole] | MS (ESI, m/z): 333, 335 (M + H)+ | Column: SiO2<br>EtOAc/n-Hexane |
| 1-6-9 | [structure: 3-phenyl-5-(2-bromo-6-(trifluoromethoxy)phenyl)-1H-pyrazole] | MS (ESI, m/z): 383, 385 (M + H)+ | Column: SiO2<br>EtOAc/n-Hexane |

TABLE 6-continued

| Ref. Ex. | Strc. | P.D. | P.C. |
|---|---|---|---|
| 1-6-10 | | MS (ESI, m/z): 367, 369 (M + H)+ | Column: SiO2<br>EtOAc/n-Hexane |

TABLE 7

| Ref. Ex. | Strc. | P.D. | P.C. |
|---|---|---|---|
| 1-6-11 | | MS (ESI, m/z): 335, 337 (M + H)+ | Column: SiO2<br>EtOAc/n-Hexane |
| 1-6-12 | | MS (ESI, m/z): 329, 331 (M + H)+ | Column: SiO2<br>EtOAc/n-Hexane |
| 1-6-13 | | MS (ESI, m/z): 367, 369 (M + H)+ | Column: SiO2<br>EtOAc/n-Hexane |
| 1-6-14 | | MS (ESI, m/z): 367, 369 (M + H)+ | Column: SiO2<br>EtOAc/n-Hexane |
| 1-6-15 | | MS (ESI, m/z): 329, 331 (M + H)+ | Column: SiO2<br>EtOAc/n-Hexane |
| 1-6-16 | | MS (ESI, m/z): 333, 335 (M + H)+ | Column: SiO2<br>EtOAc/n-Hexane |

TABLE 7-continued

| Ref. Ex. | Strc. | P.D. | P.C. |
|---|---|---|---|
| 1-6-17 | | MS (ESI, m/z): 313, 315 (M + H)+ | Column: SiO2<br>EtOAc/n-Hexane |
| 1-6-18 | | MS (ESI, m/z): 333, 335 (M + H)+ | Column: SiO2<br>EtOAc/n-Hexane |
| 1-6-19 | | MS (ESI, m/z): 359, 361 (M + H)+ | Column: SiO2<br>EtOAc/n-Hexane |
| 1-6-20 | | MS (ESI, m/z): 414, 416 (M + H)+ | Column: SiO2<br>EtOAc/n-Hexane |

TABLE 8

| Ref. Ex. | Strc. | P.D. | P.C. |
|---|---|---|---|
| 1-6-21 | | $^1$H-NMR (CDCl$_3$) δ ppm: 1.40 (9H, s), 6.98 (1H, s), 7.21-7.28 (1H, m), 7.35-7.43 (2H, m), 7.45-7.51 (1H, m), 7.65-7.72 (3H, m), 7.82-7.86 (1H, m) | Column: SiO2<br>EtOAc/n-Hexane |
| 1-6-22 | | MS (ESI, m/z): 405, 407 (M + H)+ | Column: SiO2<br>EtOAc/n-Hexane |
| 1-6-23 | | MS (ESI, m/z): 371, 373 (M + H)+ | Column: SiO2<br>EtOAc/n-Hexane |

TABLE 8-continued

| Ref. Ex. | Strc. | P.D. | P.C. |
| --- | --- | --- | --- |
| 1-6-24 | | MS (ESI, m/z): 401, 403 (M + H)$^+$ | Column: SiO2<br>EtOAc/n-Hexane |
| 1-6-25 | | MS (ESI, m/z): 335, 337 (M + H)$^+$ | Column: SiO2<br>EtOAc/n-Hexane |
| 1-6-26 | | MS (ESI, m/z): 335, 337 (M + H)$^+$ | Column: SiO2<br>EtOAc/n-Hexane |
| 1-6-27 | | MS (ESI, m/z): 335, 337 (M + H)$^+$ | Column: SiO2<br>EtOAc/n-Hexane |
| 1-6-28 | | MS (ESI, m/z): 331, 333 (M + H)$^+$ | Column: SiO2<br>EtOAc/n-Hexane |
| 1-6-29 | | MS (ESI, m/z): 401, 403 (M + H)$^+$ | Column: SiO2<br>EtOAc/n-Hexane |
| 1-6-30 | | MS (ESI, m/z): 401, 403 (M + H)$^+$ | Column: SiO2<br>EtOAc/n-Hexane |

TABLE 9

| Ref. Ex. | Strc. | P.D. | P.C. |
| --- | --- | --- | --- |
| 1-6-31 | | MS (ESI, m/z): 347, 349 (M + H)$^+$ | Column: SiO2<br>EtOAc/n-Hexane |
| 1-6-32 | | MS (ESI, m/z): 347, 349 (M + H)$^+$ | Column: SiO2<br>EtOAc/n-Hexane |
| 1-6-33 | | MS (ESI, m/z): 351, 353 (M + H)$^+$ | Column: SiO2<br>EtOAc/n-Hexane |
| 1-6-34 | | MS (ESI, m/z): 351, 353 (M + H)$^+$ | Column: SiO2<br>EtOAc/n-Hexane |
| 1-6-35 | | MS (ESI, m/z): 323, 325 (M + H)$^+$ | Column: SiO2<br>EtOAc/n-Hexane |
| 1-6-36 | | MS (ESI, m/z): 300, 302 (M + H)$^+$ | Column: SiO2<br>EtOAc/n-Hexane |
| 1-6-37 | | MS (ESI, m/z): 389, 391 (M + H)$^+$ | Column: SiO2<br>EtOAc/n-Hexane |

TABLE 9-continued

| Ref. Ex. | Strc. | P.D. | P.C. |
| --- | --- | --- | --- |
| 1-6-38 | | MS (ESI, m/z): 353, 355 (M + H)+ | Column: SiO2 EtOAc/n-Hexane |
| 1-6-39 | | MS (ESI, m/z): 407, 409 (M + H)+ | Column: SiO2 EtOAc/n-Hexane |

TABLE 10

| Ref. Ex. | Strc. | P.D. | P.C. |
| --- | --- | --- | --- |
| 1-6-40 | | MS (ESI, m/z): 300, 302 (M + H)+ | Column: SiO2 EtOAc/n-Hexane |
| 1-6-41 | | MS (ESI, m/z): 300, 302 (M + H)+ | Filtration of the DCM suspension |
| 1-6-42 | | MS (ESI, m/z): 309, 311 (M + H)+ | Column: SiO2 EtOAc/n-Hexane |

TABLE 11

| Ref. Ex. | Strc. | P.D. | P.C. |
| --- | --- | --- | --- |
| 1-7-1 | | MS (ESI, m/z): 305, 307 (M + H)+ | Column: SiO2 EtOAc/n-Hexane |

TABLE 11-continued

| Ref. Ex. | Strc. | P.D. | P.C. |
| --- | --- | --- | --- |
| 1-7-2 | | MS (ESI, m/z): 305, 307 (M + H)+ | Column: SiO2 EtOAc/n-Hexane |
| 1-7-3 | | MS (ESI, m/z): 300, 302 (M + H)+ | Filtration of the DCM suspension. |
| 1-7-4 | | MS (ESI, m/z): 365, 367 (M + H)+ | Column: SiO2 EtOAc/n-Hexane |

TABLE 12

| Ref. Ex. | Strc. | P.D. | P.C. |
| --- | --- | --- | --- |
| 1-8-1 | | MS (ESI, m/z): 343, 345 (M + H)+ | Column: SiO2 EtOAc/n-Hexane |
| 1-8-2 | | MS (ESI, m/z): 449, 451 (M + H)+ | Column: SiO2 EtOAc/n-Hexane |

TABLE 12-continued

| Ref. Ex. | Strc. | P.D. | P.C. |
| --- | --- | --- | --- |
| 1-8-3 | | MS (ESI, m/z): 409, 411 (M + H)+ | Column: SiO2<br>EtOAc/n-Hexane |
| 1-8-4 | | MS (ESI, m/z): 344, 346 (M + H)+ | Column: SiO2<br>EtOAc/n-Hexane |

TABLE 13

| Ref. Ex. | Strc. | P.D. | P.C. |
| --- | --- | --- | --- |
| 1-8-5 | | MS (ESI, m/z): 379, 381 (M + H)+ | Column: SiO2<br>EtOAc/n-Hexane |

TABLE 13-continued

| Ref. Ex. | Strc. | P.D. | P.C. |
| --- | --- | --- | --- |
| 1-8-6 | | MS (ESI, m/z): 361, 363 (M + H)⁺ | Column: SiO2 EtOAc/n-Hexane |

TABLE 14

| Ref. Ex. | Strc. | P.D. | P.C. |
| --- | --- | --- | --- |
| 1-9-1 | | MS (ESI, m/z): 309 (M + H)⁺ | Without purification |

TABLE 15

| Ref. Ex. | Strc. | P.D. | P.C. |
| --- | --- | --- | --- |
| 1-9-2 | | MS (ESI, m/z): 345 (M + H)⁺ | Without purification |

TABLE 15-continued

| Ref. Ex. | Strc. | P.D. | P.C. |
|---|---|---|---|
| 1-9-3 | | MS (ESI, m/z): 327 (M + H)+ | Without purification |
| 1-10-1 | | MS (ESI, m/z): 375 (M + H)+ | Without purification |

TABLE 16

| Ref. Ex. | Strc. | P.D. | P.C. |
|---|---|---|---|
| 1-11-1 | | MS (ESI, m/z): 319 (M + H)+ | Collected by filtration |
| 1-11-2 | | MS (ESI, m/z): 301 (M + H)+ | Without purification |

TABLE 16-continued

| Ref. Ex. | Strc. | P.D. | P.C. |
|---|---|---|---|
| 1-11-3 | | MS (ESI, m/z): 335 (M + H)$^+$ | Without purification |
| 1-11-4 | | MS (ESI, m/z): 317 (M + H)$^+$ | Without purification |

TABLE 17

| Ref. Ex. | Strc. | P.D. | P.C. |
|---|---|---|---|
| 1-12-1 | | MS (ESI, m/z): 283 (M + H)$^+$ | Without purification |
| 1-12-2 | | MS (ESI, m/z): 279 (M + H)$^+$ | Without purification |
| 1-12-3 | | MS (ESI, m/z): 299 (M + H)$^+$ | Without purification |
| 1-12-4 | | MS (ESI, m/z): 349 (M + H)$^+$ | Without purification |

TABLE 17-continued

| Ref. Ex. | Strc. | P.D. | P.C. |
|---|---|---|---|
| 1-12-5 | | MS (ESI, m/z): 333 (M + H)$^+$ | Without purification |
| 1-12-6 | | MS (ESI, m/z): 301 (M + H)$^+$ | Without purification |

TABLE 18

| Ref. Ex. | Strc. | P.D. | P.C. |
|---|---|---|---|
| 1-13-1 | | MS (ESI, m/z): 301 (M + H)$^+$ | Collected by filtration |
| 1-13-2 | | MS (ESI, m/z): 367 (M + H)$^+$ | Without purification |
| 1-13-3 | | MS (ESI, m/z): 301 (M + H)$^+$ | Without purification |
| 1-13-4 | | MS (ESI, m/z): 301 (M + H)$^+$ | Without purification |
| 1-13-5 | | MS (ESI, m/z): 301 (M + H)$^+$ | Without purification |

TABLE 18-continued

| Ref. Ex. | Strc. | P.D. | P.C. |
| --- | --- | --- | --- |
| 1-13-6 | | MS (ESI, m/z): 297 (M + H)+ | Without purification |
| 1-13-7 | | MS (ESI, m/z): 367 (M + H)+ | Without purification |
| 1-13-8 | | MS (ESI, m/z): 367 (M + H)+ | Without purification |
| 1-13-9 | | MS (ESI, m/z): 313 (M + H)+ | Without purification |

TABLE 19

| Ref. Ex. | Strc. | P.D. | P.C. |
| --- | --- | --- | --- |
| 1-13-10 | | MS (ESI, m/z): 313 (M + H)+ | Without purification |
| 1-13-11 | | MS (ESI, m/z): 373 (M + H)+ | Without purification |

TABLE 19-continued

| Ref. Ex. | Strc. | P.D. | P.C. |
|---|---|---|---|
| 1-13-12 | | MS (ESI, m/z): 317 (M + H)+ | Without purification |
| 1-13-13 | | MS (ESI, m/z): 317 (M + H)+ | Without purification |
| 1-13-14 | | MS (ESI, m/z): 289 (M + H)+ | Without purification |
| 1-13-15 | | MS (ESI, m/z): 355 (M + H)+ | Without purification |
| 1-13-16 | | MS (ESI, m/z): 319 (M + H)+ | Without purification |
| 1-13-17 | | MS (ESI, m/z): 275 (M + H)+ | Without purification |

TABLE 20
| Ref. Ex. | Strc. | P.D. | P.C. |
|---|---|---|---|
| 1-14-1 | 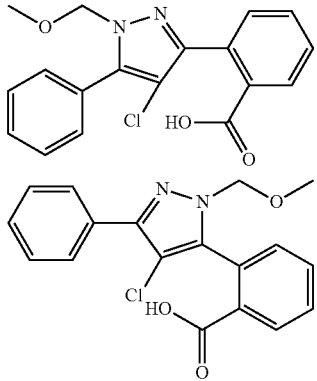 | MS (ESI, m/z): 343 (M + H)+ | Without purification |
| 1-14-2 | 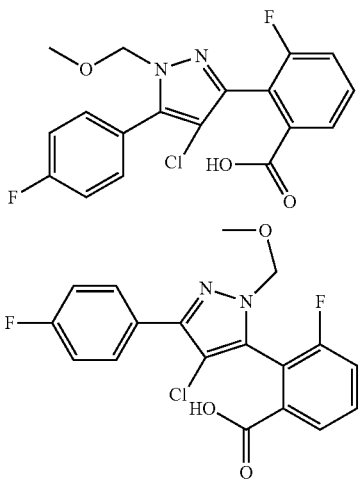 | MS (ESI, m/z): 379 (M + H)+ | Without purification |
| 1-15-1 | 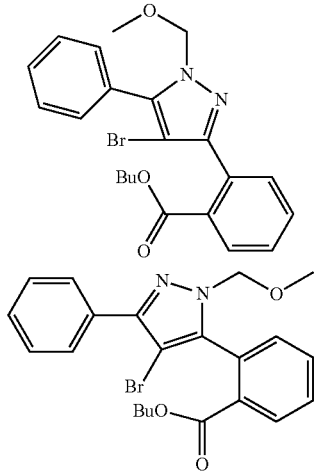 | MS (ESI, m/z): 443, 445 (M + H)+ | Column: SiO2 EtOAc/n-Hexane |

TABLE 20-continued
| Ref. Ex. | Strc. | P.D. | P.C. |
|---|---|---|---|
| 1-15-2 | 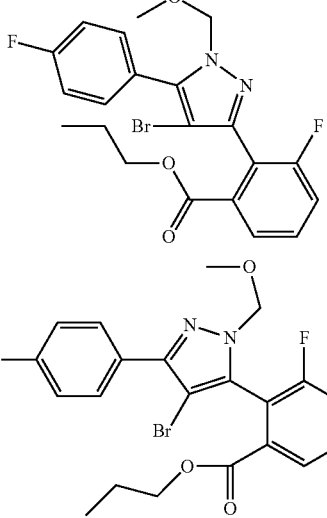 | MS (ESI, m/z): 465, 467 (M + H)+ | Without purification |
TABLE 21
| Ref. Ex. | Strc. | P.D. | P.C. |
|---|---|---|---|
| 1-16-1 | 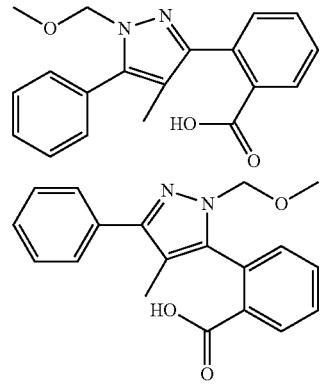 | MS (ESI, m/z): 323 (M + H)+ | Without purification |
| 1-16-2 | 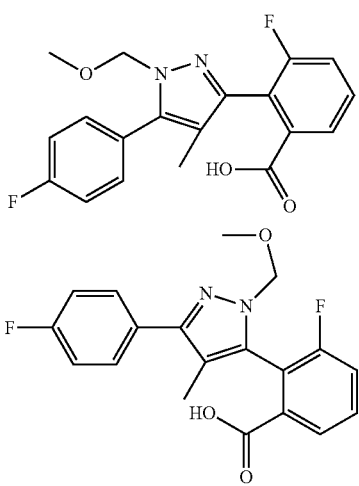 | MS (ESI, m/z): 359 (M + H)+ | Without purification |

TABLE 21-continued

| Ref. Ex. | Strc. | P.D. | P.C. |
|---|---|---|---|
| 1-17-1 | | MS (ESI, m/z): 335 (M + H)+ | Without purification |

TABLE 22

| Ref. Ex. | Strc. | P.D. | P.C. |
|---|---|---|---|
| 1-18-1 | | MS (ESI, m/z): 283 (M + H)+ | Without purification |
| 1-18-2 | | MS (ESI, m/z): 299 (M + H)+ | Without purification |
| 1-18-3 | | MS (ESI, m/z): 299 (M + H)+ | Without purification |
| 1-19-1 | | MS (ESI, m/z): 429 (M + H)+ | Column: SiO2 EtOAc/n-Hexane |

TABLE 23

| Ref. Ex. | Strc. | P.D. | P.C. |
|---|---|---|---|
| 1-20-1 | | MS (ESI, m/z): 352 (M + H)+ | Column: SiO2<br>EtOAc/MeOH |
| 1-21-1 | | MS (ESI, m/z): 401 (M + H)+ | Without purification |
| 1-22-1 | | ¹H-NMR (CDCl₃) δ ppm: 4.02-4.15 (4H, m), 5.82-5.85 (1H, s), 7.53 (1H, d, J = 8.4 Hz), 7.76-7.80 (1H, m), 7.92 (1H, d, J = 8.0 Hz, 10.36 (1H, s). | Column: SiO2<br>EtOAc/n-Hexane |

TABLE 24

| Ref. Ex. | Strc. | P.D. | P.C. |
|---|---|---|---|
| 1-23-1 | | MS (ESI, m/z): 341 (M + H)+ | Without purification |
| 1-24-1 | | MS (ESI, m/z): 361 (M + H)+ | Without purification |
| 1-25-1 | | MS (ESI, m/z): 264 (M − H)− | Without purification |
| 1-26-1 | | MS (ESI, m/z): 363 (M + H)+ | Collected by filtration |
| 1-27-1 | | MS (ESI, m/z): 282 (M + H)+ | Without purification |

REFERENCE EXAMPLE 2-1-1

(R)-2-Amino-3-(pyridin-2-yl)propionamide dihydrochloride

To a solution of (R)-2-tert-butoxycarbonylamino-3-(pyridin-2-yl)propionic acid (500 mg) in tetrahydrofuran (8 mL) was added carbonyldiimidazole (609 mg) at room temperature, and the mixture was stirred for 30 minutes. To the reaction mixture was added an aqueous solution of 28% ammonia (4 mL), and the mixture was stirred for 1 hour. The mixture was poured into water. The crude product was extracted with ethyl acetate. The extract was washed with water, and then was concentrated under reduced pressure. The residue was purified by silica gel column chromatography (eluent: ethyl acetate/methanol). The crude product was suspended in ethyl acetate, and the insoluble compound was collected by filtration to afford (R)-2-tert-butoxycarbonylamino-3-(pyridin-2-yl)propionamide (177 mg). To a suspension of the product (193 mg) in ethanol (3 mL) was added a solution of hydrogen chloride in ethyl acetate (4 mol/L, 3 mL) at room temperature. The mixture was stirred for 15 minutes, and to the mixture was added diisopropyl ether. The solvent was removed by decantation. The precipitate was washed with diisopropyl ether, and dried under reduced pressure to afford the title compound (173 mg). Structural formula, spectral data and purification condition are shown in Table 25.

REFERENCE EXAMPLE 2-1-2

Reference Example 2-1-2 was synthesized in a manner similar to that of Reference Example 2-1-1 by using the corresponding materials. Structural formula, spectral data and purification condition are shown in Table 25.

REFERENCE EXAMPLE 2-2-1

(2R)-2-Amino-N-methyl-3-(pyridin-2-yl)propionamide hydrochloride

To a suspension of (2R)-2-[(tert-butoxycarbonyl)amino]-3-(pyridin-2-yl)propionic acid (0.10 g) in N,N-dimethylformamide (1 mL) were added 1-hydroxybenzotriazole monohydrate (0.086 g), a solution of methylamine in tetrahydrofuran (2 mol/L, 0.9 mL) and 1-ethyl-3-(3-dimethylaminopropyl)carbodiimide hydrochloride (0.11 g), and the mixture was stirred at room temperature for 2 days. To the reaction mixture was added water, and the crude product was extracted with ethyl acetate. The organic layer was washed with brine, and dried over anhydrous magnesium sulfate. The solvent was removed under reduced pressure. The residue was purified by aminopropyl silica gel column chromatography (eluent: ethyl acetate/n-hexane) to afford N-[(1R)-1-(methylcarbamoyl)-2-(pyridin-2-yl)ethyl]carbamic acid tert-butyl ester (0.050 g). To a solution of the product (0.050 g) in methanol (2 mL) was added a solution of hydrogen chloride in 1,4-dioxane (4 mol/L, 2 mL), and the mixture was stirred at room temperature overnight. The precipitate was collected by filtration to afford the title compound (0.036 g). Structural formula, spectral data and purification condition are shown in Table 25.

REFERENCE EXAMPLE 2-2-2

Reference Example 2-2-2 was synthesized in a manner similar to that of Reference Example 2-2-1 by using the corresponding materials. Structural formula, spectral data and purification condition are shown in Table 25.

REFERENCE EXAMPLE 2-3-1

N-((2R)-2-Amino-3-phenylpropyl) phthalimide hydrochloride

To a solution of N-[(2R)-1-hydroxy-3-phenylpropan-2-yl] carbamic acid tert-butyl ester (0.10 g) in tetrahydrofuran (0.5 mL) were added phthalimide (0.065 g), triphenylphosphine (0.16 g) and a solution of azodicarboxylic acid diethyl ester in toluene (2.2 mol/L, 270 µL), and the mixture was stirred at room temperature for 1 hour. The reaction mixture was concentrated under reduced pressure, and the residue was purified by silica gel column chromatography (eluent: ethyl acetate/n-hexane) to afford N-[(2R)-1-(1,3-dioxo-2,3-dihydro-1H-isoindol-3-yl)-3-phenylpropan-2-yl]carbamic acid tert-butyl ester (0.115 g). To a solution of the product (0.115 g) in tetrahydrofuran (1 mL) was added a solution of hydrogen chloride in 1,4-dioxane (4 mol/L, 1 mL), and the mixture was stirred at room temperature overnight. The reaction mixture was concentrated under reduced pressure to afford the title compound (0.085 g). Structural formula, spectral data and purification condition are shown in Table 25.

REFERENCE EXAMPLES 2-3-2 TO 2-3-3

Reference Examples 2-3-2 to 2-3-3 were synthesized in a manner similar to that of Reference Example 2-3-1 by using the corresponding materials. Structural formula, spectral data and purification condition are shown in Table 25.

REFERENCE EXAMPLE 2-4-1

N-[6-(2-Aminoethyl)pyridin-2-yl]carbamic acid tert-butyl ester hydrochloride

To a solution of 6-{2-[(tert-butoxycarbonyl)amino] ethyl}pyridine-2-carboxylic acid (0.254 g) in tert-butyl alcohol (3 mL) were added triethylamine (0.065 g) and diphenylphosphoryl azide (0.34 g), and the mixture was stirred at 100° C. overnight. The reaction mixture was concentrated under reduced pressure, and the residue was purified by silica gel column chromatography (eluent: ethyl acetate/n-hexane) to afford N-(6-{2-[(tert-butoxycarbonyl)amino] ethyl}pyridin-2-yl)carbamic acid tert-butyl ester (0.30 g). To a solution of the product (0.30 g)tetrahydrofuran (2 mL) was added a solution of hydrogen chloride in 1,4-dioxane (4 mol/L, 2 mL), and the mixture was stirred at room temperature for 2 hours. The precipitate was collected by filtration to afford the title compound (0.19 g). Structural formula, spectral data and purification condition are shown in Table 26.

REFERENCE EXAMPLE 2-5-1

3-(tert-Butyldimethylsilyl)oxy-2-phenylpropylamine

To a solution of 2-phenylpropane-1,3-diol (556 mg) in tetrahydrofuran (20 mL) was added sodium hydride (60% dispersion in oil, 153 mg) at 0° C., and the mixture was stirred at room temperature for 20 minutes. To the mixture was added tert-butyldimethylchlorosilane (578 mg) at 0° C., and the mixture was stirred at room temperature for 16 hours. To the reaction mixture was added a saturated aqueous solution of sodium bicarbonate, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford 3-(tert-butyldimethylsilyloxy)-2-phenylpropan-1-ol (972 mg). To a solution of the product (972 mg) in tetrahydrofuran (20 mL) were added phthalimide (590 mg), triphenylphosphine (1.05 g) and a solution of azodicarboxylic acid diethyl ester in toluene (2.2 mol/L, 1.8 mL), and the mixture was stirred at room temperature for 16 hours. The mixture was concentrated under reduced pressure, and the residue was purified by silica gel column chromatography (eluent: ethyl acetate/n-hexane) to afford N-{3-[(tert-butyldimethylsilyl)oxy]-2-phenylpropyl}phthalimide (1.38 g). To a solution of the product (1.38 g) in ethanol (17 mL) was added hydrazine monohydrate (1.75 g), and the mixture was stirred at 80° C. for 2 hours. The insoluble compound was removed by filtration, and the filtrate was concentrated under reduced pressure. The residue was purified by aminopropyl silica gel column chromatography (eluent: ethyl acetate/n-hexane) to afford the title compound (791 mg). Structural formula, spectral data and purification condition are shown in Table 26.

REFERENCE EXAMPLE 2-5-2

Reference Example 2-5-2 was synthesized in a manner similar to that of Reference Example 2-5-1 by using the corresponding materials. Structural formula, spectral data and purification condition are shown in Table 26.

REFERENCE EXAMPLE 2-6-1

N-[2-(2-Aminoethyl)pyridin-3-yl]carbamic acid tert-butyl ester

To a solution of N-[2-(hydroxymethyl) pyridin-3-yl]carbamic acid tert-butyl ester (0.15 g) in dichloromethane (1 mL) was added thionyl chloride (0.096 g), and the mixture was stirred at room temperature for 1 hour. The reaction mixture was poured into a saturated aqueous solution of sodium bicarbonate, and the crude product was extracted with dichloromethane. The organic layer was washed with brine, and dried over anhydrous magnesium sulfate. The solvent was removed under reduced pressure, and the residue was purified by silica gel column chromatography (eluent: ethyl acetate/n-hexane) to afford N-[2-(chloromethyl)pyridin-3-yl]carbamic acid tert-butyl ester (0.12 g). A mixture of the product (0.12 g), dichloromethane (2 mL), potassium cyanide (0.039 g), tetrabutylammonium hydrogen sulfate (0.017 g) and water (0.5 mL) was stirred at room temperature for 3 hours. To the reaction mixture was added a saturated aqueous solution of sodium bicarbonate, and the crude product was extracted with ethyl acetate. The organic layer was washed with brine, and dried over anhydrous magnesian sulfate. The solvent was removed under reduced pressure, and the residue was purified by silica gel column chromatography (eluent: ethyl acetate/n-hexane) to afford N-[2-(chloromethyl)pyridin-3-yl]carbamic acid tert-butyl ester. To a mixture of the product in methanol (3 mL) and dichloromethane (3 mL) were added concentrated hydrochloric acid (0.072 g) and 10% palladium-carbon (50% wet, 0.03 g), and the mixture was stirred at room temperature overnight under a hydrogen atmosphere (0.32 MPa). The reaction mixture was filtered through a pad of celite, and the filtrate was concentrated under reduced pressure. The residue was purified by aminopropyl silica gel column chromatography (eluent: ethyl acetate/methanol) to afford the title compound (0.011 g). Structural formula, spectral data and purification condition are shown in Table 26.

REFERENCE EXAMPLE 2-7-1

(2R)-2-(Methylamino)-3-(pyridin-2-yl)propan-1-ol

To a solution of (2R)-2-amino-3-(pyridin-2-yl)propionic acid methyl ester (338 mg) and triethylamine (0.57 g) in dichloromethane (8 mL) was added 2-nitrobenzene-1-sulfonyl chloride (0.50 g) under ice-cooling, and the mixture was stirred at room temperature for 30 minutes. To the reaction mixture was added water, and the crude product was extracted with dichloromethane. The organic layer was washed with brine, and dried over anhydrous magnesium sulfate. The solvent was removed under reduced pressure. To a solution of the residue in N,N-dimethylformamide (5 mL) were added potassium carbonate (0.52 g) and iodomethane (0.80 g), and the mixture was stirred at room temperature for 4 hours. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (2R)-2-(N-methyl-2-nitrobenzenesulfonylamino)-3-(pyridin-2-yl)propionic acid methyl ester (0.32 g). A mixture of the product (0.24 g), thiophenol (77 mg), potassium carbonate (0.26 g) and acetonitrile (2 mL) was stirred at room temperature overnight. To the reaction mixture was added water, and the crude product was extracted with dichloromethane. The organic layer was washed with brine, and dried over anhydrous magnesium sulfate. The solvent was removed under reduced pressure, and the residue was purified by aminopropyl silica gel column chromatography (eluent: ethyl acetate/methanol) to afford (2R)-2-(methylamino)-3-(pyridin-2-yl)propionic acid methyl ester (0.11 g). To a solution of the product (0.10 g) in tetrahydrofuran (2 mL) was added lithium aluminium hydride (20 mg) at 0° C., and the mixture was stirred at the same temperature for 1 hour. To the reaction mixture was added water, and the mixture was filtered through a pad of celite. The filtrate was concentrated under reduced pressure. The residue was purified by aminopropyl silica gel column chromatography (eluent: ethyl acetate/methanol) to afford the title compound (0.046 g). Structural formula, spectral data and purification condition are shown in Table 26.

REFERENCE EXAMPLE 2-8-1

[(3,4-trans)-4-(Pyridin-2-y)pyrrolidine-3-yl]methanol

To a solution of (3,4-trans)-1-benzyl-4-(pyridin-2-yl)pyrrolidine-3-carboxylic acid ethyl ester (0.30 g) in tetrahydrofuran (3 mL) was added lithium aluminium hydride (36 mg) under ice-cooling, and the mixture was stirred at 0° C. for 1 hour. To the reaction mixture were added diethyl ether and water, and the mixture was filtered through a pad of celite. The filtrate was concentrated under reduced pressure to afford [(3,4-trans)-1-benzyl-4-(pyridin-2-yl)pyrrolidin-3-yl]methanol (0.26 g). To the product (0.10 g) were added ethanol (3 mL) and 10% palladium-carbon (50% wet, 0.02 g), and the mixture was stirred at room temperature overnight under a hydrogen atmosphere. The reaction mixture was filtered through a pad of celite, and the filtrate was concentrated under reduced pressure. The residue was purified by aminopropyl silica gel column chromatography (eluent: ethyl acetate/methanol) to afford the title compound (0.05 g). Structural formula, spectral data and purification condition are shown in Table 26.

REFERENCE EXAMPLE 2-9-1

4-(Benzyloxy)-1-(pyridin-2-yl)butan-2-amine

To a solution of 2-methylpyridine (0.93 g) in tetrahydrofuran (5 mL) was added a solution of n-butyllithium in n-hexane (2.6 mol/L, 4.0 mL) at −78° C., and the mixture was stirred at the same temperature for 10 Lutes and was stirred under ice-cooling for 0.5 hours. The reaction mixture was allowed to cool at −30° C. To the mixture was added dropwise a solution of 3-(benzyloxy)propanal (1.0 g) in tetrahydrofuran (2 mL), and the mixture was stirred at the same temperature for 10 minutes and was stirred under ice-cooling for 1 hour. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford 4-(benzyloxy)-1-(pyridin-2-yl)butan-2-ol (1.16 g). To a solution of the product (0.30 g) in tetrahydrofuran (2 mL) were added phthalimide (0.258 g), triphenylphosphine (0.459 g) and a solution of azodicarboxylic acid diethyl ester in toluene (2.2 mol/L, 800 µL), and the mixture was stirred at room temperature for 1 hour. The reaction mixture was concentrated under reduced pressure, and the residue was purified by silica gel column chromatography (eluent: ethyl acetate/n-hexane) to afford N-[4-(benzyloxy)-1-(pyridin-2-yl)butan-2-yl]phthalimide (0.45 g). To a solution of the product (0.45 g) in ethanol (3 mL) was added hydrazine monohydrate (0.58 g), and the mixture was stirred under reflux for 4 hours. The reaction mixture was allowed to cool to room temperature. To the mixture was added water, and the crude product was extracted with dichloromethane. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford the title compound (0.10 g). Structural formula, spectral data and purification condition are shown in Table 26.

REFERENCE EXAMPLE 2-10-1

(3R)-3-Amino-4-(pyridin-2-yl)butan-2-ol

To a solution of (2R)-2-[(tert-butoxycarbonyl)amino]-3-(pyridin-2-yl)propionic acid (0.500 g) in N,N-dimethylformamide (3.5 mL) were added N,O-dimethylhydroxylamine hydrochloride (0.238 g), 1-hydroxybenzotriazole monohydrate (0.374 g), 1-ethyl-3-(3-dimethylaminopropyl)carbodiimide hydrochloride (0.468 g) and triethylamine (0.950 g) under ice-cooling, and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford. N-[(1R)-1-(N-methoxy-N-methylcarbamoyl)-2-(pyridin-2-yl)ethyl]carbamic acid tert-butyl ester (0.432 g). To a solution of the product (0.432 g) in diethyl ether (14 mL) was added a solution of methyllithium in diethyl ether (1.13 mol/L, 1.6 mL) under ice-cooling, and the mixture was stirred at 0° C. for 1 hour. To the reaction mixture was added a saturated aqueous solution of ammonium chloride, and the crude product was extracted with ethyl acetate. The organic layer was washed with water and brine, and dried over anhydrous magnesium sulfate. The solvent was removed under reduced pressure, and the residue was purified by aminopropyl silica gel column chromatography (eluent: ethyl acetate/n-hexane) to afford N-[(2R)-3-oxo-1-(pyridin-2-yl)butan-2-yl]carbamic acid tert-butyl ester (0.261 g). To a solution of the product (0.261 g) in methanol (9 mL) was added sodium borohydride (0.045 g) under ice-cooling, and the mixture was stirred at room temperature overnight. To the reaction mixture was added a saturated aqueous solution of ammonium chloride, and the crude product was extracted with ethyl acetate. The organic layer was washed with water and brine, and dried over anhydrous magnesium sulfate. The solvent was removed under reduced pressure, and the residue was purified by silica gel column chromatography (eluent: methanol/ethyl acetate) to afford a mixture of diastereomers. The mixture was purified by preparative reverse phase liquid chromatography (Inertsil ODS-3, eluent: acetonitrile/water) to afford N-[(2R)-3-hydroxy-1-(pyridin-2-yl)butan-2-yl]carbamic acid tert-butyl ester (0.065 g) as a high polarity diastereomer. To a solution of the product (0.065 g) in 1,4-dioxane (3 mL) was added a solution of hydrogen chloride in 1,4-dioxane (4 mol/L, 0.2 mL), and the mixture was stirred 80° C. for 12 hours. The reaction mixture was concentrated under reduced pressure. The residue was purified by aminopropyl silica gel column chromatography (eluent: methanol/ethyl acetate) to afford the title compound (0.025 g). Structural formula, spectral data and purification condition are shown in Table 26.

REFERENCE EXAMPLE 2-10-2

Reference Example 2-10-2 was synthesized in a manner similar to that of Reference Example 2-10-1 by using the corresponding materials. Structural formula, spectral data and purification condition are shown in Table 26.

REFERENCE EXAMPLE 2-11-1

(3R)-3-Amino-4-(pyridin-2-yl)butan-2-ol hydrochloride

To a solution of (2R)-2-[(tert-butoxy carbonyl)amino]-3-(pyridin-2-yl)propionic acid (1.000 g) in N,N-dimethylformamide (10 mL) were added N,O-dimethylhydroxylamine hydrochloride (0.476 g), 1-hydroxybenzotriazole monohydrate (0.748 g), 1-ethyl-3-(3-dimethylaminopropyl)carbodiimide hydrochloride (0.936 g) and triethylamine (1.900 g) under ice-cooling, and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford N-[(1R)-1-(N-methoxy-N-methylcarbamoyl)-2-(pyridin-2-yl)ethyl]carbamic acid tert-butyl ester (0.563 g). To a solution of the product (0.563 g) in diethyl ether (14 mL) was added a solution of methylmagnesium bromide in diethyl ether (3.0 mol/L, 0.8 mL) under ice-cooling, and the mixture was stirred at 0° C. for 1 hour. To the reaction mixture was added a saturated aqueous solution of ammonium chloride, and the crude product was extracted with ethyl acetate. The organic layer was washed with water and brine, and dried over anhydrous magnesium sulfate. The solvent was removed under reduced pressure, and the residue was purified by aminopropyl silica gel column chromatography (eluent: ethyl acetate/n-hexane) to afford N-[(2R)-3-oxo-1-(pyridin-2-yl)butan-2-yl]carbamic acid tert-butyl ester (0.463 g). To a solution of the product (0.463 g) in tetrahydrofuran (5 mL) was added a solution of lithium tri(sec-butyl)borohydride in tetrahydrofuran (1.0 mol/L, 3.5 mL) at −78° C., and the mixture was stirred at the same temperature for 5 hours. To the reaction mixture was added a saturated aqueous solution of ammonium chloride, and the mixture was allowed to warm to room temperature. The crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford a mixture of diastereomers. The mixture was purified by preparative reverse phase liquid chromatography (Inertsil ODS-3, eluent: acetonitrile/water) to afford N-[(2R)-3-hydroxy-1-(pyridin-2-yl)butan-2-yl]carbamic acid tert-butyl ester (0.051 g) as a low polarity diastereomer. To a solution of the product (0.051 g) in 1,4-dioxane (3 mL) was added a solution of hydrogen chloride in 1,4-dioxane (4 mol/L, 0.3 mL), and the mixture was stirred at 80° C. for 12 hours. The reaction mixture was concentrated under reduced pressure, and the residue was washed with n-hexane to afford the title compound (0.046 g). Structural formula, spectral data and purification condition are shown in Table 27.

REFERENCE EXAMPLE 2-11-2

Reference Example 2-11-2 was synthesized in a manner similar to that of Reference Example 2-1.1-1 by using the corresponding materials. Structural formula, spectral data and purification condition are shown in Table 27.

REFERENCE EXAMPLE 2-12-1

(3R)-3-Amino-4-(pyridin-2-yl)butan-1-ol hydrochloride

To a solution of 3-(tert-butyldimethylsilyloxy)propanal (0.40 g) tetrahydrofuran (4 mL) were added (R)-2-methylpropane-2-sulfinamide (0.258 g) and tetraethyl orthotitanate (0.63 g), and the mixture was stirred at room temperature for 1 hour. To the reaction mixture was added brine, and the mixture was filtered through a pad of celite. The filtrate was concentrated under reduced pressure, and the residue was purified by silica gel column chromatography (eluent: ethyl acetate/n-hexane) to afford (R)-N-[(1E)-3-(tert-butyldimethylsilyloxy)propylidene]-2-methylpropane-2-sulfinamide (0.33 g). To a solution of 2-methylpyridine (0.14 g) in tetrahydrofuran (2 mL) was added a solution of n-butyllithium in n-hexane (2.6 mol/L, 0.96 mL) at −78° C., and the mixture was stirred at the same temperature for 10 minutes. To the mixture was added dropwise a solution of (R)-N-[(1E)-3-(tert-butyldimethylsilyloxy)propylidene]-2-methylpropane-2-sulfinamide (0.33 g) in tetrahydrofuran (2 mL), and the mixture was stirred at −78° C. for 0.5 hours. The reaction mixture was allowed to warm to room temperature. To the reaction mixture was added a saturated aqueous solution of ammonium chloride. The crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol). The crude product was purified by preparative reverse phase liquid chromatography (Capcell Pak C18 UG80, eluent: acetonitrile/water) to afford (R)-N-[(2R)-4-(tert-butyldimethylsilyloxy)-1-(pyridin-2-yl)butan-2-yl]-2-methylpropane-2-sulfinamide (0.174 g) as a high polarity product and (R)-N-[(2S)-4-(tert-butyldimethylsilyloxy)-1-(pyridin-2-yl)butan-2-yl]-2-methylpropane-2-sulfinamide (0.060 g) as a low polarity product. To a solution of (R)-N-[(2R)-4-(tert-butyldimethylsilyloxy)-1-(pyridin-2-yl)butan-2-yl]-2-methylpropane-2-sulfinamide (0.174 g) in methanol (1 mL) was added a solution of hydrogen chloride in 1,4-dioxane (4 mol/L, 1 mL), and the mixture was stirred at room temperature for 2 hours. The precipitate was collected by filtration to afford the title compound (0.098 g). Structural formula, spectral data and purification condition are shown in Table 28.

REFERENCE EXAMPLES 2-12-2 TO 2-12-30

Reference Examples 2-12-2 to 2-12-30 were synthesized in a manner similar to that of Reference Example 2-12-1 by using the corresponding materials. Structural formula, spectral data and purification condition are shown in Table 28 to Table 31.

REFERENCE EXAMPLE 2-13-1

4-(tert-Butyldimethylsilyloxy)-2-(pyridin-2-yl)butylamine

To a solution of 2-(pyridin-2-yl)acetic acid ethyl ester (0.50 g) in N,N-dimethylformamide (8 mL) were added potassium tert-butoxide (0.50 and 2-bromoethyl (tert-butyldimethylsilyl)ether (0.79 g) under ice-cooling, and the mixture was stirred at room temperature for 2 hours. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford 4-(tert-butyldimethylsilyloxy)-2-(pyridin-2-yl)butanoic acid ethyl ester (0.94 g). To a solution of lithium aluminium hydride (0.22 g) in tetrahydrofuran (5 mL) was added dropwise a solution of 4-(tert-butyldimethylsilyloxy)-2-(pyridin-2-yl)butanoic acid ethyl ester (0.94 g) in tetrahydrofuran (5 mL) under ice-cooling, and the mixture was stirred at 0° C. for 1 hour. The reaction mixture was diluted with diethyl ether. To the mixture was added water, and the mixture was filtered through a pad of celite. The filtrate was concentrated under reduced pressure, and the residue was purified by aminopropyl silica gel column chromatography (eluent: ethyl acetate/n-hexane) to afford 4-(tert-butyldimethylsilyloxy)-2-(pyridin-2-yl)butan-1-ol (0.37 g). To a solution of the product (0.16 g) in tetrahydrofuran (2 mL) were added phthalimide (0.12 g), triphenylphosphine (0.22 g) and a solution of azodicarboxylic acid diethyl ester in toluene (2.2 mol/L, 420 µL), and the mixture was stirred at room temperature for 1 hour. The reaction mixture was concentrated under reduced pressure, and the residue was purified by silica gel column chromatography (eluent: ethyl acetate/n-hexane) to afford N-{4-(tert-butyldimethylsilyloxy)-2-(pyridin-2-yl)butyl}phthalimide (0.22 g). To a solution of the product (0.22 g) in methanol (3 mL) was added hydrazine monohydrate (0.28 g), and the mixture was stirred under reflux for 2 hours. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol) to afford the title compound (0.10 g). Structural formula, spectral data and purification condition are shown in Table 32.

REFERENCE EXAMPLE 2-14-1

(R)-3-Amino-4-phenylbutyramide hydrochloride

To a solution of N-[(2R)-1-carbamoyl-3-phenylpropan-2-yl]carbamic acid tert-butyl ester (0.100 g) in 1,4-dioxane (2 mL) was added a solution of hydrogen chloride in 1,4-dioxane (4 mol/L, 2 mL), and the mixture was stirred at room temperature for 5 hours. The reaction mixture was concentrated, and the residue was washed with n-hexane to afford the title compound (0.076 g). Structural formula, spectral data and purification condition are shown in Table 32.

REFERENCE EXAMPLE 2-15-1

(3S)-3-Amino-4-(pyridin-2-yl)butan-1-ol hydrochloride

To a solution of 3-(tert-butyldimethylsilyloxy)propanal (0.30 g) in tetrahydrofuran (4 mL) were added (S)-2-methylpropane-2-sulfinamide (0.19 g) and tetraethyl orthotitanate (0.47 g), and the mixture was stirred at room temperature for 1 hour. To the reaction mixture was added brine, and the mixture was filtered through a pad of celite. The filtrate was concentrated under reduced pressure. The residue was purified by silica gel column chromatography (eluent: ethyl acetate/n-hexane) to afford (S)-N-[(1E)-3-(tert-butyldimethylsilyloxy)propylidene]-2-methylpropane-2-sulfinamide (0.30 g). To a solution of 2-methylpyridine (0.14 g) in tetrahydrofuran (2 mL) was added a solution of n-butyllithium in n-hexane (2.6 mol/L, 0.96 mL) at −78° C., and the mixture was stirred at the same temperature for 10 minutes. To the mixture was added dropwise a solution of (S)-N-[(1E)-3-(tert-butyldimethylsilyloxy)propylidene]-2-methylpropane-2-sulfinamide (0.30 g) in tetrahydrofuran (2 mL), and the mixture was stirred at −78° C. for 0.5 hours. The reaction mixture was allowed to warm to room temperature. To the reaction mixture was added a saturated aqueous solution of ammonium chloride. The crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol). The crude product was purified by preparative reverse phase liquid chromatography (Capcell Pak C18 UG80, eluent: acetonitrile/water) to afford (S)-N-[(2S)-4-(tert-butyldimethylsilyloxy)-1-(pyridin-2-yl)butan-2-yl]-2-methylpropane-2-sulfinamide (0.08 g) as a high polarity product and (S)-N-[(2R)-4-tert-butyldimethylsilyoxy-1-(pyridin-2-yl)butan-2-yl]-2-methylpropane-2-sulfinamide (0.030 g) as a low polarity product. To a solution of (S)-N-[(2S)-4-(tert-butyldimethylsilyloxy)-1-(pyridin-2-yl)butan-2-yl]-2-methylpropane-2-sulfinamide (0.08 g) in methanol (1 mL) was added a solution of hydrogen chloride in 1,4-dioxane (4 mol/L, 1 mL), and the mixture was stirred at the same temperature for 1 hour. The precipitate was collected by filtration to afford the title compound (0.045 g). Structural formula, spectral data and purification condition are shown in Table 32.

REFERENCE EXAMPLES 2-15-2 TO 2-15-3

Reference Examples 2-15-2 to 2-15-3 were synthesized in a manner similar to that of Reference Example 2-15-1 by using the corresponding materials. Structural formula, spectral data and purification condition are shown in Table 32.

REFERENCE EXAMPLE 2-16-1

(3R)-3-Amino-4-(6-aminopyridin-2-yl)butan-1-ol

To a solution of 3-(tert-butyldimethylsilyloxy)propanal (0.40 g) in tetrahydrofuran (4 mL) were added (R)-2-methylpropane-2-sulfinamide (0.258 g) and tetraethyl orthotitanate (0.63 g), and the mixture was stirred at room temperature for 1 hour. To the reaction mixture was added brine, and the mixture was filtered through a pad of celite. The solvent of the filtrate was removed under reduced pressure, and the residue was purified by silica gel column chromatography (eluent: ethyl acetate/n-hexane) to afford (R)-N-[(1E)-3-(tert-butyldimethylsilyloxy)propylidene]2-methylpropane-2-sulfinamide (0.33 g). To a solution of 2-azido-6-methylpyridine (0.14 g) in tetrahydrofuran (2 mL) was added a solution of n-butyllithium in n-hexane (2.6 mol/L, 0.65 mL) at −78° C., and the mixture was stirred at the same temperature for 10 minutes. To the mixture was added dropwise a solution of (R)-N-[(1E)-3-(tert-butyldimethylsilyloxy)propylidene]-2-methylpropane-2-sulfinamide (0.20 g) tetrahydrofuran (2 mL), and the mixture was stirred at −78° C. for 0.5 hours. The reaction mixture was allowed to warm to room temperature. To the reaction mixture was added a saturated aqueous solution of ammonium chloride. The crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol). The crude product was purified by preparative reverse phase liquid chromatography (Capcell Pak C18 UG80, eluent: acetonitrile/water) to afford (R)-N-[(2R)-1-(6-azidopyridin-2-yl)-4-(tert-butyldimethylsilyloxy)butan-2-yl]-2-methylpropane-2-sulfinamide (0.11 g). A mixture of the product (0.11 g), tetrahydrofuran (1 mL), water (0.3 mL) and triphenylphosphine (0.27 g) was stirred at 90° C. overnight. The reaction mixture was allowed to cool to room temperature, and then the solvent was removed under reduced pressure. The residue was purified by silica gel column chromatography (eluent: ethyl acetate/n-hexane) to afford (R)-N-[(2R)-1-(6-aminopyridin-2-yl)-4-(tert-butyldimethylsilyloxy)butan-2-yl]-2-methylpropane-2-sulfinamide. To a solution of the product in methanol (1 mL) was added a solution of hydrogen chloride in 1,4-dioxane (4 mol/L, 1 mL), and the mixture was stirred at room temperature for 2 hours. The solvent was removed under reduced pressure. The residue was purified by aminopropyl silica gel column chromatography (eluent: ethyl acetate/methanol) to afford the title compound (0.046 g). Structural formula, spectral data and purification condition are shown in Table 33.

REFERENCE EXAMPLE 2-17-1

(4S)-4-Amino-5-(pyridin-2-yl)pentan-1-ol

To a solution of (2R)-2-[(tert-butoxycarbonyl)amino]-(pyridin-2-yl)propionic acid (1.000 g) N,N-dimethylformamide (10 mL) were added N,O-dimethylhydroxylamine hydrochloride (0.476 g). 1-hydroxybenzotriazole monohydrate (0.748 g), 1-ethyl-3-(3-dimethylaminopropyl)carbodiimide hydrochloride (0.936 g) and triethylamine (1.900 g) under ice-cooling, and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford N-[(1R)-1-(N-methoxy-N-methylcarbamoyl)-2-(pyridin-2-yl)ethyl]carbamic acid tert-butyl ester (0.959 g). To a solution of the product (0.158 g) in dichloromethane (4 mL) was added a solution of diisobutylaluminium hydride in n-hexane (095 mol/L, 0.7 mL) at −78° C., and the mixture was stirred at the same temperature for 2 hours. To the reaction mixture was added an aqueous solution of potassium sodium tartrate, and the mixture was allowed to warm to room temperature. The mixture was stirred for 30 minutes. The crude product was extracted with ethyl acetate. The organic layer was washed with brine, and dried over anhydrous magnesium sulfate. The solvent was removed under reduced pressure, and the residue was dissolved in dichloromethane (1 mL). To the solution was added (carbethoxymethylene)triphenylphosphorane (0.214 g) under ice-cooling, and the mixture was stirred at room temperature for 5 hours. The solvent was removed under reduced pressure, and the residue was purified by silica gel column chromatography (eluent: n-hexane/ethyl acetate) to afford (2E,4R)-4-[(tert-butoxycarbonyl)amino]-5-(pyridin-2-yl)pent-2-enoic acid ethyl ester (0.101 g). To a solution of the product (0.101 g) in methanol (1.5 mL) was added 10% palladium-carbon (50% wet, 100 mg) under ice-cooling, and the mixture was stirred at room temperature under a hydrogen atmosphere overnight. The reaction mixture was filtered through a pad of celite, and the filtrate was concentrated under reduced pressure. The residue was purified by silica gel column chromatography (eluent: ethyl acetate/n-hexane) to afford (4S)-4-[(tert-butoxycarbonyl)amino]-5-(pyridin-2-yl)pentanoic acid ethyl ester (0.088 g). To a solution of the product (0.088 g) in tetrahydrofuran (1.5 mL) was added lithium aluminium hydride (0.026 g) under ice-cooling, and the mixture was stirred at 0° C. for 1 hour. To the reaction mixture were added water and diethyl ether, and the mixture was stirred for 30 minutes. The reaction mixture was filtered through a pad of celite, and the filtrate was concentrated under reduced pressure. The residue was purified by silica gel column chromatography (eluent: ethyl acetate/methanol) to afford N-[(2S)-5-hydroxy-1-(pyridin-2-yl)pentan-2-yl] carbamic acid tert-butyl ester (0.047 g). To a solution of the product (0.047 g) in 1,4-dioxane (3 mL) was added a solution of hydrogen chloride in 1,4-dioxane (4 mol/L, 0.5 mL), and the mixture was stirred at room temperature overnight. The reaction mixture was concentrated under reduced pressure, and the residue was purified by aminopropyl silica gel column chromatography (eluent: methanol/ethyl acetate) to afford the title compound (0.023 g). Structural formula, spectral data and purification condition are shown in Table 33.

REFERENCE EXAMPLE 2-18-1

(2R)-2-Amino-3-(pyridin-2-yl)butan-1-ol hydrochloride

To a solution of 2-ethylpyridine (0.309 g) in tetrahydrofuran (3 mL) was added a solution of n-butyllithium in n-hexane (2.6 mol/L, 1 mL) at −78° C. and the mixture was stirred at the same temperature for 30 minutes. To the mixture was added a solution of (R)-N-[(E)-2-(tert-butyldimethylsilyloxy)ethylidene]-2-methylpropane-2-sulfinamide (0.500 g) in tetrahydrofuran (3 mL) at the same temperature, and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of diastereomers. The mixture was purified by preparative reverse phase liquid chromatography (Inertsil ODS-3, eluent: acetonitrile/water) to afford (R)-N-[(2R)-1-(tert-butyldimethylsilyloxy)-3-(pyridin-2-yl)butan-2-yl]-2-methylpropane-2-sulfinamide (0.162 g) as a high polarity diastereomer. To a solution of the product (0.056 g) in 1,4-dioxane (1 mL) was added a solution of hydrogen chloride in 1,4-dioxane (4 mol/L, 1 mL), and the mixture was stirred at room temperature for 5 hours. The reaction mixture was concentrated under reduced pressure, and the residue was washed with n-hexane to afford the title compound (0.022 g). Structural formula, spectral data and purification condition are shown in Table 33.

REFERENCE EXAMPLES 2-18-2 TO 2-18-3

Reference Examples 2-18-2 to 2-18-3 were synthesized in a manner similar to that of Reference Example 2-18-1 by using the corresponding materials. Structural formula, spectral data and purification condition are shown in Table 33.

REFERENCE EXAMPLE 2-19-1

(4S)-4-Amino-3-(pyridin-2-yl)pentan-1-ol hydrochloride

To a solution of 2-(pyridin-2-yl)acetic acid methyl ester (0.46 g) in N,N-dimethylformamide (8 mL) were added potassium tert-butoxide (0.41 g) and 2-bromoethyl (tert-butyldimethylsilyl)ether (0.79 g) under ice-cooling, and the mixture was stirred at room temperature for 1 hour. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford 4-(tert-butyldimethylsilyloxy)-2-(pyridin-2-yl)butanoic acid methyl ester (0.94 g). To a solution of the product (0.40 g) in methanol (5 mL) was added an aqueous solution of sodium hydroxide (2 mol/L, 1.3 mL), and the mixture was stirred at room temperature overnight. The reaction mixture was neutralized by adding hydrochloric acid (2 mol/L, 1.30 mL). To the mixture were added N,O-dimethylhydroxylamine hydrochloride (0.19 g), triethylamine (0.39 g) and 4-(4,6-dimethoxy-1,3,5-triazin-2-yl)-4-methylmorpholinium chloride n-hydrate (0.54 g), and the mixture was stirred at room temperature for 5 hours. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford 4-(tert-butyldimethylsilyloxy)-N-methoxy-N-methyl-2-(pyridin-2-yl)butyramide (0.33 g). To a solution of the product (0.10 g) in tetrahydrofuran (1.5 mL) was added a solution of methylmagnesium bromide in tetrahydrofuran (1 mol/L, 600 μL) under ice-cooling, and the mixture was stirred at 0° C. for 1 hour. To the reaction mixture were added hydrochloric acid (1 mol/L) and water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford 5-(tert-butyldimethylsilyloxy)-3-(pyridin-2-yl)pentan-2-one (0.05 g). To a solution of the product (0.05 g) in tetrahydrofuran (2 mL) were added (S)-2-methylpropane-2-sulfinamide (0.023 g) and tetraethyl orthotitanate (0.077 g), and the mixture was stirred at 70° C. overnight. The reaction mixture was allowed to cool to 0° C., to the reaction mixture were added sodium borohydride (5 mg) and water (0.2 mL), and the mixture was stirred at the same temperature for 2 hours. The reaction mixture was quenched with acetone. To the mixture was added brine, and the mixture was filtered through a pad of celite. The filtrate was concentrated under reduced pressure, and the residue was purified by silica gel column chromatography (eluent: ethyl acetate/methanol) to afford (S)-N-[(2S)-5-(tert-butyldimethylsilyloxy)-3-(pyridin-2-yl)pentan-2-yl]-2-methylpropane-2-sulfinamide (21 mg) as a low polarity product and (S)-N-[(2R)-5-(tert-butyldimethylsilyloxy)-3-(pyridin-2-yl)pentan-2-yl]-2-methylpropane-2-sulfinamide (16 mg) as a high polarity product. To a solution of (S)-N-[(2S)-5-(tert-butyldimethylsilyloxy)-3-(pyridin-2-yl)pentan-2-yl]-2-methylpropane-2-sulfinamide (21 mg) in methanol (0.5 mL) was added a solution of hydrogen chloride in 1,4-dioxane (4 mol/L, 0.5 mL), and the mixture was stirred at room temperature overnight. The reaction mixture was concentrated under reduced pressure to afford the title compound (13 mg). Structural formula, spectral data and purification condition are shown in Table 33.

REFERENCE EXAMPLE 2-19-2

Reference Example 2-19-2 was synthesized in a manner similar to that of Reference Example 2-19-1 by using the corresponding materials. Structural formula, spectral data and purification condition are shown in Table 33.

REFERENCE EXAMPLE 2-20-1

(4R)-4-Amino-2-methyl-5-(pyridin-2-yl)pentan-2-ol dihydrochloride

To a solution of (S)-3-hydroxybutanoic acid methyl ester (2.000 g) in N,N-dimethylformamide (40 mL) was added imidazole (1.383 g) and tert-butyldimethylchlorosilane (3.062 g) under ice-cooling, and the mixture was stirred at room temperature for 3 hours. To the reaction mixture was added ice, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane) to afford (3S)-3-(tert-butyldimethylsilyloxy)butanoic acid methyl ester (3.934 g). To a solution of the product (3.934 g) in diethyl ether (60 mL) was added a solution of diisobutylaluminium hydride in n-hexane (1.02 mol/L, mL) at −78° C., and the mixture was stirred at the same temperature for 2 hours. To the reaction mixture was added an aqueous solution of potassium sodium tartrate, and the mixture was allowed to warm to room temperature. The mixture was stirred for 30 minutes. The crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (3S)-3-(tert-butyldimethylsilyloxy)butanal (3.076 g). To a solution of the product (1.600 g) in tetrahydrofuran (20 mL) were added (R)-(+)-2-methylpropane-2-sulfinamide (1.246 g) and tetraethyl orthotitanate (2.886 g), and the mixture was stirred at room temperature overnight. To the reaction mixture was added brine. The mixture was diluted with ethyl acetate, and then filtered through a pad of celite. The filtrate was concentrated under reduced pressure, and the residue was purified by silica gel column chromatography (eluent: ethyl acetate/n-hexane) to afford (R)-N-[(1E,3S)-3-(tert-butyldimethylsilyloxy)butylidene]-2-methylpropane-2-sulfinamide (2.050 g). To a solution of 2-methylpyridine (0.572 g) in tetrahydrofuran (3 mL) was added a solution of n-butyllithium in n-hexane (2.6 mol/L, 2.2 mL) at −78° C., and the mixture was stirred at the same temperature for 30 minutes. To the mixture was added a solution of (R)-N-[(1E,3S)-3-(tert-butyldimethylsilyloxy)butylidene]-2-methylpropane-2-sulfinamide (1.250 g) in tetrahydrofuran (3 mL) at the same temperature, and the mixture was further stirred at the same temperature for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (R)-N-[(2R,4S)-4-tert-butyldimethylsilyloxy)-1-(pyridin-2-yl)pentan-2-yl]-2-methylpropane-2-sulfinamide (0.639 g) as a high polarity diastereomer. To a solution of the product (0.400 g) in tetrahydrofuran (6 mL) was added a solution of tetra-n-butylammonium fluoride in tetrahydrofuran (1 mol/L, 2 mL) under ice-cooling, and the mixture was stirred at the same temperature for 30 minutes. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford (R)-N-[(2R,4S)-4-hydroxy-1-(pyridin-2-yl)pentan-2-yl]-2-methylpropane-2-sulfinamide (0.284 g). To a solution of the product (0.284 g) in dichloromethane (10 mL) was added Dess-Martin periodinane (0.509 g) under ice-cooling, and the mixture was stirred at room temperature for 4 hours. To the reaction mixture were added 10% aqueous sodium sulfite solution and a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford (R)-2-methyl-N-[(2R)-4-oxo-1-(pyridin-2-yl)pentan-2-yl]propane-2-sulfinamide (0.201 g). To a solution of the product (0.201 g) in tetrahydrofuran (3 mL) was added a solution of methylmagnesium bromide in diethyl ether (3.0 mol/L, 0.91 mL) under ice-cooling, and the mixture was stirred at the same temperature for 7 hours. To the reaction mixture was added a saturated aqueous solution of ammonium chloride, and the crude product was extracted with ethyl acetate. The organic layer was washed with water and brine, and dried over anhydrous magnesium sulfate. The solvent was removed under reduced pressure, and the residue was purified by silica gel column chromatography (eluent: methanol/ethyl acetate) to afford (R)-N-[(2R)-4-hydroxy-4-methyl-1-(pyridin-2-yl)pentan-2-yl]-2-methylpropane-2-sulfinamide (0.015 g). To a solution of the product (0.015 g) in 1,4-dioxane (0.5 mL) was added a solution of hydrogen chloride in 1,4-dioxane (4 mol/L, 0.5 mL), and the mixture was stirred at room temperature for 5 hours. The reaction mixture was concentrated under reduced pressure, and the residue was washed with n-hexane to afford the title compound (0.015 g). Structural formula, spectral data and purification condition are shown in Table 33.

REFERENCE EXAMPLE 2-21-1

(2R)-4-Methoxy-1-(pyridin-2-yl)butan-2-amine hydrochloride

To a solution of 3-(tert-butyldimethylsilyloxy)propanal (0.40 g) in tetrahydrofuran (4 mL) were added (R)-2-methylpropane-2-sulfinamide (0.258 g) and tetraethyl orthotitanate (0.63 g), and the mixture was stirred at room temperature for 1 hour. To the reaction mixture was added brine, and the mixture was filtered through a pad of celite. The solvent of the filtrate was removed under reduced pressure, and the residue was purified by silica gel column chromatography (eluent: ethyl acetate/n-hexane) to afford (R)-N-[(1E)-3-(tert-butyldimethylsilyloxy)propylidene]-2-methylpropane-2-sulfinamide (0.33 g). To a solution of 2-methylpyridine (0.14 g) in tetrahydrofuran (2 mL) was added a solution of n-butyllithium in n-hexane (2.6 mol/L, 0.96 mL) at −78° C., and the mixture was stirred at the same temperature for 10 minutes. To the mixture was added dropwise a solution of (R)-N-[(1E)-3-(tert-butyldimethylsilyloxy)propylidene]-2-methylpropane-2-sulfinamide (0.33 g) in tetrahydrofuran (2 mL), and the mixture was stirred at −78° C. for 0.5 hours. The reaction mixture was allowed to warm to room temperature. To the reaction mixture was added a saturated aqueous solution of ammonium chloride. The crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol). The crude product was purified by preparative reverse phase liquid chromatography (Capcell Pak C18 UG80, eluent: acetonitrile/water) to afford (R)-N-[(2R)-4-(tert-butyldimethylsilyloxy)-1-(pyridin-2-yl)butan-2-yl]-2-methylpropane-2-sulfinamide (0.174 g) as a high polarity product. To a solution of the product (0.15 g) in tetrahydrofuran (1 mL) was added a solution of tetra-n-butylammonium fluoride in tetrahydrofuran (1 mol/L, 580 μL), and the mixture was stirred at room temperature for 30 minutes. The reaction mixture was concentrated under reduced pressure, and the residue was purified by silica gel column chromatography (eluent:ethyl acetate/methanol) to afford (R)-N-[(2R)-4-hydroxy-1-(pyridin-2-yl)butan-2-yl]-2-methylpropane-2-sulfinamide (0.093 g). To a solution of the product (0.093 g) in tetrahydrofuran (1 mL) were added sodium hydride (60% dispersion in oil, 16 mg) and iodomethane (0.27 g) under ice-cooling, and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure. To the residue were added methanol (1 mL) and a solution of hydrogen chloride in 1,4-dioxane (4 mol/L, 1 mL), and the mixture was stirred at room temperature for 2 hours. The reaction mixture was concentrated under reduced pressure to afford the title compound (0.036 g). Structural formula, spectral data and purification condition are shown in Table 34.

REFERENCE EXAMPLE 2-21-2

Reference Example 2-21-2 was synthesized in a manner similar to that of Reference Example 2-21-1 by using the corresponding materials. Structural formula, spectral data and purification condition are shown in Table 34.

REFERENCE EXAMPLE 2-22-1

(R)-4-(tert-Butyldimethylsilyloxy)-1-(pyridin-2-yl)butan-2-amine

To a solution of (3R)-3-amino-4-(pyridin-2-yl)butan-1-ol hydrochloride (40 mg) in dichloromethane (1 ml) were added N,N-diisopropylethylamine (87 mg) and tert-butyldimethylchlorosilane (30 mg), and the mixture was stirred at room temperature for 1 hour. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford the title compound (47 mg). Structural formula, spectral data and purification condition are shown in Table 34.

REFERENCE EXAMPLES 2-22-2 TO 2-22-5

Reference Examples 2-22-2 to 2-22-5 were synthesized in a manner similar to that of Reference Example 2-22-1 by using the corresponding materials. Structural formula, spectral data and purification condition are shown in Table 34.

REFERENCE EXAMPLE 2-23-1

(2R)-2-Amino-3-(pyrimidin-2-yl)propan-1-ol hydrochloride

A suspension of (2S)-2-[(tert-butoxycarbonyl)amino]-3-iodopropionic acid methyl ester (613 mg), zinc (268 mg) in N,N-dimethylformamide (10 mL) was stirred at room temperature under an argon atmosphere for 2 hours. To the mixture were added 2-bromopyrimidine (296 mg) and bis(triphenylphosphine)palladium (II) dichloride (131 mg), and the mixture was stirred at room temperature for 4 hours. To the mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford (2R)-2-[(tert-butoxycarbonyl)amino]-3-(pyrimidin-2-yl)propionic acid methyl ester (310 mg). To a mixture of the product (310 mg), ethanol (3 mL) and water (3 mL) was added sodium borohydride (104 mg) at 0° C., and the mixture was stirred at room temperature for 12 hours. To the reaction mixture was added a saturated aqueous solution of sodium bicarbonate, and the crude product was extracted with ethyl acetate. The extract was washed with brine, and dried over sodium sulfate. The solvent was removed under reduced pressure. To a solution of the residue in methanol (3 mL) was added a solution of hydrogen chloride in 1,4-dioxane (4 mol/L, 3 mL), and the mixture was stirred at room temperature for 1 hour. The solvent was removed under reduced pressure to afford the title compound (84 mg). Structural formula, spectral data and purification condition are shown in Table 35.

REFERENCE EXAMPLES 2-23-2 TO 2-23-16

Reference Examples 2-23-2 to 2-23-16 were synthesized in a manner similar to that of Reference Example 2-23-1 by using the corresponding materials. Structural formula, spectral data and purification condition are shown in Table 35 to Table 36.

REFERENCE EXAMPLE 2-24-1

(2S,3R)-3-Amino-4-(pyrimidin-2-yl)butane-1,2-diol hydrochloride

To a mixture of N-{(1R)-1-[(4S)-2,2-dimethyl-1,3-dioxolan-4-yl]-2-hydroxyethyl}carbamic acid tert-butyl ester (1.25 g), imidazole (521 mg), triphenylphosphine (2.01 g) and tetrahydrofuran (10 mL) was added iodine (1.7 g) at 0° C., and the mixture was stirred at room temperature for 2 hours. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford N-{(1S)-1-[(4S)-2,2-dimethyl-1,3-dioxolan-4-yl]-2-iodoethyl}carbamic acid tert-butyl ester (1.45 g). A mixture of the product (1.45 g), zinc (562 mg) in N,N-dimethylformamide (5 mL) was stirred at room temperature under an argon atmosphere for 2 hours. To the mixture were added 2-bromopyrimidine (621 mg) and bis(triphenylphosphine)palladium(II)dichloride (274 mg), and the mixture was stirred at room temperature for 4 hours. To the mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford N-{(1R)-1-[(4S)-2,2-dimethyl-1,3-dioxolan-4-yl]-2-(pyrimidin-2-yl)ethyl}carbamic acid tert-butyl ester (928 mg). A mixture of the product (150 mg), 1,4-dioxane (1 mL) and a solution of hydrogen chloride in 1,4-dioxane (4 mol/L, 1 mL) was stirred at room temperature for 1 hour. The reaction mixture was concentrated under reduced pressure to afford the title compound (119 mg). Structural formula, spectral data and purification condition are shown in Table 37.

REFERENCE EXAMPLE 2-25-1

(2R)-2-Amino-3-(1 H-pyrazol-1-yl)propan-1-ol hydrochloride

A mixture of (2S)-2-[(tert-butoxycarbonyl)amino]-3-iodopropionic acid methyl ester (1.45 g), pyrazole (100 mg), cesium carbonate (957 mg) and N,N-dimethylformamide (5 mL) was stirred at 80° C. for 5 hours. The reaction mixture was allowed to cool to room temperature. To the reaction mixture was added water, and the crude product was extracted with ethyl acetate. The extract was washed with water and brine, and dried over sodium sulfate. The solvent was removed under reduced pressure, and the residue was purified by silica gel column chromatography (eluent: ethyl acetate/n-hexane) to afford (2R)-2-[(tert-butoxycarbonyl)amino]-3-(1 H-pyrazol-1-yl)propionic acid methyl ester (103 mg). To a mixture of the product (103 mg), ethanol (1 mL) and water (1 mL) was added sodium borohydride (35 mg) at 0° C., the mixture was stirred at room temperature for 2 hours. To the reaction mixture was added a saturated aqueous solution of sodium bicarbonate, and the crude product was extracted with ethyl acetate. The extract was washed with brine, and dried over sodium sulfate. The solvent was removed under reduced pressure. A mixture of the residue, methanol (1 mL) and a solution of hydrogen chloride in 1,4-dioxane (4 mol/L, 1 mL) was stirred at room temperature for 1 hour. The reaction mixture was concentrated under reduced pressure to afford the title compound (64 mg). Structural formula, spectral data and purification condition are shown in Table 37.

REFERENCE EXAMPLE 2-26-1

(2S,3R)-3-Amino-4-(1H-pyrazol-1-yl)butane-1,2-diol hydrochloride

To a mixture of N-{(1R)-1-[(4S)-2,2-dimethyl-1,3-dioxolan-4-yl]-2-hydroxyethyl}carbamic acid tert-butylester (3.32 g), imidazole (1.38 g), triphenylphosphine (5.33 g) and tetrahydrofuran (30 mL) was added iodine (4.52 g) at 0° C., and the mixture was stirred at room temperature for 2 hours. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford N-{(1S)-1-[(4S)-2,2-dimethyl-1,3-dioxolan-4-yl]-2-iodoethyl}carbamic acid tert-butyl ester (3.25 g). A mixture of the product (545 mg), pyrazole (100 mg), cesium carbonate (957 mg) and N,N-dimethylformamide (5 mL) was stirred at 80° C. for 13 hours. The reaction mixture was allowed to cool to room temperature. To the mixture was added water, and the crude product was extracted with ethyl acetate. The extract was washed with water and brine, and dried over sodium sulfate. The solvent was removed under reduced pressure. The residue was purified by silica gel column chromatography (eluent: ethyl acetate/n-hexane) to afford N-{(1R)-1-[(4S)-2,2-dimethyl-1, 3-dioxolan-4-yl]-2-(1H-pyrazol-1-yl)ethyl}carbamic acid tert-butylester (220 mg). To a solution of the product (220 mg) in 1,4-dioxane (1 mL) was added a solution of hydrogen chloride in 1,4-dioxane (4 mol/L, 1 mL), and the mixture was stirred at room temperature for 1 hour. The reaction mixture was concentrated under reduced pressure to afford the title compound (52 mg). Structural formula, spectral data and purification condition are shown in Table 37,

REFERENCE EXAMPLE 2-27-1

(3R)-3-Amino-1,2,3,4-tetrahydro-1,5-naphthyridin-2-one hydrochloride

A mixture of (2S)-2-[(tert-butoxycarbonyl amino]-3-iodopropionic acid methyl ester (1.02 g), zinc (447 mg) in N,N-dimethylformamide (5 mL) was stirred at room temperature under an argon atmosphere for 2 hours. To the mixture were added 2-bromo-3-nitropyridine (631 mg), bis(triphenylphosphine)palladium(II)dichloride (218 mg), and the mixture was stirred at room temperature for 13 hours. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by silica gel column chromatography (eluent: ethyl acetate/n-hexane) to afford (2R)-2-[(tert-butoxycarbonyl)amino]-3-(3-nitropyridin-2-yl)propionic acid methyl ester (440 mg). To a solution of the product (440 mg) in ethanol (5 mL) was added 10% palladium-carbon (50% wet, 20 mg), and the mixture was stirred at 50° C. under a hydrogen atmosphere for 10 hours. The reaction mixture was filtered through a pad of celite, and the filtrate was concentrated under reduced pressure. The residue was purified by aminopropyl silica gel column chromatography (eluent: ethyl acetate/n-hexane) to afford N-((3R)-2-oxo-1,2,3,4-tetrahydro-1,5-naphthyridin-3-yl) carbamic acid tert-butyl ester. A mixture of the product, methanol (1 mL) and a solution of hydrogen chloride in 1,4-dioxane (4 mol/L, 1 mL) was stirred at room temperature for 1 hour. The reaction mixture was concentrated under reduced pressure to afford the title compound (40 mg). Structural formula, spectral data and purification condition are shown in Table 37.

REFERENCE EXAMPLES 2-28-1, 2-28-2

(R)-N-[(2S)-1,3-di(tert-butyldimethylsilyloxy)-1-(pyridin-2-yl)propan-2-yl]-2-methylpropane-2-sulfinamide (2-28-1:HP)

(R)-N-[(2S)-1,3-di(tert-butyldimethylsilyloxy)-1-(pyridin-2-yl)propan-2-yl]-2-methylpropane-2-sulfinamide (2-28-2:LP)

To a solution of 2-(tert-butyldimethylsilyloxy)acetaldehyde (2.000 g) in tetrahydrofuran (30 mL) were added (R)-(+)-2-methylpropane-2-sulfinamide (1.808 g) and tetraethyl orthotitanate (4.188 g), and the mixture was stirred at room temperature overnight. To the reaction mixture were added brine and ethyl acetate, and the mixture was filtered through a pad of celite. The filtrate was concentrated under reduced pressure, and the residue was purified by silica gel column chromatography (eluent: ethyl acetate/n-hexane) to afford (R)-N-[(1E)-2-(tert-butyldimethylsilyloxy)ethylidene]-2-methylpropane-2-sulfinamide (2.185 g). To a solution of 2-(tert-butyldimethylsilyloxymethyl)pyridine (0.282 g) in tetrahydrofuran (2 mL) was added a solution of n-butyllithium in n-hexane (2.6 mol/L, 0.4 mL) at −78° C., and the mixture was stirred at the same temperature for 30 minutes. To the mixture was added a solution of (R)-N-[(1E)-2-(tert-butyldimethylsilyloxy)ethylidene]-2-methylpropane-2-sulfinamide (0.263 g) in tetrahydrofuran (2 mL), and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford the title compound (2-28-1: 0.085 g, 2-28-2: 0.076 g). Structural formula, spectral data and purification condition are shown in Table 37.

REFERENCE EXAMPLES 2-28-3 TO 2-28-4

Reference Examples 2-28-3 to 2-28-4 were synthesized in a manner similar to that of Reference Example 2-28-1 by using the corresponding materials. Structural formula, spectral data and purification condition are shown in Table 37.

REFERENCE EXAMPLE 2-29-1

(2R,3S)-4-(Benzyloxy)-3-methoxy-1-(pyridin-2-yl)butan-2-amine

To a solution of 3-(benzyloxy)-2-methoxypropanal (1.90 g) in tetrahydrofuran (20 mL) were added (R)-2-methylpropane-2-sulfinamide (1.53 g) and tetraethyl orthotitanate (3.53 g), and the mixture was stirred at room temperature overnight. To the reaction mixture was added brine, and the mixture was filtered through a pad of celite. The filtrate was concentrated under reduced pressure, and the residue was purified by silica gel column chromatography (eluent: ethyl acetate/n-hexane) to afford (R)-N-[(1E,2S)-3-(benzyloxy)-2-methoxypropylidene]-2-methylpropane-2-sulfinamide (0.57 g) as a high polarity product and (R)-N-[(1E,2R)-3-(benzyloxy)-2-methoxypropylidene]-2-methylpropane-2-sulfinamide (0.70 g) as a low polarity product. To a solution of 2-methylpyridine (0.27 g) in tetrahydrofuran (2 mL) was added a solution of n-butyllithium in n-hexane (2.6 mol/L, 1.0 mL) at −78° C., and the mixture was stirred at the same temperature for 10 minutes. To the mixture was added dropwise a solution of (R)-N-[(1E,2S)-3-(benzyloxy)-2-methoxypropylidene]-2-methylpropane-2-sulfinamide (0.57 g) in tetrahydrofuran (4 mL), and the mixture was stirred at the same temperature for 1.5 hours. To the reaction mixture were added water and a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol). The crude product was purified by preparative reverse phase liquid chromatography (Capcell Pak C18 UG80, eluent: acetonitrile water) to afford (R)-N-[(2R,3S)-4-(benzyloxy)-3-methoxy-1-(pyridin-2-yl)butan-2-yl]-2-methylpropane-2-sulfinamide (0.20 g) as a high polarity product. To a solution of the product (0.20 g) in methanol (2 mL) was added a solution of hydrogen chloride in 1,4-dioxane (4 mol/L, 2 mL), and the mixture was stirred at room temperature for 1 hour. The reaction mixture was concentrated under reduced pressure, and the residue was purified by aminopropyl silica gel column chromatography (eluent: ethyl acetate/methanol) to afford the title compound (0.15 g). Structural formula, spectral data and purification condition are shown in Table 38.

REFERENCE EXAMPLE 2-30-1

(2R,3R)-4-(Benzyloxy)-3-methoxy-1-(pyridin-2-yl)butan-2-amine

To a solution of 3-(benzyloxy)-2-methoxypropanal (1.90 g) in tetrahydrofuran (20 mL) were added (R)-2-methylpropane-2-sulfinamide (1.53 g) and tetraethyl orthotitanate (3.53 g), and the mixture was stirred at room temperature overnight. To the reaction mixture was added brine, and the mixture was filtered through a pad of celite. The filtrate was concentrated under reduced pressure, and the residue was purified by silica gel column chromatography (eluent: ethyl acetate/n-hexane) to afford (R)-N-[(1E,2S)-3-(benzyloxy)-2-methoxypropylidene]-2-methylpropane-2-sulfinamide (0.57 g) as a high polarity product and (R)-N-[(1E,2R)-3-(benzyloxy)-2-methoxypropylidene]-2-methylpropane-2-sulfinamide (0.70 g) as a low polarity product. To a solution of 2-methylpyridine (0.19 g) in tetrahydrofuran (2 mL) was added a solution of n-butyllithium in n-hexane (2.6 mol/L, 1.0 mL) at −78"C, and the mixture was stirred at the same temperature for 10 minutes. To the mixture was added dropwise a solution of (R)-N-[(1E,2R)-3-(benzyloxy)-2-methoxypropylidene]-2-methylpropane-2-sulfinamide (0.40 g) in tetrahydrofuran (2 mL), and the mixture was stirred at the same temperature for 1.5 hours. To the reaction mixture were added water and a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent:ethyl acetate/methanol) to afford a mixture of (R)-N-[(2R,3R)-4-(benzyloxy)-3-methoxy-1-(pyridin-2-yl)butan-2-yl]-2-methylpropane-2-sulfinamide and (R)-N-[(2S,3R)-4-(benzyloxy)-3-methoxy-1-(pyridin-2-yl)butan-2-yl]-2-methylpropane-2-sulfinamide (0.47 g). To the product (042. g) were added tetrahydrofuran (4 mL) and a solution of hydrogen chloride in 1,4-dioxane (4 mol/L, 2 mL), and the mixture was stirred at room temperature for 1 hour. The reaction mixture was concentrated under reduced pressure, and the residue was purified by silica gel column chromatography (eluent: ethyl acetate/methanol) to afford the title compound (0.15 g) as a low polarity product. Structural formula, spectral data and purification condition are shown in Table 38.

REFERENCE EXAMPLE 2-31-1

(2R)-2-Amino-2-methyl-3-(pyridin-2-yl)propanamide

To a solution of (2R)-2-amino-2-methyl-3-(pyridin-2-yl)propan-1-ol hydrochloride (64 mg) in dichloromethane (1 mL) were added N,N-diisopropylethylamine (121 mg) and chloroformic acid benzyl ester (64 mg), and the mixture was stirred at room temperature overnight. To the reaction mixture was added water, and the crude product was extracted with dichloromethane. The organic layer was washed with brine, and dried over anhydrous magnesium sulfate. The solvent was removed under reduced pressure, and the residue was purified by silica gel column chromatography (eluent: ethyl acetate/n-hexane) to afford N-[(2R)-1-hydroxy-2-(pyridin-2-ylmethyl)propan-2-yl]carbamic acid benzyl ester (35 mg). To a solution of the product (35 mg) in dichloromethane (1 mL) was added Dess-Martin periodinane (80 mg), and the mixture was stirred at room temperature for 1 hour. To the reaction mixture were added an aqueous solution of sodium thiosulfate (1 mol/L) and a saturated aqueous solution of sodium bicarbonate, and the crude product was extracted with dichloromethane. The organic layer was washed with brine, and dried over anhydrous magnesium sulfate. The solvent was removed under reduced pressure to afford N-[(2R)-1-oxo-2-(pyridin-2-ylmethyl) propan-2-yl]carbamic acid benzyl ester (34 mg). A mixture of the product (34 mg), sodium dihydrogenphosphate dihydrate (21 mg), tert-butyl alcohol (2 mL), acetonitrile (400 µL) water (800 µL), 2-methyl-2-butene (35 mg) and sodium chlorite (45 mg) was stirred at room temperature for 2 hours. To the reaction mixture were added water and a saturated aqueous solution of ammonium chloride, and the crude product was extracted with dichloromethane. The organic layer was washed with brine, and dried over anhydrous magnesium sulfate. The solvent was removed under reduced pressure to afford (2R)-2-[(benzyloxycarbonyl)amino]-2-methyl-3-(pyridin-2-yl)propionic acid (36 mg). To a suspension of the product (36 mg) in N,N-dimethylformamide (1 mL) were added ammonium chloride (61 mg), N,N-diisopropylethylamine (147 mg) and 1,1'-carbonyldiimidazole (30 mg), and the mixture was stirred at room temperature for 1 day. To the reaction mixture were added water and a saturated aqueous solution of ammonium chloride, and the crude product was extracted with dichloromethane. The organic layer was washed with brine, and dried over anhydrous magnesium sulfate. The solvent was removed under reduced pressure to afford N-[(1R)-1-carbamoyl-1-methyl-2-(pyridin-2-yl)ethyl]carbamic acid benzyl ester (13 mg). To the product (13 mg) were added ethanol (2 mL) and1.0% palladium-carbon (50% wet, 0.02 g), and the mixture was stirred at room temperature under a hydrogen atmosphere for 3 hours. The reaction mixture was filtered through a pad of celite, and the filtrate was concentrated under reduced pressure to afford the title compound (7 mg) Structural formula, spectral data and purification condition are shown in Table 38.

REFERENCE EXAMPLE 2-31-2

Reference Example 2-31-2 was synthesized in a manner similar to that of Reference Example 2-31-1 by using the corresponding materials. Structural formula and purification condition are shown in Table 38.

REFERENCE EXAMPLE 2-32-1

(3R)-3-Amino-4-hydroxybutanenitrile hydrochloride

To a solution of (2R)-2-[(tert-butoxycarbonyl)amino]-3-cyanopropionic acid (500 mg) in tetrahydrofuran (5 mL) were added triethylamine (710 mg) and chloroformic acid isobutyl ester (637 mg) at 0° C., and the mixture was stirred at the same temperature for 1 hour. The reaction mixture was filtered through a pad of celite, and the filtrate was concentrated under reduced pressure. To a solution of the residue in methanol (5 mL) was added sodium borohydride (178 mg) at 0° C., and the mixture was stirred at the same temperature for 2 hours. To the reaction mixture was added hydrochloric acid (1 mol/L), and the crude product was extracted with ethyl acetate. The extract was washed with brine, and dried over sodium sulfate. The solvent was removed under reduced pressure. To a solution of the residue in 1,4-dioxane (3 mL) was added a solution of hydrogen chloride in 1,4-dioxane (4 mol/L, 2 mL), and the mixture was stirred at room temperature for 1 hour. The precipitate was collected by filtration to afford the title compound (100 mg). Structural formula, spectral data and purification condition are shown in Table 38.

REFERENCE EXAMPLE 2-33-1

(3R)-3-Amino-4-(1,6-dihydropyrimidin-2-yl)butan-1-ol dihydrochloride

To a solution of (2S)-4-(tert-butoxy)-2-[(tert-butoxycarbonyl)amino]-4-oxobutanoic acid (2 g) in tetrahydrofuran (10 mL) were added N-methylmorpholine (840 mg) and chloroformic acid isobutyl ester (1.04 g) at 0° C., and the mixture was stirred at the same temperature for 1 hour. The reaction mixture was filtered through a pad of celite, and the filtrate was concentrated under reduced pressure. To a solution of the residue in methanol (10 mL) was added sodium borohydride (525 mg) at 0° C. and the mixture was stirred at the same temperature for 2 hours. To the reaction mixture was added hydrochloric acid (1 mol/L), and the crude product was extracted with ethyl acetate. The extract was washed with brine, and dried over sodium sulfate. The solvent was removed under reduced pressure. The residue was purified by silica gel column chromatography (eluent: ethyl acetate/n-hexane) to afford (3S)-3-[(tert-butoxycarbonyl)amino]-4-hydroxybutanoic acid tert-butyl ester (1.93 g). To a mixture of the product (1.93 g), imidazole (763 mg), triphenylphosphine (2.94 g) and tetrahydrofuran (20 mL) was added iodine (2.49 g) at 0° C., and the mixture was stirred at room temperature for 2 hours. To the reaction mixture was added a saturated aqueous solution of ammonium chloride, and the crude product was extracted with ethyl acetate. The extract was washed with brine, and dried over sodium sulfate The solvent was removed under reduced pressure, and the residue was purified by silica gel column chromatography (eluent: ethyl acetate/n-hexane) to afford (3S)-3-[(tert-butoxycarbonyl)amino]-4-iodobutanoic acid tert-butyl ester (2.3 g). A mixture of the product (1 g), zinc (374 mg) in N,N-dimethylformamide (10 mL) was stirred at room temperature under an argon atmosphere for 2 hours. To the mixture were added 2-bromopyrimidine (413 mg) and bis(triphenylphosphine)palladium (II) dichloride (182 mg), and the mixture was stirred at 40° C. for 5 hours. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by silica gel column chromatography (eluent: ethyl acetate/n-hexane) to afford (3R)-3-[(tert-butoxycarbonyl)amino]-4-(pyrimidin-2-yl)butanoic acid tert-butyl ester (460mg). To a solution of the product (350 mg) in tetrahydrofuran (5 mL) was added lithium aluminium hydride (99 mg) at 0° C. and the mixture was stirred at room temperature for 1 hour. To the reaction mixture were added water (100 μL), an aqueous solution of sodium hydroxide (15%, 100 μL) and water (300 μL) at 0° C., and the mixture was stirred at room temperature for 30 minutes. The reaction mixture was filtered through a pad of celite, and the filtrate was concentrated under reduced pressure. To the residue were added methanol (2 mL) and a solution of hydrogen chloride in 1,4-dioxane (4 mol/L, 2 mL), and the mixture was stirred at room temperature for 12 hours. The reaction mixture was concentrated under reduced pressure to afford the title compound (200 mg). Structural formula, spectral data and purification condition are shown in Table 38.

REFERENCE EXAMPLE 2-34-1

(3R)-3-Amino-2-methyl-4-(6-methyl-1,6-dihydropyrimidin-2-yl)butan-2-ol dihydrochloride A mixture of (2S)-2-[(tert-butoxycarbonyl)amino]-3-iodopropionic acid methyl ester (800 mg), zinc (350 mg) in N,N-dimethylformamide (10 mL) was stirred at room temperature under an argon atmosphere for 2 hours. To the mixture were added 2-bromopyrimidine (386 mg) and bis(triphenylphosphine)palladium (II) dichloride (171 mg), and the mixture was stirred at room temperature for 12 hours. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford (2R)-2-[(tert-butoxycarbonyl)amino]-3-(pyrimidin-2-yl)propionic acid methyl ester (450 mg). To a solution of the product (450 mg) in tetrahydrofuran (5 mL) was added a solution of methyllithium in diethyl ether (1.1 mol/L, 5.8 mL) at −78° C., and the mixture was stirred for 30 minutes. To the reaction mixture was added a saturated aqueous solution of ammonium chloride, and the crude product was extracted with ethyl acetate The extract was washed with brine, and dried over sodium sulfate. The solvent was removed under reduced pressure. To the residue were added methanol (2 mL) and a solution of hydrogen chloride in 1,4-dioxane (4 mol/L, 2 mL), and the mixture was stirred at room temperature for 12 hours. The reaction mixture was concentrated under reduced pressure to afford the title compound (40 mg). Structural formula, spectral data and purification condition are shown in Table 38.

REFERENCE EXAMPLE 2-35-1

(3R)-3-Amino-4-(pyrimidin-2-yl)butan-1-ol hydrochloride

To a solution of (2S)-2-[(tert-butoxycarbonyl)amino]-4-methoxy-4-oxobutanoic acid (2 g) in tetrahydrofuran (10 mL) were added N-methylmorpholine (981 mg) and chloroformic acid isobutyl ester (1.22 g) at 0° C. and the mixture was stirred at the same temperature for 1 hour. The reaction mixture was filtered through a pad of celite, and the filtrate was concentrated under reduced pressure. To a solution of the residue in methanol (10 mL) was added sodium borohydride (337 mg) at 0° C., and the mixture was stirred at the same temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure. The residue was purified by silica gel column chromatography (eluent: ethyl acetate/n-hexane) to afford (3S)-3-[(tert-butoxycarbonyl)amino]-4-hydroxybutanoic acid methyl ester (1.18 g). To a mixture of the product (1.18 g), imidazole (551 mg), triphenylphosphine (2.12 g) and tetrahydrofuran (40 mL) was added iodine (1.8 g) at 0° C., and the mixture was stirred at room temperature for 2 hour. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford (3S)-3-[(tert-butoxycarbonyl)amino]-4-iodobutanoic acid methyl ester (1.5 g). A mixture of the product (1.5 g) and zinc (629 mg) in N,N-dimethylformamide (10 mL) was stirred at room temperature under an argon atmosphere for 2 hours. To the mixture were added 2-bromopyrimidine (695 mg) and bis(triphenylphosphine)palladium (II) dichloride (307 mg), and the mixture was stirred at room temperature for 12 hours. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford (3R)-3-[(tert-butoxycarbonyl)amino]-4-(pyrimidin-2-yl)butanoic acid methyl ester (746 mg). To a mixture of the product (746 mg) in ethanol (3 mL) and water (3 mL) was added sodium borohydride (239 mg) at 0° C. and the mixture was stirred at room temperature for 2 hours. To the reaction mixture was added a saturated aqueous solution of sodium bicarbonate, and the crude product was extracted with ethyl acetate. The extract was washed with brine, and dried over sodium sulfate. The solvent was removed under reduced pressure. The residue was purified by aminopropyl silica gel column chromatography (eluent: ethyl acetate/n-hexane) to afford N-[(2R)-4-hydroxy-1-(pyrimidin-2-yl)butan-2-yl]carbamic acid tert-butyl ester. To the product were added methanol (3 mL) and a solution of hydrogen chloride in 1,4-dioxane (4 mol/L, 3 mL), and the mixture was stirred at room temperature for 13 hours. The reaction mixture was concentrated under reduced pressure to afford the title compound (50 mg). Structural formula, spectral data and purification condition are shown in Table 38.

REFERENCE EXAMPLE 2-36-1

N-[(2R,3R)-3-Amino-1-benzyloxy-4-(pyridin-2-yl)butan-2-yl]carbamic acid benzyl ester To a mixture of N-[1-benzyloxy-3-oxopropan-2-yl]carbamic acid benzyl ester (975 mg) and (R)-tert-butylsulfinamide (490 mg) in tetrahydrofuran (15 mL) was added tetraethyl orthotitanate (0.959 mL). The mixture was stirred overnight. To the mixture was added brine (1.5 mL), and the mixture was filtered through a pad of celite. To the filtrate were added water and ethyl acetate, and the mixture was partitioned. The organic layer was concentrated under reduced pressure. The residue was purified by silica gel column chromatography (eluent: ethyl acetate/n-hexane) to afford N-{1-benzyloxy-3-[((R)-tert-butylsulfinyl)imino]propan-2-yl}carbamic acid benzyl ester (863 mg). To a solution of 2-methylpyridine (289 mg) in tetrahydrofuran (6 mL) was added a solution of n-butyllithium in n-hexane (2.6 mol/L, 1.05 mL) at −78° C., and the mixture was stirred at the same temperature for 30 minutes. To the mixture was added a solution of N-{1-benzyloxy-3-[((R)-tert-butylsulfinyl)imino]propan-2-yl}carbamic acid benzyl ester (863 mg) in tetrahydrofuran (6 mL). The mixture was stirred at −78° C. for 1.25 hours and at room temperature for 1 hour. To the reaction mixture was added a saturated aqueous solution of ammonium chloride (5 mL), and the crude product was extracted with ethyl acetate. The organic layer was washed with brine, and then concentrated under reduced pressure. The residue was purified by silica gel column chromatography (eluent: ethyl acetate/n-hexane). The crude product was purified by preparative reverse phase liquid chromatography (Capcell Pak C18 UG80, eluent: acetonitrile/water) to afford N-{(2R,3R)-1-benzyloxy-3-[((R)-tert-butylsulfinyl)amino]-4-(pyridin-2-yl)butan-2-yl}carbamic acid benzyl ester (46 mg) and a mixture of the corresponding three diastereomers (74 mg). To a solution of N-{(2R,3R)-1-benzyloxy-3-[((R)-tert-butylsulfinyl)amino]-4-(pyridin-2-yl)butan-2-yl}carbamic acid benzyl ester (46 mg) in methanol (1 mL) was added a solution of hydrogen chloride in 1,4-dioxane (4 mol/L, 0.2 mL) at room temperature, and the mixture was stirred for 1.3 hours. The reaction mixture was purified by aminopropyl silica gel column chromatography (eluent: ethyl acetate/methanol) to afford the title compound (36 mg). Structural formula, spectral data and purification condition are shown in Table 38.

REFERENCE EXAMPLE 2-37-1

N-[(2R,3RS)-3-Amino-1-benzyloxy-4-(pyridin-2-yl)butan-2-yl]carbamic acid benzyl ester To a solution of (R)-3-benzyloxy-2-(benzyloxycarbonylamino)propionic acid methyl ester (990 mg) in dichloromethane (15 mL) was added a solution of diisobutylaluminium hydride in n-hexane (1.02 mol/L, 5.09 mL) at −78° C., and the mixture was stirred for 1.5 hours. To the mixture were added methanol (5 mL) and brine (10 mL), and the mixture was filtered through a pad of celite. The insoluble compound was washed with ethyl acetate. The organic layer of the filtrate was collected. The crude product was extracted from the aqueous layer with ethyl acetate. The combined organic layer was concentrated under reduced pressure. To a mixture of the residue and (R)-tert-butylsulfinamide (525 mg) in tetrahydrofuran (20 mL) was added tetraethyl orthotitanate (0.906 mL). The mixture was stirred at room temperature overnight. To the mixture were added brine (5 mL) and ethyl acetate (10 mL), and the mixture was filtered through a pad of celite. To the filtrate were added water and ethyl acetate, and the mixture was partitioned. The organic layer was concentrated under reduced pressure. The residue was purified by silica gel column chromatography (eluent: ethyl acetate/n-hexane) to afford N-{(S)-1-benzyloxy-3-[((R)-tert-butylsulfinyl)imino]propan-2-yl}carbamic acid benzyl ester (993 mg). To a solution of 2-methylpyridine (333 mg) in tetrahydrofuran (7 mL) was added a solution of n-butyllithium in n-hexane (2.6 mol/L, 1.19 mL) at −78° C., and the mixture was stirred for 30 minutes. To the mixture was added a solution of {(S)-1-benzyloxy-3-[((R)-tert-butylsulfinyl)imino]propan-2-yl}carbamic acid benzyl ester (993 mg) in tetrahydrofuran (7 mL). The mixture was stirred at −78° C. for 2 hours and at room temperature for 30 minutes. To the reaction mixture was added a saturated aqueous solution of ammonium chloride (2 mL). The crude product was extracted with ethyl acetate. The organic layer was concentrated under reduced pressure. The residue was purified by silica gel column chromatography (eluent: ethyl acetate/methanol) to afford N-{(S)-1-benzyloxy-3-[((R)-tert-butylsulfinyl)amino]-4-(pyridin-2-yl)butan-2-yl}carbamic acid benzyl ester (489 mg). To a solution of the product (484 mg) in methanol (15 mL) was added a solution of hydrogen chloride in 1,4-dioxane (4 mol/L, 0.461 mL) and the mixture was stirred at room temperature overnight. The reaction mixture was purified by aminopropyl silica gel column chromatography (eluent: ethyl acetate/n-hexane) to afford the title compound (350 mg). Structural formula, spectral data and purification condition are shown in Table 39.

REFERENCE EXAMPLE 2-37-2

Reference Example 2-37-2 was synthesized in a manner similar to that of Reference Example 2-37-1 by using the corresponding materials. Structural formula, spectral data and purification condition are shown in Table 39.

REFERENCE EXAMPLE 2-38-1

(2R,3S)-3,4-Dimethoxy-1-(pyridin-2-yl)butan-2-amine hydrochloride

To a solution of (2S,3R)-3-amino-4-(pyridin-2-yl)butane-1,2-diol (0.20 g) in tetrahydrofuran (3 mL) were added triethylamine (0.32 g) and di-tert-butyl dicarbonate (0.19 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford N-[(2R,3S)-3,4-dihydroxy-1-(pyridin-2-yl)butan-2-yl]carbamic acid tert-butyl ester (0.22 g). To the product (50 mg) in tetrahydrofuran (1 mL) were added sodium hydride (60% dispersion in oil, 15 mg) and iodomethane (125 mg) under ice-cooling, and the mixture was stirred at room temperature for 1 day. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford N-[(2R,3S)-3,4-dimethoxy-1-(pyridin-2-yl)butan-2-yl]carbamic acid tert-butyl ester (10 mg). To a solution of the product (10 mg) in methanol (0.5 mL) was added a solution of hydrogen chloride in 1,4-dioxane (4 mol/L, 0.5 mL) at room temperature, and the mixture was stirred at the same temperature for 2 hours. The reaction mixture was concentrated under reduced pressure to afford the title compound (9 mg). Structural formula, spectral data and purification condition are shown in Table 39.

REFERENCE EXAMPLE 2-39-1

(2S,3R)-3-Amino-1-ethoxy-4-(pyridin-2-yl)butan-2-ol

To a solution of (2R)-2-[(benzyloxy)methyl]oxirane (1.00 g) ethanol (10 mL) was added potassium hydroxide (1.03 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (2R)-1-(benzyloxy)-3-ethoxypropan-2-ol (1.25 g). To a solution of the product (1.25 g) in dichloromethane (20 mL) were added imidazole (1.01 g) and tert-butyldimethylchlorosilane (0.99 g), and the mixture was stirred at room temperature for 2 hours. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford [(2R)-1-(benzyloxy)-3-ethoxypropan-2-yl](tert-butyldimethylsilyl)ether (2.00 g). To a solution of the product (2.00 g) in ethanol (20 mL) was added 10% palladium-carbon (50% wet, 0.2 g), and the mixture was stirred at room temperature under a hydrogen atmosphere for 2 hours. The reaction mixture was filtered through a pad of celite, and the filtrate was concentrated under reduced pressure. The residue was dissolved in dichloromethane (10 mL). To the solution were added iodobenzene diacetate (2.87 g) and AZADOL® (0.046 g) under ice-cooling, and the mixture was stirred at room temperature for 2 hours. To the reaction mixture were added an aqueous solution of sodium thiosulfate (1 mol/L) and a saturated aqueous solution of sodium bicarbonate, and the crude product was extracted with dichloromethane. The organic layer was washed with brine, and dried over anhydrous magnesium sulfate. The solvent was removed under reduced pressure. To the residue were added tetrahydrofuran (20 mL), (R)-tert-butylsulfinamide (790 mg) and tetraethyl orthotitanate (1.85 mL). The mixture was stirred at room temperature overnight. To the reaction mixture were added brine and ethyl acetate, and the mixture was filtered through a pad of celite. The filtrate was concentrated under reduced pressure, and the residue was purified by silica gel column chromatography (eluent: ethyl acetate/n-hexane) to afford (R)-N-[(1E,2S)-2-(tert-butyldimethylsilyloxy)-3-ethoxypropylidene]-2-methylpropane-2-sulfinamide (0.85 g). To a solution of 2-methylpyridine (0.35 g) in tetrahydrofuran (2 mL) was added a solution of n-butyllithium in n-hexane (2,6 mol/L, 2.2 mL) at −78° C., and the mixture was stirred at the same temperature for 10 minutes. To the mixture was added dropwise a solution of (R)-N-[(1E,2S)-2-(tert-butyldimethylsilyloxy)-3-ethoxypropylidene]-2-methylpropane-2-sulfinamide (0.85 g) in tetrahydrofuran (3 mL), and the mixture was stirred at the same temperature for 1.5 hours. To the reaction mixture were added water and a saturated aqueous solution of ammonium chloride, and the crude product was extracted with ethyl acetate. The organic layer was washed with brine, and dried over anhydrous magnesian sulfate. The solvent was removed under reduced pressure, and the residue was purified by silica gel column chromatography (eluent: ethyl acetate/methanol). The crude product was purified by preparative reverse phase liquid chromatography (Capcell Pak C18 UG80, eluent: acetonitrile/water) to afford (R)-N-[(2R,3S)-3-(tert-butyldimethylsilyloxy)-4-ethoxy-1-(pyridin-2-yl)butan-2-yl]-2-methylpropane-2-sulfinamide (0.36 g) as a high polarity product. To a solution of the product (0.36 g) in methanol (2 mL) was added a solution of hydrogen chloride in 1,4-dioxane (4 mol/L, 2 mL), and the mixture was stirred at room temperature overnight. The reaction mixture was concentrated under reduced pressure, and the residue was purified by aminopropyl silica gel column chromatography (eluent: ethyl acetate/methanol) to afford the title compound (0.16 g). Structural formula, spectral data and purification condition are shown in Table 39.

REFERENCE EXAMPLES 2-39-2 TO 2-39-4

Reference Examples 2-39-2 to 2-39-4 were synthesized in a manner similar to that of Reference Example 2-39-1 by using the corresponding materials. Structural formula, spectral data and purification condition are shown in Table 39.

REFERENCE EXAMPLE 2-40-1

(2R,3S)-4-(Benzyloxy)-3-ethoxy-1-(pyridin-2-yl)butan-2-amine

To a solution of (4R)-4-[(benzyloxy)methyl]-2,2-dimethyl-1,3-dioxolane (8.00 g) in methanol was added a solution of hydrogen chloride in 1,4-dioxane (4 mol/L, 20 mL), and the mixture was stirred at room temperature for 3 hours. The reaction mixture was concentrated, and the residue was purified by silica gel column chromatography (eluent: ethyl acetate/n-hexane) to afford (2S)-3-(benzyloxy)propane-1,2-diol (7.30 g). To a solution of the product (6.90 g) in dichloromethane (30 mL) were added N,N-diisopropylethylamine (12.2 g) and chloromethyl methyl ether (3.35 g) under ice-cooling, and the mixture was stirred at room temperature for 1 hour. To the reaction mixture were added water and a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (2R)-1-benzyloxy-3-(methoxymethoxy)propan-2-ol (2.30 g). To a solution of the product (0.20 g) in tetrahydrofuran (5 mL) was added sodium hydride (60% dispersion in oil 53 mg) and iodoethane (0.42 g) under ice-cooling, and the mixture was stirred at room temperature for 5 hours. To the reaction mixture was added water, and the crude product was extracted with dichloromethane. The organic layer was washed with brine, and dried over anhydrous magnesium sulfate. The solvent was removed under reduced pressure, and the residue was purified by silica gel column chromatography (eluent: ethyl acetate/n-hexane) to afford [(2R)-1-(benzyloxy)-3-(methoxymethoxy)propan-2-yl]ethyl ether (0.21 g). To a solution of the product (0.21 g) in methanol (2 mL) was added a solution of hydrogen chloride in 1,4-dioxane (4 mol/L, 2 mL), and the mixture was stirred at room temperature for 1 hour. The reaction mixture was concentrated under reduced pressure, and the residue was purified by silica gel column chromatography (eluent: ethyl acetate/n-hexane) to afford (2S)-3-(benzyloxy)-2-ethoxypropan-1-ol (0.137 g). To a solution of the product (137 mg) in dichloromethane (2 mL) were added iodobenzene diacetate (315 mg) and AZADOL® (5 mg) under ice-cooling, and the mixture was stirred at room temperature for 2 hours. To the reaction mixture were added an aqueous solution of sodium thiosulfate (1 mol/L) and a saturated aqueous solution of sodium bicarbonate, and the crude product was extracted with dichloromethane. The organic layer was washed with brine, and dried over anhydrous magnesian sulfate. The solvent was removed under reduced pressure. To the residue were added tetrahydrofuran (3 mL), (R)-tert-butylsulfinamide (103 mg) and tetraethyl orthotitanate (215 μL). The mixture was stirred at room temperature overnight. To the reaction mixture were added brine and ethyl acetate, and the mixture was filtered through a pad of celite. The filtrate was concentrated under reduced pressure, and the residue was purified by silica gel column chromatography (eluent: ethyl acetate/n-hexane) to afford (R)-N-[(1E,2S)-3-(benzyloxy)-2-ethoxypropylidene]-2-methylpropane-2-sulfinamide (120 mg). To a solution of 2-methylpyridine (54 mg) in tetrahydrofuran (2 mL) was added a solution of n-butyllithium in n-hexane (2.6 mol/L, 0.2 mL) at −78° C., and the mixture was stirred at the same temperature for 10 minutes. To the mixture was added dropwise a solution of (R)-N-[(1E,2S)-3-(benzyloxy)-2-ethoxypropylidene]-2-methylpropane-2-sulfinamide (120 mg) in tetrahydrofuran (3 mL), and the mixture was stirred at the same temperature for 1.5 hours. To the reaction mixture were added water and a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol). The crude product was purified by preparative reverse phase liquid chromatography (Capcell Pak C18 UG80, eluent: acetonitrile/water) to afford (R)-N-[(2R,3S)-4-(benzyloxy)-3-ethoxy-1-(pyridin-2-yl)butan-2-yl]-2-methylpropane-2-sulfinamide (35 mg) as a high polarity product. To a solution of the product (35 mg) in methanol (1 mL) was added a solution of hydrogen chloride in 1,4-dioxane (4 mol/L, 1 mL), and the mixture was stirred at room temperature overnight. The reaction mixture was concentrated under reduced pressure, and the residue was purified by aminopropyl silica gel column chromatography (eluent: ethyl acetate/methanol) to afford the title compound (12 mg). Structural formula and purification condition are shown in Table 39.

REFERENCE EXAMPLE 2-41-1

(1R)-1-((4R)-2,2-Dimethyl-1,3-dioxolan-4-yl)-2-(pyrimidin-2-yl)ethan-1-amine

To a mixture of N-[(1R)-1-((4R)-2,2-dimethyl-1,3-dioxolan-4-yl)-2-hydroxyethyl]carbamic acid benzyl ester (1.78 g), imidazole (656 mg), triphenylphosphine (2.53 g) and tetrahydrofuran (20 mL) was added iodine (2.14 g) at 0° C., and the mixture was stirred at room temperature for 2 hours. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford N-[(1S)-1-((4R)-2,2-dimethyl-1,3-dioxolan-4-yl)-2-iodoethyl]carbamic acid benzyl ester (1.9 g). A mixture of the product (1.9 g), zinc (355 mg) in N,N-dimethyl formamide (10 mL) was stirred at room temperature under an argon atmosphere for 2 hours. To the mixture were added 2-bromopyrimidine (392 mg), bis(triphenylphosphine)palladium (II) dichloride (173 mg), and the mixture was stirred at room temperature for 13 hours. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford N-[(1R)-1-((4R)-2,2-dimethyl-1,3-dioxolan-4-yl)-2-(pyrimidin-2-yl)ethyl]carbamic acid benzyl ester (614 mg). A mixture of the product (400 mg), 10% palladium-carbon (50% wet, 10 mg) and ethyl acetate (5 mL) was stirred at room temperature under a hydrogen atmosphere for 5 hours. The reaction mixture was filtered through a pad of celite, and the filtrate was concentrated under reduced pressure to afford the title compound (140 mg). Structural formula, spectral data and purification condition are shown in Table 39.

REFERENCE EXAMPLE 2-42-1

(2S)-3-(Benzyloxy)-1-methoxy-1-(pyridin-2-yl)propan-2-amine hydrochloride

To a solution of 2-(tert-butyldimethylsilyloxymethyl)pyridine (1.032 g) in tetrahydrofuran (5 mL) was added a solution of n-butyllithium in n-hexane (2.6 mol/L, 1.5 mL) at −78° C., and the mixture was stirred at the same temperature for 30 minutes. To the mixture was added dropwise a solution of (R)-N-[(1E)-2-(benzyloxy)ethylidene]-2-methylpropane-2-sulfinamide (0.836 g) in tetrahydrofuran (5 mL), and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (R)-N-[(2S)-3-(benzyloxy)-1-(tert-butyldimethylsilyloxy)-1-(pyridin-2-yl)propan-2-yl]-2-methylpropane-2-sulfinamide (HP, 0.345 g) and (R)-N-[(2S)-3-(benzyloxy)-1-(tert-butyldimethylsilyloxy)-1-(pyridin-2-yl)propan-2-yl]-2-methylpropane-2-sulfinamide (LP, 0.354 g). To a solution of (R)-N-[(2S)-3-(benzyloxy)-1-(tert-butyldimethylsilyloxy)-1-(pyridin-2-yl)propan-2-yl]-2-methylpropane-2-sulfinamide (0.345 g) in tetrahydrofuran (4 mL) was added a solution of tetra-n-butylammonium fluoride in tetrahydrofuran (1 mol/L, 1 mL) under ice-cooling, and the mixture was stirred for 30 minutes. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford (R)-N-[(2S)-3-(benzyloxy)-1-hydroxy-1-(pyridin-2-yl)propan-2-yl]-2-methylpropane-2-sulfinamide (0.185 g). To a solution of the product (0.093 g) in tetrahydrofuran (1 mL) was added sodium hydride (60% dispersion in oil, 0.006 g) under ice-cooling, and the mixture was stirred at room temperature for 30 minutes. To the mixture was added iodomethane (0.145 g) and the mixture was stirred at room temperature overnight. To the reaction mixture was added ice, and the crude product was extracted with ethyl acetate. The organic layer was washed with brine, and dried over anhydrous magnesium sulfate. The solvent was removed under reduced pressure, and the residue was purified by silica gel column chromatography (eluent:ethyl acetate/n-hexane) to afford (R)-N-[(2S)-3-(benzyloxy)-1-methoxy-1-(pyridin-2-yl)propan-2-yl]-2-methylpropane-2-sulfinamide (0.042 g). To a solution of the product (0.024 g) in 1,4-dioxane (1 mL) was added a solution of hydrogen chloride in 1,4-dioxane (4 mol/L, 1 mL), and the mixture was stirred at room temperature for 5 hours. The reaction mixture was concentrated under reduced pressure, and the residue was washed with n-hexane to afford the title compound (0.015 g). Structural formula, spectral data and purification condition are shown in Table 40.

REFERENCE EXAMPLES 2-42-2 TO 2-42-4

Reference Examples 2-42-2 to 2-42-4 were synthesized in a manner similar to that of Reference Example 2-42-1 by using the corresponding materials. Structural formula, spectral data and purification condition are shown in Table 40.

REFERENCE EXAMPLE 2-43-1

(2R,3S)-4-(Benzyloxy)-1,3-dimethoxy-1-(pyridin-2-yl)butan-2-amine

To a solution of (2R)-3-benzyloxy-2-methoxypropanal (0.213 g) in tetrahydrofuran (8 mL) were added (R)-(+)-2-methylpropane-2-sulfinamide (0.145 g) and tetraethyl orthotitanate (0.401 g), and the mixture was stirred at room temperature overnight. To the reaction mixture were added brine and ethyl acetate, and the mixture was filtered through a pad of celite. The filtrate was concentrated under reduced pressure, and the residue was purified by silica gel column chromatography (eluent: ethyl acetate/n-hexane) to afford (R)-N-[(1E,2S)-3-(benzyloxy)-2-methoxypropylidene]-2-methylpropane-2-sulfinamide (0.247 g). To a solution of 2-(tert-butyldimethylsilyloxymethyl)pyridine (0.260 g) in tetrahydrofuran (2 mL) was added a solution of n-butyllithium in n-hexane (2.6 mol/L, 0.4 mL) at −78° C., and the mixture was stirred for 30 minutes. To the mixture was added dropwise a solution of (R)-N-[(1E,2S)-3-(benzyloxy)-2-methoxypropylidene]-2-methylpropane-2-sulfinamide (0.247 g) in tetrahydrofuran (3 mL) at the same temperature, and the mixture was father stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of three diastereomers. The mixture was purified by preparative reverse phase liquid chromatography (Inertsil ODS-3, eluent: acetonitrile/water) to afford (R)-N-[(2S,3S)-4-(benzyloxy)-1-(tert-butyldimethylsilyloxy)-3-methoxy-1-(pyridin-2-yl)butan-2-yl]-2-methylpropane-2-sulfinamide (LP: 0.082 g) as a single diastereomer and a mixture of (R)-N-[(2S,3S)-4-(benzyloxy)-1-(tert-butyldimethylsilyloxy)-3-methoxy-1-(pyridin-2-yl)butan-2-yl]-2-methylpropane-2-sulfinamide as a single diastereomer and (R)-N-[(2R,3S)-4-(benzyloxy)-1-(tert-butyldimethylsilyloxy)-3-methoxy-1-(pyridin-2-yl)butan-2-yl]-2-methylpropane-2-sulfinamide as a single diastereomer (HP: 0.085 g). To the mixture of (R)-N-[(2S,3S)-4-(benzyloxy)-1-(tert-butyldimethylsilyloxy)-3-methoxy-1-(pyridin-2-yl)butan-2-yl]-2-methylpropane-2-sulfinamide as a single diastereomer and (R)-N-[(2R,3S)-4-(benzyloxy)-1-(tert-butyldimethylsilyloxy)-3-methoxy-1-(pyridin-2-yl)butan-2-yl]-2-methylpropane-2-sulfinamide as a single diastereomer (0.085 g)was added tetrahydrofuran (1 mL). To the mixture was added a solution of tetra-n-butylammonium fluoride in tetrahydrofuran (1 mol/L, 0.25 mL) under ice-cooling, and the mixture was stirred for 30 minutes. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford (R)-N-[(2R,3S)-4-(benzyloxy)-1-hydroxy-3-ethoxy-1-(pyridin-2-yl)butan-2-yl]-2-methylpropane-2-sulfinamide (0.033 g) as a low polarity diastereomer. To a solution of the product (0.033 g) in tetrahydrofuran (1 mL) was added sodium hydride (60% dispersion in oil, 0.003 g) under ice-cooling, and the mixture was stirred for 30 minutes. To the mixture was added iodomethane (0.046 g), and the mixture was stirred at room temperature overnight. To the reaction mixture was added ice, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (R)-N-[(2R,3S)-4-(benzyloxy)-1,3-dimethoxy-1-(pyridin-2-yl)butan-2-yl]-2-methylpropane-2-sulfinamide (0.018 g). To a solution of the product (0.018 g) in 1,4-dioxane (1 mL) was added a solution of hydrogen chloride in 1,4-dioxane (4 mol/L, 1 mL), and the mixture was stirred at room temperature for 5 hours. The reaction mixture was concentrated under reduced pressure, and the residue was washed with n-hexane to afford the title compound (0.013 g). Structural formula, spectral data and purification condition are shown in Table 40.

REFERENCE EXAMPLE 2-43-2

Reference Example 2-43-2 was synthesized in a manner similar to that of Reference Example 2-43-1 by using the corresponding materials. Structural formula, spectral data and purification condition are shown in Table 40.

REFERENCE EXAMPLE 2-44-1

A mixture of (2R,3R)-2-amino-4-methoxy-3-(pyridin-2-yl)butan-1-ol and (2R,3S)-2-amino-4-methoxy-3-(pyridin-2-yl)butan-1-ol To a solution of 2-bromolpyridine (0.72 g) in tetrahydrofuran (10 mL) was added a solution of n-butyllithium in n-hexane (2.6 mol/L, 1.7 mL) at −78° C., and the mixture was stirred for 10 minutes. To the mixture was added a solution of (4S)-4-formyl-2,2-dimethyl-1,3-oxazolidine-3-carboxylic acid tert-butyl ester (1.0 g) in tetrahydrofuran (5 mL) at the same temperature, and the mixture was further stirred for 1.5 hours. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of (4S)-4-[(R)-hydroxy(pyridin-2-yl)methyl]-2,2-dimethyl-1,3-oxazolidine-3-carboxylic acid tert-butyl ester and (4S)-4-[(S)-hydroxy(pyridin-2-yl)methyl]-2,2-dimethyl-1,3-oxazolidine-3-carboxylic acid tert-butylester (1.16 g). To a mixture of the product (1.16 g) and dichloromethane (10 mL) was added Dess-Martin periodinane (2.39 g), and the mixture was stirred at room temperature for 2 days. To the reaction mixture were added an aqueous solution of sodium thiosulfate (1mol/L) and a saturated aqueous solution of sodium bicarbonate, and the crude product was extracted with dichloromethane. The organic layer was washed with brine, and dried over anhydrous magnesium sulfate. The solvent was removed under reduced pressure, and the residue was purified by silica gel column chromatography (eluent: ethyl acetate/n-hexane) to afford (4S)-2,2-dimethyl-4-(pyridine-2-carbonyl)-1,3-oxazolidine-3-carboxylic acid test-butyl ester (1.02 g). To a suspension of (methoxymethyl)triphenylphosphonium chloride (447 mg) in tetrahydrofuran (3 mL) was added a solution of potassium bis(trimethylsilyl)amide in tetrahydrofuran (1.0 mol/L, 1.2 mL), and the mixture was stirred at room temperature for 1 hour. To the mixture was added (4S)-2,2-dimethyl-4-(pyridine-2-carbonyl)-1,3-oxazolidine-3-carboxylic acid tert-butyl ester (200 mg) under ice-cooling, and the mixture was stirred at room temperature for 1 hour. To the reaction mixture was added a saturated aqueous solution of ammonium chloride. The organic layer was washed with brine, and dried over anhydrous magnesium sulfate. The solvent was removed under reduced pressure. The residue was purified by silica gel column chromatography (eluent: ethyl acetate/n-hexane) to afford (4R)-4-[2-methoxy-1-(pyridin-2-yl)ethenyl]-2,2-dimethyl-1,3-oxazolidine-3-carboxylic acid tert-butyl ester (100 mg). To a solution of the product (100 mg) in ethanol (3 mL) was added 10% palladium-carbon (50% wet, 10 mg), and the mixture was stirred under a hydrogen atmosphere overnight. The reaction mixture was filtered through a pad of celite, and the filtrate was concentrated under reduced pressure. The residue was purified by silica gel column chromatography (eluent: ethyl acetate/n-hexane) to afford a mixture of (4R)-4-[(1R)-2-methoxy-1-(pyridin-2-yl)ethyl]-2,2-dimethyl-1,3-oxazolidine-3-carboxylic acid tert-butyl ester and (4R)-4-[(1S)-2-methoxy-1-(pyridin-2-yl)ethyl]-2,2-dimethyl-1,3-oxazolidine-3-carboxylic acid tert-butyl ester (80 mg). To a mixture of the product (80 mg) and methanol (1 mL) was added a solution of hydrogen chloride in 1,4-dioxane (4 mol/L, 1 mL), and stirred at room temperature for 2 hours. The reaction mixture was concentrated under reduced pressure, and the residue was purified by aminopropyl silica gel column chromatography (eluent: ethyl acetate/methanol) to afford the title compound (40 mg). Structural formula, spectral data and purification condition are shown in Table 40.

REFERENCE EXAMPLE 2-45-1

(2R,3S)-4-(tert-Butyldiphenylsilyloxy)-3-methoxy-1-(1H-pyrazol-1-yl)butan-2-amine To a mixture of (1S)-2-(benzyloxy)-1-((4R)-2,2-dimethyl-1,3-dioxolan-4-yl)ethan-1-ol (9.7 g), phthalimide (11.31 g) and triphenylphosphine (20.17 g) in tetrahydrofuran (70 mL) was added a solution of azodicarboxylic acid diethyl ester in toluene (2.2 mol/L, 35 mL), and the mixture was stirred at room temperature for 6 hours. The mixture was concentrated under reduced pressure, and the residue was purified by silica gel column chromatography (eluent: ethyl acetate/n-hexane). To the purified product was added diethyl ether, and the solid was removed by filtration. The filtrate was concentrated under reduced pressure to afford N-[(1R)-2-(benzyloxy)-1-((4S)-2,2-dimethyl-1,3-dioxolan-4-yl)ethyl]phthalimide (10.6 g). To a solution of the product (10.6 g) in ethanol (50 mL) was added hydrazine monohydrate (19.24 g), and the mixture was stirred at 80° C. for 1 hour. To the reaction mixture was added a saturated aqueous solution of sodium bicarbonate, and the crude product was extracted with ethyl acetate. The extract was washed with brine, and dried over sodium sulfate. The solvent was removed under reduced pressure. To a solution of the residue in ethanol (20 mL) were added di-tert-butyl dicarbonate (6.71 g) and 20% palladium hydroxide-carbon (50% wet, 2 g), and the mixture was stirred at 50° C. under a hydrogen atmosphere for 2 hours. The reaction mixture was filtered through a pad of celite, and the filtrate was concentrated under reduced pressure. The residue was purified by silica gel column chromatography (eluent: ethyl acetate/n-hexane) to afford N-[(1R)-1-((4S)-2,2-dimethyl-1,3-dioxolan-4-yl)-

2-hydroxyethyl]carbamic acid tert-butyl ester (4.9 g). To a solution of N-[(1R)-1-((4S)-2,2-dimethyl-1,3-dioxolan-4-yl)-2-hydroxyethyl]carbamic acid tert-butyl ester (12.6 g) in dichloromethane (70 mL) were added triethylamine (9.76 g) and methanesulfonyl chloride (7.18 g) at 0° C., and the mixture was stirred at room temperature for 1 hour. To the reaction mixture was added a saturated aqueous solution of sodium bicarbonate, and the crude product was extracted with dichloromethane. The extract was washed with brine, and dried over sodium sulfate. The extract was concentrated under reduced pressure. To a solution of the residue in N,N-dimethylformamide (100 mL) were added cesium carbonate (47.13 g) and pyrazole (6.57 g), and the mixture was stirred at 80° C. for 4 hours. To the reaction mixture was added a saturated aqueous solution of ammonium chloride, and the crude product was extracted with ethyl acetate. The extract was washed with water and brine, and dried over sodium sulfate. The solvent was removed under reduced pressure. The residue was purified by silica gel column chromatography (eluent: ethyl acetate/n-hexane) to afford N-[(1R)-1-((4S)-2,2-dimethyl-1,3-dioxolan-4-yl)-2-(1H-pyrazol-1-yl)ethyl]carbamic acid tert-butyl ester (6.5 g). To a mixture of the product (6.5 g), methanol (21 mL) and water (7 mL) was added trifluoroacetic acid (1.6 mL), and the mixture was stirred at room temperature for 2 days. The reaction mixture was concentrated under reduced pressure, and the residue was purified by silica gel column chromatography (eluent:ethyl acetate/methanol) to afford N-[(2R,3S)-3,4-dihydroxy-1-(1H-pyrazol-1-yl)butan-2-yl]carbamic acid tert-butyl ester (5.0 g). To a solution of the product (5.0 g) in N,N-dimethylformamide (20 mL) were added imidazole (1.71 g) and tert-butyldiphenylchlorosilane (6.31 g) at 0° C., and the mixture was stirred at the same temperature for 3 hours. To the reaction mixture was added a saturated aqueous solution of sodium bicarbonate, and the crude product was extracted with ethyl acetate. The extract was washed with water and brine, and dried over sodium sulfate. The solvent was removed under reduced pressure, and the residue was purified by silica gel column chromatography (eluent: ethyl acetate/n-hexane) to afford. N-[(2R,3S)-4-(tert-butyldiphenylsilyloxy)-3-hydroxy-1-(1H-pyrazol-1-yl)butan-2-yl]carbamic acid tert-butyl ester (7.8 g). To a mixture of the product (7.8 g), iodomethane (2.61 g), tetrahydrofuran (30 mL) and N,N-dimethylformamide (3 mL) was added portionwise sodium hydride (60% dispersion in oil, 642 mg) at 0° C., and the mixture was stirred at the same temperature for 4 hours. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford N-[(2R,3S)-4-(tert-butyldiphenylsilyloxy)-3-methoxy-1-(1H-pyrazol-1-yl)butan-2-yl]carbamic acid tert-butyl ester (6.8 g). To a solution of the product (6.8 g) in dichloromethane (20 mL) was added trifluoroacetic acid (10 mL), and the mixture was stirred at room temperature for 3 hours. The reaction mixture was concentrated under reduced pressure. To the residue was added an aqueous solution of sodium hydroxide (2 mol/L), and the crude product was extracted with ethyl acetate. The extract was washed with water and brine, and dried over sodium sulfate. The solvent was removed under reduced pressure, and the residue was purified by aminopropyl silica gel column chromatography (eluent: ethyl acetate/n-hexane) to afford the title compound (4.5 g). Structural formula, spectral data and purification condition are shown in Table 41.

REFERENCE EXAMPLES 2-45-2 TO 2-45-8

Reference Examples 2-45-2 to 2-45-8 were synthesized in a manner similar to that of Reference Example 2-45-1 by using the corresponding materials. Structural formula, spectral data and purification condition are shown in Table 41.

REFERENCE EXAMPLE 2-46-1

N-[(2S,3S)-4-(tert-Butyldiphenylsilyloxy)-1-iodo-3-methoxybutan-2-yl]carbamic acid tert-butyl ester To a solution of (4S)-4-[(1R)-1-azido-2-(benzyloxy)ethyl]-2,2-dimethyl-1,3-dioxolane (2.3 g) in methanol (5 mL) was added a solution of hydrogen chloride in 1,4-dioxane (4 mol/L, 10 mL), and the mixture was stirred at room temperature for 4 hours. To the reaction mixture was added a solution of hydrogen chloride in 1.4-dioxane (4 mol/L, 10 mL), and the mixture was stirred at 60° C. for 2 hours. The reaction mixture was concentrated under reduced pressure. To a solution of the residue in N,N-dimethylformamide (25 mL) were added imidazole (678 mg) and tert-butyldiphenylchlorosilane (2.51 g) at 0° C., and the mixture was stirred at the same temperature for 2 hours. To the reaction mixture was added a saturated aqueous solution of sodium bicarbonate, and the crude product was extracted with ethyl acetate. The extract was washed with water and brine, and dried over sodium sulfate. The solvent was concentrated under reduced pressure, and the residue was purified by silica gel column chromatography (eluent: ethyl acetate/n-hexane) to afford (2S,3R)-3-azido-4-(benzyloxy)-1-(tert-butyldiphenylsilyloxy)butan-2-ol (4.58 g). To a mixture of the product (4.58 g), N,N-dimethylformamide (10 mL) and iodomethane (2.05 g) was added sodium hydride (60% dispersion in oil, 425 mg) at 0° C., and the mixture was stirred at the same temperature for 1 hour. To the reaction mixture was added a saturated aqueous solution of ammonium chloride, and the crude product was extracted with ethyl acetate. The extract was washed with water and brine, and dried over sodium sulfate. The solvent was removed under reduced pressure, and the residue was purified by silica gel column chromatography (eluent: ethyl acetate/n-hexane) to afford [(2S,3R)-3-azido-4-(benzyloxy)-2-methoxybutyl](tert-butdiphenylsilyl)ether (4.3 g). A mixture of the product (4.3 g), di-tert-butyl dicarbonate (2.3 g), 20% palladium hydroxide-carbon (50% wet, 2 g) and ethanol (30 mL) was stirred at 60° C. under a hydrogen atmosphere for 13 hours. The reaction mixture was filtered through a pad of celite, and the filtrate was concentrated under reduced pressure. The residue was purified by silica gel column chromatography (eluent: ethyl acetate/n-hexane) to afford N-[(2R,3S)-4-(tert-butyldiphenylsilyloxy)-1-hydroxy-3-methoxybutan-2-yl]carbamic acid tert-butyl ester (2.88 g). To a mixture of the product (2.88 g), imidazole (662 mg), triphenylphosphine (2.55 g) and tetrahydrofuran (10 mL) was added iodine (2.16 g) at 0° C., and the mixture was stirred at room temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford the title compound (3.08 g). Structural formula, spectral data and purification condition are shown in Table 42.

REFERENCE EXAMPLE 2-46-2

Reference Example 2-46-2 was synthesized in a manner similar to that of Reference Example 2-46-1 by using the corresponding materials. Structural formula, spectral data and purification condition are shown in Table 42.

REFERENCE EXAMPLE 2-47-1

(2S,3R)-3-Amino-2-methoxy-4-(pyrimidin-2-yl) butan-1-ol

A mixture of N-[(2S,3S)-4-(tert-butyldiphenylsilyloxy)-1-iodo-3-methoxybutan-2-yl]carbamic acid tert-butyl ester (1.09 g) and zinc (268 mg) in N,N-dimethylformamide (10 mL) was stirred at room temperature under an argon atmosphere for 2 hours. To the mixture were added 2-bromopyrimidine (296 mg) and bis(triphenylphosphine)palladium (II) dichloride (131 mg), and the mixture was stirred at room temperature for 4 hours. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford N-[(2R,3S)-4-(tert-butyldiphenylsilyloxy)-3-methoxy-1-(pyrimidin-2-yl)butan-2-yl]carbamic acid tert-butyl ester (455 mg). A mixture of the product (455 mg) and a solution of hydrogen chloride in 1,4-dioxane (4 mol/L, 5 mL) was stirred at 50° C. for 2 days. The reaction mixture was concentrated under reduced pressure. To a solution of the residue in tetrahydrofuran (1 mL) was added a solution of tetra-n-butylammonium fluoride in tetrahydrofuran (1 mol/L, 1 mL) and the mixture was stirred at room temperature for 30 minutes. The solution was concentrated under reduced pressure, and the residue was purified by aminopropyl silica gel column chromatography (eluent: ethyl acetate/methanol) to afford the title compound (150 mg). Structural formula, spectral data and purification condition are shown in Table 42.

REFERENCE EXAMPLE 2-48-1

(2R,3S)-4-(tert-Butyldiphenylsilyloxy)-3-methoxy-1-(pyrimidin-2-yl)butan-2-amine A mixture of N-[(2S,3S)-4-(tert-butyldiphenylsilyloxy)-1-iodo-3-methoxybutan-2-yl]carbamic acid tert-butyl ester (600 mg) and zinc (148 mg) in N,N-dimethylformamide (5 mL) was stirred at room temperature under an argon atmosphere for 2 hours. To the mixture were added 2-bromopyrimidine (163 mg) and bis(triphenylphosphine)palladium (II) dichloride (72 mg), and the mixture was stirred at room temperature for 3 days. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford N-[(2R,3S)-4-(tert-butyldiphenylsilyloxy)-3-methoxy-1-(pyrimidin-2-yl)butan-2-yl]carbamic acid tert-butyl ester (290 mg). To a solution of the product (290 mg) in dichloromethane (2 mL) was added trifluoroacetic acid (1 mL), and the mixture was stirred at room temperature for 1 hour. The reaction mixture was concentrated under reduced pressure, and the residue was purified by aminopropyl silica gel column chromatography (eluent: ethyl acetate/n-hexane) to afford the title compound (150 mg). Structural formula, spectral data and purification condition are shown in Table 42.

REFERENCE EXAMPLES 2-48-2 TO 2-48-5

Reference Examples 2-48-2 to 2-48-5 were synthesized in a manner similar to that of Reference Example 2-48-1 by using the corresponding materials. Structural formula, spectral data and purification condition are shown in Table 42.

REFERENCE EXAMPLE 2-49-1

(2R,3S)-4-(tert-Butyldiphenylsilyloxy)-1-(3-fluoropyridin-2-yl)-3-methoxybutan-2-amine trifluoroacetate A mixture of N-[(2S,3S)-4-(tert-butyldiphenylsilyloxy)-1-iodo-3-methoxybutan-2-yl]carbamic acid tert-butyl ester (200 mg), zinc (49 mg) and N,N-dimethylformamide (5 mL) was stirred at room temperature under an argon atmosphere for 2 hours. To the mixture were added 2-bromo-3-fluoropyridine (60 mg) and bis[di-tert-butyl(4-dimethylaminophenyl)phosphine]dichloropalladium (II) (24 mg), and the mixture was stirred at room temperature for 6 hours. To the mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford N-[(2R,3S)-4-(tert-butyldiphenylsilyloxy)-1-(3-fluoropyridin-2-yl)-3-methoxybutan-2-yl]carbamic acid tert-butyl ester (45 mg). To a solution of the product (45 mg) dichloromethane (1 mL) was added trifluoroacetic acid (0.2 mL), and the mixture was stirred at room temperature for 1 hour. The reaction mixture was concentrated under reduced pressure to afford the title compound (55 mg). Structural formula, spectral data and purification condition are shown in Table 43.

REFERENCE EXAMPLE 2-49-2

Reference Example 2-49-2 was synthesized in a manner similar to that of Reference Example 2-49-1 by using the corresponding materials. Structural formula, spectral data and purification condition are shown in Table 43.

REFERENCE EXAMPLE 2-50-1

(2S,3R)-4-(tert-Butyldiphenylsilyloxy)-3-methoxy-1-(pyrimidin-2-y l)butan-2-amine To a solution of (2R)-2-((4S)-2,2-dimethyl-1,3-dioxolan-4-yl)-2-hydroxyacetic acid methyl ester (5.0 g) in dichloromethane (50 mL) were added N,N-diisopropylethylamine (6.8 g) and methanesulfonyl chloride (3.91 g) at 0° C., and the mixture was stirred at the same temperature for 1 hour.

To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in N,N-dimethylformamide (40 mL) was added sodium azide (3.42 g), and the mixture was stirred at 50° C. for 15 hours. To the reaction mixture was added water, and the crude product was extracted with ethyl acetate. The extract was washed with water and brine, and dried over sodium sulfate. The solvent was removed under reduced pressure. The residue was purified by silica gel column chromatography (eluent: ethyl acetate/n-hexane) to afford (2R)-2-azido-2-((4R)-2,2-dimethyl-1,3-dioxolan-4-yl)acetic acid methyl ester (1.3 g). To a solution of the product (1.3 g) in methanol (20 mL) was added sodium borohydride (457 mg) at 0° C., and the mixture was stirred at the same temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford (2S)-2-azido-2-((4R)-2,2-dimethyl-1,3-dioxolan-4-yl)ethan-1-ol (1.1 g). To a solution of the product (1.1 g) in N,N-dimethylformamide (10 mL) was added sodium hydride (60% dispersion in oil, 380 mg) at 0° C., and the mixture was stirred at room temperature for 30 minutes. To the mixture was added benzylbromide (1.21 g) at 0° C., and the mixture was stirred at the same temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford (4R)-4-[(1S)-1-azido-2-(benzyloxy)ethyl]-2,2-dimethyl-1,3-dioxolane (1.61 g). To the product (1.61 g) was added a solution of hydrogen chloride in 1,4-dioxane (4 mol/L, 5 mL), and the mixture was stirred at room temperature for 3 days. The reaction mixture was concentrated under reduced pressure to afford (2R,3S)-3-azido-4-(benzyloxy)butane-1,2-diol (1.45 g). To a solution of the product (1.45 g) in N,N-dimethylformamide (10 mL) were added imidazole (541 mg) and tert-butyldiphenylchlorosilane (1.85 g) at 0° C., and the mixture was stirred at the same temperature for 1 hour. To the reaction mixture was added a saturated aqueous solution of sodium bicarbonate, and the crude product was extracted with ethyl acetate. The extract was washed with water and brine, and dried over sodium sulfate. The solvent was removed under reduced pressure, and the residue was purified by silica gel column chromatography (eluent: ethyl acetate/n-hexane) to afford (2R,3S)-3-azido-4-(benzyloxy)-1-(tert-butyldiphenylsilyloxy)butan-2-ol (2.49 g). To a mixture of the product (2.49 g), iodomethane (966 mg) and N,N-dimethylformamide (5 mL) was added portionwise sodium hydride (60% dispersion in oil, 315 mg) at 0° C., and the mixture was stirred at the same temperature for 1 hour. To the reaction mixture was added a saturated aqueous solution of ammonium chloride, and the crude product was extracted with ethyl acetate. The extract was washed with water and brine, and dried over sodium sulfate. The solvent was removed under reduced pressure, and the residue was purified by silica gel column chromatography (eluent: ethyl acetate/n-hexane) to afford [(2R,3S)-3-azido-4-(benzyloxy)-2-methoxybutyl](tert-butyldiphenylsilyl) ether (1.99 g). A mixture of the product (1.99 g), di-tert-butyl dicarbonate (893 mg), 20% palladium hydroxide-carbon (50% wet, 500 mg) and methanol (10 mL) was stirred at 50° C. under a hydrogen atmosphere for 12 hours. The reaction mixture was filtered through a pad of celite, and the filtrate was concentrated under reduced pressure. The residue was purified by silica gel column chromatography (eluent: ethyl acetate/n-hexane) to afford N-[(2S,3R)-4-(tert-butyldiphenylsilyloxy)-1-hydroxy-3-methoxybutan-2-yl]carbamic acid tert-butyl ester (1.73 g). To a mixture of the product (1 g), imidazole (230 mg), triphenylphosphine (886 mg) and tetrahydrofuran (5 mL) was added iodine (750 mg) at 0° C., and the mixture was stirred at room temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford N-[(2R,3R)-4-(tert-butyldiphenylsilyloxy)-1-iodo-3-methoxybutan-2-yl]carbamic acid tert-butyl ester (1.1 g). A mixture of the product (500 mg) and zinc (123 mg) in N,N-dimethyl formamide (5 mL) was stirred at room temperature under an argon atmosphere for 2 hours. To the mixture were added 2-bromopyrimidine (136 mg) and bis(triphenylphosphine)palladium (II) dichloride (60 mg), and the mixture was stirred at room temperature for 4 hours. To the reaction mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford N-[(2S,3R)-4-(tert-butyldiphenylsilyloxy)-3-methoxy-1-(pyrimidin-2-yl)butan-2-yl]carbamic acid tert-butyl ester (320 mg). To a solution of the product (320 mg) in dichloromethane (2 mL) was added trifluoroacetic acid (0.5 mL), and the mixture was stirred at room temperature for 13 hours. The reaction mixture was concentrated under reduced pressure, and the residue was purified by aminopropyl silica gel column chromatography (eluent: ethyl acetate/n-hexane) to afford the title compound (90 mg) Structural formula, spectral data and purification condition are shown in Table 43.

REFERENCE EXAMPLE 2-50-2

Reference Example 2-50-2 was synthesized in a manner similar to that of Reference Example 2-50-1 by using the corresponding materials. Structural formula, spectral data and purification condition are shown in Table 43.

REFERENCE EXAMPLE 2-51-1

(2S)-2-Amino-3,3-difluoro-3-(pyridin-2-yl)propan-1-ol

To a solution of (R)-N-[(1E)-2-(tert-butyldimethylsilyloxy)ethylidene]-2-methylpropane-2-sulfinamide (0.330 g) and 2-difluoromethylpyridine (0.153 g) in tetrahydrofuran (6 mL) was added a solution of lithium diisopropylamide in tetrahydrofuran (1.13 mol/L, 1.3 mL) at −78° C. and the mixture was stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (R)-N-[(2S)-3-(tert-butyldimethylsilyloxy)-1,1-difluoro-1-(pyridin-2-yl)propan-2-yl]-2-methylpropane-2-sulfinamide (0.064 g). To a solution of the product (0.064 g) in 1,4-dioxane (1 mL) was added a solution of hydrogen chloride in 1,4-dioxane (4 mol/L, 1 mL), and the mixture was stirred at room temperature for 5 hours. The reaction mixture was concentrated, and the residue was purified by aminopropyl silica gel column chromatography (eluent: methanol/ethyl acetate) to afford the title compound (0.026 g). Structural formula, spectral data and purification condition are shown in Table 43.

REFERENCE EXAMPLES 2-51-2 TO 2-51-3

Reference Examples 2-51-2 to 2-51-3 were synthesized in a manner similar to that of Reference Example 2-51-1 by using the corresponding materials. Structural formula, spectral data and purification condition are shown in Table 43.

REFERENCE EXAMPLE 2-52-1

(2S,3S)-4-(Benzyloxy)-1,1-difluoro-3-methoxy-1-(pyridin-2-yl)butan-2-amine

To a solution of (R)-N-[(1E,2S)-3-(benzyloxy)-2-methoxypropylidene]-2-methylpropane-2-sulfinamide (0.122 g) and 2-difluoromethylpyridine (0.053 g) in tetrahydrofuran (4 mL) was added a solution of lithium diisopropylamide in tetrahydrofuran (1.13 mol/L, 0.36 mL) at −78° C., and the mixture was stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent:ethyl acetate/methanol) to afford (R)-N-[(2S,3S)-4-benzyloxy-1,1-difluoro-3-methoxy-1-(pyridin-2-yl)butan-2-yl]-2-methylpropane-2-sulfinamide (0.036 g). To a solution of the product (0.036 g) in 1,4-dioxane (1 mL) was added a solution of hydrogen chloride in 1,4-dioxane (4 mol/L, 1 mL), and the mixture was stirred at room temperature for 5 hours. The reaction mixture was concentrated, and the residue was purified by aminopropyl silica gel column chromatography (eluent: methanol/ethyl acetate) to afford the title compound (0.041 g). Structural formula, spectral data and purification condition are shown in Table 43.

REFERENCE EXAMPLE 2-53-1

(2S)-2-Amino-3-(pyridin-2-yl)butane-1,3-diol

To a solution of 2-bromolpyridine (0.885 g) in tetrahydrofuran (15 mL) was added a solution of n-butyllithium in n-hexane (2.6 mol/L, 1.9 mL) at −78° C., and the mixture was stirred for 30 minutes. To the mixture was added a solution of (4S)-4-formyl-2,2-dimethyl-1,3-oxazolidine-3-carboxylic acid tert-butyl ester (0.917 g) in tetrahydrofuran (15 mL) at the same temperature, and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (4S)-4-[hydroxy(pyridin-2-yl)methyl]-2,2-dimethyl-1,3-oxazolidine-3-carboxylic acid tert-butylester as a mixture of diastereomers (0.903 g). The mixture of diastereomers (0.903 g) was dissolved in dichloromethane (30 mL). To the mixture was added Dess-Martin periodinane (1.491 g) under ice-cooling, and the mixture was stirred at room temperature overnight. To the reaction mixture were added 10% aqueous sodium sulfite solution and a saturated aqueous solution of sodium bicarbonate, and the crude product was extracted with ethyl acetate. The organic layer was washed with brine, and dried over anhydrous magnesium sulfate. The solvent was removed under reduced pressure to afford (4S)-2,2-dimethyl-4-(pyridine-2-carbonyl)-1,3-oxazolidine-3-carboxylic acid tert-butyl ester (0.805 g). To a solution of the product (0.200 g) in tetrahydrofuran (1 mL) was added a solution of methylmagnesium bromide in diethyl ether (3 mol/L, 0.3 mL) at −78° C., and the mixture was stirred at the same temperature for 1 hour. To the reaction mixture was added a saturated aqueous solution of ammonium chloride, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane) to afford (4S)-4-[1-hydroxy-1-(pyridin-2-yl)ethyl]-2,2-dimethyl-1,3-acid tert-butyl ester as a mixture of diastereomers (0.205 g). To a solution of the product (0.205 g) in 1,4-dioxane (3 mL) was added a solution of hydrogen chloride in 1,4-dioxane (4 mol/L, 3 mL), and the mixture was stirred at room temperature for 5 hours. The reaction mixture was concentrated under reduced pressure, and the residue was purified by aminopropyl silica gel column chromatography (eluent: methanol/ethyl acetate) to afford the title compound (0.060 g). Structural formula, spectral data and purification condition are shown in Table 44.

REFERENCE EXAMPLE 2-53-2

Reference Example 2-53-2 was synthesized in a manner similar to that of Reference Example 2-53-1 by using the corresponding materials. Structural formula, spectral data and purification condition are shown in Table 44.

REFERENCE EXAMPLE 2-54-1

(2S)-2-Amino-3-methoxy-3-(pyridin-2-yl)butan-1-ol

A diastereomeric mixture of (4S)-4-[1-hydroxy-1-(pyridin-2-yl)ethyl]-2,2-dimethyl-1,3-oxazolidine-3-carboxylic acid tert-butyl ester (0.201 g) was dissolved in tetrahydrofuran (3 mL). To the mixture was added sodium hydride (60% dispersion in oil, 0.037 g) under ice-cooling. The reaction mixture was stirred for 30 minutes. To the mixture was added idomethane (0.352 g), and the mixture was stirred at room temperature overnight. To the reaction mixture was added ice, and the crude product was extracted with ethyl acetate. The organic layer was washed with brine, and dried over anhydrous magnesium sulfate. The solvent was removed under reduced pressure to afford (4S)-4-[1-methoxy-1-(pyridin-2-yl)ethyl]-2,2-dimethyl-1,3-oxazolidine-3-carboxylic acid tert-butylester (0.169 g) as a mixture of diastereomers. The product (0.164 g) was dissolved in 1,4-dioxane (2 mL). To the mixture was added a solution of hydrogen chloride in 1,4-dioxane (4 mol/L, 2 mL), and the mixture was stirred at room temperature for 5 hours. The reaction mixture was concentrated under reduced pressure, and the residue was purified by aminopropyl silica gel column chromatography (eluent: methanol/ethyl acetate) to afford the title compound (0.025 g) Structural formula, spectral data and purification condition are shown in Table 44.

REFERENCE EXAMPLE 2-55-1

(2S)-2-Amino-3-fluoro-3-(pyridin-2-yl)propan-1-ol

To a solution of 2-bromopyridine (0.398 g) in tetrahydrofuran (8 mL) was added a solution of n-butyllithium in n-hexane (2.6 mol/L, 0.8 mL) at −78° C. and the mixture was stirred for 30 minutes. To the mixture was added a solution of (4S)-4-formyl-2,2-dimethyl-1,3-oxazolidine-3-carboxylic acid tert-butyl ester (0.412 g) in tetrahydrofuran (8 mL) at the same temperature, and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (4S)-4-[hydroxy(pyridin-2-yl)methyl]-2,2-dimethyl-1,3-oxazolidine-3-carboxylic acid tert-butylester (0.317 g) as a mixture of diastereomers. The product (0.317 g) was dissolved in dichloromethane (4 mL). To the mixture was added Deoxo-Fluor® (0.455 g) under ice-cooling, and the mixture was stirred at room temperature for 30 minutes. To the reaction mixture was added a saturated aqueous solution of sodium bicarbonate, and the crude product was extracted with dichloromethane. The solvent was removed under reduced pressure, and the residue was purified by silica gel column chromatography (eluent: ethyl acetate/n-hexane) to afford (4S)-4-[fluoro(pyridin-2-yl)methyl]-2,2-dimethyl-1,3-oxazolidine-3-carboxylic acid tert-butyl ester (0.145 g) as a single diastereomer. To the product (0.145 g) in 1,4-dioxane (3 mL) was added a solution of hydrogen chloride in 1,4-dioxane (4 mol/L, 3 mL), and the mixture was stirred at room temperature for 5 hours. The reaction mixture was concentrated under reduced pressure, and the residue was purified by aminopropyl silica gel column chromatography (eluent: methanol/ethyl acetate) to afford the title compound (0.054 g). Structural formula, spectral data and purification condition are shown in Table 44.

REFERENCE EXAMPLE 2-56-1

(2S,3R)-3-Amino-1-methoxy-4-(pyrimidin-2-yl)butan-2-ol hydrochloride

A mixture of N-[(1R)-2-(benzyloxy)-1-((4S)-2,2-dimethyl-1,3-dioxolan-4-yl)ethyl]carbamic acid tert-butyl ester (550 mg), methanol (2 mL), water (0.5 mL) and trifluoroacetic acid (60 µL) was stirred at room temperature for 12 hours. The reaction mixture was concentrated under reduced pressure. The residual water was removed by azeotropic distillation with toluene. To a solution of the residue in N,N-dimethylformamide (2 mL) were added imidazole (149 mg) and tert-butyldiphenylchlorosilane (473 mg) at 0° C., and the mixture was stirred at the same temperature for 2 hours. To the reaction mixture was added a saturated aqueous solution of sodium bicarbonate, and the crude product was extracted with ethyl acetate. The extract was washed with water and brine, and dried over sodium sulfate. The solvent was removed under reduced pressure. To a solution of the residue in toluene (5 mL) were added p-toluenesulfonic acid monohydrate (30 mg) and 2,2-dimethoxypropane (1.9 mL), and the mixture was stirred at 85° C. for 6 hours. To the reaction mixture was added a saturated aqueous solution of sodium bicarbonate, and the crude product was extracted with ethyl acetate. The extract was washed with brine, and dried over sodium sulfate. The solvent was removed under reduced pressure. To a solution of the residue in tetrahydrofuran (3 mL) was added a solution of tetra-n-butylammonium fluoride in tetrahydrofuran (1 mol/L, 3.13 mL) at 0° C., and the mixture was stirred at room temperature for 1 hour. To the reaction mixture was added a saturated aqueous solution of sodium bicarbonate, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford (4R,5S)-4-[(benzyloxy)methyl]-5-(hydroxymethyl)-2,2-dimethyl-1,3-oxazolidine-3-carboxylic acid tert-butyl ester (450 mg). To a solution of the product (450 mg) in N,N-dimethylformamide (5 mL) was added sodium hydride (60% dispersion in oil, 77 mg) at 0° C., and the mixture was stirred at room temperature for 20 minutes. To the mixture was added iodomethane (218 mg) at 0° C., and the mixture was stirred at room temperature for 30 minutes. To the reaction mixture was added a saturated aqueous solution of ammonium chloride, and the crude product was extracted with ethyl acetate. The extract was washed with water and brine, and dried over sodium sulfate. The solvent was removed under reduced pressure. The residue was purified by silica gel column chromatography (eluent: ethyl acetate/n-hexane) to afford (4R,5S)-4-[(benzyloxy)methyl]-5-(methoxymethyl)-2,2-dimethyl-1,3-oxazolidine-3-carboxylic acid tert-butyl ester (420 mg). A mixture of the product (420 mg), 20% palladium hydroxide-carbon (50% wet, 50 mg) and methanol (5 mL) was stirred at room temperature under a hydrogen atmosphere for 2 hours. The reaction mixture was filtered through a pad of celite, and the filtrate was concentrated under reduced pressure. The residue was purified by silica gel column chromatography (eluent: ethyl acetate/n-hexane) to afford (4R,5S)-4-(hydroxymethyl)-5-(methoxymethyl)-2,2-dimethyl-1,3-oxazolidine-3-carboxylic acid tert-butyl ester (310 mg). To a mixture of the product (310 mg), imidazole (123 mg), triphenylphosphine (473 mg) and tetrahydrofuran (5 mL) was added iodine (400 mg) at 0° C., and the mixture was stirred at room temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure, and the residue was purified by silica gel column chromatography (eluent: ethyl acetate/n-hexane) to afford (4S,5S)-4-(iodomethyl)-5-(methoxymethyl)-2,2-dimethyl-1,3-oxazolidine-3-carboxylic acid tert-butyl ester (370 mg). A mixture of the product (370 mg), zinc (138 mg) and N,N-dimethylformamide (5 mL) was stirred at room temperature under an argon atmosphere for 2 hours. To the mixture were added 2-bromopyrimidine (153 mg) and his(triphenylphosphine)palladium(II) dichloride (68 mg), and the mixture was stirred at room temperature for 15 hours. To the mixture was added a saturated aqueous solution of sodium bicarbonate, and the mixture was filtered through a pad of celite. The crude product was extracted with ethyl acetate. The extract was washed with water and brine, and dried over sodium sulfate. The solvent was removed under reduced pressure. The residue was purified by aminopropyl silica gel column chromatography (eluent: ethyl acetate/n-hexane) to afford (4R,5S)-5-(methoxymethyl)-2,2-dimethyl-4-(pyrimidin-2-ylmethyl)-1,3-oxazolidine-3-carboxylic acid tert-butyl ester (230 mg). To a solution of the product (230 mg) in methanol (1 mL) was added a solution of hydrogen chloride in 1,4-dioxane (4 mol/L, 1 mL), and the mixture was stirred at room temperature for 1 hour. The reaction mixture was concentrated under reduced pressure to afford the title compound (180 mg). Structural formula, spectral data and purification condition are shown in Table 44.

REFERENCE EXAMPLE 2-57-1

(2R,3S)-4-(Benzoloxy)-3-fluoro-1-(pyrimidin-2-yl)butan-2-amine

To a solution of (1S)-2-(benzyloxy)-1-[(4S)-2,2-dimethyl-1,3-dioxolan-4-yl]ethan-1-ol (1.4 g) in dichloromethane (10 mL) was added (diethylamino)sulfur trifluoride (1.34 g) at −78° C., and the mixture was stirred at the same temperature for 1 hour. The mixture was further stirred at room temperature for 2 hours. The reaction mixture was poured into a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (4S)-4-[(1R)-2-(benzyloxy)-1-fluoroethyl]-2,2-dimethyl-1,3-dioxolane (0.52 g). To the product (0.52 g) in methanol (3 mL) was added a solution of hydrogen chloride in 1,4-dioxane (4 mol/L, 3 mL), and the mixture was stirred at room temperature for 1 hour. The reaction mixture was concentrated under reduced pressure, and the residue was purified by silica gel column chromatography (eluent: ethyl acetate/n-hexane) to afford (2S,3R)-4-(benzyloxy)-3-fluorobutane-1,2-diol (0.21 g). To a solution of the product (210 mg) in N,N-dimethylformamide (2,5 mL) were added imidazole (169 mg) and tert-butyldiphenylchlorosilane (300 mg) at 0° C., and the mixture was stirred for 1 hour. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (2S,3R)-4-benzyloxy-1-(tert-butyldiphenylsilyloxy)-3-fluorobutan-2-ol (0.45 g). To a solution of the product (0.45 g) in dichloromethane (1 mL) were added N,N-diisopropylethylamine (0.322 g), 4-dimethylaminopyridine (12 mg) and methanesulfonyl chloride (0.125 g) at 0° C., and the mixture was stirred at room temperature for 0.5 hours. To the reaction mixture was added water, and the crude product was extracted with dichloromethane. The organic layer was washed with brine, and dried over anhydrous magnesium sulfate. The solvent was removed under reduced pressure. To the residue were added N,N-dimethylformamide (3 mL) and sodium azide (0.19 g), and the mixture was stirred at 100° C. overnight. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford [(2R,3S)-2-azido-4-benzyloxy-3-fluorobutan-1-yl](tert-butyldiphenylsilyl)ether (0.27 g). To a solution of the product (0.27 g) in ethanol (3 mL) were added di-tert-butyl dicarbonate (0.20 g) and 10% palladium-carbon (50% wet, 30 mg), and the mixture was stirred at room temperature under a hydrogen atmosphere overnight. The reaction mixture was filtered through a pad of celite, and the filtrate was concentrated under reduced pressure. To the residue were added tetrahydrofuran (3 mL) and a solution of tetra-n-butylammonium fluoride in tetrahydrofuran (1 mol/L, 670 µL), and the mixture was stirred at room temperature for 1 hour. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford N-[(2R,3S)-4-(benzyloxy)-3-fluoro-1-hydroxybutan-2-yl]carbamic acid tert-butyl ester (113 mg). To a mixture of the product (100 mg), imidazole (33 mg), triphenylphosphine (126 mg) and tetrahydrofuran (2 mL) was added iodine (122 mg) at 0° C., and the mixture was stirred at room temperature for 1 hour. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford N-[(2S,3S)-4-(benzyloxy)-3-fluoro-1-iodobutan-2-yl]carbamic acid tert-butyl ester (135 mg). A mixture of the product (135 mg), zinc (46 mg), one chip of iodine and N,N-dimethylformamide (1.5 mL) was stirred at room temperature under an argon atmosphere for 1 hour. To the mixture were added 2-bromopyrimidine (51 mg) and bis(triphenylphosphine)palladium(II) dichloride (22 mg), and the mixture was stirred at room temperature for 3 hours. To the reaction mixture was added a saturated aqueous solution of sodium bicarbonate, and the mixture was filtered through a pad of celite. To the filtrate was added water, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane) to afford N-[(2R,3S)-4-(benzyloxy)-3-fluoro-1-(pyrimidin-2-yl)butan-2-yl]carbamic acid tert-butyl ester (70 mg). To a solution of the product (70 mg) in methanol (1 mL) was added a solution of hydrogen chloride in 1,4-dioxane (4 mol/L, 1 mL), and the mixture was stirred at room temperature for 1 hour. The reaction mixture was concentrated under reduced pressure, and the residue was purified by aminopropyl silica gel column chromatography (eluent: ethyl acetate/methanol) to afford the title compound (50 mg). Structural formula, spectral data and purification condition are shown in Table 44.

REFERENCE EXAMPLES 2-57-2 TO 2-57-4

Reference Examples 2-57-2 to 2-57-4 were synthesized in a manner similar to that of Reference Example 2-57-1 by using the corresponding materials. Structural formula, spectral data and purification condition are shown in Table 44.

REFERENCE EXAMPLE 2-58-1

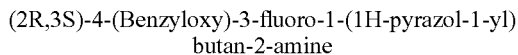
(2R,3S)-4-(Benzyloxy)-3-fluoro-1-(1H-pyrazol-1-yl)butan-2-amine

To a solution of (1S)-2-(benzyloxy)-1-[(4S)-2,2-dimethyl-1,3-dioxolan-4-yl]ethan-1-ol (1.4 g) in dichloromethane (10 mL) was added (diethylamino)sulfur trifluoride (1.34 g) at −78° C., and the mixture was stirred at the same temperature for 1 hour. The mixture was further stirred at room temperature for 2 hours. The reaction mixture was poured into a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (4S)-4-[(1R)-2-(benzyloxy)-1-fluoroethyl]-2,2-dimethyl-1,3-dioxolane (0.52 g). To a solution of the product (0.52 g) in methanol (3 mL) was added a solution of hydrogen chloride in 1,4-dioxane (4 mol/L, 3 mL), and the mixture was stirred at room temperature for 1 hour. The reaction mixture was concentrated under reduced pressure, and the residue was purified by silica gel column chromatography (eluent: ethyl acetate/n-hexane) to afford (2S,3R)-4-(benzyloxy)-3-fluorobutane-1,2-diol (0.21 g). To a solution of the product (50 mg) in toluene (1 mL) were added triphenylphosphine (67 mg) and a solution of azodicarboxylic acid diethyl ester in toluene (2.2 mol/L, 116 μL), and the mixture was stirred at 80° C. overnight. The reaction mixture was allowed to cool to room temperature, and then concentrated under reduced pressure. The residue was purified by silica gel column chromatography (eluent: ethyl acetate/n-hexane) to afford (2R)-2-[(1R)-2-(benzyloxy)-1-fluoroethyl]oxirane (40 mg). To a solution of the product (40 mg) in N,N-dimethylformamide (1 mL) were added cesium carbonate (133 mg) and pyrazole (15 mg), and the mixture was stirred at 100° C. for 1 hour. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (2S,3R)-4-(benzyloxy)-3-fluoro-1-(1H-pyrazol-1-yl)butan-2-ol (32 mg). To a solution of the product (32 mg) in dichloromethane (2 mL) were added N,N-diisopropylethylamine (40 mg), 4-dimethylaminopyridine (2 mg) and methanesulfonyl chloride (18 mg) and the mixture was stirred at room temperature for 0.5 hours. To the reaction mixture was added water, and the crude product was extracted with dichloromethane. The organic layer was washed with brine, and dried over anhydrous magnesium sulfate. The solvent was removed under reduced pressure. To the residue were added N,N-dimethylformamide (2 mL) and sodium azide (24 mg), and the mixture was stirred at 100° C. for 2 days. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford 1-[(2R,3S)-2-azido-4-(benzyloxy)-3-fluorobutyl]-1H-pyrazole (33 mg). To a solution of the product (33 mg) in ethanol (3 mL) was added 10% palladium-carbon (50% wet. 10 mg), and the mixture was stirred at room temperature under a hydrogen atmosphere for 2 hours. The reaction mixture was filtered through a pad of celite, and the filtrate was concentrated under reduced pressure. The residue was purified by aminopropyl silica gel column chromatography (eluent: ethyl acetate/methanol) to afford the title compound (21 mg). Structural formula, spectral data and purification condition are shown in Table 45.

REFERENCE EXAMPLES 2-58-2 TO 2-58-6

Reference Examples 2-58-2 to 2-58-6 were synthesized in a manner similar to that of Reference Example 2-58-1 by using the corresponding materials. Structural formula, spectral data and purification condition are shown in Table 45.

REFERENCE EXAMPLE 2-59-1

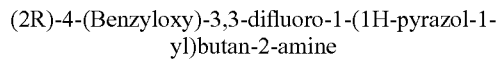
(2R)-4-(Benzyloxy)-3,3-difluoro-1-(1H-pyrazol-1-yl)butan-2-amine

To a solution of (2S)-4-(benzyloxy)-3,3-difluorobutane-1,2-diol (0.50 g) in toluene (1.5 mL) were added triphenylphosphine (678 mg) and a solution of azodicarboxylic acid diethyl ester in toluene (2.2 mol/L, 1.17 mL), and the mixture was stirred at 80° C. overnight. The reaction mixture was allowed to cool to room temperature, and then concentrated under reduced pressure. The residue was purified by silica gel column chromatography (eluent: ethyl acetate/n-hexane) to afford (2S)-2-[2-(benzyloxy)-1,1-difluoroethyl]oxirane (350 mg). To a solution of the product (350 mg) in N,N-dimethylformamide (1 mL) were added cesium carbonate (1.07 g) and pyrazole (123 mg), and the mixture was stirred at 100° C. for 1 hour. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (2S)-4-(benzyloxy)-3,3-difluoro-1-(1H-pyrazol-1-yl)butan-2-ol (400 mg). To a solution of the product (400 mg) in dichloromethane (4 mL) were added pyridine (1 mL) and trifluoromethanesulfonic anhydride (560 mg) at −20° C. and the mixture was stirred at the same temperature for 2 hours. To the reaction mixture was added hydrochloric acid (0.5 mol/L), and the crude product was extracted with dichloromethane. The organic layer was washed with brine, and dried over anhydrous magnesium sulfate. The solvent was removed under reduced pressure. To the residue were added N,N-dimethylformamide (3 mL) and sodium azide (278 mg), and the mixture was stirred at 100° C. for 1 day. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford 1-[(2R)-2-azido-4-(benzyloxy)-3,3-difluorobutyl]-1H-pyrazole (400 mg). To a solution of the product (400 mg) in ethanol (5 mL) was added 10% palladium-carbon (50% wet, 80 mg), and the mixture was stirred at room temperature under a hydrogen atmosphere for 1 hour. The reaction mixture was filtered through a pad of celite, and the filtrate was concentrated under reduced pressure. The residue was purified by aminopropyl silica gel column chromatography (eluent: ethyl acetate/n-hexane) to afford the title compound (154 mg). Structural formula, spectral data and purification condition are shown in Table 45.

REFERENCE EXAMPLE 2-59-2

(2R)-4-(Benzyloxy)-3,3-difluoro-1-(2H-1,2,3-triazol-2-yl)butan-2-amine hydrochloride To a solution of [(2R)-2-azido-4-benzyloxy-3,3-difluorobutan-1-yl](tert-butyldiphenylsilyl)ether (3.5 g) in ethanol (20 mL) were added di-tert-butyl dicarbonate (1.7 g) and 10% palladium-carbon (50% wet, 500 mg), and the mixture was stirred at room temperature under a hydrogen atmosphere for 5 hours. The reaction mixture was filtered through a pad of celite, and the filtrate was concentrated under reduced pressure. To the residue were added tetrahydrofuran (10 mL) and a solution of tetra-n-butylammonium fluoride in tetrahydrofuran (1 mol/L, 8.5 mL), and the mixture was stirred at room temperature for 1 hour. To the reaction mixture was added a saturated aqueous solution of ammonium chloride, and the crude product was extracted with ethyl acetate. The organic layer was washed with brine, and dried over sodium sulfate. The solvent was removed under reduced pressure, and the residue was purified by silica gel column chromatography (eluent: ethyl acetate/n-hexane) to afford N-[(2R)-4-(benzyloxy)-3,3-difluoro-1-hydroxybutan-2-yl]carbamic acid tert-butyl ester (1.5 g). To a solution of the product (1.0 g) in dichloromethane were added triethylamine (611 mg) and methanesulfonyl chloride (450 mg) at 0° C. and the mixture was stirred at the same temperature for 1 hour. To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in N,N-dimethylformamide (5 mL) were added cesium carbonate (2.95 g) and 1,2,3-triazole (417 mg), and the mixture was stirred at 60° C. for 3 hours. The reaction mixture was allowed to cool to room temperature. To the mixture was added a saturated aqueous solution of ammonium chloride, and the crude product was extracted with ethyl acetate. The extract was washed with water and brine successively, and dried over sodium sulfate. The solvent was removed under reduced pressure. The residue was purified by silica gel column chromatography (eluent: n-hexane/ethyl acetate) to afford N-[(2R)-4-(benzyloxy)-3,3-difluoro-1-(2H-1,2,3-triazol-2-yl)butan-2-yl]carbamic acid tert-butyl ester (590 mg). To a solution of the product (590 mg) methanol (1 mL) was added a solution of hydrogen chloride in 1,4-dioxane (4 mol/L, 1 mL), and the mixture was stirred at room temperature for 2 hours. The reaction mixture was concentrated under reduced pressure to afford the title compound (480 mg). Structural formula, spectral data and purification condition are shown in Table 45.

REFERENCE EXAMPLE 2-60-1

(2R)-4-(Benzyloxy)-3,3-difluoro-1-(pyrimidin-2-yl)butan-2-amine

To a solution of [(2R)-2-azido-4-benzyloxy-3,3-difluorobutan-1-yl](tert-butyldiphenylsilyl)ether (170 mg) in ethanol (2 mL) were added di-tert-butyl dicarbonate (112 mg) and 10% palladium-carbon (50% wet, 50 mg), and the mixture was stirred at room temperature under a hydrogen atmosphere overnight. The reaction mixture was filtered through a pad of celite, and the filtrate was concentrated under reduced pressure. To the residue were added tetrahydrofuran (2 mL) and a solution of tetra-n-butylammonium fluoride in tetrahydrofuran (1 mol/L, 500 μL), and the mixture was stirred at room temperature for 1 hour. To the reaction mixture was added water, and the crude product was extracted with dichloromethane. The organic layer was washed with brine, and dried over anhydrous magnesium sulfate. The solvent was removed under reduced pressure, and the residue was purified by silica gel column chromatography (eluent: ethyl acetate/n-hexane) to afford N-[(2R)-4-(benzyloxy)-3,3-difluoro-1-hydroxybutan-2-yl]carbamic acid tert-butyl ester (90 mg). To a mixture of the product (90 mg), imidazole (28 mg), triphenylphosphine (107 mg) and tetrahydrofuran (2 mL) was added iodine (104 mg) at 0° C., and the mixture was stirred at room temperature for 2 hours. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford N-[(2S)-4-(benzyloxy)-3,3-difluoro-1-iodobutan-2-yl]carbamic acid tert-butyl ester (56 mg). A mixture of the product (56 mg), zinc (18 mg), one chip of iodine and N,N-dimethylformamide (1 mL) was stirred at room temperature under an argon atmosphere for 1 hour. To the mixture were added 2-bromopyrimidine (20 mg) and bis(triphenylphosphine)palladium (II) dichloride (9 mg), and the mixture was stirred at room temperature for 3 hours. To the reaction mixture was added a saturated aqueous solution of sodium bicarbonate, and the mixture was filtered through a pad of celite. The crude product was extracted with ethyl acetate. The organic layer was washed with water and brine, and dried over anhydrous magnesium sulfate. The solvent was removed under reduced pressure. The residue was purified by silica gel column chromatography (eluent: ethyl acetate/n-hexane) to afford N-[(2R)-4-(benzyloxy)-3,3-difluoro-1-(pyrimidin-2-yl)butan-2-yl]carbamic acid tert-butyl ester (25 mg). To a solution of the product (25 mg) in methanol (1.5 mL) was added a solution of hydrogen chloride in 1,4-dioxane (4 mol/L, 1.5 mL), and the mixture was stirred at room temperature for 1 hour. The reaction mixture was concentrated under reduced pressure. The residue was purified by aminopropyl silica gel column chromatography (eluent: ethyl acetate/methanol) to afford the title compound (20 mg). Structural formula, spectral data and purification condition are shown in Table 46.

REFERENCE EXAMPLE 2-60-2

Reference Example 2-60-2 was synthesized in a manner similar to that of Reference Example 2-60-1 by using the corresponding materials. Structural formula, spectral data and purification condition are shown in Table 46.

REFERENCE EXAMPLE 2-61-1

[((4S)-2,2-Dimethyl-1,3-dioxolan-4-yl)methyl][2-(pyridin-2-yl)ethyl]amine

To a mixture of (4R)-2,2-dimethyl-1,3-dioxolane-4-carboxylic acid (0.5 g), 1-hydroxybenzotriazole monohydrate (0.262 g), 2-(pyridin-2-yl)ethan-1-amine (0.46 g), triethylamine (0.693 g) and dichloromethane (34.2 mL) was added 1-ethyl-3-(3-dimethylaminopropyl)carbodiimide hydrochloride (0.79 g), and the mixture was stirred at room temperature for 1 day. The reaction mixture was concentrated under reduced pressure. The residue was partitioned between water and ethyl acetate. The aqueous layer was extracted three times with ethyl acetate. The combined organic layer was dried over sodium sulfate, and concentrated under reduced pressure. The residue was purified by aminopropyl silica gel column chromatography (eluent: ethyl acetate/n-hexane) to afford (4R)-2,2-dimethyl-N-[2-(pyridin-2-yl)ethyl]-1,3-dioxolane-4-carboxamide (0.80 g). To a suspension of lithium aluminium hydride (365 mg) in tetrahydrofuran (30 mL) was added dropwise a solution of (4R)-2,2-dimethyl-N-[2-(pyridin-2-yl)ethyl]-1,3-dioxolane-4-carboxamide (0.80 g) in tetrahydrofuran (12.8 mL) at 0° C., and the mixture was stirred at room temperature for 20 hours. To the reaction mixture were added water (0.366 mL), an aqueous solution of sodium hydroxide (15%, 0.366 mL) and water (0.366 mL) successively, and the mixture was quenched. The mixture was stirred at room temperature for 21 hours. The mixture was filtered through a pad of celite. The filtrate was concentrated under reduced pressure. The residue was purified by aminopropyl silica gel column chromatography (eluent: ethyl acetate/n-hexane) to afford [((4S)-2,2-dimethyl-1,3-dioxolan-4-yl)methyl][2-(pyridin-2-yl)ethyl]amine (0.275 g). To a solution of the product (273 mg) in dichloromethane (5.78 mL) were added triethylamine (351 mg) and trifluoroacetic anhydride (364 mg) successively at 0° C. The mixture was stirred at room temperature for 36 hours. To the reaction mixture was added methanol (1 mL), and the mixture was stirred for 1 hour. To the mixture was added a saturated aqueous solution of sodium bicarbonate, and the crude product was extracted with ethyl acetate. The organic layer was washed with brine, dried over sodium sulfate, and concentrated under reduced pressure. The residue was purified by silica gel column chromatography (eluent: ethyl acetate/n-hexane) to afford N-[((4S)-2,2-dimethyl-1,3-dioxolan-4-yl)methyl]-2,2,2-trifluoro-N-[2-(pyridin-2-yl)ethyl]acetamide (211 mg). To a solution of the product (209 mg) in ethanol (6.29 mL) was added an aqueous solution of sodium hydroxide (2 mol/L, 944 µL) at room temperature, and the mixture was stirred at 60° C. for 2 hours. The reaction mixture was allowed to cool to room temperature, and diluted with water. The crude product was extracted with dichloromethane. The aqueous layer was extracted twice with dichloromethane. The combined organic layer was dried over sodium sulfate, and concentrated under reduced pressure to afford the title compound (144 mg). Structural formula, spectral data and purification condition are shown in Table 46.

REFERENCE EXAMPLE 2-61-2

Reference Example 2-61-2 was synthesized in a manner similar to that of Reference Example 2-61-1 by using the corresponding materials. Structural formula, spectral data and purification condition are shown in Table 46.

REFERENCE EXAMPLE 2-62-1

[(2R)-3-(Benzyloxy)-2-methoxypropyl][2-(pyridin-2-yl)ethyl]amine

To a solution of (2R)-2-[(benzyloxy)methyl]oxirane (0.500 g) in tert-butylalcohol (10.2 mL) was added 2-(pyridin-2-yl)ethylamine (0.744 g) at room temperature, and the mixture was stirred at 100° C. for 11.5 hours. The reaction mixture was allowed to cool to room temperature, and then concentrated under reduced pressure. The residue was dissolved in acetonitrile (10.2 mL). To the solution were added 4-dimethylaminopyridine (1.488 g) and acetic anhydride (0.836 mL), and the mixture was stirred at room temperature for 3 hours. To the mixture was added methanol (3 mL), and the mixture was further stirred for 0.5 hours. The reaction mixture was concentrated under reduced pressure. The residue was partitioned between ethyl acetate and a saturated aqueous solution of sodium bicarbonate. The organic layer was washed with brine, dried over sodium sulfate, and concentrated under reduced pressure. The residue was purified by silica gel column chromatography (eluent:ethyl acetate/methanol) to afford acetic acid ((2R)-1-(benzyloxy)-3-{N-[2-(pyridin-2-yl)ethyl]-N-acetylamino}propan-2-yl) ester (0.644 g). To a solution of the product (0.642 g) in ethanol (6.93 mL) was added an aqueous solution of sodium hydroxide (2 mol/L, 6.93 mL) at room temperature, and the mixture was stirred at 70° C. for 45.5 hours. The reaction mixture was allowed to cool to room temperature, and diluted with water. The crude product was extracted with dichloromethane. The aqueous layer was extracted once with dichloromethane. The combined organic layer was dried over sodium sulfate, and concentrated under reduced pressure to afford [(2R)-3-(benzyloxy)-2-hydroxypropyl][2-(pyridin-2-yl)ethyl]amine (0.500 g). To a solution of the product (499 mg) in tetrahydrofuran (8.71 mL) was added sodium hydride (60% dispersion in oil, 84 mg) in two parts at 0° C., and the mixture was stirred for 1 hour. To the mixture was added dropwise iodomethane (163 µL). The mixture was allowed to warm to room temperature, and stirred for 2 hours. To the reaction mixture was added a saturated aqueous solution of ammonium chloride (30 mL). The mixture was partitioned between ethyl acetate (80 mL) and water (10 mL). The organic layer was dried over sodium sulfate, and concentrated under reduced pressure. The residue was purified by aminopropyl silica gel column chromatography (eluent: ethyl acetate/methanol) to afford the title compound (214 mg). Structural formula, spectral data and purification condition are shown in Table 46.

REFERENCE EXAMPLE 2-62-2

Reference Example 2-62-2 was synthesized in a manner similar to that of Reference Example 2-62-1 by using the corresponding materials. Structural formula, spectral data and purification condition are shown in Table 46.

REFERENCE EXAMPLE 2-63-1

((2R)-2-Hydroxy-3-methoxypropyl)[2-(pyridin-2-yl)ethyl]amine

To a solution of (2R)-2-(methoxymethyl)oxirane (0.300 g) in tert-butyl alcohol (12.2 mL) was added 2-(pyridin-2-yl)ethan-1-amine (0.624 g) at room temperature, and the mixture was stirred at 100° C. for 14 hours. The reaction mixture was allowed to cool to room temperature, and then concentrated under reduced pressure. The residue was dissolved in dichloromethane (17.0 mL). To the mixture was added triethylamine (1.90 mL) at 0° C. To the mixture was added dropwise trifluoroacetic anhydride (1.92 mL), and the mixture was stirred at room temperature for 3 hours. To the mixture was added methanol (3 mL), and the mixture was further stirred for 30 minutes. The reaction mixture was concentrated under reduced pressure. The residue was partitioned between ethyl acetate and a saturated aqueous solution of sodium bicarbonate. The organic layer was washed with brine, dried over sodium sulfate, and concentrated under reduced pressure. The residue was purified by silica gel column chromatography (eluent:ethyl acetate/n-hexane) to afford 2,2,2-trifluoro-N-((2R)-2-hydroxy-3-methoxypropyl)-N-[2-(pyridin-2-yl)ethyl]acetamide (0.562 g). To a solution of the product (0.56 g) in ethanol (6.40 mL) was added an aqueous solution of sodium hydroxide (2 mol/L, 2.74 mL), and the mixture was stirred at 60° C. for 3.5 hours. The reaction mixture was allowed to cool to room temperature, and diluted with water. The crude product was extracted with dichloromethane. The aqueous layer was extracted five times with dichloromethane. The combined organic layer was dried over sodium sulfate, and concentrated under reduced pressure to afford the title compound (366 mg). Structural formula, spectral data and purification condition are shown in Table 46.

REFERENCE EXAMPLE 2-63-2

Reference Example 2-63-2 was synthesized in a manner similar to that of Reference Example 2-63-1 by using the corresponding materials. Structural formula, spectral data and purification condition are shown in Table 46.

REFERENCE EXAMPLE 2-64-1

N-((2R)-2-Amino-3-phenylpropyl)-N-methyl-2-nitrobenzene-1-sulfonamide hydrochloride To a mixture of N-((2R)-1-hydroxy-3-phenylpropan-2-yl)carbamic acid tert-butyl ester (503 mg), triphenylphosphine (630 mg), N-methyl-2-nitrobenzene-1-sulfonamide (454 mg) and tetrahydrofuran (5 mL) was added a solution of azodicarboxylic acid diethyl ester in toluene (2.2 mol/L, 1,1 mL), and the mixture was stirred at room temperature for 1 hour. To the reaction mixture was added n-hexane (5 mL), and the mixture was stirred for 30 minutes. The mixture was purified by silica gel column chromatography (eluent: ethyl acetate/n-hexane) to afford the crude product. The crude product was purified by aminopropyl silica gel column chromatography (eluent: ethyl acetate/n-hexane) to afford N-[(2R)-1-(N-methyl-2-nitrobenzenesulfonylamino)-3-phenylpropan-2-yl]carbamic acid tert-butyl ester (430 mg). To the product (430 mg) was added a solution of hydrogen chloride in 1,4-dioxane (4 mol/L, 5 mL), and the mixture was stirred at room temperature for 1 hour. The reaction mixture was diluted with diethyl ether, and the mixture was stirred for 30 minutes. The precipitate was collected by filtration to afford the title compound (323 mg). Structural formula, spectral data and purification condition are shown in Table 46.

REFERENCE EXAMPLE 2-65-1

(R)-N-[(1R)-1-((4R)-2,2-Dimethyl-1,3-dioxolan-4-yl)-2-(pyridin-2-yl)ethyl]-2-methylpropane-2-sulfinamide To a solution of 2-methylpyridine (0.120 g) in tetrahydrofuran (2 mL) was added a solution of n-butyllithium in n-hexane (2.6 mol/L, 0.46 mL) at −78° C., and the mixture was stirred for 30 minutes. To the mixture was added a solution of (R)-N-[(1E)-((4S)-2,2-dimethyl-1,3-dioxolan-4-yl)methylidene]-2-methylpropane-2-sulfinamide (0.200 g) in tetrahydrofuran (2 mL) at the same temperature, and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford the title compound (0.170 g) as a high polarity diastereomer. Structural formula, spectral data and purification condition are shown in Table 47.

REFERENCE EXAMPLES 2-65-2 TO 2-65-3

Reference Examples 2-65-2 to 2-65-3 were synthesized in a manner similar to that of Reference Example 2-65-1 by using the corresponding materials. Structural formula, spectral data and purification condition are shown in Table 47.

REFERENCE EXAMPLE 2-66-1

(S)-N-[(1S)-1-((4S)-2,2-Dimethyl-1,3-dioxolan-4-yl)-2-(pyridin-2-yl)ethyl]-2-methylpropane-2-sulfinamide To a solution of 2-methylpyridine (0.215 g) in tetrahydrofuran (3.5 mL) was added a solution of n-butyllithium in n-hexane (2.6 mol/L, 0.83 mL) at −78° C., and the mixture was stirred for 30 minutes. To the mixture was added a solution of (S)-N-[(1E)-((4S)-2,2-dimethyl-1,3-dioxolan-4-yl)methylidene]-2-methylpropane-2-sulfinamide (0.360 g) in tetrahydrofuran (7 mL) at the same temperature, and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford the title compound (0.200 g) as a high polarity diastereomer. Structural formula, spectral data and purification condition are shown in Table 47.

REFERENCE EXAMPLE 2-66-2

Reference Example 2-66-2 was synthesized in a manner similar to that of Reference Example 2-66-1 by using the corresponding materials. Structural formula, spectral data and purification condition are shown in Table 47.

REFERENCE EXAMPLE 2-67-1

(R)-N-[(1R)-1-((4S)-2,2-Dimethyl-1,3-dioxolan-4-yl)-2-(pyridin-2-yl)propyl]-2-methylpropane-2-sulfinamide To a solution of 2-ethylpyridine (0.110 g) in tetrahydrofuran (2 mL) was added a solution of n-butyllithium in n-hexane (2.6 mol/L, 0.36 mL) at −78° C., and the mixture was stirred for 30 minutes. To the mixture was added a solution of (R)-N-[(1E)-((4S)-2,2-dimethyl-1,3-dioxolan-4-yl)methylidene]-2-methylpropane-2-sulfinamide (0.200 g) in tetrahydrofuran (2 mL) at the same temperature, and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford the title compound (0.150 g) as a high polarity diastereomer. Structural formula, spectral data and purification condition are shown in Table 48.

REFERENCE EXAMPLE 2-67-2

Reference Example 2-67-2 was synthesized in a manner similar to that of Reference Example 2-67-1 by using the corresponding materials. Structural formula, spectral data and purification condition are shown in Table 48.

REFERENCE EXAMPLE 2-68-1

(R)-N-[(1R)-1-((4S)-2,2-Dimethyl-1,3-dioxolan-4-yl)-2-methoxy-2-(pyridin-2-yl)ethyl]-2-methylpropane-2-sulfinamide To a solution of 2-(tert-butyldimethylsilyloxymethyl)pyridine (0.669 g) in tetrahydrofuran (4 mL) was added a solution of n-butyllithium in n-hexane (2.6 mol/L, 1.07 mL) at −78° C., and the mixture was stirred for 30 minutes. To the mixture was added a solution of (R)-N-[(1E)-((4S)-2,2-dimethyl-1,3-dioxolan-4-yl)methylidene]-2-methylpropane-2-sulfinamide (0.467 g) in tetrahydrofuran (4 mL) at the same temperature, and the mixture was further stirred for 30 minutes. The reaction mixture was allowed to warm to room temperature. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a diastereomeric mixture of (R)-N-[(1S)-2-(tert-butyldimethylsilyloxy)-1-((4S)-2,2-dimethyl-1,3-dioxolan-4-yl)-2-(pyridin-2-yl)ethyl]-2-methylpropane-2-sulfinamide (0.554 g) as a low polarity product. The product (0.277 g) was dissolved in tetrahydrofuran (3 mL). To the mixture was added a solution of tetra-n-butylammonium fluoride in tetrahydrofuran (1 mol/L, 0.6 mL) under ice-cooling, and the mixture was stirred for 30 minutes. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford (R)-N-[(1R)-1-((4S)-2,2-dimethyl-1,3-dioxolan-4-yl)-2-hydroxy-2-(pyridin-2-yl)ethyl]-2-methylpropane-2-sulfinamide (0.119 g) as a high polarity diastereomer. To a solution of the product (0.030 g) in N,N-dimethylformamide (0.5 mL) was added sodium hydride (60% dispersion in oil, 0.003 g) under ice-cooling, and the mixture was stirred for 30 minutes. To the mixture was added iodomethane (0.049 g), and the mixture was stirred at room temperature overnight. To the reaction mixture was added ice, and the crude product was extracted with ethyl acetate. The organic layer was washed with brine, and dried over anhydrous magnesium sulfate. The solvent was removed under reduced pressure, and the residue was purified by silica gel column chromatography (eluent: methanol/ethyl acetate) to afford the title compound (0.021 g). Structural formula, spectral data and purification condition are shown in Table 48.

REFERENCE EXAMPLE 2-69-1

(2S,3R)-3-Amino-1-methoxy-4-(1H-pyrazol-1-yl)butan-2-ol hydrochloride

A mixture of N-[(2R,3S)-4-(tert-butyldiphenylsilyloxy)-3-hydroxy-1-(1H-pyrazol-1-yl)butan-2-yl]carbamic acid tert-butyl ester (1.90 g), p-toluenesulfonic acid monohydrate (71 mg), 2,2-dimethoxypropane (3.88 g) and toluene (10 mL) was stirred at 80° C. for 8 hours. The reaction mixture was allowed to cool to room temperature. To the reaction mixture was added a saturated aqueous solution of sodium bicarbonate, and the crude product was extracted with ethyl acetate. The organic layer was washed with brine, and dried over sodium sulfate. The solvent was removed under reduced pressure. To a solution of the residue in tetrahydrofuran (10 mL) was added a solution of tetra-n-butylammonium fluoride in tetrahydrofuran (1 mol/L, 4.47 mL) at 0° C., and the mixture was stirred at room temperature for 1 hour. To the reaction mixture was added a saturated aqueous solution of ammonium chloride, and the crude product was extracted with ethyl acetate. The organic layer was washed with brine, and dried over sodium sulfate. The solvent was removed under reduced pressure, and the residue was purified by silica gel column chromatography (eluent: ethyl acetate/n-hexane) to afford (4R,5S)-5-(hydroxymethyl)-2,2-dimethyl-4-(1H-pyrazol-1-ylmethyl)-1,3-oxazolidine-3-carboxylic acid tert-butyl ester (0.98 g). To a solution of the product (160 mg) in N,N-dimethylformamide (1mL) were added iodomethane (110 mg) and sodium hydride (60% dispersion in oil, 35 mg) successively at 0° C., and the mixture was stirred at room temperature for 2 hours. To the reaction mixture was added a saturated aqueous solution of ammonium chloride, and the crude product was extracted with ethyl acetate. The organic layer was washed with water and brine, and dried over sodium sulfate. The solvent was removed under reduced pressure, and the residue was purified by silica gel column chromatography (eluent: ethyl acetate/n-hexane) to afford (4R,5S)-5-(methoxymethyl)-2,2-dimethyl-4-(1H-pyrazol-1-ylmethyl)-1,3-oxazolidine-3-carboxylic acid tert-butyl ester (150 mg). To a solution of the product (150 mg) in methanol (1 mL) was added a solution of hydrogen chloride in 1,4-dioxane (4 mol/L, 1 mL) at room temperature, and the mixture was stirred at the same temperature for 1 hour. The reaction mixture was concentrated under reduced pressure to afford the title compound (100 mg). Structural formula, spectral data and purification condition are shown in Table 48.

REFERENCE EXAMPLE 2-70-1

(2S,3R)-3-Amino-1-fluoro-4-(1H-pyrazol-1-yl)butan-2-ol hydrochloride

To a solution of (4R,5S)-5-(hydroxymethyl)-2,2-dimethyl-4-(1H-pyrazol-1-ylmethyl)-1,3-oxazolidine-3-carboxylic acid tert-butyl ester (580 mg) in tetrahydrofuran (5 mL) were added 1,8-diazabicyclo[5.4.0]-7-undecene (567 mg), perfluorobutanesulfonyl fluoride (1.13 g) at 0° C., and the mixture was stirred at room temperature for 12 hours. To the reaction mixture were added water and dichloromethane, and the crude product was extracted with dichloromethane. The organic layer was washed with brine, and dried over sodium sulfate. The solvent was removed under reduced pressure, and the residue was purified by silica gel column chromatography (eluent: ethyl acetate/n-hexane) to afford (4R,5S)-5-(fluoromethyl)-2,2-dimethyl-4-(1H-pyrazol-1-yl-methyl)-1,3-oxazolidine-3-carboxylic acid tert-butyl ester (240 mg). To a solution of the product (40 mg) in methanol (1 mL) was added a solution of hydrogen chloride in 1,4-dioxane (4 mol/L, 1 mL) at room temperature, and the mixture was stirred at the same temperature for 2 hours. The reaction mixture was concentrated under reduced pressure to afford the title compound (27 mg). Structural formula, spectral data and purification condition are shown in Table 48.

REFERENCE EXAMPLE 2-71-1

(2R,3S)-4-Fluoro-3-methoxy-1-(1H-pyrazol-1-yl)butan-2-amine hydrochloride

To a solution of (2S,3R)-3-amino-1-fluoro-4-(1H-pyrazol-1-yl)butan-2-ol hydrochloride (133 mg) in methanol (1 mL) were added triethylamine (194 mg) and di-tert-butyl dicarbonate (140 mg) at room temperature, and the mixture was stirred at the same temperature for 2 hours. The reaction mixture was concentrated under reduced pressure, and the residue was purified by silica gel column chromatography (eluent: ethyl acetate/n-hexane) to afford N-[(2R,3S)-4-fluoro-3-hydroxy-1-(1H-pyrazol-1-yl)butan-2-yl]carbamic acid tert-butyl ester (170 mg). To a mixture of the product (170 mg), tetrahydrofuran (1 mL), N,N-dimethylformamide (0.1 mL) and iodomethane (97 mg) was added sodium hydride (60% dispersion in oil, 30 mg) at 0° C., and the mixture was stirred at the same temperature for 5 hours. To the reaction mixture was added a saturated aqueous solution of ammonium chloride, and the crude product was extracted with ethyl acetate. The organic layer was washed with water and brine, and dried over sodium sulfate. The solvent was removed under reduced pressure, and the residue was purified by silica gel column chromatography (eluent: ethyl acetate/n-hexane) to afford N-[(2R,3S)-4-fluoro-3-methoxy-1-(1H-pyrazol-1-yl)butan-2-yl]carbamic acid tert-butyl ester (150 mg). To a solution of the product (150 mg) in methanol (1 mL) was added a solution of hydrogen chloride in 1,4-dioxane (4 mol/L, 1 mL) at room temperature, and the mixture was stirred at the same temperature for 1 hour. The reaction mixture was concentrated under reduced pressure to afford the title compound (90 mg). Structural formula, spectral data and purification condition are shown in Table 48.

TABLE 25

| Ref. Ex. | Strc. | P.D. | P.C. |
| --- | --- | --- | --- |
| 2-1-1 | | MS (ESI, m/z): 156 (M + H)+ | Without purification |
| 2-1-2 | | MS (ESI, m/z): 156 (M + H)+ | Without purification |
| 2-2-1 | | MS (ESI, m/z): 180 (M + H)+ | Collected by filtration |
| 2-2-2 | | MS (ESI, m/z): 194 (M + H)+ | Without purification |

TABLE 25-continued

| Ref. Ex. | Strc. | | P.D. | P.C. |
|---|---|---|---|---|
| 2-3-1 | (phthalimide-CH₂-CH(NH₂)-CH₂-Ph, S-config) | HCl | MS (ESI, m/z): 281 (M + H)⁺ | Without purification |
| 2-3-2 | (phthalimide-CH₂-CH(NH₂)-CH₂-(2-pyridyl)) | 2HCl | ¹H-NMR (DMSO-d₆) δ ppm: 3.40-3.56 (2H, m), 3.93-4.07 (2H, m), 4.20-4.30 (1H, m), 7.80-8.01 (3H, m), 8.05-8.14 (1H, m), 8.48-8.59 (1H, m), 8.79-8.59 (1H, m). | Without purification |
| 2-3-3 | (phthalimide-CH₂-CH(NH₂)-CH₂-Ph, R-config) | HCl | MS (ESI, m/z): 281 (M + H)⁺ | Without purification |

TABLE 26

| Ref. Ex. | Strc. | P.D. | P.C. |
|---|---|---|---|
| 2-4-1 | Boc-NH-(6-pyridyl)-CH₂CH₂-NH₂ · HCl | MS (ESI, m/z): 238 (M + H)⁺ | Collected by filtration |
| 2-5-1 | Ph-CH(CH₂NH₂)-CH₂-OTBS | ¹H-NMR (CDCl₃) δ ppm: 0.00 (6H, d, J = 2.0 Hz), 0.88 (9H, s), 2.80-2.87 (1H, m), 2.96 (1H, dd, J = 12.6, 8.5 Hz), 3.19 (1H, dd, J = 12.6, 5.5 Hz), 3.73-3.81 (2H, m), 7.21-7.26 (3H, m), 7.31-7.35 (2H, m). | Column: APS EtOAc/n-Hexane |
| 2-5-2 | (2-pyridyl)-CH(CH₂NH₂)-CH₂-OTBS | MS (ESI, m/z): 267 (M + H)⁺ | Column: APS EtOAc/MeOH |
| 2-6-1 | (2-pyridyl with 3-NHBoc)-CH₂CH₂-NH₂ | MS (ESI, m/z): 238 (M + H)⁺ | Column: APS EtOAc/MeOH |

TABLE 26-continued

| Ref. Ex. | Strc. | P.D. | P.C. |
|---|---|---|---|
| 2-7-1 | (pyridine-CH2-CH(NHMe)-CH2OH) | MS (ESI, m/z): 167 (M + H)+ | Column: APS EtOAc/MeOH |
| 2-8-1 | Rel. (pyrrolidine with HOCH2 and pyridin-2-yl) | MS (ESI, m/z): 179 (M + H)+ | Column: APS EtOAc/MeOH |
| 2-9-1 | (BnO-CH2CH2-CH(NH2)-CH2-pyridin-2-yl) | MS (ESI, m/z): 257 (M + H)+ | Column: APS EtOAc/n-Hexane |
| 2-10-1 | (pyridine-CH2-CH(NH2)-CH(OH)-CH3) | MS (ESI, m/z): 167 (M + H)+ | Column: APS EtOAc/n-Hexane |
| 2-10-2 | (pyridine-CH2-CH(NH2)-CH(OH)-CH2CH3) | MS (ESI, m/z): 181 (M + H)+ | Column: APS EtOAc/n-Hexane |

TABLE 27

| Ref. Ex. | Strc. | P.D. | P.C. |
|---|---|---|---|
| 2-11-1 | (pyridine-CH2-CH(NH2)-CH(OH)-CH3 · HCl) | MS (ESI, m/z): 167 (M + H)+ | Without purification |
| 2-11-2 | (pyridine-CH2-CH(NH2)-CH(OH)-CH2CH3 · HCl) | MS (ESI, m/z): 181 (M + H)+ | Without purification |

TABLE 28

| Ref. Ex. | Strc. | P.D. | P.C. |
|---|---|---|---|
| 2-12-1 | (HO-CH2CH2-CH(NH2)-CH2-pyridin-2-yl · HCl) | MS (ESI, m/z): 167 (M + H)+ | Collected by filtration |

TABLE 28-continued
| Ref. Ex. | Strc. | P.D. | P.C. |
|---|---|---|---|
| 2-12-2 | 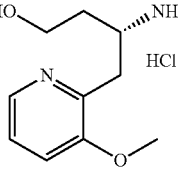 | MS (ESI, m/z): 197 (M + H)+ | Collected by filtration |
| 2-12-3 | 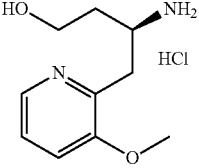 | MS (ESI, m/z): 197 (M + H)+ | Without purification |
| 2-12-4 | 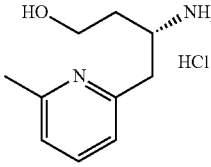 | MS (ESI, m/z): 181 (M + H)+ | Collected by filtration |
| 2-12-5 | 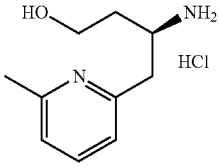 | MS (ESI, m/z): 181 (M + H)+ | Collected by filtration |
| 2-12-6 | 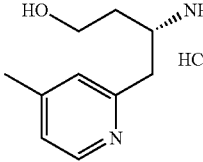 | MS (ESI, m/z): 181 (M + H)+ | Collected by filtration |
| 2-12-7 | 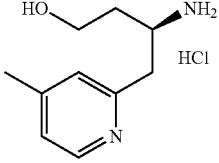 | MS (ESI, m/z): 181 (M + H)+ | Collected by filtration |
| 2-12-8 | 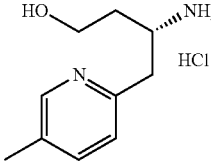 | MS (ESI, m/z): 181 (M + H)+ | Collected by filtration |
| 2-12-9 | 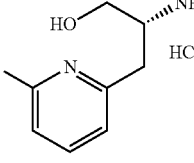 | MS (ESI, m/z): 194 (M + H)+ | Collected by filtration |

TABLE 29

| Ref. Ex. | Strc. | P.D. | P.C. |
| --- | --- | --- | --- |
| 2-12-10 | | MS (ESI, m/z): 181 (M + H)⁺ | Collected by filtration |
| 2-12-11 | | MS (ESI, m/z): 197 (M + H)⁺ | Collected by filtration |
| 2-12-12 | | MS (ESI, m/z): 185 (M + H)⁺ | Without purification |
| 2-12-13 | | MS (ESI, m/z): 181 (M + H)⁺ | Collected by filtration |
| 2-12-14 | | MS (ESI, m/z): 181 (M + H)⁺ | Collected by filtration |
| 2-12-15 | | MS (ESI, m/z): 181 (M + H)⁺ | Without purification |
| 2-12-16 | | MS (ESI, m/z): 197 (M + H)⁺ | Without purification |
| 2-12-17 | | MS (ESI, m/z): 183 (M + H)⁺ | Collected by filtration |

TABLE 29-continued

| Ref. Ex. | Strc. | P.D. | P.C. |
| --- | --- | --- | --- |
| 2-12-18 | (structure: HO-CH2CH2-C(CH3)(NH2)-CH2-(2-pyridyl), ·HCl) | MS (ESI, m/z): 181 (M + H)+ | Without purification |

TABLE 30

| Ref. Ex. | Strc. | P.D. | P.C. |
| --- | --- | --- | --- |
| 2-12-19 | (structure: HO-CH2-C(CH3)(NH2)-CH2-(2-pyridyl), ·HCl) | MS (ESI, m/z): 167 (M + H)+ | Without purification |
| 2-12-20 | (structure: 2-phenyl-5-methyl-1,3-dioxane with 5-CH(NH2)-CH2-(2-pyridyl) substituent, ·HCl) | MS (ESI, m/z): 299 (M + H)+ | Without purification |
| 2-12-21 | (structure: HO-CH2-C(CH3)2-CH(NH2)-CH2-(2-pyridyl), ·HCl) | MS (ESI, m/z): 195 (M + H)+ | Without purification |
| 2-12-22 | (structure: HO-CH2-CH(CH3)-CH(NH2)-CH2-(2-pyridyl), ·HCl) | MS (ESI, m/z): 181 (M + H)+ | Without purification |
| 2-12-23 | (structure: 2-phenyl-1,3-dioxane with 5-CH(NH2)-CH2-(2-pyridyl) substituent, ·HCl) | MS (ESI, m/z): 285 (M + H)+ | Without purification |

TABLE 30-continued

| Ref. Ex. | Strc. | P.D. | P.C. |
|---|---|---|---|
| 2-12-24 | (structure) | MS (ESI, m/z): 275 (M + H)⁺ | Column: APS EtOAc/MeOH |
| 2-12-25 | (structure) | MS (ESI, m/z): 269 (M + H)⁺ | Column: APS EtOAc/MeOH |
| 2-12-26 | (structure) | MS (ESI, m/z): 269 (M + H)⁺ | Column: APS EtOAc/MeOH |
| 2-12-27 | (structure) | MS (ESI, m/z): 287 (M + H)⁺ | Column: APS EtOAc/MeOH. |

TABLE 31

| Ref. Ex. | Strc. | P.D. | P.C. |
|---|---|---|---|
| 2-12-28 | (structure) | MS (ESI, m/z): 197 (M + H)⁺ | Column: APS EtOAc/MeOH |
| 2-12-29 | (structure) | MS (ESI, m/z): 197 (M + H)⁺ | Column: APS EtOAc/n-Hexane |

TABLE 31-continued

| Ref. Ex. | Strc. | P.D. | P.C. |
|---|---|---|---|
| 2-12-30 | BnO—CH(F)—CH(NH₂)—CH₂-(2-pyridyl) | MS (ESI, m/z): 275 (M + H)⁺ | Column: APS EtOAc/MeOH |

TABLE 32

| Ref. Ex. | Strc. | P.D. | P.C. |
|---|---|---|---|
| 2-13-1 | 2-pyridyl-CH(CH₂NH₂)-CH₂CH₂-OTBS | MS (ESI, m/z): 281 (M + H)⁺ | Column: APS EtOAc/MeOH |
| 2-14-1 | H₂N-C(O)-CH₂-CH(NH₂)-CH₂-Ph · HCl | MS (ESI, m/z): 179 (M + H)⁺ | Without purification |
| 2-15-1 | HO-CH₂CH₂-CH(NH₂)-CH₂-(2-pyridyl) · HCl | MS (ESI, m/z): 167 (M + H)⁺ | Without purification |
| 2-15-2 | HO-CH₂-C(CH₃)(NH₂)-CH₂-(2-pyridyl) · HCl | MS (ESI, m/z): 167 (M + H)⁺ | Without purification |
| 2-15-3 | HO-CH₂CH₂-C(CH₃)(NH₂)-CH₂-(2-pyridyl) · HCl | MS (ESI, m/z): 181 (M + H)⁺ | Without purification |

TABLE 33

| Ref. Ex. | Strc. | P.D. | P.C. |
| --- | --- | --- | --- |
| 2-16-1 | (structure) | MS (ESI, m/z): 182 (M + H)⁺ | Column: APS EtOAc/MeOH |
| 2-17-1 | (structure) | MS (ESI, m/z): 181 (M + H)⁺ | Column: APS EtOAc/MeOH |
| 2-18-1 | (structure) | MS (ESI, m/z): 167 (M + H)⁺ | Without purification |
| 2-18-2 | (structure) | MS (ESI, m/z): 181 (M + H)⁺ | Without purification |
| 2-18-3 | (structure) | MS (ESI, m/z): 181 (M + H)⁺ | Collected by filtration |
| 2-19-1 | (structure) | MS (ESI, m/z): 181 (M + H)⁺ | Without purification |
| 2-19-2 | (structure) | MS (ESI, m/z): 181 (M + H)⁺ | Without purification |

TABLE 33-continued
| Ref. Ex. | Strc. | P.D. | P.C. |
|---|---|---|---|
| 2-20-1 | 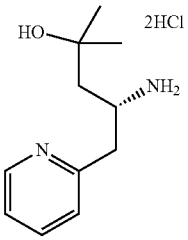 | MS (ESI, m/z): 195 (M + H)⁺ | Without purification |
TABLE 34
| Ref. Ex. | Strc. | P.D. | P.C. |
|---|---|---|---|
| 2-21-1 | 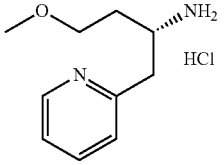 | MS (ESI, m/z): 181 (M + H)⁺ | Without purification |
| 2-21-2 | 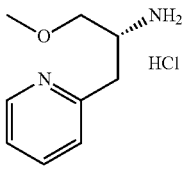 | MS (ESI, m/z): 167 (M + H)⁺ | Without purification |
| 2-22-1 | 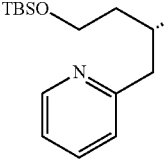 | MS (ESI, m/z): 281 (M + H)⁺ | Column: APS EtOAc/n-Hexane |
| 2-22-2 | 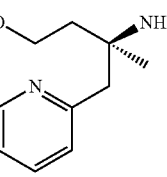 | MS (ESI, m/z): 295 (M + H)⁺ | Column: APS EtOAc/n-Hexane |
| 2-22-3 | 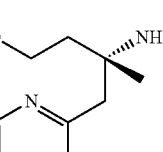 | MS (ESI, m/z): 295 (M + H)⁺ | Column: APS EtOAc/n-Hexane |
| 2-22-4 | 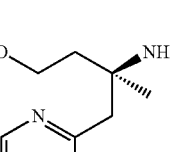 | MS (ESI, m/z): 281 (M + H)⁺ | Column: APS EtOAc/n-Hexane |

TABLE 34-continued

| Ref. Ex. | Strc. | P.D. | P.C. |
|---|---|---|---|
| 2-22-5 | TBSO, NH₂, pyridine with methyl | MS (ESI, m/z): 281 (M + H)⁺ | Column: APS EtOAc/n-Hexane |

TABLE 35

| Ref. Ex. | Strc. | P.D. | P.C. |
|---|---|---|---|
| 2-23-1 | HO, NH₂, pyrimidine, HCl | MS (ESI, m/z): 154 (M + H)⁺ | Without purification |
| 2-23-2 | HO, NH₂, 3-hydroxypyridine, HCl | MS (ESI, m/z): 169 (M + H)⁺ | Without purification |
| 2-23-3 | HO, NH₂, 3-fluoropyridine, HCl | MS (ESI, m/z): 171 (M + H)⁺ | Without purification |
| 2-23-4 | HO, NH₂, 3-chloropyridine, HCl | MS (ESI, m/z): 187 (M + H)⁺ | Without purification |
| 2-23-5 | HO, NH₂, thiazole, HCl | MS (ESI, m/z): 159 (M + H)⁺ | Without purification |
| 2-23-6 | HO, NH₂, pyrazine, HCl | MS (ESI, m/z): 154 (M + H)⁺ | Without purification |
| 2-23-7 | HO, NH₂, 3-cyanopyridine, HCl | MS (ESI, m/z): 178 (M + H)⁺ | Without purification |
| 2-23-8 | HO, NH₂, thiazol-4-yl, HCl | MS (ESI, m/z): 159 (M + H)⁺ | Without purification |
| 2-23-9 | HO, NH₂, 1-methylimidazole, HCl | MS (ESI, m/z): 156 (M + H)⁺ | Without purification |

TABLE 36

| Ref. Ex. | Strc. | P.D. | P.C. |
|---|---|---|---|
| 2-23-10 | HO, NH₂, pyridazine, HCl | MS (ESI, m/z): 154 (M + H)⁺ | Without purification |

TABLE 36-continued

| Ref. Ex. | Strc. | P.D. | P.C. |
|---|---|---|---|
| 2-23-11 | (imidazo[1,2-a]pyridin-5-ylmethyl propanol, NH₂, HCl) | MS (ESI, m/z): 192 (M + H)⁺ | Without purification |
| 2-23-12 | (3-methoxypyridin-2-yl propanol, NH₂, HCl) | MS (ESI, m/z): 183 (M + H)⁺ | Without purification |
| 2-23-13 | (3-trifluoromethylpyridin-2-yl propanol, NH₂, HCl) | MS (ESI, m/z): 221 (M + H)⁺ | Without purification |
| 2-23-14 | (1-(ethoxymethyl)imidazol-2-yl propanol, NH₂, HCl) | MS (ESI, m/z): 200 (M + H)⁺ | Without purification |
| 2-23-15 | (isoquinolin-1-yl propanol, NH₂, HCl) | MS (ESI, m/z): 203 (M + H)⁺ | Without purification |
| 2-23-16 | (1-ethylimidazol-2-yl propanol, NH₂, HCl) | $^1$H-NMR (CDCl$_3$) δ ppm: 1.37-1.45 (3H, m), 3.32-3.37 (2H, m), 3.47-3.52 (1H, m), 3.58-3.64 (1H, m), 4.18-4.24 (3H, m), 7.68-7.81 (2H, m), 8.41 (3H, br). | Without purification |

TABLE 37

| Ref. Ex. | Strc. | P.D. | P.C. |
|---|---|---|---|
| 2-24-1 | (pyrimidin-2-yl butanediol amine, NH₂, HCl) | MS (ESI, m/z): 184 (M + H)⁺ | Without purification |

TABLE 37-continued

| Ref. Ex. | Strc. | P.D. | P.C. |
|---|---|---|---|
| 2-25-1 | HO-CH₂-CH(NH₂)-CH₂-pyrazole · HCl | MS (ESI, m/z): 142 (M + H)⁺ | Without purification |
| 2-26-1 | HO-CH₂-CH(OH)-CH(NH₂)-CH₂-pyrazole · HCl | MS (ESI, m/z): 172 (M + H)⁺ | Without purification |
| 2-27-1 | 3-amino-3,4-dihydro-1,5-naphthyridin-2(1H)-one · HCl | MS (ESI, m/z): 164 (M + H)⁺ | Without purification |
| 2-28-1 | TBSO-CH₂-CH(NHS(O)tBu)-CH(OTBS)-pyridin-2-yl | MS (ESI, m/z): 501 (M + H)⁺ | Column: SiO2 EtOAc/n-Hexane |
| 2-28-2 | TBSO-CH₂-CH(NHS(O)tBu)-CH(OTBS)-pyridin-2-yl | MS (ESI, m/z): 501 (M + H)⁺ | Column: SiO2 EtOAc/n-Hexane |
| 2-28-3 | TBSO-CH₂CH₂-CH(NHS(O)tBu)-CH(OTBS)-pyridin-2-yl | MS (ESI, m/z): 515 (M + H)⁺ | Column: SiO2 EtOAc/n-Hexane |

TABLE 37-continued
| Ref. Ex. | Strc. | P.D. | P.C. |
|---|---|---|---|
| 2-28-4 | 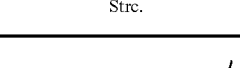 | ¹H-NMR (CDCl₃) δ ppm: −0.10 (3H, s), 0.85 (3H, s), 0.11 (3H, s), 0.12 (3H, s), 1.22 (3H, d, J = 6.0 Hz), 1.68-1.77 (1H, m), 1.86-1.95 (1H, m), 3.38-3.72 (2H, m), 4.10-4.20 (1H, m), 7.13 (1H, ddd, J = 1.2, 5.0, 7.6 Hz), 7.42 (1H, d, J = 7.8 Hz), 7.63 (1H, ddd, J = 1.7, 7.6, 7.6 Hz), 8.47-8.51 (1H, m). | Column: SiO2 EtOAc/n-Hexane |
TABLE 38
| Ref. Ex. | Strc. | P.D. | P.C. |
|---|---|---|---|
| 2-29-1 |  | MS (ESI, m/z): 287 (M + H)⁺ | Column: APS EtOAc/MeOH |
| 2-30-1 |  | MS (ESI, m/z): 287 (M + H)⁺ | Column: SiO2 EtOAc/MeOH |
| 2-31-1 |  | MS (ESI, m/z): 180 (M + H)⁺ | Without purification |
| 2-31-2 |  |  | Column: APS EtOAc/MeOH |
| 2-32-1 |  | HCl MS (ESI, m/z): 101 (M + H)⁺ | Without purification |

TABLE 38-continued
| Ref. Ex. | Strc. | P.D. | P.C. |
|---|---|---|---|
| 2-33-1 | 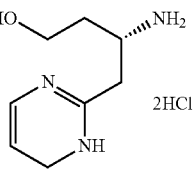 | MS (ESI, m/z): 170 (M + H)+ | Without purification |
| 2-34-1 | 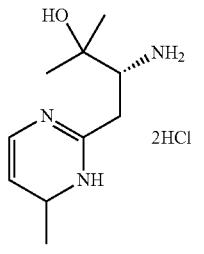 | MS (ESI, m/z): 198 (M + H)+ | Without purification |
| 2-35-1 | 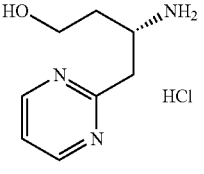 [SMILES: N[C@@H](CCO)Cc1ncccn1 ; Cl] | MS (ESI, m/z): 168 (M + H)+ | Without purification |
| 2-36-1 | 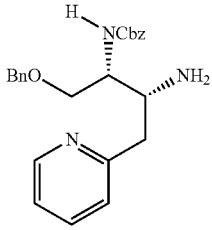 [SMILES: N[C@H](Cc1ccccn1)[C@H](COCc1ccccc1)NC(=O)OCc1ccccc1] | MS (ESI, m/z): 406 (M + H)+ | Column: APS EtOAc/MeOH |
TABLE 39
| Ref. Ex. | Strc. | P.D. | P.C. |
|---|---|---|---|
| 2-37-1 | 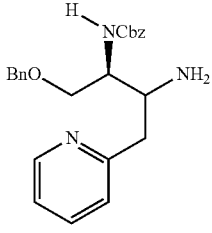 [SMILES: NC(Cc1ccccn1)[C@@H](COCc1ccccc1)NC(=O)OCc1ccccc1] | MS (ESI, m/z): 406 (M + H)+ | Column: APS EtOAc/n-Hexane |
| 2-37-2 | 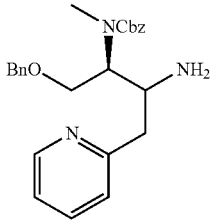 [SMILES: CN(C(=O)OCc1ccccc1)[C@H](COCc1ccccc1)C(N)Cc1ccccn1] | MS (ESI, m/z): 420 (M + H)+ | Column: APS EtOAc/n-Hexane |

TABLE 39-continued

| Ref. Ex. | Strc. | P.D. | P.C. |
|---|---|---|---|
| 2-38-1 | | MS (ESI, m/z): 211 (M + H)$^+$ | Without purification |
| 2-39-1 | | MS (ESI, m/z): 211 (M + H)$^+$ | Column: APS EtOAc/MeOH |
| 2-39-2 | | MS (ESI, m/z): 197 (M + H)$^+$ | Column: APS EtOAc/MeOH |
| 2-39-3 | | MS (ESI, m/z): 225 (M + H)$^+$ | Column: APS EtOAc/MeOH |
| 2-39-4 | | MS (ESI, m/z): 311 (M + H)$^+$ | Column: APS EtOAc/MeOH |
| 2-40-1 | | | Column: APS EtOAc/MeOH |
| 2-41-1 | | MS (ESI, m/z): 224 (M + H)$^+$ | Without purification |

TABLE 40

| Ref. Ex. | Strc. | P.D. | P.C. |
| --- | --- | --- | --- |
| 2-42-1 | (structure) | MS (ESI, m/z): 273 (M + H)+ | Without purification |
| 2-42-2 | (structure) | MS (ESI, m/z): 287 (M + H)+ | Without purification |
| 2-42-3 | (structure) | MS (ESI, m/z): 273 (M + H)+ | Without purification |
| 2-42-4 | (structure) | MS (ESI, m/z): 287 (M + H)+ | Without purification |
| 2-43-1 | (structure) | MS (ESI, m/z): 317 (M + H)+ | Without purification |
| 2-43-2 | (structure) | MS (ESI, m/z): 317 (M + H)+ | Without purification |
| 2-44-1 | (structure) | MS (ESI, m/z): 197 (M + H)+ | Column: APS EtOAc/MeOH |

TABLE 41
| Ref. Ex. | Stre. | P.D. | P.C. |
|---|---|---|---|
| 2-45-1 | 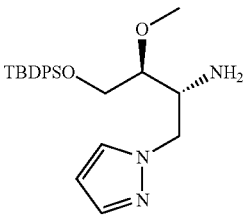 | MS (ESI, m/z): 424 (M + H)$^+$ | Column: APS EtOAc/n-Hexane |
| 2-45-2 | 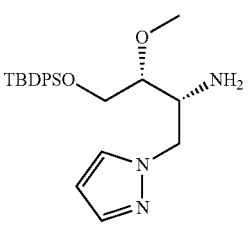 | MS (ESI, m/z): 424 (M + H)$^+$ | Column: APS EtOAc/n-Hexane |
| 2-45-3 | 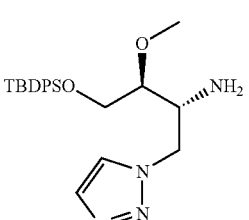 | MS (ESI, m/z): 425 (M + H)$^+$ | Column: APS EtOAc/n-Hexane |
| 2-45-4 | 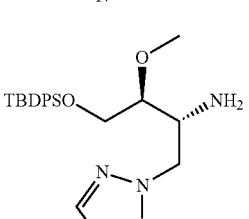 | MS (ESI, m/z): 425 (M + H)$^+$ | Column: APS EtOAc/n-Hexane |
| 2-45-5 | 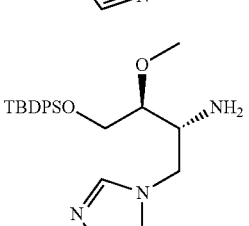 | MS (ESI, m/z): 425 (M + H)$^+$ | Column: APS EtOAc/MeOH |
| 2-45-6 | 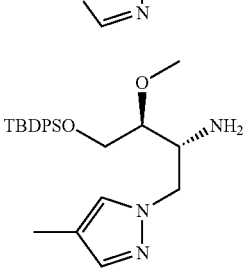 | MS (ESI, m/z): 438 (M + H)$^+$ | Column: APS EtOAc/MeOH |
| 2-45-7 | 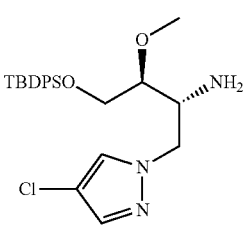 | MS (ESI, m/z): 458 (M + H)$^+$ | Column: APS EtOAc/MeOH |

TABLE 41-continued

| Ref. Ex. | Stre. | P.D. | P.C. |
|---|---|---|---|
| 2-45-8 | TBDPSO, OMe, NH₂, imidazole | MS (ESI, m/z): 424 (M + H)⁺ | Column: APS EtOAc/MeOH |

TABLE 42

| Ref. Ex. | Stre. | P.D. | P.C. |
|---|---|---|---|
| 2-46-1 | TBDPSO, OMe, NHBoc, I | ¹H-NMR (CDCl₃) δ ppm: 1.06 (9H, s), 1.42 (9H, s), 3.24-3.35 (2H, m), 3.38 (3H, s), 3.59-3.72 (2H, m), 3.98-4.04 (1H, m), 5.08 (1H, d, J = 8.8 Hz), 7.38-7.44 (6H, m). 7.65-7.70 (4H, m). | Column: S102 EtOAc/ n-Hexane |
| 2-46-2 | TBDPSO, OMe, NHBoc, I | ¹H-NMR (CDCl₃) δ ppm: 1.07 (9H, s), 1.42 (9H, s), 3.24-3.28 (1H, m), 3.38 (3H, m), 3.38-3.41 (1H, m), 3.51-3.66 (2H, m), 3.77 (2H, d, J = 3.7 Hz), 8.16 (1H, d, J = 8.0 Hz), 7.38-7.46 (6H, m), 7.67-7.72 (4H, m). | Column: S102 EtOAc/ n-Hexane |
| 2-47-1 | HO, OMe, NH₂, pyrimidine | MS (ESI, m/z): 198 (M + H)⁺ | Column: APS EtOAc/MeOH |
| 2-48-1 | TBDPSO, OMe, NH₂, pyrimidine | MS (ESI, m/z): 436 (M + H)⁺ | Column: APS EtOAc/ n-Hexane |
| 2-48-2 | TBDPSO, OMe, NH₂, pyrimidine | MS (ESI, m/z): 436 (M + H)⁺ | Column: APS EtOAc/ n-Hexane |

TABLE 42-continued

| Ref. Ex. | Stre. | P.D. | P.C. |
|---|---|---|---|
| 2-48-3 | (structure) | MS (ESI, m/z): 436 (M + H)+ | Without purification |
| 2-48-4 | (structure) | MS (ESI, m/z): 460 (M + H)+ | Column: APS EtOAc/ n-Hexane |
| 2-48-5 | (structure) | MS (ESI, m/z): 441 (M + H)+ | Without purification |

TABLE 43

| Ref. Ex. | Stre. | P.D. | P.C. |
|---|---|---|---|
| 2-49-1 | (structure) | MS (ESI, m/z): 453 (M + H)+ | Without purification |
| 2-49-2 | (structure) | MS (ESI, m/z): 441 (M + H)+ | Without purification |
| 2-50-1 | (structure) | MS (ESI, m/z): 436 (M + H)+ | Column: APS EtOAc/ n-Hexane |

TABLE 43-continued

| Ref. Ex. | Stre. | P.D. | P.C. |
|---|---|---|---|
| 2-50-2 | (structure) | MS (ESI, m/z): 460 (M + H)+ | Column: APS EtOAc/n-Hexane |
| 2-51-1 | (structure) | $^1$H-NMR (CDCl$_3$) δ ppm: 3.60-3.71 (3H, m), 7.39-7.45 (1H, m), 7.65-7.71 (1H, m), 7.83-7.89 (1H, m), 8.63-8.66 (1H, m).<br>MS (ESI, m/z): 189 (M + H)+ | Column: APS EtOAc/n-Hexane |
| 2-51-2 | (structure) | MS (ESI, m/z): 203 (M + H)+ | Column: APS EtOAc/n-Hexane |
| 2-51-3 | (structure) | MS (ESI, m/z): 219 (M + H)+ | Without purification |
| 2-52-1 | (structure) | $^1$H-NMR (CDCl$_3$) δ ppm: 3.34 (3H, m), 3.64-3.80 (5H, m), 4.50-4.65 (3H, m), 7.25-7.40 (6H, m), 7.64-7.69 (1H, m), 7.81 (1H, ddd, J = 1.8, 7.8, 7.8 Hz), 8.65-8.70 (1H, m).<br>MS (ESI, m/z): 323 (M + H)+ | Column: APS EtOAc/MeOH |

TABLE 44

| Ref. Ex. | Stre. | P.D. | P.C. |
|---|---|---|---|
| 2-53-1 | (structure) | $^1$H-NMR (CDCl$_3$) δ ppm: 1.51 (3H, m), 3.10 (1H, dd, J = 4.3, 7.0 Hz), 3.77 (1H, dd, J = 7.1, 10.8 Hz), 3.83 (1H, dd, J = 4.4, 10.8 Hz), 7.22-7.28 (1H, m), 7.40-7.44 (1H, m), 7.73-7.79 (1H, m), 8.52-8.55 (1H, m). | Column: APS EtOAc/MeOH |
| 2-53-2 | (structure) | $^1$H-NMR (CDCl$_3$) δ ppm: 0.58 (3H, t, J = 7.4 Hz), 1.77-2.00 (2H, m), 3.08-3.11 (1H, m), 3.74 (1H, dd, J = 7.2, 10.8 Hz), 3.84 (1H, dd, J = 4.3, 10.8 Hz), 7.21-7.27 (1H, m), 7.35-7.40 (1H, m), 7.73-7.79 (1H, m), 8.53-8.57 (1H, m). | Column: APS EtOAc/MeOH |

TABLE 44-continued

| Ref. Ex. | Stre. | P.D. | P.C. |
|---|---|---|---|
| 2-54-1 | (structure) | $^1$H-NMR (CDCl$_3$) δ ppm: 1.63 (3H, m), 3.02 (1H, dd, J = 4.3, 7.9 Hz), 3.02 (3H, s), 3.35 (1H, dd, J = 7.9, 10.7 Hz), 3.51 (1H, dd, J = 4.4, 10.7 Hz), 7.20 (1H, ddd, J = 1.2, 4.2, 7.5 Hz), 7.45-7.50 (1H, m), 7.71 (1H, ddd, J = 1.0, 7.9, 7.9 Hz), 8.58-8.61 (1H, m), MS (ESI, m/z): 197 (M + H)$^+$ | Column: APS EtOAc/MeOH |
| 2-55-1 | (structure) | $^1$H-NMR (CDCl$_3$) δ ppm: 3.46-3.60 (2H, m), 3.72-3.80 (1H, m), 5.06 (1H, dd, J = 4.6, 45 Hz), 7.26-7.32 (1H, m), 7.50 (1H, d, J = 7.8 Hz), 7.80 (1H, ddd, J = 1.8, 7.7, 7.7 Hz), 8.55-8.60 (1H, m). MS (ESI, m/z): 171 (M + H)$^+$ | Column: APS EtOAc/MeOH |
| 2-56-1 | (structure) HCl | MS (ESI, m/z): 198 (M + H)$^+$ | Without purification |
| 2-57-1 | (structure) | MS (ESI, m/z): 276 (M + H)$^+$ | Column: APS EtOAc/MeOH |
| 2-57-2 | (structure) | MS (ESI, m/z): 276 (M + H)$^+$ | Column: APS EtOAc/MeOH |
| 2-57-3 | (structure) | MS (ESI, m/z): 275 (M + H)$^+$ | Column: APS EtOAc/MeOH |
| 2-57-4 | (structure) HCl | MS (ESI, m/z): 293 (M + H)$^+$ | Without purification |

TABLE 45

| Ref. Ex. | Stre. | P.D. | P.C. |
| --- | --- | --- | --- |
| 2-58-1 | (structure) | MS (ESI, m/z): 264 (M + H)⁺ | Column: APS EtOAc/MeOH |
| 2-58-2 | (structure) | MS (ESI, m/z): 264 (M + H)⁺ | Column: APS EtOAc/n-Hexane |
| 2-58-3 | (structure) | MS (ESI, m/z): 264 (M + H)⁺ | Column: APS EtOAc/MeOH |
| 2-58-4 | (structure) | MS (ESI, m/z): 264 (M + H)⁺ | Column: APS EtOAc/MeOH |
| 2-58-5 | (structure) | MS (ESI, m/z): 265 (M + H)⁺ | Without purification |
| 2-58-6 | (structure) | MS (ESI, m/z): 265 (M + H)⁺ | Without purification |
| 2-59-1 | (structure) | MS (ESI, m/z): 282 (M + H)⁺ | Column: APS EtOAc/n-Hexane |

TABLE 45-continued

| Ref. Ex. | Stre. | P.D. | P.C. |
| --- | --- | --- | --- |
| 2-59-2 | BnO-CF$_2$-CH(NH$_2$)-CH$_2$-(2H-1,2,3-triazol-2-yl) · HCl | MS (ESI, m/z): 283 (M + H)$^+$ | Without purification |

TABLE 46

| Ref. Ex. | Stre. | P.D. | P.C. |
| --- | --- | --- | --- |
| 2-60-1 | BnO-CF$_2$-CH(NH$_2$)-CH$_2$-(pyrimidin-2-yl) | MS (ESI, m/z): 294 (M + H)$^+$ | Column: APS EtOAc/MeOH |
| 2-60-2 | BnO-CF$_2$-CH(NH$_2$)-CH$_2$-(pyridin-2-yl) | MS (ESI, m/z): 293 (M + H)$^+$ | Column: APS EtOAc/MeOH |
| 2-61-1 | pyridin-2-yl-CH$_2$CH$_2$-NH-CH$_2$-(2,2-dimethyl-1,3-dioxolan-4-yl) | $^1$H-NMR (CDCl3) δ ppm: 1.34 (3H, m), 1.39 (3H, m), 2.72-2.83 (2H, m), 2.95-3.01 (2H, m), 3.02-3.09 (2H, m), 3.66 (1H, dd, J = 6.7, 8.0 Hz), 4.03 (1H, dd, J = 6.4, 8.0 Hz), 4.18-4.27 (1H, m), 7.09-7.14 (1H, m), 7.15-7.20 (1H, m), 7.59 (1H, td, J = 1.8, 7.7 Hz), 8.51-8.56 (1H, m). | Without purification |
| 2-61-2 | pyridin-2-yl-CH$_2$CH$_2$-NH-CH$_2$-(2,2-dimethyl-1,3-dioxolan-4-yl) | $^1$H-NMR (CDCl$_3$) δ ppm: 1.34 (3H, m), 1.40 (3H, m), 2.72-2.83 (2H, m), 2.95-3.01 (2H, m), 3.02-3.09 (2H, m), 3.66 (1H, dd, J = 6.7, 8.0 Hz), 4.03 (1H, dd, J = 6.3, 8.0 Hz), 4.18-4.27 (1H, m), 7.09-7.14 (1H, m), 7.15-7.20 (1H, m), 7.59 (1H, td, J = 1.9, 7.7 Hz), 8.51-8.56 (1H, m). | Without purification |
| 2-62-1 | pyridin-2-yl-CH$_2$CH$_2$-NH-CH$_2$-CH(OMe)-CH$_2$-OBn | $^1$H-NMR (CDCl$_3$) δ ppm: 2.71-2.84 (2H, m), 2.93-3.08 (4H, m), 3.42 (3H, m), 3.48-3.56 (3H, m), 4.53 (2H, s), 7.08-7.13 (1H, m), 7.14-7.19 (1H, m), 7.25-7.38 (5H, m), 7.58 (1H, td, J = 1.9, 7.7 Hz), 8.49-8.56 (1H, m). | Column: APS EtOAc/MeOH |
| 2-62-2 | pyridin-2-yl-CH$_2$CH$_2$-NH-CH$_2$-CH(OMe)-CH$_2$-OBn | $^1$H-NMR (CDCl$_3$) δ ppm: 2.71-2.84 (2H, m), 2.98-3.08 (4H, m), 3.42 (3H, m), 3.47-3.57 (3H, m), 4.53 (2H, s), 7.08-7.14 (1H, m), 7.14-7.19 (1H, m), 7.25-7.40 (5H, m), 7.58 (1H, d, J = 1.9, 7.7 Hz), 8.49-8.56 (1H, m). | Column: APS EtOAc/MeOH |

TABLE 46-continued

| Ref. Ex. | Stre. | P.D. | P.C. |
| --- | --- | --- | --- |
| 2-63-1 | | ¹H-NMR (DMSO-d₆) δ ppm: 1.55-1.80 (1H, br), 2.45 (1H, dd, J = 7.2, 11.8 Hz), 2.56 (1H, dd, J = 4.5, 11.8 Hz), 2.84 (4H, s), 3.17-3.28 (5H, m), 3.57-3.70 (1H, m), 4.62-4.70 (1H, m), 7.16-7.22 (1H, m), 7.23-7.29 (1H, m), 7.68 (1H, td, J = 1.9, 7.7 Hz), 8.44-8.49 (1H, m). | Column: APS EtOAc/MeOH |
| 2-63-2 | | ¹H-NMR (DMSO-d₆) δ ppm: 1.55-1.88 (1H, br), 2.45 (1H, dd, J = 7.2, 11.8 Hz), 2.56 (1H, dd, J = 4.5, 11.8 Hz), 2.84 (4H, s), 3.17-3.28 (5H, m), 3.57-3.69 (1H, m), 4.62-4.70 (1H, m), 7.15-7.22 (1H, m), 7.23-7.30 (1H, m), 7.68 (1H, td, J = 1.9, 7.7 Hz), 8.44-8.49 (1H, m). | Column: APS EtOAc/MeOH |
| 2-64-1 | | MS (ESI, m/z): 350 (M + H)⁺ | Collected by filtration |

TABLE 47

| Ref. Ex. | Stre. | P.D. | P.C. |
| --- | --- | --- | --- |
| 2-65-1 | | MS (ESI, m/z): 327 (M + H)⁺ | Column: S102 EtOAc/MeOH |
| 2-65-2 | | ¹H-NMR (CDCl₃) δ ppm: 1.09 (9H, s), 1.37 (3H, s), 1.41 (3H, s), 1.88-1.94 (2H, m), 3.06-3.10 (2H, m), 3.51 (1H, t, J = 7.7 Hz), 3.98-4.10 (2H, m), 4.40-4.50 (1H, m), 4.56 (1H, d, J = 7.7 Hz), 7.09-7.21 (2H, m), 7.56-7.62 (1H, m), 8.49-8.54 (1H, m). | Column: S102 EtOAc/MeOH |
| 2-65-3 | | MS (ESI, m/z): 345 (M + H)⁺ | Column: S102 EtOAc/MeOH |

TABLE 47-continued
| Ref. Ex. | Stre. | P.D. | P.C. |
|---|---|---|---|
| 2-66-1 | 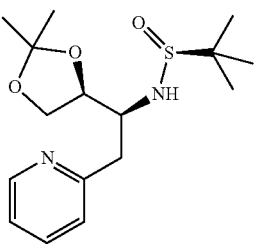 [SMILES: CC1(C)OC[C@H]([C@H](Cc2ccccn2)N[S@@](=O)C(C)(C)C)O1] | MS (ESI, m/z): 327 (M + H)+ | Column: S102<br>EtOAc/MeOH |
| 2-66-2 | 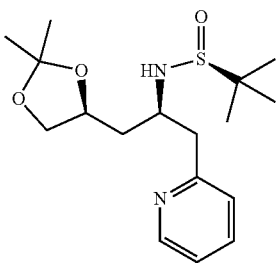 [SMILES: CC1(C)OC[C@H](C[C@H](Cc2ccccn2)N[S@@](=O)C(C)(C)C)O1] | MS (ESI, m/z): 341 (M + H)+ | Column: S102<br>EtOAc/MeOH |
TABLE 48
| Ref. Ex. | Stre. | P.D. | P.C. |
|---|---|---|---|
| 2-67-1 | 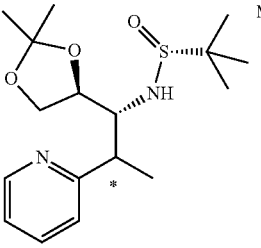 | MS (ESI, m/z): 341 (M + H)+ | Column: S102<br>EtOAc/MeOH |
| 2-67-2 | 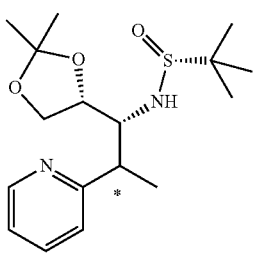 [SMILES: CC(c1ccccn1)[C@@H](N[S@](=O)C(C)(C)C)[C@@H]1COC(C)(C)O1] | MS (ESI, m/z): 341 (M + H)+ | Column: S102<br>EtOAc/MeOH |
| 2-68-1 | 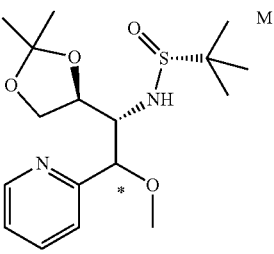 | MS (ESI, m/z): 357 (M + H)+ | Column: S102<br>EtOAc/MeOH |

TABLE 48-continued

| Ref. Ex. | Stre. | P.D. | P.C. |
|---|---|---|---|
| 2-69-1 | (structure) | MS (ESI, m/z): 186 (M + H)$^+$ | Without purification |
| 2-70-1 | (structure) | MS (ESI, m/z): 174 (M + H)$^+$ | Without purification |
| 2-71-1 | (structure) | MS (ESI, m/z): 188 (M + H)$^+$ | Without purification |

EXAMPLES

Example 1-1

3-Fluoro-2-[5-(4-fluorophenyl)-1H-pyrazol-3-yl]-N-[(2R)-4-hydroxy-1-(pyridin-2-yl)butan-2-yl]benzamide To a suspension of 3-fluoro-2-[5-(4-fluorophenyl)-1H-pyrazol-3-yl]benzoic acid (0.35 g) in N,N-dimethylformamide (1 mL) were added 1-hydroxybenzotriazole monohydrate (0.23 g), (3R)-3-amino-4-(pyridin-2-yl)butan-1-ol hydrochloride (0.28 g), N,N-diisopropylethylamine (0.75 g) and 1-ethyl-3-(3-dimethylaminopropyl)carbodiimide hydrochloride (0.29 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol). The crude product was purified by silica gel column chromatography (eluent: ethyl acetate/methanol) to afford the title compound (0.18 g). Structural formula, spectral data and purification condition are shown in Table 49.

Examples 1-2 to 1-204, 1-208 to 1-209, 1-212 to 1-246 and 43-26

Examples 1-2 to 1-204, 1-208 to 1-209, 1-212 to 1-246 and 43-26 were synthesized in a manner similar to that of Example 1-1 by using the corresponding materials. Structural formula, spectral data and purification condition are shown in Table 49 to Table 84 and Table 118.

Example 2-1

2-(4-Ethyl-5-phenyl-1H-pyrazol-3-yl)-N-[2-(pyridin-2-yl)ethyl]benzamide

A mixture of 2-(1-methoxymethyl-5-phenyl-4-vinyl-1H-pyrazol-3-yl)benzoic acid and 2-(2-methoxymethyl-5-phenyl-4-vinyl-2H-pyrazol-3-yl)benzoic acid (480 mg), 1-hydroxybenzotriazole monohydrate (220 mg), 2-(pyridin-2-yl)ethylamine (351 mg) and triethylamine (436 mg) were dissolved in N,N-dimethylformamide (5 mL). To the mixture was added 1-ethyl-3-(3-dimethylaminopropyl)carbodiimide hydrochloride (551 mg) at room temperature, and the mixture was stirred overnight. The reaction mixture was poured into water, and the crude product was extracted with ethyl acetate. The extract was washed with water, and then was concentrated under reduced pressure. The residue was purified by silica gel column chromatography (eluent: ethyl acetate/methanol) to afford a mixture of 2-(1-methoxymethyl-5-phenyl-4-vinyl-1H-pyrazol-3-yl)-N-[2-(pyridin-2-yl)ethyl]benzamide and 2-(2-methoxymethyl-5-phenyl-4-vinyl-2H-pyrazol-3-yl)-N-[2-(pyridin-2-yl)ethyl]benzamide (453 mg). To a mixture of the product (50 mg) and tetrahydrofuran (2 mL) was added 10% palladium-carbon (50% wet, 10 mg). The mixture was stirred at room temperature under a hydrogen atmosphere overnight. The reaction mixture was filtered through a pad of celite, and the filtrate was concentrated under reduced pressure. The residue was dissolved in ethanol (1 mL), and to the mixture was added a solution of hydrogen chloride in ethyl acetate (4 mol/L, 2 mL). The mixture was stirred at 60° C. for 5 hours and the mixture was poured into a saturated aqueous solution of sodium bicarbonate. The crude product was extracted with ethyl acetate. The extract was washed with a saturated aqueous solution of sodium bicarbonate and water, and then concentrated under reduced pressure to afford the title compound (42 mg). Structural formula, spectral data and purification condition are shown in Table 85.

Example 3-1

2-(4-Formyl-5-phenyl-1H-pyrazol-3-yl)-N-[2-(pyridin-2-yl)ethyl]benzamide

To a mixture of tetrahydrofuran (2 mL) and water (0.5 mL) were added a mixture of 2-(1-methoxymethyl-5-phenyl-4-vinyl-1H-pyrazol-3-yl)-N-[2-(pyridin-2-yl)ethyl]benzamide and 2-(2-methoxymethyl-5-phenyl-4-vinyl-2H-pyrazol-3-yl)-N-[2-(pyridin-2-yl)ethyl]benzamide (100 mg) and an aqueous solution of N-methylmorpholine-N-oxide (4.8 mol/L, 0.071 mL). To the mixture was added a solution of osmium tetroxide in tert-butyl alcohol (0.1 mol/L, 0.012 mL), and the mixture was stirred at room temperature overnight. To the mixture was added sodium periodate (146 mg), and the mixture was stirred at room temperature overnight. The mixture was filtered through a pad of celite, and the insoluble compound was washed with ethyl acetate. The filtrate was washed with brine and water, and then concentrated under reduced pressure. The residue was purified by aminopropyl silica gel column chromatography (eluent: ethyl acetate/methanol) to afford a mixture of 2-(4-formyl-1-methoxymethyl-5-phenyl-1H-pyrazol-3-yl)-N-[2-(pyridin-2-yl)ethyl]benzamide and 2-(4-formyl-2-methoxymethyl-5-phenyl-2H-pyrazol-3-yl)-N-[2-(pyridin-2-yl)ethyl]benzamide (30 mg). The product (30 mg) was dissolved in tetrahydrofuran (1 mL). To the mixture was added hydrochloric acid (6 mol/L 1 mL), and the mixture was stirred at 50° C. for 3 hours. The mixture was poured into a saturated aqueous solution of sodium bicarbonate, and the crude product was extracted with ethyl acetate. The extract was washed with a saturated aqueous solution of sodium bicarbonate and water, and then concentrated under reduced pressure. The residue was purified by silica gel column chromatography (eluent: ethyl acetate/methanol) to afford the title compound (11 mg). Structural formula, spectral data and purification condition are shown in Table 85.

Example 4-1

2-(5-Phenyl-1H-pyrazol-3-yl)-N-[2-(pyridin-2-yl)ethyl]-3-trifluoromethoxybenzamide To a solution of 3-(2-bromo-6-trifluoromethoxyphenyl)-5-phenyl-1H-pyrazole (100 mg) in dimethylsulfoxide (4 mL) were added 1,3-bis(diphenylphosphino)propane (22 mg), N,N-diisopropylethylamine (169 mg) and 2-(pyridin-2-yl)ethylamine (191 mg), and the mixture was placed under an argon atmosphere. To the mixture was added palladium (II) acetate (12 mg), and the mixture was stirred at 110° C. under a carbon monoxide atmosphere for 5 hours. The reaction mixture was filtered through a pad of celite, and to the filtrate was added water. The crude product was extracted with ethyl acetate. The extract was washed with water, and then was concentrated under reduced pressure. The residue was purified by silica gel column chromatography (eluent: ethyl acetate/methanol) to afford the title compound (43 mg). Structural formula, spectral data and purification condition are shown in Table 86.

Examples 4-2 to 4-11 and 5-4 to 5-7

Examples 4-2 to 4-11 and 5-4 to 5-7 were synthesized in a manner similar to that of Example 4-1 by using the corresponding materials. Structural formula, spectral data and purification condition are shown in Table 86 to Table 88.

Example 5-1

2-[5-(3-Formylphenyl)-1H-pyrazol-3-yl]-N-[2-(pyridin-2-yl)ethyl]benzamide

To a solution of 2-{5-[3-(1,3-dioxolan-2-yl)phenyl]-1H-pyrazol-3-yl}-N-[2-(pyridin-2-yl)ethyl]benzamide (0.202 g) in tetrahydrofuran (1.5 mL) was added hydrochloric acid (1 mol/L, 3 mL), and the mixture was stirred at 60° C. overnight. The reaction mixture was poured into a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford the title compound (0.134 g). Structural formula, spectral data and purification condition are shown in Table 88.

Examples 5-2 to 5-3

Examples 5-2 to 5-3 were synthesized in a manner similar to that of Example 5-1 by using the corresponding materials. Structural formula, spectral data and purification condition are shown in Table 88.

Example 6-1

2-{5-[3-(Hydroxymethyl)phenyl]-1H-pyrazol-3-yl}-N-[2-(pyridin-2-yl)ethyl]benzamide To a solution of 2-[5-(3-formylphenyl)-1H-pyrazol-3-yl]-N-[2-(pyridin-2-yl)ethyl]benzamide (0.112 g) in methanol (3 mL) was added sodium borohydride (0.016 g) under ice-cooling, and the mixture was stirred at room temperature for 1.5 hours. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford the title compound (0.114 g). Structural formula, spectral data and purification condition are shown in Table 89.

Examples 6-2 to 6-3

Examples 6-2 to 6-3 were synthesized in a manner similar to that of Example 6-i by using the corresponding materials. Structural formula, spectral data and purification condition are shown in Table 89.

Example 7-1

2-[5-(2-Acetylaminophenyl)-1H-pyrazol-3-yl]-N-[2-(pyridin-2-yl)ethyl]benzamide

To a mixture of 2-[5-(2-aminophenyl)-1H-pyrazol-3-yl]-N-[2-(pyridin-2-yl)ethyl]benzamide (40 mg) and triethylamine (21 mg) in dichloromethane (2 mL) was added acetic anhydride (12 mg) at room temperature. The mixture was stirred overnight, and diluted with water. The crude product was extracted with ethyl acetate. The extract was washed with water, and then concentrated under reduced pressure.

The residue was purified by silica gel column chromatography (eluent: ethyl acetate/methanol) and aminopropyl silica gel column chromatography (eluent: ethyl acetate/methanol) to afford the title compound (31 mg). Structural formula, spectral data and purification condition are shown in Table 89.

Examples 7-2 to 7-3

Examples 7-2 to 7-3 were synthesized in a manner similar to that of Example 7-1 by using the corresponding materials. Structural formula, spectral data and purification condition are shown in Table 89.

Example 8-1

2-[5-(2-Methanesulfonylaminophenyl)-1H-pyrazol-3-yl]-N-[2-(pyridin-2-yl)ethyl]benzamide To a mixture of 2-[5-(2-aminophenyl)-1H-pyrazol-3-yl]-N-[2-(pyridin-2-yl)ethyl]benzamide (44 mg) and triethylamine (23 mg) in dichloromethane. (2 mL) was added methanesulfonyl chloride (15 mg) at room temperature. The mixture was stirred at room temperature overnight, and diluted with water. The crude product was extracted with ethyl acetate. The extract was washed with water, and then concentrated under reduced pressure. The residue was purified by silica gel column chromatography (eluent: ethyl acetate/methanol). The crude product was purified by aminopropyl silica gel column chromatography (eluent: ethyl acetate/methanol) to afford the title compound (18 mg). Structural formula, spectral data and purification condition are shown in Table 89.

Example 9-1

(S)-3-Phenyl-2-[2-(5-phenyl-1H-pyrazol-3-yl)benzoylamino]propionic acid

To a suspension of 2-(5-phenyl-1H-pyrazol-3-yl)benzoic acid (0.50 g) in N,N-dimethylformamide (5 mL) were added 1-hydroxybenzotriazole monohydrate (0.44 g), (2S)-2-amino-3-phenylpropionic acid benzyl ester p-toluenesulfonate (0.97 g), N,N-diisopropylethylamine (0.73 g) and 1-ethyl-3-(3-dimethylaminopropyl)carbodiimide hydrochloride (0.54 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford (S)-3-phenyl-2-[2-(5-phenyl-1H-pyrazol-3-yl)benzoylamino]propionic acid benzyl ester (0.95 g). To a solution of the product (0.95 g) tetrahydrofuran (6 mL) was added 10% palladium-carbon (50% wet, 0.1 g) at room temperature, and the mixture was stirred under a hydrogen atmosphere for 2 hours. The reaction mixture was filtered through a pad of celite. The filtrate was concentrated under reduced pressure to afford the title compound (0.80 g). Structural formula, spectral data and purification condition are shown in Table 90.

Example 9-2

Example 9-2 was synthesized in a manner similar to that of Example 9-1 by using the corresponding materials. Structural formula, spectral data and purification condition are shown in Table 90.

Example 10-1

N-((S)-1-Dimethylcarbamoyl-2-phenylethyl)-2-(5-phenyl-1H-pyrazol-3-yl)benzamide

To a suspension of (S)-3-phenyl-2-[2-(5-phenyl-1H-pyrazol-3-yl)benzoylamino]propionic acid (0.06 g) in N,N-dimethylformamide (1 mL) were added 1-hydroxybenzotriazole monohydrate (0.034 g), a solution of dimethylamine in tetrahydrofuran (2 mol/L, 0.36 mL) and 1-ethyl-3-(3-dimethylaminopropyl)carbodiimide hydrochloride (0.042 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford the title compound (0.015 g). Structural formula, spectral data and purification condition are shown in Table 90.

Examples 10-2 to 10-3

Examples 10-2 to 10-3 were synthesized in a manner similar to that of Example 10-1 by using the corresponding materials. Structural formula, spectral data and purification condition are shown in Table 90.

Example 11-1

3-Benzyloxy-2-(5-phenyl-1H-pyrazol-3-yl)-N-[2-(pyridin-2-yl)ethyl]benzamide

A mixture of 3-(2-benzyloxy-6-bromophenyl)-1-methoxymethyl-5-phenyl-1H-pyrazole and 3-(2-benzyloxy-6-bromophenyl)-2-methoxymethyl-5-phenyl-2H-pyrazole (1.63 g) was dissolved in dimethylsulfoxide (20 mL). To the mixture were added 1,3-bis(diphenylphosphino)propane (302 mg), N,N-diisopropylethylamine (1.41 g) and 2-(pyridin-2-yl)ethylamine (1.33 g), and the mixture was placed under an argon atmosphere. To the mixture was added palladium(II) acetate (164 mg), and the mixture was stirred at 110° C. under a carbon monoxide atmosphere for 5 hours. The reaction mixture was filtered through a pad of celite, and to the filtrate was added water. The crude product was extracted with ethyl acetate. The extract was washed with water, and then concentrated under reduced pressure. The residue was purified by silica gel column chromatography (eluent: ethyl acetate/methanol) to afford a mixture of 3-benzyloxy-2-(1-methoxymethyl-5-phenyl-1H-pyrazol-3-yl)-N-[2-(pyridin-2-yl)ethyl]benzamide and 3-benzyloxy-2-(2-methoxymethyl-5-phenyl-2H-pyrazol-3-yl)-N-[2-(pyridin-2-yl)ethyl]benzamide (1.13 g). The mixture (50 mg) was dissolved in ethanol (1 mL). To the solution was added a solution of hydrogen chloride in ethyl acetate (4 mol/L, 2 mL), and the mixture was stirred at 60° C. for 2. hours. The mixture was poured into a saturated aqueous solution of sodium bicarbonate, and the crude product was extracted with ethyl acetate. The extract was washed with a saturated aqueous solution of sodium bicarbonate and water, and then dried over anhydrous magnesium sulfate. The solvent was removed under reduced pressure to afford the title compound (44 mg). Structural formula, spectral data and purification condition are shown in Table 90.

Example 12-1

(2-(5-Phenyl-1H-pyrazol-3-yl)-3-{N-[2-(pyridin-2-yl)ethyl]carbamoyl}phenoxy)acetic acid ethyl ester To 3-hydroxy-2-(2-methoxymethyl-5-phenyl-2H-pyrazol-3-yl)-N-[2-(pyridin-2-yl)ethyl]benzamide (200 mg) was dissolved in N,N-dimethylformamide (3 mL). To the mixture were added potassium carbonate (193 mg) and ethyl bromoacetate (117 mg), and the mixture was stirred at room temperature overnight. The mixture was poured into water, and the crude product was extracted with ethyl acetate. The extract was washed with water, and then was concentrated under reduced pressure. The residue was purified by silica gel column chromatography (eluent: ethyl acetate/methanol) to afford 2-(2-methoxymethly-5-phenyl-2H-pyrazol-3-yl)-3-{N-[2-(pyridin-2-yl)ethyl]carbamoyl}phenoxy)acetic acid ethyl ester (299 mg). The product (204 mg) was dissolved in ethanol (2 mL). To the solution was added a solution of hydrogen chloride in ethyl acetate (4 mol/L, 4 mL), and the mixture was stirred at 60° C. for 4 hours. The mixture was poured into a saturated aqueous solution of sodium bicarbonate, and the crude product was extracted with ethyl acetate. The extract was washed with a saturated aqueous solution of sodium bicarbonate and water, and then dried over anhydrous magnesium sulfate. The solvent was removed under reduced pressure to afford the title compound (134 mg). Structural formula, spectral data and purification condition are shown in Table 91.

Examples 12-2 to 12-4

Examples 12-2 to 12-4 were synthesized in a manner similar to that of Example 12-1 by using the corresponding materials. Structural formula, spectral data and purification condition are shown in Table 91.

Example 13-1

3-(2-Hydroxyethoxy)-2-(5-phenyl-1H-pyrazol-3-yl)-N-[2-(pyridin-2-yl)ethyl]benzamide To 2-(2-methoxymethyl-5-phenyl-2H-pyrazol-3-yl)-3-{N-[2-(pyridin-2-yl)ethyl]carbamoyl}phenoxy)acetic acid ethyl ester (95 mg) was added ethanol (2 mL). To the mixture was added sodium borohydride (21 mg) at room temperature, and the mixture was stirred for 3 hours. To the mixture was added sodium borohydride (42 mg), and the mixture was stirred overnight. The reaction mixture was diluted with water. The mixture was poured into a saturated aqueous solution of sodium bicarbonate, and the crude product was extracted with ethyl acetate. The extract was washed with water, and then was concentrated under reduced pressure. The residue was purified by silica gel column chromatography (eluent: ethyl acetate/methanol) to afford a mixture of 3-(2-hydroxyethoxy)-2-(1-methoxymethyl-5-phenyl-1H-pyrazol-3-yl)-N-[2-(pyridin-2-yl)ethyl]benzamide and 3-(2-hydroxyethoxy)-2-(2-methoxymethyl-5-phenyl-2H-pyrazol-3-yl)-N-[2-(pyridin-2-yl)ethyl]benzamide (58 mg). The mixture (58 mg) was dissolved in ethanol (1 mL). To the solution was added a solution of hydrogen chloride in ethyl acetate (4 mol/L, 2 mL), and the mixture was stirred at 60° C. for 2 hours. The reaction mixture was poured into a saturated aqueous solution of sodium bicarbonate, and the crude product was extracted with ethyl acetate. The extract was washed with a saturated aqueous solution of sodium bicarbonate and water, and then concentrated under reduced pressure. The residue was purified by silica gel column chromatography (eluent: ethyl acetate/methanol) to afford the title compound (38 mg). Structural formula, spectral data and purification condition are shown in Table 91.

Example 14-1

(2S)-3-Phenyl-2-[2-(5-phenyl-1H-pyrazol-3-yl)benzoylamino]-N-(pyrrolidin-3-yl)propanamide To a suspension of (S)-3-phenyl-2-[2-(5-phenyl-1H-pyrazol-3-yl)benzoylamino]propionic acid (0.06 g) in dichloromethane (1 mL) were added 3-aminopyrrolidine-1-carboxylic acid tert-butyl ester (0.03 g), N,N-diisopropylethylamine (0.066 g) and a solution of T3P® in ethyl acetate (1.7 mol/L, 0.17 mL), and the mixture was stirred at room temperature for 1.5 hours. To the reaction mixture was added water, and the insoluble compound was collected by filtration to afford 3-{(2S)-3-phenyl-2-[2-(5-phenyl-1H-pyrazol-3-yl)benzoylamino]propylamino}pyrrolidine-1-carboxylic acid tert-butyl ester. To the product were added tetrahydrofuran (1 mL) and a solution of hydrogen chloride in 1,4-dioxane (4 mol/L, 1 mL), and the mixture was stirred at room temperature for 3 hours. The reaction mixture was concentrated under reduced pressure. To the residue was added a saturated aqueous solution of sodium bicarbonate, and the crude product was extracted with dichloromethane. The organic layer was washed with brine, and dried over anhydrous magnesium sulfate. The solvent was removed under reduced pressure. To the residue were added ethyl acetate and n-hexane. The insoluble compound was collected by filtration to afford the title compound (0.037 g). Structural formula, spectral data and purification condition are shown in Table 91.

Example 14-2

Example 14-2 was synthesized in a manner similar to that of Example 14-1 by using the corresponding materials. Structural formula, spectral data and purification condition are shown in Table 91.

Example 15-1

N-[(2S)-1-((3S)-3-Hydroxypyrrolidin-1-yl)-1-oxo-3-phenylpropan-2-yl]-2-(5-phenyl-1H-pyrazol-3-yl)benzamide To a solution of (S)-3-phenyl-2-[2-(5-phenyl-1H-pyrazol-3-yl)benzoylamino]propionic acid (0.05 g) in methanol (2 mL) were added (3S)-pyrrolidin-3-ol (0.016 g) and 4-(4,6-dimethoxy-1,3,5-triazin-2-yl)-4-methylmorpholinium chloride n-hydrate (0.05 g), and the mixture was stirred at room temperature for 2 days. To the reaction mixture was added a saturated aqueous solution of sodium bicarbonate, and the crude product was extracted with dichloromethane. The organic layer was washed with brine, and dried over anhydrous magnesium sulfate. The solvent was removed under reduced pressure, and the residue was purified by aminopropyl silica gel column chromatography (eluent: ethyl acetate/methanol) to afford the title compound (0.05 g). Structural formula, spectral data and purification condition are shown in Table 92.

Example 15-2

Example 15-2 was synthesized in a manner similar to that of Example 15-1 by using the corresponding materials. Structural formula, spectral data and purification condition are shown in Table 92.

Example 16-1

N-((2R)-1-Amino-3-phenylpropan-2-yl)-2-(5-phenyl-1H-pyrazol-3-yl)benzamide

To a suspension of 2-(5-phenyl-1H-pyrazol-3-yl)benzoic acid (0.105 g) in N,N-dimethylformamide (1 mL) were added 1-hydroxybenzotriazole monohydrate (0.092 g), N-((2R)-2-amino-3-phenylpropyl)phthalimide (0.126 g), N,N-diisopropylethylamine (0.154 g) and 1-ethyl-3-(3-dimethylaminopropyl) carbodiimide hydrochloride (0.114 g), and the mixture was stirred at room temperature for 2 hours. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford N-[(2R)-1-(1,3-dioxo-2,3-dihydro-1H-isoindol-2-yl)-3-phenylpropan-2-yl]-2-(5-phenyl-1H-pyrazol-3-yl)benzamide (0.10 g). The product (0.10 g) was dissolved in methanol (1 mL). To the mixture was added hydrazine monohydrate (0.10 g), and the mixture was stirred under reflux for 2 hours. The reaction mixture was concentrated under reduced pressure. To the residue was added water, and the crude product was extracted with ethyl acetate. The organic layer was washed with brine, and dried over anhydrous magnesium sulfate. The solvent was removed under reduced pressure. The residue was purified by aminopropyl silica gel column chromatography (eluent: ethyl acetate/methanol) to afford the title compound (0.03 g). Structural formula, spectral data and purification condition are shown in Table 92.

Examples 16-2 to 6-11

Examples 16-2 to 6-11 were synthesized in a manner similar to that of Example 16-1 by using the corresponding materials. Structural formula, spectral data and purification condition are shown in Table 92 to Table 93.

Example 17-1

2-[5-(3,4-Difluorophenyl)-1H-pyrazol-3-yl]-N-[2-(pyridin-2-yl)ethyl]benzamide

To a solution of 3-(2-bromophenyl)-5-(3,4-difluorophenyl)-1H-pyrazole (0.200 g) in 1,4-dioxane (3.4 mL) were added triethylamine (0.091 g), palladium (II) acetate (0.007 g), bis(adamantan-1-yl)(butyl)phosphine (0.011 g) and 2-(2-aminoethyl)pyridine (0.109 g), and the mixture was stirred at 100° C. under a carbon monoxide atmosphere for 23 hours. The reaction mixture was allowed to cool to room temperature, and then filtered through a pad of celite. The filtrate was concentrated under reduced pressure, and the residue was purified by silica gel column chromatography (eluent: ethyl acetate/methanol) to afford the title compound (0.070 g). Structural formula, spectral data and purification condition are shown in Table 94.

Examples 17-2 to 17-11

Examples 17-2 to 17-11 were synthesized in a manner similar to that of Example 17-1 by using the corresponding materials. Structural formula, spectral data and purification condition are shown in Table 94 to Table 95.

Example 18-1

2-[5-(3-Aminophenyl)-1H-pyrazol-3-yl]-N-[2-(pyridin-2-yl)ethyl]benzamide

To a solution of N-{3-[3-(2-bromophenyl)-1H-pyrazol-5-yl]phenyl}carbamic acid tert-butyl ester (0.352 g) in 1,4-dioxane (5 mL) were added triethylamine (0.129 g), palladium (II) acetate (0.010 g), bis(adamantan-1-yl)(butyl)phosphine (0.015 g) and 2-(2-aminoethyl)pyridine (0.156 g), and the mixture was stirred at 100° C. under a carbon monoxide atmosphere for 19 hours. The reaction mixture was allowed to cool to room temperature, and then filtered through a pad of celite. The filtrate was concentrated under reduced pressure, and the residue was purified by silica gel column chromatography (eluent: ethyl acetate/methanol) to afford N-{3-[3-(2-{[2-(pyridin-2-yl)ethyl]carbamoyl}phenyl)-1H-pyrazol-5-yl]phenyl}carbamic acid tert-butyl ester (0.094 g). To a solution of the product (0.094 g) in ethyl acetate (2 mL) was added a solution of hydrogen chloride in ethyl acetate (4 mol/L, 2 mL), and the mixture was stirred at room temperature for 2 hours. The reaction mixture was concentrated under reduced pressure, and the residue was purified by silica gel column chromatography (eluent: ethyl acetate/methanol) to afford the title compound (0.053 g). Structural formula, spectral data and purification condition are shown in Table 95.

Example 18-2

Example 18-2 was synthesized in a manner similar to that of Example 18-1 by using the corresponding materials. Structural formula, spectral data and purification condition are shown in Table 95.

Example 19-1

2-[5-(4-Fluoro-2-hydroxyphenyl)-1H-pyrazol-3-yl]-N-[(2R)-1-hydroxy-3-(pyridin-2-yl)propan-2-yl]benzamide To a solution of 2-[5-(4-fluoro-2-methoxyphenyl)-1H-pyrazol-3-yl]-N-[(2R)-1-hydroxy-3-(pyridin-2-yl)propan-2-yl]benzamide (0.041 g) in dichloromethane (1 mL) was added a solution of boron tribromide in dichloromethane (1 mol/L, 0.46 mL) under ice-cooling, and the mixture was stirred at the same temperature for 2 hours. The mixture was further stirred at room temperature overnight. To the reaction mixture was added a saturated aqueous solution of sodium bicarbonate, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford the title compound (0.017 g). Structural formula, spectral data and purification condition are shown in Table 96.

Examples 19-2 to 19-8

Examples 19-2 to 19-8 were synthesized in a manner similar to that of Example 19-1 by using the corresponding materials. Structural formula, spectral data and purification condition are shown in Table 96 to Table 97.

Example 20-1

N-[2-(4-Aminophenyl)ethyl]-2-(5-phenyl-1H-pyrazol-3-yl)benzamide

To a suspension of 2-(5-phenyl-1H-pyrazol-3-yl)benzoic acid (0.05 g) in N,N-dimethylformamide (1 mL) were added 1-hydroxybenzotriazole monohydrate (0.043 g), 2-(4-nitrophenyl)ethylamine hydrochloride (0.038 g), triethylamine (0.057 g) and 1-ethyl-3-(3-dimethylaminopropyl)carbodiimide hydrochloride (0.055 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure. The residue was dissolved in tetrahydrofuran (1 mL). To the mixture was added 10% palladium-carbon (50% wet, 20 mg), and the mixture was stirred at room temperature under a hydrogen atmosphere for 2 hours. The reaction mixture was filtered through a pad of celite. The filtrate was concentrated under reduced pressure, and the residue was purified by aminopropyl silica gel column chromatography (eluent: ethyl acetate/methanol) to afford the title compound (0.056 g). Structural formula, spectral data and purification condition are shown in Table 97.

Examples 20-2 to 20-3

Examples 20-2 to 20-3 were synthesized in a manner similar to that of Example 20-1 by using the corresponding materials. Structural formula, spectral data and purification condition are shown in Table 97.

Example 21-1

N-[2-(2-Carbamoylphenyl)ethyl]-2-(5-phenyl-1H-pyrazol-3-yl)benzamide

To a suspension of 2-(5-phenyl-1H-pyrazol-3-yl)benzoic acid (0.05 g) in N,N-dimethylformamide (1 mL) were added 1-hydroxybenzotriazole monohydrate (0.043 g), 2-(2-aminoethyl)benzoic acid methyl ester (0.034 g), triethylamine (0.06 g) and 1-ethyl-3-(3-dimethylaminopropyl)carbodiimide hydrochloride (0.055 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford 2-{2-[2-(5-phenyl-1H-pyrazol-3-yl)benzoylamino]ethyl}benzoic acid methyl ester (0.063 g). To a solution of the product (0.063 g) in ethanol (2 mL) was added an aqueous solution of sodium hydroxide (2 mol/L, 0.22 mL), and the mixture was stirred at 60° C. for 1 hour. The reaction mixture was allowed to cool to room temperature, and then neutralized by adding hydrochloric acid (2 mol/L). To the mixture was added water, and the crude product was extracted with ethyl acetate. The organic layer was washed with brine, and dried over anhydrous magnesian sulfate. The solvent was removed under reduced pressure. To a suspension of the residue in N,N-dimethylformamide (1 mL) were added 1-hydroxybenzotriazole monohydrate (0.031 g), ammonium chloride (0.036 g), triethylamine (0.095 g) and 1-ethyl-3-(3-dimethylaminopropyl)carbodiimide hydrochloride (0.039 g), and the mixture was stirred at room temperature for 1 day. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford the title compound (0.007 g). Structural formula, spectral data and purification condition are shown in Table 97.

Example 22-1

N-[2-(3-Aminopyridin-2-yl)ethyl]-2-(5-phenyl-1H-pyrazol-3-yl)benzamide

To a suspension of 2-(5-phenyl-1H-pyrazol-3-yl)benzoic acid (0.011 g) in N,N-dimethylformamide (1 mL) were added 1-hydroxybenzotriazole monohydrate (0.010 g), N-[2-(2-aminoethyl)pyridin-3-yl]carbamic acid tert-butyl ester (0.01 g), N,N-diisopropylethylamine (0.022 g) and 1-ethyl-3(3-dimethylaminopropyl)carbodiimide hydrochloride (0.012 g), and the mixture was stirred at room temperature for 2 hours. To the reaction mixture was added water, and the crude product was extracted with ethyl acetate. The organic layer was washed with brine, and dried over anhydrous magnesium sulfate. The solvent was removed under reduced pressure. To the residue were added dichloromethane (1 mL) and trifluoroacetic acid (1 mL), and the mixture was stirred at room temperature for 2 hours. The reaction mixture was concentrated under reduced pressure. To the residue was added a saturated aqueous solution of sodium bicarbonate, and the crude product was extracted with dichloromethane. The organic layer was washed with brine, and dried over anhydrous magnesium sulfate. The solvent was removed under reduced pressure, and the residue was purified by aminopropyl silica gel column chromatography (eluent: ethyl acetate/methanol) to afford the title compound (0.007 g). Structural formula, spectral data and purification condition are shown in Table 97.

Example 22-2

Example 22-2 was synthesized in a manner similar to that of Example 22-1 by using the corresponding materials. Structural formula, spectral data and purification condition are shown in Table 97.

Example 23-1

3-Fluoro-2-{5-[4-fluoro-3-(hydroxymethyl)phenyl]-1H-pyrazol-3-yl}-N-[(2R)-1-hydroxy-3-(pyridin-2-yl)propan-2-yl]benzamide To a solution of 2-{5-[3-(1,3-dioxolan-2-yl)-4-fluorophenyl]-1H-pyrazol-3-yl}-3-fluorobenzoic acid (0.086 g) in N,N-dimethylformamide (1 mL) were added (2R)-2-amino-3-(pyridin-2-yl)propan-1-ol (0.053 g), 1-hydroxybenzotriazole monohydrate (0.53 g), 1-ethyl-3-(3-dimethylaminopropyl)carbodiimide hydrochloride (0.067 g) and N,N-diisopropylethylamine (0.12 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol) to afford 2-{5-[3-(1,3-dioxolan-2-yl)-4-fluorophenyl]-1H-pyrazol-3-yl}-3-fluoro-N-[(2R)-1-hydroxy-3-(pyridin-2-yl)propan-2-yl]benzamide (0.07 g). To a solution of the product (0.070 g) in tetrahydrofuran (1 mL) was added hydrochloric acid (2 mol/L, 3 mL), and the mixture was stirred at 60° C. overnight. The reaction mixture was poured into a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford 3-fluoro-2-[5-(4-fluoro-3-formylphenyl)-1H-pyrazol-3-yl]-N-[(2R)-1-hydroxy-3-(pyridin-2-yl)propan-2-yl]benzamide (0.062 g). To a solution of the product (0.062 g) in methanol (1.5 mL) was added sodium borohydride (0.008 g) under ice-cooling, and the mixture was stirred at room temperature for 1.5 hours. To the reaction mixture was added a saturated aqueous solution of ammonium chloride, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford the title compound (0.057 g). Structural formula, spectral data and purification condition are shown in Table 98.

Examples 23-2 to 23-3

Examples 23-2 to 23-3 were synthesized in a manner similar to that of Example 23-1 by using the corresponding materials. Structural formula, spectral data and purification condition are shown in Table 98.

Example 24-1

(2S)-2-{3-Fluoro-2-[5-(4-fluorophenyl)-1H-pyrazol-3-yl]benzoylamino}-2-methyl-3-phenylpropanamide To a mixture of 3-fluoro-2-[5-(4-fluorophenyl)-1-(methoxymethyl)-1H-pyrazol-3-yl]benzoic acid and 3-fluoro-2-[5-(4-fluorophenyl)-2-(methoxymethyl)-2H-pyrazol-3-yl]benzoic acid (0.15 g) was added dichloromethane (2 mL). To the suspension was added 1-chloro-N,N,2-trimethylpropenylamine (0.116 g), and the mixture was stirred at room temperature for 2 hours. The reaction mixture was concentrated under reduced pressure. To the residue were added dichloromethane (2 mL), (S)-2-amino-2-methyl-3-phenylpropanamide hydrochloride (0.094 g), triethylamine (0.44 g) and 4-dimethylaminopyridine (10 mg), and the mixture was stirred under reflux overnight. The reaction mixture was allowed to cool to room temperature. To the mixture was added water, and the crude product was extracted with dichloromethane. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford a mixture of (2S)-2-{3-fluoro-2-[5-(4-fluorophenyl)-1-(methoxymethyl)-1H-pyrazol-3-yl]benzoylamino}-2-methyl-3-phenylpropanamide and (2S)-2-{3-fluoro-2-[5-(4-fluorophenyl)-2-(methoxymethyl)-2H-pyrazol-3-yl]benzoylamino}-2-methyl-3-phenylpropanamide. To the mixture were added methanol (1 mL) and a solution of hydrogen chloride in 1,4-dioxane (4 mol/L, 1 mL), and the mixture was stirred at 50° C. for 4 hours. The reaction mixture was allowed to cool to room temperature. To the reaction mixture was added a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol) to afford the title compound (0.064 g). Structural formula, spectral data and purification condition are shown in Table 99.

Examples 24-2 to 24-7

Examples 24-2 to 24-7 were synthesized in a manner similar to that of Example 24-1 by using the corresponding materials. Structural formula, spectral data and purification condition are shown in Table 99.

Example 25-1

2-[5-(4-Fluorophenyl)-1H-pyrazol-3-yl]-N-(3,4-trans-4-phenylpyrrolidin-3-yl)benzamide To a solution of N-(3,4-trans-1-benzyl-4-phenylpyrrolidin-3-yl)-2-[5-(4-fluorophenyl)-1H-pyrazol-3-yl]benzamide (0.12 g) in ethanol (2 mL) was added 10% palladium-carbon (50% wet, 0.05 g) at room temperature, and the mixture was stirred at 60° C. under a hydrogen atmosphere for 3 hours. The reaction mixture was allowed to cool to room temperature. The catalyst was removed by filtration through a pad of celite. The filtrate was concentrated under reduced pressure. The residue was purified by aminopropyl silica gel column chromatography (eluent: ethyl acetate/methanol) to afford the title compound (0.082 g). Structural formula, spectral data and purification condition are shown in Table 100.

Example 26-1

3-Fluoro-2-[5-(4-fluorophenyl)-1H-pyrazol-3-yl]-N-[4-hydroxy-1-(pyridin-2-yl)butan-2-yl]benzamide To a suspension of 3-fluoro-2-[5-(4-fluorophenyl)-1H-pyrazol-3-yl]benzoic acid (0.041 g) in N,N-dimethylformamide (1 mL) were added 1-hydroxybenzotriazole monohydrate (0.031 g), 4-(benzyloxy)-1-(pyridin-2-yl)butan-2-amine (0.035 g), N,N-diisopropylethylamine (0.071 g) and 1-ethyl-3-(3-dimethylaminopropyl)carbodiimide hydrochloride (0.040 g), and the mixture was stirred at room temperature overnight. To the reaction mixture was added water, and the crude product was extracted with dichloromethane. The organic layer was washed with brine, and dried over anhydrous magnesium sulfate. The solvent was removed under reduced pressure, and the residue was purified by aminopropyl silica gel column chromatography (eluent: ethyl acetate/methanol) to afford N-[4-(benzyloxy)-1-(pyridin-2-yl)butan-2-yl]-3-fluoro-2-[5-(4-fluorophenyl)-1H-pyrazol-3-yl]benzamide (0.05 g). To a solution of the product (0.05 g) in trifluoroacetic acid (0.95 mL) were added water (0.1 mL) and dimethylsulfide (0.2 mL), and the mixture was stirred at room temperature for 3 days. The reaction mixture was purified by aminopropyl silica gel column chromatography (eluent: ethyl acetate/methanol) to afford the title compound (0.028 g). Structural formula, spectral data and purification condition are shown in Table 100.

Example 26-2

Example 26-2 was synthesized in a manner similar to that of Example 26-1 by using the corresponding materials. Structural formula, spectral data and purification condition are shown in Table 100.

Example 27-1

3-Fluoro-2-[5-(4-fluorophenyl)-1H-pyrazol-3-yl]-N-[(2R,3S)-4-hydroxy-3-methoxy-1-(1H-pyrazol-1-yl)butan-2-yl]benzamide To a solution of 3-fluoro-2-[5-(4-fluorophenyl)-1H-pyrazol-3-yl]benzoic acid (40 mg) in N,N-dimethylformamide (1 mL) were added (2R,3S)-4-(tert-butyldiphenylsilyloxy)-3-methoxy-1-(1H-pyrazol-1-yl)butan-2-amine (56 mg), 1-hydroxybenzotriazole monohydrate (22 mg), 1-ethyl-3-(3-dimethylaminopropyl)carbodiimide hydrochloride (28 mg) and N,N-diisopropylethylamine (68 μL), and the mixture was stirred at room temperature for 14 hours. To the reaction mixture was added water, and the crude product was extracted with ethyl acetate. The organic layer was washed with water and brine, dried over sodium sulfate, and filtered. The filtrate was concentrated under reduced pressure. The residue was purified by silica gel column chromatography (eluent: ethyl acetate/n-hexane) to afford N-[(2R,3S)-4-(tert-butyldiphenylsilyloxy)-3-methoxy-1-(1H-pyrazol-1-yl)butan-2-yl]-3-fluoro-2-[5-(4-fluorophenyl)-1H-pyrazol-3-yl]benzamide (47 mg). To a solution of the product (47 mg) in tetrahydrofuran (1 mL) was added a solution of tetra-n-butylammonium fluoride in tetrahydrofuran (1 mol/L, 150 μL), and the mixture was stirred at room temperature for 30 minutes. To the reaction mixture was added a saturated aqueous solution of ammonium chloride, and the crude product was extracted with ethyl acetate. The organic layer was washed with brine, dried over sodium sulfate, and filtered. The filtrate was concentrated under reduced pressure. The residue was purified by silica gel column chromatography (eluent: ethyl acetate/methanol) to afford the title compound (27 mg). Structural formula, spectral data and purification condition are shown in Table 101.

Examples 27-2 to 27-31

Examples 27-2 to 27-31 were synthesized in a manner similar to that of Example 27-1 by using the corresponding materials. Structural formula, spectral data and purification condition are shown in Table 101 to Table 105.

Example 28-1

3-Fluoro-2-[4-fluoro-5-(4-fluorophenyl)-1H-pyrazol-3-yl]-N-[(2R)-4-hydroxy-1-(pyridin-2-yl)butan-2-yl]benzamide To a mixture of 3-fluoro-2-[4-fluoro-5-(4-fluorophenyl)-1-(methoxymethyl)-1H-pyrazol-3-yl]benzoic acid and 3-fluoro-2-[4-fluoro-5-(4-fluorophenyl)-2-(methoxymethyl)-2H-pyrazol-3-yl]benzoic acid (0.112 g) was added N,N-dimethylformamide (2.5 mL). To the mixture were added (3R)-3-amino-4-(pyridin-2-yl)butan-1-ol hydrochloride (0.074 g), 1-hydroxybenzotriazole monohydrate (0.057 g), 1-ethyl-3-(3-dimethylaminopropyl)carbodiimide hydrochloride (0.71 g) and triethylamine (0.125 g), and the mixture was stirred at room temperature overnight. To the reaction mixture was added wafer, and the crude product was extracted with ethyl acetate. The organic layer was washed with brine, and dried over sodium sulfate. The solvent was removed under reduced pressure, and the residue was purified by silica gel column chromatography to afford a mixture of 3-fluoro-2-[4-fluoro-5-(4-fluorophenyl)-1-(methoxymethyl)-1H-pyrazol-3-yl]-N-[(2R)-4-hydroxy-1-(pyridin-2-yl)butan-2-yl]benzamide and 3-fluoro-2-[4-fluoro-5-(4-fluorophenyl)-2-(methoxymethyl)-2H-pyrazol-3-yl]-N-[(2R)-4-hydroxy-1-(pyridin-2-yl)butan-2-yl]benzamide (0.086 g). To the mixture (0.086 g) were added 1,4-dioxane mL) and a solution of hydrogen chloride in 1,4-dioxane (4 mol/L, 1 mL), and the mixture was stirred at 60° C. for 2 hours. The reaction mixture was allowed to cool to room temperature, and then concentrated under reduced pressure. The residue was purified by silica gel column chromatography (eluent: ethyl acetate/methanol) to afford the title compound (0.047 g). Structural formula, spectral data and purification condition are shown in Table 106.

Examples 28-2 to 28-9

Examples 28-2 to 28-9 were synthesized in a manner similar to that of Example 28-1 by using the corresponding materials. Structural formula, spectral data and purification condition are shown in Table 106 to Table 107.

Example 29-1

2-(5-Phenyl-1H-pyrazol-3-yl)-N-[2-(piperidin-2-yl)ethyl]benzamide hydrochloride

To a suspension of 2-(5-phenyl-1H-pyrazol-3-yl)benzoic acid (0.07 g) in N,N-dimethylformamide (1 mL) were added 1-hydroxybenzotriazole monohydrate (0.061 g), 2-(2-aminoethyl)piperidine-1-carboxylic acid tert-butyl ester (0.073 g), triethylamine (0.08 g) and 1-ethyl-3-(3-dimethylaminopropyl)carbodiimide hydrochloride (0.076 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford 2-{2-[2-(5-phenyl-1H-pyrazol-3-yl)benzoylamino]ethyl}piperidine-1-carboxylic acid tert-butyl ester. To a solution of the product in tetrahydrofuran (2 mL) was added a solution of hydrogen chloride in ethyl acetate (4 mol/L, 2 mL), and the mixture was stirred at room temperature for 4 hours. To the reaction mixture was added diethyl ether, and then the precipitate was collected by filtration to afford the title compound (0.11 g). Structural formula, spectral data and purification condition are shown in Table 108.

Example 29-2

Example 29-2 was synthesized in a manner similar to that of Example 29-1 by using the corresponding materials. Structural formula, spectral data and purification condition are shown in Table 108.

Example 30-1

3-Fluoro-2-[5-(4-fluorophenyl)-1H-pyrazol-3-yl]-N-[3-hydroxy-2-(pyridin-2-yl)propyl]benzamide To a mixture of 3-fluoro-2-[5-(4-fluorophenyl)-1-(methoxymethyl)-1H-pyrazol-3-yl]benzoic acid and 3-fluoro-2-[5-(4-fluorophenyl)-2-(methoxymethyl)-2H-pyrazol-3-yl]benzoic acid (0.07 g) was added N,N-dimethylformamide (1 mL). To the mixture were added 1-hydroxybenzotriazole monohydrate (0.046 g), 2-{1-amino-3-(tert-butyldimethylsilyloxy)propan-2-yl}pyridine (0.054 g), N,N-diisopropylethylamine (0.11 g) and 1-ethyl-3-(3-dimethylaminopropyl)carbodiimide hydrochloride (0.058 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol) to afford a mixture of N-{3-(tert-butyldimethylsilyloxy)-2-(pyridin-2-yl)propyl}-3-fluoro-2-[5-(4-fluorophenyl)-1-(methoxymethyl)-1H-pyrazol-3-yl]benzamide and N-{3-(tert-butyldimethylsilyloxy)-2-(pyridin-2-yl)propyl}-3-fluoro-2-[5-(4-fluorophenyl)-2-(methoxymethyl)-2H-pyrazol-3-yl]benzamide. To the mixture were added methanol (1 mL) and a solution of hydrogen chloride in 1,4-dioxane (4 mol/L, 1 mL), and the mixture was stirred at 50° C. for 2 hours. The reaction mixture was allowed to cool to room temperature, and then concentrated under reduced pressure. The residue was purified by aminopropyl silica gel column chromatography (eluent: ethyl acetate/methanol) to afford the title compound (0.05 g). Structural formula, spectral data and purification condition are shown in Table 108.

Example 30-2

Example 30-2 was synthesized in a manner similar to that of Example 30-1 by using the corresponding materials. Structural formula, spectral data and purification condition are shown in Table 108.

Example 31-1

N-[(2R,3R)-3,4-Dihydroxy-1-(pyrimidin-2-yl)butan-2-yl]-3-fluoro-2-[5-(4-fluorophenyl)-1H-pyrazol-3-yl]benzamide To a solution of 3-fluoro-2-[5-(4-fluorophenyl)-1H-pyrazol-3-yl]benzoic acid (38 mg) in N,N-dimethylformamide (1 mL) were added (1R)-1-((4R)-2,2-dimethyl-1,3-dioxolan-4-yl)-2-(pyrimidin-2-yl)ethylamine (31 mg), 1-hydroxybenzotriazole monohydrate (21 mg), 1-ethyl-3-(3-dimethylaminopropyl)carbodiimide hydrochloride (27 mg) and N,N-diisopropylethylamine (33 µL), and the mixture was stirred at room temperature for 2 hours. To the reaction mixture was added water, and the crude product was extracted with ethyl acetate. The organic layer was washed with water and brine, and dried over sodium sulfate. The filtrate was concentrated under reduced pressure. The residue was purified by aminopropyl silica gel column chromatography (eluent: ethyl acetate/methanol) to afford N-[(1R)-1-((4R)-2,2-dimethyl-1,3-dioxolan-4-yl)-2-(pyrimidin-2-yl)ethyl]-3-fluoro-2-[5-(4-fluorophenyl)-1H-pyrazol-3-yl]benzamide. To a solution of the product in methanol (1 mL) was added a solution of hydrogen chloride in ethyl acetate (4 mol/L, 1 mL), and the mixture was stirred at room temperature for 1 hour. The reaction mixture was concentrated under reduced pressure, and the residue was purified by silica gel column chromatography (eluent: ethyl acetate/methanol) to afford the title compound (28 mg). Structural formula, spectral data and purification condition are shown in Table 108.

Example 32-1

N-[(2R,3S)-3-Amino-4-benzyloxy-1-(pyridin-2-yl)butan-2-yl]-3-fluoro-2-[5-(4-fluorophenyl)-1H-pyrazol-3-yl]benzamide A mixture of 3-fluoro-2-[5-(4-fluorophenyl)-1H-pyrazol-3-yl]benzoic acid (76 mg), N-[(2S)-3-amino-1-benzyloxy-4-(pyridin-2-yl)butan-2-yl]carbamic acid benzyl ester (100 mg), 1-ethyl-3-(3-dimethylaminopropyl)carbodiimide hydrochloride (62 mg), 1-hydroxybenzotriazole monohydrate (49 mg) and triethylamine (75 mg) in N,N-dimethylformamide (2 mL) was stirred at room temperature for 11.5 hours. The mixture was purified by silica gel column chromatography (eluent: ethyl acetate/n-hexane) to afford a mixture of diastereomers (138 mg). The mixture was purified by preparative reverse phase liquid chromatography (Capcell Pak C18 UG80, eluent: acetonitrile/water) to afford N-[(2S,3R)-1-benzyloxy-3-{3-fluoro-2-[5-(4-fluorophenyl)-1H-pyrazol-3-yl]benzoylamino}-4-(pyridin-2-yl)butan-2-yl]carbamic acid benzyl ester (78 mg) and N-[(2S,3S)-1-benzyloxy-3-{3-fluoro-2-[5-(4-fluorophenyl)-1H-pyrazol-3-yl]benzoylamino}-4-(pyridin-2-yl)butan-2-yl] carbamic acid benzyl ester (25 mg). A mixture of N-[(2S,3R)-1-benzyloxy-3-{3-fluoro-2-[5-(4-fluorophenyl)-1H-pyrazol-3-yl]benzoylamino}-4-(pyridin-2-yl)butan-2-yl] carbamic acid benzyl ester (72 mg) and 10% palladium-carbon (50% wet, 40 mg) in ethanol (3 mL) was stirred at room temperature under a hydrogen atmosphere for 3 hours. The reaction mixture was filtered through a pad of celite. The filtrate was concentrated under reduced pressure to afford the title compound (57 mg). Structural formula, spectral data and purification condition are shown in Table 108.

Example 32-2

Example 32-2 was synthesized in a manner similar to that of Example 32-1 by using the corresponding materials. Structural formula, spectral data and purification condition are shown in Table 108.

Example 33-1

3-Fluoro-2-[-5-(4-fluorophenyl)-1H-pyrazol-3-yl]-N-[(2R)-3-hydroxy-3-methyl-1-(pyridin-2-yl)butan-2-yl]benzamide To a solution of 3-fluoro-2-[-5-(4-fluorophenyl)-1H-pyrazol-3-yl]benzoic acid (0.060 g) in N,N-dimethylformamide (3 mL) were added (2R)-2-amino-3-(pyridin-2-yl)propionic acid methyl ester (0.036 g), 1-hydroxybenzotriazole monohydrate (0.037 g), 1-ethyl-3-(3-dimethylaminopropyl)carbodiimide hydrochloride (0.046 g) and triethylamine (0.081 g), and the mixture was stirred at room temperature overnight. To the reaction mixture was added water, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford (2R)-2-{3-fluoro-2-[5-(4-fluorophenyl)-1H-pyrazol-3-yl]benzoylamino}-3-(pyridin-2-yl)propionic acid methyl ester (0.059 g). To a solution of the product (0.059 g) in tetrahydrofuran (1 mL)

was added a solution of methylmagnesium bromide in diethyl ether (3 mol/L, 1.13 mL) under ice-cooling, and the mixture was stirred at room temperature for 1 hour. To the reaction mixture was added a saturated aqueous solution of ammonium chloride, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford the title compound (0.037 g). Structural formula, spectral data and purification condition are shown in Table 109.

Examples 33-2 to 33-5

Examples 33-2 to 33-5 were synthesized in a manner similar to that of Example 33-1 by using the corresponding materials. Structural formula, spectral data and purification condition are shown in Table 109.

Examples 34-1HP and 34-1LP

2-[-5-(4-Chlorophenyl)-1H-pyrazol-3-yl]-3-fluoro-N-[(2R)-3-hydroxy-3-methyl-1-(pyridin-2-yl)butan-2-yl]benzamide (Example 34-1HP)

2-[-5-(4-Chlorophenyl)-1H-pyrazol-3-yl]-3-fluoro-N-[(2R)-3-oxo-1-(pyridin-2-yl)butan-2-yl]benzamide (Example 34-1LP)

To a solution of 3-fluoro-2-[-5-(4-chlorophenyl)-1H-pyrazol-3-yl]benzoic acid (0.063 g) in N,N-dimethylformamide (3 mL) were added (2R)-2-amino-3-(pyridin-2-yl)propionic acid methyl ester (0.047 g), 1-hydroxybenzotriazole monohydrate (0.037 g), 1-ethyl-3-(3-dimethylaminopropyl)carbodiimide hydrochloride (0.046 g) and triethylamine (0.081 g), and the mixture was stirred at room temperature overnight. To the reaction mixture was added water, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford (2R)-2-{3-fluoro-2-[-5-(4-chlorophenyl)-1H-pyrazol-3-yl]benzoylamino}-3-(pyridin-2-yl)propionic acid methyl ester (0.068 g). To a solution of the product (0.034 g) in tetrahydrofuran (1 mL) was added a solution of methyllithium in diethyl ether (1.1 mol/L, 0.32 mL) under ice-cooling, and the mixture was stirred at the same temperature for 2 hours. To the reaction mixture was added a saturated aqueous solution of ammonium chloride, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford the title compounds (HP: 0.015 g, LP: 0.004 g). Structural formula, spectral data and purification condition are shown in Table 110.

Example 35-1

2-[5-(4-Chlorophenyl)-1H-pyrazol-3-yl]-3-fluoro-N-[(2R)-4-hydroxy-3-(hydroxymethyl)-3-methyl-1-(pyridin-2-yl)butan-2-yl]benzamide To a solution of 3-fluoro-2-[-5-(4-chlorophenyl)-1H-pyrazol-3-yl]benzoic acid (0.022 g) in N,N-dimethylformamide (1 mL) were added (1R)-1-(5-methyl-2-phenyl-1,3-dioxan-5-yl)-2-(pyridin-2-yl)ethylamine hydrochloride (0.033 g), 1-hydroxybenzotriazole monohydrate (0.013 g), 1-ethyl-3-(3-dimethylaminopropyl)carbodiimide hydrochloride (0.016 g) and triethylamine (0.028 g), and the mixture was stirred at room temperature overnight. To the reaction mixture as added water, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford 2-[-5-(4-chlorophenyl)-1H-pyrazol-3-yl]-3-fluoro-N-[(1R)-1-(5-methyl-2-phenyl-1,3-dioxan-5-yl)-2-(pyridin-2-yl)ethyl]benzamide (0.021 g). To a solution of the product (0.021 g) in acetic acid (0.8 mL) was added water (0.2 mL), and the mixture was stirred at 70° C. for 12 hours. To the reaction mixture was added a saturated aqueous solution of sodium bicarbonate, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford the title compound (0.004 g). Structural formula, spectral data and purification condition are shown in Table 110.

Examples 35-2 to 35-5

Examples 35-2 to 35-5 were synthesized in a manner similar to that of Example 35-1 by using the corresponding materials. Structural formula, spectral data and purification condition are shown in Table 110.

Example 36-1

3-Chloro-2-[5-(4-fluorophenyl)-1H-pyrazol-3-yl]-N-[(2R)-4-hydroxy-1-(pyridin-2-yl)butan-2-yl]benzamide To a suspension of 4-chloro-2-(4-fluorophenyl)-8H-pyrazolo[5,1-a]isoindol-8-one (0.05 g) in tetrahydrofuran (1 mL) was added (2R)-4-(tert-butyldimethylsilyloxy)-1-(pyridin-2-yl)butan-2-amine (0.047 g), and the mixture was stirred at room temperature for 3 hours. The reaction mixture was concentrated under reduced pressure. The residue was purified by aminopropyl silica gel column chromatography (eluent: ethyl acetate/n-hexane) to afford N-[(2R)-4-(tert-butyldimethylsilyloxy)-1-(pyridin-2-yl)butan-2-yl]-3-chloro-2-[-5-(4-fluorophenyl)-1H-pyrazol-3-yl]benzamide. To the product was added a solution of tetra-n-butylammonium fluoride in tetrahydrofuran (1 mol/L, 180 μL), and the mixture was stirred at room temperature for 30 minutes. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford the title compound (0.043 g). Structural formula, spectral data and purification condition are shown in Table 111.

Example 36-2

Example 36-2 was synthesized in a manner similar to that of Example 36-1 by using the corresponding materials. Structural formula, spectral data and purification condition are shown in Table 111.

Example 37-1

(2R)-2-{3-Fluoro-2-[-5-(4-fluorophenyl)-1H-pyrazol-3-yl]benzoylamino}-3-(pyridin-2-yl)propanamide To a suspension of 3-fluoro-2-[-5-(4-fluorophenyl)-1H-pyrazol-3-yl]benzoic acid (0.047 g) in dichloromethane (1 mL) were added (2R)-2-amino-3-(pyridin-2-yl)propanamide dihydrochloride (0.038 g), N,N-diisopropylethylamine (0.112 g) and a solution of T3P (registered trademark) in N,N-dimethylformamide (1.6 mol/L, 0.2 mL), and the mixture was stirred at room temperature for 5 days. To the reaction mixture was added water, and the crude product was extracted with ethyl acetate. The organic layer was washed with brine, and dried over anhydrous magnesium sulfate. The solvent was removed under reduced pressure. To the residue was added ethyl acetate/n-hexane. The insoluble compound was collected by filtration to afford the title compound (0.022 g). Structural formula, spectral data and purification condition are shown in Table 111.

Examples 37-2 to 37-3

Examples 37-2 to 37-3 were synthesized in a manner similar to that of Example 37-1 by using the corresponding materials. Structural formula, spectral data and purification condition are shown in Table 111.

Example 38-1

3-(2-{3-Fluoro-2-[5-(4-fluorophenyl)-1H-pyrazol-3-yl]benzoylamino}ethyl)benzoic acid To a solution of 3-fluoro-2-[-5-(4-fluorophenyl)-1H-pyrazol-3-yl]benzoic acid (0.057g) in N,N-dimethylformamide (1.5 mL) were added 2-(3-bromophenyl)ethylamine (0.038 g), 1-hydroxybenzotriazole monohydrate (0.035 g), 1-ethyl-3-(3-dimethylaminopropyl)carbodiimide hydrochloride (0.044 g) and triethylamine (0.058 g), and the mixture was stirred at room temperature overnight. To the reaction mixture was added water, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford N-[2-(3-bromophenyl)ethyl]-3-fluoro-2-[-5-(4-fluorophenyl)-1H-pyrazol-3-yl]benzamide (0.052 g). To a suspension of the product (0.052 g) in n-propanol (1.5 mL) were added N-methylpyrrolidone (0.5 mL), triethylamine (0.033 g), 1,1'-bis(diphenylphosphino)ferrocene (0.006 g) and 1,1'-bis(diphenylphosphino)ferrocene palladium(II) dichloride dichloromethane adduct (0.009 g), and the mixture was stirred at 100° C. under a carbon monoxide atmosphere for 13 hours. The reaction mixture was allowed to cool to room temperature. To the mixture was added hydrochloric acid (1 mol/L). The crude product was extracted with ethyl acetate. The organic layer was washed with water and brine, and dried over sodium sulfate. The solvent was removed under reduced pressure, and the residue was purified by silica gel column chromatography (eluent: ethyl acetate/n-hexane) to afford 3-(2-{3-fluoro-2-[5-(4-fluorophenyl)-1H-pyrazol-3-yl]benzoylamino}ethyl) benzoic acid propyl ester (0.026 g). To a solution of the product (0.026 g) in methanol (0.5 mL) was added an aqueous solution of sodium hydroxide (2 mol/L, 0.5 mL), and the mixture was stirred at 60° C. for 2 hours. The reaction mixture was allowed to cool to room temperature. To the mixture was added hydrochloric acid (2 mol/L, 0.5 mL). The precipitate was collected by filtration to afford the title compound (0.021 g). Structural formula, spectral data and purification condition are shown in Table 112.

Examples 38-2 to 38-3

Examples 38-2 to 38-3 were synthesized in a manner similar to that of Example 38-1 by using the corresponding materials. Structural formula, spectral data and purification condition are shown in Table 112.

Example 39-1

3-Fluoro-2-[5-(4-fluorophenyl)-1H-pyrazol-3-yl]-N-((2R,3S)-3,4-dihydroxy-1-phenylbutan-2-yl)benzamide To a solution of 4-fluoro-2-(4-fluorophenyl)-8H-pyrazolo[5,1-a]isoindol-8-one (0.030 g) in tetrahydrofuran (1 mL) were added (2S,3R)-3-amino-2-hydroxy-4-phenyl-1-butanol hydrochloride (0.020 g) and triethylamine (0.016 g), and the mixture was stirred at room temperature for 2 hours. To the reaction mixture was added methanol, and the reaction mixture was concentrated under reduced pressure. The residue was purified by silica gel column chromatography (eluent: ethyl acetate/methanol) to afford the title compound (0.023 g). Structural formula, spectral data and purification condition are shown in Table 113.

Example 39-2

Example 39-2 was synthesized in a manner similar to that of Example 39-1 by using the corresponding materials. Structural formula, spectral data and purification condition are shown in Table 113.

Example 40-1

(2R)-2-{3-Fluoro-2-[5-(4-fluorophenyl)-1H-pyrazol-3-yl]benzoylamino}-2-methyl-3-(pyridin-2-yl)propanamide To a solution of 4-fluoro-2-(4-fluorophenyl)-8H-pyrazolo[5,1-a]isoindol-8-one (11 mg) in tetrahydrofuran (0.5 mL) were added (2R)-2-amino-2-methyl-3-(pyridin-2-yl)propanamide (7 mg), N,N-diisopropylethylamine (10 mg) and 4-dimethylaminopyridine (1 mg), and the mixture was stirred at 60° C. for 7 days. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford the title compound (5 mg). Structural formula, spectral data and purification condition are shown in Table 113.

Example 40-2

Example40-2 was synthesized in a manner similar to that of Example 40-1 by using the corresponding materials. Structural formula, spectral data and purification condition are shown in Table 113.

Example 41-1

3-Fluoro-2-[5-(4-fluorophenyl)-1H-pyrazol-3-yl]-N-((3R)-2H,3H,4H-pyrano[3,2-b]pyridin-3-yl)benzamide To a solution of 3-fluoro-2-[5-(4-fluorophenyl)-1H-pyrazol-3-yl]-N-[(2R)-1-(3-fluoropyridin-2-yl)-3-hydroxypropan-2-yl]benzamide (0.074 g) in N,N-dimethylformamide (2 mL) were added N,N'-dimethylpropyleneurea (0.031 g) and sodium hydride (60% dispersion in oil, 0.039 g) under ice-cooling, and the mixture was stirred at 40° C. for 18 hours. To the reaction mixture was added water, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford the title compound (0.045 g). Structural formula, spectral data and purification condition are shown in Table 113.

Example 41-2

Example 41-2 was synthesized in a manner similar to that of Example 41-1 by using the corresponding materials. Structural formula, spectral data and purification condition are shown in Table 113.

Example 42-1

2-[5-(4-Chlorophenyl)-1H-pyrazol-3-yl]-3-fluoro-N-[(2R)-1-(methylamino)-3-phenylpropan-2-yl]benzamide To a suspension of 2-[5-(4-chlorophenyl)-1H-pyrazol-3-yl]-3-fluorobenzoic acid (0.05g) in N,N-dimethylformamide (1 mL) were added N-((2R)-2-amino-3-phenylpropyl)-N-methyl-2-nitrobenzene-1-sulfonamide hydrochloride (0.061 g), 1-hydroxybenzotriazole monohydrate (0.029 g), 1-ethyl-3 (3-dimethylaminopropyl)carbodiimide hydrochloride (0.036 g) and triethylamine (0.064 g), and the mixture was stirred at room temperature for 1 day. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford 2-[5-(4-chlorophenyl)-1H-pyrazol-3-yl]-3-fluoro-N-[(2R)-1-(N-methyl-2-nitrobenzenesulfonylamino)-3-phenylpropan-2-yl]benzamide (0.1 g). To a solution of the product (0.1 g) in acetonitrile (2 mL) were added thiophenol (0.021 g) and cesium carbonate (0.154 g), and the mixture was stirred at room temperature for 2 hours. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford the title compound (0.05 g). Structural formula, spectral data and purification condition are shown in Table 114.

Example 42-2

Example 42-2 was synthesized in a manner similar to that of Example 42-1 by using the corresponding materials. Structural formula, spectral data and purification condition are shown in Table 114.

Example 43-1

2-[5-(4-Chlorophenyl)-1H-pyrazol-3-yl]-3-fluoro-N-[(2R,3 S)-4-hydroxy-3-methoxy-1-(pyridin-2-yl)butan-2-yl]benzamide To a suspension of 2-[5-(4-chlorophenyl)-1H-pyrazol-3-yl]-3-fluorobenzoic acid (0.03g) in N,N-dimethylformamide (1 mL) were added (2R,3S)-4-(benzyloxy)-3-methoxy-1-(pyridin-2-yl)butan-2-amine (0.027 g), 1-hydroxybenzotriazole monohydrate (0.016 g), 1-ethyl-3-(3-dimethylaminopropyl)carbodiimide hydrochloride (0.02 g) and triethylamine (0.038 g), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/methanol) to afford N-[(2R,3S)-4-(benzyloxy)-3-methoxy-1-(pyridin-2-yl)butan-2-yl]-2-[5-(4-chlorophenyl)-1H-pyrazol-3-yl]-3-fluorobenzamide (0.035 g). To a solution of the product (0.035 g) in trifluoroacetic acid (0.95 mL) were added water (0.1 mL) and dimethylsulfide (0.2 mL), and the mixture was stirred at 60° C. for 1 day. The reaction mixture was allowed to cool to room temperature. The reaction mixture was poured into a saturated aqueous solution of sodium bicarbonate, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol) to afford the title compound (0.02 g). Structural formula, spectral data and purification condition are shown in Table 115.

Examples 43-2 to 43-9, 43-11 to 43-25 and 43-27 to 43-46

Examples 43-2 to 43-9, 43-11 to 43-25 and 43-27 to 43-46 were synthesized in a manner similar to that of Example 43-1 by using the corresponding materials. Structural formula, spectral data and purification condition are shown in Table 115 to Table 121.

Example 44-1

3-Fluoro-2-[5-(4-fluorophenyl)-1H-pyrazol-3-yl]-N-[(2R)-1-hydroxy-3-[3-(2H-1,2,3,4-tetrazol-5-yl)pyridin-2-yl]propan-2-yl]benzamide To a solution of N-[(2R)-1-(3-cyanopyridin-2-yl)-3-hydroxypropan-2-yl]-3-fluoro-2-[5-(4-fluorophenyl)-1H-pyrazol-3-yl]benzamide (55 mg) in N-methylpyrrolidone (2 mL) were added sodium azide (39 mg), ammonium chloride (32 mg) and lithium chloride (7 mg), and the mixture was stirred at 120° C. for 28 hours. The reaction mixture was allowed to cool to room temperature. To the mixture was added water, and the crude product was extracted with ethyl acetate. The organic layer was washed with brine, dried over sodium sulfate, and filtered. The filtrate was concentrated under reduced pressure, and the residue was purified by silica gel column chromatography (eluent: ethyl acetate/methanol) to afford the title compound (5 mg). Structural formula, spectral data and purification condition are shown in Table 122.

Example 44-2

Example 44-2 was synthesized in a manner similar to that of Example 44-1 by using the corresponding materials. Structural formula, spectral data and purification condition are shown in Table 122.

Example 45-1

3-Fluoro-2-[5-(4-fluorophenyl)-1H-pyrazol-3-yl]-N-[(2R,3S)-4-hydroxy-3-methylamino-1-(pyridin-2-yl)butan-2-yl]benzamide A mixture of 3-fluoro-2-[5-(4-fluorophenyl)-1H-pyrazol-3-yl]benzoic acid (77 mg), N-[(2S)-3-amino-1-benzyloxy-4-(pyridin-2-yl)butan-2-yl]-N-methylcarbamic acid benzyl ester (103 mg), 1-ethyl-3-(3-dimethylaminopropyl)carbodiimide hydrochloride (62 mg), 1-hydroxybenzotriazole monohydrate (49 mg) and triethylamine (75 mg) in N,N-dimethylformamide (2 mL) was stirred at room temperature for 12 hours. To the reaction mixture was added dichloromethane. The mixture was washed twice with water. The organic layer was concentrated under reduced pressure, and the residue was purified by silica gel column chromatography (eluent: ethyl acetate/n-hexane) to afford a mixture of diastereomers. The mixture was purified by preparative reverse phase liquid chromatography (Capcell Pak C18 UG80, eluent: acetonitrile/water) to afford N-[(2S,3R)-1-benzyloxy-3-{3-fluoro-2-[5-(4-fluorophenyl)-1H-pyrazol-3-yl]benzoylamino}-4-(pyridin-2-yl)butan-2-yl]-N-methylcarbamic acid benzyl ester (83 mg) and N-[(2S,3S)-1-benzyloxy-3-{3-fluoro-2-[5-(4-fluorophenyl)-1H-pyrazol-3-yl]benzoylamino}-4-(pyridin-2-yl)butan-2-yl]-N-methylcarbamic acid benzyl ester (25 mg). A mixture of N-[(2S,3R)-1-benzyloxy-3-{3-fluoro-2-[5-(4-fluorophenyl)-1H-pyrazol-3-yl]benzoylamino}-4-(pyridin-2-yl)butan-2-yl]-N-methylcarbamic acid benzyl ester (83 mg) and 10% palladium-carbon (50% wet, 50 mg) in ethanol (2 mL) was stirred at room temperature under a hydrogen atmosphere for 4 hours. The reaction mixture was filtered through a pad of celite. The filtrate was concentrated under reduced pressure to afford N-[(2R,3S)-4-benzyloxy-3-methylamino-1-(pyridin-2-yl)butan-2-yl]-3-fluoro-2-[5-(4-fluorophenyl)-1H-pyrazol-3-yl]benzamide (61 mg). A mixture of the product (61 mg), water (0.2 mL), dimethylsulfide (0.4 mL) in trifluoroacetic acid (1.9 mL) was stirred at 60° C. for 34 hours. The pH of the reaction mixture was adjusted to 7 by addition of a saturated aqueous solution of sodium bicarbonate. To the mixture was added ethyl acetate, and the organic layer was washed with water and brine, and concentrated under reduced pressure. The residue was purified by aminopropyl silica gel column chromatography (eluent: ethyl acetate/methanol) to afford the title compound (37 mg). Structural formula, spectral data and purification condition are shown in Table 122.

Examples 45-2 to 45-3 and 43-10

Examples 45-2 to 45-3 and 43-10 were synthesized in a manner similar to that of Example 45-1 by using the corresponding materials. Structural formula, spectral data and purification condition are shown in Table 122 and Table 116.

Example 46-1

3-Fluoro-2-[5-(4-fluorophenyl)-1H-pyrazol-3-yl]-N-[(2R)-3-hydroxy-3-methyl-1-(4-methylpyrimidin-2-yl)butan-2-yl]benzamide To a solution of 3-fluoro-2-[5-(4-fluorophenyl)-1H-pyrazol-3-yl]-N-[(2R)-3-hydroxy-3-methyl-1-(6-methyl-1,6-dihydropyrimidin-2-yl)butan-2-yl]benzamide (20 mg) in toluene (1 mL) was added 2,3-dichloro-5,6-dicyano-p-benzoquinone (19 mg), and the mixture was stirred at 80° C. for 30 minutes. The reaction mixture was allowed to cool to room temperature, and purified by aminopropyl silica gel column chromatography (eluent: ethyl acetate/methanol) to afford the title compound (4 mg). Structural formula, spectral data and purification condition are shown in Table 122.

Example 47-1

3-Fluoro-2-[5-(4-fluorophenyl)-1H-pyrazol-3-yl]-N-[(1R)-1-((4S)-2-oxo-1,3-oxazolidin-4-yl)-2-(pyridin-2-yl)ethyl]benzamide To a solution of N-[(2R,3S)-3-amino-4-hydroxy-1-(pyridin-2-yl)butan-2-yl]-3-fluoro-2-[5-(4-fluorophenyl)-1H-pyrazol-3-yl]benzamide (13 mg) in tetrahydrofuran (2 mL) was added carbonyldiimidazole (9 mg), and the mixture was stirred at room temperature for 1.5 hours. The mixture was purified by silica gel column chromatography (eluent: ethyl acetate/methanol) to afford the title compound (13 mg). Structural formula, spectral data and purification condition are shown in Table 123.

Examples 47-2 to 47-3

Examples 47-2 to 47-3 were synthesized in a manner similar to that of Example 47-1 by using the corresponding materials. Structural formula, spectral data and purification condition are shown in Table 123.

Example 48-1

N-[(2R,3S)-3-Dimethylamino-4-hydroxy-1-(pyridin-2-yl)butan-2-yl]-3-fluoro-2-[5-(4-fluorophenyl)-1H-pyrazol-3-yl]benzamide To a mixture of N-[(2R,3S)-3-amino-4-hydroxy-1-(pyridin-2-yl)butan-2-yl]-3-fluoro-2-[5-(4-fluorophenyl)-1H-pyrazol-3-yl]benzamide (29 mg), an aqueous solution of 35% formaldehyde (0.106 mL) in tetrahydrofuran (0.5 mL) was added sodium triacetoxyborohydride (46 mg) at the room temperature, and the mixture was stirred for 15 minutes. The reaction mixture was purified by aminopropyl silica gel column chromatography (eluent: ethyl acetate/methanol) to afford the title compound (23 mg). Structural formula, spectral data and purification condition are shown in Table 123.

Example 48-2

Example 48-2 was synthesized in a manner similar to that of Example 48-1 by using the corresponding materials. Structural formula, spectral data and purification condition are shown in Table 123.

Example 49-1

N-[(2S,3S)-1,1-Difluoro-4-hydroxy-3-methoxy-1-(pyridin-2-yl)butan-2-yl]-3-fluoro-2-[5-(4-fluorophenyl)-1H-pyrazol-3-yl]benzamide To a mixture of 3-fluoro-2-[5-(4-fluorophenyl)-1-(methoxymethyl)-1H-pyrazol-3-yl]benzoic acid and 3-fluoro-2-[5-(4-fluorophenyl)-2-(methoxymethyl)-2H-pyrazol-3-yl]benzoic acid (0.052 g) was added dichloromethane (1 mL). To the mixture was added 1-chloro-N,N,2-trimethylpropenylamine (0.034 g) under ice-cooling, and the mixture was stirred at room temperature for 2 hours. The reaction mixture was concentrated under reduced pressure to afford a mixture of 3-fluoro-2-[5-(4-fluorophenyl)-1-(methoxymethyl)-1H-pyrazol-3-yl]benzoyl chloride and 3-fluoro-2-[5-(4-fluorophenyl)-2-(methoxymethyl)-2H-pyrazol-3-yl]benzoyl chloride. To a mixture of (2S,3S)-4-(benzyloxy)-1,1-difluoro-3-methoxy-1-(pyridin-2-yl)butan-2-amine (0.041 g), triethylamine (0.038 g), 4-dimethylaminopyridine (0.003 g) and dichloromethane (1 mL) was added a mixture of 3-fluoro-2-[5-(4-fluorophenyl)-1-(methoxymethyl)-1H-pyrazol-3-yl]benzoyl chloride and 3-fluoro-2-[5-(4-fluorophenyl)-2-(methoxymethyl)-2H-pyrazol-3-yl]benzoyl chloride in dichlorometane (1 mL), and the mixture was stirred at room temperature for 1 hour. To the reaction mixture was added water, and the crude product was extracted with dichloromethane. The solvent was removed under reduced pressure, and the residue was purified by silica gel column chromatography (eluent: ethyl acetate/n-hexane) to afford a mixture of N-[(2S,3S)-4-(benzyloxy)-1 1-difluoro-3-methoxy-1-(pyridin-2-yl)butan-2-yl]-3-fluoro-2-[5-(4-fluorophenyl)-1-(methoxymethyl)-1H-pyrazol-3-yl]benzamide and N-[(2S,3S)-4-(benzyloxy)-1,1-difluoro-3-methoxy-1-(pyridin-2-yl)butan-2-yl]-3-fluoro-2-[5-(4-fluorophenyl)-2-(methoxymethyl)-2H-pyrazol-3-yl]benzamide (0.064 g). To a solution of the product (0.064 g) in trifluoroacetic acid (0.95 mL) were added water (0.1 mL) and dimethylsulfide (0.2 mL), and the mixture was stirred at 60° C. overnight. The reaction mixture was purified by aminopropyl silica gel column chromatography (eluent: ethyl acetate/methanol) to afford the title compound (0.015 g). Structural formula, spectral data and purification condition are shown in Table 123.

Example 50-1

N-[(2R)-3,3-Difluoro-4-hydroxy-1-(1H-pyrazol-1-yl)butan-2-yl]-3-fluoro-2-[5-(4-fluorophenyl)-1H-pyrazol-3-yl]benzamide To a suspension of 4-fluoro-2-(4-fluorophenyl)-8H-pyrazolo[5,1-a]isoindol-8-one (35 mg) in tetrahydrofuran (0.5 mL) were added (2R)-4-(benzyloxy)-3,3-difluoro-1-(1H-pyrazol-1-yl)butan-2-amine (35 mg) and N,N-diisopropylethylamine (16 mg), and the mixture was stirred at 85° C. for 20 hours. The reaction mixture was allowed to cool to room temperature. To the mixture was added water, and the crude product was extracted with dichloromethane. The organic layer was washed with brine, and dried over anhydrous magnesium sulfate. The solvent was removed under reduced pressure. To the residue were added trifluoroacetic acid (0.95 mL), water (0.1 mL) and dimethylsulfide (0.2 mL), and the mixture was stirred at 85° C. for 5 hours. The reaction mixture was allowed to cool to room temperature, and then concentrated under reduced pressure. The residue was purified by aminopropyl silica gel column chromatography (eluent: ethyl acetate/methanol) to afford the title compound (30 mg). Structural formula, spectral data and purification condition are shown in Table 124.

Examples 50-2 to 50-11

Examples 50-2 to 50-11 were synthesized in a manner similar to that of Example 50-1 by using the corresponding materials. Structural formula, spectral data and purification condition are shown in Table 124 to Table 125.

Example 50-12

N-[(2R)-3,3-Difluoro-4-hydroxy-1-(2H-1,2,3-triazol-2-yl)butan-2-yl]-3-fluoro-2-[5-(4-fluorophenyl)-1H-pyrazol-3-yl]benzamide To a suspension of 4-fluoro-2-(4-fluorophenyl)-8H-pyrazolo[5,1-a]isoindol-8-one (48 mg) in cyclopentylmethylether (1 mL) were added (2R)-4-(benzyloxy)-3,3-difluoro-1-(2H-1,2,3-triazol-2-yl)butan-2-amine hydrochloride (54 mg) and N,N-diisopropylethylamine (66 mg), and the mixture was stirred at 80° C. for 2 days. The reaction mixture was allowed to cool to room temperature. To the mixture was added a saturated aqueous solution of sodium bicarbonate, and the crude product was extracted with ethyl acetate. The organic layer was washed with brine, and dried over sodium sulfate. The solvent was removed under reduced pressure, and the residue was purified by silica gel column chromatography (eluent: ethyl acetate/n-hexane) to afford N-[(2R)-4-(benzyloxy)-3,3-difluoro-1-(2H-1,2,3-triazol-2-yl)butan-2-yl]-3-fluoro-2-[5-(4-fluorophenyl)-1H-pyrazol-3-yl]benzamide (48 mg). To the product (48 mg) were added trifluoroacetic acid (1 mL), water (0.1 mL) and dimethylsulfide (0.2 mL), and the mixture was stirred at 60° C. for 5 hours. The reaction mixture was allowed to cool to room temperature, and then concentrated under reduced pressure. The residue was purified by aminopropyl silica gel column chromatography (eluent: ethyl acetate/methanol) to afford the title compound (13 mg). Structural formula, spectral data and purification condition are shown in Table 125.

Example 51-1

2-{5-[4-(1,3-Dioxolan-2-yl)phenyl]-1H-pyrazol-3-yl}-N-[2-(pyridin-2-yl)ethyl]benzamide To a solution of 2-(4-ethynylphenyl)-1,3-dioxolane (0.209 g) in tetrahydrofuran (5 mL) was added a solution of n-butyllithium in n-hexane (1.6 mol/L, 0.75 mL) at −78° C., and the mixture was allowed to warm to 0° C. To the mixture was added a solution of N-[2-(pyridin-2-yl)ethyl]phthalimide (0.5 g) in tetrahydrofuran (5 mL), and the mixture was stirred for 10 minutes. To the reaction mixture was added water, and the reaction mixture was concentrated under reduced pressure. To the residue were added ethanol (5 mL) and hydrazine (0.192 g), and the mixture was stirred at 60° C. for 3 hours. After cooling the reaction mixture, insoluble compound was removed by filtration. The filtrate was concentrated under reduced pressure. To the residue was added water, and the crude product was extracted with ethyl acetate. The organic layer was washed with brine, and dried over sodium sulfate. The solvent was removed under reduced pressure, and the residue was purified by aminopropyl silica gel column chromatography (eluent: ethyl acetate/methanol) to afford the title compound (0.038 g). Structural formula, spectral data and purification condition are shown in Table 126.

Example 52-1

N-{3-Fluoro-2-[5-(4-fluorophenyl)-1H-pyrazol-3-yl]benzoyl}-N-[2-(pyridin-2-yl)ethyl]glycine To a mixture of (N-{3-fluoro-2-[5-(4-fluorophenyl)-1H-pyrazol-3-yl]benzoyl}-N-[2-(pyridin-2-yl)ethyl]glycine methyl ester (58 mg), tetrahydrofuran (1 mL), methanol (1 mL) and water (0.3 mL) was added lithium hydroxide monohydrate (15 mg), and the mixture was stirred at 40° C. for 3 hours. The reaction mixture was allowed to cool to room temperature. To the reaction mixture was added hydrochloric acid (1 mol/L), and the crude product was extracted with ethyl acetate. The organic layer was washed with brine, dried over sodium sulfate, and filtered. The filtrate was concentrated under reduced pressure, and the residue was purified by silica gel column chromatography (eluent: ethyl acetate/methanol) to afford the title compound (39 mg). Structural formula, spectral data and purification condition are shown in Table 126.

Example 52-2

Example 52-2 was synthesized in a manner similar to that of Example 52-1 by using the corresponding materials. Structural formula, spectral data and purification condition are shown in Table 126.

Example 53-1

2-[5-(4-Fluorophenyl)-1H-pyrazol-3-yl]-N-[(2R)-1-hydroxy-3-(pyridin-2-yl)propan-2-yl]benzene-1,3-dicarboxamide To a suspension of a mixture of 3-bromo-2-[5-(4-fluorophenyl)-1-(methoxymethyl)-1H-pyrazol-3-yl]benzamide and 3-bromo-2-[5-(4-fluorophenyl)-2-(methoxymethyl)-2H-pyrazol-3-yl]benzamide (5 mg) in n-propanol (2 mL) were added N-methylpyrrolidone (0.5 mL), triethylamine (5 mg), 1,1'-bis(diphenylphosphino)ferrocene (2 mg) and 1,1'-bis(diphenylphosphino)ferrocene palladium (II) dichloride dichloromethane adduct (2 mg), and the mixture was stirred at 100° C. under a carbon monoxide atmosphere for 5 hours. The reaction mixture was allowed to cool to room temperature. To the mixture was added water, and the crude product was extracted with ethyl acetate. The organic layer was washed with brine, and dried over anhydrous magnesium sulfate. The solvent was removed under reduced pressure, and the residue was purified by silica gel column chromatography (eluent: ethyl acetate/n-hexane) to afford a mixture of 3-carbamoyl-2-[5-(4-fluorophenyl)-1-(methoxymethyl)-1H-pyrazol-3-yl]benzoic acid propyl ester and 3-carbamoyl-2-[5-(4-fluorophenyl)-2-(methoxymethyl)-2H-pyrazol-3-yl] benzoic acid propyl ester (5 mg). To the mixture (5 mg) were added methanol (1 mL), an aqueous solution of sodium hydroxide (2 mol/L, 100 µL), and the mixture was stirred at 60° C. for 1.5 hours. The reaction mixture was acidified with hydrochloric acid (2 mol/L). The crude product was extracted with ethyl acetate. The organic layer was washed with water and brine, and dried over anhydrous magnesium sulfate. The solvent was removed under reduced pressure to afford a mixture of 3-carbamoyl-2-[5-(4-fluorophenyl)-1-(methoxymethyl)-1H-pyrazol-3-yl]benzoic acid and 3-carbamoyl-2-[5-(4-fluorophenyl)-2-(methoxymethyl)-2H-pyrazol-3-yl]benzoic acid (4.5 mg). To the mixture (4.5 mg) were added N,N-dimethylformamide (1 mL), (2R)-2-amino-3-(pyridin-2-yl)propan-1-ol (3 mg), 1-hydroxybenzotriazole monohydrate (3 mg), 1-ethyl-3-(3-dimethylaminopropyl) carbodiimide hydrochloride (4 mg) and triethylamine (7 mg), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/methanol) to afford a mixture of 2-[5-(4-fluorophenyl)-1-(methoxymethyl)-1H-pyrazol-3-yl]-N-[(2R)-1-hydroxy-3-(pyridin-2-yl)propan-2-yl]benzene-1,3-dicarboxamide and 2-[5-(4-fluorophenyl)-2-(methoxymethyl)-2H-pyrazol-3-yl]-N-[(2R)-1-hydroxy-3-(pyridin-2-yl)propan-2-yl]benzene-1,3-dicarboxamide. To the mixture were added tetrahydrofuran (1 mL) and a solution of hydrogen chloride in ethyl acetate (4 mol/L, 1 mL), and the mixture was stirred at 50° C. for 1 hour. The reaction mixture was allowed to cool to room temperature, and then concentrated under reduced pressure. The residue was purified by aminopropyl silica gel column chromatography (eluent: ethyl acetate/methanol) to afford the title compound (0.5 mg). Structural formula and purification condition are shown in Table 126.

Example 54-1

N-[(2S)-1,3-Dihydroxy-1-(pyridin-2-yl)propan-2-yl]-3-fluoro-2-[5-(4-fluorophenyl)-1H-pyrazol-3-yl] benzamide To a solution of (R)-N-[(2S)-1,3-di(tert-butyldimethylsilyloxy)-1-(pyridin-2-yl)propan-2-yl]-2-methylpropane-2-sulfinamide (0.085 g) in 1,4-dioxane (1 mL) was added a solution of hydrogen chloride in 1,4-dioxane (4 mol/L, 1 mL), and the mixture was further stirred at 60° C. for 24 hours. The reaction mixture was allowed to cool to room temperature, and then concentrated under reduced pressure. To a solution of the residue in N,N-dimethylformamide (1 mL) were added 3-fluoro-2-[5-(4-fluorophenyl)-1H-pyrazol-3-yl]benzoic acid (0.030 g), 1-hydroxybenzotriazole monohydrate (0.019 g), 1-ethyl-3-(3-dimethylaminopropyl) carbodiimide hydrochloride (0.023 g) and triethylamine (0.040 g), and the mixture was stirred at room temperature overnight. To the reaction mixture was added water, and the crude product was extracted with ethyl acetate. The organic layer was washed with brine, and dried over sodium sulfate. The solvent was removed under reduced pressure, and the residue was purified by silica gel column chromatography (eluent: ethyl acetate/methanol) to afford the title compound (0.013 g). Structural formula, spectral data and purification condition are shown in Table 127.

Examples 54-2 to 54-20, 1-205 to 1-207 and 1-210 to 1-211

Examples 54-2 to 54-20, 1-205 to 1-207 and 1-210 to 1-211 were synthesized in a manner similar to that of Example 54-1 by using the corresponding materials. Structural formula, spectral data and purification condition are shown in Table 78 to Table 79 and Table 127 to Table 130.

Example 55-1

N-[(2R)-1-(6-Aminopyridin-2-yl)-3-hydroxypropan-2-yl]-3-fluoro-2-[5-(4-fluorophenyl)-1H-pyrazol-3-yl]benzamide A mixture of N-[(2R)-1-(6-azidopyridin-2-yl)-3-hydroxypropan-2-yl]-3-fluoro-2-[5-(4-fluorophenyl)-1H-pyrazol-3-yl]benzamide (36 mg), tetrahydrofuran (2 mL), water (0.2 mL) and triphenylphosphine (77 mg) was stirred at 80° C. for 2 days. The reaction mixture was allowed to cool to room temperature, and then concentrated under reduced pressure. The residue was purified by aminopropyl silica gel column chromatography (eluent: ethyl acetate/methanol) to afford the title compound (8 mg) Structural formula, spectral data and purification condition are shown in Table 130.

Example 56-1

N-[(2R)-3,3-Difluoro-4-hydroxy-1-(2H-1,2,3-triazol-2-yl)butan-2-yl]-3-fluoro-2-[4-fluoro-5-(4-fluorophenyl)-1H-pyrazol-3-yl]benzamide A mixture of 3-fluoro-2-[4-fluoro-5-(4-fluorophenyl)-1H-pyrazol-3-yl]benzoic acid (40 mg), (2R)-4-(benzyloxy)-3,3-difluoro-1-(2H-1,2,3-triazol-2-yl)butan-2-amine hydrochloride (44 mg), N,N-diisopropylethylamine (163 mg), a solution of T3P (registered trademark) in ethyl acetate (1.7 mol/L, 0.15 mL) and N-methylpyrrolidone (1 mL) was stirred at 80° C. for 2 days. To the reaction mixture was added a saturated aqueous solution of sodium bicarbonate, and the crude product was extracted with ethyl acetate. The organic layer was washed with water and brine successively, and dried over sodium sulfate. The solvent was removed under reduced pressure, and the residue was purified by silica gel column chromatography (eluent: ethyl acetate/n-hexane). To a solution of the product in trifluoroacetic acid (1 mL) were added water (0.1 mL) and dimethylsulfide (0.2 mL), and the mixture was stirred at 60° C. for 5 hours. The reaction mixture was allowed to cool to room temperature, and then concentrated under reduced pressure. The residue was purified by aminopropyl silica gel column chromatography (eluent: ethyl acetate/methanol) to afford the title compound (28 mg). Structural formula, spectral data and purification condition are shown in Table 131.

Example 57-1

2-(5-Phenyl-1H-pyrazol-3-yl)-N-(pyridin-2-ylmethyl)benzamide

To a solution of 2-(5-phenyl-1H-pyrazol-3-yl)benzoic acid (50 mg) in N,N-dimethylformamide (1 mL) were added 2-amino-2-(pyridin-2-yl)acetic acid ethyl ester hydrochloride (49 mg), 1-hydroxybenzotriazole monohydrate (44 mg), 1-ethyl-3-(3-dimethylaminopropyl)carbodiimide hydrochloride (54 mg) and N,N-diisopropylethylamine (73 mg), and the mixture was stirred at room temperature overnight. To the reaction mixture was added water, and the crude product was extracted with ethyl acetate. The organic layer was washed with brine, and dried over anhydrous magnesium sulfate. The solvent was removed under reduced pressure, and the residue was purified by aminopropyl silica gel column chromatography (eluent: ethyl acetate/n-hexane) to afford 2-[2-(5-phenyl-1H-pyrazol-3-yl)benzoylamino]-2-(pyridin-2-yl)acetic acid ethyl ester (29 mg). To a solution of the product (29 mg) in ethanol (1 mL) and tetrahydrofuran (1 mL) was added an aqueous solution of sodium hydroxide (2 mol/L, 0.05 mL), and the mixture was stirred at room temperature for 2 hours. To the reaction mixture were added hydrochloric acid (2 mol/L, 0.06 mL) and water, and the crude product was extracted with ethyl acetate. The organic layer was washed with brine, and dried over anhydrous magnesium sulfate. The solvent was removed under reduced pressure to afford the title compound (0.021 g). Structural formula, spectral data and purification condition are shown in Table 131.

Example 57-2

Example 57-2 was synthesized in a manner similar to that of Example 57-1 by using the corresponding materials. Structural formula, spectral data and purification condition are shown in Table 131.

TABLE 49

| Ex. No. | Stre. | P.D. | P.C. |
| --- | --- | --- | --- |
| 1-1 | 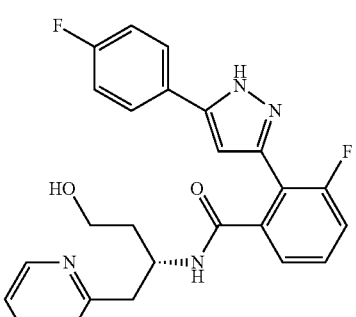 | $^1$H-NMR (CDCl$_3$) δ ppm: 1.36-1.46 (1H, m), 1.76-1.86 (1H, m), 2.90 (1H, dd, J = 6.0, 14.4 Hz), 3.13 (1H, dd, J = 4.7, 14.4 Hz), 3.56-3.68 (2H, m), 4.57-4.69 (1H, m), 6.83 (1H, d, J = 3.2 Hz), 7.04-7.15 (4H, m), 7.24-7.33 (2H, m), 7.36-7.43 (1H, m), 7.56 (1H, td, J = 1.9, 7.7 Hz), 7.68-7.76 (2H, m), 7.79 (1H, d, J = 8.1 Hz), 8.35-8.40 (1H, m). RT (min): 1.792 (Method A) MS (ESI, m/z): 449.1789 (M + H)$^+$ | Column: APS EtOAc/MeOH |
| 1-2 | 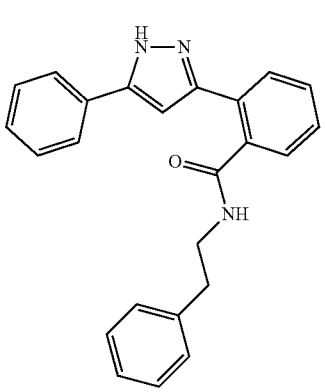 [SMILES: O=C(NCCc1ccccc1)c1ccccc1-c1cc(-c2ccccc2)[nH]n1] | RT (min): 3.321 (Method A) MS (ESI, m/z): 368.1755 (M + H)$^+$ | Column: S102 EtOAc/n-Hexane |

TABLE 49-continued

| Ex. No. | Stre. | P.D. | P.C. |
| --- | --- | --- | --- |
| 1-3 | | ¹H-NMR (DMSO-d₆) δ ppm: 2.94 (2H, t, J = 7.3 Hz), 3.51-3.59 (2H, m), 6.82 (1H, s), 7.15-7.67 (6H, m), 7.61-7.83 (4H, m), 8.26-8.54 (2H, m), 13.13-13.45 (1H, m).<br>RT (min): 1.599 (Method A)<br>MS (ESI, m/z): 369.1708 (M + H)⁺ | Column: S102<br>EtOAc/MeOH |
| 1-4 | | RT (min): 3.420 (Method A)<br>MS (ESI, m/z): 386.1661 (M + H)⁺ | Column: S102<br>EtOAc/n-Hexane |
| 1-5 | | RT (min): 3.468 (Method A)<br>MS (ESI, m/z): 386.1662 (M + H)⁺ | Column: S102<br>EtOAc/n-Hexane |
| 1-6 | | RT (min): 3.573 (Method A)<br>MS (ESI, m/z): 382.1912 (M + H)⁺ | Column: S102<br>EtOAc/MeOH |

TABLE 49-continued

| Ex. No. | Stre. | P.D. | P.C. |
|---|---|---|---|
| 1-7 | | RT (min): 2.058 (Method B)<br>MS (ESI, m/z): 370.1660 (M + H)+ | Column: S102<br>EtOAc/MeOH |

TABLE 50

| Ex. No. | Stre. | P.D. | P.C. |
|---|---|---|---|
| 1-8 | | RT (min): 1.787 (Method A)<br>MS (ESI, m/z): 387.1614 (M + H)+ | Column: S102<br>EtOAc/MeOH |
| 1-9 | | RT (min): 1.794 (Method A)<br>MS (ESI, m/z): 387.1614 (M + H)+ | Column: S102<br>EtOAc/MeOH |
| 1-10 | | RT (min): 1.785 (Method A)<br>MS (ESI, m/z): 383.1863 (M + H)+ | Column: S102<br>EtOAc/MeOH |

TABLE 50-continued

| Ex. No. | Stre. | P.D. | P.C. |
| --- | --- | --- | --- |
| 1-11 | | RT (min): 2.924 (Method A)<br>MS (ESI, m/z): 398.1861 (M + H)⁺ | Column: S102<br>EtOAc/n-Hexane |
| 1-12 | | ¹H-NMR (CD₃OD) δ ppm: 2.74 (1H, dd, J = 8.7, 13.8 Hz), 2.93 (1H, dd, J = 6.1, 13.8 Hz), 3.55-3.63 (2H, m), 4.25-4.35 (1H, m), 6.83 (1H, s), 7.11-7.19 (1H, m), 7.20-7.27 (5H, m), 7.29-7.52 (5H, m), 7.64-7.77 (3H, m).<br>RT (min): 2.935 (Method A)<br>MS (ESI, m/z): 396.1861 (M + H)⁺ | Column: S102<br>EtOAc/n-Hexane |
| 1-13 | | ¹H-NMR (DMSO-d₆) δ ppm: 2.81-2.95 (1H, m), 3.06-3.22 (1H, m), 4.54-4.67 (1H, m), 6.80-7.00 (2H, m), 7.06-7.55 (11H, m), 7.60-7.85 (4H, m), 8.65-8.82 (1H, m), 13.00-13.44 (1H, m).<br>RT (min): 2.844 (Method A)<br>MS (ESI, m/z): 411.1814 (M + H)⁺ | Column: S102<br>EtOAc/MeOH |
| 1-14 | | ¹H-NMR (DMSO-d₆) δ ppm: 2.81-2.95 (1H, m), 3.06-3.22 (1H, m), 4.54-4.67 (1H, m), 6.80-7.00 (2H, m), 7.06-7.56 (11H, m), 7.60-7.85 (4H, m), 8.65-8.82 (1H, m), 13.01-13.44 (1H, m).<br>RT (min): 2.876 (Method A)<br>MS (ESI, m/z): 411.1812 (M + H)⁺ | Column: S102<br>EtOAc/MeOH |

TABLE 51

| Ex. No. | Stre. | P.D. | P.C. |
|---|---|---|---|
| 1-15 | | ¹H-NMR (DMSO-d₆) δ ppm: 3.01-3.15 (1H, m), 3.21-3.34 (1H, m), 4.75-4.88 (1H, m), 6.81-7.03 (2H, m), 7.13-7.55 (8H, m), 7.56-7.83 (5H, m), 8.45-8.52 (1H, m), 8.63-8.77 (1H, m), 13.04-13.28 (1H, m).<br>RT (min): 1.673 (Method A)<br>MS (ESI, m/z): 412.1765 (M + H)⁺ | Column: S102<br>EtOAc/MeOH |
| 1-16 | | RT (min): 1.659 (Method A)<br>MS (ESI, m/z): 412.1763 (M + H)⁺ | Column: S102<br>EtOAc/MeOH |
| 1-17 | | RT (min): 1.674 (Method A)<br>MS (ESI, m/z): 426.1920 (M + H)⁺ | Column: APS<br>EtOAc/MeOH |
| 1-18 | | RT (min): 1.796 (Method A)<br>MS (ESI, m/z): 440.2078 (M + H)⁺ | Column: APS<br>EtOAc/MeOH |

TABLE 51-continued

| Ex. No. | Stre. | P.D. | P.C. |
|---|---|---|---|
| 1-19 | | RT (min): 1.608 (Method A)<br>MS (ESI, m/z): 412.1765 (M + H)$^+$ | Filtration of the EtOAc suspension |
| 1-20 | | $^1$H-NMR (DMSO-d$_6$) δ ppm: 2.74-2.87 (1H, m), 3.02-3.19 (1H, m), 4.41-4.57 (1H, m), 6.69-7.65 (14H, m), 7.71-7.80 (2H, m), 8.70-8.82 (1H, m), 12.95-13.44 (1H, m).<br>RT (min): 3.316 (Method A)<br>MS (ESI, m/z): 495.1635 (M + H)$^+$ | Filtration of the EtOAc suspension |
| 1-21 | | $^1$H-NMR (DMSO-d$_6$) δ ppm: 2.61 (1H, dd, J = 8.7, 13.7 Hz), 2.84 (1H, dd, J = 5.5, 13.7 Hz), 3.20-3.43 (2H, m), 3.89-4.01 (1H, m), 4.67-4.91 (1H, m), 6.70-6.80 (1H, m), 7.14-7.84 (13H, m), 8.09-8.38 (1H, m). 12.95-13.68 (1H, m).<br>RT (min): 3.375 (Method A)<br>MS (ESI, m/z): 482.1683 (M + H)$^+$ | Column: S102<br>EtOAc/n-Hexane |

TABLE 52

| Ex. No. | Stre. | P.D. | P.C. |
|---|---|---|---|
| 1-22 | | RT (min): 3.020 (Method A)<br>MS (ESI, m/z): 456.1923 (M + H)$^+$ | Column: APS<br>EtOAc/MeOH |
| 1-23 | | RT (min): 1.482 (Method A)<br>MS (ESI, m/z): 401.1726 (M + H)$^+$ | Column: APS<br>EtOAc/MeOH |
| 1-24 | | RT (min): 2.374 (Method A)<br>MS (ESI, m/z): 370.1660 (M + H)$^+$ | Column: APS<br>EtOAc/MeOH |
| 1-25 | | RT (min): 2.427 (Method A)<br>MS (ESI, m/z): 370.1658 (M + H)$^+$ | Column: APS<br>EtOAc/MeOH |

TABLE 52-continued

| Ex. No. | Stre. | P.D. | P.C. |
|---|---|---|---|
| 1-26 | | RT (min): 1.712 (Method A)<br>MS (ESI, m/z): 377.1972 (M + H)+ | Column: APS<br>EtOAc/MeOH |
| 1-27 | | $^1$H-NMR (CDCl$_3$) δ ppm: 3.13 (1H, dd, J = 5.13, 14.3 Hz),<br>3.30 (1H, dd, J = 6.8, 14.3 Hz), 3.69-3.76 (1H, m),<br>3.76-3.83 (1H, m), 4.41-4.53 (1H, m), 6.76 (1H, s),<br>6.90-6.99 (1H, m), 7.65-7.14 (2H, m), 7.31-7.52<br>(7H, m), 7.61-7.67 (1H, m), 7.76-7.82 (2H, m),<br>8.36-8.41 (1H, m).<br>RT (min): 1.654 (Method A)<br>MS (ESI, m/z): 399.1814 (M + H)+ | Column: APS<br>EtOAc/MeOH |
| 1-28 | | Rt (min): 3.588 (Method A)<br>MS (ESI, m/z): 425.1968 (M + H)+ | Column: S102<br>EtOAc/n-Hexane |

TABLE 53

| Ex. No. | Stre. | P.D. | P.C. |
|---|---|---|---|
| 1-29 | | $^1$H-NMR (CDCl$_3$) δ ppm: 3.15 (1H, dd, J = 4.9 Hz, 14.2<br>Hz), 3.28-3.38 (1H, m), 3.69-3.76 (1H, m),<br>3.77-3.86 (1H, m), 4.43-4.52 (1H, m), 6.70 (1H, m),<br>6.95-7.00 (1H, m), 7.08-7.24 (3H, m), 7.34-7.38<br>(2H, m), 7.46-7.58 (3H, m), 7.61-7.72 (2H, m),<br>8.39-8.43 (1H, m).<br>RT (min): 2.081 (Method A)<br>MS (ESI, m/z): 435.1624 (M + H)+ | Column: S102<br>EtOAc/MeOH |

TABLE 53-continued

| Ex. No. | Stre. | P.D. | P.C. |
|---|---|---|---|
| 1-30 | | RT (min): 3.720 (Method A)<br>MS (ESI, m/z): 382.1912 (M + H)⁺ | Column: S102<br>EtOAc/<br>n-Hexane |
| 1-31 | | RT (min): 3.766 (Method A)<br>MS (ESI, m/z): 382.1912 (M + H)⁺ | Column: S102<br>EtOAc/<br>n-Hexane |
| 1-32 | | RT (min): 3.632 (Method A)<br>MS (ESI, m/z): 398.1860 (M + H)⁺ | Column: S102<br>EtOAc/<br>n-Hexane |
| 1-33 | | RT (min): 3.437 (Method A)<br>MS (ESI, m/z): 398.1861 (M + H)⁺ | Column: S102<br>EtOAc/<br>n-Hexane |
| 1-34 | | RT (min): 3.574 (Method A)<br>MS (ESI, m/z): 412.2019 (M + H)⁺ | Column: S102<br>EtOAc/<br>n-Hexane |

TABLE 53-continued

| Ex. No. | Stre. | P.D. | P.C. |
|---|---|---|---|
| 1-35 | (structure) | RT (min): 1.640 (Method A)<br>MS (ESI, m/z): 399.1812 (M + H)⁺ | Column: APS<br>EtOAc/MeOH |

TABLE 54

| Ex. No. | Stre. | P. D. | P. C. |
|---|---|---|---|
| 1-36 | (structure) | ¹H-NMR(CDCl₃) δ ppm: 1.27 (3H, s), 1.32 (3H, s), 2.64 (1H, dd, J = 11.5, 14.2 Hz), 3.18 (1H, dd, J = 4.0, 14.2 Hz), 4.37-4.47 (1H, m), 5.93-6.04 (1H, m), 6.74 (1H, s), 6.85-6.91 (1H, m), 7.12-7.21 (3H, m), 7.21-7.36 (4H, m), 7.37-7.46 (3H, m), 7.58-7.64 (1H, m), 7.72-7.80 (2H, m).<br>RT(min): 3.400 (Method A)<br>MS(ESI, m/z): 426.2172 (M + H)⁺ | Column: APS<br>EtOAc/MeOH |
| 1-37 | (structure) | RT(min): 3.671 (Method A)<br>MS(ESI, m/z): 402.1366 (M + H)⁺ | Column: SiO2<br>EtOAc/n-Hexane |
| 1-38 | (structure) | RT(min): 3.890 (Method A)<br>MS(ESI, m/z): 402.1366 (M + H)⁺ | Column: SiO2<br>EtOAc/n-Hexane |

TABLE 54-continued
| Ex. No. | Strc. | P. D. | P. C. |
|---|---|---|---|
| 1-39 | 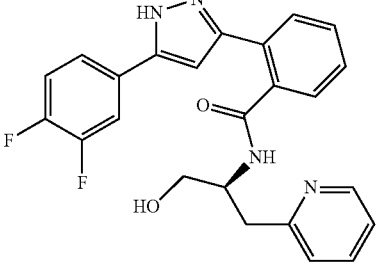 | RT(min): 2.000 (Method A)<br>MS(ESI, m/z): 435.1624 (M + H)$^+$ | Column: SiO2<br>EtOAc/MeOH |
| 1-40 | 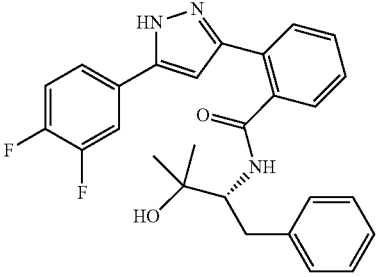 [SMILES: CC(C)(O)[C@@H](Cc1ccccc1)NC(=O)c1ccccc1-c1cc(-c2ccc(F)c(F)c2)[nH]n1] | RT(min): 3.885 (Method A)<br>MS(ESI, m/z): 462.1986 (M + H)$^+$ | Column: SiO2<br>EtOAc/MeOH |
| 1-41 | 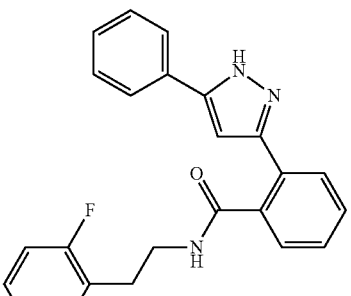 | RT(min): 3.591 (Method A)<br>MS(ESI, m/z): 386.1659 (M + H)$^+$ | Column: SiO2<br>EtOAc/n-Hexane |
| 1-42 | 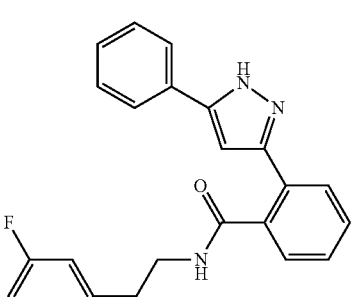 | RT(min): 3.785 (Method A)<br>MS(ESI, m/z): 386.1661 (M + H)$^+$ | Column: SiO2<br>EtOAc/n-Hexane |

TABLE 55
| Ex. No. | Strc. | P. D. | P. C. |
|---|---|---|---|
| 1-43 | 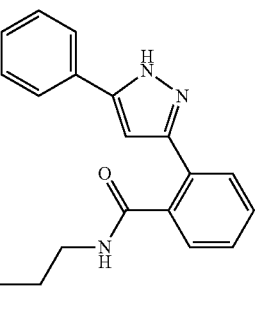 | RT(min): 2.906 (Method A)<br>MS(ESI, m/z): 384.1704 (M + H)+ | Column: SiO2<br>EtOAc/n-Hexane |
| 1-44 | 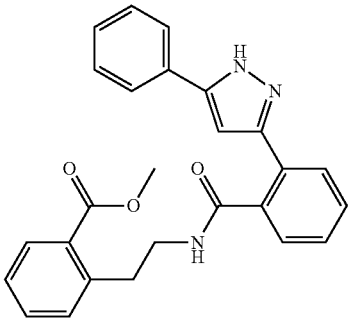 | RT(min): 3.555 (Method A)<br>MS(ESI, m/z): 426.1809 (M + H)+ | Column: SiO2<br>EtOAc/n-Hexane |
| 1-45 | 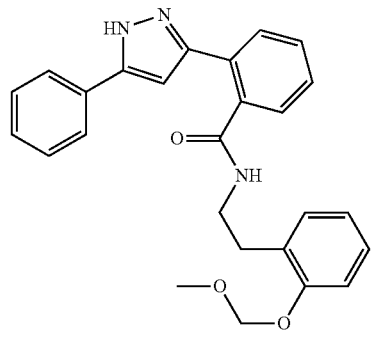 [SMILES: COCOc1ccccc1CCNC(=O)c1ccccc1-c1cc(-c2ccccc2)[nH]n1] | RT(min): 3.582 (Method A)<br>MS(ESI, m/z): 428.1965 (M + H)+ | Column: APS<br>EtOAc/n-Hexane |
| 1-46 | 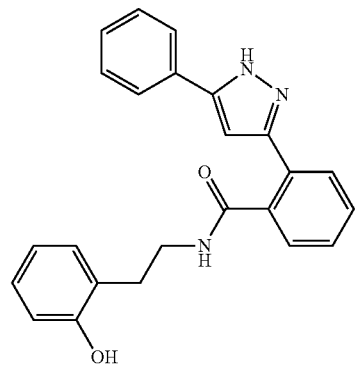 [SMILES: O=C(NCCc1ccccc1O)c1ccccc1-c1cc(-c2ccccc2)[nH]n1] | RT(min): 3.175 (Method A)<br>MS(ESI, m/z): 384.1703 (M + H)+ | Column: APS<br>EtOAc/n-Hexane |

TABLE 55-continued
| Ex. No. | Strc. | P. D. | P. C. |
|---|---|---|---|
| 1-47 | 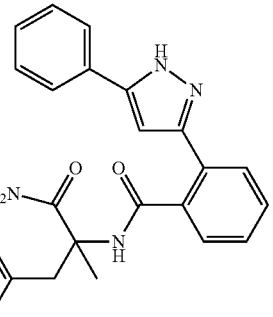 | ¹H-NMR(CDCl₃) δ ppm: 1.60 (3H, s), 3.26 (1H, d, J = 13.6 Hz), 3.54 (1H, d, J = 13.6 Hz), 6.02-6.30 (2H, m), 6.78 (1H, s), 7.01-7.24 (5H, m), 7.30-7.51 (7H, m), 7.60-7.66 (1H, m), 7.67-7.74 (2H, m).<br>RT(min): 3.497 (Method A)<br>MS(ESI, m/z): 425.1969 (M + H)⁺ | Column: APS<br>EtOAc/MeOH |
| 1-48 | 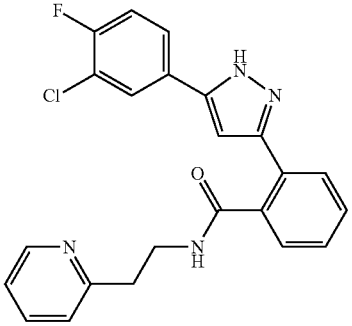 [SMILES: O=C(NCCc1ccccn1)c1ccccc1-c1cc(-c2ccc(F)c(Cl)c2)[nH]n1] | RT(min): 2.457 (Method A)<br>MS(ESI, m/z): 421.1224 (M + H)⁺ | Column: SiO2<br>EtOAc/MeOH |
| 1-49 | 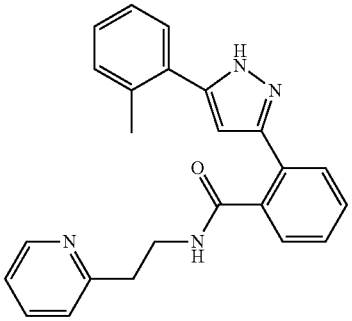 [SMILES: Cc1ccccc1-c1cc(-c2ccccc2C(=O)NCCc2ccccn2)n[nH]1] | RT(min): 2.065 (Method A)<br>MS(ESI, m/z): 383.1864 (M + H)⁺ | Column: SiO2<br>EtOAc/MeOH |
TABLE 56
| Ex. No. | Strc. | P. D. | P. C. |
|---|---|---|---|
| 1-50 | 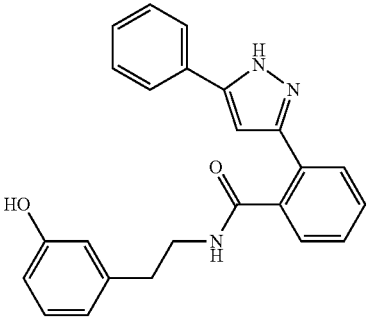 [SMILES: O=C(NCCc1cccc(O)c1)c1ccccc1-c1cc(-c2ccccc2)[nH]n1] | RT(min):3.118 (Method A)<br>MS(ESI, m/z): 384.1705 (M + H)⁺ | Column: SiO2<br>EtOAc/n-Hexane |

TABLE 56-continued

| Ex. No. | Strc. | P. D. | P. C. |
|---|---|---|---|
| 1-51 | | RT(min): 2.606 (Method A)<br>MS(ESI, m/z): 417.1473 (M + H)⁺ | Column: SiO2<br>EtOAc/MeOH |
| 1-52 | | $^1$H-NMR(DMSO-d$_6$) δ ppm: 3.33-3.44 (2H, m), 4.67-4.83 (1H, m), 5.41-5.58 (1H, m), 6.85-6.95 (1H, m), 7.18-7.86 (14 H, m), 8.28-8.56 (1H, m), 13.1-13.5 (1H, m).<br>RT(min): 3.168 (Method A)<br>MS(ESI, m/z): 384.1705 (M + H)⁺ | Column: SiO2<br>EtOAc/n-Hexane |
| 1-53 | | $^1$H-NMR(DMSO-d$_6$) δ ppm: 3.35-3.42 (2H, m), 4.70-4.80 (1H, m), 5.41-5.58 (1H, m), 6.85-6.95 (1H, m), 7.18-7.87 (14H, m), 8.28-8.59 (1H, m), 13.1-13.5 (1H, m).<br>RT(min): 3.195 (Method A)<br>MS(ESI, m/z): 384.1705 (M + H)⁺ | Column: SiO2<br>EtOAc/n-Hexane |
| 1-54 | | RT(min): 2.019 (Method A)<br>MS(ESI, m/z): 417.1717 (M + H)⁺ | Column: SiO2<br>EtOAc/MeOH |

TABLE 56-continued

| Ex. No. | Strc. | P. D. | P. C. |
|---|---|---|---|
| 1-55 | 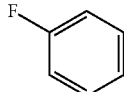 | ¹H-NMR(CDCl₃) δ ppm: 2.40 (3H, s), 3.013-3.09 (2H, m), 3.80-3.86 (2H, m), 6.76 (1H, s), 6.80-6.86 (1H, m), 6.99-7.06 (1H, m), 7.07-7.15 (2H, m), 7.29-7.35 (1H, m), 7.38 (1H, ddd, J = 1.3 Hz, 7.6 Hz, 7.6 Hz), 7.44-7.59 (4H, m), 7.65-7.71 (1H, m), 8.40-8.44 (1H, m). RT(min): 2.443 (Method A) MS(ESI, m/z): 441.1918 (M + H)⁺ | Column: SiO2 EtOAc/MeOH |
| 1-56 | 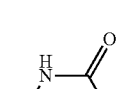 | RT(min): 1.824 (Method A) MS(ESI, m/z): 441.1918 (M + H)⁺ | Column: SiO2 EtOAc/MeOH |

TABLE 57

| Ex. No. | Strc. | P. D. | P. C. |
|---|---|---|---|
| 1-57 | 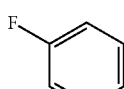 | RT(min): 3.434 (Method A) MS(ESI, m/z): 427.1563 (M + H)⁺ | Column: SiO2 EtOAc/n-Hexane |
| 1-58 | 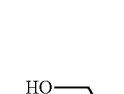 | ¹H-NMR(CDCl₃) δ ppm: 3.07 (1H, dd, J = 6.0 Hz, 14.1 Hz), 3.16 (1H, dd, J = 6.6 Hz, 14.1 Hz), 3.62 (1H, dd, J = 4.0 Hz, 11.7 Hz), 3.67 (1H, dd, J = 4.4 Hz, 11.7 Hz), 4.10-4.50 (1H, m), 6.66 (1H, s), 6.99-7.10 (3H, m), 7.15 (1H, d, J = 7.8 Hz), 7.25-7.45 (4H, m), 7.48-7.58 (2H, m), 7.62-7.71 (2H, m), 8.33-8.37 (1H, m). RT(min): 1.855 (Method A) MS(ESI, m/z): 417.1719 (M + H)⁺ | Column: SiO2 EtOAc/MeOH |

TABLE 57-continued

| Ex. No. | Strc. | P. D. | P. C. |
|---|---|---|---|
| 1-59 | 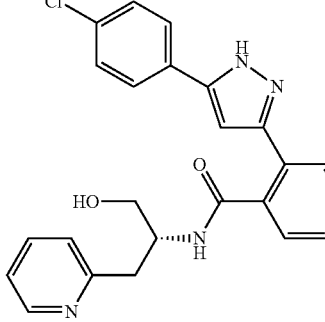 | ¹H-NMR(CDCl₃) δ ppm: 3.08 (1H, dd, J = 5.8 Hz, 14.1 Hz), 3.21 (1H, dd, J = 6.9 Hz, 14.2 Hz), 3.64 (1H, dd, J = 4.1 Hz, 11.7 Hz), 3.71 (1H, dd, J = 4.1 Hz, 11.7 Hz), 4.40-4.50 (1H, m), 6.70 (1H, s), 7.07 (1H, dd, J = 5.4 Hz, 7.7 Hz), 7.14 (1H, d, J = 7.8 Hz), 7.21 (1H, d, J = 7.8 Hz), 7.30-7.40 (4H, m), 7.43 (1H, dt, J = 1.7 Hz, 7.8 Hz), 7.51 (1H, dt, J = 1.8 Hz, 7.7 Hz), 7.57 (1H, d, J = 7.8 Hz), 7.63-7.69 (2H, m), 8.36 (1H, d, J = 4.9 Hz). RT(min): 2.291 (Method A) MS(ESI, m/z): 433.1422 (M + H)⁺ | Column: SiO2 EtOAc/MeOH |
| 1-60 | 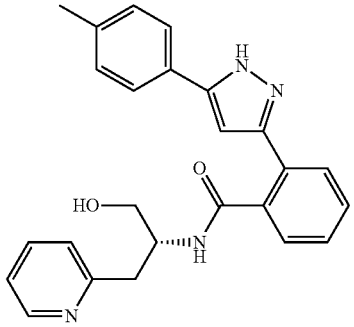 | RT(min): 2.068 (Method A) MS(ESI, m/z): 413.1971 (M + H)⁺ | Column: SiO2 EtOAc/MeOH |
| 1-61 | 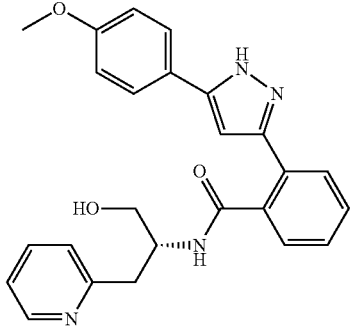 [SMILES: O=C(N[C@@H](CO)Cc1ccccn1)c1ccccc1-c1cc(-c2ccc(Cl)cc2)[nH]n1] | ¹H-NMR(CDCl₃) δ ppm: 3.12 (1H, dd, J = 5.4 Hz, 14.2 Hz), 3.26 (1H, dd, J = 6.9 Hz, 14.3 Hz), 3.69-3.79 (2H, m), 3.85 (3H, s), 4.42-4.51 (1H, m) 6.67 (1H, s), 6.92-7.02 (3H, m), 7.05-7.15 (2H, m), 7.30-7.40 (2H, m) 7.43-7.54 (2H, m), 7.62 (1H, d, J = 7.7 Hz), 7.66-7.73 (2H, m), 8.37-8.41 (1H, m). RT(min) : 1.743 (Method A) MS(ESI, m/z): 429.1917 (M + H)⁺ | Column: SiO2 EtOAc/MeOH |
| 1-62 | 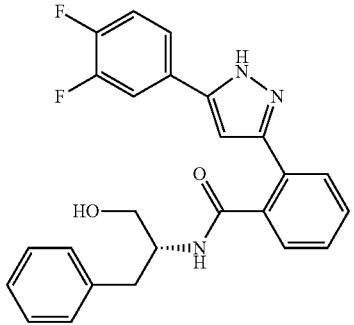 [SMILES: O=C(N[C@@H](CO)Cc1ccccc1)c1ccccc1-c1cc(-c2ccc(F)c(F)c2)[nH]n1] | ¹H-NMR(CDCl₃) δ ppm: 2.88 (2H, d, J = 7.3 Hz), 3.57 (1H, dd, J = 5.5 Hz, 12.2 Hz), 3.78 (1H, dd, J = 3.6 Hz, 11.3 Hz), 4.32-4.49 (1H, m), 6.19 (1H, d, J = 8.5 Hz), 6.67 (1H, s), 7.05-7.24 (4H, m), 7.24-7.56 (7H, m), 7.59 (1H, d, J = 7.8 Hz). RT(min): 3.464 (Method A) MS(ESI, m/z): 434.1673 (M + H)⁺ | Column: SiO2 EtOAc/MeOH |

TABLE 57-continued

| Ex. No. | Strc. | P. D. | P. C. |
|---|---|---|---|
| 1-63 | 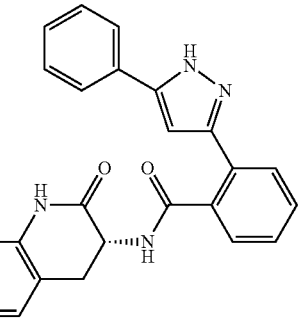 | RT(min): 3.394 (Method A)<br>MS(ESI, m/z): 409.1656 (M + H)+ | Column: APS<br>EtOAc/MeOH |

TABLE 58

| Ex. No. | Strc. | P. D. | P. C. |
|---|---|---|---|
| 1-64 | | ¹H-NMR(CDCl₃) δ ppm: 3.00-3.17 (2H, m), 3.55-3.66 (2H, m), 4.31-4.43 (1H, m), 6.71 (1H, s), 7.01-7.16 (5H, m), 7.36-7.46 (3H, m), 7.52 (1H, td, J = 1.8, 7.8 Hz), 7.60-7.70 (2H, m), 8.35-8.41 (1H, m).<br>RT(min): 2.533 (Method A)<br>MS(ESI, m/z): 501.1543 (M + H)+ | Column: APS<br>EtOAc/MeOH |
| 1-65 | | ¹H-NMR(CDCl₃) δ ppm: 2.95-3.10 (2H, m), 3.65 (1H, dd, J = 5.5, 11.3 Hz), 3.86 (1H, dd, J = 3.4, 11.3 Hz), 4.37-4.51 (1H, m), 6.16-6.30 (1H, m), 6.76 (1H, s), 7.12-7.21 (2H, m), 7.23-7.43 (7H, m), 7.43-7.50 (1H, m), 7.60-7.65 (1H, m), 7.65-7.72 (2H, m).<br>RT(min): 3.549 (Method A)<br>MS(ESI, m/z): 432.1472 (M + H)+ | Column: SiO2<br>EtOAc/n-Hexane |
| 1-66 | | RT(min): 3.172 (Method A)<br>MS(ESI, m/z): 409.1656 (M + H)+ | Column: SiO2<br>EtOAc/MeOH |

TABLE 58-continued

| Ex. No. | Strc. | P. D. | P. C. |
|---|---|---|---|
| 1-67 | 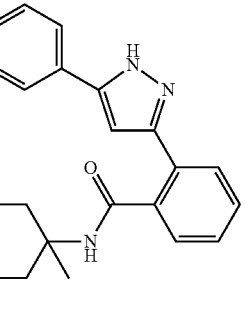 | RT(min): 3.865 (Method A)<br>MS(ESI, m/z): 412.2017 (M + H)$^+$ | Column: SiO2<br>EtOAc/n-Hexane |
| 1-68 | 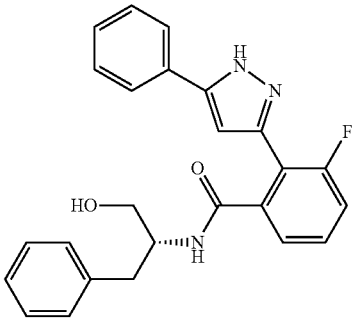 [SMILES: O=C(N[C@@H](CO)Cc1ccccc1)c1cccc(F)c1-c1cc(-c2ccccc2)[nH]n1] | $^1$H-NMR(CDCl$_3$) δ ppm: 2.82 (2H, d, J = 7.4 Hz), 3.50 (1H, dd, J = 5.7, 11.4 Hz), 3.82 (1H, dd, J = 3.6, 11.4 Hz), 4.30-4.42 (1H, m), 6.24 (1H, d, J = 8.5 Hz), 6.80 (1H, d, J = 3.0 Hz), 7.09 (1H, d, J = 7.7 Hz), 7.12-7.38 (10H, m), 7.53-7.61 (2H, m).<br>RT(min): 3.278 (Method A)<br>MS(ESI, m/z): 416.1766 (M + H)$^+$ | Column: SiO2<br>EtOAc/n-Hexane |
| 1-69 | 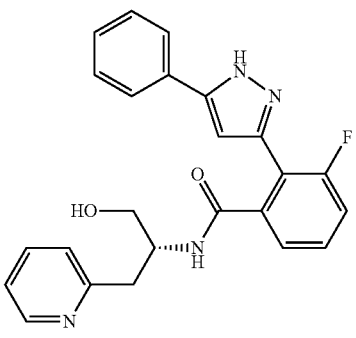 [SMILES: O=C(N[C@@H](CO)Cc1ccccn1)c1cccc(F)c1-c1cc(-c2ccccc2)[nH]n1] | $^1$H-NMR(CDCl$_3$) δ ppm: 3.09 (1H, dd, J = 5.7, 14.3 Hz), 3.19 (1H, dd, J = 6.5, 14.3 Hz), 3.70 (2H, d, J = 4.0 Hz), 4.36-4.49 (1H, m), 6.84 (1H, d, J = 3.1 Hz), 7.04-7.10 (2H, m), 7.12 (1H, d, J = 7.8 Hz), 7.17-7.25 (2H, m), 7.30-7.37 (2H, m), 7.38-7.45 (2H, m), 7.51 (1H, td, J = 1.8, 7.8 Hz), 7.73 (2H, d, J = 7.6 Hz), 8.35-8.40 (1H, m).<br>RT(min): 1.907 (Method A)<br>MS(ESI, m/z): 417.1719 (M + H)$^+$ | Column: APS<br>EtOAc/MeOH |
| 1-70 | 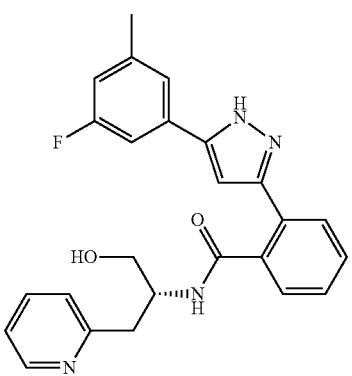 [SMILES: Cc1cc(F)cc(-c2cc(-c3ccccc3C(=O)N[C@@H](CO)Cc3ccccn3)n[nH]2)c1] | $^1$H-NMR(CDCl$_3$) δ ppm: 2.40 (3H, s), 3.13 (1H, dd, J = 5.1 Hz, 14.5 Hz), 3.30 (1H, dd, J = 6.8 Hz, 14.1 Hz), 3.71 (1H, dd, J = 4.0 Hz, 11.7 Hz), 3.79 (1H, dd, J = 3.8 Hz, 11.8 Hz), 4.41-4.52 (1H, m), 6.73 (1H, s), 6.81-6.86 (1H, m), 6.99-7.03 (1H, m), 7.06-7.15 (2H, m), 7.25-7.31 (1H, m), 7.32-7.40 (2H, m), 7.40-7.44 (1H, br), 7.45-7.53 (2H, m), 7.60-7.65 (1H, m), 8.36-8.42 (1H, m).<br>RT(min): 2.255 (Method A)<br>MS(ESI, m/z): 431.1873 (M + H)$^+$ | Column: SiO2<br>EtOAc/MeOH |

TABLE 59

| Ex. No. | Strc. | P. D. | P. C. |
|---|---|---|---|
| 1-71 | | RT(min): 2.597 (Method A)<br>MS(ESI, m/z): 421.1223 (M + H)⁺ | Column: SiO2<br>EtOAc/MeOH |
| 1-72 | | ¹H-NMR(CDCl₃) δ ppm: 3.05-3.10 (2H, m), 3.84 (2H, dd, J = 6.0 Hz, 11.9 Hz), 6.71-6.78 (2H, m), 7.01-7.08 (1H, m), 7.09-7.17 (2H, m), 7.36-7.43 (3H, m), 7.46-7.62 (3H, m), 7.68 (1H, d, J = 8.0 Hz), 8.41-8.46 (1H, m).<br>RT(min): 2.343 (Method A)<br>MS(ESI, m/z): 405.1520 (M + H)⁺ | Column: SiO2<br>EtOAc/MeOH |
| 1-73 | | ¹H-NMR(CDCl₃) δ ppm: 2.30 (3H, s), 3.04-3.09 (2H, m), 3.80-3.87 (2H, m), 6.75 (1H, s), 6.97-7.03 (1H, m), 7.07-7.14 (2H, m), 7.18-7.24 (1H, m), 7.34-7.42 (1H, m), 7.44-7.59 (5H, m), 7.65-7.71 (1H, m), 8.41-8.45 (1H, m).<br>RT(min): 2.285 (Method A)<br>MS(ESI, m/z): 401.1769 (M + H)⁺ | Column: SiO2<br>EtOAc/MeOH |
| 1-74 | | RT(min): 2.179 (Method A)<br>MS(ESI, m/z): 403.1563 (M + H)⁺ | Column: SiO2<br>EtOAc/MeOH |

TABLE 59-continued

| Ex. No. | Strc. | P. D. | P. C. |
|---|---|---|---|
| 1-75 | (structure) | RT(min): 4.054 (Method A)<br>MS(ESI, m/z): 402.1610 (M + H)⁺ | Column: SiO2<br>EtOAc/MeOH |
| 1-76 | (structure) | $^1$H-NMR(CDCl$_3$) δ ppm: 1.41-1.52 (1H, m), 1.86-1.97 (1H, m), 2.82 (1H, dd, J = 7.2, 14.2 Hz), 2.91 (1H, dd, (J = 6.5, 13.9 Hz), 3.56-3.68 (2H, m), 4.52-4.64 (1H, m), 6.02 (1H, d, J = 8.8 Hz), 6.70 (1H, s), 7.06-7.25 (8H, m), 7.31-7.37 (1H, m), 7.45-7.51 (1H, m), 7.61 (1H, d, J = 7.8 Hz), 7.71-7.78 (1H, m).<br>RT(min): 3.448 (Method A)<br>MS(ESI, m/z): 430.1925 (M + H)⁺ | Column: SiO2<br>EtOAc/MeOH |
| 1-77 | (structure) | $^1$H-NMR(CDCl$_3$) δ ppm: 2.42 (1H, dd, J = 5.8, 15.8 Hz), 2.50-2.58 (1H, m), 2.90-2.99 (1H, m), 3.07-3.15 (1H, m), 4.55-4.64 (1H, m), 6.72 (1H, s), 6.98-7.03 (1H, m), 7.07-7.13 (2H, m), 7.19-7.24 (3H, m), 7.25-7.34 (2H, m), 7.34-7.39 (2H, m), 7.47-7.54 (1H, m), 7.63-7.68 (1H, m), 7.76-7.83 (2H, m).<br>RT(min): 3.211 (Method A)<br>MS(ESI, m/z): 443.1875 (M + H)⁺ | Column: SiO2<br>EtOAc/MeOH |

TABLE 60

| Ex. No. | Strc. | P. D. | P. C. |
|---|---|---|---|
| 1-78 | (structure) | RT(min): 3.971 (Method A)<br>MS(ESI, m/z): 398.1660 (M + H)⁺ | Column: SiO2<br>EtOAc/n-Hexane |

TABLE 60-continued

| Ex. No. | Strc. | P. D. | P. C. |
|---|---|---|---|
| 1-79 | (structure) | $^1$H-NMR(CDCl$_3$) δ ppm: 1.64 (3H, s), 3.32 (1H, d, J = 13.6 Hz), 3.49 (1H, d, J = 3.4, 13.6 Hz), 5.91-6.37 (2H, m), 6.73 (1H, s), 7.04-7.16 (4H, m), 7.18-7.24 (3H, m), 7.32-7.38 (2H, m), 7.45-7.53 (1H, m), 7.60-7.66 (1H, m), 7.66-7.73 (2H, m).<br>RT(min): 3.710 (Method A)<br>MS(ESI, m/z): 443.1875 (M + H)$^+$ | Column: APS<br>EtOAc/n-Hexane |
| 1-80 | (structure) | RT(min): 1.916 (Method A)<br>MS(ESI, m/z): 413.1605 (M + H)$^+$ | Column: SiO2<br>EtOAc/MeOH |
| 1-81 | (structure) | $^1$H-NMR(CDCl$_3$) δ ppm: 2.85-3.02 (2H, m), 3.63 (1H, dd, J = 5.6, 11.4 Hz), 3.86 (1H, dd, J = 3.7, 11.4 Hz), 4.34-4.47 (1H, m), 6.11-6.22 (1H, m), 6.78 (1H, s), 6.98-7.11 (2H, m), 7.16-7.24 (2H, m), 7.30-7.51 (6H, m), 7.61-7.67 (1H, m), 7.67-7.75 (2H, m).<br>RT(min): 3.457 (Method A)<br>MS(ESI, m/z): 416.1765 (M + H)$^+$ | Column: SiO2<br>EtOAc/n-Hexane |
| 1-82 | (structure) | RT(min): 2.012 (Method A)<br>MS(ESI, m/z): 412.1566 (M + H)$^+$ | Column: SiO2<br>EtOAc/MeOH |

TABLE 60-continued

| Ex. No. | Strc. | P. D. | P. C. |
|---|---|---|---|
| 1-83 | | RT(min): 1.846 (Method A)<br>MS(ESI, m/z): 394.1659 (M + H)$^+$ | Column: SiO2<br>EtOAc/MeOH |
| 1-84 | | $^1$H-NMR(CDCl$_3$) δ ppm: 3.10 (1H, dd, J = 5.6 Hz, 14.2 Hz), 3.22 (1H, dd, J = 6.5 Hz, 14.2 Hz), 3.69 (1H, dd, J = 4.2 Hz, 11.7 Hz), 3.73 (1H, dd, J = 4.1 Hz, 11.6 Hz), 4.40-4.47 (1H, m), 6.81 (1H, d, J = 3.5 Hz), 6.97-7.01 (1H, m), 7.06-7.14 (4H, m), 7.16-7.37 (3H, m), 7.50 (1H, dt, J = 1.8 Hz, 7.7 Hz), 7.70-7.76 (2H, m), 8.36-8.40 (1H, m).<br>RT(min): 2.089 (Method A)<br>MS(ESI, m/z): 435.1625 (M + H)$^+$ | Column: SiO2<br>EtOAc/MeOH |

TABLE 61

| Ex. No. | Strc. | P. D. | P. C. |
|---|---|---|---|
| 1-85 | | $^1$H-NMR(CDCl$_3$) δ ppm: 3.15 (1H, dd, J = 4.8 Hz, 14.1 Hz), 3.32 (1H, dd, J = 6.9 Hz, 14.3 Hz), 3.72 (1H, dd, J = 4.2 Hz, 11.8 Hz), 3.81 (1H, dd, J = 3.7 Hz, 11.7 Hz), 4.42-4.51 (1H, m), 6.74 (1H, s), 6.96-7.01 (1H, m), 7.08-7.15 (2H, m), 7.35-7.45 (3H, m), 7.47-7.58 (3H, m), 7.60-7.68 (2H, m), 8.38-8.42 (1H, m).<br>RT(min): 2.390 (Method A)<br>MS(ESI, m/z): 451.1330 (M + H)$^+$ | Column: SiO2<br>EtOAc/MeOH |
| 1-86 | | $^1$H-NMR(CDCl$_3$) δ ppm: 2.85 (2H, d, J = 7.5 Hz), 3.50 (1H, dd, J = 5.8, 11.5 Hz), 3.86 (1H, dd, J = 3.7, 11.5 Hz), 4.33-4.46 (1H, m), 6.20 (1H, d, J = 8.6 Hz), 6.73 (1H, d, J = 3.0 Hz), 6.96-7.05 (2H, m), 7.05-7.10 (1H, m), 7.13-7.38 (7H, m), 7.48-7.57 (2H, m).<br>RT(min): 3.093 (Method A)<br>MS(ESI, m/z): 434.1673 (M + H)$^+$ | Column: SiO2<br>EtOAc/n-Hexane |

TABLE 61-continued

| Ex. No. | Strc. | P. D. | P. C. |
|---|---|---|---|
| 1-87 | | RT(min): 3.021 (Method A)<br>MS(ESI, m/z): 428.1766 (M + H)⁺ | Column: APS<br>EtOAc/MeOH |
| 1-88<br>Ref | | RT(min): 2.671 (Method A)<br>MS(ESI, m/z): 517.2395 (M + H)⁺ | Column: APS<br>EtOAc/n-Hexane |
| 1-89 | | RT(min): 1.879 (Method A)<br>MS(ESI, m/z): 431.1875 (M + H)⁺ | Column: SiO2<br>EtOAc/MeOH |
| 1-90 | | RT(min): 2.669 (Method A)<br>MS(ESI, m/z): 521.2343 (M + H)⁺ | Column: APS<br>EtOAc/MeOH |

TABLE 61-continued

| Ex. No. | Strc. | P. D. | P. C. |
|---|---|---|---|
| 1-91 | | ¹H-NMR(CDCl₃) δ ppm: 3.15 (1H, dd, J = 5.1 Hz, 14.1 Hz), 3.30 (1H, dd, J = 6.9 Hz, 14.2 Hz), 3.72 (1H, dd, J = 4.1 Hz, 11.8 Hz), 3.79 (1H, dd, J = 3.8 Hz, 11.7 Hz), 3.96 (3H, s), 4.42-4.51 (1H, m), 6.72 (1H, s), 6.96-7.01 (1H, m), 7.08-7.15 (3H, m), 7.25-7.30 (1H, m), 7.34-7.39 (2H, m), 7.46-7.55 (3H, m), 7.63-7.67 (1H, m), 8.39-8.42 (1H, m).<br>RT(min): 1.805 (Method A)<br>MS(ESI, m/z): 447.1823 (M + H)⁺ | Column: SiO2<br>EtOAc/MeOH |

TABLE 62

| Ex. No. | Strc. | P. D. | P. C. |
|---|---|---|---|
| 1-92 | | RT(min): 1.764 (Method A)<br>MS(ESI, m/z): 447.1823 (M + H)⁺ | Column: SiO2<br>EtOAc/MeOH |
| 1-93 | | ¹H-NMR(CDCl₃) δ ppm: 2.87-2.98 (2H, m), 3.63 (1H, dd, J = 5.6 Hz, 11.4 Hz), 3.83 (1H, dd, J = 3.8 Hz, 11.4 Hz), 4.36-4.46 (1H, m), 6.19 (1H, d, J = 8.7 Hz), 6.72 (1H, s), 6.98-7.12 (4H, m), 7.15-7.25 (2H, m), 7.30-7.40 (2H, m), 7.46-7.52 (1H, m), 7.60-7.72 (3H, m).<br>RT(min): 3.088 (Method A)<br>MS(ESI, m/z): 434.1670 (M + H)⁺ | Column: SiO2<br>EtOAc/n-Hexane |
| 1-94 | | ¹H-NMR(CDCl₃) δ ppm: 3.15 (1H, dd, J = 5.8, 14.3 Hz), 3.27 (1H, dd, J = 6.8, 14.2 Hz), 3.73 (1H, dd, J = 3.9, 11.6 Hz), 3.78 (1H, dd, J = 4.0 Hz, 11.8 Hz), 4.48-4.66 (1H, m), 6.71 (1H, s), 6.99-7.17 (7H, m), 7.36-7.42 (2H, m), 7.49-7.55 (1H, m), 7.67-7.75 (2H, m), 8.37-8.41 (1H, m).<br>RT(min): 1.630 (Method A)<br>MS(ESI, m/z): 435.1626 (M + H)⁺ | Column: SiO2<br>EtOAc/MeOH |

TABLE 62-continued

| Ex. No. Strc. | P. D. | P. C. |
| --- | --- | --- |
| 1-95 | RT(min): 1.749 (Method A)<br>MS(ESI, m/z): 435.1625 (M + H)$^+$ | Column: SiO2<br>EtOAc/MeOH |
| 1-96 | RT(min): 1.850 (Method A)<br>MS(ESI, m/z): 435.1624 (M + H)$^+$ | Column: SiO2<br>EtOAc/MeOH |
| 1-97 | $^1$H-NMR(CDCl$_3$) δ ppm: 3.14 (1H, dd, J = 6.3, 14.2 Hz), 3.30 (1H, dd, J = 6.7, 14.2 Hz), 3.72 (1H, dd, J = 4.0, 11.7 Hz), 3.79 (1H, dd, J = 4.0, 11.7 Hz), 4.40-4.53 (1H, m), 7.06-7.20 (5H, m), 7.32-7.44 (2H, m), 7.47-7.58 (2H, m), 7.70-7.76 (1H, m), 7.79-7.88 (2H, m), 8.36-8.43 (1H, m).<br>RT(min): 1.888 (Method A)<br>MS(ESI, m/z): 435.1624 (M + H)$^+$ | Column: SiO2<br>EtOAc/MeOH |
| 1-98 | RT(min): 1.938 (Method A)<br>MS(ESI, m/z): 431.1873 (M + H)$^+$ | Column: SiO2<br>EtOAc/MeOH |

TABLE 63
| Ex. No. Strc. | | P. D. | P. C. |
|---|---|---|---|
| 1-99 | 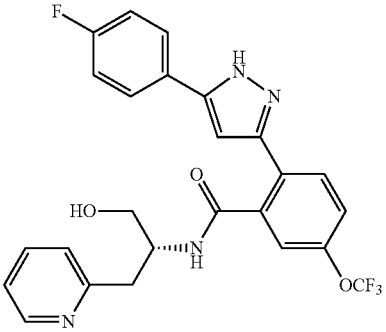 [SMILES: O=C(N[C@@H](CO)Cc1ccccn1)c1cc(OC(F)(F)F)ccc1-c1cc(-c2ccc(F)cc2)[nH]n1] | RT(min): 2.387 (Method A)<br>MS(ESI, m/z): 501.1541 (M + H)+ | Column: SiO2<br>EtOAc/MeOH |
| 1-100 | 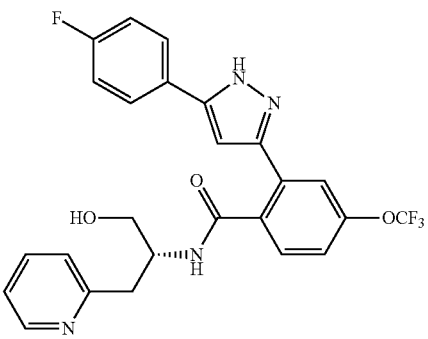 [SMILES: O=C(N[C@@H](CO)Cc1ccccn1)c1ccc(OC(F)(F)F)cc1-c1cc(-c2ccc(F)cc2)[nH]n1] | RT(min): 2.341 (Method A)<br>MS(ESI, m/z): 501.1540 (M + H)+ | Column: SiO2<br>EtOAc/MeOH |
| 1-101 | 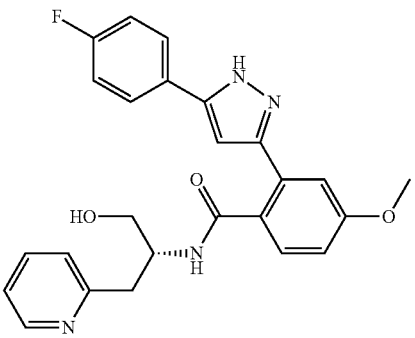 [SMILES: COc1ccc(C(=O)N[C@@H](CO)Cc2ccccn2)c(-c2cc(-c3ccc(F)cc3)[nH]n2)c1] | RT(min): 1.851 (Method A)<br>MS(ESI, m/z): 447.1823 (M + H)+ | Column: SiO2<br>EtOAc/MeOH |
| 1-102 | 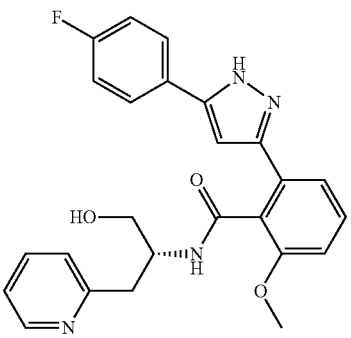 [SMILES: COc1cccc(-c2cc(-c3ccc(F)cc3)[nH]n2)c1C(=O)N[C@@H](CO)Cc1ccccn1] | RT(min): 1.625 (Method A)<br>MS(ESI, m/z): 447.1824 (M + H)+ | Column: SiO2<br>EtOAc/MeOH |

TABLE 63-continued

| Ex. No. | Strc. | P. D. | P. C. |
|---|---|---|---|
| 1-103 | (structure) | ¹H-NMR(CDCl₃) δ ppm: 2.97-3.07 (2H, m), 3.47 (1H, dd, J = 4.0, 11.7 Hz), 3.55 (1H), dd, J = 4.0, 11.7 Hz), 4.25-4.37 (1H, m ), 6.68 (1H, s), 7.01-7.11 (3H, m), 7.16 (1H, d, J = 7.8 Hz), 7.22-7.35 (3H, m), 7.48 (1H, dd, J = 2.1, 7.0 Hz), 7.53 (1H, td, J = 1.8 Hz, 7.7 Hz), 7.60-7.68 (2H, m), 8.33-8.39 (1H, m).<br>RT(min): 1.932 (Method A)<br>MS(ESI, m/z): 451.1329 (M + H)⁺ | Column: SiO2<br>EtOAc/MeOH |
| 1-104 | (structure) | ¹H-NMR(CDCl₃) δ ppm: 1.12 (3H, d, J = 6.4 Hz), 2.81 (1H, dd, J = 8.1 Hz, 13.9 Hz), 2.89 (1H, dd, J = 7.0 Hz, 13.9 Hz), 3.82-3.92 (1H, m), 3.69 (1H, dd, J = 4.2 Hz, 11.7 Hz), 4.14-4.24 (1H, m), 6.17 (1H, d, J = 9.4 Hz), 6.82 (1H, d, J = 3.4 Hz), 6.99 (1H, d, J = 7.2 Hz), 7.02-7.09 (2H, m), 7.15-7.35 (6H, m), 7.62-7.69 (2H, m).<br>RT(min): 3.194 (Method A)<br>MS(ESI, m/z): 448.1827 (M + H)⁺ | Column: SiO2<br>EtOAc/MeOH |
| 1-105 | (structure) | ¹H-NMR(CDCl₃) δ ppm: 3.04-3.21 (2H, m), 3.64 (1H, dd, J = 4.6, 11.7 Hz), 3.73 (1H, dd, J = 4.2, 11.7 Hz), 4.35-4.51 (1H, m), 7.00-7.11 (3H, m), 7.15 (1H, d, J = 7.9 Hz), 7.18-7.25 (2H, m), 7.34-7.41 (1H, m), 7.46 (1H, d, J = 7.9 Hz), 7.53 (1H, td, J = 1.8 Hz, 7.7 Hz), 7.62-7.72 (2H, m), 8.35-8.43 (1H, m).<br>RT(min): 1.986 (Method A)<br>MS(ESI, m/z): 453.1530 (M + H)⁺ | Column: SiO2<br>EtOAc/MeOH |

TABLE 64

| Ex. No. | Strc. | P. D. | P. C. |
|---|---|---|---|
| 1-106 | (structure) | ¹H-NMR(CDCl₃) δ ppm: 1.17 (3H, d, J = 6.6 Hz), 2.71 (1H, dd, J = 10.4, 14.4 Hz), 2.96 (1H, dd, J = 5.2, 14.4 Hz), 4.09-4.19 (1H, m), 4.35-4.46 (1H, m), 6.05 (1H, d, J = 8.7 Hz), 6.78 (1H, d, J = 3.21 Hz), 6.84-6.90 (1H, m), 7.01-7.11 (2H, m), 7.13-7.24 (4H, m), 7.24-7.33 (3H, m), 7.57-7.66 (2H, m).<br>RT(min): 3.167 (Method A)<br>MS(ESI, m/z): 448.1827 (M + H)⁺ | Column: SiO2<br>EtOAc/n-Hexane |

TABLE 64-continued

| Ex. No. | Strc. | P. D. | P. C. |
|---|---|---|---|
| 1-107 | 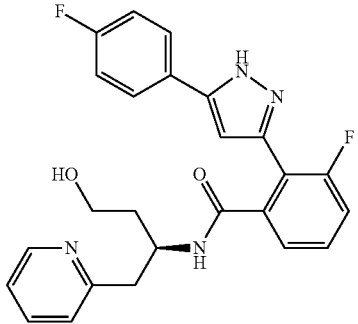 [SMILES: O=C(N[C@H](CCO)Cc1ccccn1)c1cccc(F)c1-c1cc(-c2ccc(F)cc2)[nH]n1] | RT(min): 1.764 (Method A)<br>MS(ESI, m/z): 449.1780 (M + H)+ | Column: APS<br>EtOAc/MeOH |
| 1-108 | 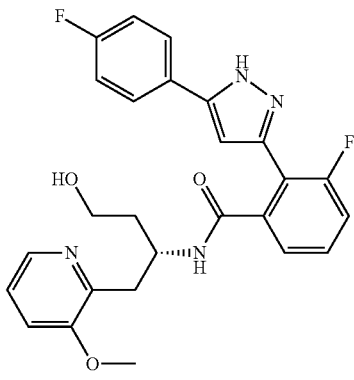 [SMILES: COc1cccnc1C[C@H](CCO)NC(=O)c1cccc(F)c1-c1cc(-c2ccc(F)cc2)[nH]n1] | ¹H-NMR(CDCl₃) δ ppm: 1.40-1.55 (1H, m), 1.83-1.94 (1H, m), 2.98-3.11 (2H, m), 3.57-3.70(2H, m), 3.79 (3H, s), 4.59-4.73 (1H, m), 6.80 (1H, d, J = 3.3 Hz), 7.03-7.06 (2H, m), 7.06-7.13 (2H, m), 7.20-7.30 (2H, m), 7.33-7.40 (1H, m), 7.41-7.46 (1H, m), 7.69-7.78 (2H, m), 7.94-7.99 (1H, m).<br>RT(min): 1.870 (Method A)<br>MS(ESI, m/z): 479.1887(M + H)+ | Column: APS<br>EtOAc/MeOH |
| 1-109 | 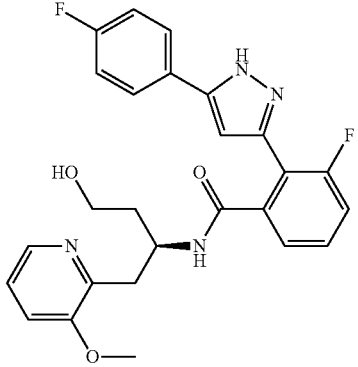 [SMILES: COc1cccnc1C[C@@H](CCO)NC(=O)c1cccc(F)c1-c1cc(-c2ccc(F)cc2)[nH]n1] | RT(min): 1.877 (Method A)<br>MS(ESI, m/z): 479.1884(M + H)+ | Column: APS<br>EtOAc/MeOH |
| 1-110 | 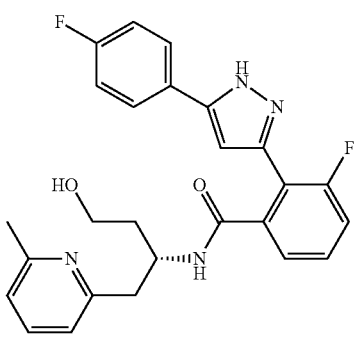 [SMILES: Cc1cccc(C[C@H](CCO)NC(=O)c2cccc(F)c2-c2cc(-c3ccc(F)cc3)[nH]n2)n1] | ¹H-NMR(CDCl₃) δ ppm: 1.36-1.48 (1H, m), 1.76-1.88 (1H, m), 2.38 (3H, s), 2.85 (1H, dd, J = 6.0, 14.3 Hz), 3.10 (1H, dd, J = 4.7, 14.3 Hz), 3.56-3.70 (2H, m), 4.53-4.66 (1H, m), 6.84 (1H, d, J = 3.5 Hz), 6.95 (1H, d, J = 7.7 Hz), 7.05-7.14 (2H, m), 7.24-7.35 (3H, m), 7.36-7.43 (1H, m), 7.47 (1H, t, J = 7.7 Hz), 7.70-7.79 (2H, m), 8.09 (1H, d, J = 7.7 Hz).<br>RT(min): 1.841 (Method A)<br>MS(ESI, m/z): 463.1938 (M + H)+ | Column: APS<br>EtOAc/MeOH |

TABLE 64-continued

| Ex. No. | Strc. | P. D. | P. C. |
|---|---|---|---|
| 1-111 | 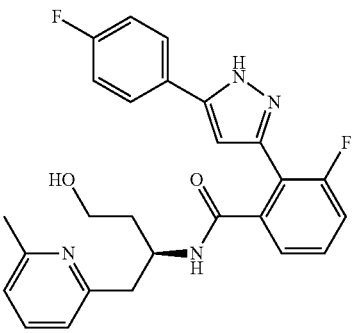 [SMILES: Cc1cccc(C[C@@H](CCO)NC(=O)c2cccc(F)c2-c2cc(-c3ccc(F)cc3)[nH]n2)n1] | RT(min): 1.816 (Method A)<br>MS(ESI, m/z): 463.1937 (M + H)⁺ | Column: APS<br>EtOAc/MeOH |
| 1-112 | 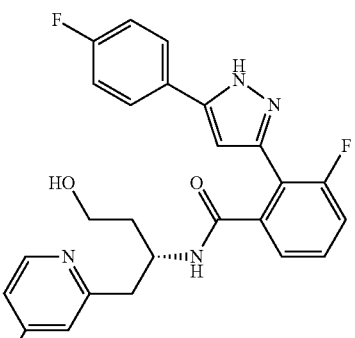 | ¹H-NMR(CDCl₃) δ ppm: 1.35-1.46 (1H, m), 1.70-1.84 (1H, m), 2.26 (3H, s), 2.83 (1H, dd, J = 6.0, 14.4 Hz), 3.05 (1H, dd, J = 4.8, 14.4 Hz), 3.54-3.67 (2H, m), 4.51-4.64 (1H, m), 6.79 (1H, d, J = 3.0 Hz), 6.89-6.90 (1H, m), 6.91 (1H, s), 7.03-7.11 (2H, m), 7.20-7.33 (2H, m), 7.33-7.42 (1H, m), 7.66-7.75 (2H, m), 7.91 (1H, d, J = 8.4 Hz), 8.20 (1H, d, J = 5.1 Hz).<br>RT(min): 1.854 (Method A)<br>MS(ESI, m/z): 463.1938 (M + H)⁺ | Column: APS<br>EtOAc/MeOH |

TABLE 65

| Ex. No. | Strc. | P. D. | P. C. |
|---|---|---|---|
| 1-113 | 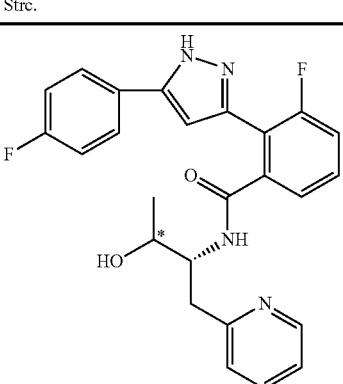 | ¹H-NMR(CDCl₃) δ ppm: 1.27 (3H, d, J = 6.9 Hz), 3.17 (1H, dd, J = 5.7 Hz, 14.7 Hz), 3.24 (1H, dd, J = 5.2 Hz, 14.7 Hz), 3.88-3.95 (1H, m), 4.29-3.37 (1H, m), 6.75-6.78 (1H, m), 6.88 (1H, d, J = 8.2 Hz), 7.00-7.07 (3H, m), 7.08-7.14 (2H, m), 7.18 (1H, ddd, J = 1.3 Hz, 8.3 Hz, 9.9 Hz), 7.24-7.32 (1H, m), 7.42 (1H, dt, J = 1.8 Hz, 7.8 Hz), 7.71-7.78 (2H, m), 8.32-8.36 (1H, m).<br>RT(min): 1.824 (Method A)<br>MS(ESI, m/z): 449.1782 (M + H)⁺ | Column: SiO2<br>EtOAc/MeOH |
| 1-114 | 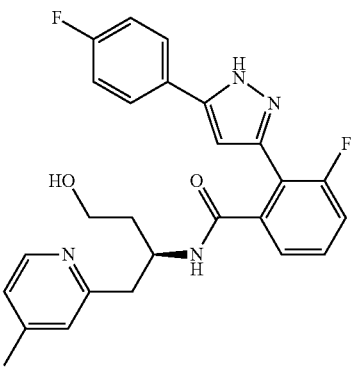 [SMILES: Cc1ccnc(C[C@H](CCO)NC(=O)c2cccc(F)c2-c2cc(-c3ccc(F)cc3)[nH]n2)c1] | RT(min): 1.834 (Method A)<br>MS(ESI, m/z): 463.1937 (M + H)⁺ | Column: APS<br>EtOAc/MeOH |

TABLE 65-continued

| Ex. No. Strc. | P. D. | P. C. |
|---|---|---|
| 1-115 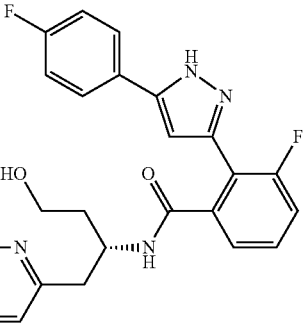 | RT(min): 1.870 (Method A)<br>MS(ESI, m/z): 463.1937 (M + H)⁺ | Column: APS<br>EtOAc/MeOH |
| 1-116 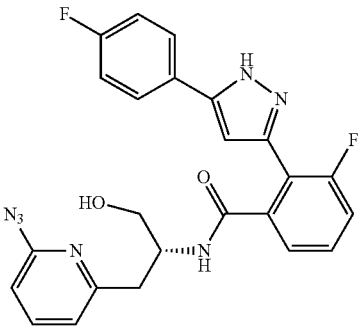 [SMILES: [N-]=[N+]=Nc1cccc(C[C@H](CO)NC(=O)c2cccc(F)c2-c2cc(-c3ccc(F)cc3)[nH]n2)n1] | RT(min): 2.400 (Method A)<br>MS(ESI, m/z): 476.1638 (M + H)⁺ | Column: APS<br>EtOAc/MeOH |
| 1-117 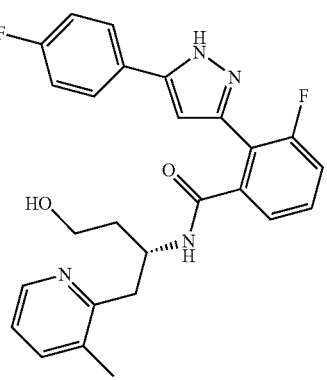 | $^1$H-NMR(CDCl$_3$) δ ppm: 1.47-1.59 (1H, m), 1.76-1.87 (1H, m), 2.26 (3H, s), 2.95-3.03 (2H, m), 3.57-3.66 (2H, m), 4.57-4.66 (1H, m), 6.78 (1H, d, J = 3.1 Hz), 6.99 (1H, dd, J = 4.9, 7.6 Hz), 7.04-7.12 (2H, m), 7.22-7.31 (2H, m), 7.33-7.42 (2H, m), 7.65-7.76 (2H, m), 8.00 (1H, d, J = 8.3 Hz), 8.16-8.22 (1H, m).<br>RT(min): 1.841 (Method A)<br>MS(ESI, m/z): 463.1937 (M + H)⁺ | Column: APS<br>EtOAc/MeOH |
| 1-118 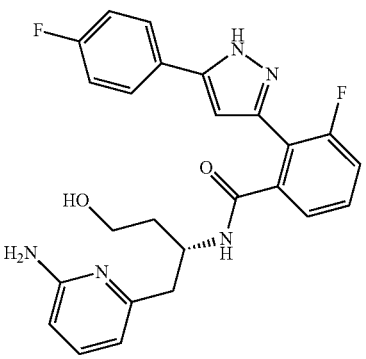 [SMILES: Nc1cccc(C[C@H](CCO)NC(=O)c2cccc(F)c2-c2cc(-c3ccc(F)cc3)[nH]n2)n1] | $^1$H-NMR(CDCl$_3$) δ ppm: 1.27-1.40 (1H, m), 1.70-1.83 (1H, m), 2.69 (1H, dd, J = 5.6, 14.3 Hz), 2.92 (1H, dd, J = 4.7, 14.3 Hz), 3.48-3.70 (2H, m), 4.30-4.68 (3H, m), 6.32 (1H, d, J = 8.2 Hz), 6.46 (1H, d, J = 7.2 Hz), 6.82 (1H, d, J = 3.0 Hz), 7.04-7.15 (2H, m), 7.24-7.45 (4H, m), 7.65-7.74 (2H, m), 7.96-8.04 (1H, m).<br>RT(min): 1.790 (Method A)<br>MS(ESI, m/z): 464.1888 (M + H)⁺ | Column: APS<br>EtOAc/MeOH |

TABLE 65-continued
| Ex. No. | Strc. | P. D. | P. C. |
|---|---|---|---|
| 1-119 | 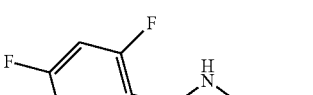 | RT(min): 1.976 (Method A)<br>MS(ESI, m/z): 423.1424 (M + H)+ | Column: SiO2<br>EtOAc/MeOH |
TABLE 66
| Ex. No. | Strc. | P. D. | P. C. |
|---|---|---|---|
| 1-120 | 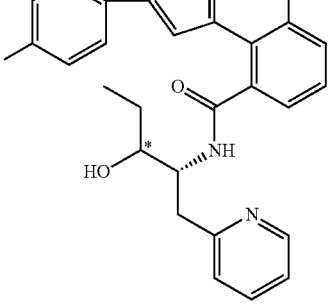 | RT(min): 1.959 (Method A)<br>MS(ESI, m/z): 463.1938 (M + H)+ | Column: SiO2<br>EtOAc/MeOH |
| 1-121 | 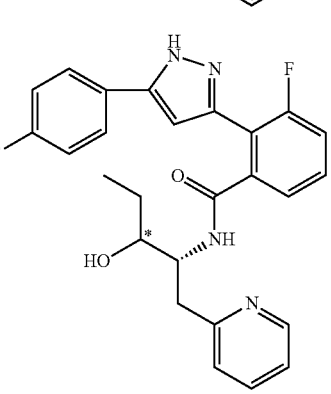 | RT(min): 1.969 (Method A)<br>MS(ESI, m/z): 463.1938 (M + H)+ | Column: SiO2<br>EtOAc/MeOH |
| 1-122 | 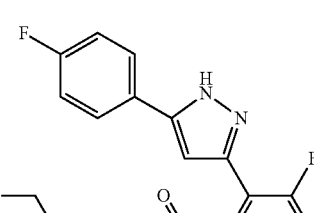 | RT(min): 1.767 (Method A)<br>MS(ESI, m/z): 463.1937 (M + H)+ | Column: SiO2<br>EtOAc/MeOH |

TABLE 66-continued

| Ex. No. Strc. | P. D. | P. C. |
|---|---|---|
| 1-123 | ¹H-NMR(CDCl₃) δ ppm: 1.36-1.46 (1H, m), 1.71-1.86 (1H, m), 2.83 (1H, dd, J = 5.9, 14.4 Hz), 3.08 (1H, dd, J = 4.6, 14.4 Hz), 3.52-3.68 (2H, m), 3.78 (3H, s), 4.57-4.69 (1H, m), 6.55-6.63 (1H, m), 6.63-6.67 (1H, m), 6.82 (1H, d, J = 3.2 Hz), 7.05-7.12 (3H, m), 7.25-7.43 (2H, m), 7.68-7.77 (2H, m), 7.93-8.03 (1H, m), 8.18 (1H, d, J = 5.9 Hz).<br>RT(min): 1.851 (Method A)<br>MS(ESI, m/z): 479.1885 (M + H)⁺ | Column: APS EtOAc/MeOH |
| 1-124 | ¹H-NMR(CDCl₃) δ ppm: 1.13 (3H, d, J = 6.3 Hz), 3.08 (1H, dd, J = 5.2 Hz, 14.2 Hz), 3.24 (1H, dd, J = 7.2 Hz, 14.4 Hz), 3.92-4.00 (1H, m), 4.22-4.30 (1H, m), 6.77 (1H, d, J = 3.5 Hz), 6.85-6.93 (1H, m), 7.02-7.12 (4H, m), 7.13-7.22 (2H, m), 7.25-7.33 (1H, m), 7.42-7.50 (1H, m), 7.70-7.76 (2H, m), 8.30-8.35 (1H, m).<br>RT(min): 1.847 (Method A)<br>MS(ESI, m/z): 449.1777 (M + H)⁺ | Column: SiO2 EtOAc/MeOH |
| 1-125 | ¹H-NMR(CDCl₃) δ ppm: 1.41-1.52 (1H, m), 1.80-1.94 (1H, m), 3.00-3.18 (2H, m), 3.57-3.72 (2H, m), 4.64-4.79 (1H, m), 6.83 (1H, d, J = 3.3 Hz), 7.05-7.15 (3H, m), 7.25-7.36 (4H, m), 7.36-7.44 (1H, m), 7.67-7.78 (2H, m), 8.18-8.25 (1H, m).<br>RT(min): 2.575 (Method A)<br>MS(ESI, m/z): 467.1686 (M + H)⁺ | Column: APS EtOAc/MeOH |
| 1-126 | ¹H-NMR(CDCl₃) δ ppm: 1.07 (3H, d, J = 6.2 Hz), 1.28-1.37 (1H, m), 1.46-1.55 (1H, m), 2.86 (1H, dd, J = 6.0, 14.6 Hz), 3.08 (1H, dd, J = 4.5, 14.6 Hz), 3.65-3.75 (1H, m), 4.57-4.70 (1H, m), 6.80 (1H, d, J = 3.0 Hz), 7.04-7.16 (4H, m), 7.24-7.33 (2H, m), 7.35-7.44 (1H, m), 7.56 (1H, td, J = 1.9, 7.7 Hz), 7.68-7.76 (2H, m), 7.96 (1H, d, J = 8.2 Hz), 8.33-8.40 (1H, m).<br>RT(min): 1.896 (Method A)<br>MS(ESI, m/z): 463.1937 (M + H)⁺ | Column: APS EtOAc/MeOH |

TABLE 67

| Ex. No. | Strc. | P. D. | P. C. |
|---|---|---|---|
| 1-127 | | RT (min): 1.831 (Method A)<br>MS (ESI, m/z): 463.1938 (M + H)⁺ | Column: APS<br>EtOAc/MeOH |
| 1-128 | | ¹H-NMR (DMSO-d₆) δ ppm: 2.15-2.35 (2H, m), 2.65-2.80 (2H, m), 4.23-4.38 (1H, m), 6.70-6.90 (2H, m), 7.00-7.60 (11H, m), 7.77-7.86 (2H, m).<br>RT (min): 2.855 (Method A)<br>MS (ESI, m/z): 461.1782 (M + H)⁺ | Column: SiO2<br>EtOAc/MeOH |
| 1-129 | | RT (min): 2.567 (Method A)<br>MS (ESI, m/z): 496.1548 (M + H)⁺ | Column: SiO2<br>EtOAc/MeOH |
| 1-130 | | ¹H-NMR (CDCl₃) δ ppm: 1.18 (3H, d, J = 6.3 Hz), 1.54-1.62 (2H, m), 2.88-2.97 (1H, m), 3.15 (1H, dd, J = 4.7 Hz, 14.4 Hz), 3.90-3.97 (2H, m), 4.52-4.60 (1H, m), 6.83-6.87 (1H, m), 7.03-7.15 (4H, m), 7.20-7.32 (2H, m), 7.34-7.40 (2H, m), 7.52-7.60 (1H, m), 7.70-7.80 (2H, m), 8.35-8.40 (1H, m).<br>RT (min): 1.804 (Method A)<br>MS (ESI, m/z): 463.1936 (M + H)⁺ | Column: SiO2<br>EtOAc/MeOH |

TABLE 67-continued

| Ex. No. | Strc. | P. D. | P. C. |
|---|---|---|---|
| 1-131 | | ¹H-NMR (CDCl₃) δ ppm: 1.35-1.46 (1H, m), 1.74-1.89 (1H, m), 2.90 (1H, dd, J = 6.0, 14.4 Hz), 3.13 (1H, dd, J = 4.6, 14.4 Hz), 3.56-3.70 (2H, m), 4.55-4.71 (1H, m), 6.87 (1H, d, J = 3.4 Hz), 7.05-7.10 (1H, m), 7.11-7.16 (1H, m), 7.24-7.34 (2H, m), 7.35-7.44 (3H, m), 7.57 (1H, td, J = 1.9, 7.7 Hz), 7.68-7.73 (2H, m), 7.77-7.83 (1H, m), 8.35-8.40 (1H, m).<br>RT (min): 2.045 (Method A)<br>MS (ESI, m/z): 465.1484 (M + H)⁺ | Column: APS EtOAc/MeOH |
| 1-132 | | ¹H-NMR (CDCl₃) δ ppm: 1.31-1.43 (1H, m), 1.74-1.88 (1H, m), 2.80 (1H, dd, J = 5.3, 14.3 Hz), 3.01 (1H, dd, J = 4.8, 14.3 Hz), 3.51-3.67 (5H, m), 4.56-4.70 (1H, m), 6.56 (1H, d, J = 8.4 Hz), 6.69 (1H, d, J = 7.1 Hz), 6.85 (1H, d, J = 3.4 Hz), 7.06-7.13 (2H, m), 7.25-7.32 (2H, m), 7.35-7.42 (1H, m), 7.45 (1H, dd, J = 7.1, 8.4 Hz), 7.69-7.77 (2H, m), 8.05-8.14 (1H, m).<br>RT (min): 2.786 (Method A)<br>MS (ESI, m/z): 479.1887 (M + H)⁺ | Column: APS EtOAc/MeOH |
| 1-133 | | RT (min): 2.661 (Method A)<br>MS (ESI, m/z): 384.1702 (M + H)⁺ | Column: APS EtOAc/MeOH |

TABLE 68

| Ex. No. | Strc. | P. D. | P. C. |
|---|---|---|---|
| 1-134 | | ¹H-NMR (CDCl₃) δ ppm: 1.29-1.38 (1H, m), 1.69-1.80 (1H, m), 2.82-2.90 (1H, m), 3.06 (1H, dd, J = 4.8 Hz, 14.4 Hz), 3.50-3.63 (2H, m), 6.72 (1H, s), 7.08-7.14 (4H, m), 7.43-7.50 (3H, m), 7.52-7.59 (1H, m), 7.62-7.70 (2H, m), 8.36-8.42 (1H, m).<br>RT (min): 2.218 (Method A)<br>MS (ESI, m/z): 515.1697 (M + H)⁺ | Column: SiO2 EtOAc/MeOH |

TABLE 68-continued

| Ex. No. | Strc. | P. D. | P. C. |
|---|---|---|---|
| 1-135 | | RT (min): 3.084 (Method A)<br>MS (ESI, m/z): 396.1703 (M + H)⁺ | Column: APS<br>EtOAc/n-Hexane |
| 1-136 | | RT (min): 2.752 (Method A)<br>MS (ESI, m/z): 501.1301 (M + H)⁺ | Column: SiO2<br>EtOAc/MeOH |
| 1-137 | | ¹H-NMR (CDCl₃) δ ppm: 3.10 (1H, dd, J = 5.4, 14.3 Hz), 3.22 (1H, dd, J = 6.7, 14.3 Hz), 3.63-3.77 (2H, m), 4.38-4.48 (1H, m), 6.82 (1H, d, J = 3.4 Hz), 7.00-7.14 (3H, m), 7.16-7.28 (2H, m), 7.29-7.40 (3H, m), 7.49 (1H, td, J = 1.9, 7.7 Hz), 7.65-7.72 (2H, m), 8.34-8.41 (1H, m).<br>RT (min): 2.038 (Method A)<br>MS (ESI, m/z): 451.1328 (M + H)⁺ | Column: APS<br>EtOAc/MeOH |
| 1-138 | | ¹H-NMR (CDCl₃) δ ppm: 1.08-1.18 (1H, m), 1.26 (3H, d, J = 7.0 Hz), 1.66-1.78 (1H, m), 2.94-3.05 (1H, m), 3.47-3.62 (2H, m), 4.43-4.54 (1H, m), 6.88 (1H, d, J = 3.4 Hz), 7.03-7.13 (4H, m), 7.26-7.34 (1H, m), 7.36-7.47 (2H, m), 7.57 (1H, td, J = 1.9, 7.7 Hz), 7.69-7.77 (2H, m), 8.32-8.37 (1H, m), 8.68 (1H, d, J = 8.4 Hz).<br>RT (min): 1.919 (Method A)<br>MS (ESI, m/z): 463.1937 (M + H)⁺ | Column: APS<br>EtOAc/MeOH |

TABLE 68-continued

| Ex. No. | Strc. | P. D. | P. C. |
|---|---|---|---|
| 1-139 | | $^1$H-NMR (CDCl$_3$) δ ppm: 3.13 (1H, dd, J = 5.8, 14.3 Hz), 3.26 (1H, dd, J = 7.2, 14.0 Hz), 3.49 (1H, dd, J = 6.0, 12.0 Hz), 3.56 (1H, dd, J = 6.2, 11.6 Hz), 3.80-3.87 (1H, m), 4.50-4.59 (1H, m), 6.74 (1H, d, J = 3.0 Hz), 6.95-7.02 (1H, m), 7.04-7.17 (5H, m), 7.17-7.36 (2H, m), 7.49-7.56 (1H, m), 7.64-7.71 (2H, m), 8.35-8.39 (1H, m).<br>RT (min): 1.699 (Method A)<br>MS (ESI, m/z): 465.1730 (M + H)$^+$ | Column: SiO2<br>EtOAc/MeOH |
| 1-140 | | RT (min): 2.456 (Method A)<br>MS (ESI, m/z): 406.1471 (M + H)$^+$ | Column: APS<br>EtOAc/MeOH |

TABLE 69

| Ex. No. | Strc. | P. D. | P. C. |
|---|---|---|---|
| 1-141 | | RT (min): 2.001 (Method A)<br>MS (ESI, m/z): 463.1937 (M + H)$^+$ | Column: APS<br>EtOAc/MeOH |
| 1-142 | | RT (min): 1.969 (Method A)<br>MS (ESI, m/z): 463.1936 (M + H)$^+$ | Column: APS<br>EtOAc/MeOH |

TABLE 69-continued

| Ex. No. | Strc. | P. D. | P. C. |
|---|---|---|---|
| 1-143 | | RT (min): 2.083 (Method A)<br>MS (ESI, m/z): 463.1937 (M + H)⁺ | Column: APS<br>EtOAc/MeOH |
| 1-144 | | RT (min): 2.936 (Method A)<br>MS (ESI, m/z): 485.15911 (M + H)⁺ | Column: SiO2<br>EtOAc/MeOH |
| 1-145 | | RT (min): 2.690 (Method A)<br>MS (ESI, m/z): 412.1766 (M + H)⁺ | Column: SiO2<br>EtOAc/MeOH |
| 1-146 | | RT (min): 2.774 (Method A)<br>MS (ESI, m/z): 399.1813 (M + H)⁺ | Column: SiO2<br>EtOAc/MeOH |

TABLE 69-continued

| Ex. No. | Strc. | P. D. | P. C. |
|---|---|---|---|
| 1-147 | | RT (min): 2.222 (Method A)<br>MS (ESI, m/z): 479.1886 (M + H)⁺ | Column: SiO2<br>EtOAc/MeOH |

TABLE 70

| Ex. No. | Strc. | P. D. | P. C. |
|---|---|---|---|
| 1-148 | | ¹H-NMR (CDCl₃) δ ppm: 3.13 (1H, dd, J = 5.9, 14.8 Hz), 3.26 (1H, dd, J = 6.7, 14.7 Hz), 3.51 (1H, dd, J = 6.0, 11.1 Hz), 3.57 (1H, dd, J = 6.2, 11.6 Hz), 3.81-3.86 (1H, m), 4.50-4.58 (1H, m), 6.77 (1H, d, J = 3.2 Hz), 6.96-7.02 (1H, m), 7.07-7.16 (3H, m), 7.17-7.24 (1H, m), 7.28-7.38 (3H, m), 7.52 (1H, dt, J = 1.8, 7.8 Hz), 7.62-7.68 (2H, m), 8.35-8.39 (1H, m).<br>RT (min): 1.976 (Method A)<br>MS (ESI, m/z): 481.1435 (M + H)⁺ | Column: SiO2<br>EtOAc/MeOH |
| 1-149 | | RT (min): 2.015 (Method A)<br>MS (ESI, m/z): 477.2092 (M + H)⁺ | Column: SiO2<br>EtOAc/MeOH |
| 1-150 | | RT (min): 1.845 (Method A)<br>MS (ESI, m/z): 503.2087 (M + H)⁺ | Column: SiO2<br>EtOAc/MeOH |

TABLE 70-continued

| Ex. No. | Strc. | P. D. | P. C. |
|---|---|---|---|
| 1-151 | | RT (min): 2.194 (Method A)<br>MS (ESI, m/z): 493.2042 (M + H)+ | Column: SiO2<br>EtOAc/MeOH |
| 1-152 | | RT (min): 2.168 (Method A)<br>MS (ESI, m/z): 493.2045 (M + H)+ | Column: SiO2<br>EtOAc/MeOH |
| 1-153 | | RT (min): 1.993 (Method A)<br>MS (ESI, m/z): 463.1938 (M + H)+ | Column: APS<br>EtOAc/MeOH |
| 1-154 | | $^1$H-NMR (CDCl$_3$) δ ppm: 1.35-1.46 (1H, m), 1.73-1.85 (1H, m), 2.89 (1H, dd, J = 5.8, 14.5 Hz), 3.14 (1H, dd, J = 4.4, 14.5 Hz), 3.52-3.71 (2H, m), 4.52-4.69 (1H, m), 7.03-7.09 (1H, m), 7.12 (1H, d, J = 7.7 Hz), 7.25-7.34 (1H, m), 7.35-7.42 (3H, m), 7.43-7.50 (1H, m), 7.56 (1H, td, J = 1.8, 7.7 Hz), 7.71-7.77 (2H, m), 7.89-7.98 (1H, m), 8.35-8.40 (1H, m).<br>RT (min): 2.221 (Method A)<br>MS (ESI, m/z): 483.1391 (M + H)+ | Filtration of EtOAc/n-Hexane suspension |

TABLE 71

| Ex. No. | Strc. | P. D. | P. C. |
|---|---|---|---|
| 1-155 | | ¹H-NMR (CDCl₃) δ ppm: 3.11 (1H, dd, J = 5.3, 14.5 Hz), 3.24 (1H, dd, J = 6.1, 14.5 Hz), 3.73 (2H, d, J = 4.2 Hz), 4.36-4.47 (1H, m), 7.05-7.17 (3H, m), 7.20-7.32 (2H, m), 7.34-7.44 (3H, m), 7.49 (1H, td, J = 1.8, 7.7 Hz), 7.72-7.79 (2H, m), 8.35-8.43 (1H, m).<br>RT (min): 2.240 (Method A)<br>MS (ESI, m/z): 469.1235 (M + H)⁺ | Filtration of EtOAc/n-Hexane suspension |
| 1-156 | | ¹H-NMR (CDCl₃) δ ppm: 3.10-3.20 (1H, m), 3.21-3.31 (1H, m), 3.50-3.65 (2H, m), 3.78-3.89 (1H, m), 4.44-4.61 (1H, m), 7.02-7.28 (7H, m), 7.3-7.43 (1H, m), 7.48-7.57 (1H, m), 7.68-7.80 (2H, m), 8.31-8.40 (1H, m).<br>RT (min): 1.941 (Method A)<br>MS (ESI, m/z): 483.1636 (M + H)⁺ | Column: SiO2 EtOAc/MeOH |
| 1-157 | | RT (min): 2.149 (Method A)<br>MS (ESI, m/z): 531.1646 (M + H)⁺ | Column: SiO2 EtOAc/MeOH |
| 1-158 | | ¹H-NMR (CDCl₃) δ ppm: 1.65 (3H, s), 3.35 (3H, s), 3.40-3.47 (1H, m), 3.78 (1H, dd, J = 4.0, 11.5 Hz), 4.59-4.67 (1H, m), 6.84 (1H, d, J = 3.7 Hz), 7.03-7.10 (3H, m), 7.20-7.32 (2H, m), 7.35-7.42 (1H, m), 7.43-7.48 (1H, m), 7.53-7.69 (4H, m), 8.39-8.42 (1H, m).<br>Rt (min): 2.254 (Method A)<br>MS (ESI, m/z): 479.1890 (M + H)⁺ | Column: SiO2 EtOAc/MeOH |

TABLE 71-continued

| Ex. No. | Strc. | P. D. | P. C. |
| --- | --- | --- | --- |
| 1-159 | | RT (min): 2.460 (Method A)<br>MS (ESI, m/z): 495.1596 (M + H)⁺ | Column: SiO2<br>EtOAc/MeOH |
| 1-160 | | ¹H-NMR (CDCl₃) δ ppm: 0.73 (3H, s), 1.10 (3H, s), 2.82 (1H, dd, J = 10.4, 14.2 Hz), 3.10-3.18 (2H, m), 3.48 (1H, d, J = 11.7 Hz), 4.35-4.43 (1H, m), 6.79 (1H, d, J = 3.5 Hz), 6.94-7.02 (2H, m), 7.11 (1H, d, J = 7.4 Hz), 7.17-7.26 (2H, m), 7.30-7.37 (1H, m), 7.38-7.43 (2H, m), 7.48-7.54 (1H, m), 7.70-7.77 (2H, m), 8.27-8.31 (1H, m).<br>RT (min): 2.251 (Method A)<br>MS (ESI, m/z): 493.1799 (M + H)⁺ | Column: SiO2<br>EtOAc/MeOH |
| 1-161 | | ¹H-NMR (CDCl₃) δ ppm: 0.71 (3H, s), 1.10 (3H, s), 2.82 (1H, dd, J = 10.4, 14.2 Hz), 3.12 (1H, d, J = 12.0 Hz), 3.16 (1H, dd, J = 3.5, 14.0 Hz), 3.48 (1H, d, J = 11.6 Hz), 4.36-4.44 (1H, m), 6.75 (1H, d, J = 3.2 Hz), 6.95-7.02 (2H, m), 7.08-7.15 (3H, m), 7.18-7.25 (2H, m), 7.26-7.36 (2H, m), 7.52 (1H, dt, J = 1.7, 7.7 Hz), 7.72-7.79 (2H, m), 8.28-8.32 (1H, m).<br>RT (min): 1.987 (Method A)<br>MS (ESI, m/z): 477.2095 (M + H)⁺ | Column: SiO2<br>EtOAc/MeOH |

TABLE 72

| Ex. No. | Strc. | P. D. | P. C. |
| --- | --- | --- | --- |
| 1-162 | | RT (min): 2.135 (Method A)<br>MS (ESI, m/z): 479.1642 (M + H)⁺ | Column: SiO2<br>EtOAc/MeOH |

TABLE 72-continued

| Ex. No. | Strc. | P. D. | P. C. |
|---|---|---|---|
| 1-163 | | ¹H-NMR (DMSO-d₆) δ ppm: 2.90-3.13 (1H, m), 3.15-3.41 (1H, m), 4.62-4.83 (1H, m), 6.75-7.87 (13H, m), 8.44-8.53 (1H, m), 8.60-8.86 (1H, m), 13.0-13.6 (1H, m). RT (min): 2.211 (Method A) MS (ESI, m/z): 464.1278 (M + H)⁺ | Filtration of EtOAc/n-Hexane suspension |
| 1-164 | | RT (min): 1.963 (Method A) MS (ESI, m/z): 463.1939 (M + H)⁺ | Column: SiO2 EtOAc/MeOH |
| 1-165 | | RT (min): 1.995 (Method A) MS (ESI, m/z): 437.2344 (M + H)⁺ | Column: SiO2 EtOAc/MeOH |
| 1-166 | | ¹H-NMR (CDCl₃) δ ppm: 1.12-2.05 (10H, m), 2.60-2.60 (1H, m), 3.07 (1H, dd, J = 6.5, 14.01 Hz), 3.15 (1H, dd, J = 7.4, 14.1 Hz), 3.41 (1H, dd, J = 6.7, 11.7 Hz), 3.53 (1H, dd, J = 6.0, 11.9 Hz), 3.70-3.76 (1H, m), 4.45-4.55 (1H, m), 6.30 (1H, d, J = 2.7 Hz), 7.02-7.34 (6H, m), 7.60-7.67 (1H, m), 8.43-8.47 (1H, m). RT (min): 1.901 (Method A) MS (ESI, m/z): 453.2290 (M + H)⁺ | Column: SiO2 EtOAc/MeOH |

TABLE 72-continued

| Ex. No. | Strc. | P. D. | P. C. |
|---|---|---|---|
| 1-167 | | ¹H-NMR (CDCl₃) δ ppm: 3.14 (2H, dd, J = 1.6 Hz, 6.4 Hz), 3.62 (1H, dd, J = 5.1 Hz, 11.6 Hz), 3.81 (1H, dd, J = 3.8 Hz, 11.6 Hz), 4.51-4.58 (1H, m), 6.74 (1H, d, J = 2.5 Hz), 6.99 (1H, d, J = 8.2 Hz), 7.03 (2H, t, J = 8.6 Hz), 7.12 (1H, dt, J = 4.6, 8.6 Hz) 7.19-7.24 (2H, m), 7.29-7.36 (2H, m), 7.57-7.63 (2H, m), 8.23 (1H, d, J = 4.7 Hz). RT (min): 2.535 (Method A) MS (ESI, m/z): 453.1531 (M + H)⁺ | Column: SiO2 EtOAc/MeOH |
| 1-168 | | ¹H-NMR (CDCl₃) δ ppm: 1.57 (3H, s), 3.91 (1H, dd, J = 3.8, 11.6 Hz), 4.10-4.16 (1H, m), 4.56-4.62 (1H, m), 5.91-5.98 (1H, brd), 6.64-6.74 (2H, m), 6.77 (1H, d, J = 3.7 Hz), 7.07-7.11 (1H, m), 7.16-7.21 (1H, m), 7.22-7.26 (1H, m), 7.33-7.36 (2H, m), 7.48 (1H, d, J = 8.2 Hz), 7.58-7.64 (2H, m), 7.65-7.70 (1H, m), 8.37-8.41 (1H, m). RT (min): 2.274 (Method A) MS (ESI, m/z): 481.1434 (M + H)⁺ | Column: SiO2 EtOAc/MeOH |

TABLE 73

| Ex. No. | Strc. | P. D. | P. C. |
|---|---|---|---|
| 1-169 | | ¹H-NMR (CDCl₃) δ ppm: 2.98-3.16 (2H, m), 3.33 (1H, dd, J = 6.4, 11.5 Hz), 3.43 (1H, dd, J = 6.4, 11.5 Hz), 3.67-3.75 (1H, m), 4.38-4.49 (1H, m), 6.67 (1H, s), 7.00-7.13 (4H, m), 7.16 (1H, d, J = 7.8 Hz), 7.21-7.33 (2H, m), 7.47-7.60 (2H, m), 7.60-7.69 (2H, m), 8.32-8.38 (1H, m). RT (min): 1.849 (Method A) MS (ESI, m/z): 481.1435 (M + H)⁺ | Column: SiO2 EtOAc/MeOH |
| 1-170 | | ¹H-NMR (CDCl₃) δ ppm: 3.18-3.29 (1H, m), 3.33-3.47 (1H, m), 3.48-3.57 (1H, m), 3.63-3.73 (1H, m), 3.88-4.02 (1H, m), 6.79-6.85 (1H, m), 7.01-7.09 (1H, m), 7.13-7.31 (3H, m), 7.33-7.43 (3H, m), 7.44-7.56 (1H, m), 7.59-7.67 (2H, m), 7.69-7.77 (1H, m). RT (min): 2.014 (Method A) MS (ESI, m/z): 467.1278 (M + H)⁺ | Column: SiO2 EtOAc/MeOH |

TABLE 73-continued

| Ex. No. | Strc. | P. D. | P. C. |
|---|---|---|---|
| 1-171 | | ¹H-NMR (CDCl₃) δ ppm: 3.19-3.30 (1H, m), 3.35-3.57 (2H, m), 3.63-3.72 (1H, m), 3.88-4.00 (1H, m), 6.76-6.83 (1H, m), 7.00-7.06 (1H, m), 7.07-7.13 (3H, m), 7.15-7.19 (1H, m), 7.20-7.30 (1H, m), 7.33-7.42 (1H, m), 7.46-7.59 (1H, m), 7.63-7.75 (3H, m).<br>RT (min): 1.713 (Method A)<br>MS (ESI, m/z): 451.1573 (M + H)⁺ | Column: SiO2<br>EtOAc/MeOH |
| 1-172 | | ¹H-NMR (CDCl₃) δ ppm: 3.19 (1H, dd, J = 5.2, 14.6 Hz), 3.37 (1H, dd, J = 7.0, 14.6 Hz), 3.56-3.70 (2H, m), 3.88-3.96 (1H, m), 4.51-4.63 (1H, m), 6.86-6.95 (1H, m), 7.04-7.20 (4H, m), 7.31-7.41 (2H, m), 7.47-7.61 (2H, m), 7.71 (1H, d, J = 7.8 Hz), 7.79-7.88 (2H, m), 8.36-8.42 (1H, m).<br>RT (min): 1.825 (Method A)<br>MS (ESI, m/z): 465.1730 (M + H)⁺ | Column: SiO2<br>EtOAc/MeOH |
| 1-173 | | ¹H-NMR (CDCl₃) δ ppm: 1.44-1.55 (1H, m), 1.81-1.92 (1H, m), 2.97 (1H, dd, J = 6.6, 14.5 Hz), 3.21 (1H, dd, J = 4.5, 14.5 Hz), 3.59-3.75 (2H, m), 4.60-4.77 (1H, m), 7.04-7.18 (3H, m), 7.21 (1H, d, J = 7.7 hz), 7.38-7.45 (1H, m), 7.51-7.69 (3H, m), 7.71-7.78 (1H, m), 7.80-7.90 (2H, m), 7.98-8.08 (1H, m), 8.34-8.40 (1H, m).<br>RT (min): 1.921 (Method A)<br>MS (ESI, m/z): 449.1782 (M + H)⁺ | Column: SiO2<br>EtOAc/MeOH |
| 1-174 | | ¹H-NMR (DMSO-d₆) δ ppm: 2.96 (1H, dd, J = 14.0, 8.0), 3.11 (1H, br), 3.42-3.48 (1H, m), 4.34-4.43 (1H, m), 4.68 (0.5H, br), 4.87 (0.5H, br), 6.81 (1H, s), 7.16-7.53 (6H, m), 7.80-7.82 (2H, m), 8.00 (0.5H, br), 8.32 (0.5H, br), 8.69 (2H, d, J = 4.9 Hz), 13.01 (0.5H, br), 13.44 (0.5H, br).<br>RT (min): 2.248 (Method A)<br>MS (ESI, m/z): 436.1579 (M + H)⁺ | Column: APS<br>EtOAc/MeOH |

TABLE 73-continued

| Ex. No. | Strc. | P. D. | P. C. |
|---|---|---|---|
| 1-175 | | RT (min): 3.684 (Method A)<br>MS (ESI, m/z): 418.1724 (M + H)$^+$ | Column: SiO2<br>EtOAc/n-Hexane |

TABLE 74

| Ex. No. | Strc. | P. D. | P. C. |
|---|---|---|---|
| 1-176 | | RT (min): 3.542 (Method A)<br>MS (ESI, m/z): 476.1778 (M + H)$^+$ | Column: SiO2<br>EtOAc/n-Hexane |
| 1-177 | | $^1$H-NMR (DMSO-d$_6$) δ ppm: 3.03-3.10 (1H, m), 3.27-3.43 (2H, m), 4.13 (1H, br), 4.84 (0.5H, br), 4.98 (0.5H, br), 6.80 (1H, s), 7.19-7.82 (9H, m), 8.19 (0.5H, br), 8.50 (0.5H, m), 13.07 (0.5H, m), 13.47 (0.5H, m).<br>RT (min): 2.508 (Method A)<br>MS (ESI, m/z): 441.1189 (M + H)$^+$ | Column: SiO2<br>EtOAc/MeOH |
| 1-178 | | RT (min): 2.255 (Method A)<br>MS (ESI, m/z): 436.1580 (M + H)$^+$ | Column: APS<br>EtOAc/MeOH |

TABLE 74-continued

| Ex. No. | Strc. | P. D. | P. C. |
|---|---|---|---|
| 1-179 | 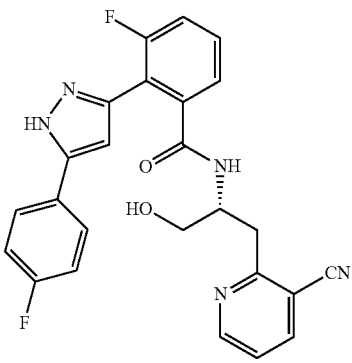 [SMILES: N#Cc1cccnc1C[C@H](CO)NC(=O)c1cccc(F)c1-c1cc(-c2ccc(F)cc2)[nH]n1] | ¹H-NMR (CDCl₃) δ ppm: 3.30-3.32 (2H, m), 3.65 (1H, dd, J = 11.4, 5.3 Hz), 3.89 (1H, dd, J = 11.4, 4.1 Hz), 4.63-4.68 (1H, m), 6.74 (1H, d, J = 3.0 Hz), 6.94 (1H, d, J = 8.3 Hz), 7.03 (2H, t, J = 8.8 Hz), 7.20-7.29 (3H, m), 7.34-7.39 (1H, m), 7.57 (2H, br), 7.85 (1H, dd, J = 7.9, 1.8 Hz), 8.62 (1H, dd, J = 4.9, 1.8 Hz).<br>RT (min): 2.591 (Method A)<br>MS (ESI, m/z): 460.1577 (M + H)⁺ | Column: SiO2<br>EtOAc/MeOH |
| 1-180 | 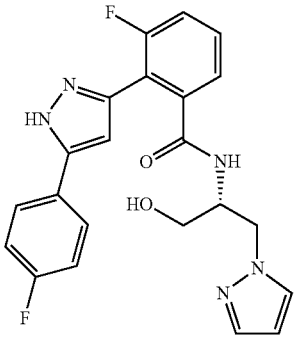 [SMILES: O=C(N[C@@H](CO)Cn1cccn1)c1cccc(F)c1-c1cc(-c2ccc(F)cc2)[nH]n1] | ¹H-NMR (CDCl₃) δ ppm: 3.41 (1H, d, J = 11.0 Hz), 3.61 (1H, d, J = 11.0 Hz), 4.32-4.38 (3H, m), 6.15 (1H, s), 6.71 (1H, s), 7.03 (2H, t, J = 8.2 Hz), 7.16-7.40 (6H, m), 7.60 (2H, t, J = 7.1 Hz).<br>RT (min): 2.538 (Method A)<br>MS (ESI, m/z): 424.1579 (M + H)⁺ | Column: SiO2<br>EtOAc/MeOH |
| 1-181 | 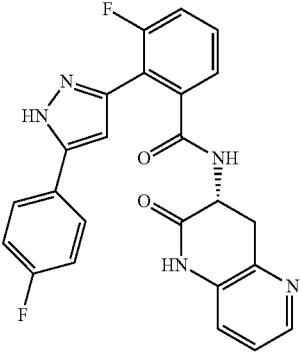 [SMILES: O=C(N[C@@H]1Cc2ncccc2NC1=O)c1cccc(F)c1-c1cc(-c2ccc(F)cc2)[nH]n1] | RT (min): 2.248 (Method A)<br>MS (ESI, m/z): 446.1421 (M + H)⁺ | Column: SiO2<br>EtOAc/MeOH |
| 1-182 | 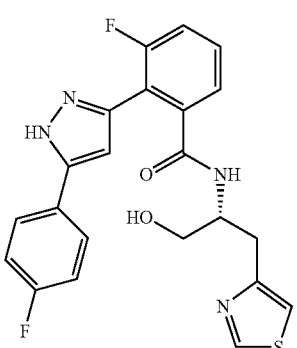 | ¹H-NMR (CDCl₃) δ ppm: 3.05-3.15 (2H, m), 3.62 (2H, ddd, J = 22.5, 11.7, 5.0 Hz), 3.66 (1H, dd, J = 11.7, 5.0 Hz), 4.38-4.45 (1H, m), 6.73 (1H, d, J = 2.8 Hz), 6.99-7.08 (4H, m), 7.18-7.23 (2H, m), 7.31-7.36 (1H, m), 7.58-7.61 (2H, m), 8.65 (1H, d, J = 1.9 Hz).<br>RT (min): 2.488 (Method A)<br>MS (ESI, m/z): 441.1189 (M + H)⁺ | Column: SiO2<br>EtOAc/MeOH |

TABLE 75

| Ex. No. | Strc. | P. D. | P. C. |
|---|---|---|---|
| 1-183 | 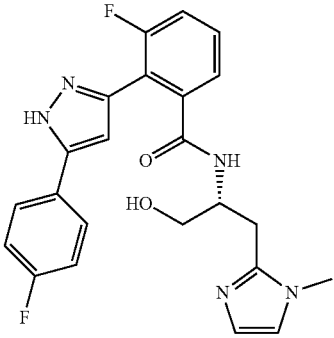 [SMILES: Cn1ccnc1C[C@H](CO)NC(=O)c1cccc(F)c1-c1cc(-c2ccc(F)cc2)[nH]n1] | ¹H-NMR (CDCl₃) δ ppm: 2.89 (1H, dd, J = 14.6, 3.5 Hz), 3.25 (1H, dd, J = 14.6, 9.1 Hz), 3.50 (1H, dd, J = 12.0, 3.5 Hz), 3.59 (3H, s), 3.75 (1H, dd, J = 12.0, 1.8 Hz), 4.09-4.13 (1H, m), 6.73 (1H, d, J = 1.0 Hz), 6.76 (1H, d, J = 2.0 Hz), 6.80 (1H, d, J = 1.3 Hz), 7.08-7.13 (2H, m), 7.17-7.23 (2H, m), 7.31-7.37 (2H, m), 7.71-7.75 (2H, m). RT (min): 1.751 (Method A) MS (ESI, m/z): 438.1734 (M + H)⁺ | Column: SiO2 EtOAc/MeOH |
| 1-184 | 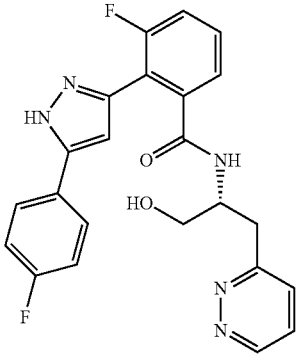 [SMILES: O=C(N[C@@H](CO)Cc1cccnn1)c1cccc(F)c1-c1cc(-c2ccc(F)cc2)[nH]n1] | ¹H-NMR (CDCl₃) δ ppm: 3.21 (2H, d, J = 6.4 Hz), 3.64 (2H, d, J = 3.3 Hz), 4.39-4.44 (1H, m), 6.67 (1H, br), 7.03 (2H, t, J = 8.3 Hz), 7.10-7.15 (2H, m), 7.28-7.33 (2H, m), 7.42-7.47 (2H, m), 7.62-7.65 (2H, m), 8.93 (1H, d, J = 4.0 Hz). RT (min): 2.060 (Method A) MS (ESI, m/z): 436.1578 (M + H)⁺ | Column: SiO2 EtOAc/MeOH |
| 1-185 | 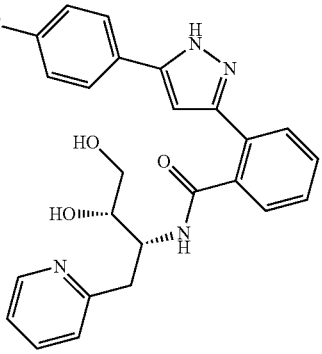 | ¹H-NMR (CDCl₃) δ ppm: 3.16 (1H, dd, J = 5.0, 14.7 Hz), 3.33 (1H, dd, J = 7.1, 14.7 Hz), 3.50-3.68 (2H, m), 3.85-3.93 (1H, m), 4.52-4.63 (1H, m), 6.67 (1H, s), 6.80-6.95 (1H, m), 7.04-7.13 (3H, m), 7.15 (1H, d, J = 7.8 Hz), 7.30-7.37 (2H, m), 7.43-7.55 (2H, m), 7.59 (1H, d, J = 7.6 Hz), 7.70-7.78 (2H, m), 8.35-8.41 (1H, m). RT (min): 1.628 (Method A) MS (ESI, m/z): 447.1825 (M + H)⁺ | Column: SiO2 EtOAc/MeOH |
| 1-186 | 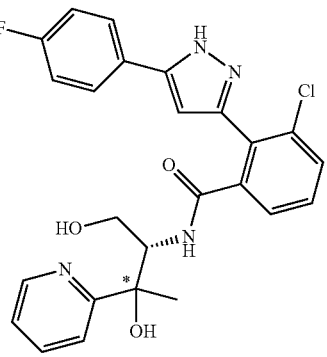 | ¹H-NMR (CDCl₃) δ ppm: 1.51 (3H, s), 3.78-3.85 (1H, m), 3.88-3.96 (1H, m), 4.45-4.54 (1H, m), 6.64 (1H, s), 6.80-6.90 (2H, m), 6.97-7.05 (2H, m), 7.11-7.17 (1H, m), 7.18-7.25 (1H, m), 7.45-7.70 (6H, m), 8.41-8.45 (1H, m). RT (min): 2.151 (Method A) MS (ESI, m/z): 481.1440 (M + H)⁺ | Column: SiO2 EtOAc/MeOH |

TABLE 75-continued

| Ex. No. | Strc. | P. D. | P. C. |
|---|---|---|---|
| 1-187 | | RT (min): 1.709 (Method A)<br>MS (ESI, m/z): 474.1736 (M + H)⁺ | Column: SiO2<br>EtOAc/MeOH |
| 1-188 | | RT (min): 1.808 (Method A)<br>MS (ESI, m/z): 452.1891 (M + H)⁺ | Column: APS<br>EtOAc/MeOH |
| 1-189 | | RT (min): 2.033 (Method A)<br>MS (ESI, m/z): 480.2204 (M + H)⁺ | Column: APS<br>EtOAc/MeOH |

TABLE 76

| Ex. No. | Strc. | P. D. | P. C. |
|---|---|---|---|
| 1-190 | | $^1$H-NMR (DMSO-d$_6$) δ ppm: 2.93-3.11 (1H, m), 3.14-3.41 (1H, m), 4.62-4.84 (1H, m), 6.73-7.74 (11H, m), 7.76-7.87 (2H, m), 8.45-8.52 (1H, m), 8.64-8.82 (1H, m), 13.0-13.4 (1H, m).<br>RT (min): 1.944 (Method A)<br>MS (ESI, m/z): 448.1579 (M + H)⁺ | Filtration of EtOAc suspension |

TABLE 76-continued

| Ex. No. | Strc. | P. D. | P. C. |
|---|---|---|---|
| 1-191 | | ¹H-NMR (CDCl₃) δ ppm: 1.49-1.53 (1H, m), 1.80-1.90 (1H, m), 3.12 (1H, dd, J = 14.9, 6.3 Hz), 3.25 (1H, dd, J = 14.9, 5.2 Hz), 3.66-3.68 (2H, m), 4.72-4.79 (1H, m, 6.81 (1H, d, J = 3.0 Hz), 7.04-7.11 (3H, m), 7.24-7.29 (1H, m), 7.34-7.44 (3H, m), 7.69-7.73 (2H, m), 8.55 (2H, d, J = 5.0 Hz).<br>RT (min): 2.269 (Method A)<br>MS (ESI, m/z): 450.1735 (M + H)⁺ | Column: APS<br>EtOAc/MeOH |
| 1-192 | | RT (min): 3.484 (Method A)<br>MS (ESI, m/z): 476.1778 (M + H)⁺ | Column: SiO2<br>EtOAc/n-Hexane |
| 1-193 | | ¹H-NMR (CDCl₃) δ ppm: 3.47-3.59 (1H, m), 3.65-3.75 (1H, m), 4.28-4.49 (3H, m), 6.13-6.17 (1H, m), 7.02-7.16 (3H, m), 7.18-7.32 (3H, m), 7.38-7.48 (2H, m), 7.66-7.77 (2H, m).<br>RT (min): 2.757 (Method A)<br>MS (ESI, m/z): 442.1485 (M + H)⁺ | Column: SiO2<br>EtOAc/MeOH |
| 1-194 | | RT (min): 1.947 (Method A)<br>MS (ESI, m/z): 421.1468 (M + H)⁺ | Column: SiO2<br>EtOAc/MeOH |

TABLE 76-continued

| Ex. No. | Strc. | P. D. | P. C. |
| --- | --- | --- | --- |
| 1-195 | | RT (min): 3.031 (Method A)<br>MS (ESI, m/z): 420.1515 (M + H)⁺ | Column: SiO2<br>EtOAc/MeOH |
| 1-196 | | ¹H-NMR (CDCl₃) δ ppm: 3.10 (2H, d, J = 6.5 Hz), 3.58 (1H, dd, J = 11.5, 5.2 Hz), 3.76 (3H, s), 3.77 (1H, dd, J = 11.5, 3.8 Hz), 4.50-4.57 (1H, m), 6.71 (1H, d, J = 2.8 Hz), 6.99-7.18 (6H, m), 7.22-7.30 (2H, m), 7.59-7.62 (2H, m), 7.97 (1H, dd, J = 4.0, 2.0 Hz).<br>RT (min): 1.901 (Method A)<br>MS (ESI, m/z): 465.1730 (M + H)⁺ | Column: SiO2<br>EtOAc/MeOH |

TABLE 77

| Ex. No. | Strc. | P. D. | P. C. |
| --- | --- | --- | --- |
| 1-197 | | ¹H-NMR (CDCl₃) δ ppm: 3.21 (2H, d, J = 5.9 Hz), 3.57 (1H, dd, J = 11.4, 5.2 Hz), 3.85 (1H, dd, J = 11.6, 3.4 Hz), 4.56-4.64 (1H, m), 6.72 (1H, d, J = 2.9 Hz), 6.97-7.02 (2H, m), 7.19-7.24 (4H, m), 7.31-7.37 (1H, m), 7.53-7.56 (2H, m), 7.89 (1H, dbr, J = 7.8 Hz), 8.57 (1H, dbr, J = 4.4 Hz).<br>RT (min): 3.000 (Method A)<br>MS (ESI, m/z): 503.1501 (M + H)⁺ | Column: SiO2<br>EtOAc/MeOH |
| 1-198 | | ¹H-NMR (CDCl₃) δ ppm: 0.99 (3H, t, J = 7.1 Hz), 3.04 (1H, dd, J = 14.8, 3.6 Hz), 3.31 (1H, d, J = 8.4 Hz), 3.37 (2H, q, J = 7.1 Hz), 3.51 (1H, dd, J = 12.2, 4.5 Hz), 3.74 (1H, dd, J = 12.2, 2.1 Hz), 4.13-4.19 (1H, m), 5.25 (1H, d, J = 10.9), 5.35-5.43 (1H, m), 6.80 (1H, d, J = 2.3 Hz), 6.84 (1H, d, J = 1.3 Hz), 6.90 (1H, d, J = 1.3 Hz), 7.09-7.13 (2H, m), 7.19-7.30 (3H, m), 7.34-7.39 (1H, m), 7.72-7.76 (2H, m).<br>RT (min): 1.989 (Method A)<br>MS (ESI, m/z): 482.1995 (M + H)⁺ | Column: SiO2<br>EtOAc/MeOH |

TABLE 77-continued

| Ex. No. | Strc. | P. D. | P. C. |
|---|---|---|---|
| 1-199 | | RT (min): 2.092 (Method A)<br>MS (ESI, m/z): 485.1780 (M + H)⁺ | Column: SiO2<br>EtOAc/MeOH |
| 1-200 | | ¹H-NMR (CDCl₃): δ 1.33 (3H, d, J = 7.1 Hz), 3.17-3.25 (1H, m), 3.45 (1H, dd, J = 7.5, 11.2 Hz), 3.56 (1H, dd, J = 4.7, 11.2 Hz), 4.40-4.48 (1H, m), 6.84 (1H, d, J = 3.2 Hz), 7.00-7.14 (5H, m), 7.20-7.30 (1H, m), 7.31-7.41 (2H, m), 7.55 (1H, dt, J = 1.8, 7.5 Hz), 7.60-7.67 (2H, m), 7.94-8.00 (1H, m), 8.32-8.38 (1H, m).<br>RT (min): 1.908 (Method A)<br>MS (ESI, m/z): 449.1781 (M + H)⁺ | Column: SiO2<br>EtOAc/MeOH |
| 1-201 | | RT (min): 3.134 (Method A)<br>MS (ESI, m/z): 446.1673 (M + H)⁺ | Column: SiO2<br>EtOAc/n-Hexane |
| 1-202 | | ¹H-NMR (CDCl₃) δ ppm: 1.51-1.55 (1H, m), 1.86-1.94 (1H, m), 3.18 (1H, dd, J = 14.6, 6.2 Hz), 3.33 (1H, dd, J = 14.6, 3.4 Hz), 3.66-3.73 (2H, m), 4.76-4.83 (1H, m), 7.06 (1H, t, J = 4.7 Hz), 7.11-7.15 (2H, m), 7.42-7.46 (1H, m), 7.56-7.61 (2H, m), 7.66-7.86 (4H, m), 8.57 (2H, d, J = 5.0 Hz).<br>RT (min): 2.418 (Method A)<br>MS (ESI, m/z): 450.1733 (M + H)⁺ | Column: APS<br>EtOAc/MeOH |

TABLE 77-continued

| Ex. No. | Strc. | P. D. | P. C. |
|---|---|---|---|
| 1-203 | | RT (min): 2.387 (Method A)<br>MS (ESI, m/z): 436.1579 (M + H)⁺ | Column: SiO2<br>EtOAc/MeOH |

TABLE 78

| Ex. No. | Strc. | P. D. | P. C. |
|---|---|---|---|
| 1-204 | | $^1$H-NMR (CDCl$_3$) δ ppm: 1.24 (3H, t, J = 7.2 Hz), 2.88 (1H, dd, J = 14.6, 3.3 Hz), 3.27 (1H, dd, J = 14.6, 9.0 Hz), 3.49 (1H, dd, J = 12.1, 3.3 Hz), 3.75 (1H, dd, J = 12.1, 1.5 Hz), 3.90-4.11 (3H, m), 6.76 (1H, d, J = 1.8 Hz), 6.81 (2H, dd, J = 9.6, 1.3 Hz), 7.06-7.12 (2H, m), 7.17-7.24 (2H, m), 7.32-7.39 (2H, m), 7.71-7.74 (2H, m).<br>RT (min): 1.831 (Method A)<br>MS (ESI, m/z): 452.1891 (M + H)⁺ | Column: APS<br>EtOAc/MeOH |
| 1-205 | | $^1$H-NMR (CDCl$_3$) δ ppm: 3.68 (1H, dd, J = 4.7 Hz, 12.4 Hz), 3.97 (1H, dd, J = 2.8 Hz, 11.7 Hz), 4.47-4.53 (1H, m), 5.11 (1H, d, J = 1.7 Hz), 7.03 (1H, d, J = 6.9 Hz), 7.14 (2H, t, J = 8.8 Hz), 7.19 (1H, dd, J = 5.4, 7.3 Hz), 7.34-7.41 (2H, m), 7.50-7.58 (2H, m), 7.64 (1H, dt, J = 1.7, 7.3 Hz), 7.74 (1H, d, J = 7.3 Hz), 7.84 (1H, dd, J = 5.6, 8.4 Hz), 8.47 (1H, d, J = 5.0 Hz).<br>RT (min): 1.927 (Method A)<br>MS (ESI, m/z): 451.1574 (M + H)⁺ | Column: SiO2<br>EtOAc/MeOH |
| 1-206 | | $^1$H-NMR (CDCl$_3$) δ ppm: 1.94-2.04 (1H, m), 2.08-2.20 (1H, m), 3.62-3.74 (1H, m), 3.82 (1H, dt, J = 4.5 Hz, 11.8 Hz), 4.71-4.80 (1H, m), 4.90-4.93 (1H, m), 6.45 (1H, d, J = 9.3 Hz), 7.07-7.16 (3H, m), 7.34 (1H, dt, J = 1.2, 7.8 Hz), 7.36-7.40 (1H, m), 7.52 (1H, dt, J = 1.4, 7.7 Hz), 7.61 (1H, dt, J = 1.7, 7.7 Hz), 7.66-7.70 (1H, m), 7.83-7.93 (2H, m), 8.37-8.40 (1H, m).<br>RT (min): 1.890 (Method A)<br>MS (ESI, m/z): 465.1730 (M + H)⁺ | Column: SiO2<br>EtOAc/MeOH |

TABLE 78-continued

| Ex. No. | Strc. | P. D. | P. C. |
|---|---|---|---|
| 1-207 | | ¹H-NMR (CDCl₃) δ ppm: 1.66-2.02 (2H, m), 3.41-3.50 (1H, m), 3.58-3.64 (1H, m), 4.56-4.66 (1H, m), 4.77-4.82 (1H, m), 6.65 (1H, s), 6.98-7.02 (1H, m), 7.09-7.17 (3H, m), 7.22-7.30 (2H, m), 7.32-7.39 (1H, m), 7.48-7.53 (1H, m), 7.61-7.70 (3H, m), 8.41-8.46 (1H, m).<br>RT (min): 1.923 (Method A)<br>MS (ESI, m/z): 481.1439 (M + H)⁺ | Column: SiO2<br>EtOAc/MeOH |
| 1-208 | | ¹H-NMR (CDCl₃) δ ppm: 1.39-1.51 (1H, m), 1.78-1.91 (1H, m), 2.93 (1H, dd, J = 6.1, 14.4 Hz), 3.18 (1H, d, J = 4.6, 14.4 Hz), 3.55-3.72 (2H, m), 4.60-4.75 (1H, m), 6.73 (1H, s), 7.04-7.13 (3H, m), 7.16 (1H, d, J = 7.8 Hz), 7.37-7.44 (1H, m), 7.48-7.55 (2H, m), 7.58 (1H, td, J = 1.8, 7.8 Hz), 7.63-7.68 (1H, m), 7.73-7.80 (2H, m), 7.85-7.94 (1H, m), 8.34-8.40 (1H, m).<br>RT (min): 1.635 (Method A)<br>MS (ESI, m/z): 431.1876 (M + H)⁺ | Column: SiO2<br>EtOAc/MeOH |
| 1-209 | | RT (min): 2.142 (Method A)<br>MS (ESI, m/z): 493.2045 (M + H)⁺ | Column: SiO2<br>EtOAc/MeOH |
| 1-210 | | ¹H-NMR (CDCl₃) δ ppm: 3.44-3.54 (1H, m), 3.68-3.80 (2H, m), 4.28-4.34 (1H, m), 4.97-5.05 (1H, m), 6.69 (1H, s), 7.07 (2H, t, J = 8.6 Hz), 7.12-7.17 (1H, m), 7.20-7.30 (2H, m), 7.40-7.49 (3H, m), 7.60-7.67 (4H, m), 8.37-8.42 (1H, m).<br>RT (min): 1.989 (Method A)<br>MS (ESI, m/z): 467.1281 (M + H)⁺ | Column: SiO2<br>EtOAc/MeOH |

TABLE 79

| Ex. No. | Strc. | P. D. | P. C. |
|---|---|---|---|
| 1-211 | | ¹H-NMR (CDCl₃) δ ppm: 3.60-3.91 (2H, m), 4.40-4.47 (1H, m), 5.06-5.12 (1H, m), 7.08-7.20 (3H, m), 7.20-7.50 (4H, m), 7.60-7.64 (1H, m), 7.71-7.78 (2H, m), 8.41-8.44 (1H, m).<br>RT (min): 2.020 (Method A)<br>MS (ESI, m/z): 469.1481 (M + H)⁺ | Column: SiO2<br>EtOAc/MeOH |
| 1-212 | | RT (min): 2.015 (Method A)<br>MS (ESI, m/z): 449.1781 (M + H)⁺ | Column: SiO2<br>EtOAc/MeOH |
| 1-213 | | ¹H-NMR (CDCl₃) δ ppm: 3.13 (1H, dd, J = 5.6, 14.3 Hz), 3.25-3.40 (6H, m), 3.94-4.02 (1H, m), 4.40-4.54 (1H, m), 6.73-6.84 (1H, m), 7.04-7.18 (4H, m), 7.20-7.34 (2H, m), 7.36-7.45 (1H, m), 7.45-7.53 (1H, m), 7.82-7.92 (2H, m), 8.35-8.42 (1H, m).<br>RT (min): 2.062 (Method A)<br>MS (ESI, m/z): 497.1795 (M + H)⁺ | Column: SiO2<br>EtOAc/MeOH |
| 1-214 | | RT (min): 2.013 (Method A)<br>MS (ESI, m/z): 493.2043 (M + H)⁺ | Column: SiO2<br>EtOAc/MeOH |

TABLE 79-continued

| Ex. No. | Strc. | P. D. | P. C. |
|---|---|---|---|
| 1-215 | | RT (min): 2.149 (Method A)<br>MS (ESI, m/z): 509.1748 (M + H)⁺ | Column: SiO2<br>EtOAc/MeOH |
| 1-216 | | RT (min): 2.254 (Method A)<br>MS (ESI, m/z): 509.1752 (M + H)⁺ | Column: SiO2<br>EtOAc/MeOH |
| 1-217 | | $^1$H-NMR (CDCl$_3$) δ ppm: 0.99 (3H, s), 2.99 (1H, dd, J = 8.0, 14.6 Hz), 3.31 (1H, d, J = 12.0 Hz), 3.38 (1H, dd, J = 4.3, 14.6 Hz), 3.60 (1H, d, J = 12.0 Hz), 4.31-4.42 (1H, m), 6.74 (1H, d, J = 3.0 Hz), 7.01-7.15 (4H, m), 7.20-7.41 (4H, m), 7.48-7.56 (1H, m), 7.65-7.75 (2H, m), 8.30-8.35 (1H, m).<br>RT (min): 1.742 (Method A)<br>MS (ESI, m/z): 479.1888 (M + H)⁺ | Column: SiO2<br>EtOAc/MeOH |

TABLE 80

| Ex. No. | Strc. | P.D. | P.C. |
|---|---|---|---|
| 1-218 | | $^1$H-NMR (CDCl$_3$) δ ppm: 0.84 (3H, s), 2.84-2.93 (1H, m), 3.06-3.13 (1H, m), 3.21-3.30 (1H, m), 3.39-3.46 (1H, m), 4.25-4.35 (1H, m), 6.64 (1H, s), 7.01-7.24 (6H, m), 7.29-7.35 (1H, m), 7.49-7.70 (4H, m), 8.32-8.40 1H, m).<br>RT (min): 1.916 (Method A)<br>MS (ESI, m/z): 495.1592 (M + H)⁺ | Column: SiO2<br>EtOAc/MeOH |

TABLE 80-continued

| Ex. No. | Strc. | P.D. | P.C. |
|---|---|---|---|
| 1-219 | | ¹H-NMR (CDCl₃) δ ppm: 1.00 (3H, s), 2.96-3.05 (1H, m), 3.34 (1H, d, J = 1.0 Hz), 3.38 (1H, dd, J = 4.4,) 15.0 Hz), 3.60 (1H, d, J = 12.0 Hz), 4.30-4.43 (1H, m), 6.77 (1H, d, J = 3.0 Hz), 7.01-7.07 (1H, m), 7.08-7.13 (1H, m), 7.15-7.21 (2H, m), 7.32-7.43 (3H, m), 7.48-7.54 (1H, m), 7.65-7.72 (2H, m), 8.30-8.36 (1H, m). RT (min): 2.007 (Method A) MS (ESI, m/z): 495.1592 (M + H)⁺ | Column: SiO2 EtOAc/MeOH |
| 1-220 | | ¹H-NMR (CDCl₃) δ ppm: 3.27-3.29 (2H, m), 3.58 (2H, d, J = 5.7 Hz), 3.79-3.83 (1H, m), 4.67-4.73 (1H, m), 6.75 (1H, d, J = 2.8 Hz), 7.02-7.08 (3H, m), 7.18-7.34 (4H, m), 7.61-7.64 (2H, m), 8.57 (2H, d, J = 6.0 Hz). RT (min): 2.099 (Method A) MS (ESI, m/z): 466.1687 (M + H)⁺ | Column: SiO2 EtOAc/MeOH |
| 1-221 | | RT (min): 2.181 (Method A) MS (ESI, m/z): 507.2200 (M + H)⁺ | Column: SiO2 EtOAc/MeOH |
| 1-222 | | RT (min): 2.403 (Method A) MS (ESI, m/z): 523.1904 (M + H)⁺ | Column: SiO2 EtOAc/MeOH |
| 1-223 | | ¹H-NMR (CDCl₃) δ ppm: 1.41-1.53 (1H, m), 1.80-1.91 (1H, m), 2.94 (1H, dd, J = 6.0, 14.4 Hz), 3.21 (1H, dd, J = 4.5, 14.4 Hz), 3.59-3.73 (2H, m), 4.60-4.75 (1H, m), 7.05-7.11 (1H, m), 7.16 (1H, d, J = 7.7 Hz), 7.37-7.48 (3H, m), 7.54-7.62 (3H, m), 7.75-7.88 (3H, m), 8.03-8.13 (1H, m), 8.36-8.41 (1H, m). RT (min): 2.172 (Method A) MS (ESI, m/z): 465.1485 (M + H)⁺ | Column: SiO2 EtOAc/MeOH |

TABLE 80-continued

| Ex. No. | Strc. | P.D. | P.C. |
|---|---|---|---|
| 1-224 |  | $^1$H-NMR (CDCl$_3$) δ ppm: 1.28 (3H, s), 3.16 (1H, dd, J = 6.9 15.1 Hz), 3.33 (1H, dd, J = 5.2, 15.1 Hz), 3.42 (2H, s), 4.51-4.58 (1H, m), 6.70-6.73 (1H, m), 6.89-6.98 (2H, m), 7.04-7.21 (5H, m), 7.25-7.30 (1H, m), 7.47-7.54 (1H, m), 7.64-7.71 (2H, m), 8.34-8.38 (1H, m). RT (min): 1.730 (Method A) MS (ESI, m/z): 479.1889 (M + H)$^+$ | Column: SiO2 EtOAc/MeOH |

TABLE 81

| Ex. No. | Strc. | P.D. | P.C. |
|---|---|---|---|
| 1-225 | 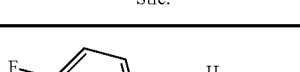 | $^1$H-NMR (CDCl$_3$) δ ppm: 1.23 (3H, s), 3.08-3.16 (1H, m), 3.20-3.30 (3H, m), 4.39-4.47 (1H, m), 6.66 (1H, s), 6.89-6.94 (1H, m), 6.99-7.16 (6H, m), 7.45-7.57 (2H, m), 7.62-7.69 (2H, m), 8.34-8.39 (1H, m). RT (min): 1.901 (Method A) MS (ESI, m/z): 495.1593 (M + H)$^+$ | Column: SiO2 EtOAc/n-Hexane |
| 1-226 | | $^1$H-NMR (CDCl$_3$) δ ppm: 3.44 (1H, dd, J = 11.9, 6.1 Hz), 3.51 (1H, dd, J = 11.9, 6.1 Hz), 3.80-3.83 (1H, m), 4.34-4.50 (3H, m), 6.19 (1H, t, J = 2.1 Hz), 6.75 (1H, d, J = 2.5 Hz), 6.88-6.90 (1H, m), 7.04-7.08 (2H, m), 7.13 (1H, dbr, J = 7.5 Hz), 7.19-7.24 (1H, m), 7.32-7.37 (2H, m), 7.45 (1H, d, J = 1.5 Hz), 7.62-7.65 (2H, m). RT (min): 2.354 (Method A) MS (ESI, m/z): 454.1682 (M + H)$^+$ | Column: SiO2 EtOAc/MeOH |
| 1-227 | | $^1$H-NMR (CDCl$_3$) δ ppm: 3.24-3.27 (2H, m), 3.30 (3H, s), 3.42-3.48 (2H, m), 3.67 (1H, dd, J = 15.6, 8.7 Hz), 4.85-4.91 (1H, m), 6.79 (1H, d, J = 3.2 Hz), 6.93 (1H, dbr, J = 9.3 Hz), 7.03-7.10 (3H, m), 7.21-7.28 (1H, m), 7.32-7.38 (1H, m), 7.68-7.75 (2H, m), 8.57 (2H, d, J = 4.9 Hz). RT (min): 2.341 (Method A) MS (ESI, m/z): 480.1839 (M + H)$^+$ | Column: SiO2 EtOAc/MeOH |

TABLE 81-continued

| Ex. No. | Strc. | P.D. | P.C. |
|---|---|---|---|
| 1-228 | | ¹H-NMR (CDCl₃) δ ppm: 1.27 (3H, s), 3.15 (1H, dd, J = 7.4, 14.8 Hz), 3.34 (1H, dd, J = 4.9, 14.8 Hz), 3.39-3.47 (2H, m), 4.54-4.62 (1H, m), 6.60 (1H, s), 7.00-7.20 (6H, m), 7.22-7.28 (1H, m), 7.36-7.42 (1H, m), 7.46-7.54 (2H, m), 7.64-7.72 (2H, m), 8.32-8.37 (1H, m).<br>RT (min): 1.695 (Method A)<br>MS (ESI, m/z): 461.1981 (M + H)⁺ | Column: SiO2<br>EtOAc/MeOH |
| 1-229 | | ¹H-NMR (CDCl₃) δ ppm: 3.50-3.63 (2H, m), 4.05-4.10 (1H, m), 5.00-5.15 (1H, m), 6.74 (1H, d, 2.4 Hz), 6.97-7.06 (2H, t, J = 8.7 Hz), 7.22-7.31 (3H, m), 7.35-7.42 (1H, dt, J = 5.1 Hz, 7.9 Hz), 7.56-7.64 (3H, m), 7.70 (1H, dt, J = 1.5 Hz, 8.0 Hz), 8.55 (1H, d, J = 4.7 Hz).<br>RT (min): 2.608 (Method A)<br>MS (ESI, m/z): 501.1540 (M + H)⁺ | Column: SiO2<br>EtOAc/MeOH |
| 1-230 | | ¹H-NMR (CDCl₃) δ ppm: 3.80 (1H, dd, J = 5.4 Hz, 12.3 Hz), 3.92 (1H, dd, J = 4.0 Hz, 12.1 Hz), 5.00-5.15 (1H, m), 6.75 (1H, s), 6.97-7.06 (2H, m), 7.15-7.42 (5H, m), 7.51-7.64 (3H, m), 7.76 (1H, dt, J = 1.7 Hz, 8.6 Hz), 8.56 (1H, d, J = 4.7 Hz).<br>RT (min): 2.769 (Method A)<br>MS (ESI, m/z): 471.1435 (M + H)⁺ | Column: SiO2<br>EtOAc/MeOH |
| 1-231 | | ¹H-NMR (CDCl₃) δ ppm: 3.78 (1H, dd, J = 3.8 Hz, 11.8 Hz), 3.89 (1H, dd, J = 3.8 Hz, 12.0 Hz), 4.70-4.82 (1H, m), 5.70 (1H, dd, J = 5.5, 46.3 Hz), 6.78 (1H, d, J = 3.3 Hz), 6.87 (1H, d, J = 9. Hz), 7.08-7.10 (2H, m), 7.18-7.28 (2H, m), 7.30-7.38 (1H, m), 7.44 (1H, d, J = 7.3 Hz), 7.61-7.75 (3H, m), 8.46-8.51 (1H, m).<br>RT (min): 2.573 (Method A)<br>MS (ESI, m/z): 453.1532 (M + H)⁺ | Column: SiO2<br>EtOAc/MeOH |

TABLE 82

| Ex. No. | Strc. | P.D. | P.C. |
|---|---|---|---|
| 1-232 | | ¹H-NMR (CDCl₃) δ ppm: 3.59-3.67 (1H, m), 3.73 (1H, dd, J = 4.4 Hz, 12.0 Hz), 4.60-4.74 (1H, m), 5.60 (1H, dd, J = 5.5, 46.4 Hz), 6.68 (1H, s), 6.97-6.99 (1H, m), 7.01-7.08 (2H, m), 7.20-7.25 (1H, m), 7.28-7.37 (2H, m), 7.38-7.45 (1H, m), 7.52 (1H, dd, J = 2.3, 7.1 Hz), 7.55-7.63 (2H, m), 7.67-7.74 (1H, m), 8.46-8.50 (1H, m).<br>RT (min): 2.711 (Method A)<br>MS (ESI, m/z): 469.1239 (M + H)⁺ | Column: SiO2<br>EtOAc/MeOH |
| 1-233 | | ¹H-NMR (CDCl₃) δ ppm: 3.29 (3H, s), 3.58-3.70 (2H, m), 3.71-3.79 (2H, m), 3.80-3.88 (1H, m), 4.48-4.58 (1H, m), 6.70-6.76 (1H, m), 6.80 (1H, d, J = 3.9 Hz), 7.03-7.17 (5H, m), 7.18-7.37 (2H, m), 7.38-7.46 (1H, m), 7.75-7.84 (2H, m), 8.38-8.43 (1H, m).<br>RT (min): 2.036 (Method A)<br>MS (ESI, m/z): 479.1886 (M + H)⁺ | Column: SHISEIDO CAPCELL PAK C18 UG80<br>H2O/MeCN<br>IIP product |
| 1-234 | | ¹H-NMR (CDCl₃) δ ppm: 3.24 (3H, s), 3.31-3.40 (1H, m), 3.49-3.77 (4H, m), 4.62-4.74 (1H, m), 6.86 (1H, d, J = 3.4 Hz), 7.02-7.12 (3H, m), 7.12-7.18 (1H, m), 7.22-7.33 (2H, m), 7.35-7.43 (1H, m), 7.52-7.61 (1H, m), 7.64-7.74 (2H, m), 7.87-8.00 (1H, m), 8.33-8.41 (1H, m).<br>RT (min): 2.166 (Method A)<br>MS (ESI, m/z): 479.1887 (M + H)⁺ | Column: SHISEIDO CAPCELL PAK C18 UG80<br>H2O/MeCN<br>LP product |
| 1-235 | | RT (min): 2.174 (Method A)<br>MS (ESI, m/z): 495.1591 (M + H)⁺ | Column: SHISEIDO CAPCELL PAK C18 UG80<br>H2O/MeCN<br>IIP product |

TABLE 82-continued

| Ex. No. | Strc. | P.D. | P.C. |
|---|---|---|---|
| 1-236 | 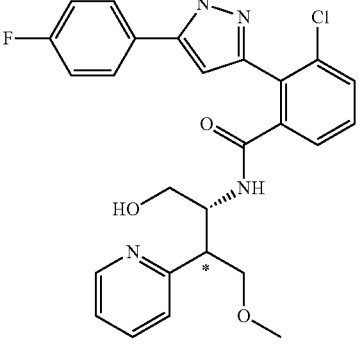 | RT (min): 2.324 (Method A)<br>MS (ESI, m/z): 495.1590 (M + H)+ | Column: SHISEIDO<br>CAPCELL PAK C18<br>UG80<br>H2O/MeCN<br>LP product |
| 1-237 | 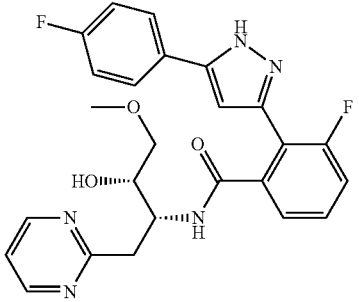 [SMILES: COC[C@@H](O)[C@@H](Cc1ncccn1)NC(=O)c1cccc(F)c1-c1cc(-c2ccc(F)cc2)[nH]n1] | RT (min): 2.292 (Method A)<br>MS (ESI, m/z): 480.1841 (M + H)+ | Column: SiO2<br>EtOAc/MeOH |
| 1-238 | 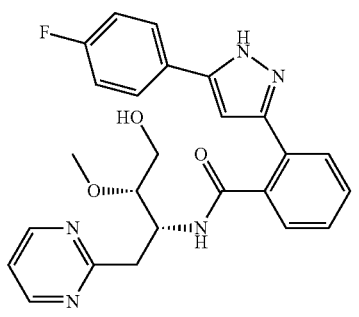 [SMILES: CO[C@H](CO)[C@@H](Cc1ncccn1)NC(=O)c1ccccc1-c1cc(-c2ccc(F)cc2)[nH]n1] | $^1$H-NMR (CDCl$_3$) δ ppm: 3.20-3.40 (5H, m), 3.42-3.51 (2H, m), 3.68-3.74 (1H, m), 4.88-4.97 (1H, m), 6.67-6.72 (1H, m), 6.92-7.12 (4H, m), 7.35-7.39 (1H, m), 7.44-7.54 (2H, m), 7.59-7.65 (1H, m), 7.74-7.81 (2H, m), 8.54-8.57 (2H, m).<br>RT (min): 2.279 (Method A)<br>MS (ESI, m/z): 462.1935 (M + H)+ | Column: SiO2<br>EtOAc/MeOH |

TABLE 83

| Ex. No. | Strc. | P.D. | P.C. |
|---|---|---|---|
| 1-239 | 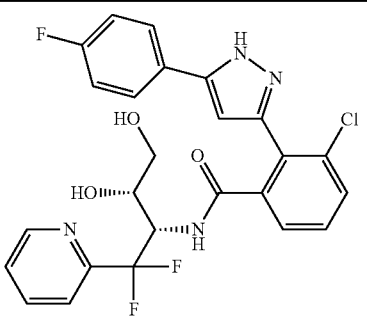 | $^1$H-NMR (CDCl$_3$) δ ppm: 3.40-3.47 (2H, m), 3.99-4.05 (1H, m), 4.76-4.88 (1H, m), 6.73 (1H, s), 7.03-7.11 (2H, m), 7.15-7.24 (2H, m), 7.38-7.47 (2H, m), 7.51-7.57 (1H, m), 7.58-7.68 (4H, m), 8.52-8.58 (1H, m).<br>RT (min): 2.744 (Method A)<br>MS (ESI, m/z): 517.1248 (M + H)+ | Column: SiO2<br>EtOAc/MeOH |

TABLE 83-continued

| Ex. No. | Strc. | P.D. | P.C. |
|---|---|---|---|
| 1-240 | | RT (min): 1.933 (Method A)<br>MS (ESI, m/z): 449.1782 (M + H)+ | Column: SiO2<br>EtOAc/MeOH |
| 1-241 | | ¹H-NMR (CDCl₃) δ ppm: 1.58 (3H, s), 3.93 (1H, dd, J = 4.1 Hz, 11.6 Hz), 4.12 (1H, dd, J = 5.5 Hz, 12.8 Hz), 4.56-4.64 (1H, m), 5.90-6.02 (1H, br), 6.64-6.71 (2H, m), 6.75 (1H, d, J = 4.0 Hz), 7.03-7.12 (3H, m), 7.15-7.28 (2H, m), 7.47-7.51 (1H, m), 7.61-7.72 (3H, m), 8.38-8.42 (1H, m).<br>RT (min): 1.905 (Method A)<br>MS (ESI, m/z): 465.1733 (M + H)+ | Column: SiO2<br>EtOAc/MeOH |
| 1-242 | | ¹H-NMR (CDCl₃) δ ppm: 3.24-3.27 (2H, m), 3.30 (3H, s), 3.42-3.47 (2H, m), 3.66 (1H, dd, J = 14.8, 8.4 Hz), 4.84-4.90 (1H, m), 6.83 (1H, d, J = 3.3 Hz), 6.90 (1H, dbr, J = 9.5 Hz), 7.03 (1H, t, J = 5.0 Hz), 7.23-7.30 (2H, m), 7.34-7.40 (3H, m), 7.71 (2H, d, J = 8.5 Hz), 8.57 (2H, d, J = 5.0 Hz).<br>RT (min): 2.663 (Method A)<br>MS (ESI, m/z): 496.1548 (M + H)+ | Column: SiO2<br>EtOAc/MeOH |
| 1-243 | | RT (min): 1.652 (Method A)<br>MS (ESI, m/z): 439.2138 (M + H)+ | Column: SiO2<br>EtOAc/MeOH. |
| 1-244 | | RT (min): 2.571 (Method A)<br>MS (ESI, m/z): 468.1839 (M + H)+ | Column: SiO2<br>EtOAc/MeOH. |

TABLE 84

| Ex. No. | Strc. | P.D. | P.C. |
|---|---|---|---|
| 1-245 | | ¹H-NMR (CDCl₃) δ ppm: 3.66-3.73 (1H, m), 4.07-4.34 (5H, m), 5.48 (1H, br), 6.23 (1H, t, J = 2.1 Hz), 6.72 (1H, br), 7.06 (1H, d, J = 7.2 Hz), 7.26-7.31 (2H, m), 7.37-7.51 (2H, m), 7.66 (1H, d, J = 1.8 Hz), 7.80-7.83 (2H, m), 8.22 (1H, br). RT (min): 2.686 (Method A) MS (ESI, m/z): 456.1638 (M + H)⁺ | Column: SiO2 EtOAc/MeOH. |
| 1-246 | | RT (min): 3.057 (Method A) MS (ESI, m/z): 470.1797 (M + H)⁺ | Column: SiO2 EtOAc/MeOH. |

TABLE 85

| Ex. No. | Strc. | P.D. | P.C. |
|---|---|---|---|
| 2-1 | | RT (min): 2.070 (Method A) MS (ESI, m/z): 397.2019 (M + H)⁺ | Without purification |
| 3-1 | | RT (min): 1.126 (Method A) MS (ESI, m/z): 397.1658 (M + H)⁺ | Column: SiO2 EtOAc/MeOH |

TABLE 86

| Ex. No. | Strc. | P.D. | P.C. |
|---|---|---|---|
| 4-1 | | ¹H-NMR (DMSO-d₆) δ ppm: 2.80 (2H, t, J = 7.4 Hz), 3.38-3.48 (2H, m), 6.72-6.80 (1H, m), 7.08-7.84 (11H, m), 8.25-8.49 (2H, m), 13.08-13.55 (1H, m), RT (min): 2.228 (Method A) MS (ESI, m/z): 453.1530 (M + H)⁺ | Column: SiO2 EtOAc/MeOH |
| 4-2 | | RT (min): 1.397 (Method A) MS (ESI, m/z): 375.1271 (M + H)⁺ | Column: SiO2 EtOAc/MeOH |
| 4-3 | | RT (min): 1.390 (Method A) MS (ESI, m/z): 375.1272 (M + H)⁺ | Column: SiO2 EtOAc/MeOH |
| 4-4 | | RT (min): 1.617 (Method A) MS (ESI, m/z): 429.1917 (M + H)⁺ | Column: SiO2 EtOAc/MeOH |
| 4-5 | | RT (min): 1.912 (Method A) MS (ESI, m/z): 370.1662 (M + H)⁺ | Column: SiO2 EtOAc/MeOH |

TABLE 87

| Ex. No. | Strc. | P.D. | P.C. |
| --- | --- | --- | --- |
| 4-6 | | RT (min): 1.926 (Method B)<br>MS (ESI, m/z): 370.1659 (M + H)⁺ | Column: SiO2<br>EtOAc/MeOH |
| 4-7 | | RT (min): 0.734 (Method A)<br>MS (ESI, m/z): 384.1817 (M + H)⁺ | Column: SiO2<br>EtOAc/MeOH |
| 4-8 | | RT (min): 2.156 (Method A)<br>MS (ESI, m/z): 493.2205 (M + Na)⁺ | Column: SiO2<br>EtOAc/MeOH |
| 4-9 | | $^1$H-NMR (DMSO-d$_6$) δ ppm: 2.80-2.88 (2H, m), 3.40-3.52 (2H, m), 6.75-6.85 (1H, m), 7.11-7.55 (8H, m), 7.64 (1H, dd, J = 1.7, 7.6 Hz), 7.73-7.83 (2H, m), 8.16-8.49 (2H, m), 13.11-13.52 (1H, m).<br>RT (min): 1.735 (Method A)<br>MS (ESI, m/z): 387.1613 (M + H)⁺ | Column: SiO2<br>EtOAc/MeOH |
| 4-10 | | RT (min): 1.905 (Method A)<br>MS (ESI, m/z): 403.1317 (M + H)⁺ | Column: SiO2<br>EtOAc/MeOH |

TABLE 87-continued

| Ex. No. | Strc. | P.D. | P.C. |
| --- | --- | --- | --- |
| 4-11 | | RT (min): 2.241 (Method A)<br>MS (ESI, m/z): 437.1585 (M + H)$^+$ | Column: SiO2<br>EtOAc/MeOH |

TABLE 88

| Ex. No. | Strc. | P.D. | P.C. |
| --- | --- | --- | --- |
| 5-1 | | RT (min): 1.676 (Method A)<br>MS (ESI, m/z): 397.1655 (M + H)$^+$ | Column: SiO2<br>EtOAc/MeOH |
| 5-2 | | RT (min): 1.408 (Method A)<br>MS (ESI, m/z): 397.1656 (M + H)$^+$ | Column: SiO2<br>EtOAc/MeOH |
| 5-3 | | RT (min): 1.635 (Method A)<br>MS (ESI, m/z): 397.1656 (M + H)$^+$ | Column: SiO2<br>EtOAc/MeOH |

TABLE 88-continued

| Ex. No. | Strc. | P.D. | P.C. |
|---|---|---|---|
| 5-4 | | RT (min): 0.786 (Method A)<br>MS (ESI, m/z): 370.1659 (M + H)+ | Column: SiO2<br>EtOAc/MeOH |
| 5-5 | | RT (min): 0.749 (Method A)<br>MS (ESI, m/z): 370.1658 (M + H)+ | Column: SiO2<br>EtOAc/MeOH |
| 5-6 | | RT (min): 2.228 (Method A)<br>MS (ESI, m/z): 412.1764 (M + H)+ | Column: SiO2<br>EtOAc/MeOH |
| 5-7 | | RT (min): 1.093 (Method A)<br>MS (ESI, m/z): 370.1658 (M + H)+ | Column: SiO2<br>EtOAc/MeOH |

TABLE 89

| Ex. No. | Strc. | P.D. | P.C. |
|---|---|---|---|
| 6-1 | | RT (min): 1.199 (Method A)<br>MS (ESI, m/z): 399.1812 (M + H)$^+$ | Column: SiO2<br>EtOAc/MeOH |
| 6-2 | | RT (min): 1.082 (Method A)<br>MS (ESI, m/z): 399.1812 (M + H)$^+$ | Column: SiO2<br>EtOAc/MeOH |
| 6-3 | | RT (min): 1.079 (Method A)<br>MS (ESI, m/z): 399.1813 (M + H)$^+$ | Column: SiO2<br>EtOAc/MeOH |
| 7-1 | | RT (min): 1.207 (Method A)<br>MS (ESI, m/z): 426.1922 (M + H)$^+$ | Column: APS<br>EtOAc/MeOH |
| 7-2 | | RT (min): 2.989 (Method A)<br>MS (ESI, m/z): 439.2126 (M + H)$^+$ | Column: APS<br>EtOAc/MeOH |

TABLE 89-continued

| Ex. No. | Strc. | P.D. | P.C. |
|---|---|---|---|
| 7-3 | | RT (min): 3.059 (Method A)<br>MS (ESI, m/z): 439.2125 (M + H)$^+$ | Column: APS<br>EtOAc/MeOH |
| 8-1 | | RT (min): 1.842 (Method A)<br>MS (ESI, m/z): 462.1592 (M + H)$^+$ | Column: APS<br>EtOAc/MeOH |

TABLE 90

| Ex. No. | Strc. | P.D. | P.C. |
|---|---|---|---|
| 9-1 | | RT (min): 2.956 (Method A)<br>MS (ESI, m/z): 412.1652 (M + H)$^+$ | Without<br>purification |
| 9-2 | | RT (min): 1.628 (Method A)<br>MS (ESI, m/z): 385.1657 (M + H)$^+$ | Column: SiO2<br>EtOAc/MeOH |

TABLE 90-continued

| Ex. No. | Strc. | P.D. | P.C. |
|---|---|---|---|
| 10-1 | | RT (min): 3.083 (Method A)<br>MS (ESI, m/z): 439.2125 (M + H)+ | Column: APS<br>EtOAc/n-Hexane |
| 10-2 | | RT (min): 2.777 (Method A)<br>MS (ESI, m/z): 455.2075 (M + H)+ | Column: APS<br>EtOAc/MeOH |
| 10-3 | | RT (min): 2.143 (Method A)<br>MS (ESI, m/z): 482.2547 (M + H)+ | Column: APS<br>EtOAc/MeOH |
| 11-1 | | RT (min): 2.463 (Method A)<br>MS (ESI, m/z): 475.2125 (M + H)+ | Without<br>purification |

TABLE 91

| Ex. No. | Strc. | P.D. | P.C. |
|---|---|---|---|
| 12-1 | | RT (min): 1.943 (Method A)<br>MS (ESI, m/z): 471.2023 (M + H)⁺ | Without purification |
| 12-2 | | RT (min): 2.452 (Method A)<br>MS (ESI, m/z): 519.2387 (M + H)⁺ | Without purification |
| 12-3 | | RT (min): 1.558 (Method A)<br>MS (ESI, m/z): 399.1810 (M + H)⁺ | Column: SiO2<br>EtOAc/MeOH |
| 12-4 | | RT (min): 1.756 (Method A)<br>MS (ESI, m/z): 443.2074 (M + H)⁺ | Without purification |

TABLE 91-continued

| Ex. No. | Strc. | P.D. | P.C. |
|---|---|---|---|
| 13-1 | | RT (min): 0.893 (Method A)<br>MS (ESI, m/z): 429.1917 (M + H)+ | Column: SiO2<br>EtOAc/MeOH |
| 14-1 | | RT (min): 2.094 (Method A)<br>MS (ESI, m/z): 480.2391 (M + H)+ | Filtration of<br>EtOAc/n-Hexane<br>suspension |
| 14-2 | | RT (min): 2.055 (Method A)<br>MS (ESI, m/z): 494.2548 (M + H)+ | Filtration of<br>EtOAc/n-Hexane<br>suspension |

TABLE 92

| Ex. No. | Strc. | P.D. | P.C. |
|---|---|---|---|
| 15-1 | | RT (min): 2.740 (Method A)<br>MS (ESI, m/z): 481.2231 (M + H)+ | Column: APS<br>EtOAc/MeOH |

TABLE 92-continued

| Ex. No. | Strc. | P.D. | P.C. |
|---|---|---|---|
| 15-2 | 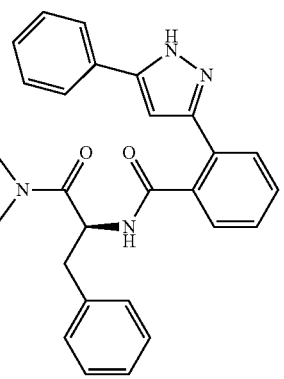 | RT (min): 2.725 (Method A)<br>MS (ESI, m/z): 481.2231 (M + H)⁺ | Column: APS<br>EtOAc/MeOH |
| 16-1 | 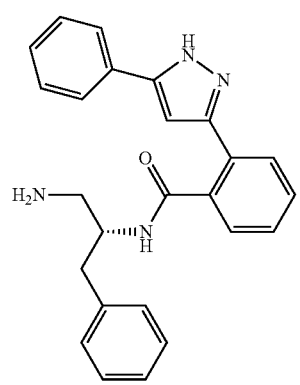 [SMILES: NC[C@@H](Cc1ccccc1)NC(=O)c1ccccc1-c1cc(-c2ccccc2)[nH]n1] | ¹H-NMR (DMSO-d₆) δ ppm: 2.54-2.75 (3H, m), 2.82 (1H, dd, J = 6.0, 13.8 Hz), 3.98-4.12 (1H, m), 6.86 (1H, s), 7.09-7.52 (12H, m), 7.68-7.74 (3H, m), 8.21-8.31 (1H, m).<br>RT (min): 2.419 (Method A)<br>MS (ESI, m/z): 397.2023 (M + H)⁺ | Column: APS<br>EtOAc/MeOH |
| 16-2 | 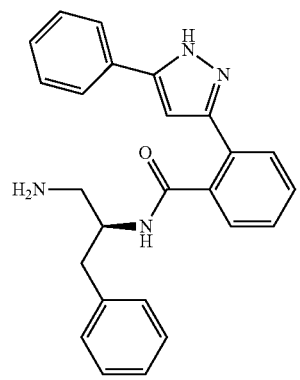 [SMILES: NC[C@H](Cc1ccccc1)NC(=O)c1ccccc1-c1cc(-c2ccccc2)[nH]n1] | ¹H-NMR (DMSO-d₆) δ ppm: 2.54-2.76 (3H, m), 2.82 (1H, dd, J = 6.0, 13.6 Hz), 3.98-4.13 (1H, m), 6.86 (1H, s), 7.09-7.53 (12H, m), 7.66-7.79 (3H, m), 8.21-8.31 (1H, m).<br>RT (min): 2.446 (Method A)<br>MS (ESI, m/z): 397.2020 (M + H)⁺ | Column: APS<br>EtOAc/MeOH |
| 16-3 | 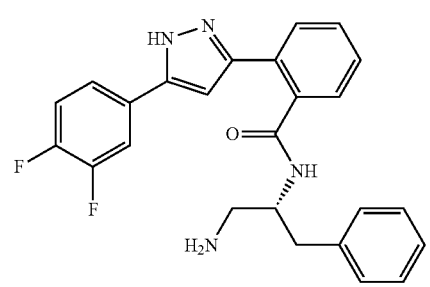 [SMILES: NC[C@@H](Cc1ccccc1)NC(=O)c1ccccc1-c1cc(-c2ccc(F)c(F)c2)[nH]n1] | ¹H-NMR (CDCl₃) δ ppm: 2.74 (1H, dd, J = 8.2 Hz, 13.0 Hz), 2.87 (2H, d, J = 6.9 Hz), 3.00 (1H, dd, J = 4.2, 13.0 Hz), 4.39-4.50 (1H, m), 6.17 (1H, d, J = 8.6 Hz), 6.74 (1H, s), 7.12-7.24 (4H, m), 7.25-7.40 (4H, m), 7.45-7.54 (2H, m), 7.57-7.66 (2H, m).<br>RT (min): 2.583 (Method A)<br>MS (ESI, m/z): 433.1832 (M + H)⁺ | Column: APS<br>EtOAc/MeOH |

TABLE 92-continued

| Ex. No. | Strc. | P.D. | P.C. |
|---|---|---|---|
| 16-4 | | RT (min): 2.567 (Method A)<br>MS (ESI, m/z): 433.1834 (M + H)+ | Column: APS<br>EtOAc/MeOH |
| 16-5 | | ¹H-NMR (CDCl₃) δ ppm: 2.43-2.79 (4H, m), 4.11-4.25 (1H, m), 6.76 (1H, s), 7.03-7.11 (2H, m), 7.14-7.25 (3H, m), 7.28-7.40 (5H, m), 7.48-7.54 (1H, m), 7.57-7.65 (2H, m).<br>RT (min): 2.532 (Method A)<br>MS (ESI, m/z): 431.1632 (M + H)+ | Column: APS<br>EtOAc/MeOH |

TABLE 93

| Ex. No. | Strc. | P.D. | P.C. |
|---|---|---|---|
| 16-6 | | RT (min): 2.663 (Method A)<br>MS (ESI, m/z): 465.1894 (M + H)+ | Column: APS<br>EtOAc/MeOH |
| 16-7 | | ¹H-NMR (CDCl₃) δ ppm: 2.64-2.92 (4H, m), 4.25-4.38 (1H, m), 6.88 (1H, d, J = 3.0 Hz), 7.11-7.40 (12H, m), 7.61-7.67 (2H, m).<br>RT (min): 2.611 (Method A)<br>MS (ESI, m/z): 415.1927 (M + H)+ | Column: APS<br>EtOAc/MeOH |

TABLE 93-continued

| Ex. No. | Strc. | P.D. | P.C. |
|---|---|---|---|
| 16-8 | 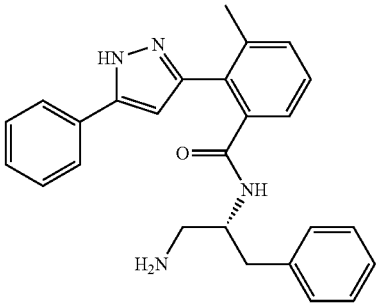 | $^1$H-NMR (CDCl$_3$) δ ppm: 2.28 (3H, s), 2.37-2.47 (1H, m), 2.54-2.63 (2H, m), 2.68-2.76 (1H, m), 4.10-4.23 (1H, m), 6.61 (1H, s), 7.03-7.10 (2, m), 7.13-7.25 (3H, m), 7.28-7.41 (7H, m), 7.64-7.71 (2H, m). RT (min): 2.513 (Method A) MS (ESI, m/z): 411.2176 (M + H)$^+$ | Column: APS EtOAc/MeOH |
| 16-9 | 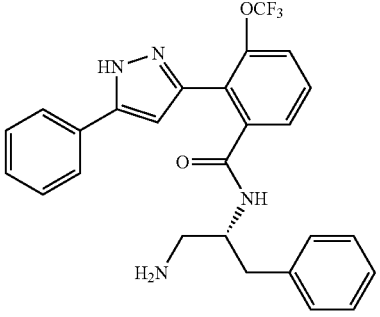 [SMILES: NC[C@@H](Cc1ccccc1)NC(=O)c1cccc(C(F)(F)F)c1-c1cc(-c2ccccc2)[nH]n1] | $^1$H-NMR (CDCl$_3$) δ ppm: 2.56-2.86 (4H, m), 4.14-4.31 (1H, m), 6.78 (1H, s), 7.07-7.14 (2, m), 7.13-7.25 (3H, m), 7.28-7.45 (6H, m), 7.56-7.64 (2H, m). RT (min): 2.821 (Method A) MS (ESI, m/z): 481.1844 (M + H)$^+$ | Column: APS EtOAc/MeOH |
| 16-10 | 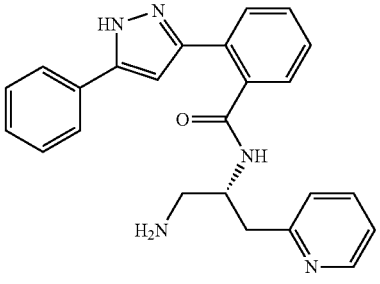 [SMILES: NC[C@@H](Cc1ccccn1)NC(=O)c1ccccc1-c1cc(-c2ccccc2)[nH]n1] | $^1$H-NMR (CDCl$_3$) δ ppm: 2.69-2.77 (1H, m), 2.87-3.03 (2H, m), 3.07-3.14 (1H, m), 4.47-4.61 (1H, m), 6.83 (1H, s), 6.98-7.06 (1H, m), 7.12-7.19 (1H, m), 7.27-7.44 (5H, m), 7.45-7.60 (3H, m), 7.64-7.71 (1H, m), 7.74-7.82 (2H, m), 8.31-8.39 (1H, m). RT (min): 1.447 (Method A) MS (ESI, m/z): 398.1972 (M + H)$^+$ | Column: APS EtOAc/MeOH |
| 16-11 | 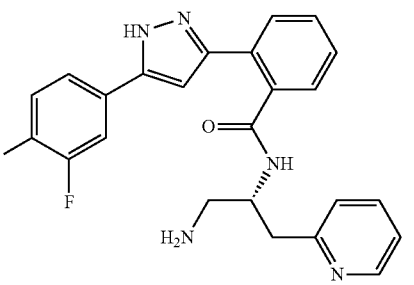 | $^1$H-NMR (CDCl$_3$) δ ppm: 2.74 (1H, dd, J = 8.0 Hz, 12.6 Hz), 2.95 (1H, dd, J = 4.8 Hz, 12.6 Hz), 3.00 (1H, dd, J = 6.6 Hz, 14.3 Hz), 3.14 (1H, dd, J = 5.0, 14.2 Hz), 4.50-4.60 (1H, m), 6.78 (1H, s), 7.02-7.09 (1H, m), 7.14-7.22 (2H, m), 7.36-7.55 (5H, m), 7.56-7.70 (3H, m), 8.33-8.37 (1H, m). RT (min): 1.864 (Method A) MS (ESI, m/z): 434.1785 (M + H)$^+$ | Column: APS EtOAc/MeOH |

TABLE 94

| Ex. No. | Strc. | P.D. | P.C. |
| --- | --- | --- | --- |
| 17-1 | | RT (min): 2.115 (Method A)<br>MS (ESI, m/z): 405.1522 (M + H)⁺ | Column: SiO2<br>EtOAc/MeOH |
| 17-2 | | RT (min): 1.827 (Method A)<br>MS (ESI, m/z): 399.1812 (M + H)⁺ | Column: SiO2<br>EtOAc/MeOH |
| 17-3 | | RT (min): 2.032 (Method A)<br>MS (ESI, m/z): 383.1863 (M + H)⁺ | Column: SiO2<br>EtOAc/MeOH |
| 17-4 | | RT (min): 2.235 (Method A)<br>MS (ESI, m/z): 437.1582 (M + H)⁺ | Column: SiO2<br>EtOAc/MeOH |
| 17-5 | | RT (min): 1.834 (Method A)<br>MS (ESI, m/z): 387.1613 (M + H)⁺ | Column: SiO2<br>EtOAc/MeOH |

TABLE 94-continued

| Ex. No. | Strc. | P.D. | P.C. |
|---|---|---|---|
| 17-6 | | RT (min): 2.496 (Method A)<br>MS (ESI, m/z): 437.1582 (M + H)+ | Column: SiO2<br>EtOAc/MeOH |
| 17-7 | | RT (min): 1.909 (Method A)<br>MS (ESI, m/z): 399.1812 (M + H)+ | Column: SiO2<br>EtOAc/MeOH |
| 17-8 | | RT (min): 2.327 (Method A)<br>MS (ESI, m/z): 403.1318 (M + H)+ | Column: SiO2<br>EtOAc/MeOH |

TABLE 95

| Ex. No. | Strc. | P.D. | P.C. |
|---|---|---|---|
| 17-9 | | RT (min): 2.092 (Method A)<br>MS (ESI, m/z): 383.1864 (M + H)+ | Column: SiO2<br>EtOAc/MeOH |
| 17-10 | | RT (min): 2.306 (Method A)<br>MS (ESI, m/z): 403.1316 (M + H)+ | Column: SiO2<br>EtOAc/MeOH |

TABLE 95-continued

| Ex. No. | Strc. | P.D. | P.C. |
|---|---|---|---|
| 17-11 | | RT (min): 3.774 (Method A)<br>MS (ESI, m/z): 430.1922 (M + H)+ | Column: SiO2<br>EtOAc/MeOH |
| 18-1 | | RT (min): 2.811 (Method A)<br>MS (ESI, m/z): 384.1817 (M + H)+ | Column: APS<br>EtOAc/MeOH |
| 18-2 | | RT (min): 2.132 (Method A)<br>MS (ESI, m/z): 384.1813 (M + H)+ | Column: APS<br>EtOAc/MeOH |

TABLE 96

| Ex. No. | Strc. | P.D. | P.C. |
|---|---|---|---|
| 19-1 | | 1H-NMR (CDCl3) δ ppm: 3.15 (1H, dd, J = 4.7 Hz, 14.0 Hz), 3.36 (1H, dd, J = 6.8 Hz, 14.2 Hz), 3.75 (1H, dd, J = 4.1 Hz, 11.7 Hz), 3.84 (1H, dd, J = 3.5 Hz, 11.7 Hz), 4.43-4.52 (1H, m), 6.65 (1H, ddd, J = 2.5 8.4, 8.4 Hz), 6.72-6.78 (2H, m), 6.96-7.02 (1H, m), 7.06-7.15 (2H, m), 7.38-7.42 (2H, m), 7.46-7.67 (4H, m), 7.66-7.71 (1H, m), 8.37-8.41 (1H, m).<br>RT (min): 1.781 (Method A)<br>MS (ESI, m/z): 433.1667 (M + H)+ | Column: SiO2<br>EtOAc/MeOH |
| 19-2 | | RT (min): 1.077 (Method A)<br>MS (ESI, m/z): 385.1656 (M + H)+ | Column: SiO2<br>EtOAc/MeOH |

TABLE 96-continued

| Ex. No. | Strc. | P.D. | P.C. |
|---|---|---|---|
| 19-3 | | RT (min): 1.158 (Method A)<br>MS (ESI, m/z): 385.1658 (M + H)+ | Column: SiO2<br>EtOAc/MeOH |
| 19-4 | | RT (min): 1.510 (Method A)<br>MS (ESI, m/z): 403.1562 (M + H)+ | Column: SiO2<br>EtOAc/MeOH |
| 19-5 | | RT (min): 0.958 (Method A)<br>MS (ESI, m/z): 415.1762 (M + H)+ | Column: SiO2<br>EtOAc/MeOH |
| 19-6 | | 1H-NMR (CDCl3) δ ppm: 2.86 (1H, dd, J = 8.9 Hz, 13.9 Hz), 3.03 (1H, dd, J = 5.8 Hz, 13.9 Hz), 3.38-3.45 (1H, m), 3.47-3.55 (1H, m), 4.29-4.38 (1H, m), 6.75 (1H, s), 7.09-7.21 (4H, m), 7.21-7.50 (4H, m), 7.60-7.80 (2H, m), 8.45-8.49 (1H, m).<br>RT (min): 1.108 (Method A)<br>MS (ESI, m/z): 433.1669 (M + H)+ | Column: SiO2<br>EtOAc/MeOH |
| 19-7 | | RT (min): 1.395 (Method A)<br>MS (ESI, m/z): 433.1668 (M + H)+ | Column: SiO2<br>EtOAc/MeOH |

TABLE 97

| Ex. No. | Strc. | P.D. | P.C. |
|---|---|---|---|
| 19-8 | | RT (min): 1.143 (Method A)<br>MS (ESI, m/z): 433.1668 (M + H)$^+$ | Column: SiO2<br>EtOAc/MeOH |
| 20-1 | | RT (min): 1.997 (Method A)<br>MS (ESI, m/z): 383.1863 (M + H)$^+$ | Column: APS<br>EtOAc/MeOH |
| 20-2 | | RT (min): 2.812 (Method A)<br>MS (ESI, m/z): 383.1863 (M + H)$^+$ | Column: APS<br>EtOAc/MeOH |
| 20-3 | | RT (min): 2.192 (Method A)<br>MS (ESI, m/z): 383.1864 (M + H)$^+$ | Column: APS<br>EtOAc/MeOH |

TABLE 97-continued

| Ex. No. | Strc. | P.D. | P.C. |
|---|---|---|---|
| 21-1 | | RT (min): 2.730 (Method A)<br>MS (ESI, m/z): 411.1813 (M + H)⁺ | Column: SiO2<br>EtOAc/MeOH |
| 22-1 | | RT (min): 1.978 (Method A)<br>MS (ESI, m/z): 384.1816 (M + H)⁺ | Column: APS<br>EtOAc/MeOH |
| 22-2 | | RT (min): 2.020 (Method A)<br>MS (ESI, m/z): 384.1816 (M + H)⁺ | Column: APS<br>EtOAc/MeOH |

TABLE 98

| Ex. No. | Strc. | P.D. | P.C. |
|---|---|---|---|
| 23-1 | | RT (min): 1.355 (Method A)<br>MS (ESI, m/z): 465.1732 (M + H)⁺ | Column: SiO2<br>EtOAc/MeOH. |

TABLE 98-continued
| Ex. No. | Strc. | P.D. | P.C. |
| --- | --- | --- | --- |
| 23-2 | 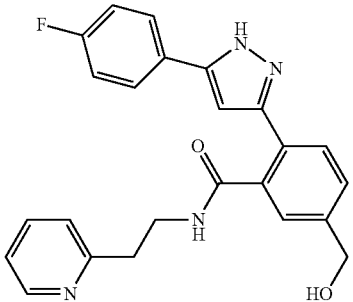 [SMILES: O=C(NCCc1ccccn1)c1cc(CO)ccc1-c1cc(-c2ccc(F)cc2)[nH]n1] | RT (min): 1.523 (Method A)<br>MS (ESI, m/z): 417.1720 (M + H)+ | Column: SiO2<br>EtOAc/MeOH. |
| 23-3 | 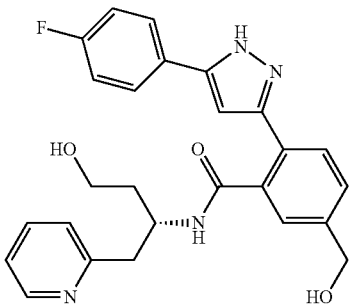 [SMILES: O=C(N[C@@H](CCO)Cc1ccccn1)c1cc(CO)ccc1-c1cc(-c2ccc(F)cc2)[nH]n1] | RT (min): 1.370 (Method A)<br>MS (ESI, m/z): 461.1983 (M + H)+ | Column: SiO2<br>EtOAc/MeOH. |
TABLE 99
| Ex. No. | Strc. | P.D. | P.C. |
| --- | --- | --- | --- |
| 24-1 | 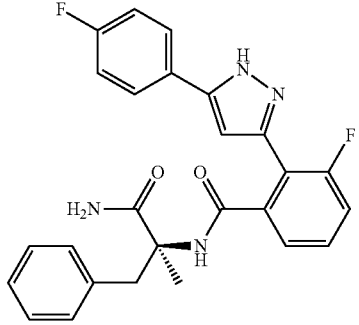 [SMILES: C[C@@](Cc1ccccc1)(NC(=O)c1cccc(F)c1-c1cc(-c2ccc(F)cc2)[nH]n1)C(N)=O] | 1H-NMR (CDCl3) δ ppm: 1.55 (3H, s), 3.21 (1H, d, J = 13.6 Hz), 3.54 (1H, d, J = 13.6 Hz), 6.11 (1H, s), 6.22-6.44 (1H, m), 6.82 (1H, d, J = 3.9 Hz), 6.98-7.07 (2H, m), 7.08-7.17 (3H, m), 7.18-7.35 (6H, m), 7.58-7.67 (2H, m).<br>RT (min): 3.186 (Method A)<br>MS (ESI, m/z): 461.1783 (M + H)+ | Column: APS<br>EtOAc/MeOH |
| 24-2 | 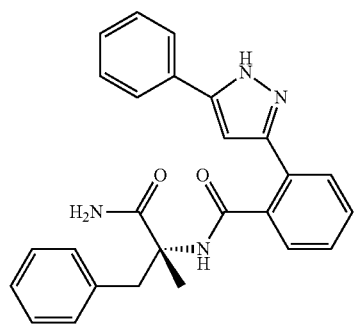 [SMILES: C[C@](Cc1ccccc1)(NC(=O)c1ccccc1-c1cc(-c2ccccc2)[nH]n1)C(N)=O] | RT (min): 3.104 (Method A)<br>MS (ESI, m/z): 425.1968 (M + H)+ | Column: APS<br>EtOAc/MeOH |

TABLE 99-continued

| Ex. No. | Strc. | P.D. | P.C. |
|---|---|---|---|
| 24-3 | 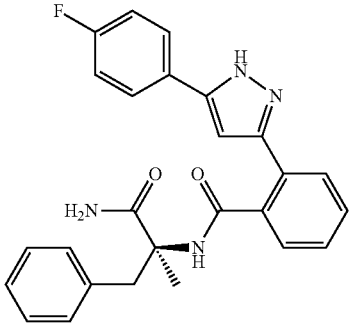 [SMILES: C[C@@](Cc1ccccc1)(NC(=O)c1ccccc1-c1cc(-c2ccc(F)cc2)[nH]n1)C(N)=O] | ¹H-NMR (CDCl₃) δ ppm: 1.62 (3H, s), 3.31 (1H, d, J = 13.6 Hz), 3.55 (1H, d, J = 13.6 Hz), 6.00-6.40 (2H, m), 6.73 (1H, s), 7.02-7.10 (2H, m)s, 7.11-7.17 (2H, m), 7.18-7.24 (3H, m), 7.29-7.38 (3H, m), 7.44-7.52 (1H, m), 7.60-7.72 (3H, m).<br>RT (min): 3.160 (Method A)<br>MS (ESI, m/z): 443.1875 (M + H)⁺ | Column: APS<br>EtOAc/MeOH |
| 24-4 | 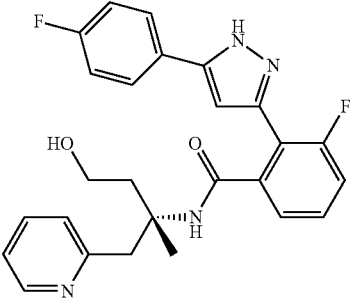 [SMILES: C[C@](CCO)(Cc1ccccn1)NC(=O)c1cccc(F)c1-c1cc(-c2ccc(F)cc2)[nH]n1] | ¹H-NMR (CDCl₃) δ ppm: 1.50 (3H, m), 1.94-2.12 (2H, m), 3.21 (2H, s), 3.72-3.85 (2H, m), 6.87 (1H, d, J = 3.8 Hz), 7.04-7.19 (5H, m), 7.21-7.29 (2H, m), 7.31-7.40 (1H, m), 7.52-7.60 (1H, m), 7.73-7.84 (2H, m), 8.40-8.46 (1H, m).<br>RT (min): 1.967 (Method A)<br>MS (ESI, m/z): 463.1938 (M + H)⁺ | Column: APS<br>EtOAc/MeOH |
| 24-5 | 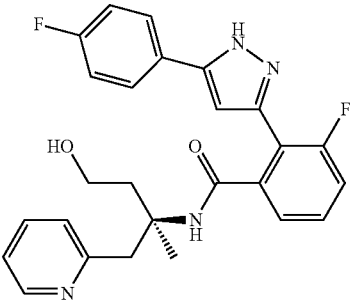 [SMILES: C[C@@](CCO)(Cc1ccccn1)NC(=O)c1cccc(F)c1-c1cc(-c2ccc(F)cc2)[nH]n1] | RT (min): 1.971 (Method A)<br>MS (ESI, m/z): 463.1936 (M + H)⁺ | Column: APS<br>EtOAc/MeOH |
| 24-6 | 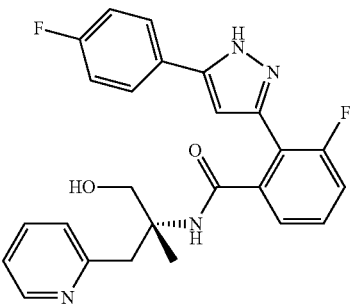 [SMILES: C[C@](CO)(Cc1ccccn1)NC(=O)c1cccc(F)c1-c1cc(-c2ccc(F)cc2)[nH]n1] | RT (min): 2.048 (Method A)<br>MS (ESI, m/z): 449.1779 (M + H)⁺ | Column: APS<br>EtOAc/MeOH |

TABLE 99-continued

| Ex. No. | Strc. | P.D. | P.C. |
|---|---|---|---|
| 24-7 | | ¹H-NMR (CDCl₃) δ ppm: 1.70 (3H, s), 3.07-3.17 (1H, m), 3.32-3.41 (1H, m), 6.88 (1H, d, J = 4.2 Hz), 6.98-7.10 (3H, m), 7.17-7.30 (3H, m), 7.30-7.42 (1H, m), 7.54-7.68 (3H, m), 8.26-8.33 (1H, m), 8.40-8.45 (1H, m).<br>RT (min): 2.058 (Method A)<br>MS (ESI, m/z): 462.1736 (M + H)⁺ | Column: SiO2<br>EtOAc/MeOH |

TABLE 100

| Ex. No. | Strc. | P.D. | P.C. |
|---|---|---|---|
| 25-1 | | RT (min): 2.149 (Method A)<br>MS (ESI, m/z): 427.1926 (M + H)⁺ | Column: APS<br>EtOAc/MeOH |
| 26-1 | | ¹H-NMR (CDCl₃) δ ppm: 1.35-1.47 (1H, m), 1.75-1.87 (1H, m), 2.90 (1H, dd, J = 6.1, 14.4 Hz), 3.12 (1H, dd, J = 4.5, 14.4 Hz), 3.55-3.69 (2H, m), 4.56-4.68 (1H, m), 6.82 (1H, d, J = 3.0 Hz), 7.03-7.17 (4H, m), 7.22-7.33 (2H, m), 7.34-7.44 (1H, m), 7.53-7.61 (1H, m), 7.66-7.75 (2H, m), 7.75-7.83 (1H, m), 8.33-8.41 (1H, m).<br>RT (min): 1.776 (Method A)<br>MS (ESI, m/z): 449.1782 (M + H)⁺ | Column: APS<br>EtOAc/MeOH |
| 26-2 | | ¹H-NMR (CDCl₃) δ ppm: 1.39-1.49 (1H, m), 1.79-1.93 (1H, m), 2.93 (1H, dd, J = 6.0, 14.4 Hz), 3.19 (1H, dd, J = 4.6, 14.4 Hz), 3.57-3.72 (2H, m), 4.60-4.75 (1H, m), 6.74 (1H, s), 7.05-7.18 (4H, m), 7.39-7.45 (1H, m), 7.49-7.61 (3H, m), 7.65-7.70 (1H, m), 7.74-7.82 (2H, m), 7.89-7.99 (1H, m), 8.35-8.40 (1H, m).<br>RT (min): 1.662 (Method A)<br>MS (ESI, m/z): 431.1874 (M + H)⁺ | Column: APS<br>EtOAc/MeOH |

TABLE 101

| Ex. No. | Strc. | P.D. | P.C. |
|---|---|---|---|
| 27-1 | | ¹H-NMR (CDCl₃) δ ppm: 3.28-3.32 (1H, m), 3.34 (3H, s), 3.41 (1H, dd, J = 11.7, 7.3 Hz), 3.59 (1H, dd, J = 4.3, 11.7 Hz), 4.31-4.41 (2H, m), 4.69-7.76 (1H, m), 6.24 (1H, t, J = 2.0 Hz), 6.61 (1H, d, J = 8.7 Hz), 6.80 (1H, d, J = 3.1 Hz), 7.05-7.11 (2H, m), 7.21-7.27 (2H, m), 7.35-7.40 (1H, m), 7.42 (1H, d, J = 2.2 Hz), 7.47 (1H, d, J = 1.5 Hz), 7.68-7.73 (2H, m). RT (min): 2.615 (Method A) MS (ESI, m/z): 468.1841 (M + H)⁺ | Column: SiO2 EtOAc/MeOH |
| 27-2 | | RT (min): 1.861 (Method A) MS (ESI, m/z): 449.1779 (M + H)⁺ | Column: SHISEIDO CAPCELL PAK C18 UG80 H2O/MeCN |
| 27-3 | | RT (min): 1.787 (Method A) MS (ESI, m/z): 468.1841 (M + H)⁺ | Column: APS EtOAc/MeOH |
| 27-4 | | ¹H-NMR (CDCl₃) δ ppm: 3.02 (1H, dd, J = 5.8, 14.3 Hz), 3.07-3.23 (6H, m), 3.80-3.87 (1H, m), 4.30-4.45 (1H, m), 6.70 (1H, s), 6.80-6.91 (1H, m), 7.05-7.12 (3H, m), 7.12-7.17 (1H, m), 7.22-7.35 (2H, m), 7.47-7.57 (2H, m), 7.68-7.77 (2H, m), 8.34-8.38 (1H, m). RT (min): 1.871 (Method A) MS (ESI, m/z): 479.1885 (M + H)⁺ | Column: SiO2 EtOAc/MeOH |
| 27-5 | | ¹H-NMR (CDCl₃) δ ppm: 3.13 (1H, dd, J = 5.4, 14.4 Hz), 3.26 (3H, s), 3.26-3.42 (3H, m), 3.93-4.00 (1H, m), 4.46-4.56 (1H, m), 6.75 (1H, d, J = 8.8 Hz), 6.81 (1H, d, J = 3.6 Hz), 7.04-7.16 (5H, m), 7.18-7.27 (1H, m), 7.28-7.37 (1H, m), 7.49 (1H, td, J = 1.8, 7.7 Hz), 7.74-7.82 (2H, m), 8.34-8.41 (1H, m). RT (min): 2.013 (Method A) MS (ESI, m/z): 495.1592 (M + H)⁺ | Column: SiO2 EtOAc/MeOH |

TABLE 101-continued

| Ex. No. | Strc. | P.D. | P.C. |
|---|---|---|---|
| 27-6 | 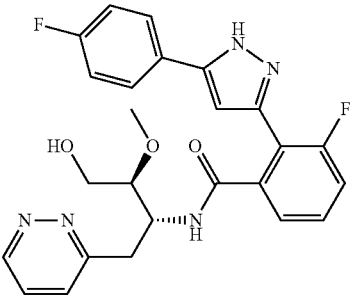 [SMILES: CO[C@H](CO)[C@@H](Cc1cccnn1)NC(=O)c1cccc(F)c1-c1cc(-c2ccc(F)cc2)[nH]n1] | ¹H-NMR (CDCl₃) δ ppm: 3.20-3.25 (1H, m), 3.33-3.45 (3H, m), 3.38 (3H, s), 3.64 (1H, dd, J = 16.5, 9.4 Hz), 4.71-4.77 (1H, m), 6.73-6.76 (2H, m), 7.07-7.11 (2H, m), 7.16-7.24 (2H, m), 7.29-7.38 (2H, m), 7.43 (1H, dd, J = 8.6, 1.5 Hz), 7.70-7.74 (2H, m), 8.94 (1H, dd, J = 5.0, 1.5 Hz).<br>RT (min): 2.214 (Method A)<br>MS (ESI, m/z): 480.1841 (M + H)⁺ | Column: SiO2<br>EtOAc/MeOH |
| 27-7 | 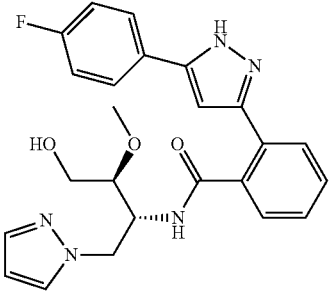 [SMILES: CO[C@H](CO)[C@@H](Cn1cccn1)NC(=O)c1ccccc1-c1cc(-c2ccc(F)cc2)[nH]n1] | ¹H-NMR (CDCl₃) δ ppm: 3.31-3.35 (1H, m), 3.35 (3H, s), 3.43 (1H, dd, J = 11.6, 7.3 Hz), 3.62 (1H, dd, J = 11.6, 4.6 Hz), 4.33-4.44 (2H, m), 4.74-4.80 (1H, m), 6.23 (1H, t, J = 2.0 Hz), 6.66-6.73 (2H, m), 7.05-7.10 (2H, m), 7.35-7.50 (5H, m), 7.59 (1H, dbr, J = 7.4 Hz), 7.71-7.75 (2H, m).<br>RT (min): 2.554 (Method A)<br>MS (ESI, m/z): 450.1936 (M + H)⁺ | Column: SiO2<br>EtOAc/MeOH |

TABLE 102

| Ex. No. | Strc. | P.D. | P.C. |
|---|---|---|---|
| 27-8 | 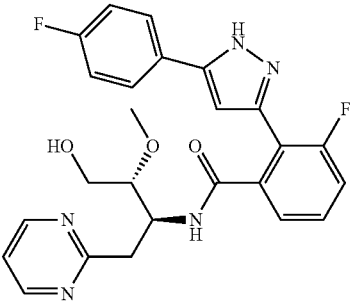 [SMILES: CO[C@@H](CO)[C@H](Cc1ncccn1)NC(=O)c1cccc(F)c1-c1cc(-c2ccc(F)cc2)[nH]n1] | RT (min): 2.371 (Method A)<br>MS (ESI, m/z): 480.1844 (M + H)⁺ | Column: SiO2<br>EtOAc/MeOH |
| 27-9 | 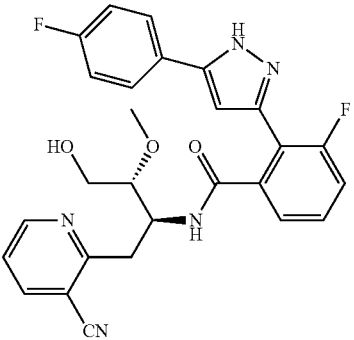 [SMILES: CO[C@@H](CO)[C@H](Cc1ncccc1C#N)NC(=O)c1cccc(F)c1-c1cc(-c2ccc(F)cc2)[nH]n1] | RT (min): 2.742 (Method A)<br>MS (ESI, m/z): 504.1840 (M + H)⁺ | Column: SiO2<br>EtOAc/MeOH |

TABLE 102-continued

| Ex. No. | Strc. | P.D. | P.C. |
|---|---|---|---|
| 27-10 | | RT (min): 2.300 (Method A)<br>MS (ESI, m/z): 480.1841 (M + H)⁺ | Column: APS<br>EtOAc/MeOH |
| 27-11 | | $^1$H-NMR (CDCl$_3$) δ ppm: 3.14-3.38 (3H, m), 3.27 (3H, s), 3.67 (1H, d, J = 12.5 Hz), 3.82 (1H, d, J = 12.5 Hz), 4.73 (1H, br), 7.06-7.13 (3H, m), 7.26-7.32 (1H, m), 7.41-7.47 (2H, m), 7.61 (1H, d, J = 7.0 Hz), 7.78 (2H, br), 8.56 (2H, d, J = 4.4 Hz).<br>RT (min): 2.525 (Method A)<br>MS (ESI, m/z): 498.1750 (M + H)⁺ | Column: APS<br>EtOAc/MeOH |
| 27-12 | | $^1$H-NMR (CDCl$_3$) δ ppm: 3.19-3.35 (3H, m), 3.30 (3H, s), 3.71 (1H, dd, J = 12.5, 2.7 Hz), 3.83 (1H, dd, J = 12.5, 3.6 Hz), 4.77-4.84 (1H, m), 6.85 (1H, d, J = 3.3 Hz), 7.07 (1H, t, J = 5.0 Hz), 7.24-7.45 (6H, m), 7.70 (2H, d, J = 8.6 Hz), 8.57 (2H, d, J = 4.8 Hz).<br>RT (min): 2.588 (Method A)<br>MS (ESI, m/z): 496.1548 (M + H)⁺ | Column: APS<br>EtOAc/MeOH |
| 27-13 | | RT (min): 2.443 (Method A)<br>MS (ESI, m/z): 496.1544 (M + H)⁺ | Column: APS<br>EtOAc/MeOH |
| 27-14 | | $^1$H-NMR (CDCl$_3$) δ ppm: 3.29-3.33 (1H, m), 3.34 (3H, s), 3.41 (1H, dd, J = 11.6, 7.5 Hz), 3.59 (1H, dd, J = 11.6, 4.6 Hz), 4.31-4.41 (2H, m), 4.69-4.76 (1H, m), 6.24 (1H, t, J = 2.2 Hz), 6.62 (1H, d, J = 9.1 Hz), 6.82 (1H, d, J = 3.2 Hz), 7.21-7.27 (2H, m), 7.35-7.40 (3H, m), 7.42 (1H, d, J = 2.2 Hz), 7.46 (1H, d, J = 1.4 Hz), 7.67 (2H, d, J = 8.4 Hz).<br>RT (min): 2.898 (Method A)<br>MS (ESI, m/z): 484.1546 (M + H)⁺ | Column: APS<br>EtOAc/MeOH |

TABLE 103

| Ex. No. | Strc. | P.D. | P.C. |
|---|---|---|---|
| 27-15 | | $^1$H-NMR (CDCl$_3$) δ ppm: 3.17-3.21 (1H, m), 3.24-3.29 (1H, m), 3.26 (3H, s), 3.47 (1H, dd, J = 11.5, 4.5 Hz), 4.21-4.31 (1H, m), 4.59-4.66 (1H, m), 6.23 (1H, t, J = 2.2 Hz), 6.61 (1H, d, J = 8.9 Hz), 6.74 (1H, s), 7.06-7.11 (2H, m), 7.32-7.37 (2H, m), 7.38 (1H, d, J = 1.8 Hz), 7.45 (1H, d, J = 1.8 Hz), 7.55 (1H, d, J = 7.4, 2.2 Hz), 7.67-7.7 (2H, m). RT (min): 2.864 (Method A) MS (ESI, m/z): 484.1548 (M + H)$^+$ | Column: APS EtOAc/MeOH |
| 27-16 | | $^1$H-NMR (CDCl$_3$) δ ppm: 3.33-3.37 (2H, m), 3.39 (3H, s), 3.47-3.53 (2H, m), 3.68-3.76 (1H, m), 4.85-4.92 (1H, m), 6.66 (1H, d, J = 8.1 Hz), 6.80 (1H, d, J = 2.4 Hz), 7.09-7.17 (3H, m), 7.23-7.32 (2H, m), 7.37-7.42 (1H m), 7.71-7.74 (2H, m), 7.81 (1H, dd, J = 7.6, 1.1 Hz), 8.63 (1H, d, J = 4.9 Hz). RT (min): 2.857 (Method A) MS (ESI, m/z): 504.1842 (M + H)$^+$ | Column: APS EtOAc/MeOH |
| 27-17 | | $^1$H-NMR (CDCl$_3$) δ ppm: 2.44 (2H, d, J = 9.2 Hz), 3.27 (3H, s), 3.49 (1H, d, J = 13.6 Hz), 3.79 (1H, dd, J = 13.6 2.2 Hz), 4.20 (1H, dd, J = 13.9, 2.1 Hz), 4.49-4.55 (1H, m), 4.60 (1H, dd, J = 13.9, 4.3 Hz), 6.23 (1H, t, J = 2.1 z), 6.84 (1H, d, J = 3.1 Hz), 7.07-7.12 (2H, m), 7.28-7.45 (5H, m), 7.68-7.72 (2H, m), 7.86 (1H, d, J = 8.2 Hz). RT (min): 2.663 (Method A) MS (ESI, m/z): 468.1843 (M + H)$^+$ | Column: SiO2 EtOAc/MeOH |
| 27-18 | | $^1$H-NMR (CDCl$_3$) δ ppm: 3.20-3.32 (5H, m), 3.42-3.49 (2H, m), 3.63-3.69 (1H, m), 4.80-4.85 (1H, m), 7.05 (2H, t, J = 4.9 Hz), 7.10 (2H, t, J = 8.0 Hz), 7.28-7.32 (1H m), 7.39-7.48 (2H, m), 7.78 (2H, br), 8.57 (2H, d; J = 5.0 Hz). RT (min): 2.708 (Method A) MS (ESI, m/z): 498.1747 (M + H)$^+$ | Column: APS EtOAc/MeOH |
| 27-19 | | $^1$H-NMR (CDCl$_3$) δ ppm: 3.32-3.35 (2H, m), 3.34 (3H, s), 3.40-3.42 (2H, m), 3.61-3.66 (1H, m), 4.71-7.77 (1H, m), 6.69 (1H, d, J = 9.2 Hz), 6.80 (1H, d, J = 2.8 Hz), 7.07-7.11 (2H, m), 7.17 (1H, d, J = 3.1 Hz), 7.23-7.29 (2H, m), 7.34-7.40 (1H, m), 7.65 (1H, d, J = 3.1 Hz), 7.71-7.74 (2H, m). RT (min): 2.794 (Method A) MS (ESI, m/z): 485.1454 (M + H)$^+$ | Column: SiO2 EtOAc/MeOH |

TABLE 103-continued

| Ex. No. | Strc. | P.D. | P.C. |
|---|---|---|---|
| 27-20 | | ¹H-NMR (CDCl₃) δ ppm: 3.17 (1H, dd, J = 7.4, 2.3 Hz), 3.35 (3H, s), 3.40-3.47 (2H, m), 3.62-3.68 (1H, m), 4.79 (1H, dd, J = 15.0, 7.4 Hz), 6.71 (1H, d, J = 9.4 Hz), 6.76 (1H, d, J = 3.0 Hz), 7.05-7.11 (3H, m), 7.21-7.38 (4H, m), 7.68-7.71 (2H, m), 8.24 (1H, dt, J = 4.5, 1.2 Hz), RT (min): 2.869 (Method A)<br>MS (ESI, m/z): 497.1794 (M + H)⁺ | Column: SiO2<br>EtOAc/MeOH |
| 27-21 | | ¹H-NMR (CDCl₃) δ ppm: 3.12-3.17 (2H, m), 3.35 (3H, s), 3.35-3.42 (2H, m), 3.63-3.65 (1H, m), 4.71-4.78 (1H, m), 6.64-6.67 (1H, m), 6.80 (1H, br), 7.04 (1H, br), 7.07-7.12 (2H, m), 7.23-7.29 (2H, m), 7.35-7.40 (1H, m), 7.72-7.76 (2H, m), 8.70 (1H, br).<br>RT (min): 2.726 (Method A)<br>MS (ESI, m/z): 485.1452 (M + H)⁺ | Column: APS<br>EtOAc/MeOH |

TABLE 104

| Ex. No. | Strc. | P.D. | P.C. |
|---|---|---|---|
| 27-22 | | ¹H-NMR (CDCl₃) δ ppm: 3.33 (3H, s), 3.35-3.46 (2H, m), 3.64 (1H, dd, J = 11.9, 4.5 Hz), 4.66-4.68 (2H, m), 4.84-4.92 (1H, m), 6.54-6.56 (1H, m), 6.79 (1H, br), 7.06-7.10 (2H, m), 7.23-7.30 (2H, m), 7.37-7.42 (1H, m), 7.57 (2H, s), 7.67-7.71 (2H, m).<br>RT (min): 2.691 (Method A)<br>MS (ESI, m/z): 469.1794 (M + H)⁺ | Column: APS<br>EtOAc/MeOH |
| 27-23 | | RT (min): 2.445 (Method A)<br>MS (ESI, m/z): 469.1793 (M + H)⁺ | Column: SiO2<br>EtOAc/MeOH |

TABLE 104-continued

| Ex. No. | Strc. | P.D. | P.C. |
|---|---|---|---|
| 27-24 | | ¹H-NMR (CDCl₃) δ ppm: 2.47 (1H, d, J = 9.9 Hz), 3.27 (3H, s), 3.46-3.49 (1H, m), 3.80 (1H, dd, J = 13.8, 1.8 Hz), 4.23 (1H, dd, J = 14.6, 1.8 Hz), 4.46-4.53 (1H, m), 4.61 (1H, dd, J = 13.8, 4.6 Hz), 6.23 (1H, t, J = 2.3 Hz), 7.08-7.13 (2H, m), 7.31-7.38 (2H, m), 7.45-7.54 (3H, m), 7.73-7.78 (2H, m), 7.94-7.96 (1H, m).<br>RT (min): 2.951 (Method A)<br>MS (ESI, m/z): 486.1746 (M + H)⁺ | Column: APS EtOAc/MeOH |
| 27-25 | | ¹H-NMR (CDCl₃) δ ppm: 3.31-3.34 (1H, m), 3.34 (3H, s), 3.43-3.48 (1H, m), 3.61 (1H, dd, J = 11.5, 4.5 Hz), 4.33-4.44 (2H, m), 4.67-4.74 (1H, m), 6.24 (1H, t, J = 2.1 Hz), 6.67-6.69 (1H, m), 7.09 (2H, t, J = 8.8 Hz), 7.30-7.34 (2H, m), 7.41-7.47 (3H, m), 7.75 (2H, br).<br>RT (min): 2.913 (Method A)<br>MS (ESI, m/z): 486.1747 (M + H)⁺ | Column: APS EtOAc/MeOH |
| 27-26 | | RT (min): 2.355 (Method A)<br>MS (ESI, m/z): 469.1793 (M + H)⁺ | Column: APS EtOAc/MeOH |
| 27-27 | | RT (min): 2.600 (Method A)<br>MS (ESI, m/z): 487.1699 (M + H)⁺ | Column: APS EtOAc/MeOH |
| 27-28 | | ¹H-NMR (CDCl₃) δ ppm: 2.01 (3H, s), 3.27-3.43 (2H, m), 3.34 (3H, s), 3.58 (1H, dd, J = 11.5, 4.5 Hz), 4.24-4.30 (2H, m), 4.64-4.70 (1H, m), 6.67 (1H, d, J = 8.7 Hz), 6.79 (1H, d, J = 2.4 Hz), 7.07 (2H, t, J = 8.7 Hz), 7.17 (1H, s), 7.22-7.25 (3H, m), 7.33-7.39 (1H, m), 7.68-7.73 (1H, m).<br>RT (min): 2.905 (Method A)<br>MS (ESI, m/z): 482.1997 (M + H)⁺ | Column: APS EtOAc/MeOH |

TABLE 105

| Ex. No. | Strc. | P.D. | P.C. |
|---|---|---|---|
| 27-29 | | RT (min): 3.116 (Method A)<br>MS (ESI, m/z): 502.1451 (M + H)$^+$ | Column: APS<br>EtOAc/MeOH |
| 27-30 | | $^1$H-NMR (CDCl$_3$) δ ppm: 3.31 (3H, s), 3.37 3.40 (1H, m), 3.46-3.54 (1H, m), 3.60-3.67 (1H, m), 4.68-4.71 (2H, m), 4.82-4.89 (1H, m), 6.58-6.67 (1H, m), 7.04-7.09 (2H, m), 7.29-7.33 (1H, m), 7.40-7.51 (2H, m), 7.57 (2H, s), 7.63-7.78 (2H, m).<br>RT (min): 2.814 (Method A)<br>MS (ESI, m/z): 487.1701 (M + H)$^+$ | Column: APS<br>EtOAc/MeOH |
| 27-31 | | RT (min): 2.560 (Method A)<br>MS (ESI, m/z): 442.2247 (M + H)$^+$ | Column: APS<br>EtOAc/MeOH |

TABLE 106

| Ex. No. | Strc. | P.D. | P.C. |
|---|---|---|---|
| 28-1 | | $^1$H-NMR (CDCl$_3$) δ ppm: 1.34-1.46 (1H, m), 1.74-1.86 (1H, m), 2.89 (1H, dd, J = 5.8 Hz, 14.5 Hz), 3.14 (1H, dd, J = 4.3 Hz, 14.2 Hz), 3.54-3.69 (2H, m), 4.56-4.66 (1H, m), 7.03-7.14 (4H, m), 7.24-7.35 (2H, m), 7.38-7.42 (1H, m), 7.46 (1H, dd, J = 5.0 Hz, 8.0 Hz), 7.56 (1H, dt, J = 1.8 Hz, 7.6 Hz), 7.74-7.82 (2H, m), 8.37-8.40 (1H, m).<br>RT (min): 1.974 (Method A)<br>MS (ESI, m/z): 467.1688 (M + H)$^+$ | Column: SiO2<br>EtOAc/MeOH |

TABLE 106-continued

| Ex. No. | Strc. | P.D. | P.C. |
|---|---|---|---|
| 28-2 | | RT (min): 0.961 (Method A)<br>MS (ESI, m/z): 385.1658 (M + H)⁺ | Column: APS<br>EtOAc/MeOH |
| 28-3 | | RT (min): 2.336 (Method A)<br>MS (ESI, m/z): 435.1923 (M + H)⁺ | Without purification |

TABLE 107

| Ex. No. | Strc. | P.D. | P.C. |
|---|---|---|---|
| 28-4 | | RT (min): 1.989 (Method A)<br>MS (ESI, m/z): 403.1316 (M + H)⁺ | Column: SiO2<br>EtOAc/MeOH |
| 28-5 | | RT (min): 1.856 (Method A)<br>MS (ESI, m/z): 383.1863 (M + H)⁺ | Column: APS<br>EtOAc/MeOH |

TABLE 107-continued
| Ex. No. | Strc. | P.D. | P.C. |
|---|---|---|---|
| 28-6 | 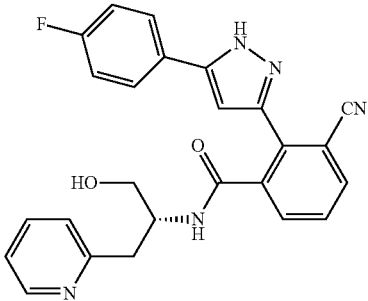 [SMILES: N#Cc1cccc(C(=O)N[C@@H](CO)Cc2ccccn2)c1-c1cc(-c2ccc(F)cc2)[nH]n1] | RT (min): 1.525 (Method A)<br>MS (ESI, m/z): 442.1672 (M + H)+ | Column: APS<br>EtOAc/MeOH |
| 28-7 | 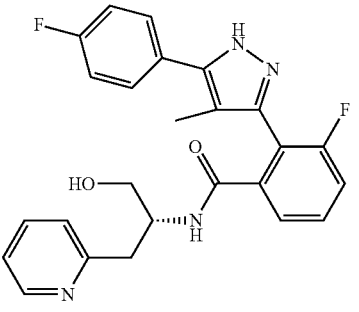 [SMILES: Cc1c(-c2c(F)cccc2C(=O)N[C@@H](CO)Cc2ccccn2)n[nH]c1-c1ccc(F)cc1] | RT (min): 1.965 (Method A)<br>MS (ESI, m/z): 449.1780 (M + H)+ | Column: SiO2<br>EtOAc/MeOH |
| 28-8 | 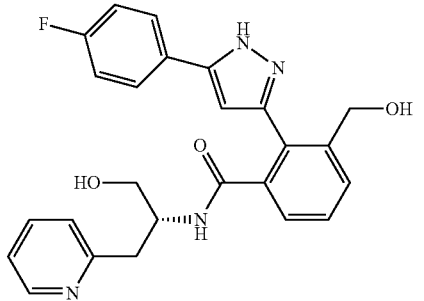 [SMILES: O=C(N[C@@H](CO)Cc1ccccn1)c1cccc(CO)c1-c1cc(-c2ccc(F)cc2)[nH]n1] | RT (min): 0.765 (Method A)<br>MS (ESI, m/z): 447.1824 (M + H)+ | Column: APS<br>EtOAc/MeOH |
| 28-9 | 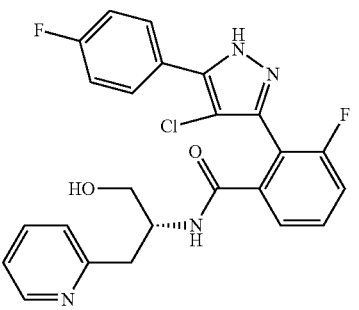 [SMILES: O=C(N[C@@H](CO)Cc1ccccn1)c1cccc(F)c1-c1n[nH]c(-c2ccc(F)cc2)c1Cl] | RT (min): 2.064 (Method A)<br>MS (ESI, m/z): 469.1236 (M + H)+ | Column: SiO2<br>EtOAc/MeOH |

TABLE 108

| Ex. No. | Strc. | P.D. | P.C. |
|---|---|---|---|
| 29-1 | | RT (min): 2.303 (Method A)<br>MS (ESI, m/z): 375.2177 (M + H)+ | Filtration of Et2O suspension |
| 29-2 | Rel. | RT (min): 2.281 (Method A)<br>MS (ESI, m/z): 427.1926 (M + H)+ | Column: APS EtOAc/MeOH |
| 30-1 | | RT (min): 1.867 (Method A)<br>MS (ESI, m/z): 435.1624 (M + H)+ | Column: APS EtOAc/MeOH |
| 30-2 | | 1H-NMR (CDCl3) δ ppm: 2.91-3.10 (1H, m), 3.39-3.67 (4H, m), 6.77 (1H, s), 7.11-7.29 (6H, m), 7.31-7.38 (2H, m), 7.43-7.51 (3H, m), 7.67-7.80 (3H, m), 8.25-8.31 (1H, m).<br>RT (min): 3.168 (Method A)<br>MS (ESI, m/z): 398.1859 (M + H)+ | Collected by filtration |

TABLE 108-continued

| Ex. No. | Strc. | P.D. | P.C. |
| --- | --- | --- | --- |
| 31-1 | | RT (min): 2.084 (Method A)<br>MS (ESI, m/z): 466.1683 (M + H)$^+$ | Column: SiO2<br>EtOAc/MeOH |
| 32-1 | | RT (min): 2.451 (Method A)<br>MS (ESI, m/z): 554.2357 (M + H)$^+$ | Without purification |
| 33-2 | | RT (min): 2.452 (Method A)<br>MS (ESI, m/z): 554.2357 (M + H)$^+$ | Without purification |

TABLE 109

| Ex. No. | Strc. | P. D. | P. C. |
| --- | --- | --- | --- |
| 33-1 | | $^1$H-NMR (CDCl$_3$) δ ppm: 1.24 (3H, s), 1.40 (3H, s), 3.22 (1H, dd, J = 4.9, 15.3 Hz), 3.38 (1H, dd, J = 5.6, 15.3 Hz), 4.26-4.33 (1H, m), 6.63-6.69 (1H, m), 6.75 (1H, d, J = 3.8 Hz), 6.95-7.05 (3H, m), 7.09-7.16 (2H, m), 7.16-7.22 (1H, m), 7.24-7.33 (2H, m), 7.74-7.82 (2H, m), 8.27-8.32 (1H, m).<br>RT (min): 1.890 (Method A)<br>MS (ESI, m/z): 463.1937 (M + H)$^+$ | Column: SiO2<br>EtOAc/MeOH |

TABLE 109-continued

| Ex. No. | Strc. | P. D. | P. C. |
| --- | --- | --- | --- |
| 33-2 | | ¹H-NMR (CDCl₃) δ ppm: 1.26 (3H, s), 1.42 (3H, s), 3.23 (1H, dd, J = 4.7, 15.3 Hz), 3.37 (1H, dd, J = 5.6, 15.3 Hz), 4.20-4.25 (1H, m), 6.63-6.70 (1H, m), 6.93 (1H, d, J = 7.7 Hz), 6.99-7.05 (1H, m), 7.12-7.19 (3H, m), 7.20-7.40 (3H, m), 7.85-7.92 (2H, m), 8.30-8.34 (1H, m).<br>RT (min): 2.093 (Method A)<br>MS (ESI, m/z): 481.1841 (M + H)⁺ | Column: SiO2<br>EtOAc/MeOH |
| 33-3 | | ¹H-NMR (CDCl₃) δ ppm: 1.12 (3H, s), 1.31 (3H, s), 3.15 (1H, dd, J = 5.1, 15.5 Hz), 3.28 (1H, dd, J = 5.4, 15.5 Hz), 4.17-4.25 (1H, m), 6.58-6.64 (1H, m), 6.66 (1H, s), 6.98-7.06 (2H, m), 7.09-7.15 (2H, m), 7.16-7.19 (1H, m), 7.24-7.30 (1H, m), 7.35-7.41 (1H, m), 7.50 (1H, dd, J = 1.2, 8.1 Hz), 7.69-7.76 (2H, m), 8.28-8.32 (1H, m).<br>RT (min): 2.093 (Method A)<br>MS (ESI, m/z): 479.1642 (M + H)⁺ | Column: SiO2<br>EtOAc/MeOH |
| 33-4 | | RT (min): 2.295 (Method A)<br>MS (ESI, m/z): 507.1958 (M + H)⁺ | Column: SiO2<br>EtOAc/MeOH |
| 33-5 | | RT (min): 2.189 (Method A)<br>MS (ESI, m/z): 491.2252 (M + H)⁺ | Column: SiO2<br>EtOAc/MeOH |

TABLE 110

| Ex. No. | Strc. | P. D. | P. C. |
|---|---|---|---|
| 34-1HP | | $^1$H-NMR (CDCl$_3$) δ ppm: 1.25 (3H, s), 1.41 (3H, s), 3.23 (1H, dd, J = 4.6, 15.5 Hz), 3.39 (1H, dd, J = 5.6, 15.6 Hz), 4.25-4.32 (1H, m), 6.59 (1H, d, J = 8.1 Hz), 6.79 (1H, d, J = 4.0 Hz), 6.94 (1H, d, J = 7.9 Hz), 6.97-7.06 (2H, m), 7.17-7.24 (1H, m), 7.26-7.34 (2H, m), 7.39-7.43 (2H, m), 7.77 (2H, d, J = 8.8 Hz), 8.28-8.31 (1H, m).<br>RT (min): 2.153 (Method A)<br>MS (ESI, m/z): 479.1639 (M + H)$^+$ | Column: SiO2<br>EtOAc/MeOH |
| 34-1LP | | RT (min): 2.200 (Method A)<br>MS (ESI, m/z): 463.1329 (M + H)$^+$ | Column: SiO2<br>EtOAc/MeOH |
| 35-1 | | $^1$H-NMR (CDCl$_3$) δ ppm: 0.55 (3H, s), 2.85-2.93 (1H, m), 3.25-3.31 (1H, m), 3.42-3.48 (1H, m), 3.52-3.58 (1H, m), 3.63-3.67 (2H, m), 3.75-3.81 (2H, m), 4.82-4.89 (1H, m), 6.78 (1H, d, J = 3.3 Hz), 6.97-7.08 (2H, m), 7.17-7.42 (5H, m), 7.54 (1H, dt, J = 1.8, 7.5 Hz), 7.66-7.73 (2H, m), 8.30-8.33 (1H, m).<br>RT (min): 2.071 (Method A)<br>MS (ESI, m/z): 509.1746 (M + H)$^+$ | Column: SiO2<br>EtOAc/MeOH |
| 35-2 | | RT (min): 1.796 (Method A)<br>MS (ESI, m/z): 493.2044 (M + H)$^+$ | Column: SiO2<br>EtOAc/MeOH |

TABLE 110-continued

| Ex. No. | Strc. | P. D. | P. C. |
|---|---|---|---|
| 35-3 | | ¹H-NMR (CD₃OD) δ ppm: 1.78-1.86 (1H, m), 2.98 (1H, dd, J = 9.6, 13.7 Hz), 3.12 (1H, dd, J = 5.1, 14.1 Hz), 3.58-3.72 (4H, m), 4.53-4.61 (1H, m), 6.70 (1H, d, J = 1.0 Hz), 6.94-7.06 (1H, m), 7.12-7.24 (3H, m), 7.24-7.36 (2H, m), 7.38-7.48 (1H, m), 7.63-7.84 (3H, m), 8.37-8.43 (1H, m). RT (min): 1.700 (Method A) MS (ESI, m/z): 479.1885 (M + H)⁺ | Column: SiO2 EtOAc/MeOH |
| 35-4 | | RT (min): 1.922 (Method A) MS (ESI, m/z): 479.1880 (M + H)⁺ | Column: SiO2 EtOAc/MeOH |
| 35-5 | | RT (min): 1.929 (Method A) MS (ESI, m/z): 479.1890 (M + H)⁺ | Column: SiO2 EtOAc/MeOH |

TABLE 111

| Ex. No. | Strc. | P. D. | P. C. |
|---|---|---|---|
| 36-1 | | ¹H-NMR (CDCl₃) δ ppm: 1.19-1.34 (1H, m), 1.58-1.71 (1H, m), 2.81 (1H, dd, J = 6.0, 14.4 Hz), 2.97 (1H, dd, J = 5.0, 14.4 Hz), 3.42-3.56 (2H, m), 4.43-4.57 (1H, m), 6.68 (1H, s), 7.00-7.13 (4H, m), 7.31-7.42 (2H, m), 7.49-7.58 (2H, m), 7.58-7.74 (3H, m), 8.35-8.42 (1H, m). RT (min): 1.919 (Method A) MS (ESI, m/z): 465.1486 (M + H)⁺ | Column: SiO2 EtOAc/MeOH |

TABLE 111-continued

| Ex. No. | Strc. | P. D. | P. C. |
| --- | --- | --- | --- |
| 36-2 | | ¹H-NMR (CDCl₃) δ ppm: 1.40 (3H, s), 3.18 (1H, d, J = 13.9 Hz), 3.32 (1H, d, J = 13.9 Hz), 3.74 (2H, s), 6.83 (1H, d, J = 3.8 Hz), 7.03-7.15 (5H, m), 7.15-7.36 (3H, m), 7.50-7.57 (1H, m), 7.70-7.80 (2H, m), 8.38-8.43 (1H, m).<br>RT (min): 2.061 (Method A)<br>MS (ESI, m/z): 449.1782 (M + H)⁺ | Column: SiO2<br>EtOAc/MeOH |
| 37-1 | | ¹H-NMR (DMSO-d₆) δ ppm: 2.91-3.13 (1H, m), 3.14-3.41 (1H, m), 4.62-4.84 (1H, m), 6.69-7.75 (11H, m), 7.76-7.87 (2H, m), 8.46-8.50 (1H, m), 8.60-8.85 (1H, m), 12.9-13.5 (1H, m).<br>RT (min): 1.939 (Method A)<br>MS (ESI, m/z): 448.1575 (M + H)⁺ | Filtration of EtOAc/n-Hexane suspension |
| 37-2 | | RT (min): 3.953 (Method A)<br>MS (ESI, m/z): 476.1779 (M + H)⁺ | Column: SiO2<br>EtOAc/n-Hexane |
| 37-3 | | RT (min): 2.357 (Method A)<br>MS (ESI, m/z): 477.1729 (M + H)⁺ | Column: SiO2<br>EtOAc/MeOH |

TABLE 112

| Ex. No. | Strc. | P. D. | P. C. |
|---|---|---|---|
| 38-1 | | RT (min): 2.903 (Method A)<br>MS (ESI, m/z): 448.1468 (M + H)$^+$ | Collected by filtration |
| 38-2 | | RT (min): 3.206 (Method A)<br>MS (ESI, m/z): 462.1620 (M + H)$^+$ | Without purification |
| 38-3 | | RT (min): 2.944 (Method A)<br>MS (ESI, m/z): 448.1465 (M + H)$^+$ | Collected by filtration |

TABLE 113

| Ex. No. | Strc. | P. D. | P. C. |
|---|---|---|---|
| 39-1 | | RT (min): 2.857 (Method A)<br>MS (ESI, m/z): 464.1778 (M + H)$^+$ | Column: SiO2<br>EtOAc/MeOH |

TABLE 113-continued

| Ex. No. | Strc. | P. D. | P. C. |
|---|---|---|---|
| 39-2 | | ¹H-NMR (DMSO-d₆) δ ppm: 2.87-2.94 (1H, m), 3.12-3.18 (1H, m), 3.45 (1H, br), 4.37-4.45 (1H, m), 4.70 (0.5H, br), 4.92 (0.5H, br), 6.81 (1H, s), 7.17-7.51 (6H, m), 7.81 (3H, s), 7.98 (0.5H, br), 8.12 (0.5H, br), 8.44 (1H, d, J = 2.8 Hz), 13.00 (0.5H, br), 13.45 (0.5H, br). RT (min): 2.722 (Method A) MS (ESI, m/z): 469.1237 (M + H)⁺ | Column: APS EtOAc/MeOH |
| 40-1 | | RT (min): 2.078 (Method A) MS (ESI, m/z): 462.1735 (M + H)⁺ | Column: SiO2 EtOAc/MeOH |
| 40-2 Ref. | | RT (min): 2.260 (Method A) MS (ESI, m/z): 461.1780 (M + H)⁺ | Column: SHISEIDO CAPCELL PAK C18 UG80 H2O/MeCN |
| 41-1 | | RT (min): 2.047 (Method A) MS (ESI, m/z): 433.1467 (M + H)⁺ | Column: SiO2 EtOAc/MeOH |

TABLE 113-continued

| Ex. No. | Strc. | P. D. | P. C. |
|---|---|---|---|
| 41-2 | | RT (min): 1.882 (Method A)<br>MS (ESI, m/z): 463.1575 (M + H)$^+$ | Column: SiO2<br>EtOAc/MeOH. |

TABLE 114

| Ex. No. | Strc. | P. D. | P. C. |
|---|---|---|---|
| 42-1 | | $^1$H-NMR (CDCl$_3$) δ ppm: 2.41 (3H, s), 2.60-2.78 (2H, m), 2.80-2.94 (2H, m), 4.44-4.58 (1H, m), 6.15-6.26 (1H, m), 6.91 (1H, d, J = 3.9 Hz), 7.06-7.40 (10H, m), 7.64-7.73 (2H, m).<br>RT (min): 2.580 (Method A)<br>MS (ESI, m/z): 463.1694 (M + H)$^+$ | Column: SiO2<br>EtOAc/MeOH |
| 42-2 | | $^1$H-NMR (CDCl$_3$) δ ppm: 2.49 (3H, s), 2.68-2.94 (4H, m), 4.48-4.63 (1H, m), 6.05-6.21 (1H, m), 6.89 (1H, d, J = 4.0 Hz), 7.00-7.11 (3H, m), 7.13-7.37 (7H, m), 7.70-7.80 (2H, m).<br>RT (min): 2.435 (Method A)<br>MS (ESI, m/z): 447.1987 (M + H)$^+$ | Column: APS<br>EtOAc/MeOH |

TABLE 115

| Ex. No. | Strc. | P. D. | P. C. |
| --- | --- | --- | --- |
| 43-1 | | ¹H-NMR (CDCl₃) δ ppm: 3.07-3.13 (2H, m), 3.35 (3H, s), 3.37-3.44 (2H, m), 3.60-3.68 (1H, m), 4.67-4.77 (1H, m), 6.79 (1H, d, J = 8.8 Hz), 6.83 (1H, d, J = 3.5 Hz), 7.06 (1H, ddd, J = 1.0, 5.0, 7.5 Hz), 7.16-7.28 (3H, m), 7.32-7.41 (3H, m), 7.56 (1H, td, J = 1.8, 7.8 Hz), 7.68-7.75 (2H, m), 8.39-8.44 (1H, m).<br>RT (min): 2.134 (Method A)<br>MS (ESI, m/z): 495.1593 (M + H)⁺ | Column: APS<br>EtOAc/MeOH |
| 43-2 | | ¹H-NMR (CDCl₃) δ ppm: 2.84-2.91 (1H, m), 3.02-3.10 (1H, m), 3.17 (1H, dd, J = 6.3, 14.5 Hz), 3.26 (3H, s), 3.61 (1H, dd, J = 2.3, 13.1 Hz), 3.79 (1H, dd, J = 3.1, 13.1 Hz), 4.55-4.65 (1H, m), 6.82 (1H, d, J = 3.1 Hz), 7.03 (1H, d, J = 7.7 Hz), 7.23-7.33 (2H, m), 7.36-7.44 (1H, m), 7.58 (1H, td, J = 1.9, 7.7 Hz), 7.66-7.74 (2H, m), 8.08 (1H, d, J = 8.4 Hz), 8.34-8.39 (1H, m).<br>RT (min): 1.866 (Method A)<br>MS (ESI, m/z): 479.1889 (M + H)⁺ | Column: APS<br>EtOAc/MeOH |
| 43-3 | | ¹H-NMR (CDCl₃) δ ppm: 3.05-3.13 (2H, m), 3.34 (3H, s), 3.36-3.45 (2H, m), 3.57-3.68 (1H, m), 4.66-4.78 (1H, m), 6.79 (1H, d, J = 3.2 Hz), 6.82 (1H, d, J = 9.0 Hz), 7.03-7.14 (3H, m), 7.16-7.28 (3H, m), 7.31-7.39 (1H, m), 7.56 (1H, td, J = 1.8, 7.7 Hz), 7.69-7.78 (2H, m), 8.39-8.44 (1H, m).<br>RT (min): 1.881 (Method A)<br>MS (ESI, m/z): 479.1888 (M + H)⁺ | Column: APS<br>EtOAc/MeOH |
| 43-4 | | ¹H-NMR (CDCl₃) δ ppm: 2.96-3.05 (2H, m), 3.21-3.32 (5H, m), 3.44-3.56 (1H, m), 4.58-4.70 (1H, m), 6.72 (1H, s), 6.82-6.89 (1H, m), 7.03-7.11 (3H, m), 7.15 (1H, d, J = 7.9 Hz), 7.20-7.27 (1H, m), 7.29-7.35 (1H, m), 7.50-7.60 (2H, m), 7.65-7.73 (2H, m), 8.36-8.42 (1H, m).<br>RT (min): 2.036 (Method A)<br>MS (ESI, m/z): 495.1591 (M + H)⁺ | Column: APS<br>EtOAc/MeOH |

TABLE 115-continued

| Ex. No. | Strc. | P. D. | P. C. |
|---|---|---|---|
| 43-5 | | ¹H-NMR (CDCl₃) δ ppm: 3.12-3.18 (2H, m), 3.39 (3H, s), 3.43-3.51 (2H, m), 3.67-3.75 (1H, m), 4.70-4.82 (1H, m), 6.82-6.90 (1H, m), 7.03-7.08 (1H, m), 7.10-7.18 (2H, m), 7.19-7.24 (1H, m), 7.36-7.43 (1H, m), 7.44-7.49 (1H, m), 7.51-7.60 (2H, m), 7.72-7.77 (1H, m), 7.84-7.93 (2H, m), 8.39-8.45 (1H, m).<br>RT (min): 2.010 (Method A)<br>MS (ESI, m/z): 479.1888 (M + H)⁺ | Column: APS<br>EtOAc/MeOH |
| 43-6 | | ¹H-NMR (CDCl₃) δ ppm: 3.32 (3H, s), 3.68-3.75 (2H, m), 4.45-4.53 (1H, m), 4.58 (1H, d, J = 4.6 Hz), 6.76 (1H, d, J = 3.2 Hz), 6.92 (1H, d, J = 8.8 Hz), 7.01 (2H, d, J = 8.8 Hz), 7.15 (1H, ddd, J = 1.1, 4.6, 7.5 Hz), 7.18-7.25 (2H, m), 7.31-7.38 (2H, m), 7.58-7.66 (3H, m), 8.47-8.52 (1H, m).<br>RT (min): 2.062 (Method A)<br>MS (ESI, m/z): 465.1729 (M + H)⁺ | Column: APS<br>EtOAc/MeOH |
| 43-7 | | RT (min): 2.147 (Method A)<br>MS (ESI, m/z): 461.1783 (M + H)⁺ | Column: APS<br>EtOAc/MeOH |

TABLE 116

| Ex. No. | Strc. | P. D. | P. C. |
|---|---|---|---|
| 43-8 |  | ¹H-NMR (CDCl₃) δ ppm: 0.80-0.91 (1H, m), 0.95-1.07 (3H, m), 3.48-3.60 (1H, m), 3.62-3.78 (1H, m), 5.03-5.15 (1H, m), 6.78-6.83 (1H, m), 7.05-7.30 (3H, m), 7.38-7.48 (2H, m), 7.52-7.62 (1H, m), 7.70-7.80 (3H, m), 8.16-8.29 (1H, m), 8.50-8.60 (1H, m).<br>RT (min): 2.150 (Method A)<br>MS (ESI, m/z): 461.1782 (M + H)⁺ | Column: APS<br>EtOAc/MeOH |

TABLE 116-continued

| Ex. No. | Strc. | P. D. | P. C. |
|---|---|---|---|
| 43-9 | | ¹H-NMR (CDCl₃) δ ppm: 1.44-1.54 (1H, m), 1.88-1.99 (1H, m), 3.38 (3H, s), 3.56-3.72 (2H, m), 4.42 (1H, d, J = 3.3 Hz), 4.56-4.65 (1H, m), 6.81 (1H, d, J = 3.2 Hz), 6.98-7.14 (4H, m), 7.21-7.42 (4H, m), 7.56-7.65 (1H, m), 7.67-7.77 (2H, m), 8.42-8.48 (1H, m).<br>RT (min): 2.062 (Method A)<br>MS (ESI, m/z): 479.1888 (M + H)⁺ | Column: APS<br>EtOAc/MeOH |
| 43-10 | | RT (min): 1.646 (Method A)<br>MS (ESI, m/z): 464.1890 (M + H)⁺ | Column: APS<br>EtOAc/MeOH |
| 43-11 | | ¹H-NMR (CDCl₃) δ ppm: 3.27 (3H, s), 3.63 (1H, dd, J = 4.0 Hz, 11.6 Hz), 3.75 (1H, dd, J = 4.3 Hz, 11.6 Hz), 4.42-4.45 (2H, m), 6.81 (1H, d, J = 3.3 Hz), 7.03-7.11 (2H, m), 7.14-7.28 (3H, m), 7.30-7.37 (1H, m), 7.38-7.46 (2H, m), 7.64-7.76 (3H, m), 8.46-8.51 (1H, m).<br>RT (min): 2.090 (Method A)<br>MS (ESI, m/z): 465.1731 (M + H)⁺ | Column: APS<br>EtOAc/MeOH |
| 43-12 | | ¹H-NMR (CDCl₃) δ ppm: 3.29 (3H, s), 3.34-3.39 (1H, m), 3.77 (1H, dd, J = 3.3 Hz, 11.3 Hz), 4.16-4.24 (1H, m), 4.65 (1H, d, J = 8.2 Hz), 6.80 (1H, d, J = 3.4 Hz), 7.07 (2H, t, J = 8.6 Hz), 7.14-7.27 (3H, m), 7.31-7.46 (3H, m), 7.64-7.76 (3H, m), 8.48-8.52 (1H, m). | Column: APS<br>EtOAc/MeOH |

TABLE 116-continued

| Ex. No. | Strc. | P. D. | P. C. |
|---|---|---|---|
| 43-13 | | ¹H-NMR (CDCl₃) δ ppm: 3.11-3.16 (2H, m), 3.38 (3H, s), 3.41-3.47 (2H, m), 3.63-3.73 (1H, m), 4.72-4.82 (1H, m), 6.65 (1H, s), 7.07-7.16 (1H, m), 7.28-7.34 (1H, m), 7.39-7.55 (4H, m), 7.70-7.78 (2H, m), 7.80-7.86 (1H, m), 8.06-8.12 (1H, m), 8.50-8.52 (1H, m).<br>RT (min): 1.795 (Method A)<br>MS (ESI, m/z): 461.1980 (M + H)⁺ | Column: APS<br>EtOAc/MeOH |
| 43-14 | | ¹H-NMR (CDCl₃) δ ppm: 3.11 (2H, d, J = 6.9 Hz), 3.33 (3H, s), 3.35-3.48 (2H, m), 3.64 (1H, dd, J = 4.6, 11.2 Hz), 4.63-4.74 (1H, m), 6.89-6.96 (1H, m), 7.03-7.14 (3H, m), 7.19 (1H, dt, J = 1.1, 7.8 Hz), 7.27-7.32 (2H, m), 7.38-7.48 (1H, m), 7.56 (1H, td, J = 1.8, 7.7 Hz), 7.75-7.84 (2H, m), 8.38-8.42 (1H, m).<br>RT (min): 2.069 (Method A)<br>MS (ESI, m/z): 497.1794 (M + H)⁺ | Column: APS<br>EtOAc/MeOH |

TABLE 117

| Ex. No. | Strc. | P. D. | P. C. |
|---|---|---|---|
| 43-15 | | ¹H-NMR (CDCl₃) δ ppm: 1.04 (3H, t, J = 7.0 Hz), 3.10 (1H, d, J = 7.0 Hz), 3.34-3.52 (3H, m), 3.54-3.64 (2H, m), 4.66-4.77 (1H, m), 6.78 (1H, d, J = 3.2 Hz), 6.82-6.89 (1H, m), 7.03-7.12 (3H, m), 7.15-7.25 (3H, m), 7.31-7.39 (1H, m), 7.56 (1H, td, J = 1.8, 7.7 Hz), 7.66-7.77 (2H, m), 8.38-8.44 (1H, m).<br>RT (min): 2.047 (Method A)<br>MS (ESI, m/z): 493.2046 (M + H)⁺ | Column: APS<br>EtOAc/MeOH |
| 43-16 | | ¹H-NMR (CDCl₃) δ ppm: 3.28 (3H, s), 3.69-3.75 (2H, m), 4.45-4.52 (2H, m), 7.03 (2H, t, J = 8.8 Hz), 7.15-7.29 (4H, m), 7.36-7.45 (2H, m), 7.61-7.67 (2H, m), 7.69 (1H, dt, J = 1.5, 7.7 Hz), 8.51-8.54 (1H, m).<br>RT (min): 2.334 (Method A)<br>MS (ESI, m/z): 483.1639 (M + H)⁺ | Column: APS<br>EtOAc/MeOH |

TABLE 117-continued

| Ex. No. | Strc. | P. D. | P. C. |
|---|---|---|---|
| 43-17 | | ¹H-NMR (CDCl₃) δ ppm: 3.35 (3H, s), 3.69 (1H, dd, J = 4.4 Hz, 11.6 Hz), 3.89 (1H, dd, J = 4.0 Hz, 11.7 Hz), 4.49-4.56 (1H, m), 4.62 (1H, d, 5.5 Hz), 7.13 (2H, t, J = 8.8 Hz), 7.20 (1H, ddd, J = 1.0, 5.0, 7.6 Hz), 7.37-7.49 (4H, m), 7.55 (1H, dt, J = 1.3, 7.6 Hz), 7.72 (1H, dt, J = 1.8, 7.6 Hz), 7.75-7.79 (1H, m), 7.82-7.89 (2H, m), 8.51-8.55 (1H, m). <br> RT (min): 2.235 (Method A) <br> MS (ESI, m/z): 465.1731 (M + H)⁺ | Column: APS <br> EtOAc/MeOH |
| 43-18 | | ¹H-NMR (CDCl₃) δ ppm: 3.10-3.20 (2H, m), 3.39 (3H, s), 3.43-3.52 (2H, m), 3.71 (1H, dd, J = 3.6, 10.3 Hz), 4.71-4.82 (1H, m), 6.82-6.90 (1H, m), 7.01-7.07 (1H, m), 7.21 (1H, d, J = 7.8 Hz), 7.36-7.49 (4H, m), 7.52-7.59 (2H, m), 7.71-7.77 (1H, m), 7.81-7.88 (2H, m), 8.39-8.43 (1H, m). <br> RT (min): 2.286 (Method A) <br> MS (ESI, m/z): 495.1595 (M + H)⁺ | Column: APS <br> EtOAc/MeOH |
| 43-19 | | RT (min): 2.352 (Method A) <br> MS (ESI, m/z): 525.1697 (M + H)⁺ | Column: APS <br> EtOAc/MeOH |
| 43-20 | | RT (min): 2.370 (Method A) <br> MS (ESI, m/z): 525.1696 (M + H)⁺ | Column: APS <br> EtOAc/MeOH |

TABLE 117-continued

| Ex. No. | Strc. | P. D. | P. C. |
|---|---|---|---|
| 43-21 |  | RT (min): 2.384 (Method A)<br>MS (ESI, m/z): 495.1592 (M + H)$^+$ | Column: APS<br>EtOAc/MeOH |

TABLE 118

| Ex. No. | Strc. | P. D. | P. C. |
|---|---|---|---|
| 43-22 | | $^1$H-NMR (CDCl$_3$) δ ppm: 1.14 (3H, t, J = 6.9 Hz), 3.35-3.50 (2H, m), 3.65-3.70 (1H, m), 3.82 (1H, dd, J = 4.3 Hz, 11.7 Hz), 4.40-4.48 (1H, m), 4.64 (1H, d, 5.9 Hz), 6.81-6.89 (2H, m), 7.07 (2H, t, J = 8.7 Hz), 7.14-7.40 (4H, m), 7.44 (1H, d, J = 7.8 Hz), 7.66-7.74 (3H, m), 8.50-8.54 (1H, m).<br>RT (min): 2.278 (Method A)<br>MS (ESI, m/z): 479.1889 (M + H)$^+$ | Column: APS<br>EtOAc/MeOH |
| 43-23 | | $^1$H-NMR (CDCl$_3$) δ ppm: 3.03-3.22 (2H, m), 3.66-3.89 (2H, m), 3.95-4.15 (1H, m), 4.62-4.76 (1H, m), 6.78 (1H, d, J = 2.8 Hz), 7.03-7.13 (3H, m), 7.18 (1H, d, J = 7.8 Hz), 7.24-7.37 (2H, m), 7.38-7.45 (1H, m), 7.54-7.68 (3H, m), 8.31-8.44 (2H, m).<br>RT (min): 1.919 (Method A)<br>MS (ESI, m/z): 467.1689 (M + H)$^+$ | Column: APS<br>EtOAc/MeOH |
| 43-24 | | $^1$H-NMR (CDCl$_3$) δ ppm: 3.05-3.21 (2H, m), 3.53-3.75 (2H, m), 4.58-4.76 (2H, m), 6.77-6.80 (1H, m), 7.03-7.20 (5H, m), 7.35-7.42 (1H, m), 7.54-7.60 (1H, m), 7.68-7.74 (2H, m), 8.41-8.45 (1H, m).<br>RT (min): 1.846 (Method A)<br>MS (ESI, m/z): 467.1689 (M + H)$^+$ | Column: SiO2<br>EtOAc/MeOH |

TABLE 118-continued

| Ex. No. | Strc. | P. D. | P. C. |
|---|---|---|---|
| 43-25 | | $^1$H-NMR (CDCl$_3$) δ ppm: 3.05-3.21 (2H, m), 3.66-3.88 (2H, m), 3.96-4.14 (1H, m), 4.65-4.75 (1H, m), 6.78-6.81 (1H, m), 7.05-7.14 (3H, m), 7.17-7.21 (1H, m), 7.25-7.47 (4H, m), 7.56-7.68 (3H, m), 8.34-8.44 (2H, m).<br>RT (min): 1.884 (Method A)<br>MS (ESI, m/z): 467.1688 (M + H)$^+$ | Column: SiO2<br>EtOAc/MeOH |
| 43-26 | | RT (min): 2.899 (Method A)<br>MS (ESI, m/z): 487.1143 (M + H)$^+$ | Column: APS<br>EtOAc/MeOH |
| 43-27 | | $^1$H-NMR (CDCl$_3$) δ ppm: 2.99 (1H, dd, J = 7.6, 14.5 Hz), 3.07 (1H, dd, J = 6.0, 14.5 Hz), 3.34-3.46 (1H, m), 3.47-3.58 (1H, m), 4.43-4.62 (1H, m), 4.62-4.78 (1H, m), 6.67 (1H, s), 7.04-7.17 (5H, m), 7.24-7.39 (2H, m), 7.53-7.69 (4H, m), 8.38-8.44 (1H, m).<br>RT (min): 2.004 (Method A)<br>MS (ESI, m/z): 483.1393 (M + H)$^+$ | Column: APS<br>EtOAc/MeOH |
| 43-28 | | RT (min): 2.043 (Method A)<br>MS (ESI, m/z): 483.1394 (M + H)$^+$ | Column: APS<br>EtOAc/MeOH |

TABLE 119

| Ex. No. | Strc. | P. D. | P. C. |
| --- | --- | --- | --- |
| 43-29 | | ¹H-NMR (CDCl₃) δ ppm: 3.26 (1H, dd, J = 8.2, 14.7 Hz), 3.35 (1H, dd, J = 5.1, 14.7 Hz), 3.56-3.67 (1H, m), 3.69-3.79 (1H, m), 4.63-4.84 (1H, m), 4.88-5.05 (1H, m), 6.79 (1H, d, J = 3.1 Hz), 6.97-7.07 (2H, m), 7.08-7.17 (2H, m), 7.22-7.36 (2H, m), 7.36-7.45 (1H, m), 7.65-7.79 (2H, m), 8.56 (2H, d, J = 5.0 Hz), RT (min): 2.376 (Method A) MS (ESI, m/z): 468.1642 (M + H)⁺ | Column: APS EtOAc/MeOH |
| 43-30 | | RT (min): 2.551 (Method A) MS (ESI, m/z): 484.1351 (M + H)⁺ | Column: APS EtOAc/MeOH |
| 43-31 | | RT (min): 2.042 (Method A) MS (ESI, m/z): 493.2045 (M + H)⁺ | Column: APS EtOAc/MeOH |
| 43-32 | | RT (min): 2.043 (Method A) MS (ESI, m/z): 493.2045 (M + H)⁺ | Column: APS EtOAc/MeOH |

TABLE 119-continued

| Ex. No. | Strc. | P. D. | P. C. |
|---|---|---|---|
| 43-33 | | RT (min): 2.269 (Method A)<br>MS (ESI, m/z): 495.1593 (M + H)+ | Column: APS<br>EtOAc/MeOH |
| 43-34 | | $^1$H-NMR (CDCl$_3$) δ 2.95-2.98 (1H, m), 3.11 (2H, d, J = 7.0 Hz), 3.32-3.45- (5H, m), 3.65 (1H, dd, J = 4.0, 10.7 Hz), 4.69-4.78 (1H, m), 6.80-7.00 (4H, m), 7.02-7.12 (1H, m), 7.14-7.24 (3H, m), 7.30-7.38 (1H, m), 7.40-7.48 (1H, m), 7.55-7.62 (1H, m), 7.82-7.92 (1H, m), 8.41-8.45 (1H, m).<br>RT (min): 2.058 (Method A)<br>MS (ESI, m/z): 497.1794 (M + H)+ | Column: APS<br>EtOAc/MeOH |
| 43-35 | | RT (min): 2.093 (Method A)<br>MS (ESI, m/z): 475.2137 (M + H)+ | Column: APS<br>EtOAc/MeOH |

TABLE 120

| Ex. No. | Strc. | P. D. | P. C. |
|---|---|---|---|
| 43-36 | | RT (min): 2.314 (Method A)<br>MS (ESI, m/z): 513.1498 (M + H)+ | Column: APS<br>EtOAc/MeOH |

TABLE 120-continued

| Ex. No. | Strc. | P. D. | P. C. |
|---|---|---|---|
| 43-37 | | ¹H-NMR (CDCl₃) δ ppm: 2.05 (3H, s), 2.99-3.06 (2H, m), 3.24-3.30 (5H, m), 3.50-3.58 (1H, m), 4.62-4.70 (1H, m), 6.83-6.94 (1H, m), 7.05-7.18 (5H, m), 7.20-7.32 (1H, m), 7.38-7.48 (1H, m), 7.50-7.60 (2H, m), 7.70-7.80 (1H, m), 8.38-8.42 (1H, m)<br>RT (min): 2.197 (Method A)<br>MS (ESI, m/z): 493.2043 (M + H)⁺ | Column: APS<br>EtOAc/MeOH |
| 43-38 | | RT (min): 2.814 (Method A)<br>MS (ESI, m/z): 456.1642 (M + H)⁺ | Column: APS<br>EtOAc/MeOH |
| 43-39 | | ¹H-NMR (CDCl₃) δ ppm: 3.55-3.73 (2H, m), 4.42 (2H, d, J = 6.7 Hz), 4.50-4.68 (1H, m), 4.70-4.84 (1H, m), 6.23 (1H, dd, J = 2.1, 2.1 Hz), 6.98-7.03 (1H, m), 7.07-7.14 (2H, m), 7.24-7.36 (2H, m), 7.40 (1H, d, J = 2.1 Hz), 7.43-7.50 (2H, m), 7.68-7.78 (2H, m)<br>RT (min): 2.836 (Method A)<br>MS (ESI, m/z): 474.1574 (M + H)⁺ | Column: APS<br>EtOAc/MeOH |
| 43-40 | | RT (min): 2.438 (Method A)<br>MS (ESI, m/z): 457.1592 (M + H)⁺ | Column: APS<br>EtOAc/MeOH |

TABLE 120-continued

| Ex. No. | Strc. | P. D. | P. C. |
|---|---|---|---|
| 43-41 | | ¹H-NMR (CDCl₃) δ ppm: 3.20 (2H, dd, J = 7.0, 2.0 Hz), 3.56-3.64 (1H, m), 3.67-3.75 (1H, m), 4.63-4.93 (2H, m), 6.76 (1H, d, J = 2.4 Hz), 6.87-6.90 (1H, m), 7.08-7.12 (3H, m), 7.23-7.32 (3H, m), 7.36-7.41 (1H, m), 7.67-7.70 (2H, m), 8.24 (1H, d, J = 4.9 Hz). RT (min): 2.686 (Method A) MS (ESI, m/z): 485.1596 (M + H)⁺ | Column: APS EtOAc/MeOH |
| 43-42 | | ¹H-NMR (CDCl₃) δ ppm: 3.56-3.73 (2H, m), 4.51-4.77 (3H, m), 4.89-5.02 (1H, m), 6.74-6.77 (2H, m), 7.06-7.11 (2H, m), 7.24-7.31 (2H, m), 7.38-7.43 (1H, m), 7.56 (2H, s), 7.63-7.66 (2H, m). RT (min): 2.508 (Method A) MS (ESI, m/z): 457.1594 (M + H)⁺ | Column: APS EtOAc/MeOH |

TABLE 121

| Ex. No. | Strc. | P. D. | P. C. |
|---|---|---|---|
| 43-43 | | ¹H-NMR (CDCl₃) δ ppm: 3.65-3.74 (2H, m), 4.58-4.75 (3H, m), 4.88-5.02 (1H, m), 6.82-6.85 (1H, m), 7.08 (2H, t, J = 8.8 Hz), 7.30-7.34 (1H, m), 7.38-7.40 (1H, m), 7.47-7.52 (1H, m), 7.57 (2H, s), 7.67 (2H, br). RT (min): 2.718 (Method A) MS (ESI, m/z): 475.1500 (M + H)⁺ | Column: APS EtOAc/MeOH |
| 43-44 | | ¹H-NMR (CDCl₃) δ ppm: 3.50-3.70 (2H, m), 4.37 (2H, d, J = 6.4 Hz), 4.46-4.65 (1H, m), 4.70-4.88 (1H, m), 6.22-6.25 (1H, m), 6.80 (1H, d, J = 2.8 Hz), 6.83-6.89 (1H, m), 7.20-7.25 (1H, m), 7.34-7.44 (5H, m), 7.45-7.48 (1H, m), 7.62-7.67 (2H, m). RT (min): 2.785 (Method A) MS (ESI, m/z): 472.1345 (M + H)⁺ | Column: APS EtOAc/MeOH |

TABLE 121-continued

| Ex. No. | Strc. | P. D. | P. C. |
|---|---|---|---|
| 43-45 | | ¹H-NMR (CDCl₃) δ ppm: 3.32-3.54 (2H, m), 4.24-4.31 (2H, m), 4.32-4.50 (1H, m), 4.60-4.78 (1H, m), 6.21-6.25 (1H, m), 6.70 (1H, s), 6.90-7.06 (1H, m), 7.07-7.13 (2H, m), 7.24-7.38 (3H, m), 7.45 (1H, d, J = 1.8 Hz), 7.56 (1H, dd, J = 1.7, 7.6 Hz), 7.60-7.67 (2H, m).<br>RT (min): 2.679 (Method A)<br>MS (ESI, m/z): 472.1343 (M + H)⁺ | Column: APS<br>EtOAc/MeOH |
| 43-46 | | RT (min): 2.600 (Method A)<br>MS (ESI, m/z): 474.1545 (M + H)⁺ | Column: APS<br>EtOAc/MeOH |

TABLE 122

| Ex. No. | Strc. | P.D. | P.C. |
|---|---|---|---|
| 44-1 | | RT(min): 2.087 (Method A)<br>MS(ESI, m/z): 503.1749 (M + H)⁺ | Column: SiO2<br>EtOAc/MeOH |
| 44-2 | | RT(min): 2.223 (Method A)<br>MS(ESI, m/z): 426.1484 (M + H)⁺ | Column: SiO2<br>CH₂Cl₂/MeOH |

TABLE 122-continued

| Ex. No. | Strc. | P.D. | P.C. |
|---|---|---|---|
| 45-1 | | ¹H-NMR(CD₃OD) δ ppm: 2.40 (3H, s), 2.56-2.64 (1H, m), 2.86-2.95 (1H, m), 3.13-3.19 (1H, m), 3.56-3.60 (2H, m), 4.53-4.60 (1H, m), 6.73-6.76 (1H, m), 6.94-6.99 (1H, m), 7.14-7.35 (5H, m), 7.39-7.46 (1H, m), 7.68-7.81 (3H, m), 8.40-8.44 (1H, m). RT(min): 1.721 (Method A) MS(ESI, m/z): 478.2044 (M + H)⁺ | Column: APS EtOAc/MeOH |
| 45-2 | | ¹H-NMR(CD₃OD) δ ppm: 2.84-2.96 (2H, m), 3.11-3.17 (1H, m), 3.50 (1H, dd, J = 6.3, 11.3 Hz), 3.61 (1H, dd, J = 4.4, 11.3 Hz), 4.39-4.46 (1H, m), 6.73-6.75 (1H, m), 6.96-7.00 (1H, m), 7.13-7.25 (3H, m), 7.26-7.33 (2H, m), 7.38-7.47 (1H, m), 7.67-7.80 (3H, m), 8.40-8.45 (1H, m). RT(min): 1.641 (Method A) MS(ESI, m/z): 464.1894 (M + H)⁺ | Column: APS EtOAc/MeOH |
| 45-3 | | ¹H-NMR(CD₃OD) δ ppm: 2.96-2.92 (1H, m), 2.96 (1H, dd, J = 9.7, 13.8 Hz), 3.10 (1H, dd, J = 5.2, 13.8 Hz), 3.52 (1H, dd, J = 6.1, 11.4 Hz), 3.51 (1H, dd, J = 5.5, 11.4 Hz), 4.44-4.51 (1H, m), 6.75-6.78 (1H, m), 6.92-6.96 (1H, m), 7.14-7.36 (5H, m), 7.38-7.46 (1H, m), 7.71-7.79 (3H, m), 8.43-8.47 (1H, m). RT(min): 1.701 (Method A) MS(ESI, m/z): 464.1889 (M + H)⁺ | Column: APS EtOAc/MeOH |
| 46-1 | | RT(min): 2.450 (Method A) MS(ESI, m/z): 478.2048 (M + H)⁺ | Column: APS EtOAc/MeOH |

TABLE 123

| Ex. No. | Strc. | P.D. | P.C. |
|---|---|---|---|
| 47-1 | 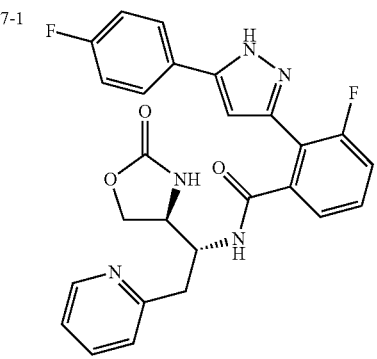 | RT(min): 1.891 (Method A)<br>MS(ESI, m/z): 490.1685 (M + H)+ | Column: SiO2<br>EtOAc/MeOH |
| 47-2 | 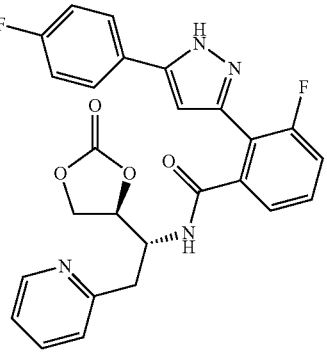 | 1H-NMR(CDCl3) δ ppm: 3.00-3.20 (2H, m), 4.33 (1H, dd, J = 7.3, 8.7 Hz), 4.45 (1H, dd, J = 8.7, 8.7 Hz), 4.79-4.88 (1H, m), 4.89-4.96 (1H, m), 6.76 (1H, d, J = 2.9 Hz), 7.07-7.18 (5H, m), 7.18-7.29 (2H, m), 7.32-7.42 (1H, m), 7.57 (1H, td, J = 1.8, 7.8 Hz), 7.67-7.75 (2H, m), 8.42-8.48 (1H, m).<br>RT(min): 2.144 (Method A)<br>MS(ESI, m/z): 491.1525 (M + H)+ | Column: SiO2<br>EtOAc/MeOH |
| 47-3 | 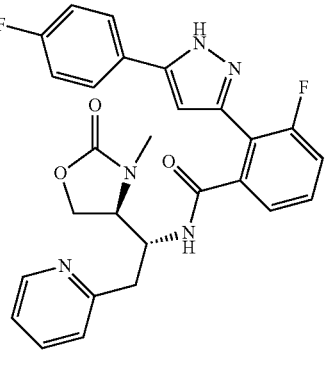 | RT(min): 2.025 (Method A)<br>MS(ESI, m/z): 504.1841 (M + H)+ | Column: SiO2<br>EtOAc/MeOH |
| 48-1 | 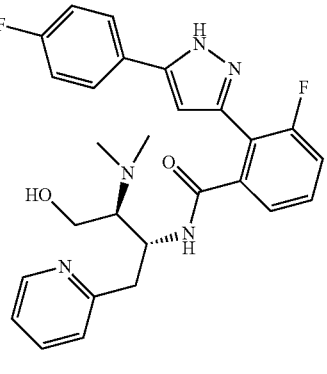 | 1H-NMR(CDCl3) δ ppm: 2.33 (6H, s), 2.61-2.69 (1H, m), 3.04 (1H, dd, J = 5.3, 14.8 Hz), 3.32 (1H, dd, J = 4.5, 14.8 Hz), 3.64-3.74 (2H, m), 4.47-4.56 (1H, m), 6.82-6.86 (1H, m), 7.04-7.27 (7H, m), 7.31-7.39 (1H, m), 7.50-7.57 (1H, m), 7.71-7.81 (2H, m), 8.37-8.41 (1H, m).<br>RT(min): 1.797 (Method A)<br>MS(ESI, m/z): 492.2202 (M + H)+ | Column: APS<br>EtOAc/MeOH |

TABLE 123-continued

| Ex. No. | Strc. | P.D. | P.C. |
|---|---|---|---|
| 48-2 | 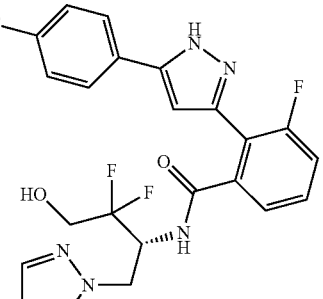 | RT(min): 1.717 (Method A)<br>MS(ESI, m/z): 492.2204 (M + H)$^+$ | Column: APS<br>EtOAc/MeOH |
| 49-1 |  | $^1$H-NMR(CDCl$_3$) δ ppm: 3.14 (3H, s), 3.49 (1H, dd, J = 7.8, 11.2 Hz), 3.61 (1H, dd, J = 5.1, 11.5 Hz), 3.65-3.72 (1H, m), 5.10-5.22 (1H, m), 6.75 (1H, d, J = 3.0 Hz), 7.00-7.08 (2H, m), 7.26-7.36 (2H, m), 7.38-7.44 (3H, m), 7.60-7.68 (3H, m), 7.74-7.81 (1H, m), 8.58-8.63 (1H, m).<br>RT(min): 2.977 (Method A)<br>MS(ESI, m/z): 515.1701 (M + H)$^+$ | Column: APS<br>EtOAc/MeOH |

TABLE 124

| Ex. No. | Strc. | P.D. | P.C. |
|---|---|---|---|
| 50-1 | 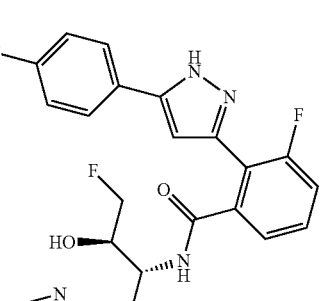 | $^1$H-NMR(DMSO-d$_6$) δ ppm: 3.47-3.80 (2H, m), 4.22-4.41 (1H, m), 4.45-4.59 (1H, m), 4.66-4.92 (1H, m), 5.14-5.63 (1H, m), 6.18-6.32 (1H, m), 6.42-7.09 (2H, m), 7.15-7.61 (5H, m), 7.68-7.72 (1H, m), 7.74-7.86 (2H, m), 8.74-8.98 (1H, m), 12.9-13.5 (1H, m).<br>RT(min): 3.094 (Method A)<br>MS(ESI, m/z): 474.1547 (M + H)$^+$ | Column: APS<br>EtOAc/MeOH |
| 50-2 |  | $^1$H-NMR(CDCl$_3$) δ ppm: 3.23-3.40 (2H, m), 3.98-4.12 (1H, m), 4.45-4.52 (1H, m), 4.58-4.70 (2H, m), 6.78 (1H, d, J = 3.2 Hz), 6.90-7.03 (1H, m), 7.04-7.14 (3H, m), 7.21-7.30 (2H, m), 7.33-7.41 (1H, m), 7.62-7.72 (2H, m), 8.58 (2H, d, J = 5.0 Hz).<br>RT(min): 2.398 (Method A)<br>MS(ESI, m/z): 468.1643 (M + H)$^+$ | Column: APS<br>EtOAc/MeOH |

TABLE 124-continued

| Ex. No. | Strc. | P.D. | P.C. |
|---|---|---|---|
| 50-3 | | ¹H-NMR(CDCl₃) δ ppm: 3.18 (1H, dd, J = 4.4, 14.5 Hz), 3.27 (1H, dd, J = 7.3, 14.5 Hz), 3.92-4.04 (1H, m), 4.32-4.66 (3H, m), 6.67 (1H, s), 6.95-7.11 (4H, m), 7.33 (1H, t, J = 7.7 Hz), 7.40 (1H, dd, J = 1.4, 7.7 Hz), 7.50-7.58 (3H, m), 8.57 (2H, d, J = 5.0 Hz).<br>RT(min): 2.563 (Method A)<br>MS(ESI, m/z): 484.1346 (M + H)⁺ | Column: APS EtOAc/MeOH |
| 50-4 | | ¹H-NMR(CDCl₃) δ ppm: 3.29 (1H, dd, J = 8.7, 15.2 Hz), 3.47 (1H, dd, J = 4.0, 15.2 Hz), 3.66-3.91 (2H, m), 5.04-5.22 (1H, m), 6.74 (1H, d, J = 2.9 Hz), 7.04 (1H, t, J = 5.0 Hz), 7.07-7.17 (2H, m), 7.24-7.33 (2H, m), 7.36-7.44 (1H, m), 7.55-7.68 (3H, m), 8.55 (2H, d, J = 5.0 Hz).<br>RT(min): 2.727 (Method A)<br>MS(ESI, m/z): 486.1548 (M + H)⁺ | Column: APS EtOAc/MeOH |
| 50-5 | | ¹H-NMR(CDCl₃) δ ppm: 3.12 (1H, dd, J = 8.2, 14.8 Hz), 3.28 (1H, dd, J = 4.4, 14.8 Hz), 3.59-3.87 (2H, m), 4.80-5.01 (1H, m), 6.75 (1H, d, J = 2.8 Hz), 7.05-7.15 (3H, m), 7.17-7.31 (3H, m), 7.33-7.43 (1H, m), 7.55-7.68 (3H, m), 7.84-7.98 (1H, m), 8.34-8.41 (1H, m).<br>RT(min): 2.186 (Method A)<br>MS(ESI, m/z): 485.1596 (M + H)⁺ | Column: APS EtOAc/MeOH |
| 50-6 | | ¹H-NMR(CDCl₃) δ ppm: 3.47-3.69 (2H, m), 4.38 (1H, d, J = 6.6 Hz), 4.44-4.64 (1H, m), 4.68-4.86 (1H, m), 6.22-6.25 (1H, m), 6.76 (1H, d, J = 2.5 Hz), 6.95 (1H, d, J = 8.7 Hz), 7.05-7.14 (2H, m), 7.17-7.31 (2H, m), 7.32-7.43 (2H, m), 7.44-7.47 (1H, m), 7.63-7.72 (2H, m).<br>RT(min): 2.649 (Method A)<br>MS(ESI, m/z): 456.1640 (M + H)⁺ | Column: APS EtOAc/MeOH |

TABLE 124-continued

| Ex. No. | Strc. | P.D. | P.C. |
|---|---|---|---|
| 50-7 | | ¹H-NMR(CDCl₃) δ ppm: 3.08 (1H, dd, J = 8.0, 14.3 Hz), 3.17 (1H, dd, J = 5.7, 14.3 Hz), 3.52-3.76 (2H, m), 4.56-4.88 (2H, m), 6.80 (1H, d, J = 3.0 Hz), 7.04-7.14 (2H, m), 7.15-7.19 (1H, m), 7.20-7.30 (2H, m), 7.34-7.42 (3H, m), 7.56 (1H, td, J = 1.8, 7.7 Hz), 7.63-7.77 (2H, m), 8.38-8.44 (1H, m).<br>RT(min): 2.222 (Method A)<br>MS(ESI, m/z): 483.1391 (M + H)⁺ | Column: APS<br>EtOAc/MeOH |

TABLE 125

| Ex. No. | Strc. | P.D. | P.C. |
|---|---|---|---|
| 50-8 | | ¹H-NMR(DMSO-d₆) δ ppm: 3.48-3.68 (1H, m), 4.00-4.57 (5H, m), 5.40-5.70 (1H, m), 6.22-6.25 (1H, m), 6.56-7.74 (8H, m), 7.75-7.88 (2H, m), 8.12-8.60 (1H, m), 12.9-13.6 (1H, m).<br>RT(min): 2.767 (Method A)<br>MS(ESI, m/z): 456.1642 (M + H)⁺ | Column: APS<br>EtOAc/MeOH |
| 50-9 | | ¹H-NMR(CDCl₃) δ ppm: 2.95-3.11 (1H, m), 3.12-3.24 (1H, m), 3.38-3.72 (2H, m), 4.63-4.94 (1H, m), 6.67 (1H, s), 7.03-7.15 (3H, m), 7.15-7.22 (1H, m), 7.22-7.42 (2H, m), 7.50-7.95 (5H, m), 8.35-8.46 (1H, m).<br>RT(min): 2.405 (Method A)<br>MS(ESI, m/z): 501.1299 (M + H)⁺ | Column: APS<br>EtOAc/MeOH |
| 50-10 | | ¹H-NMR(CDCl₃) δ ppm: 3.28 (1H, dd, J = 7.7, 14.8 Hz), 3.34 (1H, dd, J = 5.0, 14.8 Hz), 3.56-3.67 (1H, m), 3.69-3.79 (1H, m), 4.64-4.83 (1H, m), 4.84-4.99 (1H, m), 7.03 (1H, t, J = 5.0 Hz), 7.09-7.17 (2H, m), 7.22-7.37 (2H, m), 7.38-7.44 (1H, m), 7.45-7.54 (1H, m), 7.72-7.81 (2H, m), 8.56 (2H, d, J = 5.0 Hz).<br>RT(min): 2.587 (Method A)<br>MS(ESI, m/z): 486.1546 (M + H)⁺ | Column: APS<br>EtOAc/MeOH |

TABLE 125-continued

| Ex. No. | Strc. | P.D. | P.C. |
|---|---|---|---|
| 50-11 | | ¹H-NMR(CDCl₃) δ ppm: 3.58-3.92 (3H, m), 4.23-4.33 (1H, m), 4.47-4.58 (1H, m), 4.61-4.73 (1H, m), 6.20-6.26 (1H, m), 6.82 (1H, d, J = 2.8 Hz), 7.07-7.15 (2H, m), 7.28-7.36 (1H, m), 7.37-7.50 (4H, m), 7.62-7.71 (2H, m), 7.88-7.98 (1H, m).<br>RT(min): 2.757 (Method A)<br>MS(ESI, m/z): 456.1640 (M + H)⁺ | Column: APS<br>EtOAc/MeOH |
| 50-12 | | ¹H-NMR(CDCl₃) δ ppm: 3.70-3.91 (2H, m), 4.78-4.90 (2H, m), 5.08-5.20 (1H, m), 6.74 (1H, d, J = 2.7 Hz), 7.03-7.11 (3H, m), 7.22-7.30 (2H, m), 7.38-7.43 (1H, m), 7.58 (2H, s), 7.58-7.62 (2H, m).<br>RT(min): 2.774 (Method A)<br>MS(ESI, m/z): 475.1501 (M + H)⁺ | Column: APS<br>EtOAc/MeOH |

TABLE 126

| Ex. No. | Strc. | P.D. | P.C. |
|---|---|---|---|
| 51-1 | | RT(min): 1.746 (Method A)<br>MS(ESI, m/z): 441.1916 (M + H)⁺ | Column: APS<br>EtOAc/MeOH |
| 52-1 | | RT(min): 2.099 (Method A)<br>MS(ESI, m/z): 463.1576 (M + H)⁺ | Column: SiO2<br>EtOAc/MeOH |

TABLE 126-continued

| Ex. No. | Strc. | P.D. | P.C. |
|---|---|---|---|
| 52-2 | 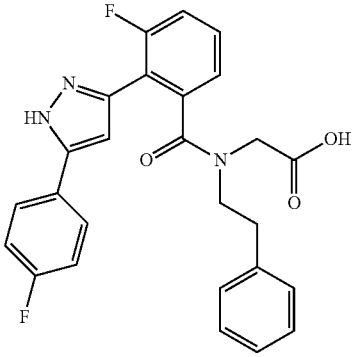 [SMILES: O=C(O)CN(CCc1ccccc1)C(=O)c1cccc(F)c1-c1cc(-c2ccc(F)cc2)[nH]n1] | RT(min): 3.601 (Method A)<br>MS(ESI, m/z): 462.1622 (M + H)+ | Column: SiO2<br>EtOAc/MeOH |
| 53-1 | 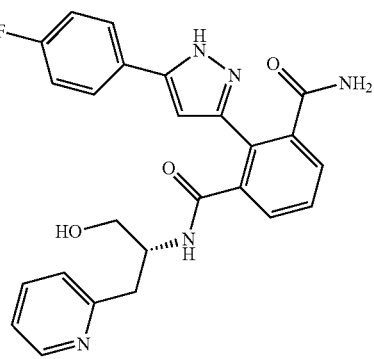 | ¹H-NMR(CDCl₃) δ ppm: 2.93-2.98 (2H, m), 3.36-3.45 (1H, m), 3.46-3.54 (1H, m), 3.61-3.68 (1H, m), 4.20-4.33 (1H, m), 5.54-5.63 (1H, m), 6.07-6.18 (1H, m), 6.68 (1H, s), 6.96-7.03 (1H, m), 7.03-7.11 (3H, m), 7.07-7.15 (2H, m), 7.40-7.55 (2H, m), 7.60-7.70 (3H, m), 8.32-8.36 (1H, m). | Column: APS<br>EtOAc/MeOH |

TABLE 127

| Ex. No. | Strc. | P.D. | P.C. |
|---|---|---|---|
| 54-1 | 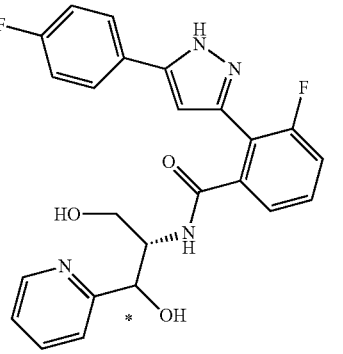 | ¹H-NMR(CDCl₃) δ ppm: 3.68-3.75 (2H, m), 4.36-4.45 (1H, m), 5.06-5.12 (1H, m), 6.76 (1H, d, J = 2.8 Hz), 7.07 (2H, t, J = 8.8 Hz), 7.11-7.22 (3H, m), 7.28-7.34 (1H, m), 7.42-7.48 (2H, m), 7.60-7.78 (4H, m), 8.40-8.55 (2H, m).<br>RT(min): 1.820 (Method A)<br>MS(ESI, m/z): 451.1576 (M + H)+ | Column: SiO2<br>EtOAc/MeOH. |
| 54-2 | 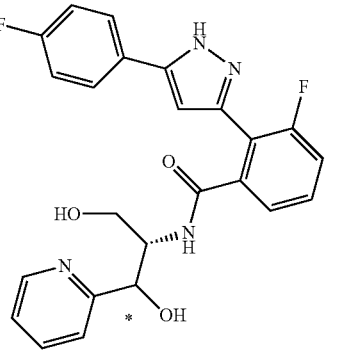 | ¹H-NMR(CDCl₃) δ ppm: 3.88-3.96 (2H, m), 4.51-4.59 (1H, m), 5.04-5.08 (1H, m), 6.60-6.77 (2H, m), 6.95-7.01 (1H, m), 7.02-7.30 (6H, m), 7.39-7.46 (1H, m), 7.60-7.70 (3H, m), 8.40-8.44 (1H, m).<br>RT(min): 1.740 (Method A)<br>MS(ESI, m/z): 451.1575 (M + H)+ | Column: SiO2<br>EtOAc/MeOH |

TABLE 127-continued

| Ex. No. | Strc. | P.D. | P.C. |
|---|---|---|---|
| 54-3 | | $^1$H-NMR(CDCl$_3$) δ ppm: 1.84-1.95 (1H, m), 2.02-2.12 (1H, m), 3.59-3.67 (1H, m), 3.71-3.78 (1H, m), 4.67-4.76 (1H, m), 4.86 (1H, d, J = 1.8 Hz), 6.50 (1H, d, J = 9.0 Hz), 6.72 (1H, d, J = 3.4 Hz), 6.86 (1H, d, J = 7.6 Hz), 7.05-7.15 (3H, m), 7.17-7.32 (2H, m), 7.38 (1H, d, J = 7.8 Hz), 7.63 (1H, dt, J = 1.5, 7.7 Hz), 7.68-7.74 (1H, m), 8.40 (1H, d, J = 4.9 Hz), RT(min): 1.751 (Method A) MS(ESI, m/z): 465.1732 (M + H)$^+$ | Column: SiO2 EtOAc/MeOH |
| 54-4 | | $^1$H-NMR(CDCl$_3$) δ ppm: 1.17 (3H, d, J = 6.0 Hz), 1.72-1.82 (1H, m), 1.87-1.95 (1H, m), 3.89-3.98 (1H, m), 4.61-4.70 (1H, m), 4.93, (1H, d, J = 2.5 Hz), 6.67-6.75 (2H, m), 6.87 (1H, d, J = 7.5 Hz), 7.04-7.11 (3H, m), 7.15 (1H, ddd, J = 1.2, 8.4, 9.9 Hz), 7.23-7.26 (1H, m), 7.41 (1H, d, J = 7.9 Hz), 7.64 (1H, dt, J = 1.6, 7.6 Hz), 7.66-7.72 (3H, m), 8.39 (1H, d, J = 4.9 Hz). RT(min): 1.788 (Method A) MS(ESI, m/z): 479.1887 (M + H)$^+$ | Column: SiO2 EtOAc/MeOH |
| 54-5 | | $^1$H-NMR(CDCl$_3$) δ ppm: 1.27-1.33 (1H, m), 1.50-1.59 (1H, m), 2.88 (1H, dd, J = 6.2, 14.3 Hz), 3.13 (1H, dd, J = 4.5, 14.3 Hz), 3.41-3.50 (2H, m), 3.97-4.07 (1H, m), 4.62-4.73 (1H, m), 6.77 (1H, d, J = 3.0 Hz), 7.03-7.15 (5H, m), 7.21-7.28 (2H, m), 7.33-7.41 (1H, m), 7.55-7.65 (3H, m), 7.92-7.97 (1H, m), 8.38-8.42 (1H, m). RT(min): 1.658 (Method A) MS(ESI, m/z): 479.1885 (M + H)$^+$ | Column: SiO2 EtOAc/MeOH |
| 54-6 | | $^1$H-NMR(CDCl$_3$) δ ppm: 3.11 (1H, dd, J = 4.7, 14.7 Hz), 3.23 (1H, dd, J = 5.3, 14.7 Hz), 3.33-3.39 (1H, m), 3.59 (1H, dd, J = 3.3, 12.4 Hz), 3.69 (1H, dd, J = 3.3, 12.4 Hz), 4.35-4.44 (1H, m), 6.78 (1H, d, J = 3.0 Hz), 6.96-7.02 (1H, m), 7.05-7.16 (5H, m), 7.20-7.32 (2H, m), 7.36-7.44 (1H, m), 7.50-7.57 (1H, m), 7.65-7.80 (3H, m), 8.35-8.39 (1H, m). RT(min): 1.684 (Method A) MS(ESI, m/z): 465.1729 (M + H)$^+$ | Column: SiO2 EtOAc/MeOH |

TABLE 128

| Ex. No. | Strc. | P.D. | P.C. |
|---|---|---|---|
| 54-7 | 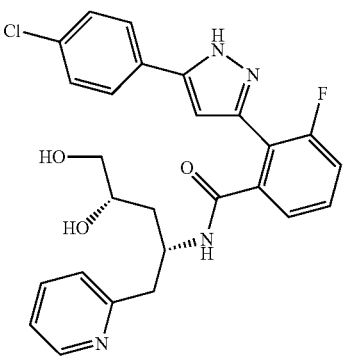 [SMILES: O=C(N[C@H](Cc1ccccn1)C[C@H](O)CO)c1cccc(F)c1-c1cc(-c2ccc(Cl)cc2)[nH]n1] | ¹H-NMR(CDCl₃) δ ppm: 1.22-1.35 (1H, m), 1.50-1.60 (1H, m), 2.89 (1H, dd, J = 6.0, 14.5 Hz), 3.15 (1H, dd, J = 4.7, 14.5 Hz), 3.44-3.49 (2H, m), 3.98-4.05 (1H, m), 4.62-4.73 (1H, m), 6.83 (1H, d, J = 3.0 Hz), 7.09-7.15 (2H, m), 7.21-7.31 (1H, m), 7.34-7.39 (4H, m), 7.56-7.63 (3H, m), 7.93 (1H, d, J = 7.7 Hz), 8.39-8.43 (1H, m). RT(min): 1.928 (Method A) MS(ESI, m/z): 495.1590 (M + H)⁺ | Column: SiO2 EtOAc/MeOH |
| 54-8 | 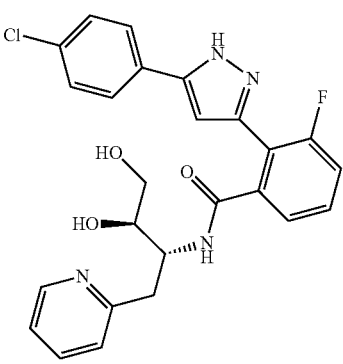 [SMILES: O=C(N[C@H](Cc1ccccn1)[C@@H](O)CO)c1cccc(F)c1-c1cc(-c2ccc(Cl)cc2)[nH]n1] | ¹H-NMR(CDCl₃) δ ppm: 3.08 (1H, dd, J = 4.2, 14.6 Hz), 3.17 (1H, dd, J = 6.1, 14.9 Hz), 3.45-3.55 (1H, m), 3.57-3.64 (1H, m), 3.65-3.72 (1H, m), 4.40-4.50 (1H, m), 6.71-7.75 (1H, m), 7.05-7.10 (1H, m), 7.12-7.24 (3H, m), 7.28-7.38 (3H, m), 7.50-7.60 (3H, m), 7.77-7.85 (1H, m), 8.32-8.38 (1H, m). RT(min): 1.977 (Method A) MS(ESI, m/z): 481.1434 (M + H)⁺ | Column: SiO2 EtOAc/MeOH |
| 54-9 | 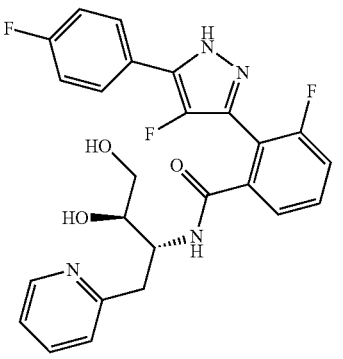 [SMILES: O=C(N[C@H](Cc1ccccn1)[C@@H](O)CO)c1cccc(F)c1-c1n[nH]c(-c2ccc(F)cc2)c1F] | ¹H-NMR(CDCl₃) δ ppm: 3.06 (1H, dd, J = 4.5, 14.4 Hz), 3.20 (1H, dd, J = 6.3, 14.3 Hz), 3.50-3.72 (3H, m), 4.42-4.53 (1H, m), 6.99-7.20 (5H, m), 7.22-7.34 (2H, m), 7.41-7.49 (1H, m), 7.51-7.62 (3H, m), 8.04-8.09 (1H, m), 8.37-8.41 (1H, m). RT(min): 1.970 (Method A) MS(ESI, m/z): 483.1636 (M + H)⁺ | Column: SiO2 EtOAc/MeOH |
| 54-10 | 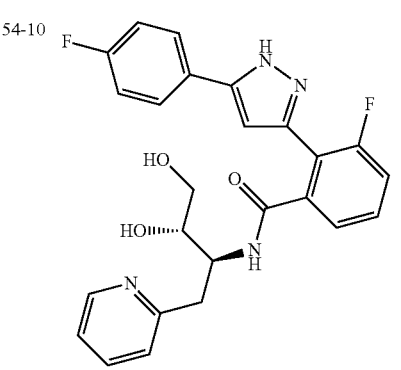 | ¹H-NMR(CDCl₃) δ ppm: 3.09 (1H, dd, J = 4.5 Hz, 14.5 Hz), 3.18 (1H, dd, J = 6.1 Hz, 14.5 Hz), 3.44-3.52 (1H, m), 3.60 (1H, dd, J = 3.3 Hz, 12.3 Hz), 3.73 (1H, dd, J = 3.6 Hz, 12.0 Hz), 4.40-4.50 (1H, m), 6.71 (1H, d, J = 2.6 Hz), 6.98-7.11 (3H, m), 7.12-7.30 (3H, m), 7.31-7.40 (1H, m), 7.53 (1H, dt, J = 1.6 Hz, 7.6 Hz), 7.56-7.62 (2H, m), 7.76-7.84 (1H, m), 8.35 (1H, d, J = 4.5 Hz). RT(min): 1.704 (Method A) MS(ESI, m/z): 465.1728 (M + H)⁺ | Column: SiO2 EtOAc/MeOH |

TABLE 128-continued
| Ex. No. | Strc. | P.D. | P.C. |
|---|---|---|---|
| 54-11 | 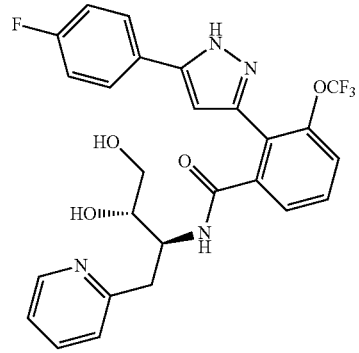 [SMILES: O=C(N[C@@H](Cc1ccccn1)[C@H](O)CO)c1cccc(OC(F)(F)F)c1-c1cc(-c2ccc(F)cc2)[nH]n1] | RT(min): 2.141 (Method A)<br>MS(ESI, m/z): 531.1645 (M + H)+ | Column: SiO2<br>EtOAc/MeOH |
| 54-12 | 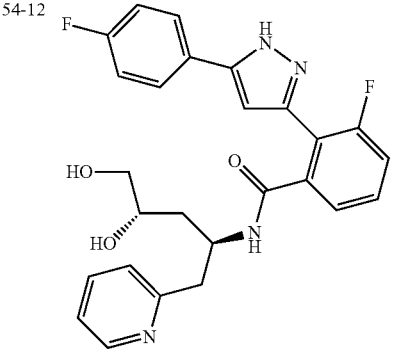 | RT(min): 1.658 (Method A)<br>MS(ESI, m/z): 479.1882 (M + H)+ | Column: SiO2<br>EtOAc/MeOH |
TABLE 129
| Ex. No. | Strc. | P.D. | P.C. |
|---|---|---|---|
| 54-13 | 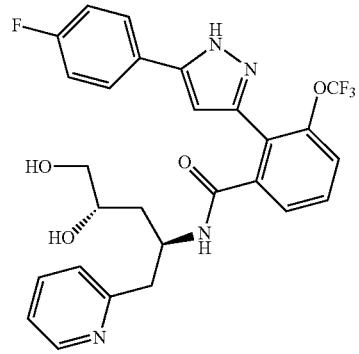 [SMILES: O=C(N[C@@H](Cc1ccccn1)C[C@H](O)CO)c1cccc(OC(F)(F)F)c1-c1cc(-c2ccc(F)cc2)[nH]n1] | RT(min): 2.106 (Method A)<br>MS(ESI, m/z): 545.1801 (M + H)+ | Column: SiO2<br>EtOAc/MeOH |
| 54-14 | 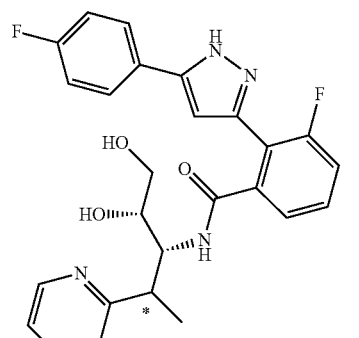 | $^1$H-NMR(CDCl$_3$) δ ppm: 1.36 (3H, d, J = 7.2 Hz), 3.18-3.27 (1H, m), 3.55 (2H, d, J = 4.8 Hz), 3.61-3.69 (1H, m), 4.43-4.51 (1H, m), 6.79 (1H, d, J = 3.3 Hz), 6.97-7.11 (6H, m), 7.19-7.36 (2H, m), 7.50 (1H, ddd, 1.8, 7.7, 7.7 Hz), 7.57-7.64 (2H, m), 7.97-8.04 (1H, m), 8.32-8.36 (1H, m).<br>RT(min): 1.812 (Method A)<br>MS(ESI, m/z): 479.1884 (M + H)+ | Column: SiO2<br>EtOAc/MeOH |

TABLE 129-continued

| Ex. No. | Strc. | P.D. | P.C. |
|---|---|---|---|
| 54-15 | 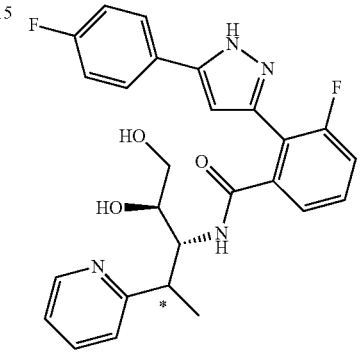 | ¹H-NMR(CDCl₃) δ ppm: 1.21 (3H, d, J = 7.3 Hz), 2.90-2.96 (1H, m), 3.48-3.62 (2H, m), 3.64-3.71 (1H, m), 4.17-4.25 (1H, m), 6.83 (1H, d, J = 3.0 Hz), 6.96-7.14 (4H, m), 7.18-7.22 (1H, m), 7.27-7.34 (1H, m), 7.38-7.48 (2H, m), 7.56-7.71 (4H, m), 8.80-8.90 (1H, m). RT(min): 1.930 (Method A) MS(ESI, m/z): 479.1883 (M + H)⁺ | Column: SiO2 EtOAc/MeOH |
| 54-16 | 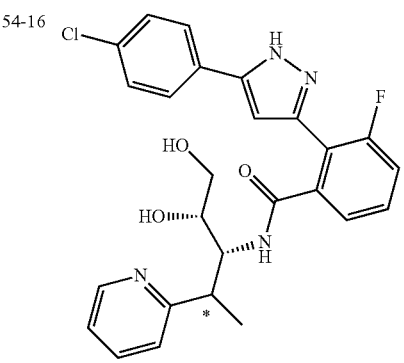 | ¹H-NMR(CDCl₃) δ ppm: 1.38 (3H, d, J = 7.0 Hz), 3.23-3.28 (1H, m), 3.57 (2H, d, J = 5.7 Hz), 3.69-3.76 (1H, m), 4.44-4.51 (1H, m), 6.85 (1H, d, J = 3.5 Hz), 7.02-7.08 (1H, m), 7.09-7.14 (2H, m), 7.24-7.40 (4H, m), 7.54 (1H, dt, J = 1.8, 7.8 Hz), 7.57-7.63 (2H, m), 7.90-7.95 (1H, m), 8.34-8.39 (1H, m). RT(min): 2.047 (Method A) MS(ESI, m/z): 495.1590 (M + H)⁺ | Column: SiO2 EtOAc/MeOH |
| 54-17 | 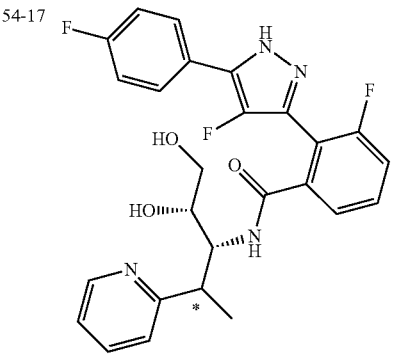 | ¹H-NMR(CDCl₃) δ ppm: 1.35 (3H, d, J = 7.2 Hz), 3.19-3.28 (1H, m), 3.52-3.57 (2H, m), 3.63-3.72 (1H, m), 4.39-4.46 (1H, m), 6.98-7.23 (7H, m), 7.38-7.46 (1H, m), 7.48-7.54 (1H, m), 7.66-7.72 (2H, m), 8.34-8.38 (1H, m). RT(min): 2.022 (Method A) MS(ESI, m/z): 497.1793 (M + H)⁺ | Column: SiO2 EtOAc/MeOH |
| 54-18 | 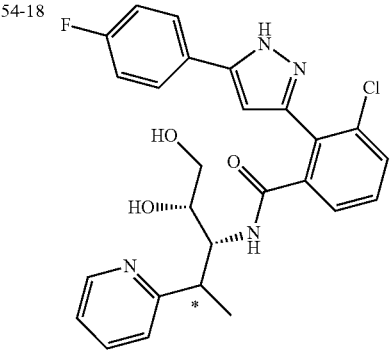 | ¹H-NMR(CDCl₃) δ ppm: 1.28-1.36 (3H, d, J = 7.0 Hz), 3.15-3.25 (1H, m), 3.40-3.50 (2H, m), 3.67-3.80 (1H, m), 4.27-4.38 (1H, m), 6.76 (1H, s), 6.97-7.15 (5H, m), 7.27-7.34 (1H, m), 7.43-7.70 (5H, m), 8.38-8.44 (1H, m). RT(min): 1.954 (Method A) MS(ESI, m/z): 495.1590 (M + H)⁺ | Column: SiO2 EtOAc/MeOH |

TABLE 130

| Ex. No. | Strc. | P.D. | P.C. |
|---|---|---|---|
| 54-19 | | ¹H-NMR(CDCl₃) δ ppm: 3.24 (3H, s), 3.43-3.57 (2H, m), 4.05-4.12 (1H, m), 4.42-4.48 (1H, m), 4.52 (1H, d), J = 6.8 Hz), 6.76 (1H, d, J = 2.8 Hz), 6.86 (1H, d, J = 7.3 Hz), 6.96-7.03 (1H, m), 7.06 (2H, t, J = 8.6 Hz), 7.15-7.24 (2H, m), 7.45 (1H, d, J = 7.7 Hz), 7.63-7.74 (3H, m), 8.47-8.52 (1H, d, J = 4.8 Hz). RT(min): 2.335 (Method A) MS(ESI, m/z): 495.1833 (M + H)⁺ | Column: SiO2 EtOAc/MeOH |
| 54-20 | | RT(min): 2.394 (Method A) MS(ESI, m/z): 483.1634 (M + H)⁺ | Column: SiO2 EtOAc/MeOH |
| 55-1 | | RT(min): 1.744 (Method A) MS(ESI, m/z): 450.1733 (M + H)⁺ | Column: APS EtOAc/MeOH |

TABLE 131

| Ex. No. | Strc. | P.D. | P.C. |
|---|---|---|---|
| 56-1 | | ¹H-NMR(CDCl₃) δ ppm: 3.67-3.89 (2H, m), 4.80-4.93 (2H, m), 5.03-5.16 (1H, m), 7.10-7.14 (2H, m), 7.20-7.23 (1H, m), 7.32-7.40 (2H, m), 7.47-7.53 (1H, m), 7.57 (2H, s), 7.64-7.69 (2H, m). RT(min): 2.970 (Method A) MS(ESI, m/z): 493.1407 (M + H)⁺ | Column: APS EtOAc/MeOH |

TABLE 131-continued

| Ex. No. Strc. | P.D. | P.C. |
|---|---|---|
| 57-1 | RT(min): 1.786 (Method A)<br>MS(ESI, m/z): 355.1550 (M + H)+ | Without purification |
| 57-2 | RT(min): 1.978 (Method A)<br>MS(ESI, m/z): 449.1414 (M + H)+ | Without purification |

REFERENCE EXAMPLE 2-72-1

Reference Example 2-72-1 was synthesized in a manner similar to that of Reference Example 2-69-1 by using the corresponding materials. Structural formula, spectral data and purification condition are shown in Table 132.

REFERENCE EXAMPLE 2-73-1

(2S,3R)-4-Benzyloxy-3-fluoro-1-(2H-1,2,3-triazol-2-yl)butan-2-amine hydrochloride To a solution of (1R)-2-(benzyloxy)-1-[(4R)-2,2-dimethyl-1,3-dioxolan-4-yl]ethan-1-ol (660 mg) tetrahydrofuran (10 mL) were added 1,8-diazabicyclo[5.4.0]-7-undecene (798 mg) and perfluoro-1-butanesulfonyl fluoride (1.58 g) at 0° C., and the mixture was stirred at room temperature for 2 hours. To the reaction mixture was added water, and the crude product was extracted with dichloromethane. The extract was washed with brine, and dried over sodium sulfate. The solvent was removed under reduced pressure. To a solution of the residue (228 mg) methanol (4 mL) was added a solution of hydrogen chloride in 1,4-dioxane (4 mol/L, 1 mL), and the mixture was stirred at room temperature for 1 hour. The reaction mixture was concentrated under reduced pressure. The residue was purified by silica gel column chromatography (eluent: n-hexane/ethyl acetate) to afford (2R,3S)-4-(benzyloxy)-3-fluorobutane-1,2-diol (156 mg). To a solution of the product (156 mg) in pyridine (2 mL) was added p-toluenesulfonyl chloride (153 mg) at 0° C., and the mixture was stirred at room temperature for 2 hours. To the reaction mixture was added p-toluenesulfonyl chloride (200 mg) at 0° C. and the mixture was stirred at room temperature for 1 hour. To the reaction mixture was added water, and the crude product was extracted with dichloromethane. The extract was washed with brine, and dried over sodium sulfate. The solvent was removed under reduced pressure. The residue was purified by silica gel column chromatography (eluent: n-hexane/ethyl acetate) to afford (2R,3S)-1-(benzyloxy)-3-fluoro-4-[(4-methylbenzenesulfonyl)oxy]butan-2-ol (305 mg). A mixture of the product (305 mg), methanol (1 mL), tetrahydrofuran (1 mL) and an aqueous solution of 28% ammonia (2 mL) was stirred at room temperature for 20 hours. The reaction mixture was concentrated under reduced pressure. To a solution of the residue in tetrahydrofuran (5 mL) were added di-tert-butyl dicarbonate (271 mg) and triethylamine (252 mg), and the mixture was stirred at room temperature for 2 hours. To the reaction mixture was added water, and the crude product was extracted with ethyl acetate. The extract was washed with brine, and dried over sodium sulfate. The solvent was removed under reduced pressure. The residue was purified by silica gel column chromatography (eluent: n-hexane/ethyl acetate) to afford N-[(2R,3S)-4-(benzyloxy)-3-fluoro-2-hydroxybutan-1-yl]carbamic acid tert-butyl ester (101 mg). To a solution of the product (101 mg) in dichloromethane (3 mL) were added triethylamine (65 mg) and methanesulfonyl chloride (48 mg) at 0° C., and the mixture was stirred at the same temperature for 1 hour. To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in N,N-dimethylformamide (1 mL) were added cesium carbonate (315 mg) and 1,2,3-triazole (33 mg) at room temperature, and the mixture was stirred at 70° C. for 3 hours. To the reaction mixture was added water, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate) to afford N-[(2S,3R)-4-(benzyloxy)-3-fluoro-1-(2H-1,2,3-triazol-2-yl)butan-2-yl]carbamic acid tert-butyl ester (37 mg). A mixture of the product (37 mg), methanol (1 mL) and a solution of hydrogen chloride in 1,4-dioxane (4 mol/L, 0.5 mL) was stirred at room temperature for 1 hour. The reaction mixture was concentrated under reduced pressure to afford the title compound (30 mg). Structural formula, spectral data and purification condition are shown in Table 132.

REFERENCE EXAMPLE 2-74-1

A mixture of (2R,3S)-3-fluoro-4-methoxy-1-(2H-1,2,3-triazol-2-yl)butan-2-amine hydrochloride and (2R,3R)-3-fluoro-4-methoxy-1-(2H-1,2,3-triazol-2-yl)butan-2-amine hydrochloride To a solution of (1S)-2-(benzyloxy)-1-[(4S)-2,2-dimethyl-1,3-dioxolan-4-yl]ethan-1-ol (5.0 g) in tetrahydrofuran (30 mL) were added 1,8-diazabicyclo[5.4,0]-7-undecene (6.03 g) and perfluoro-1-butanesulfonyl fluoride (12.0 g) at 0° C., and the mixture was stirred at room temperature for 2 hours. To the reaction mixture was added a saturated aqueous solution of ammonium chloride, and the crude product was extracted with dichloromethane. The extract was washed with brine, and dried over sodium sulfate. The solvent was removed under reduced pressure. To a solution of the residue in methanol (15 mL) was added a solution of hydrogen chloride in 1,4-dioxane (4 mol/L, 5 mL), and the mixture was stirred at room temperature for 2 hours. The reaction mixture was concentrated under reduced pressure. The residue was purified by silica gel column chromatography (eluent: n-hexane/ethyl acetate) to afford (2S,3R)-4-(benzyloxy)-3-fluorobutane-1,2-diol (1.4 g). To a solution of the product (1.4 g) in toluene (10 mL) were added triphenylphosphine (2.57 g) and a solution of azodicarboxylic acid diethyl ester in toluene (2.2 mol/L, 4.5 mL) at room temperature, and the mixture was stirred at 80° C. for 15 hours. The reaction mixture was allowed to cool to room temperature, and then concentrated under reduced pressure. The residue was purified by silica gel column chromatography (eluent: n-hexane/ethyl acetate) to afford (2S)-2-[(1R)-2-(benzyloxy)-1-fluoroethyl]oxirane (550 mg). A mixture of the product (670 mg), methanol (4 mL) and an aqueous solution of 28% ammonia (20 mL) was stirred at room temperature for 5 hours. The reaction mixture was concentrated under reduced pressure. To a solution of the residue in tetrahydrofuran (5 mL) was added di-tert-butyl dicarbonate (745 mg), and the mixture was stirred at room temperature for 1 hour. The reaction mixture was concentrated under reduced pressure. The residue was purified by silica gel column chromatography (eluent: n-hexane/ethyl acetate) to afford N-[(2S,3R)-4-(benzyloxy)-3-fluoro-2-hydroxybutan-1-yl]carbamic acid tert-butyl ester (940 mg). To a solution of the product (940 mg) in dichloromethane (5 mL) were added triethylamine (607 mg) and methanesulfonyl chloride (447 mg) at 0° C., and the mixture was stirred at the same temperature for 1 hour. To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in N,N-dimethylformamide (5 mL) were added cesium carbonate (2.9 g) and 1,2,3-triazole (311 mg) at room temperature, and the mixture was stirred at 70° C. for 12 hours. To the reaction mixture was added water, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate) to afford N-[(2R,3S)-4-(benzyloxy)-3-fluoro-1-(2H-1,2,3-triazol-2-yl)butan-2-yl]carbamic acid tert-butyl ester (400 mg). To a solution of the product (400 mg) in tetrahydrofuran (3 mL) was added 20% palladium hydroxide-carbon (50% wet, 100 mg), and the mixture was stirred at room temperature under a hydrogen atmosphere for 4 hours. The reaction mixture was filtered through a pad of celite, and then the filtrate was concentrated under reduced pressure. To a mixture of the residue, tetrahydrofuran (3 mL), N,N-dimethylformamide (0.3 mL) and iodomethane (190 mg) was added sodium hydride (60% dispersion in oil, 43 mg) at 0° C., and the mixture was stirred at room temperature for 1 hour. To the reaction mixture was added a saturated aqueous solution of ammonium chloride, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate). A mixture of the product (220 mg), methanol (1 mL) and a solution of hydrogen chloride in 1,4-dioxane (4 mol/L, 1 mL) was stirred at room temperature for 1 hour. The reaction mixture was concentrated under reduced pressure to afford the title compound (170 mg). Structural formula, spectral data and purification condition are shown in Table 132.

REFERENCE EXAMPLE 2-75-1

N-[(2R,3R)-3-Amino-2-hydroxy-4-(1H-pyrazol-1-yl)butan-1-yl]phthalimide

To a solution of (1S)-2-amino-1-[(4R)-2,2-dimethyl-1,3-dioxolan-4-yl]ethan-1-ol (1.0 g) in dichloromethane (10 mL) were added triethylamine (1.26 g) and benzyl chloroformate (1.06 g) at 0° C., and the mixture was stirred at room temperature for 13 hours. To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in dichloromethane (10 mL) added triethylamine (1.26 g) and methanesulfonyl chloride (853 mg) at 0° C., and the mixture was stirred at room temperature for 1 hour. To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in N,N-dimethylformamide (10 mL) were added cesium carbonate (6.06 g) and pyrazole (634 mg) and the mixture was stirred at 70° C. for 16 hours. To the reaction mixture were added cesium carbonate (3.0 g) and pyrazole (300 mg), and the mixture was stirred at 80° C. for 2 hours. The reaction mixture was allowed to cool to room temperature. To the mixture was added water, and the crude product was extracted with ethyl acetate. The extract was washed with water and brine, and dried over sodium sulfate. The solvent was removed under reduced pressure, and the residue was purified by silica gel column chromatography (eluent: n-hexane/ethyl acetate) to afford N-{(1R)-1-[(4S)-2,2-dimethyl-1,3-dioxolan-4-yl]-2-(1H-pyrazol-1-yl)ethyl}carbamic acid benzyl ester (890 mg). A mixture of the product (890 mg), methanol (1 mL), water (0.3 mL) and trifluoroacetic acid (294 mg) was stirred at room temperature for 2 days. The reaction mixture was concentrated under reduced pressure. The residue was removed azeotropically twice with toluene. To a solution of the residue in N,N-dimethylformamide (3 mL) were added imidazole (440 mg) and tert-butyldiphenylchlorosilane (1.06 g) at 0° C., and the mixture was stirred at the same temperature for 1 hour. To the reaction mixture was added a saturated aqueous solution of sodium bicarbonate, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate) to afford N-[(2R,3S)-4-(tert-butyldiphenylsilyloxy)-3-hydroxy-1-(1H-pyrazol-1-yl)butan-2-yl]carbamic acid benzyl ester (650 mg). To a solution of the product (650 mg) in toluene (5 mL) were added p-toluenesulfonic acid monohydrate (23 mg), 2,2-dimethoxypropane (1.25 g), and the mixture was stirred at 85° C. for 14 hours. To the reaction mixture was added a saturated aqueous solution of sodium bicarbonate, and the crude product was extracted with ethyl acetate. The extract was washed with brine, and dried over sodium sulfate. The solvent was removed under reduced pressure. To a solution of the residue in tetrahydrofuran (5 mL) was added a solution of tetra-n-butylammonium fluoride in tetrahydrofuran (1 mol/L, 1.43 mL) at 0° C., and the mixture was stirred at room temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure. The residue was purified by silica gel column chromatography (eluent: n-hexane/ethyl acetate) to afford (4R,5S)-5-(hydroxymethyl)-2,2-dimethyl-4-(1H-pyrazol-1-ylmethyl)-1,3-oxazolidine-3-carboxylic acid benzyl ester (330 mg). To a solution of the product (330 mg) in tetrahydrofuran (5 mL) were added phthalimide (281 mg), triphenylphosphine (501 mg) and a solution of azodicarboxylic acid diethyl ester in toluene (2.2 mol/L, 0.87 mL), and the mixture was stirred at room temperature for 20 hours. The reaction mixture was concentrated under reduced pressure. The residue was purified by silica gel column chromatography (eluent: n-hexane/ethyl acetate) to afford (4R,5R)-5-[(1,3-dioxo-2,3-dihydro-1H-isoindol-2-yl)methyl]-2,2-dimethyl-4-(1H-pyrazol-1-ylmethyl)-1,3-oxazolidine-3-carboxylic acid benzyl ester (500 mg). A mixture of the product (290 mg), methanol (2 mL) and a solution of hydrogen chloride in 1,4-dioxane (4 mol/L, 2 mL) was stirred at room temperature for 12 hours. The reaction mixture was concentrated under reduced pressure. To the residue were added methanol (2 mL) and 10% palladium-carbon (50% wet, 20 mg), and the mixture was stirred at room temperature under a hydrogen atmosphere for 3 hours. The reaction mixture was filtered through a pad of celite. The filtrate was concentrated under reduced pressure to afford the title compound (180 mg). Structural formula, spectral data and purification condition are shown in Table 132.

REFERENCE EXAMPLE 2-76-1

N-[(2R,3R)-3-Amino-2-hydroxy-4-(2H-1,2,3-triazol-2-yl)butan-1-yl]acetamide

To a solution of (1S)-2-amino-1-[(4R)-2,2-dimethyl-1,3-dioxolan-4-yl]ethan-1-ol (3.3 g) in dichloromethane (30 mL) were added N,N-diisopropylethylamine (6.3 g) and chloroformic acid benzyl ester (5.06 g) at 0° C., and the mixture was stirred at room temperature for 13 hours. To the reaction mixture was added a saturated aqueous solution of sodium bicarbonate, and the crude product was extracted with dichloromethane. The extract was washed with brine, and dried over sodium sulfate. The solvent was removed under reduced pressure. The residue was purified by silica gel column chromatography (eluent: n-hexane/ethyl acetate) to afford N-{(2S)-2-[(4R)-2,2-dimethyl-1,3-dioxolan-4-yl]-2-hydroxyethyl}carbamic acid benzyl ester (4.1 g). To a solution of the product (2.0 g) in dichloromethane (10 mL) were added triethylamine (1.37 g) and methanesulfonyl chloride (930 mg) at 0° C., and the mixture was stirred at room temperature for 1 hour. To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in N,N-dimethylformamide (10 mL) were added cesium carbonate (6.62 g) and 1,2,3-triazole (702 mg), and the mixture was stirred at 70° C. for 6 hour. The reaction mixture was allowed to cool to room temperature. To the mixture was added water, and the crude product was extracted with ethyl acetate. The extract was washed with water and brine, and dried over sodium sulfate. The solvent was removed under reduced pressure, and the residue was purified by silica gel column chromatography (eluent: n-hexane/ethyl acetate) to afford N-{(1R)-1-[(4S)-2,2-dimethyl-1,3-dioxolan-4-yl]-2-(2H-1,2,3-triazol-2-yl)ethyl}carbamic acid benzyl ester (800 mg). A mixture of the product (800 mg), methanol (5 mL) and a solution of hydrogen chloride in 1,4-dioxane (4 mol/L, 3 mL) was stirred at room temperature for 2 hours. The reaction mixture was concentrated under reduced pressure. The residue was removed azeotropically twice with toluene. To a solution of the residue in N,N-dimethylformamide (3 mL) were added imidazole (393 mg) and tert-butyldiphenylchlorosilane (952 mg) at 0° C., and the mixture was stirred at the same temperature for 1 hour. To the reaction mixture was added a saturated aqueous solution of sodium bicarbonate, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate) to afford N-[(2R,3S)-4-(tert-butyldiphenylsilyloxy)-3-hydroxy-1-(2H-1,2,3-triazol-2-yl)butan-2-yl]carbamic acid benzyl ester (1.0 g). To a solution of the product (1.0 g) in toluene (5 mL) were added p-toluenesulfonic acid monohydrate (35 mg), 2,2-dimethoxypropane (1.91 g), and the mixture was stirred at 85° C. for 3 hours. To the reaction mixture was added a saturated aqueous solution of sodium bicarbonate, and the crude product was extracted with ethyl acetate. The extract was washed with brine, and dried over sodium sulfate. The solvent was removed under reduced pressure. To a solution of the residue in tetrahydrofuran (5 mL) was added a solution of tetra-n-butylammonium fluoride in tetrahydrofuran (1 mol/L, 2.2 mL) at 0° C., and the mixture was stirred at the same temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure. The residue was purified by silica gel column chromatography (eluent: n-hexane/ethyl acetate) to afford (4R,5S)-5-(hydroxymethyl)-2,2-dimethyl-4-(2H-1,2,3-triazol-2-ylmethyl)-1,3-oxazolidine-3-carboxylic acid benzyl ester (470 mg). To a solution of the product (470 mg) in tetrahydrofuran (3 mL) were added phthalimide (399 mg), triphenylphosphine (711 mg) and a solution of azodicarboxylic acid diethyl ester in toluene (2.2 mol/L, 1.23 mL), and the mixture was stirred at room temperature for 5 hours. The reaction mixture was concentrated under reduced pressure. The residue was purified by silica gel column chromatography (eluent: n-hexane/ethyl acetate) to afford (4R,5R)-5-[(1,3-dioxo-2,3-dihydro-1H-isoindol-2-yl)methyl]-2,2-dimethyl-4-(2H-1,2,3-triazol-2-ylmethyl)-1,3-oxazolidine-3-carboxylic acid benzyl ester (620 mg). A mixture of the product (620 mg), ethanol (3 mL) and hydrazine monohydrate (680 mg) was stirred at 80° C. for 1 hour. To the reaction mixture was added a saturated aqueous solution of sodium bicarbonate, and the crude product was extracted with ethyl acetate. The extract was washed with brine, and dried over sodium sulfate. The solvent was removed under reduced pressure. The residue was purified by aminopropyl silica gel column chromatography (eluent: n-hexane/ethyl acetate) to afford (4R,5R)-5-(aminomethyl)-2,2-dimethyl-4-(2H-1,2,3-triazol-2-ylmethyl)-1,3-oxazolidine-3-carboxylic acid benzyl ester (430 mg). A mixture of the product (430 mg), methanol (2 mL) and a solution of hydrogen chloride in 1,4-dioxane (4 mol/L, 2 mL) was stirred at room temperature for 12 hours. The mixture was concentrated under reduced pressure to afford N-[(2R,3R)-4-amino-3-hydroxy-1-(2H-1,2,3-triazol-2-yl)butan-2-yl]carbamic acid benzyl ester hydrochloride (420 mg). A mixture of the product (200 mg), tetrahydrofuran (3 mL), triethylamine (178 mg) and acetic anhydride (120 mg) was stirred at room temperature for 3 hours. To the reaction mixture was added water, and the crude product was extracted with ethyl acetate. The extract was washed with brine, and dried over sodium sulfate. The solvent was removed under reduced pressure. To a solution of the residue in methanol (2 mL) was added 10% palladium-carbon (50% wet, 50 mg), and the mixture was stirred at room temperature under a hydrogen atmosphere for 2 hours. The reaction mixture was filtered through a pad of celite. The filtrate was concentrated under reduced pressure to afford the title compound (110 mg). Structural formula, spectral data and purification condition are shown in Table 132.

REFERENCE EXAMPLE 2-76-2

Reference Example 2-76-2 was synthesized in a manner similar to that of Reference Example 2-76-1 by using the corresponding materials. Structural formula, spectral data and purification condition are shown in Table 132.

REFERENCE EXAMPLE 2-77-1

(5R)-5[(1R)-1-amino-2-(2H-1,2,3-triazol-2-yl)ethyl]-1,3-oxazolidin-2-one

A mixture of N-[(2R,3R)-4-amino-3-hydroxy-1-(2H-1,2,3-triazol-2-yl)butan-2-yl]carbamic acid benzyl ester hydrochloride (320 mg), triethylamine (284 mg), carbonyldiimidazole (303 mg) and tetrahydrofuran (3 mL) was stirred at room temperature for 3 hours. To the reaction mixture was added water, and the crude product was extracted with ethyl acetate. The extract was washed with brine, and dried over sodium sulfate. The solvent was removed under reduced pressure. To a solution of the residue in methanol (2 mL) was added 10% palladium-carbon (50% wet, 50 mg), and the mixture was stirred at room temperature under a hydrogen atmosphere for 5 hours. The reaction mixture was filtered through a pad of celite. The filtrate was concentrated under reduced pressure to afford the title compound (160 mg). Structural formula, spectral data and purification condition are shown in Table 133.

REFERENCE EXAMPLE 2-77-2

Reference Example 2-77-2 was synthesized in a manner similar to that of Reference Example 2-77-1 by using the corresponding materials. Structural formula, spectral data and purification condition are shown in Table 133.

REFERENCE EXAMPLE 2-78-1

(2S,3R)-3-Amino-1-methoxy-4-(2H-1,2,3-triazol-2-yl)butan-2-ol hydrochloride

To a solution of N-[(2S)-2-((4R)-2,2-dimethyl-1,3-dioxolan-4-yl)-2-hydroxyethyl]carbamic acid tert-butyl ester (850 mg) in dichloromethane (5 mL) were added triethylamine (660 mg) and methanesulfonyl chloride (485 mg) at 0° C., and the mixture was stirred at the same temperature for 1 hour. To the reaction mixture was added a saturated aqueous solution of sodium bicarbonate, and the crude product was extracted with dichloromethane. The extract was washed with brine, and dried over sodium sulfate. The solvent was removed under reduced pressure. To a solution of the residue in N,N-dimethylformamide (5 mL) were added cesium carbonate (3.18 g) and 1,2,3-triazole (337 mg), and the mixture was stirred at 70° C. for 4 hours. To the reaction mixture was added water, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate) to afford N-[(1R)-1-((4S)-2,2-dimethyl-1,3-dioxolan-4-yl)-2-(2H-1,2,3-triazol-2-yl)ethyl}carbamic acid tert-butyl ester (500 mg). A mixture of the product (500 mg), methanol (3 mL), water (1 mL) and trifluoroacetic acid (182 mg) was stirred at room temperature for 2 days. The reaction mixture was concentrated under reduced pressure. The residue was removed azeotropically twice with toluene. To a solution of the residue in N,N-dimethylformamide (3 mL) was added imidazole (272 mg), then to the mixture was added tert-butyldiphenylchlorosilane (660 mg) at 0° C., and the mixture was stirred at the same temperature for 3 hours. To the reaction mixture was added a saturated aqueous solution of sodium bicarbonate, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate) to afford N-[(2R,3S)-4-(tert-butyldiphenylsilyloxy)-3-hydroxy-1-(2H-1,2,3-triazol-2-yl)butan-2-yl]carbamic acid tert-butyl ester (610 mg). To a solution of the product (610 mg) in toluene (5 mL) were added p-toluenesulfonic acid monohydrate (23 mg) and 2,2-dimethoxypropane (1.25 g) at room temperature, and the mixture was stirred at 80° C. for 3 days. To the reaction mixture was added a saturated aqueous solution of sodium bicarbonate, and the crude product was extracted with ethyl acetate. The extract was washed with brine, and dried over sodium sulfate. The solvent was removed under reduced pressure. To a solution of the residue in tetrahydrofuran (5 mL) was added a solution of tetra-n-butylammonium fluoride in tetrahydrofuran (1 mol/L, 1.4 mL) at 0° C., and the mixture was stirred at room temperature for 1 hour. To the reaction mixture was added a saturated aqueous solution of ammonium chloride, and the crude product was extracted with ethyl acetate. The extract was washed with brine, and dried over sodium sulfate. The solvent was removed under reduced pressure. The residue was purified by silica gel column chromatography (eluent: n-hexane/ethyl acetate) to afford (4R,5S)-5-(hydroxymethyl)-2,2-dimethyl-4-(2H-1,2,3-triazol-2-ylmethyl)-1,3-oxazolidine-3-carboxylic acid tert-butyl ester (240 mg). To a solution of the product (240 mg) in N,N-dimethylformamide (1 mL) was added iodomethane (164 mg), then to the mixture was added sodium hydride (60% dispersion in oil, 55 mg) at 0° C., and the mixture was stirred at room temperature for 1 hour. To the reaction mixture was added a saturated aqueous solution of ammonium chloride, and the crude product was extracted with ethyl acetate. The extract was washed with water and brine, and dried over sodium sulfate. The solvent was removed under reduced pressure. The residue was purified by silica gel column chromatography (eluent: n-hexane/ethyl acetate) to afford (4R,5S)-5-(methoxymethyl)-2,2-dimethyl-4-(2H-1,2,3-triazol-2-ylmethyl)-1,3-oxazolidine-3-carboxylic acid tert-butyl ester (220 mg). A mixture of the product (220 mg), methanol (1 mL) and a solution of hydrogen chloride in 1,4-dioxane (4 mol/L, 1 mL) was stirred at room temperature for 1 hour. The reaction mixture was concentrated under reduced pressure to afford the title compound (100 mg). Structural formula, spectral data and purification condition are shown in Table 133.

REFERENCE EXAMPLE 2-79-1

N-[(2R,3R)-3-Amino-2-hydroxy-4-(pyridin-2-yl)butan-1-yl]phthalimide

To a solution of N-[(2R.,3S)-3,4-dihydroxy-1-(pyridin-2-yl)butan-2-yl]carbamic acid tert-butyl ester (140 mg) in N,N-dimethylformamide (2 mL) were added imidazole (44 mg) and tert-butyldiphenylchlorosilane (163 mg) at 0° C., and the mixture was stirred at room temperature overnight. To the reaction mixture was added water, and the crude product was extracted with ethyl acetate. The extract was washed with brine, and then dried over anhydrous magnesium sulfate. The solvent was removed under reduced pressure. The residue was purified by silica gel column chromatography (eluent: n-hexane/ethyl acetate) to afford N-[(2R,3S)-4-(tert-butyldiphenylsilyloxy)-3-hydroxy-1-(pyridin-2-yl)butan-2-yl]carbamic acid tert-butyl ester (277 mg). To a solution of the product (130 mg) in toluene (2 mL) were added p-toluenesulfonic acid monohydrate (5 mg) and 2,2-dimethoxypropane (260 mg), and the mixture was stirred at 85° C. overnight. To the reaction mixture was added a saturated aqueous solution of sodium bicarbonate, and the crude product was extracted with ethyl acetate. The extract was washed with brine, and then dried over anhydrous magnesium sulfate. The solvent was removed under reduced pressure. The residue was purified by silica gel column chromatography (eluent: n-hexane/ethyl acetate) to afford (4R,5S)-5-[(tert-butyldiphenylsilyloxy)methyl]-2,2-dimethyl-4-(pyridin-2-ylmethyl)-1,3-oxazolidine-3-carboxylic acid tert-butyl ester. To a solution of the product in tetrahydrofuran (1 mL) was added a solution of tetra-n-butylammonium fluoride in tetrahydrofuran (1 mol/L, 0.42 mL) at 0° C., and the mixture was stirred at room temperature for 1 hour. To the reaction mixture was added a saturated aqueous solution of ammonium chloride, and the crude product was extracted with ethyl acetate. The extract was washed with brine, and then dried over anhydrous magnesium sulfate. The solvent was removed under reduced, pressure. To the residue were added tetrahydrofuran (1 mL), phthalimide (53 mg), triphenylphosphine (95 mg) and a solution of azodicarboxylic acid diethyl ester in toluene (2.2 mol/L, 164 µL ), and the mixture was stirred at room temperature for 1 hour. The reaction mixture was concentrated under reduced pressure. The residue was purified by silica gel column chromatography (eluent: n-hexane/ethyl acetate) to afford (4R,5R)-5-[(1,3-dioxo-2,3-dihydro-1H-isoindol-2-yl)methyl]-2,2-dimethyl-4-(pyridin-2-ylmethyl)-1,3-oxazolidine-3-carboxylic acid tert-butyl ester (40 mg). A mixture of the product (40 mg), methanol (0.5 mL) and a solution of hydrogen chloride in 1,4-dioxane (4 mol/L, 0.5 mL) was stirred at room temperature for 2 hours. The reaction mixture was concentrated under reduced pressure. The residue was purified by aminopropyl silica gel column chromatography (eluent: methanol/ethyl acetate) to afford the title compound (22 mg). Structural formula, spectral data and purification condition are shown in Table 133.

TABLE 132

| Ref. Ex. Strc. | | P.D. | P.C. |
| --- | --- | --- | --- |
| 2-72-1 | (structure) | MS(ESI, m/z): 186(M + H)+ | Without purification |

TABLE 132-continued

| Ref. Ex. | Strc. | P.D. | P.C. |
|---|---|---|---|
| 2-73-1 | (structure) | MS(ESI, m/z): 265(M + H)⁺ | Without purification |
| 2-74-1 | (structure) | MS(ESI, m/z): 189 (M + H)⁺ | Without purification |
| | (structure) | | |
| 2-75-1 | (structure) | MS(ESI, m/z): 301 (M + H)⁺ | Without purification |
| 2-76-1 | (structure) | MS(ESI, m/z): 214 (M + H)⁺ | Without purification |
| 2-76-2 | (structure) | MS(ESI, m/z): 213 (M + H)⁺ | Without purification |

TABLE 133

| Ref. Ex. | Strc. | P.D. | P.C. |
|---|---|---|---|
| 2-77-1 | (structure) | MS(ESI, m/z): 198 (M + H)⁺ | Without purification |
| 2-77-2 | (structure) | MS(ESI, m/z): 197 (M + H)⁺ | Without purification |

TABLE 133-continued

| Ref. Ex. | Strc. | P.D. | P.C. |
|---|---|---|---|
| 2-78-1 | (structure) | MS(ESI, m/z): 187 (M + H)$^+$ | Without purification |
| 2-79-1 | (structure) | MS(ESI, m/z): 312 (M + H)$^+$ | Column: APS EtOAc/MeOH |

Examples 58-1 to 58-2

Examples 58-1 to 58-2 were synthesized in a manner similar to that of Example 1-1 by using the corresponding materials. Structural formula, spectral data and purification condition are shown in Table 134.

Example 59-1

Example 59-1 was synthesized in a manner similar to that of Example 16-1 by using the corresponding materials. Structural formula, spectral data and purification condition are shown in Table 134.

Example 60-1

Example 60-1 was synthesized in a manner similar to that of Example 39-1 by using the corresponding materials. Structural formula, spectral data and purification condition are shown in Table 134.

Example 61-1

Example 61-1 was synthesized in a manner similar to that of Example 43-1 by using the corresponding materials. Structural formula, spectral data and purification condition are shown in Table 134.

Example 62-1

Example 62-1 was synthesized in a manner similar to that of Example 47-1 by using the corresponding materials. Structural formula, spectral data and purification condition are shown in Table 135.

Example 63-1

Example 63-1 was synthesized in a manner similar to that of Example 50-1 by using the corresponding materials. Structural formula, spectral data and purification condition are shown in Table 135.

Example 64-1

N-((2R,3R)-3-{3-Fluoro-2-[5-(4-fluorophenyl)-1H-pyrazol-3-yl]benzoylamino}-2-hydroxy-4-(2H-1,2,3-triazol-2-yl)butan-1-yl)acetamide A mixture of 4-fluoro-2-(4-fluorophenyl)-8H-pyrazolo[5,1-a]isoindol-8-one (50 mg), N-[(2R,3R)-3-amino-2-hydroxy-4-(2H-1,2,3-triazol-2-yl)butan-1-yl]acetamide (40 mg), N,N-diisopropylethylamine (115 mg), a solution of T3P® in ethyl acetate (1.7 mol/L, 0.2. mL) and N-methylpyrrolidone (1 mL) was stirred at 80° C. for 17 hours. To the reaction mixture was added a saturated aqueous solution of sodium bicarbonate, and the crude product was extracted with ethyl acetate. The extract was washed with water and brine, and dried over sodium sulfate. The solvent was removed under reduced pressure, and the residue was purified by aminopropyl silica gel column chromatography (eluent: ethyl acetate/methanol). The crude product was purified by silica gel column chromatography (eluent: ethyl acetate/methanol) to afford the title compound (14 mg). Structural formula, spectral data and purification condition are shown in Table 135.

Examples 64-2 to 64-4

Examples 64-2 to 64-4 were synthesized in a manner similar to that of Example 64-1 by using the corresponding materials. Structural formula, spectral data and purification condition are shown in Table 135.

Example 65-1

N-[(2R,3R)-4-Amino-3-hydroxy-1-(1H-pyrazol-1-yl)butan-2-yl]-3-fluoro-2-[5-(4-fluorophenyl)-1H-pyrazol-3-yl]benzamide A mixture of 4-fluoro-2-(4-fluorophenyl)-8H-pyrazolo[5,1-a]isoindol-8-one (100 mg), N-[(2R,3R)-3-amino-2-hydroxy-4-(1H-pyrazol-1-yl)butan-1-yl]phthalimide (111 mg), N,N-diisopropylethylamine (230 mg), a solution of T3P® in ethyl acetate (1.7 mol/L, 0.2 mL) and N-methylpyrrolidone (1 mL) was stirred at 80° C. for 2 days. To the reaction mixture was added a saturated aqueous solution of sodium bicarbonate, and the crude product was extracted with ethyl acetate. The extract was washed with water and brine, and dried over sodium sulfate. The solvent was removed under reduced pressure, and the residue was purified by silica gel column chromatography (eluent: n-hexane/ethyl acetate) to afford N-[(2R,3R)-4-(1,3-dioxo-2,3-dihydro-1H-isoindol-2-yl)-3-hydroxy-1-(1H-pyrazol-1-yl)butan-2-yl]-3-fluoro-2-[5-(4-fluorophenyl)-1H-pyrazol-3-yl]benzamide (60 mg).

To a solution of the product (60 mg) ethanol (2 mL) was added hydrazine monohydrate (177 mg), and the mixture was stirred at 60° C. for 5 hours. The reaction mixture was allowed to cool to room temperature, and then concentrated under reduced pressure. The residue was purified by aminopropyl silica gel column chromatography (eluent: ethyl acetate/methanol) to afford the title compound (23 mg). Structural formula, spectral data and purification condition are shown in Table 135.

TABLE 134

| Ex. No. | Strc. | P.D. | P.C. |
|---|---|---|---|
| 58-1 | 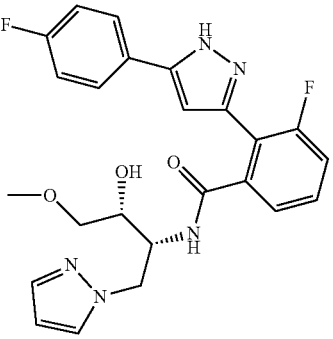 [SMILES: COC[C@H](O)[C@@H](Cn1cccn1)NC(=O)c1cccc(F)c1-c1cc(-c2ccc(F)cc2)[nH]n1] | RT(min): 2.511 (Method A)<br>MS(ESI, m/z): 468.1839 (M + H)⁺ | Column: SiO2<br>EtOAc/MeOH |
| 58-2HP | 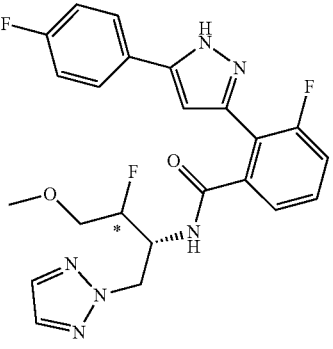 [SMILES: COCC(F)[C@@H](Cn1nccn1)NC(=O)c1cccc(F)c1-c1cc(-c2ccc(F)cc2)[nH]n1] | $^1$H-NMR(CDCl$_3$) δ ppm: 3.23 (3H, s), 3.37-3.50 (2H, m), 4.61-4.77 (3H, m), 4.82-4.96 (1H, m), 6.55-6.57 (1H, m), 6.84 (1H, d, J = 3.0 Hz), 7.08-7.14 (2H, m), 7.28-7.33 (2H, m), 7.38-7.44 (1H, m), 7.58 (2H, s), 7.74-7.78 (2H, m).<br>RT(min): 2.791 (Method A)<br>MS(ESI, m/z): 471.1751 (M + H)⁺ | Column: ODS C18<br>SHISEIDO UG80<br>H2O/MeCN |
| 58-2LP | 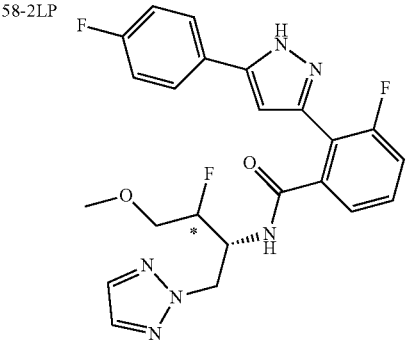 | $^1$H-NMR(CDCl$_3$) δ ppm: 3.39 (3H, s), 3.42-3.67 (2H, m), 3.91-4.02 (1H, m), 4.12-4.25 (1H, m), 5.01-5.32 (2H, m), 6.54-6.61 (1H, m), 6.79-6.84 (1H, m), 7.10-7.16 (2H, m), 7.20-7.38 (2H, m), 7.57-7.80 (5H, m).<br>RT(min): 2.900 (Method A)<br>MS(ESI, m/z): 471.1748 (M + H)⁺ | Column: ODS C18<br>SHISEIDO UG80<br>H2O/MeCN |

TABLE 134-continued

| Ex. No. | Strc. | P.D. | P.C. |
|---|---|---|---|
| 59-1 | | $^1$H-NMR(CDCl$_3$) δ ppm: 2.60-2.72 (1H, m), 2.73-2.81 (1H, m), 3.13 (1H, dd, J = 5.7, 14.3 Hz), 3.27 (1H, dd, J = 6.9, 14.3 Hz), 3.67-3.77 (1H, m), 4.40-4.51 (1H, m), 6.80 (1H, d, J = 3.5 Hz), 6.82-6.90 (1H, m), 7.04-7.37 (7H, m), 7.50-7.58 (1H, m), 7.71-7.81 (2H, m), 8.37-8.44 (1H, m).<br>RT(min): 1.021 (Method A)<br>MS(ESI, m/z): 464.1897 (M + H)$^+$ | Column: APS EtOAc/MeOH |
| 60-1 | | $^1$H-NMR(CDCl$_3$) δ ppm: 3.15-3.22 (1H, m), 3.21 (3H, s), 3.31-3.40 (2H, m), 3.85-3.90 (1H, m), 4.58-4.65 (1H, m), 4.70-4.73 (2H, m), 6.55-6.60 (1H, m), 6.85 (1H, d, J = 3.5 Hz), 7.07-7.13 (2H, m), 7.26-7.29 (2H, m), 7.37-7.42 (1H, m), 7.59 (2H, s), 7.73-7.77 (2H, m).<br>RT(min): 2.467 (Method A)<br>MS(ESI, m/z): 469.1792 (M + H)$^+$ | Column: SiO2 EtOAc/MeOH |
| 61-1 | | RT(min): 2.663 (Method A)<br>MS(ESI, m/z): 475.1498 (M + H)$^+$ | Column: APS EtOAc/MeOH |

TABLE 135

| Ex. No. | Strc. | P.D. | P.C. |
|---|---|---|---|
| 62-1 | | $^1$H-NMR(CDCl$_3$) δ ppm: 3.08 (2H, d, J = 7.2 Hz), 3.28-3.36 (1H, m), 3.46-3.54 (1H, m), 4.70-4.82 (2H, m), 5.00-5.15 (1H, m), 6.76 (1H, d, J = 2.4 Hz), 7.07-7.41 (8H, m), 7.54-7.62 (1H, m), 7.71-7.81 (2H, m), 8.46-8.53 (1H, m).<br>RT(min): 1.715 (Method A)<br>MS(ESI, m/z): 490.1695 (M + H)$^+$ | Column: APS EtOAc/MeOH |

TABLE 135-continued

| Ex. No. | Strc. | P.D. | P.C. |
|---|---|---|---|
| 63-1 | 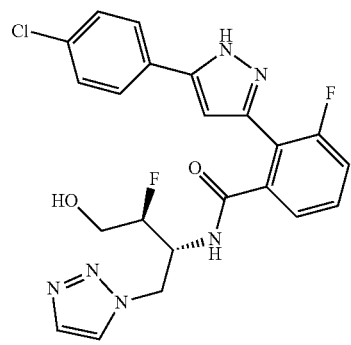 [SMILES: O=C(N[C@H](Cn1ccnn1)[C@H](F)CO)c1cccc(F)c1-c1cc(-c2ccc(Cl)cc2)[nH]n1] | RT(min): 2.467 (Method A)<br>MS(ESI, m/z): 473.1299 (M + H)+ | Column: APS<br>EtOAc/MeOH |
| 64-1 | 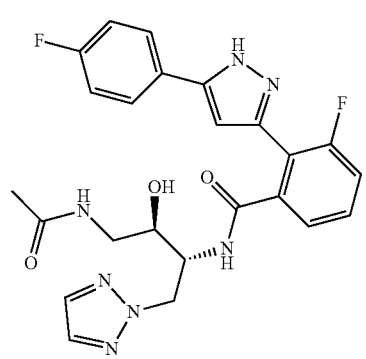 [SMILES: CC(=O)NC[C@@H](O)[C@@H](Cn1nccn1)NC(=O)c1cccc(F)c1-c1cc(-c2ccc(F)cc2)[nH]n1] | ¹H-NMR(DMSO-d₆) δ ppm: 1.77 (3H, s), 2.94-3.63 (4H, m), 4.36-4.64 (3H, m), 5.00-5.30 (1H, m), 6.61-6.88 (1H, m), 7.10-7.58 (5H, m), 7.63-7.92(5H, m), 13.00-13.50 (1H, m).<br>RT(min): 2.222 (Method A)<br>MS(ESI, m/z): 496.1902 (M + H)+ | Column: SiO2<br>EtOAc/MeOH |
| 64-2 | 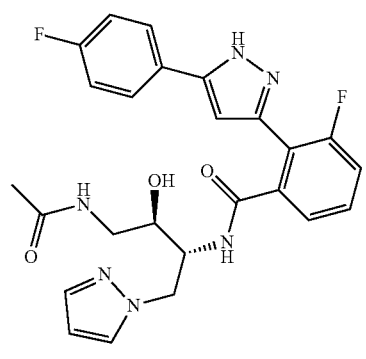 [SMILES: CC(=O)NC[C@@H](O)[C@@H](Cn1cccn1)NC(=O)c1cccc(F)c1-c1cc(-c2ccc(F)cc2)[nH]n1] | ¹H-NMR(DMSO-d₆) δ ppm: 1.77 (3H, s), 3.01-3.54 (3H, m), 4.11-4.33 (3H, m), 6.22 (1H, t, J = 2.0 Hz), 6.60-7.86 (11H, m), 12.99-13.57 (1H, m).<br>RT(min): 2.290 (Method A)<br>MS(ESI, m/z): 495.1949 (M + H)+ | Column: SiO2<br>EtOAc/MeOH |
| 64-3 | 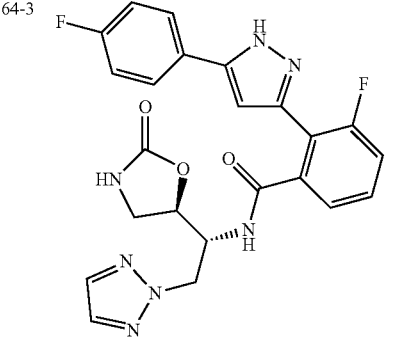 | ¹H-NMR(DMSO-d₆) δ ppm: 3.13-3.57 (2H, m), 3.90-4.15 (1H, m), 4.47-4.73 (3H, m), 6.61-9.03 (12H, m).<br>RT(min): 2.346 (Method A)<br>MS(ESI, m/z): 480.1589 (M + H)+ | Column: APS<br>EtOAc/MeOH |

TABLE 135-continued

| Ex. No. Strc. | P.D. | P.C. |
|---|---|---|
| 64-4 | $^1$H-NMR(DMSO-$d_6$) δ ppm: 3.30-3.51 (2H, m), 4.19-4.38 (2H, m), 4.44-4.62 (2H, m), 6.19-6.25 (1H, m), 6.60-7.15 (1H, m), 7.25-7.56 (6H, m), 7.67-7.72 (1H, m), 7.77-7.86 (2H, m), 8.70-8.85 (1H, m), 13.06-13.33 (1H, m).<br>RT(min): 2.387 (Method A)<br>MS(ESI, m/z): 479.1637 (M + H)$^+$ | Column: APS<br>EtOAc/MeOH |
| 65-1 | $^1$H-NMR(DMSO-$d_6$) δ ppm: 2.40-2.48 (5H, m), 4.13-4.40 (3H, m), 6.21 (1H, t, J = 2.0 Hz), 6.70-6.71 (1H, m), 7.08-7.10 (1H, m), 7.26-7.31 (2H, m), 7.37-7.51 (3H, m), 7.63-7.66 (1H, m), 7.80-7.85 (2H, m), 8.08-8.21 (1H, m).<br>RT(min): 1.855 (Method A)<br>MS(ESI, m/z): 453.1842 (M + H)$^+$ | Column: APS<br>EtOAc/MeOH |

Test Example 1

Confirmation Test of Inhibitory Effects on Icilin-induced Wet-dog Shakes

Test compounds were dissolved in dimethylacetamide (wako), and 0.5% methylcellulose solution (wako) was added to make the solution or suspension containing 5% of dimethylacetatnide. At a dose of 0.3 to 10 mg/kg/5mL of test compounds were orally administered to female SD rats. After 1 hour, wet-dog shakes were induced by the intraperitoneal injection of icilin (1 mg/kg) which was dissolved in polyethylene glycol 400 (wako). From 5 minutes after the administration of icilin, wet-dog shakes were counted for 5 minutes. For control example, vehicle (a mixture of dimethylacetamide (wako): 0.5% methylcellulose (wako)=5:95) was administrated similarly, and the number of wet-dog shakes was counted in the same manner. A percent inhibition of wet-dog shakes by test compound was calculated from the following formula: [1-(test compound wet-dog shake count/vehicle wet-dog shake count)]×100. Results are shown in Tables 136 to 138.

TABLE 136

| Ex. No. | Dose (mg/kg) | % inhibition of Wet-Dog Shake | Ex. No. | Dose (mg/kg) | % inhibition of Wet-Dog Shake |
|---|---|---|---|---|---|
| 1-3 | 10 | 66 | 1-154 | 3 | 75 |
| 1-15 | 10 | 54 | 1-156 | 3 | 99 |
| 1-27 | 10 | 68 | 1-162 | 3 | 48 |
| 1-69 | 10 | 93 | 1-169 | 3 | 34 |
| 1-76 | 10 | 72 | 1-174 | 3 | 60 |
| 1-77 | 10 | 59 | 1-177 | 3 | 59 |
| 1-85 | 10 | 86 | 1-182 | 3 | 37 |
| 1-94 | 10 | 100 | 1-183 | 3 | 36 |

TABLE 136-continued

| Ex. No. | Dose (mg/kg) | % inhibition of Wet-Dog Shake | Ex. No. | Dose (mg/kg) | % inhibition of Wet-Dog Shake |
|---|---|---|---|---|---|
| 1-128 | 10 | 59 | 1-185 | 3 | 56 |
| 4-1 | 10 | 70 | 1-191 | 3 | 31 |
| 16-11 | 10 | 51 | 1-194 | 3 | 60 |
| 1-29 | 3 | 66 | 1-196 | 3 | 63 |
| 1-58 | 3 | 86 | 1-197 | 3 | 44 |
| 1-59 | 3 | 46 | 1-200 | 3 | 91 |
| 1-62 | 3 | 55 | 1-205 | 3 | 70 |
| 1-64 | 3 | 69 | 1-206 | 3 | 55 |
| 1-68 | 3 | 41 | 1-208 | 3 | 100 |
| 1-86 | 3 | 76 | 1-210 | 3 | 47 |
| 1-103 | 3 | 45 | 1-217 | 3 | 75 |
| 1-104 | 3 | 60 | 1-218 | 3 | 40 |
| 1-105 | 3 | 90 | 1-219 | 3 | 45 |
| 1-108 | 3 | 61 | 1-223 | 3 | 100 |
| 1-113 | 3 | 98 | 1-224 | 3 | 82 |
| 1-117 | 3 | 46 | 1-225 | 3 | 37 |
| 1-124 | 3 | 42 | 1-226 | 3 | 53 |
| 1-130 | 3 | 92 | 1-228 | 3 | 97 |
| 1-131 | 3 | 94 | 1-231 | 3 | 88 |
| 1-134 | 3 | 49 | 1-241 | 3 | 100 |
| 1-137 | 3 | 84 | 24-1 | 3 | 71 |
| 1-138 | 3 | 100 | 24-3 | 3 | 46 |

TABLE 137

| Ex. No. | Dose (mg/kg) | % inhibition of Wet-Dog Shake | Ex. No. | Dose (mg/kg) | % inhibition of Wet-Dog Shake |
|---|---|---|---|---|---|
| 24-4 | 3 | 31 | 43-22 | 3 | 98 |
| 24-7 | 3 | 56 | 43-25 | 3 | 100 |
| 26-1 | 3 | 89 | 43-27 | 3 | 80 |
| 26-2 | 3 | 69 | 43-34 | 3 | 100 |
| 27-5 | 3 | 52 | 43-36 | 3 | 31 |

TABLE 137-continued

| Ex. No. | Dose (mg/kg) | % inhibition of Wet-Dog Shake | Ex. No. | Dose (mg/kg) | % inhibition of Wet-Dog Shake |
|---|---|---|---|---|---|
| 27-16 | 3 | 56 | 43-44 | 3 | 69 |
| 27-17 | 3 | 86 | 43-45 | 3 | 40 |
| 27-24 | 3 | 99 | 43-46 | 3 | 70 |
| 27-29 | 3 | 47 | 47-1 | 3 | 48 |
| 31-1 | 3 | 36 | 47-2 | 3 | 78 |
| 33-1 | 3 | 100 | 50-2 | 3 | 89 |
| 33-3 | 3 | 32 | 50-4 | 3 | 100 |
| 34-1HP | 3 | 92 | 50-7 | 3 | 99 |
| 35-1 | 3 | 42 | 50-8 | 3 | 82 |
| 35-3 | 3 | 69 | 50-11 | 3 | 100 |
| 36-1 | 3 | 39 | 54-1 | 3 | 70 |
| 36-2 | 3 | 72 | 54-2 | 3 | 48 |
| 37-1 | 3 | 38 | 54-3 | 3 | 62 |
| 39-2 | 3 | 50 | 54-4 | 3 | 50 |
| 43-2 | 3 | 100 | 54-6 | 3 | 47 |
| 43-4 | 3 | 77 | 54-7 | 3 | 41 |
| 43-6 | 3 | 49 | 54-9 | 3 | 40 |
| 43-9 | 3 | 89 | 54-14 | 3 | 77 |
| 43-11 | 3 | 88 | 54-16 | 3 | 86 |
| 43-12 | 3 | 92 | 54-17 | 3 | 42 |
| 43-16 | 3 | 97 | 54-19 | 3 | 68 |
| 43-17 | 3 | 78 | 60-1 | 1 | 92 |

TABLE 138

| Ex. No. | Dose (mg/kg) | % inhibition of Wet-Dog Shake | Ex. No. | Dose (mg/kg) | % inhibition of Wet-Dog Shake |
|---|---|---|---|---|---|
| 1-1 | 1 | 82 | 28-1 | 1 | 62 |
| 1-84 | 1 | 59 | 33-2 | 1 | 88 |
| 1-97 | 1 | 50 | 43-1 | 1 | 90 |
| 1-125 | 1 | 56 | 43-14 | 1 | 100 |
| 1-164 | 1 | 38 | 43-15 | 1 | 73 |
| 1-167 | 1 | 65 | 43-18 | 1 | 85 |
| 1-172 | 1 | 100 | 43-23 | 1 | 100 |
| 1-173 | 1 | 85 | 43-24 | 1 | 100 |
| 1-213 | 1 | 68 | 43-29 | 1 | 79 |
| 1-227 | 1 | 66 | 43-39 | 1 | 81 |
| 1-229 | 1 | 56 | 43-42 | 1 | 100 |
| 1-230 | 1 | 59 | 50-1 | 1 | 92 |
| 1-238 | 1 | 82 | 50-5 | 1 | 100 |
| 1-242 | 1 | 73 | 50-6 | 1 | 54 |
| 1-245 | 1 | 55 | 50-10 | 1 | 56 |
| 27-1 | 1 | 84 | 27-20 | 0.3 | 56 |
| 27-4 | 1 | 72 | 27-30 | 0.3 | 62 |
| 27-7 | 1 | 88 | 43-3 | 0.3 | 58 |
| 27-14 | 1 | 51 | 43-5 | 0.3 | 98 |
| 27-18 | 1 | 86 | 43-13 | 0.3 | 90 |
| 27-19 | 1 | 80 | 43-41 | 0.3 | 54 |
| 27-21 | 1 | 32 | 43-43 | 0.3 | 93 |
| 27-22 | 1 | 100 | 50-12 | 0.3 | 99 |
| 27-25 | 1 | 90 | 56-1 | 0.3 | 91 |

Test Example 2

Confirmation Test of Elongation Action of Micturition Interval of Overactive Bladder Induced by Acetic Acid Urethane (sigma) was dissolved into pure water by 25% w/v, and female SD rats were anesthetized with 1.25 g/kg urethane by subcutaneous administration. Cannulae were placed in femoral vein and bladder, and the bladder cannula was connected to both a syringe pump and a pressure transducer. Detrusor overactivity was induced by intravesical infusion of 0.25% acetic acid in saline at a rate of 3.6 mL/h, and intravesical pressure was monitored via pressure transducer concurrently. Test compounds were dissolved into a mixture of dimethylacetamide and saline (20:80), and were administered via, the femoral vein. Elongation of micturition interval (%) by test compound was calculated from the following formula: [an average of the three micturition interval after administration/an average of the three micturition interval before administration]×100. Dose and results are shown in table 139.

TABLE 139

| Ex. No. | Dose Volume | Elongation of micturition interval (%) |
|---|---|---|
| 1-1 | 1 mg/kg/mL | 169 |
| 1-14 | 1 mg/kg/mL | 138 |
| 1-58 | 1 mg/kg/mL | 159 |
| 1-84 | 1 mg/kg/mL | 183 |
| 1-125 | 1 mg/kg/mL | 223 |
| 1-139 | 1 mg/kg/mL | 163 |
| 1-172 | 1 mg/kg/mL | 194 |
| 1-227 | 1 mg/kg/mL | 193 |
| 1-238 | 1 mg/kg/mL | 136 |
| 27-1 | 1 mg/kg/mL | 158 |
| 27-7 | 1 mg/kg/mL | 176 |
| 27-14 | 1 mg/kg/mL | 195 |
| 27-25 | 1 mg/kg/mL | 167 |
| 43-1 | 1 mg/kg/mL | 156 |
| 43-3 | 1 mg/kg/mL | 158 |
| 43-27 | 1 mg/kg/mL | 185 |
| 43-42 | 1 mg/kg/mL | 158 |
| 43-43 | 1 mg/kg/mL | 172 |
| 50-1 | 1 mg/kg/mL | 217 |
| 50-6 | 1 mg/kg/mL | 197 |
| 50-12 | 1 mg/kg/mL | 191 |
| 54-16 | 1 mg/kg/mL | 132 |
| 56-1 | 1 mg/kg/mL | 150 |

As shown in Tables 136 to 138, the compounds of the present invention exhibited potent TRPM8 inhibitory effects. Further, as shown in Table 139, the compounds of the present invention have the elongation action against micturition interval and were proved to be effective for suppression of detrusor overactivity.

INDUSTRIAL APPLICABILITY

The compounds of the present invention exhibit potent TRPM8 inhibitory activity and thus are useful as an agent for treating or preventing of diseases or symptoms caused by the activation of TRPM8, in particular lower urinary tract symptoms (LUTS), especially, overactive bladder syndrome (OAB).

The invention claimed is:

1. A compound represented by the formula (I) or a pharmaceutically acceptable salt thereof:

[Chem.1]

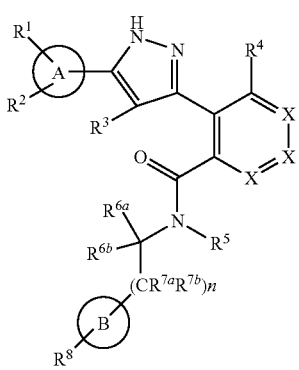

(I)

wherein ring A is $C_{3-6}$ cycloalkyl, $C_{6-10}$ aryl or heterocycle;

X is independently $CR^{4a}$ or a nitrogen atom;

$R^1$ and $R^2$ are independently a hydrogen atom, a halogen atom, hydroxy, amino, formyl, hydroxy $C_{1-6}$ alkyl, $C_{1-6}$ alkoxy, $C_{1-6}$ alkyl, halo $C_{1-6}$ alkyl, cyano, $C_{1-6}$ alkylsulfonylamino, imidazolyl, 1,3-dioxolyl or mono(di) $C_{1-6}$ alkoxy $C_{1-6}$ alkyl;

$R^3$ is a hydrogen atom, a halogen atom, $C_{1-6}$ alkyl or formyl;

$R^4$ and $R^{4a}$ are independently a hydrogen atom, a halogen atom, hydroxy, $C_{1-6}$ alkyl, $C_{1-6}$ alkoxy, $C_{1-6}$ alkoxy $C_{1-6}$ alkoxy, halo $C_{1-6}$ alkyl, halo $C_{1-6}$ alkoxy, hydroxy $C_{1-6}$ alkyl, hydroxy $C_{1-6}$ alkoxy, cyano, carbamoyl, $C_{1-6}$ alkoxycarbonyl $C_{1-6}$ alkoxy, $C_{7-10}$ aralkyloxy, $C_{7-10}$ aralkyloxy $C_{1-6}$ alkoxy or 1,3-dioxolyl;

ring B is $C_{6-10}$ aryl or heterocycle;

$R^5$ is a hydrogen atom, $C_{1-6}$ alkyl, mono(di)hydroxy $C_{1-6}$ alkyl, $C_{1-6}$ alkoxy(hydroxy)$C_{1-6}$ alkyl, carboxy $C_{1-6}$ alkyl or $C_{1-6}$ alkoxycarbonyl $C_{1-6}$ alkyl;

$R^{6a}$ is a hydrogen atom, $C(=O)R^9$, $C(=O)NR^{10}R^{11}$, $-CR^{12}R^{13}R^{14}$ or a group selected from the following formula:

[Chem.2]

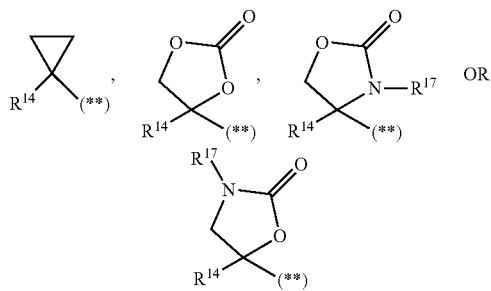

wherein, (**) is a bonding site;

$R^{7a}$ is independently a hydrogen atom, a fluorine atom, hydroxy, hydroxy $C_{1-6}$ alkyl, $C_{1-6}$ alkyl, $C_{1-6}$ alkoxy, $C_{1-6}$ alkoxy $C_{1-6}$ alkyl or amino $C_{1-6}$ alkyl;

$R^{7b}$ is independently a hydrogen atom, a fluorine atom or $C_{1-6}$ alkyl, or one of $R^5$ and $R^{6a}$ may bind together with ring B to form 6-membered ring or may bind together with $R^{7a}$ to form 5-membered ring;

$R^{6b}$ is a hydrogen atom or $C_{1-6}$ alkyl;

$R^8$ is a hydrogen atom, a halogen atom, $C_{1-6}$ alkyl, $C_{1-6}$ alkoxy, hydroxy, amino, cyano, $C_{1-6}$ alkoxycarbonyl, $C_{1-6}$ alkoxy $C_{1-6}$ alkoxy, carbamoyl, $C_{1-6}$ alkoxy $C_{1-6}$ alkyl, carboxy, azido, halo $C_{1-6}$ alkyl or tetrazolyl;

$R^9$ is hydroxy, $C_{1-6}$ alkyl or hydroxy pyrrolidinyl;

$R^{10}$ and $R^{11}$ are independently a hydrogen atom, $C_{1-6}$ alkyl, hydroxy $C_{1-6}$ alkyl, mono(di)$C_{1-6}$ alkylamino $C_{1-6}$ alkyl, pyrrolidinyl or piperidinyl;

$R^{12}$, $R^{13}$ and $R^{14}$ are independently a hydrogen atom, hydroxy, $C_{1-6}$ alkyl, $NR^{15}R^{16}$, $R^{15}R^{16}N-C_{1-6}$ alkyl, $C_{1-6}$ alkoxy, mono(di)hydroxy $C_{1-6}$ alkyl, carbamoyl, $C_{7-10}$ aralkyloxy $C_{1-6}$ alkyl, $C_{1-6}$ alkoxy $C_{1-6}$ alkyl, a fluorine atom or fluoro $C_{1-6}$ alkyl;

$R^{15}$ is a hydrogen atom, $C_{1-6}$ alkyl, ($C_{1-6}$ alkyl)carbonyl or $C_{7-10}$ aralkyl;

$R^{16}$ is a hydrogen atom, $C_{1-6}$ alkyl or $C_{7-10}$ aralkyl;

$R^{17}$ is a hydrogen atom or $C_{1-6}$ alkyl;

n is 0, 1 or 2.

2. The compound according to claim 1 or a pharmaceutical acceptable salt thereof:

wherein, ring A is $C_{3-6}$ cycloalkyl, $C_{6-10}$ aryl, pyridyl, benzo[1, 3]dioxolyl or thienyl;

ring B is $C_{6-10}$ aryl or heterocycle selected from the group consisting of the following: pyridyl, pyrimidyl, piperidinyl, morpholinyl, thiazolyl, pyrazinyl, pyrazolyl, imidazolyl, pyridazinyl, azaindolizinyl, indolyl, isoquinolyl, triazolyl, tetrazolyl and dihydropyrimidinyl.

3. The compound according to claim 2 or a pharmaceutically acceptable salt thereof, wherein n is 1.

4. The compound according to claim 3 or a pharmaceutical acceptable salt thereof:

wherein ring A is phenyl;

X is $CR^{4a}$.

5. The compound according to claim 4 or a pharmaceutically acceptable salt thereof:

wherein $R^5$ is a hydrogen atom.

6. The compound according to claim 5 or a pharmaceutically acceptable salt thereof:

wherein $R^{6a}$ is a hydrogen atom, $C(=O)R^9$, $C(=O)NR^{10}R^{11}$, $-CR^{12}R^{13}R^{14}$ or a group selected from the following formula:

[Chem.3]

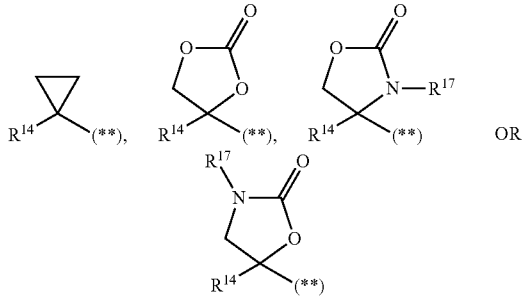

wherein, (**) is a bonding site;

$R^{7a}$ is a hydrogen atom, a fluorine atom, hydroxy, hydroxy $C_{1-6}$ alkyl, $C_{1-6}$ alkyl, $C_{1-6}$ alkoxy, $C_{1-6}$ alkoxy $C_{1-6}$ alkyl or amino $C_{1-6}$ alkyl;

$R^{7b}$ is a hydrogen atom, a fluorine atom or $C_{1-6}$ alkyl, or $R^{6a}$ may bind together with ring B or $R^{7a}$ to form the following formula:

[Chem.4]

wherein, (**) is a bonding site.

7. The compound according to claim 6 or a pharmaceutically acceptable salt thereof:
wherein X is CH.

8. The compound according to claim 7 or a pharmaceutically acceptable salt thereof:
wherein $R^1$ and $R^2$ are not hydrogen atoms at the same time.

9. The compound according to claim 8 or a pharmaceutically acceptable salt thereof:
wherein $R^{6b}$, $R^{7a}$ and $R^{7b}$ are a hydrogen atom.

10. The compound according to claim 1 or a pharmaceutically acceptable salt thereof:
wherein $R^{6a}$ is —$CR^{12}R^{13}R^{14}$; and
$R^{12}$ is hydroxy or mono(di)hydroxy $C_{1-6}$ alkyl.

11. A pharmaceutical composition comprising the compound according to claim 1 or a pharmaceutically acceptable salt thereof, and pharmaceutical additive.

12. A method for treating a disease or a symptom caused by hyperexcitability or a disorder of afferent neurons, comprising administering an effective amount of the compound according to claim 1 or a pharmaceutically acceptable salt thereof, and the disease or the symptom being selected from the group consisting of anxietas, depression, lower urinary tract symptoms, algi, and itch.

13. A compound represented by the following formula:

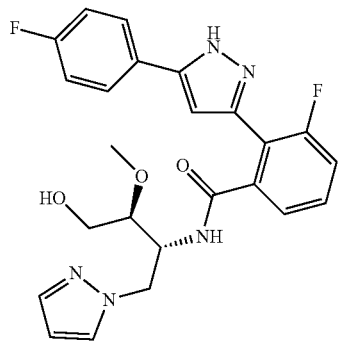 [SMILES: CO[C@H](CO)[C@@H](Cn1cccn1)NC(=O)c1cccc(F)c1-c1cc(-c2ccc(F)cc2)[nH]n1]

or a pharmaceutically acceptable salt thereof.

14. A compound represented by the following formula:

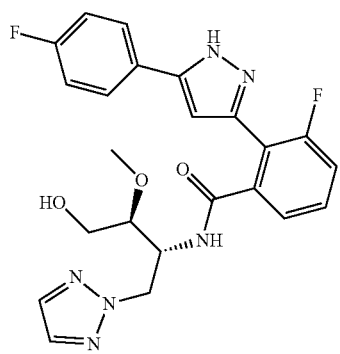 [SMILES: CO[C@H](CO)[C@@H](Cn1nccn1)NC(=O)c1cccc(F)c1-c1cc(-c2ccc(F)cc2)[nH]n1]

or a pharmaceutically acceptable salt thereof.

15. A compound represented by the following formula:

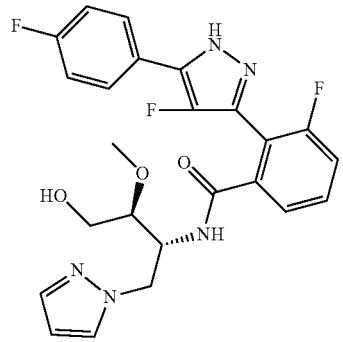 [SMILES: CO[C@H](CO)[C@@H](Cn1cccn1)NC(=O)c1cccc(F)c1-c1n[nH]c(-c2ccc(F)cc2)c1F]

or a pharmaceutically acceptable salt thereof.

16. A compound represented by the following formula:

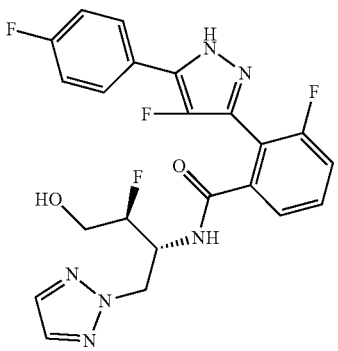 [SMILES: O=C(N[C@H](Cn1nccn1)[C@H](F)CO)c1cccc(F)c1-c1n[nH]c(-c2ccc(F)cc2)c1F]

or a pharmaceutically acceptable salt thereof.

17. A compound represented by the following formula:

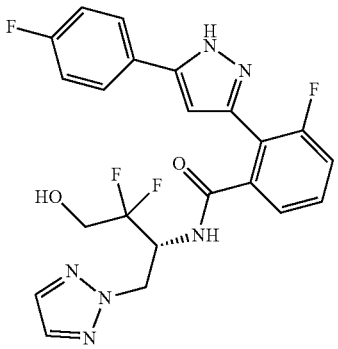 [SMILES: O=C(N[C@H](Cn1nccn1)C(F)(F)CO)c1cccc(F)c1-c1cc(-c2ccc(F)cc2)[nH]n1]

or a pharmaceutically acceptable salt thereof.

18. A compound represented by the following formula:

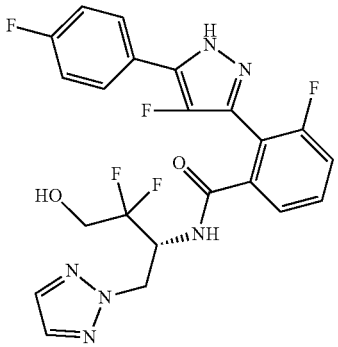 [SMILES: O=C(N[C@H](Cn1nccn1)C(F)(F)CO)c1cccc(F)c1-c1n[nH]c(-c2ccc(F)cc2)c1F]

or a pharmaceutically acceptable salt thereof.

* * * * *